US011883024B2

(12) United States Patent
Bakos et al.

(10) Patent No.: US 11,883,024 B2
(45) Date of Patent: Jan. 30, 2024

(54) METHOD OF OPERATING A SURGICAL INSTRUMENT

(71) Applicant: Cilag GmbH International, Zug (CH)

(72) Inventors: Gregory J. Bakos, Mason, OH (US); Darryl A. Parks, Mason, OH (US); Benjamin D. Dickerson, San Francisco, CA (US); Steven G. Hall, Cincinnati, OH (US); Robert J. Simms, Liberty Township, OH (US); Spencer J. Witte, Los Altos, CA (US); Taylor W. Aronhalt, Loveland, OH (US); Paul Moubarak, West Chester, OH (US); William C. Ryle, Covington, KY (US)

(73) Assignee: Cilag GmbH International, Zug (CH)

( * ) Notice: Subject to any disclaimer, the term of this patent is extended or adjusted under 35 U.S.C. 154(b) by 48 days.

(21) Appl. No.: 17/360,199

(22) Filed: Jun. 28, 2021

(65) Prior Publication Data
US 2022/0031315 A1    Feb. 3, 2022

Related U.S. Application Data

(60) Provisional application No. 63/057,430, filed on Jul. 28, 2020, provisional application No. 63/057,432, filed on Jul. 28, 2020.

(51) Int. Cl.
*A61B 17/068* (2006.01)
*A61B 17/072* (2006.01)
(Continued)

(52) U.S. Cl.
CPC .... *A61B 17/0686* (2013.01); *A61B 17/00234* (2013.01); *A61B 17/068* (2013.01);
(Continued)

(58) Field of Classification Search
CPC . A61B 17/0686; A61B 17/072; A61B 17/068; A61B 2034/301;
(Continued)

(56) References Cited

U.S. PATENT DOCUMENTS

| 66,052 A | 6/1867 | Smith |
|---|---|---|
| 662,587 A | 11/1900 | Blake |

(Continued)

FOREIGN PATENT DOCUMENTS

| AU | 2012200594 A1 | 2/2012 |
|---|---|---|
| AU | 2012203035 A1 | 6/2012 |

(Continued)

OTHER PUBLICATIONS

ASTM procedure D2240-00, "Standard Test Method for Rubber Property-Durometer Hardness," (Published Aug. 2000).
(Continued)

*Primary Examiner* — Robert F Long
*Assistant Examiner* — Xavier A Madison
(74) *Attorney, Agent, or Firm* — Frost Brown Todd LLP

(57) ABSTRACT

A method of operating an articulatable surgical instrument. The method includes providing a rotary drive motion to a rotary drive member of a surgical end effector and converting the rotary drive motion to an upper axial motion and a lower axial motion at locations that are distal to the articulation joint. The method further includes applying the upper axial motion to an upper portion of a firing member and applying the lower axial motion to a lower portion of the firing member such that the upper axial motion and lower axial motion drives the firing member distally through the surgical end effector from a starting position to an ending position.

20 Claims, 167 Drawing Sheets

(51) Int. Cl.
*A61B 17/32* (2006.01)
*A61B 17/29* (2006.01)
*A61B 34/30* (2016.01)
*A61B 17/00* (2006.01)

(52) U.S. Cl.
CPC ...... *A61B 17/072* (2013.01); *A61B 17/07207* (2013.01); *A61B 17/29* (2013.01); *A61B 17/320092* (2013.01); *A61B 34/30* (2016.02); *A61B 2017/00314* (2013.01); *A61B 2017/00323* (2013.01); *A61B 2017/00336* (2013.01); *A61B 2017/00367* (2013.01); *A61B 2017/00389* (2013.01); *A61B 2017/00398* (2013.01); *A61B 2017/00477* (2013.01); *A61B 2017/07214* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2017/320071* (2017.08); *A61B 2017/320093* (2017.08); *A61B 2017/320094* (2017.08); *A61B 2017/320095* (2017.08); *A61B 2017/320097* (2017.08); *A61B 2034/301* (2016.02)

(58) Field of Classification Search
CPC ....... A61B 2017/320097; A61B 2017/320071; A61B 2017/00323; A61B 2017/07214; A61B 2017/07257
USPC .......................................... 227/175.1–180.1
See application file for complete search history.

(56) References Cited

U.S. PATENT DOCUMENTS

| | | | |
|---|---|---|---|
| 670,748 A | 3/1901 | Weddeler |
| 719,487 A | 2/1903 | Minor |
| 804,229 A | 11/1905 | Hutchinson |
| 903,739 A | 11/1908 | Lesemann |
| 951,393 A | 3/1910 | Hahn |
| 1,075,556 A | 10/1913 | Fenoughty |
| 1,082,105 A | 12/1913 | Anderson |
| 1,188,721 A | 6/1916 | Bittner |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,028,635 A | 1/1936 | Wappler |
| 2,037,727 A | 4/1936 | Chapelle |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Lee |
| 2,420,552 A | 5/1947 | Morrill |
| 2,441,096 A | 5/1948 | Happe |
| 2,448,741 A | 9/1948 | Scott et al. |
| 2,450,527 A | 10/1948 | Smith |
| 2,491,872 A | 12/1949 | Neuman |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,724,289 A | 11/1955 | Wight |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,856,192 A | 10/1958 | Schuster |
| 2,887,004 A | 5/1959 | Stewart |
| 2,957,353 A | 10/1960 | Lewis |
| 2,959,974 A | 11/1960 | Emrick |
| 3,026,744 A | 3/1962 | Rouse |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,315,863 A | 4/1967 | O'Dea |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,339 A | 5/1972 | Shimizu |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,724,237 A | 4/1973 | Wood |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,826,978 A | 7/1974 | Kelly |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |

(56) References Cited

U.S. PATENT DOCUMENTS

| | | |
|---|---|---|
| 3,863,940 A | 2/1975 | Cummings |
| 3,883,624 A | 5/1975 | McKenzie et al. |
| 3,885,491 A | 5/1975 | Curtis |
| 3,887,393 A | 6/1975 | La Rue, Jr. |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,973,179 A | 8/1976 | Weber et al. |
| 3,981,051 A | 9/1976 | Brumlik |
| 3,999,110 A | 12/1976 | Ramstrom et al. |
| 4,025,216 A | 5/1977 | Hives |
| 4,027,746 A | 6/1977 | Kine |
| 4,034,143 A | 7/1977 | Sweet |
| 4,038,987 A | 8/1977 | Komiya |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,154,122 A | 5/1979 | Severin |
| 4,160,857 A | 7/1979 | Nardella et al. |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,203,444 A | 5/1980 | Bonnell et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,282,573 A | 8/1981 | Imai et al. |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,369,013 A | 1/1983 | Abildgaard et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,389,963 A | 6/1983 | Pearson |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,421,264 A | 12/1983 | Arter et al. |
| 4,423,456 A | 12/1983 | Zaidenweber |
| 4,425,915 A | 1/1984 | Ivanov |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,459,519 A | 7/1984 | Erdman |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,476,864 A | 10/1984 | Tezel |
| 4,478,220 A | 10/1984 | Di Giovanni et al. |
| 4,480,641 A | 11/1984 | Failla et al. |
| 4,481,458 A | 11/1984 | Lane |
| 4,483,562 A | 11/1984 | Schoolman |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,514,477 A | 4/1985 | Kobayashi |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |

(56) References Cited

U.S. PATENT DOCUMENTS

| | | |
|---|---|---|
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,980 A | 9/1986 | Aihara |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |
| 4,619,262 A | 10/1986 | Taylor |
| 4,619,391 A | 10/1986 | Sharkany et al. |
| 4,624,401 A | 11/1986 | Gassner et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,642,738 A | 2/1987 | Meller |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,651,734 A | 3/1987 | Doss et al. |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,722,340 A | 2/1988 | Takayama et al. |
| 4,724,840 A | 2/1988 | McVay et al. |
| 4,726,247 A | 2/1988 | Hormann |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,755,070 A | 7/1988 | Cerutti |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,788,485 A | 11/1988 | Kawagishi et al. |
| D298,967 S | 12/1988 | Hunt |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,495 A | 4/1989 | Hormann |
| 4,819,853 A | 4/1989 | Green |
| 4,821,939 A | 4/1989 | Green |
| 4,827,552 A | 5/1989 | Bojar et al. |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,096 A | 5/1989 | Oh et al. |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |

(56) References Cited

U.S. PATENT DOCUMENTS

| | | |
|---|---|---|
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,954,960 A | 9/1990 | Lo et al. |
| 4,955,959 A | 9/1990 | Tompkins et al. |
| 4,957,212 A | 9/1990 | Duck et al. |
| 4,962,681 A | 10/1990 | Yang |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,970,656 A | 11/1990 | Lo et al. |
| 4,973,274 A | 11/1990 | Hirukawa |
| 4,973,302 A | 11/1990 | Armour et al. |
| 4,976,173 A | 12/1990 | Yang |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,001,649 A | 3/1991 | Lo et al. |
| 5,002,543 A | 3/1991 | Bradshaw et al. |
| 5,002,553 A | 3/1991 | Shiber |
| 5,005,754 A | 4/1991 | Van Overloop |
| 5,009,222 A | 4/1991 | Her |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,033,552 A | 7/1991 | Hu |
| 5,035,040 A | 7/1991 | Kerrigan et al. |
| 5,037,018 A | 8/1991 | Matsuda et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,056,953 A | 10/1991 | Marot et al. |
| 5,060,658 A | 10/1991 | Dejter, Jr. et al. |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,151,102 A | 9/1992 | Kamiyama et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,222 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,181,514 A | 1/1993 | Solomon et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,193,731 A | 3/1993 | Aranyi |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |

(56) References Cited

U.S. PATENT DOCUMENTS

| | | |
|---|---|---|
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,456 A | 9/1993 | Nash et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,135 A | 11/1993 | Mitchell |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,269,794 A | 12/1993 | Rexroth |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,281,400 A | 1/1994 | Berry, Jr. |
| 5,282,806 A | 2/1994 | Haber et al. |
| 5,282,826 A | 2/1994 | Quadri |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,291,133 A | 3/1994 | Gokhale et al. |
| 5,292,053 A | 3/1994 | Bilotti et al. |
| 5,293,024 A | 3/1994 | Sugahara et al. |
| 5,297,714 A | 3/1994 | Kramer |
| 5,303,606 A | 4/1994 | Kokinda |
| 5,304,204 A | 4/1994 | Bregen |
| D347,474 S | 5/1994 | Olson |
| 5,307,976 A | 5/1994 | Olson et al. |
| 5,308,353 A | 5/1994 | Beurrier |
| 5,308,358 A | 5/1994 | Bond et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,486 A | 7/1994 | Wilk |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,338,317 A | 8/1994 | Hasson et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,104 A | 9/1994 | Main et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,353,798 A | 10/1994 | Sieben |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |

(56) References Cited

U.S. PATENT DOCUMENTS

| | | |
|---|---|---|
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,460 A | 1/1995 | Jang et al. |
| 5,383,874 A | 1/1995 | Jackson et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,355 A | 6/1995 | Kulick |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,645 A | 7/1995 | Smith et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,441,499 A | 8/1995 | Fritzsch |
| 5,443,197 A | 8/1995 | Malis et al. |
| 5,443,198 A | 8/1995 | Viola et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,446,646 A | 8/1995 | Miyazaki |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,474,738 A | 12/1995 | Nichols et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,377 A | 1/1996 | Smith et al. |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |

(56) References Cited

U.S. PATENT DOCUMENTS

| | | |
|---|---|---|
| 5,496,317 A | 3/1996 | Goble et al. |
| 5,497,933 A | 3/1996 | DeFonzo et al. |
| 5,498,164 A | 3/1996 | Ward et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Zlglloll |
| 5,507,426 A | 4/1996 | Young et al. |
| 5,507,773 A | 4/1996 | Huitema et al. |
| 5,509,596 A | 4/1996 | Green et al. |
| 5,509,916 A | 4/1996 | Taylor |
| 5,509,918 A | 4/1996 | Romano |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,945 A | 8/1996 | Fritzsch |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,436 A | 3/1997 | Pratt et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,979 A | 5/1997 | Mitsui et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |

(56) References Cited

U.S. PATENT DOCUMENTS

| | | |
|---|---|---|
| 5,630,782 A | 5/1997 | Adair |
| 5,631,973 A | 5/1997 | Green |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,638,582 A | 6/1997 | Klatt et al. |
| 5,639,008 A | 6/1997 | Gallagher et al. |
| D381,077 S | 7/1997 | Hunt |
| 5,643,291 A | 7/1997 | Pier et al. |
| 5,643,293 A | 7/1997 | Kogasaka et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,664,404 A | 9/1997 | Ivanov et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,667,864 A | 9/1997 | Landoll |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,672,945 A | 9/1997 | Krause |
| 5,673,840 A | 10/1997 | Schulze et al. |
| 5,673,841 A | 10/1997 | Schulze et al. |
| 5,673,842 A | 10/1997 | Bittner et al. |
| 5,674,184 A | 10/1997 | Hassler, Jr. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,690,675 A | 11/1997 | Sawyer et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,711,960 A | 1/1998 | Shikinami |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,836 A | 2/1998 | Kliegis et al. |
| 5,715,987 A | 2/1998 | Kelley et al. |
| 5,715,988 A | 2/1998 | Palmer |
| 5,716,352 A | 2/1998 | Viola et al. |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Ri |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,712 A | 3/1998 | Adair |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,736,271 A | 4/1998 | Cisar et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,752,973 A | 5/1998 | Kieturakis |
| 5,755,717 A | 5/1998 | Yates et al. |
| 5,755,726 A | 5/1998 | Pratt et al. |
| 5,758,814 A | 6/1998 | Gallagher et al. |
| 5,762,255 A | 6/1998 | Chrisman et al. |
| 5,762,256 A | 6/1998 | Mastri et al. |
| 5,762,458 A | 6/1998 | Wang et al. |
| 5,765,565 A | 6/1998 | Adair |
| 5,766,186 A | 6/1998 | Faraz et al. |
| 5,766,188 A | 6/1998 | Igaki |
| 5,766,205 A | 6/1998 | Zvenyatsky et al. |

(56) References Cited

U.S. PATENT DOCUMENTS

| | | |
|---|---|---|
| 5,769,303 A | 6/1998 | Knodel et al. |
| 5,769,640 A | 6/1998 | Jacobus et al. |
| 5,769,748 A | 6/1998 | Eyerly et al. |
| 5,769,791 A | 6/1998 | Benaron et al. |
| 5,769,892 A | 6/1998 | Kingwell |
| 5,772,099 A | 6/1998 | Gravener |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,900 A | 8/1998 | Madhani et al. |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,241 A | 9/1998 | Heimberger |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,812,188 A | 9/1998 | Adair |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,827,323 A | 10/1998 | Klieman et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Llvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,664 A | 2/1999 | Speier et al. |
| 5,868,760 A | 2/1999 | McGuckin, Jr. |
| 5,868,790 A | 2/1999 | Vincent et al. |
| 5,871,135 A | 2/1999 | Williamson IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,881,943 A | 3/1999 | Heck et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,907,664 A | 5/1999 | Wang et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |

(56) References Cited

U.S. PATENT DOCUMENTS

| | | |
|---|---|---|
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,957,831 A | 9/1999 | Adair |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,013,991 A | 1/2000 | Philipp |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,019,780 A | 2/2000 | Lombardo et al. |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,126 A | 3/2000 | Hsieh |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| 6,055,062 A | 4/2000 | Dina et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,072,299 A | 6/2000 | Kurle et al. |
| 6,074,386 A | 6/2000 | Goble et al. |
| 6,074,401 A | 6/2000 | Gardiner et al. |
| 6,075,441 A | 6/2000 | Maloney |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,090,123 A | 7/2000 | Culp et al. |
| 6,093,186 A | 7/2000 | Goble |
| D429,252 S | 8/2000 | Haitani et al. |
| 6,099,537 A | 8/2000 | Sugai et al. |
| 6,099,551 A | 8/2000 | Gabbay |
| 6,102,271 A | 8/2000 | Longo et al. |
| 6,102,926 A | 8/2000 | Tartaglia et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| RE36,923 E | 10/2000 | Hiroi et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,134,962 A | 10/2000 | Sugitani |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |

(56) References Cited

U.S. PATENT DOCUMENTS

| | | |
|---|---|---|
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,186,957 B1 | 2/2001 | Milam |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,311 B1 | 3/2001 | Danek et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,903 B1 | 3/2001 | Ramans |
| 6,206,904 B1 | 3/2001 | Ouchi |
| 6,209,414 B1 | 4/2001 | Uneme |
| 6,210,403 B1 | 4/2001 | Klicek |
| 6,211,626 B1 | 4/2001 | Lys et al. |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,246 B1 | 7/2001 | Pantages et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,269,997 B1 | 8/2001 | Balazs et al. |
| 6,270,508 B1 | 8/2001 | Klieman et al. |
| 6,270,916 B1 | 8/2001 | Sink et al. |
| 6,273,252 B1 | 8/2001 | Mitchell |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,317,616 B1 | 11/2001 | Glossop |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| 6,349,868 B1 | 2/2002 | Mattingly et al. |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Ass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,364,828 B1 | 4/2002 | Yeung et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |

(56) References Cited

U.S. PATENT DOCUMENTS

| | | |
|---|---|---|
| 6,402,766 B2 | 6/2002 | Bowman et al. |
| 6,402,780 B2 | 6/2002 | Williamson, IV et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,415,542 B1 | 7/2002 | Bates et al. |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| 6,424,885 B1 | 7/2002 | Niemeyer et al. |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,457,338 B1 | 10/2002 | Frenken |
| 6,457,625 B1 | 10/2002 | Tormala et al. |
| 6,458,077 B1 | 10/2002 | Boebel et al. |
| 6,458,142 B1 | 10/2002 | Faller et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,491,702 B2 | 12/2002 | Heilbrun et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,888 B1 | 12/2002 | Laufer et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,189 B1 | 12/2002 | Lang et al. |
| 6,500,194 B2 | 12/2002 | Benderev et al. |
| D468,749 S | 1/2003 | Friedman |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,506,399 B2 | 1/2003 | Donovan |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| D471,206 S | 3/2003 | Buzzard et al. |
| 6,527,782 B2 | 3/2003 | Hogg et al. |
| 6,527,785 B2 | 3/2003 | Sancoff et al. |
| 6,530,942 B2 | 3/2003 | Fogarty et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,540,737 B2 | 4/2003 | Bacher et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,844 B2 | 4/2003 | Lee et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,572 B1 | 7/2003 | Suzuta |
| 6,592,597 B2 | 7/2003 | Grant et al. |
| 6,594,552 B1 | 7/2003 | Nowlin et al. |
| 6,595,914 B2 | 7/2003 | Kato |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,295 B1 | 7/2003 | Tornier et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |

(56) References Cited

U.S. PATENT DOCUMENTS

| | | |
|---|---|---|
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,161 B2 | 9/2003 | Schulze et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,860 B1 | 12/2003 | Takahashi |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,695,849 B2 | 2/2004 | Michelson |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,215 B1 | 4/2004 | David et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,106 B1 | 4/2004 | Charles et al. |
| 6,723,109 B2 | 4/2004 | Solingen |
| 6,726,651 B1 | 4/2004 | Robinson et al. |
| 6,726,697 B2 | 4/2004 | Nicholas et al. |
| 6,726,705 B2 | 4/2004 | Peterson et al. |
| 6,726,706 B2 | 4/2004 | Dominguez |
| 6,729,119 B2 | 5/2004 | Schnipke et al. |
| 6,731,976 B2 | 5/2004 | Penn et al. |
| 6,736,810 B2 | 5/2004 | Hoey et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,825 B2 | 6/2004 | Shoenman et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,763,307 B2 | 7/2004 | Berg et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,770,078 B2 | 8/2004 | Bonutti |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,778,846 B1 | 8/2004 | Martinez et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,784,775 B2 | 8/2004 | Mandell et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,801,009 B2 | 10/2004 | Makaran et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,806,867 B1 | 10/2004 | Arruda et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |

(56) References Cited

U.S. PATENT DOCUMENTS

| | | |
|---|---|---|
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,840,938 B1 | 1/2005 | Morley et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,668 B2 | 3/2005 | Giannetti et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,876,850 B2 | 4/2005 | Maeshima et al. |
| 6,877,647 B2 | 4/2005 | Green et al. |
| 6,878,106 B1 | 4/2005 | Herrmann |
| 6,882,127 B2 | 4/2005 | Konigbauer |
| 6,883,199 B1 | 4/2005 | Lundell et al. |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,244 B1 | 5/2005 | Walker et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,899,705 B2 | 5/2005 | Niemeyer |
| 6,899,915 B2 | 5/2005 | Yelick et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,949,196 B2 | 9/2005 | Schmitz et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| D511,525 S | 11/2005 | Hernandez et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,991,146 B2 | 1/2006 | Sinisi et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 6,999,821 B2 | 2/2006 | Jenney et al. |

(56) References Cited

U.S. PATENT DOCUMENTS

| | | |
|---|---|---|
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,213 B2 | 3/2006 | Clark et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,399 B2 | 4/2006 | Driessen |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,033,378 B2 | 4/2006 | Smith et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,038,421 B2 | 5/2006 | Trifilo |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,165 B2 | 5/2006 | Haramiishi |
| 7,048,687 B1 | 5/2006 | Reuss et al. |
| 7,048,716 B1 | 5/2006 | Kucharczyk et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,123 B2 | 6/2006 | Gregorio et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,081,318 B2 | 7/2006 | Lee et al. |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,191 B2 | 8/2006 | Laredo et al. |
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,363 B2 | 9/2006 | Nishizawa et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| D530,339 S | 10/2006 | Hernandez et al. |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |

(56) References Cited

U.S. PATENT DOCUMENTS

| | | |
|---|---|---|
| 7,150,748 B2 | 12/2006 | Ebbutt et al. |
| 7,153,300 B2 | 12/2006 | Goble |
| 7,153,314 B2 | 12/2006 | Laufer et al. |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,117 B2 | 1/2007 | Hellenkamp |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,202 B2 | 2/2007 | Bladen et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,193,199 B2 | 3/2007 | Jang |
| 7,195,627 B2 | 3/2007 | Amoah et al. |
| 7,196,911 B2 | 3/2007 | Takano et al. |
| D541,418 S | 4/2007 | Schechter et al. |
| 7,199,537 B2 | 4/2007 | Okamura et al. |
| 7,199,545 B2 | 4/2007 | Oleynikov et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,205,959 B2 | 4/2007 | Henriksson |
| 7,206,626 B2 | 4/2007 | Quaid, III |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,226,467 B2 | 6/2007 | Lucatero et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| 7,273,488 B2 | 9/2007 | Nakamura et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,283,096 B2 | 10/2007 | Geisheimer et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,335,401 B2 | 2/2008 | Finke et al. |
| 7,336,045 B2 | 2/2008 | Clermonts |
| 7,336,048 B2 | 2/2008 | Lohr |
| 7,336,183 B2 | 2/2008 | Reddy et al. |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,554 B2 | 3/2008 | Sekine et al. |
| 7,341,555 B2 | 3/2008 | Ootawara et al. |
| 7,341,591 B2 | 3/2008 | Grinberg |

(56) References Cited

U.S. PATENT DOCUMENTS

| | | |
|---|---|---|
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,367,973 B2 | 5/2008 | Manzo et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,375,493 B2 | 5/2008 | Calhoon et al. |
| 7,377,918 B2 | 5/2008 | Amoah |
| 7,377,928 B2 | 5/2008 | Zubik et al. |
| 7,378,817 B2 | 5/2008 | Calhoon et al. |
| RE40,388 E | 6/2008 | Gines |
| D570,868 S | 6/2008 | Hosokawa et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| D575,793 S | 8/2008 | Ording |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,446,131 B1 | 11/2008 | Liu et al. |
| 7,448,525 B2 | 11/2008 | Shelton, IV et al. |
| 7,450,010 B1 | 11/2008 | Gravelle et al. |
| 7,450,991 B2 | 11/2008 | Smith et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,455,687 B2 | 11/2008 | Saunders et al. |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,147 B2 | 1/2009 | Honeycutt et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,492,261 B2 | 2/2009 | Cambre et al. |
| 7,494,039 B2 | 2/2009 | Racenet et al. |
| 7,494,460 B2 | 2/2009 | Haarstad et al. |
| 7,494,499 B2 | 2/2009 | Nagase et al. |
| 7,494,501 B2 | 2/2009 | Ahlberg et al. |
| 7,497,137 B2 | 3/2009 | Tellenbach et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |

(56) References Cited

U.S. PATENT DOCUMENTS

| | | |
|---|---|---|
| 7,534,259 B2 | 5/2009 | Lashinski et al. |
| 7,540,867 B2 | 6/2009 | Jinno et al. |
| 7,540,872 B2 | 6/2009 | Schechter et al. |
| 7,542,807 B2 | 6/2009 | Bertolero et al. |
| 7,543,730 B1 | 6/2009 | Marczyk |
| 7,544,197 B2 | 6/2009 | Kelsch et al. |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,572,285 B2 | 8/2009 | Frey et al. |
| 7,575,144 B2 | 8/2009 | Ortiz et al. |
| 7,578,825 B2 | 8/2009 | Huebner |
| D600,712 S | 9/2009 | LaManna et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,595,642 B2 | 9/2009 | Doyle |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,605,826 B2 | 10/2009 | Sauer |
| 7,607,557 B2 | 10/2009 | Shelton, IV et al. |
| 7,608,091 B2 | 10/2009 | Goldfarb et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,006 B2 | 11/2009 | Abe |
| 7,615,067 B2 | 11/2009 | Lee et al. |
| 7,617,961 B2 | 11/2009 | Viola |
| 7,618,427 B2 | 11/2009 | Ortiz et al. |
| D605,201 S | 12/2009 | Lorenz et al. |
| D606,992 S | 12/2009 | Liu et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,625,388 B2 | 12/2009 | Boukhny et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,055 B2 | 1/2010 | Marczyk |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,003 B2 | 2/2010 | Lorang et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,666,195 B2 | 2/2010 | Kelleher et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,678,121 B1 | 3/2010 | Knodel |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,690,547 B2 | 4/2010 | Racenet et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,706,853 B2 | 4/2010 | Hacker et al. |
| 7,708,180 B2 | 5/2010 | Murray et al. |
| 7,708,181 B2 | 5/2010 | Cole et al. |

(56) References Cited

U.S. PATENT DOCUMENTS

| | | |
|---|---|---|
| 7,708,182 B2 | 5/2010 | Viola |
| 7,708,758 B2 | 5/2010 | Lee et al. |
| 7,708,768 B2 | 5/2010 | Danek et al. |
| 7,709,136 B2 | 5/2010 | Touchton et al. |
| 7,712,182 B2 | 5/2010 | Zeller et al. |
| 7,713,190 B2 | 5/2010 | Brock et al. |
| 7,713,542 B2 | 5/2010 | Xu et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,932 B2 | 5/2010 | Cole et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,735,704 B2 | 6/2010 | Bilotti |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,749,240 B2 | 7/2010 | Takahashi et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,758,613 B2 | 7/2010 | Whitman |
| 7,762,462 B2 | 7/2010 | Gelbman |
| 7,762,998 B2 | 7/2010 | Birk et al. |
| D622,286 S | 8/2010 | Umezawa |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,614 B1 | 8/2010 | McGonagle et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,651 B2 | 8/2010 | Madhani et al. |
| 7,780,663 B2 | 8/2010 | Yates et al. |
| 7,780,685 B2 | 8/2010 | Hunt et al. |
| 7,782,382 B2 | 8/2010 | Fujimura |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,885 B2 | 10/2010 | Cooper |
| 7,819,886 B2 | 10/2010 | Whitfield et al. |
| 7,819,894 B2 | 10/2010 | Mitsuishi et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,829,416 B2 | 11/2010 | Kudou et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,687 B2 | 11/2010 | Harp |
| 7,837,694 B2 | 11/2010 | Tethrake et al. |
| 7,838,789 B2 | 11/2010 | Stotters et al. |
| 7,839,109 B2 | 11/2010 | Carmen, Jr. et al. |
| 7,840,253 B2 | 11/2010 | Tremblay et al. |
| 7,841,503 B2 | 11/2010 | Sonnenschein et al. |
| 7,842,025 B2 | 11/2010 | Coleman et al. |

(56) References Cited

U.S. PATENT DOCUMENTS

| | | |
|---|---|---|
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,845,538 B2 | 12/2010 | Whitman |
| 7,845,912 B2 | 12/2010 | Sung et al. |
| 7,846,085 B2 | 12/2010 | Silverman et al. |
| 7,846,149 B2 | 12/2010 | Jankowski |
| 7,846,161 B2 | 12/2010 | Dumbauld et al. |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,853,813 B2 | 12/2010 | Lee |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,883,540 B2 | 2/2011 | Niwa et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,671 B2 | 3/2011 | Kim et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,896,900 B2 | 3/2011 | Frank et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,926,692 B2 | 4/2011 | Racenet et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,939,152 B2 | 5/2011 | Haskin et al. |
| 7,941,865 B2 | 5/2011 | Seman, Jr. et al. |
| 7,942,300 B2 | 5/2011 | Rethy et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,954,688 B2 | 6/2011 | Argentine et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,508 B2 | 7/2011 | Hoag |

(56) References Cited

U.S. PATENT DOCUMENTS

| | | |
|---|---|---|
| 7,976,563 B2 | 7/2011 | Summerer |
| 7,979,137 B2 | 7/2011 | Tracey et al. |
| 7,980,443 B2 | 7/2011 | Scheib et al. |
| 7,981,025 B2 | 7/2011 | Pool et al. |
| 7,981,102 B2 | 7/2011 | Patel et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,008,598 B2 | 8/2011 | Whitman et al. |
| 8,010,180 B2 | 8/2011 | Quaid et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,033,442 B2 | 10/2011 | Racenet et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,044 B2 | 10/2011 | Viola |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,306 B2 | 11/2011 | Nobis et al. |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,859 B2 | 12/2011 | Kostrzewski |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,320 B2 | 1/2012 | Manzo |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,114,345 B2 | 2/2012 | Dlugos, Jr. et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |

(56) References Cited

U.S. PATENT DOCUMENTS

| | | |
|---|---|---|
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,157,834 B2 | 4/2012 | Conlon |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,190,238 B2 | 5/2012 | Moll et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,193,129 B2 | 6/2012 | Tagawa et al. |
| 8,196,795 B2 | 6/2012 | Moore et al. |
| 8,196,796 B2 | 6/2012 | Shelton, IV et al. |
| 8,197,472 B2 | 6/2012 | Lau et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,207,863 B2 | 6/2012 | Neubauer et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,402 B2 | 7/2012 | Francischelli et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,235,274 B2 | 8/2012 | Cappola |
| 8,236,010 B2 | 8/2012 | Ortiz et al. |
| 8,236,011 B2 | 8/2012 | Harris et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,252,009 B2 | 8/2012 | Weller et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,261,958 B1 | 9/2012 | Knodel |
| 8,262,560 B2 | 9/2012 | Whitman |
| 8,262,655 B2 | 9/2012 | Ghabrial et al. |
| 8,266,232 B2 | 9/2012 | Piper et al. |
| 8,267,300 B2 | 9/2012 | Boudreaux |
| 8,267,849 B2 | 9/2012 | Wazer et al. |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,268,344 B2 | 9/2012 | Ma et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,594 B2 | 10/2012 | Shah |

(56) References Cited

U.S. PATENT DOCUMENTS

| | | |
|---|---|---|
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,286,847 B2 | 10/2012 | Taylor |
| 8,287,487 B2 | 10/2012 | Estes |
| 8,287,522 B2 | 10/2012 | Moses et al. |
| 8,287,561 B2 | 10/2012 | Nunez et al. |
| 8,288,984 B2 | 10/2012 | Yang |
| 8,289,403 B2 | 10/2012 | Dobashi et al. |
| 8,290,883 B2 | 10/2012 | Takeuchi et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,158 B2 | 10/2012 | Sapienza |
| 8,292,801 B2 | 10/2012 | Dejima et al. |
| 8,292,888 B2 | 10/2012 | Whitman |
| 8,292,906 B2 | 10/2012 | Taylor et al. |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,303,621 B2 | 11/2012 | Miyamoto et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| D672,784 S | 12/2012 | Clanton et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,271 B2 | 12/2012 | Humayun et al. |
| 8,323,789 B2 | 12/2012 | Rozhin et al. |
| 8,324,585 B2 | 12/2012 | McBroom et al. |
| 8,327,514 B2 | 12/2012 | Kim |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,065 B2 | 12/2012 | Shah |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| D676,866 S | 2/2013 | Chaudhri |
| 8,365,972 B2 | 2/2013 | Aranyi et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,368,327 B2 | 2/2013 | Benning et al. |
| 8,369,056 B2 | 2/2013 | Senriuchi et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,374,723 B2 | 2/2013 | Zhao et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,377,059 B2 | 2/2013 | Deville et al. |
| 8,381,828 B2 | 2/2013 | Whitman et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,972 B2 | 3/2013 | Kostrzewski |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,108 B2 | 3/2013 | Powell et al. |
| 8,400,851 B2 | 3/2013 | Byun |
| 8,403,138 B2 | 3/2013 | Weisshaupt et al. |
| 8,403,195 B2 | 3/2013 | Beardsley et al. |
| 8,403,196 B2 | 3/2013 | Beardsley et al. |

(56) References Cited

U.S. PATENT DOCUMENTS

| | | |
|---|---|---|
| 8,403,198 B2 | 3/2013 | Sorrentino et al. |
| 8,403,832 B2 | 3/2013 | Cunningham et al. |
| 8,403,926 B2 | 3/2013 | Nobis et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| D680,646 S | 4/2013 | Hunt et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,211 B2 | 4/2013 | Baroud |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,469 B2 | 4/2013 | Diolaiti |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,419,755 B2 | 4/2013 | Deem et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,439,830 B2 | 5/2013 | McKinley et al. |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,449,536 B2 | 5/2013 | Selig |
| 8,449,560 B2 | 5/2013 | Roth et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,551 B2 | 6/2013 | Allen et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| D686,244 S | 7/2013 | Moriya et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,483,509 B2 | 7/2013 | Matsuzaka |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,487,487 B2 | 7/2013 | Dietz et al. |
| 8,490,851 B2 | 7/2013 | Blier et al. |
| 8,490,852 B2 | 7/2013 | Viola |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,498,691 B2 | 7/2013 | Moll et al. |
| 8,499,673 B2 | 8/2013 | Keller |
| 8,499,966 B2 | 8/2013 | Palmer et al. |
| 8,499,992 B2 | 8/2013 | Whitman et al. |
| 8,499,993 B2 | 8/2013 | Shelton, IV et al. |
| 8,499,994 B2 | 8/2013 | D'Arcangelo |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,938 B2 | 8/2013 | Eisenhardt et al. |
| 8,518,024 B2 | 8/2013 | Williams et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,787 B2 | 9/2013 | Ludwin et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,599 B2 | 9/2013 | Holsten |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,539,866 B2 | 9/2013 | Nayak et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,646 B2 | 9/2013 | Mendez-Coll |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |

(56) References Cited

U.S. PATENT DOCUMENTS

| | | |
|---|---|---|
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,592 B2 | 10/2013 | Conlon et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,125 B2 | 12/2013 | King |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,431 B2 | 12/2013 | Timm et al. |
| 8,617,155 B2 | 12/2013 | Johnson et al. |
| 8,620,473 B2 | 12/2013 | Diolaiti et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,467 B2 | 1/2014 | Whitman et al. |
| 8,628,518 B2 | 1/2014 | Blumenkranz et al. |
| 8,628,544 B2 | 1/2014 | Farascioni |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,539 B2 | 1/2014 | Twomey et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,652,155 B2 | 2/2014 | Houser et al. |
| 8,656,929 B2 | 2/2014 | Miller et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,209 B2 | 3/2014 | Crainich |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Bale et al. |
| 8,678,263 B2 | 3/2014 | Viola |
| 8,678,994 B2 | 3/2014 | Sonnenschein et al. |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,706,316 B1 | 4/2014 | Hoevenaar |
| 8,708,210 B2 | 4/2014 | Zemlok et al. |
| 8,708,211 B2 | 4/2014 | Zemlok et al. |
| 8,708,212 B2 | 4/2014 | Williams |
| 8,708,213 B2 | 4/2014 | Shelton, IV et al. |
| 8,709,012 B2 | 4/2014 | Muller |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,611 B2 | 5/2014 | Milliman |

(56) References Cited

U.S. PATENT DOCUMENTS

| | | |
|---|---|---|
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,734,831 B2 | 5/2014 | Kim et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,765,942 B2 | 7/2014 | Feraud et al. |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,496 B2 | 8/2014 | Scirica |
| 8,794,497 B2 | 8/2014 | Zingman |
| 8,795,159 B2 | 8/2014 | Moriyama |
| 8,795,276 B2 | 8/2014 | Dietz et al. |
| 8,795,308 B2 | 8/2014 | Valin |
| 8,795,324 B2 | 8/2014 | Kawai et al. |
| 8,796,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,815,594 B2 | 8/2014 | Harris et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,828,046 B2 | 9/2014 | Stefanchik et al. |
| 8,831,779 B2 | 9/2014 | Ortmaier et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,465 B2 | 9/2014 | Ramstein et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,844,790 B2 | 9/2014 | Demmy et al. |
| 8,845,622 B2 | 9/2014 | Paik et al. |
| 8,851,215 B2 | 10/2014 | Goto |
| 8,851,354 B2 | 10/2014 | Swensgard et al. |
| 8,851,355 B2 | 10/2014 | Aranyi et al. |
| 8,852,174 B2 | 10/2014 | Burbank |
| 8,852,185 B2 | 10/2014 | Twomey |
| 8,852,199 B2 | 10/2014 | Deslauriers et al. |
| 8,852,218 B2 | 10/2014 | Hughett, Sr. et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,547 B2 | 10/2014 | Brogna |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,864,750 B2 | 10/2014 | Ross et al. |
| 8,869,912 B2 | 10/2014 | Roßkamp et al. |
| 8,869,913 B2 | 10/2014 | Matthias et al. |
| 8,870,050 B2 | 10/2014 | Hodgkinson |
| 8,870,867 B2 | 10/2014 | Walberg et al. |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,882,660 B2 | 11/2014 | Phee et al. |
| 8,882,792 B2 | 11/2014 | Dietz et al. |
| 8,884,560 B2 | 11/2014 | Ito |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |

(56) References Cited

U.S. PATENT DOCUMENTS

| | | |
|---|---|---|
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,910,847 B2 | 12/2014 | Nalagatla et al. |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,912,746 B2 | 12/2014 | Reid et al. |
| 8,915,842 B2 | 12/2014 | Weisenburgh, II et al. |
| 8,920,368 B2 | 12/2014 | Sandhu et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,939,898 B2 | 1/2015 | Omoto |
| 8,944,069 B2 | 2/2015 | Miller et al. |
| 8,945,095 B2 | 2/2015 | Blumenkranz et al. |
| 8,945,098 B2 | 2/2015 | Seibold et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,542 B2 | 3/2015 | Fujimoto et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,984,711 B2 | 3/2015 | Ota et al. |
| 8,985,240 B2 | 3/2015 | Winnard |
| 8,985,429 B2 | 3/2015 | Balek et al. |
| 8,986,302 B2 | 3/2015 | Aldridge et al. |
| 8,989,903 B2 | 3/2015 | Weir et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,000,720 B2 | 4/2015 | Stulen et al. |
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,437 B2 | 4/2015 | Woodruff et al. |
| 9,011,439 B2 | 4/2015 | Shalaby et al. |
| 9,011,471 B2 | 4/2015 | Timm et al. |
| 9,014,856 B2 | 4/2015 | Manzo et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,017,849 B2 | 4/2015 | Stulen et al. |
| 9,017,851 B2 | 4/2015 | Felder et al. |
| D729,274 S | 5/2015 | Clement et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,468 B2 | 5/2015 | Scarfogliero et al. |
| 9,028,494 B2 | 5/2015 | Shelton, IV et al. |
| 9,028,495 B2 | 5/2015 | Mueller et al. |
| 9,028,510 B2 | 5/2015 | Miyamoto et al. |
| 9,028,511 B2 | 5/2015 | Weller et al. |
| 9,028,519 B2 | 5/2015 | Yates et al. |
| 9,030,166 B2 | 5/2015 | Kano |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,040,062 B2 | 5/2015 | Maeda et al. |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,238 B2 | 6/2015 | Orszulak |
| 9,044,241 B2 | 6/2015 | Barner et al. |
| 9,044,261 B2 | 6/2015 | Houser |

(56) References Cited

U.S. PATENT DOCUMENTS

| | | |
|---|---|---|
| 9,044,281 B2 | 6/2015 | Pool et al. |
| 9,050,083 B2 | 6/2015 | Yates et al. |
| 9,050,084 B2 | 6/2015 | Schmid et al. |
| 9,050,089 B2 | 6/2015 | Orszulak |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,050,192 B2 | 6/2015 | Mansmann |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,070,068 B2 | 6/2015 | Coveley et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,654 B2 | 7/2015 | Whitman et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,338 B2 | 7/2015 | Smith et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,096,033 B2 | 8/2015 | Holop et al. |
| 9,098,153 B2 | 8/2015 | Shen et al. |
| 9,099,863 B2 | 8/2015 | Smith et al. |
| 9,099,877 B2 | 8/2015 | Banos et al. |
| 9,099,922 B2 | 8/2015 | Toosky et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,101,621 B2 | 8/2015 | Zeldis |
| 9,107,663 B2 | 8/2015 | Swensgard |
| 9,107,667 B2 | 8/2015 | Hodgkinson |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,868 B2 | 8/2015 | Felder et al. |
| 9,113,873 B2 | 8/2015 | Marczyk et al. |
| 9,113,874 B2 | 8/2015 | Shelton, IV et al. |
| 9,113,875 B2 | 8/2015 | Viola et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,651 B2 | 9/2015 | Mandakolathur Vasudevan et al. |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D740,414 S | 10/2015 | Katsura |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,769 B2 | 10/2015 | Stoddard et al. |
| 9,161,803 B2 | 10/2015 | Yates et al. |
| 9,161,807 B2 | 10/2015 | Garrison |
| 9,161,855 B2 | 10/2015 | Rousseau et al. |
| 9,164,271 B2 | 10/2015 | Ebata et al. |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,171,244 B2 | 10/2015 | Endou et al. |
| 9,179,832 B2 | 11/2015 | Diolaiti |
| 9,179,911 B2 | 11/2015 | Morgan et al. |
| 9,179,912 B2 | 11/2015 | Yates et al. |
| 9,180,223 B2 | 11/2015 | Yu et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,376 B2 | 11/2015 | Almodovar |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| D746,459 S | 12/2015 | Kaercher et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,881 B2 | 12/2015 | Penna |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,504 B2 | 12/2015 | Viola et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,750 B2 | 1/2016 | Weir et al. |
| 9,226,751 B2 | 1/2016 | Shelton, IV et al. |

(56) References Cited

U.S. PATENT DOCUMENTS

| | | |
|---|---|---|
| 9,226,754 B2 | 1/2016 | D'Agostino et al. |
| 9,226,760 B2 | 1/2016 | Shelton, IV |
| 9,226,761 B2 | 1/2016 | Burbank |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,900 B2 | 1/2016 | Boudreaux et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,711 B2 | 1/2016 | Ivanko |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,241,758 B2 | 1/2016 | Franer et al. |
| 9,244,524 B2 | 1/2016 | Inoue et al. |
| D748,668 S | 2/2016 | Kim et al. |
| D749,128 S | 2/2016 | Perez et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,254,170 B2 | 2/2016 | Parihar et al. |
| 9,259,265 B2 | 2/2016 | Harris et al. |
| 9,259,274 B2 | 2/2016 | Prisco |
| 9,259,275 B2 | 2/2016 | Burbank |
| 9,261,172 B2 | 2/2016 | Solomon et al. |
| 9,265,500 B2 | 2/2016 | Sorrentino et al. |
| 9,265,510 B2 | 2/2016 | Dietzel et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,277,969 B2 | 3/2016 | Brannan et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,467 B2 | 3/2016 | Scirica |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,565 B2 | 3/2016 | McLean |
| 9,295,784 B2 | 3/2016 | Eggert et al. |
| D753,167 S | 4/2016 | Yu et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,811 B2 | 4/2016 | Goldberg et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,313,915 B2 | 4/2016 | Niu et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,291 B2 | 4/2016 | Schall et al. |
| 9,314,339 B2 | 4/2016 | Mansmann |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,326,824 B2 | 5/2016 | Inoue et al. |
| 9,327,061 B2 | 5/2016 | Govil et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | van der Walt et al. |
| 9,339,342 B2 | 5/2016 | Prisco et al. |
| 9,345,477 B2 | 5/2016 | Anim et al. |
| 9,345,479 B2 | 5/2016 | (Tarinelli) Racenet et al. |
| 9,345,480 B2 | 5/2016 | Hessler et al. |
| 9,345,481 B2 | 5/2016 | Hall et al. |
| 9,345,503 B2 | 5/2016 | Ishida et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,352,071 B2 | 5/2016 | Landgrebe et al. |
| D758,433 S | 6/2016 | Lee et al. |
| D759,063 S | 6/2016 | Chen |
| 9,358,003 B2 | 6/2016 | Hall et al. |
| 9,358,004 B2 | 6/2016 | Sniffin et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,358,065 B2 | 6/2016 | Ladtkow et al. |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,223 B2 | 6/2016 | Scirica |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |

(56) References Cited

U.S. PATENT DOCUMENTS

| | | |
|---|---|---|
| 9,370,362 B2 | 6/2016 | Petty et al. |
| 9,370,364 B2 | 6/2016 | Smith et al. |
| 9,370,400 B2 | 6/2016 | Parihar |
| 9,375,206 B2 | 6/2016 | Vidal et al. |
| 9,375,218 B2 | 6/2016 | Wheeler et al. |
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,383,881 B2 | 7/2016 | Day et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,392,885 B2 | 7/2016 | Vogler et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,393,354 B2 | 7/2016 | Freedman et al. |
| 9,396,369 B1 | 7/2016 | Whitehurst et al. |
| 9,396,669 B2 | 7/2016 | Karkanias et al. |
| 9,398,905 B2 | 7/2016 | Martin |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |
| 9,402,625 B2 | 8/2016 | Coleman et al. |
| 9,402,626 B2 | 8/2016 | Ortiz et al. |
| 9,402,627 B2 | 8/2016 | Stevenson et al. |
| 9,402,629 B2 | 8/2016 | Ehrenfels et al. |
| 9,402,679 B2 | 8/2016 | Ginnebaugh et al. |
| 9,402,688 B2 | 8/2016 | Min et al. |
| 9,408,604 B2 | 8/2016 | Shelton, IV et al. |
| 9,408,605 B1 | 8/2016 | Knodel et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,421,682 B2 | 8/2016 | McClaskey et al. |
| 9,427,223 B2 | 8/2016 | Park et al. |
| 9,427,231 B2 | 8/2016 | Racenet et al. |
| 9,429,204 B2 | 8/2016 | Stefan et al. |
| D767,624 S | 9/2016 | Lee et al. |
| 9,433,411 B2 | 9/2016 | Racenet et al. |
| 9,433,414 B2 | 9/2016 | Chen et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,445,816 B2 | 9/2016 | Swayze et al. |
| 9,445,817 B2 | 9/2016 | Bettuchi |
| 9,446,226 B2 | 9/2016 | Zilberman |
| 9,451,938 B2 | 9/2016 | Res et al. |
| 9,451,958 B2 | 9/2016 | Shelton, IV et al. |
| D768,152 S | 10/2016 | Gutierrez et al. |
| D768,156 S | 10/2016 | Frincke |
| D768,167 S | 10/2016 | Jones et al. |
| D769,315 S | 10/2016 | Scotti |
| D769,930 S | 10/2016 | Agrawal |
| 9,461,340 B2 | 10/2016 | Li et al. |
| 9,463,012 B2 | 10/2016 | Bonutti et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,513 B2 | 10/2016 | Ishida et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| D770,476 S | 11/2016 | Jitkoff et al. |
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,215 B2 | 11/2016 | Olson et al. |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,172 B2 | 11/2016 | Weisshaupt et al. |
| 9,492,189 B2 | 11/2016 | Williams et al. |
| 9,492,192 B2 | 11/2016 | To et al. |
| 9,492,237 B2 | 11/2016 | Kang et al. |
| 9,498,213 B2 | 11/2016 | Marczyk et al. |
| 9,498,219 B2 | 11/2016 | Moore et al. |
| 9,498,231 B2 | 11/2016 | Haider et al. |
| 9,504,455 B2 | 11/2016 | Whitman et al. |
| 9,504,483 B2 | 11/2016 | Houser et al. |
| 9,504,520 B2 | 11/2016 | Worrell et al. |
| 9,504,521 B2 | 11/2016 | Deutmeyer et al. |
| 9,504,528 B2 | 11/2016 | Ivinson et al. |
| 9,507,399 B2 | 11/2016 | Chien |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,065 B2 | 12/2016 | Simms et al. |
| 9,517,068 B2 | 12/2016 | Shelton, IV et al. |
| 9,517,326 B2 | 12/2016 | Hinman et al. |
| 9,521,996 B2 | 12/2016 | Armstrong |
| 9,522,003 B2 | 12/2016 | Weir et al. |
| 9,522,014 B2 | 12/2016 | Nishizawa et al. |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| 9,526,921 B2 | 12/2016 | Kimball et al. |
| D776,683 S | 1/2017 | Gobinski et al. |
| D777,773 S | 1/2017 | Shi |
| 9,532,783 B2 | 1/2017 | Swayze et al. |
| 9,539,060 B2 | 1/2017 | Lightcap et al. |
| 9,539,726 B2 | 1/2017 | Simaan et al. |
| 9,545,253 B2 | 1/2017 | Worrell et al. |
| 9,545,258 B2 | 1/2017 | Smith et al. |
| 9,549,732 B2 | 1/2017 | Yates et al. |
| 9,549,733 B2 | 1/2017 | Knodel |
| 9,549,735 B2 | 1/2017 | Shelton, IV et al. |
| 9,549,750 B2 | 1/2017 | Shelton, IV et al. |
| 9,554,794 B2 | 1/2017 | Baber et al. |
| 9,554,796 B2 | 1/2017 | Kostrzewski |
| 9,554,803 B2 | 1/2017 | Smith et al. |
| 9,554,812 B2 | 1/2017 | Inkpen et al. |
| 9,559,624 B2 | 1/2017 | Philipp |
| 9,561,013 B2 | 2/2017 | Tsuchiya |

(56) References Cited

U.S. PATENT DOCUMENTS

| | | |
|---|---|---|
| 9,561,029 B2 | 2/2017 | Scheib et al. |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,561,072 B2 | 2/2017 | Ko |
| 9,566,061 B2 | 2/2017 | Aronhalt et al. |
| 9,566,062 B2 | 2/2017 | Boudreaux |
| 9,566,065 B2 | 2/2017 | Knodel |
| 9,566,067 B2 | 2/2017 | Milliman et al. |
| 9,572,574 B2 | 2/2017 | Shelton, IV et al. |
| 9,572,576 B2 | 2/2017 | Hodgkinson et al. |
| 9,572,577 B2 | 2/2017 | Lloyd et al. |
| 9,572,592 B2 | 2/2017 | Price et al. |
| 9,574,644 B2 | 2/2017 | Parihar |
| 9,579,088 B2 | 2/2017 | Farritor et al. |
| 9,579,143 B2 | 2/2017 | Ullrich et al. |
| 9,579,158 B2 | 2/2017 | Brianza et al. |
| D780,803 S | 3/2017 | Gill et al. |
| D781,879 S | 3/2017 | Butcher et al. |
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,078 B2 | 3/2017 | Scirica et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,068 B2 | 4/2017 | Kappel et al. |
| 9,610,079 B2 | 4/2017 | Kamei et al. |
| 9,610,080 B2 | 4/2017 | Whitfield et al. |
| 9,610,412 B2 | 4/2017 | Zemlok et al. |
| 9,614,258 B2 | 4/2017 | Takahashi et al. |
| 9,615,826 B2 | 4/2017 | Shelton, IV et al. |
| 9,622,745 B2 | 4/2017 | Ingmanson et al. |
| 9,622,746 B2 | 4/2017 | Simms et al. |
| 9,629,623 B2 | 4/2017 | Lytle, IV et al. |
| 9,629,626 B2 | 4/2017 | Soltz et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,629,631 B2 | 4/2017 | Nicholas et al. |
| 9,629,632 B2 | 4/2017 | Linder et al. |
| 9,629,652 B2 | 4/2017 | Mumaw et al. |
| 9,629,814 B2 | 4/2017 | Widenhouse et al. |
| D785,794 S | 5/2017 | Magno, Jr. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,091 B2 | 5/2017 | Beardsley et al. |
| 9,636,111 B2 | 5/2017 | Wenchell |
| 9,636,112 B2 | 5/2017 | Penna et al. |
| 9,636,113 B2 | 5/2017 | Wenchell |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |
| 9,642,642 B2 | 5/2017 | Lim |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,649,190 B2 | 5/2017 | Mathies |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,616 B2 | 5/2017 | Aranyi |
| 9,655,624 B2 | 5/2017 | Shelton, IV et al. |
| 9,661,991 B2 | 5/2017 | Glossop |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,668,735 B2 | 6/2017 | Beetel |
| 9,675,344 B2 | 6/2017 | Combrowski et al. |
| 9,675,348 B2 | 6/2017 | Smith et al. |
| 9,675,351 B2 | 6/2017 | Hodgkinson et al. |
| 9,675,354 B2 | 6/2017 | Weir et al. |
| 9,675,355 B2 | 6/2017 | Shelton, IV et al. |
| 9,675,368 B2 | 6/2017 | Guo et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,872 B2 | 6/2017 | Jankowski et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,775 B2 | 7/2017 | Agarwal et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,314 B2 | 7/2017 | Marczyk |
| 9,700,315 B2 | 7/2017 | Chen et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |
| 9,700,321 B2 | 7/2017 | Shelton, IV et al. |
| 9,700,334 B2 | 7/2017 | Hinman et al. |
| 9,706,674 B2 | 7/2017 | Collins et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,003 B2 | 7/2017 | Hoell, Jr. et al. |
| 9,707,005 B2 | 7/2017 | Strobl et al. |
| 9,707,026 B2 | 7/2017 | Malackowski et al. |
| 9,707,033 B2 | 7/2017 | Parihar et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,713,474 B2 | 7/2017 | Lorenz |
| D795,919 S | 8/2017 | Bischoff et al. |
| 9,717,497 B2 | 8/2017 | Zerkle et al. |

(56) References Cited

U.S. PATENT DOCUMENTS

| | | |
|---|---|---|
| 9,717,498 B2 | 8/2017 | Aranyi et al. |
| 9,718,190 B2 | 8/2017 | Larkin et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,095 B2 | 8/2017 | Gupta et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,299 B2 | 8/2017 | Yan |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,503 B2 | 9/2017 | Milliman |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,618 B2 | 10/2017 | Bettuchi et al. |
| 9,775,635 B2 | 10/2017 | Takei |
| 9,775,678 B2 | 10/2017 | Lohmeier |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,187 B2 | 10/2017 | Zergiebel et al. |
| 9,782,193 B2 | 10/2017 | Thistle |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,248 B2 | 11/2017 | Hoffman |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,814,530 B2 | 11/2017 | Weir et al. |
| 9,814,561 B2 | 11/2017 | Forsell |
| 9,815,118 B1 | 11/2017 | Schmitt et al. |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,235 B2 | 12/2017 | Penna et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,839,481 B2 | 12/2017 | Blumenkranz et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,850,994 B2 | 12/2017 | Schena |
| D808,989 S | 1/2018 | Ayvazian et al. |
| 9,855,039 B2 | 1/2018 | Racenet et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,362 B2 | 1/2018 | Whitman et al. |
| 9,861,366 B2 | 1/2018 | Aranyi |
| 9,861,382 B2 | 1/2018 | Smith et al. |
| 9,861,446 B2 | 1/2018 | Lang |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,867,617 B2 | 1/2018 | Ma |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |

(56) References Cited

U.S. PATENT DOCUMENTS

| | | |
|---|---|---|
| 9,872,683 B2 | 1/2018 | Hopkins et al. |
| 9,872,684 B2 | 1/2018 | Hall et al. |
| 9,872,722 B2 | 1/2018 | Lech |
| 9,877,721 B2 | 1/2018 | Schellin et al. |
| 9,877,722 B2 | 1/2018 | Schellin et al. |
| 9,877,723 B2 | 1/2018 | Hall et al. |
| 9,877,776 B2 | 1/2018 | Boudreaux |
| D810,099 S | 2/2018 | Riedel |
| 9,883,843 B2 | 2/2018 | Garlow |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,552 B2 | 3/2018 | Measamer et al. |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,641 B2 | 3/2018 | Takemoto et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czernik |
| 9,918,730 B2 | 3/2018 | Trees et al. |
| 9,924,941 B2 | 3/2018 | Burbank |
| 9,924,942 B2 | 3/2018 | Swayze et al. |
| 9,924,943 B2 | 3/2018 | Mohan Pinjala et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,118 B2 | 4/2018 | Shelton, IV et al. |
| 9,931,120 B2 | 4/2018 | Chen et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,952 B2 | 4/2018 | Demmy |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,949,754 B2 | 4/2018 | Newhauser et al. |
| 9,953,193 B2 | 4/2018 | Butler et al. |
| D819,072 S | 5/2018 | Clediere |
| 9,955,954 B2 | 5/2018 | Destoumieux et al. |
| 9,955,965 B2 | 5/2018 | Chen et al. |
| 9,955,966 B2 | 5/2018 | Zergiebel |
| 9,956,677 B2 | 5/2018 | Baskar et al. |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,630 B2 | 5/2018 | Larkin et al. |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,008 B2 | 6/2018 | Scirica et al. |
| 9,987,095 B2 | 6/2018 | Chowaniec et al. |
| 9,987,097 B2 | 6/2018 | van der Weide et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,993,284 B2 | 6/2018 | Boudreaux |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,010,395 B2 | 7/2018 | Puckett et al. |
| 10,013,049 B2 | 7/2018 | Leimbach et al. |
| 10,016,199 B2 | 7/2018 | Baber et al. |
| 10,016,656 B2 | 7/2018 | Devor et al. |
| 10,022,120 B2 | 7/2018 | Martin et al. |
| 10,022,123 B2 | 7/2018 | Williams et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,108 B2 | 7/2018 | Powers et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,869 B2 | 8/2018 | Forsell |
| 10,052,044 B2 | 8/2018 | Shelton, IV et al. |
| 10,052,099 B2 | 8/2018 | Morgan et al. |

(56) References Cited

U.S. PATENT DOCUMENTS

| | | |
|---|---|---|
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,622 B2 | 9/2018 | Murthy Aravalli |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,076,340 B2 | 9/2018 | Belagali et al. |
| 10,080,552 B2 | 9/2018 | Nicholas et al. |
| D830,550 S | 10/2018 | Miller et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,746 B2 | 10/2018 | Fischvogt |
| 10,085,748 B2 | 10/2018 | Morgan et al. |
| 10,085,749 B2 | 10/2018 | Cappola et al. |
| 10,085,750 B2 | 10/2018 | Zergiebel et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,290 B2 | 10/2018 | Yigit et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,101,861 B2 | 10/2018 | Kiyoto |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,105,142 B2 | 10/2018 | Baxter, III et al. |
| 10,105,149 B2 | 10/2018 | Haider et al. |
| 10,106,932 B2 | 10/2018 | Anderson et al. |
| 10,111,657 B2 | 10/2018 | McCuen |
| 10,111,658 B2 | 10/2018 | Chowaniec et al. |
| 10,111,660 B2 | 10/2018 | Hemmann |
| 10,111,665 B2 | 10/2018 | Aranyi et al. |
| 10,111,679 B2 | 10/2018 | Baber et al. |
| 10,111,698 B2 | 10/2018 | Scheib et al. |
| 10,111,702 B2 | 10/2018 | Kostrzewski |
| D833,608 S | 11/2018 | Miller et al. |
| 10,117,649 B2 | 11/2018 | Baxter, III et al. |
| 10,117,650 B2 | 11/2018 | Nicholas et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,382 B2 | 11/2018 | Gladstone |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| D835,659 S | 12/2018 | Anzures et al. |
| D836,124 S | 12/2018 | Fan |
| 10,143,474 B2 | 12/2018 | Bucciaglia et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,152,789 B2 | 12/2018 | Carnes et al. |
| 10,154,841 B2 | 12/2018 | Weaner et al. |
| 10,159,481 B2 | 12/2018 | Whitman et al. |
| 10,159,482 B2 | 12/2018 | Swayze et al. |
| 10,159,483 B2 | 12/2018 | Beckman et al. |
| 10,159,506 B2 | 12/2018 | Boudreaux et al. |
| 10,163,065 B1 | 12/2018 | Koski et al. |
| 10,163,589 B2 | 12/2018 | Zergiebel et al. |
| 10,164,466 B2 | 12/2018 | Calderoni |
| D837,244 S | 1/2019 | Kuo et al. |
| D837,245 S | 1/2019 | Kuo et al. |
| 10,166,023 B2 | 1/2019 | Vendely et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,618 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,172,669 B2 | 1/2019 | Felder et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,182,868 B2 | 1/2019 | Meier et al. |
| 10,188,385 B2 | 1/2019 | Kerr et al. |
| 10,188,389 B2 | 1/2019 | Vendely et al. |
| 10,188,393 B2 | 1/2019 | Smith et al. |
| 10,188,394 B2 | 1/2019 | Shelton, IV et al. |
| 10,190,888 B2 | 1/2019 | Hryb et al. |
| D839,900 S | 2/2019 | Gan |
| D841,667 S | 2/2019 | Coren |
| 10,194,801 B2 | 2/2019 | Elhawary et al. |
| 10,194,904 B2 | 2/2019 | Viola et al. |
| 10,194,907 B2 | 2/2019 | Marczyk et al. |
| 10,194,908 B2 | 2/2019 | Duque et al. |
| 10,194,910 B2 | 2/2019 | Shelton, IV et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |

(56) References Cited

U.S. PATENT DOCUMENTS

| | | |
|---|---|---|
| 10,213,203 B2 | 2/2019 | Swayze et al. |
| 10,213,204 B2 | 2/2019 | Aranyi et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |
| 10,220,522 B2 | 3/2019 | Rockrohr |
| 10,226,239 B2 | 3/2019 | Nicholas et al. |
| 10,226,249 B2 | 3/2019 | Jaworek et al. |
| 10,226,250 B2 | 3/2019 | Beckman et al. |
| 10,226,251 B2 | 3/2019 | Scheib et al. |
| 10,226,274 B2 | 3/2019 | Worrell et al. |
| 10,231,634 B2 | 3/2019 | Zand et al. |
| 10,231,653 B2 | 3/2019 | Bohm et al. |
| 10,231,734 B2 | 3/2019 | Thompson et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| D847,199 S | 4/2019 | Whitmore |
| 10,244,991 B2 | 4/2019 | Shademan et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,038 B2 | 4/2019 | Hopkins et al. |
| 10,245,058 B2 | 4/2019 | Omori et al. |
| 10,251,648 B2 | 4/2019 | Harris et al. |
| 10,251,649 B2 | 4/2019 | Schellin et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,363 B2 | 4/2019 | Worrell et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,073 B2 | 4/2019 | Scheib et al. |
| 10,265,074 B2 | 4/2019 | Shelton, IV et al. |
| 10,265,090 B2 | 4/2019 | Ingmanson et al. |
| 10,271,840 B2 | 4/2019 | Sapre |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,847 B2 | 4/2019 | Racenet et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,703 B2 | 5/2019 | Nativ et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,700 B2 | 5/2019 | Scheib |
| 10,285,705 B2 | 5/2019 | Shelton, IV et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,789 B2 | 5/2019 | Marczyk et al. |
| 10,299,790 B2 | 5/2019 | Beardsley |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| 10,303,851 B2 | 5/2019 | Nguyen et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,161 B2 | 6/2019 | Jankowski |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,559 B2 | 6/2019 | Razzaque et al. |
| 10,314,577 B2 | 6/2019 | Laurent et al. |
| 10,314,578 B2 | 6/2019 | Leimbach et al. |
| 10,314,580 B2 | 6/2019 | Scheib et al. |
| 10,314,582 B2 | 6/2019 | Shelton, IV et al. |
| 10,314,584 B2 | 6/2019 | Scirica et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,743 B2 | 6/2019 | St. Goar et al. |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,032 S | 7/2019 | Jones et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,337,148 B2 | 7/2019 | Rouse et al. |
| 10,342,533 B2 | 7/2019 | Shelton, IV et al. |
| 10,342,535 B2 | 7/2019 | Scheib et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,937 B2 | 7/2019 | Williams |
| 10,349,939 B2 | 7/2019 | Shelton, IV et al. |
| 10,349,941 B2 | 7/2019 | Marczyk et al. |
| 10,349,963 B2 | 7/2019 | Fiksen et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 10,363,031 B2 | 7/2019 | Alexander, III et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| D855,634 S | 8/2019 | Kim |
| D856,359 S | 8/2019 | Huang et al. |
| 10,368,838 B2 | 8/2019 | Williams et al. |
| 10,368,861 B2 | 8/2019 | Baxter, III et al. |

(56) References Cited

U.S. PATENT DOCUMENTS

| | | |
|---|---|---|
| 10,368,863 B2 | 8/2019 | Timm et al. |
| 10,368,864 B2 | 8/2019 | Harris et al. |
| 10,368,865 B2 | 8/2019 | Harris et al. |
| 10,368,867 B2 | 8/2019 | Harris et al. |
| 10,368,892 B2 | 8/2019 | Stulen et al. |
| 10,376,263 B2 | 8/2019 | Morgan et al. |
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,830 B2 | 8/2019 | Schulz |
| 10,390,841 B2 | 8/2019 | Shelton, IV et al. |
| 10,390,897 B2 | 8/2019 | Kostrzewski |
| D860,219 S | 9/2019 | Rasmussen et al. |
| D861,035 S | 9/2019 | Park et al. |
| 10,398,433 B2 | 9/2019 | Boudreaux et al. |
| 10,398,434 B2 | 9/2019 | Shelton, IV et al. |
| 10,398,436 B2 | 9/2019 | Shelton, IV et al. |
| 10,398,460 B2 | 9/2019 | Overmyer |
| 10,404,136 B2 | 9/2019 | Oktavec et al. |
| 10,405,854 B2 | 9/2019 | Schmid et al. |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,405,914 B2 | 9/2019 | Manwaring et al. |
| 10,405,932 B2 | 9/2019 | Overmyer |
| 10,405,937 B2 | 9/2019 | Black et al. |
| 10,413,155 B2 | 9/2019 | Inoue |
| 10,413,291 B2 | 9/2019 | Worthington et al. |
| 10,413,293 B2 | 9/2019 | Shelton, IV et al. |
| 10,413,294 B2 | 9/2019 | Shelton, IV et al. |
| 10,413,297 B2 | 9/2019 | Harris et al. |
| 10,413,370 B2 | 9/2019 | Yates et al. |
| 10,413,373 B2 | 9/2019 | Yates et al. |
| 10,420,548 B2 | 9/2019 | Whitman et al. |
| 10,420,549 B2 | 9/2019 | Yates et al. |
| 10,420,550 B2 | 9/2019 | Shelton, IV |
| 10,420,551 B2 | 9/2019 | Calderoni |
| 10,420,552 B2 | 9/2019 | Shelton, IV et al. |
| 10,420,553 B2 | 9/2019 | Shelton, IV et al. |
| 10,420,554 B2 | 9/2019 | Collings et al. |
| 10,420,555 B2 | 9/2019 | Shelton, IV et al. |
| 10,420,558 B2 | 9/2019 | Nalagatla et al. |
| 10,420,559 B2 | 9/2019 | Marczyk et al. |
| 10,420,560 B2 | 9/2019 | Shelton, IV et al. |
| 10,420,561 B2 | 9/2019 | Shelton, IV et al. |
| 10,420,577 B2 | 9/2019 | Chowaniec et al. |
| D861,707 S | 10/2019 | Yang |
| D862,518 S | 10/2019 | Niven et al. |
| D863,343 S | 10/2019 | Mazlish et al. |
| D864,388 S | 10/2019 | Barber |
| D865,174 S | 10/2019 | Auld et al. |
| D865,175 S | 10/2019 | Widenhouse et al. |
| 10,426,463 B2 | 10/2019 | Shelton, IV et al. |
| 10,426,466 B2 | 10/2019 | Contini et al. |
| 10,426,467 B2 | 10/2019 | Miller et al. |
| 10,426,468 B2 | 10/2019 | Contini et al. |
| 10,426,469 B2 | 10/2019 | Shelton, IV et al. |
| 10,426,471 B2 | 10/2019 | Shelton, IV et al. |
| 10,426,476 B2 | 10/2019 | Harris et al. |
| 10,426,477 B2 | 10/2019 | Harris et al. |
| 10,426,478 B2 | 10/2019 | Shelton, IV et al. |
| 10,426,481 B2 | 10/2019 | Aronhalt et al. |
| 10,426,555 B2 | 10/2019 | Crowley et al. |
| 10,433,837 B2 | 10/2019 | Worthington et al. |
| 10,433,839 B2 | 10/2019 | Scheib et al. |
| 10,433,840 B2 | 10/2019 | Shelton, IV et al. |
| 10,433,844 B2 | 10/2019 | Shelton, IV et al. |
| 10,433,845 B2 | 10/2019 | Baxter, III et al. |
| 10,433,846 B2 | 10/2019 | Vendely et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,280 B2 | 10/2019 | Timm et al. |
| 10,441,281 B2 | 10/2019 | Shelton, IV et al. |
| 10,441,285 B2 | 10/2019 | Shelton, IV et al. |
| 10,441,286 B2 | 10/2019 | Shelton, IV et al. |
| 10,441,345 B2 | 10/2019 | Aldridge et al. |
| 10,441,369 B2 | 10/2019 | Shelton, IV et al. |
| 10,448,948 B2 | 10/2019 | Shelton, IV et al. |
| 10,448,950 B2 | 10/2019 | Shelton, IV et al. |
| 10,448,952 B2 | 10/2019 | Shelton, IV et al. |
| 10,456,122 B2 | 10/2019 | Koltz et al. |
| 10,456,132 B2 | 10/2019 | Gettinger et al. |
| 10,456,133 B2 | 10/2019 | Yates et al. |
| 10,456,137 B2 | 10/2019 | Vendely et al. |
| 10,456,140 B2 | 10/2019 | Shelton, IV et al. |
| D865,796 S | 11/2019 | Xu et al. |
| 10,463,367 B2 | 11/2019 | Kostrzewski et al. |
| 10,463,369 B2 | 11/2019 | Shelton, IV et al. |
| 10,463,370 B2 | 11/2019 | Yates et al. |
| 10,463,371 B2 | 11/2019 | Kostrzewski |
| 10,463,372 B2 | 11/2019 | Shelton, IV et al. |
| 10,463,373 B2 | 11/2019 | Mozdzierz et al. |
| 10,463,382 B2 | 11/2019 | Ingmanson et al. |
| 10,463,383 B2 | 11/2019 | Shelton, IV et al. |
| 10,463,384 B2 | 11/2019 | Shelton, IV et al. |
| 10,470,762 B2 | 11/2019 | Leimbach et al. |
| 10,470,763 B2 | 11/2019 | Yates et al. |
| 10,470,764 B2 | 11/2019 | Baxter, III et al. |
| 10,470,767 B2 | 11/2019 | Gleiman et al. |
| 10,470,768 B2 | 11/2019 | Harris et al. |
| 10,470,769 B2 | 11/2019 | Shelton, IV et al. |
| 10,470,770 B2 | 11/2019 | Shelton, IV et al. |
| 10,471,282 B2 | 11/2019 | Kirk et al. |
| 10,471,576 B2 | 11/2019 | Totsu |
| 10,471,607 B2 | 11/2019 | Butt |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,187 B2 | 11/2019 | Shelton, IV et al. |
| 10,478,188 B2 | 11/2019 | Harris et al. |
| 10,478,189 B2 | 11/2019 | Bear et al. |
| 10,478,190 B2 | 11/2019 | Miller et al. |
| 10,478,207 B2 | 11/2019 | Lathrop |
| 10,482,292 B2 | 11/2019 | Clouser et al. |
| 10,485,536 B2 | 11/2019 | Ming et al. |
| 10,485,537 B2 | 11/2019 | Yates et al. |
| 10,485,539 B2 | 11/2019 | Shelton, IV et al. |
| 10,485,541 B2 | 11/2019 | Shelton, IV et al. |
| 10,485,542 B2 | 11/2019 | Shelton, IV et al. |
| 10,485,543 B2 | 11/2019 | Shelton, IV et al. |
| 10,485,546 B2 | 11/2019 | Shelton, IV et al. |
| 10,485,547 B2 | 11/2019 | Shelton, IV et al. |
| D869,655 S | 12/2019 | Shelton, IV et al. |
| D870,742 S | 12/2019 | Cornell |
| 10,492,783 B2 | 12/2019 | Shelton, IV et al. |
| 10,492,785 B2 | 12/2019 | Overmyer et al. |
| 10,492,787 B2 | 12/2019 | Smith et al. |
| 10,492,814 B2 | 12/2019 | Snow et al. |
| 10,492,847 B2 | 12/2019 | Godara et al. |
| 10,492,851 B2 | 12/2019 | Hughett, Sr. et al. |
| 10,498,269 B2 | 12/2019 | Zemlok et al. |
| 10,499,890 B2 | 12/2019 | Shelton, IV et al. |
| 10,499,914 B2 | 12/2019 | Huang et al. |
| 10,499,917 B2 | 12/2019 | Scheib et al. |
| 10,499,918 B2 | 12/2019 | Schellin et al. |
| 10,500,000 B2 | 12/2019 | Swayze et al. |
| 10,500,309 B2 | 12/2019 | Shah et al. |
| 10,508,720 B2 | 12/2019 | Nicholas |
| 10,512,461 B2 | 12/2019 | Gupta et al. |
| 10,517,590 B2 | 12/2019 | Giordano et al. |
| 10,517,592 B2 | 12/2019 | Shelton, IV et al. |
| 10,517,594 B2 | 12/2019 | Shelton, IV et al. |
| 10,517,595 B2 | 12/2019 | Hunter et al. |
| 10,517,596 B2 | 12/2019 | Hunter et al. |
| 10,517,599 B2 | 12/2019 | Baxter, III et al. |
| 10,517,682 B2 | 12/2019 | Giordano et al. |

(56) References Cited

U.S. PATENT DOCUMENTS

| | | |
|---|---|---|
| 10,524,784 B2 | 1/2020 | Kostrzewski |
| 10,524,787 B2 | 1/2020 | Shelton, IV et al. |
| 10,524,788 B2 | 1/2020 | Vendely et al. |
| 10,524,789 B2 | 1/2020 | Swayze et al. |
| 10,524,790 B2 | 1/2020 | Shelton, IV et al. |
| 10,524,795 B2 | 1/2020 | Nalagatla et al. |
| 10,531,874 B2 | 1/2020 | Morgan et al. |
| 10,531,887 B2 | 1/2020 | Shelton, IV et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,908 B2 | 1/2020 | Mei et al. |
| 10,542,974 B2 | 1/2020 | Yates et al. |
| 10,542,976 B2 | 1/2020 | Calderoni et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,985 B2 | 1/2020 | Zhan et al. |
| 10,542,988 B2 | 1/2020 | Schellin et al. |
| 10,542,991 B2 | 1/2020 | Shelton, IV et al. |
| 10,548,504 B2 | 2/2020 | Shelton, IV et al. |
| 10,548,593 B2 | 2/2020 | Shelton, IV et al. |
| 10,548,600 B2 | 2/2020 | Shelton, IV et al. |
| 10,548,673 B2 | 2/2020 | Harris et al. |
| 10,561,418 B2 | 2/2020 | Richard et al. |
| 10,561,419 B2 | 2/2020 | Beardsley |
| 10,561,420 B2 | 2/2020 | Harris et al. |
| 10,561,422 B2 | 2/2020 | Schellin et al. |
| 10,561,432 B2 | 2/2020 | Estrella et al. |
| 10,561,474 B2 | 2/2020 | Adams et al. |
| 10,562,160 B2 | 2/2020 | Iwata et al. |
| 10,568,493 B2 | 2/2020 | Blase et al. |
| 10,568,621 B2 | 2/2020 | Shelton, IV et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,629 B2 | 2/2020 | Shelton, IV et al. |
| 10,568,632 B2 | 2/2020 | Miller et al. |
| 10,568,652 B2 | 2/2020 | Hess et al. |
| 10,569,071 B2 | 2/2020 | Harris et al. |
| D879,808 S | 3/2020 | Harris et al. |
| D879,809 S | 3/2020 | Harris et al. |
| 10,575,868 B2 | 3/2020 | Hall et al. |
| 10,580,320 B2 | 3/2020 | Kamiguchi et al. |
| 10,582,928 B2 | 3/2020 | Hunter et al. |
| 10,588,231 B2 | 3/2020 | Sgroi, Jr. et al. |
| 10,588,623 B2 | 3/2020 | Schmid et al. |
| 10,588,625 B2 | 3/2020 | Weaner et al. |
| 10,588,626 B2 | 3/2020 | Overmyer et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,835 B2 | 3/2020 | Kerr et al. |
| 10,595,862 B2 | 3/2020 | Shelton, IV et al. |
| 10,595,882 B2 | 3/2020 | Parfett et al. |
| 10,595,887 B2 | 3/2020 | Shelton, IV et al. |
| 10,595,929 B2 | 3/2020 | Boudreaux et al. |
| 10,603,036 B2 | 3/2020 | Hunter et al. |
| 10,603,039 B2 | 3/2020 | Vendely et al. |
| 10,603,041 B2 | 3/2020 | Miller et al. |
| 10,603,117 B2 | 3/2020 | Schings et al. |
| 10,603,128 B2 | 3/2020 | Zergiebel et al. |
| 10,610,224 B2 | 4/2020 | Shelton, IV et al. |
| 10,610,236 B2 | 4/2020 | Baril |
| 10,610,313 B2 | 4/2020 | Bailey et al. |
| 10,610,346 B2 | 4/2020 | Schwartz |
| 10,617,411 B2 | 4/2020 | Williams |
| 10,617,412 B2 | 4/2020 | Shelton, IV et al. |
| 10,617,413 B2 | 4/2020 | Shelton, IV et al. |
| 10,617,414 B2 | 4/2020 | Shelton, IV et al. |
| 10,617,416 B2 | 4/2020 | Leimbach et al. |
| 10,617,417 B2 | 4/2020 | Baxter, III et al. |
| 10,617,418 B2 | 4/2020 | Barton et al. |
| 10,617,420 B2 | 4/2020 | Shelton, IV et al. |
| 10,617,438 B2 | 4/2020 | O'Keefe et al. |
| 10,624,616 B2 | 4/2020 | Mukherjee et al. |
| 10,624,630 B2 | 4/2020 | Deville et al. |
| 10,624,633 B2 | 4/2020 | Shelton, IV et al. |
| 10,624,634 B2 | 4/2020 | Shelton, IV et al. |
| 10,624,635 B2 | 4/2020 | Harris et al. |
| 10,624,709 B2 | 4/2020 | Remm |
| 10,624,861 B2 | 4/2020 | Widenhouse et al. |
| 10,625,062 B2 | 4/2020 | Matlock et al. |
| 10,631,857 B2 | 4/2020 | Kostrzewski |
| 10,631,858 B2 | 4/2020 | Burbank |
| 10,631,859 B2 | 4/2020 | Shelton, IV et al. |
| 10,631,860 B2 | 4/2020 | Bakos et al. |
| 10,636,104 B2 | 4/2020 | Mazar et al. |
| 10,639,018 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,089 B2 | 5/2020 | Manwaring et al. |
| 10,639,115 B2 | 5/2020 | Shelton, IV et al. |
| 10,645,905 B2 | 5/2020 | Gandola et al. |
| 10,646,220 B2 | 5/2020 | Shelton, IV et al. |
| 10,646,292 B2 | 5/2020 | Solomon et al. |
| 10,653,413 B2 | 5/2020 | Worthington et al. |
| 10,653,417 B2 | 5/2020 | Shelton, IV et al. |
| 10,653,435 B2 | 5/2020 | Shelton, IV et al. |
| 10,660,640 B2 | 5/2020 | Yates et al. |
| 10,667,408 B2 | 5/2020 | Sgroi, Jr. et al. |
| D888,953 S | 6/2020 | Baxter, III et al. |
| 10,667,808 B2 | 6/2020 | Baxter, III et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,818 B2 | 6/2020 | McLain et al. |
| 10,674,895 B2 | 6/2020 | Yeung et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,028 B2 | 6/2020 | Shelton, IV et al. |
| 10,675,035 B2 | 6/2020 | Zingman |
| 10,675,102 B2 | 6/2020 | Forgione et al. |
| 10,677,035 B2 | 6/2020 | Balan et al. |
| 10,682,134 B2 | 6/2020 | Shelton, IV et al. |
| 10,682,136 B2 | 6/2020 | Harris et al. |
| 10,682,138 B2 | 6/2020 | Shelton, IV et al. |
| 10,682,141 B2 | 6/2020 | Moore et al. |
| 10,682,142 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,812 B2 | 6/2020 | Shelton, IV et al. |
| 10,687,813 B2 | 6/2020 | Shelton, IV et al. |
| 10,687,817 B2 | 6/2020 | Shelton, IV et al. |
| 10,687,819 B2 | 6/2020 | Stokes et al. |
| 10,687,904 B2 | 6/2020 | Harris et al. |
| 10,695,053 B2 | 6/2020 | Hess et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,062 B2 | 6/2020 | Leimbach et al. |
| 10,695,063 B2 | 6/2020 | Morgan et al. |
| 10,695,074 B2 | 6/2020 | Carusillo |
| 10,695,081 B2 | 6/2020 | Shelton, IV et al. |
| 10,695,123 B2 | 6/2020 | Allen, IV |
| 10,695,187 B2 | 6/2020 | Moskowitz et al. |
| D890,784 S | 7/2020 | Shelton, IV et al. |
| 10,702,266 B2 | 7/2020 | Parihar et al. |
| 10,702,267 B2 | 7/2020 | Hess et al. |
| 10,702,270 B2 | 7/2020 | Shelton, IV et al. |
| 10,702,271 B2 | 7/2020 | Aranyi et al. |
| 10,705,660 B2 | 7/2020 | Xiao |
| 10,709,446 B2 | 7/2020 | Harris et al. |
| 10,709,468 B2 | 7/2020 | Shelton, IV et al. |
| 10,709,469 B2 | 7/2020 | Shelton, IV et al. |
| 10,709,496 B2 | 7/2020 | Moua et al. |
| 10,716,563 B2 | 7/2020 | Shelton, IV et al. |

(56) References Cited

U.S. PATENT DOCUMENTS

| | | |
|---|---|---|
| 10,716,565 B2 | 7/2020 | Shelton, IV et al. |
| 10,716,568 B2 | 7/2020 | Hall et al. |
| 10,716,614 B2 | 7/2020 | Yates et al. |
| 10,717,179 B2 | 7/2020 | Koenig et al. |
| 10,722,232 B2 | 7/2020 | Yates et al. |
| 10,722,233 B2 | 7/2020 | Wellman |
| 10,722,292 B2 | 7/2020 | Arya et al. |
| 10,722,293 B2 | 7/2020 | Arya et al. |
| 10,722,317 B2 | 7/2020 | Ward et al. |
| D893,717 S | 8/2020 | Messerly et al. |
| 10,729,432 B2 | 8/2020 | Shelton, IV et al. |
| 10,729,436 B2 | 8/2020 | Shelton, IV et al. |
| 10,729,443 B2 | 8/2020 | Cabrera et al. |
| 10,729,458 B2 | 8/2020 | Stoddard et al. |
| 10,729,501 B2 | 8/2020 | Leimbach et al. |
| 10,729,509 B2 | 8/2020 | Shelton, IV et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,630 B2 | 8/2020 | Huang et al. |
| 10,736,633 B2 | 8/2020 | Vendely et al. |
| 10,736,634 B2 | 8/2020 | Shelton, IV et al. |
| 10,736,636 B2 | 8/2020 | Baxter, III et al. |
| 10,736,644 B2 | 8/2020 | Windolf et al. |
| 10,743,849 B2 | 8/2020 | Shelton, IV et al. |
| 10,743,851 B2 | 8/2020 | Swayze et al. |
| 10,743,868 B2 | 8/2020 | Shelton, IV et al. |
| 10,743,870 B2 | 8/2020 | Hall et al. |
| 10,743,872 B2 | 8/2020 | Leimbach et al. |
| 10,743,873 B2 | 8/2020 | Overmyer et al. |
| 10,743,874 B2 | 8/2020 | Shelton, IV et al. |
| 10,743,875 B2 | 8/2020 | Shelton, IV et al. |
| 10,743,877 B2 | 8/2020 | Shelton, IV et al. |
| 10,743,930 B2 | 8/2020 | Nagtegaal |
| 10,751,048 B2 | 8/2020 | Whitman et al. |
| 10,751,053 B2 | 8/2020 | Harris et al. |
| 10,751,076 B2 | 8/2020 | Laurent et al. |
| 10,751,138 B2 | 8/2020 | Giordano et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,233 B2 | 9/2020 | Scheib et al. |
| 10,758,259 B2 | 9/2020 | Demmy et al. |
| 10,765,425 B2 | 9/2020 | Yates et al. |
| 10,765,427 B2 | 9/2020 | Shelton, IV et al. |
| 10,765,429 B2 | 9/2020 | Leimbach et al. |
| 10,765,430 B2 | 9/2020 | Wixey |
| 10,765,432 B2 | 9/2020 | Moore et al. |
| 10,765,442 B2 | 9/2020 | Strobl |
| 10,772,625 B2 | 9/2020 | Shelton, IV et al. |
| 10,772,628 B2 | 9/2020 | Chen et al. |
| 10,772,629 B2 | 9/2020 | Shelton, IV et al. |
| 10,772,630 B2 | 9/2020 | Wixey |
| 10,772,631 B2 | 9/2020 | Zergiebel et al. |
| 10,772,632 B2 | 9/2020 | Kostrzewski |
| 10,772,651 B2 | 9/2020 | Shelton, IV et al. |
| 10,779,818 B2 | 9/2020 | Zemlok et al. |
| 10,779,820 B2 | 9/2020 | Harris et al. |
| 10,779,821 B2 | 9/2020 | Harris et al. |
| 10,779,822 B2 | 9/2020 | Yates et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,826 B2 | 9/2020 | Shelton, IV et al. |
| 10,779,903 B2 | 9/2020 | Wise et al. |
| 10,780,539 B2 | 9/2020 | Shelton, IV et al. |
| 10,786,248 B2 | 9/2020 | Rousseau et al. |
| 10,786,253 B2 | 9/2020 | Shelton, IV et al. |
| 10,786,255 B2 | 9/2020 | Hodgkinson et al. |
| 10,792,038 B2 | 10/2020 | Becerra et al. |
| 10,796,471 B2 | 10/2020 | Leimbach et al. |
| 10,799,240 B2 | 10/2020 | Shelton, IV et al. |
| 10,799,306 B2 | 10/2020 | Robinson et al. |
| 10,806,448 B2 | 10/2020 | Shelton, IV et al. |
| 10,806,449 B2 | 10/2020 | Shelton, IV et al. |
| 10,806,450 B2 | 10/2020 | Yates et al. |
| 10,806,451 B2 | 10/2020 | Harris et al. |
| 10,806,453 B2 | 10/2020 | Chen et al. |
| 10,806,479 B2 | 10/2020 | Shelton, IV et al. |
| 10,813,638 B2 | 10/2020 | Shelton, IV et al. |
| 10,813,639 B2 | 10/2020 | Shelton, IV et al. |
| 10,813,640 B2 | 10/2020 | Adams et al. |
| 10,813,641 B2 | 10/2020 | Setser et al. |
| 10,813,683 B2 | 10/2020 | Baxter, III et al. |
| 10,813,705 B2 | 10/2020 | Hares et al. |
| 10,813,710 B2 | 10/2020 | Grubbs |
| 10,820,939 B2 | 11/2020 | Sartor |
| 10,828,028 B2 | 11/2020 | Harris et al. |
| 10,828,030 B2 | 11/2020 | Weir et al. |
| 10,828,032 B2 | 11/2020 | Leimbach et al. |
| 10,828,033 B2 | 11/2020 | Shelton, IV et al. |
| 10,828,089 B2 | 11/2020 | Clark et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,249 B2 | 11/2020 | Schellin et al. |
| 10,835,251 B2 | 11/2020 | Shelton, IV et al. |
| 10,835,330 B2 | 11/2020 | Shelton, IV et al. |
| 10,842,357 B2 | 11/2020 | Moskowitz et al. |
| 10,842,473 B2 | 11/2020 | Scheib et al. |
| 10,842,488 B2 | 11/2020 | Swayze et al. |
| 10,842,489 B2 | 11/2020 | Shelton, IV |
| 10,842,490 B2 | 11/2020 | DiNardo et al. |
| 10,842,491 B2 | 11/2020 | Shelton, IV et al. |
| 10,842,492 B2 | 11/2020 | Shelton, IV et al. |
| D904,612 S | 12/2020 | Wynn et al. |
| D906,355 S | 12/2020 | Messerly et al. |
| 10,849,621 B2 | 12/2020 | Whitfield et al. |
| 10,849,623 B2 | 12/2020 | Dunki-Jacobs et al. |
| 10,849,697 B2 | 12/2020 | Yates et al. |
| 10,856,866 B2 | 12/2020 | Shelton, IV et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,863,981 B2 | 12/2020 | Overmyer et al. |
| 10,863,984 B2 | 12/2020 | Shelton, IV et al. |
| 10,863,986 B2 | 12/2020 | Yates et al. |
| 10,869,664 B2 | 12/2020 | Shelton, IV |
| 10,869,665 B2 | 12/2020 | Shelton, IV et al. |
| 10,869,666 B2 | 12/2020 | Shelton, IV et al. |
| 10,869,669 B2 | 12/2020 | Shelton, IV et al. |
| 10,874,290 B2 | 12/2020 | Walen et al. |
| 10,874,391 B2 | 12/2020 | Shelton, IV et al. |
| 10,874,392 B2 | 12/2020 | Scirica et al. |
| 10,874,393 B2 | 12/2020 | Satti, III et al. |
| 10,874,396 B2 | 12/2020 | Moore et al. |
| 10,874,399 B2 | 12/2020 | Zhang |
| 10,879,275 B2 | 12/2020 | Li et al. |
| D907,647 S | 1/2021 | Siebel et al. |
| D907,648 S | 1/2021 | Siebel et al. |
| D908,216 S | 1/2021 | Messerly et al. |
| 10,881,395 B2 | 1/2021 | Merchant et al. |
| 10,881,396 B2 | 1/2021 | Shelton, IV et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,888,318 B2 | 1/2021 | Parihar et al. |
| 10,888,321 B2 | 1/2021 | Shelton, IV et al. |
| 10,888,322 B2 | 1/2021 | Morgan et al. |
| 10,888,325 B2 | 1/2021 | Harris et al. |
| 10,888,328 B2 | 1/2021 | Shelton, IV et al. |
| 10,888,329 B2 | 1/2021 | Moore et al. |
| 10,888,330 B2 | 1/2021 | Moore et al. |
| 10,888,369 B2 | 1/2021 | Messerly et al. |
| 10,892,899 B2 | 1/2021 | Shelton, IV et al. |
| 10,893,853 B2 | 1/2021 | Shelton, IV et al. |
| 10,893,863 B2 | 1/2021 | Shelton, IV et al. |
| 10,893,864 B2 | 1/2021 | Harris et al. |
| 10,893,867 B2 | 1/2021 | Leimbach et al. |
| 10,898,183 B2 | 1/2021 | Shelton, IV et al. |
| 10,898,184 B2 | 1/2021 | Yates et al. |
| 10,898,185 B2 | 1/2021 | Overmyer et al. |
| 10,898,186 B2 | 1/2021 | Bakos et al. |

(56) References Cited

U.S. PATENT DOCUMENTS

| | | |
|---|---|---|
| 10,898,190 B2 | 1/2021 | Yates et al. |
| 10,898,193 B2 | 1/2021 | Shelton, IV et al. |
| 10,898,194 B2 | 1/2021 | Moore et al. |
| 10,898,195 B2 | 1/2021 | Moore et al. |
| 10,903,685 B2 | 1/2021 | Yates et al. |
| D910,847 S | 2/2021 | Shelton, IV et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,905,422 B2 | 2/2021 | Bakos et al. |
| 10,905,423 B2 | 2/2021 | Baber et al. |
| 10,905,426 B2 | 2/2021 | Moore et al. |
| 10,905,427 B2 | 2/2021 | Moore et al. |
| 10,911,515 B2 | 2/2021 | Blasi et al. |
| 10,912,559 B2 | 2/2021 | Harris et al. |
| 10,912,562 B2 | 2/2021 | Dunki-Jacobs et al. |
| 10,912,575 B2 | 2/2021 | Shelton, IV et al. |
| 10,918,364 B2 | 2/2021 | Applegate et al. |
| 10,918,380 B2 | 2/2021 | Morgan et al. |
| 10,918,385 B2 | 2/2021 | Overmyer et al. |
| 10,918,386 B2 | 2/2021 | Shelton, IV et al. |
| 10,925,600 B2 | 2/2021 | McCuen |
| 10,925,605 B2 | 2/2021 | Moore et al. |
| D914,878 S | 3/2021 | Shelton, IV et al. |
| 10,932,772 B2 | 3/2021 | Shelton, IV et al. |
| 10,932,774 B2 | 3/2021 | Shelton, IV |
| 10,932,775 B2 | 3/2021 | Shelton, IV et al. |
| 10,932,778 B2 | 3/2021 | Smith et al. |
| 10,932,779 B2 | 3/2021 | Vendely et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,944,728 B2 | 3/2021 | Wiener et al. |
| 10,945,727 B2 | 3/2021 | Shelton, IV et al. |
| 10,945,728 B2 | 3/2021 | Morgan et al. |
| 10,945,729 B2 | 3/2021 | Shelton, IV et al. |
| 10,945,731 B2 | 3/2021 | Baxter, III et al. |
| 10,952,708 B2 | 3/2021 | Scheib et al. |
| 10,952,726 B2 | 3/2021 | Chowaniec |
| 10,952,727 B2 | 3/2021 | Giordano et al. |
| 10,952,728 B2 | 3/2021 | Shelton, IV et al. |
| 10,952,759 B2 | 3/2021 | Messerly et al. |
| 10,952,767 B2 | 3/2021 | Kostrzewski et al. |
| 10,959,722 B2 | 3/2021 | Morgan et al. |
| 10,959,725 B2 | 3/2021 | Kerr et al. |
| 10,959,727 B2 | 3/2021 | Hunter et al. |
| 10,959,731 B2 | 3/2021 | Casasanta, Jr. et al. |
| 10,959,744 B2 | 3/2021 | Shelton, IV et al. |
| 10,959,797 B2 | 3/2021 | Licht et al. |
| D917,500 S | 4/2021 | Siebel et al. |
| 10,966,627 B2 | 4/2021 | Shelton, IV et al. |
| 10,966,717 B2 | 4/2021 | Shah et al. |
| 10,966,718 B2 | 4/2021 | Shelton, IV et al. |
| 10,966,791 B2 | 4/2021 | Harris et al. |
| 10,973,515 B2 | 4/2021 | Harris et al. |
| 10,973,516 B2 | 4/2021 | Shelton, IV et al. |
| 10,973,517 B2 | 4/2021 | Wixey |
| 10,973,519 B2 | 4/2021 | Weir et al. |
| 10,973,520 B2 | 4/2021 | Shelton, IV et al. |
| 10,980,534 B2 | 4/2021 | Yates et al. |
| 10,980,535 B2 | 4/2021 | Yates et al. |
| 10,980,536 B2 | 4/2021 | Weaner et al. |
| 10,980,537 B2 | 4/2021 | Shelton, IV et al. |
| 10,980,538 B2 | 4/2021 | Nalagatla et al. |
| 10,980,539 B2 | 4/2021 | Harris et al. |
| 10,980,560 B2 | 4/2021 | Shelton, IV et al. |
| 10,983,646 B2 | 4/2021 | Yoon et al. |
| 10,987,102 B2 | 4/2021 | Gonzalez et al. |
| 10,987,178 B2 | 4/2021 | Shelton, IV et al. |
| 10,993,713 B2 | 5/2021 | Shelton, IV et al. |
| 10,993,715 B2 | 5/2021 | Shelton, IV et al. |
| 10,993,716 B2 | 5/2021 | Shelton, IV et al. |
| 10,993,717 B2 | 5/2021 | Shelton, IV et al. |
| 11,000,274 B2 | 5/2021 | Shelton, IV et al. |
| 11,000,275 B2 | 5/2021 | Shelton, IV et al. |
| 11,000,277 B2 | 5/2021 | Giordano et al. |
| 11,000,278 B2 | 5/2021 | Shelton, IV et al. |
| 11,000,279 B2 | 5/2021 | Shelton, IV et al. |
| 11,006,951 B2 | 5/2021 | Giordano et al. |
| 11,006,955 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,511 B2 | 5/2021 | Huang et al. |
| 11,013,552 B2 | 5/2021 | Widenhouse et al. |
| 11,013,563 B2 | 5/2021 | Shelton, IV et al. |
| 11,020,016 B2 | 6/2021 | Wallace et al. |
| 11,020,112 B2 | 6/2021 | Shelton, IV et al. |
| 11,020,113 B2 | 6/2021 | Shelton, IV et al. |
| 11,020,114 B2 | 6/2021 | Shelton, IV et al. |
| 11,020,115 B2 | 6/2021 | Scheib et al. |
| 11,026,678 B2 | 6/2021 | Overmyer et al. |
| 11,026,680 B2 | 6/2021 | Shelton, IV et al. |
| 11,026,684 B2 | 6/2021 | Shelton, IV et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,033,267 B2 | 6/2021 | Shelton, IV et al. |
| 11,039,834 B2 | 6/2021 | Harris et al. |
| 11,039,836 B2 | 6/2021 | Shelton, IV et al. |
| 11,039,837 B2 | 6/2021 | Shelton, IV et al. |
| 11,045,189 B2 | 6/2021 | Yates et al. |
| 11,045,191 B2 | 6/2021 | Shelton, IV et al. |
| 11,045,192 B2 | 6/2021 | Harris et al. |
| 11,045,197 B2 | 6/2021 | Shelton, IV et al. |
| 11,045,270 B2 | 6/2021 | Shelton, IV et al. |
| 11,051,807 B2 | 7/2021 | Shelton, IV et al. |
| 11,051,810 B2 | 7/2021 | Harris et al. |
| 11,051,811 B2 | 7/2021 | Shelton, IV et al. |
| 11,051,813 B2 | 7/2021 | Shelton, IV et al. |
| 11,051,836 B2 | 7/2021 | Shelton, IV et al. |
| 11,051,840 B2 | 7/2021 | Shelton, IV et al. |
| 11,051,873 B2 | 7/2021 | Wiener et al. |
| 11,058,418 B2 | 7/2021 | Shelton, IV et al. |
| 11,058,420 B2 | 7/2021 | Shelton, IV et al. |
| 11,058,422 B2 | 7/2021 | Harris et al. |
| 11,058,423 B2 | 7/2021 | Shelton, IV et al. |
| 11,058,424 B2 | 7/2021 | Shelton, IV et al. |
| 11,058,425 B2 | 7/2021 | Widenhouse et al. |
| 11,058,426 B2 | 7/2021 | Nalagatla et al. |
| 11,058,498 B2 | 7/2021 | Shelton, IV et al. |
| 11,064,997 B2 | 7/2021 | Shelton, IV et al. |
| 11,064,998 B2 | 7/2021 | Shelton, IV |
| 11,065,048 B2 | 7/2021 | Messerly et al. |
| 11,069,012 B2 | 7/2021 | Shelton, IV et al. |
| 11,071,543 B2 | 7/2021 | Shelton, IV et al. |
| 11,071,545 B2 | 7/2021 | Baber et al. |
| 11,071,554 B2 | 7/2021 | Parfett et al. |
| 11,071,560 B2 | 7/2021 | Deck et al. |
| 11,076,853 B2 | 8/2021 | Parfett et al. |
| 11,076,854 B2 | 8/2021 | Baber et al. |
| 11,076,921 B2 | 8/2021 | Shelton, IV et al. |
| 11,076,929 B2 | 8/2021 | Shelton, IV et al. |
| 11,083,452 B2 | 8/2021 | Schmid et al. |
| 11,083,453 B2 | 8/2021 | Shelton, IV et al. |
| 11,083,454 B2 | 8/2021 | Harris et al. |
| 11,083,455 B2 | 8/2021 | Shelton, IV et al. |
| 11,083,456 B2 | 8/2021 | Shelton, IV et al. |
| 11,083,457 B2 | 8/2021 | Shelton, IV et al. |
| 11,083,458 B2 | 8/2021 | Harris et al. |
| 11,090,045 B2 | 8/2021 | Shelton, IV |
| 11,090,046 B2 | 8/2021 | Shelton, IV et al. |
| 11,090,047 B2 | 8/2021 | Shelton, IV et al. |
| 11,090,048 B2 | 8/2021 | Fanelli et al. |
| 11,090,049 B2 | 8/2021 | Bakos et al. |
| 11,090,075 B2 | 8/2021 | Hunter et al. |
| 11,096,688 B2 | 8/2021 | Shelton, IV et al. |
| 11,096,689 B2 | 8/2021 | Overmyer et al. |
| 11,100,631 B2 | 8/2021 | Yates et al. |
| 11,103,241 B2 | 8/2021 | Yates et al. |
| 11,103,248 B2 | 8/2021 | Shelton, IV et al. |
| 11,103,268 B2 | 8/2021 | Shelton, IV et al. |
| 11,103,269 B2 | 8/2021 | Shelton, IV et al. |
| 11,109,858 B2 | 9/2021 | Shelton, IV et al. |

(56) References Cited

U.S. PATENT DOCUMENTS

| | | |
|---|---|---|
| 11,109,859 B2 | 9/2021 | Overmyer et al. |
| 11,109,860 B2 | 9/2021 | Shelton, IV et al. |
| 11,109,866 B2 | 9/2021 | Shelton, IV et al. |
| 11,109,878 B2 | 9/2021 | Shelton, IV et al. |
| 11,109,925 B2 | 9/2021 | Cooper et al. |
| 11,116,485 B2 | 9/2021 | Scheib et al. |
| 11,116,502 B2 | 9/2021 | Shelton, IV et al. |
| 11,116,594 B2 | 9/2021 | Beardsley |
| 11,123,070 B2 | 9/2021 | Shelton, IV et al. |
| 11,129,611 B2 | 9/2021 | Shelton, IV et al. |
| 11,129,613 B2 | 9/2021 | Harris et al. |
| 11,129,615 B2 | 9/2021 | Scheib et al. |
| 11,129,616 B2 | 9/2021 | Shelton, IV et al. |
| 11,129,634 B2 | 9/2021 | Scheib et al. |
| 11,129,636 B2 | 9/2021 | Shelton, IV et al. |
| 11,129,666 B2 | 9/2021 | Messerly et al. |
| 11,129,680 B2 | 9/2021 | Shelton, IV et al. |
| 11,132,462 B2 | 9/2021 | Shelton, IV et al. |
| 11,133,106 B2 | 9/2021 | Shelton, IV et al. |
| 11,134,938 B2 | 10/2021 | Timm et al. |
| 11,134,940 B2 | 10/2021 | Shelton, IV et al. |
| 11,134,942 B2 | 10/2021 | Harris et al. |
| 11,134,943 B2 | 10/2021 | Giordano et al. |
| 11,134,944 B2 | 10/2021 | Wise et al. |
| 11,134,947 B2 | 10/2021 | Shelton, IV et al. |
| 11,135,352 B2 | 10/2021 | Shelton, IV et al. |
| 11,141,153 B2 | 10/2021 | Shelton, IV et al. |
| 11,141,154 B2 | 10/2021 | Shelton, IV et al. |
| 11,141,155 B2 | 10/2021 | Shelton, IV |
| 11,141,156 B2 | 10/2021 | Shelton, IV |
| 11,141,160 B2 | 10/2021 | Shelton, IV et al. |
| 11,147,547 B2 | 10/2021 | Shelton, IV et al. |
| 11,147,549 B2 | 10/2021 | Timm et al. |
| 11,147,551 B2 | 10/2021 | Shelton, IV |
| 11,147,553 B2 | 10/2021 | Shelton, IV |
| 11,147,554 B2 | 10/2021 | Aronhalt et al. |
| 11,154,296 B2 | 10/2021 | Aronhalt et al. |
| 11,154,297 B2 | 10/2021 | Swayze et al. |
| 11,154,298 B2 | 10/2021 | Timm et al. |
| 11,154,299 B2 | 10/2021 | Shelton, IV et al. |
| 11,154,300 B2 | 10/2021 | Nalagatla et al. |
| 11,154,301 B2 | 10/2021 | Beckman et al. |
| 11,160,551 B2 | 11/2021 | Shelton, IV et al. |
| 11,160,553 B2 | 11/2021 | Simms et al. |
| 11,160,601 B2 | 11/2021 | Worrell et al. |
| 11,166,716 B2 | 11/2021 | Shelton, IV et al. |
| 11,166,717 B2 | 11/2021 | Shelton, IV et al. |
| 11,166,720 B2 | 11/2021 | Giordano et al. |
| 11,166,772 B2 | 11/2021 | Shelton, IV et al. |
| 11,172,927 B2 | 11/2021 | Shelton, IV |
| 11,172,929 B2 | 11/2021 | Shelton, IV |
| 11,179,150 B2 | 11/2021 | Yates et al. |
| 11,179,151 B2 | 11/2021 | Shelton, IV et al. |
| 11,179,152 B2 | 11/2021 | Morgan et al. |
| 11,179,153 B2 | 11/2021 | Shelton, IV |
| 11,179,155 B2 | 11/2021 | Shelton, IV et al. |
| 11,179,208 B2 | 11/2021 | Yates et al. |
| 11,185,325 B2 | 11/2021 | Shelton, IV et al. |
| 11,185,330 B2 | 11/2021 | Huitema et al. |
| 11,191,539 B2 | 12/2021 | Overmyer et al. |
| 11,191,540 B2 | 12/2021 | Aronhalt et al. |
| 11,191,543 B2 | 12/2021 | Overmyer et al. |
| 11,191,545 B2 | 12/2021 | Vendely et al. |
| 11,197,668 B2 | 12/2021 | Shelton, IV et al. |
| 11,197,670 B2 | 12/2021 | Shelton, IV et al. |
| 11,197,671 B2 | 12/2021 | Shelton, IV et al. |
| 11,202,570 B2 | 12/2021 | Shelton, IV et al. |
| 11,202,631 B2 | 12/2021 | Shelton, IV et al. |
| 11,207,064 B2 | 12/2021 | Shelton, IV et al. |
| 11,207,065 B2 | 12/2021 | Harris et al. |
| 11,207,067 B2 | 12/2021 | Shelton, IV et al. |
| 11,207,090 B2 | 12/2021 | Shelton, IV et al. |
| 11,207,146 B2 | 12/2021 | Shelton, IV et al. |
| 11,213,293 B2 | 1/2022 | Worthington et al. |
| 11,213,294 B2 | 1/2022 | Shelton, IV et al. |
| 11,213,302 B2 | 1/2022 | Parfett et al. |
| 11,213,359 B2 | 1/2022 | Shelton, IV et al. |
| 11,219,453 B2 | 1/2022 | Shelton, IV et al. |
| 11,219,455 B2 | 1/2022 | Shelton, IV et al. |
| 11,224,423 B2 | 1/2022 | Shelton, IV et al. |
| 11,224,426 B2 | 1/2022 | Shelton, IV et al. |
| 11,224,427 B2 | 1/2022 | Shelton, IV et al. |
| 11,224,428 B2 | 1/2022 | Scott et al. |
| 11,224,454 B2 | 1/2022 | Shelton, IV et al. |
| 11,224,497 B2 | 1/2022 | Shelton, IV et al. |
| 11,229,436 B2 | 1/2022 | Shelton, IV et al. |
| 11,229,437 B2 | 1/2022 | Shelton, IV et al. |
| 11,234,698 B2 | 2/2022 | Shelton, IV et al. |
| 11,234,700 B2 | 2/2022 | Ragosta et al. |
| 11,241,229 B2 | 2/2022 | Shelton, IV et al. |
| 11,241,230 B2 | 2/2022 | Shelton, IV et al. |
| 11,241,235 B2 | 2/2022 | Shelton, IV et al. |
| 11,246,590 B2 | 2/2022 | Swayze et al. |
| 11,246,592 B2 | 2/2022 | Shelton, IV et al. |
| 11,246,616 B2 | 2/2022 | Shelton, IV et al. |
| 11,246,618 B2 | 2/2022 | Hall et al. |
| 11,246,678 B2 | 2/2022 | Shelton, IV et al. |
| 11,253,254 B2 | 2/2022 | Kimball et al. |
| 11,253,256 B2 | 2/2022 | Harris et al. |
| 11,259,799 B2 | 3/2022 | Overmyer et al. |
| 11,259,803 B2 | 3/2022 | Shelton, IV et al. |
| 11,259,805 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,266,406 B2 | 3/2022 | Leimbach et al. |
| 11,266,409 B2 | 3/2022 | Huitema et al. |
| 11,266,410 B2 | 3/2022 | Shelton, IV et al. |
| 11,266,468 B2 | 3/2022 | Shelton, IV et al. |
| 11,272,927 B2 | 3/2022 | Swayze et al. |
| 11,272,928 B2 | 3/2022 | Shelton, IV |
| 11,272,931 B2 | 3/2022 | Boudreaux et al. |
| 11,272,938 B2 | 3/2022 | Shelton, IV et al. |
| 11,278,279 B2 | 3/2022 | Morgan et al. |
| 11,278,280 B2 | 3/2022 | Shelton, IV et al. |
| 11,278,284 B2 | 3/2022 | Shelton, IV et al. |
| 11,284,890 B2 | 3/2022 | Nalagatla et al. |
| 11,284,891 B2 | 3/2022 | Shelton, IV et al. |
| 11,284,898 B2 | 3/2022 | Baxter, III et al. |
| 11,284,953 B2 | 3/2022 | Shelton, IV et al. |
| 11,291,440 B2 | 4/2022 | Harris et al. |
| 11,291,441 B2 | 4/2022 | Giordano et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,449 B2 | 4/2022 | Swensgard et al. |
| 11,291,451 B2 | 4/2022 | Shelton, IV |
| 11,291,465 B2 | 4/2022 | Parihar et al. |
| 11,291,510 B2 | 4/2022 | Shelton, IV et al. |
| 11,298,125 B2 | 4/2022 | Ming et al. |
| 11,298,127 B2 | 4/2022 | Shelton, IV |
| 11,298,128 B2 | 4/2022 | Messerly et al. |
| 11,298,129 B2 | 4/2022 | Bakos et al. |
| 11,298,130 B2 | 4/2022 | Bakos et al. |
| 11,298,132 B2 | 4/2022 | Shelton, IV et al. |
| 11,298,134 B2 | 4/2022 | Huitema et al. |
| 11,304,695 B2 | 4/2022 | Shelton, IV et al. |
| 11,304,696 B2 | 4/2022 | Shelton, IV et al. |
| 11,304,699 B2 | 4/2022 | Shelton, IV et al. |
| 11,311,290 B2 | 4/2022 | Shelton, IV et al. |
| 11,311,292 B2 | 4/2022 | Shelton, IV et al. |
| 11,311,294 B2 | 4/2022 | Swayze et al. |
| 11,311,342 B2 | 4/2022 | Parihar et al. |
| 11,317,910 B2 | 5/2022 | Miller et al. |
| 11,317,913 B2 | 5/2022 | Shelton, IV et al. |
| 11,317,915 B2 | 5/2022 | Boudreaux et al. |
| 11,317,917 B2 * | 5/2022 | Shelton, IV ......... A61B 17/072 |
| 11,317,919 B2 | 5/2022 | Shelton, IV et al. |
| 11,324,501 B2 | 5/2022 | Shelton, IV et al. |
| 11,324,503 B2 | 5/2022 | Shelton, IV et al. |
| 11,324,506 B2 | 5/2022 | Beckman et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |

(56) References Cited

U.S. PATENT DOCUMENTS

| | | |
|---|---|---|
| 11,337,691 B2 | 5/2022 | Widenhouse et al. |
| 11,337,693 B2 | 5/2022 | Hess et al. |
| 11,337,698 B2 | 5/2022 | Baxter, III et al. |
| 11,344,299 B2 | 5/2022 | Yates et al. |
| 11,344,303 B2 | 5/2022 | Shelton, IV et al. |
| 11,350,843 B2 | 6/2022 | Shelton, IV et al. |
| 11,350,916 B2 | 6/2022 | Shelton, IV et al. |
| 11,350,928 B2 | 6/2022 | Shelton, IV et al. |
| 11,350,929 B2 | 6/2022 | Giordano et al. |
| 11,350,932 B2 | 6/2022 | Shelton, IV et al. |
| 11,350,934 B2 | 6/2022 | Bakos et al. |
| 11,350,935 B2 | 6/2022 | Shelton, IV et al. |
| 11,350,938 B2 | 6/2022 | Shelton, IV et al. |
| 11,357,503 B2 | 6/2022 | Bakos et al. |
| 11,361,176 B2 | 6/2022 | Shelton, IV et al. |
| 11,364,027 B2 | 6/2022 | Harris et al. |
| 11,364,046 B2 | 6/2022 | Shelton, IV et al. |
| 11,369,368 B2 | 6/2022 | Shelton, IV et al. |
| 11,369,376 B2 | 6/2022 | Simms et al. |
| 11,369,377 B2 | 6/2022 | Boudreaux et al. |
| 11,373,755 B2 | 6/2022 | Shelton, IV et al. |
| 11,376,001 B2 | 7/2022 | Shelton, IV et al. |
| 11,376,098 B2 | 7/2022 | Shelton, IV et al. |
| 11,382,625 B2 | 7/2022 | Huitema et al. |
| 11,382,626 B2 | 7/2022 | Shelton, IV et al. |
| 11,382,627 B2 | 7/2022 | Huitema et al. |
| 11,382,628 B2 | 7/2022 | Baxter, III et al. |
| 11,382,638 B2 | 7/2022 | Harris et al. |
| 11,382,697 B2 | 7/2022 | Shelton, IV et al. |
| 11,389,160 B2 | 7/2022 | Shelton, IV et al. |
| 11,389,161 B2 | 7/2022 | Shelton, IV et al. |
| 11,389,162 B2 | 7/2022 | Baber et al. |
| 11,389,164 B2 | 7/2022 | Yates et al. |
| 11,395,651 B2 | 7/2022 | Shelton, IV et al. |
| 11,395,652 B2 | 7/2022 | Parihar et al. |
| 11,399,828 B2 | 8/2022 | Swayze et al. |
| 11,399,829 B2 | 8/2022 | Leimbach et al. |
| 11,399,831 B2 | 8/2022 | Overmyer et al. |
| 11,399,837 B2 | 8/2022 | Shelton, IV et al. |
| 11,406,377 B2 | 8/2022 | Schmid et al. |
| 11,406,378 B2 | 8/2022 | Baxter, III et al. |
| 11,406,380 B2 | 8/2022 | Yates et al. |
| 11,406,381 B2 | 8/2022 | Parihar et al. |
| 11,406,382 B2 | 8/2022 | Shelton, IV et al. |
| 11,406,386 B2 | 8/2022 | Baber et al. |
| 11,406,390 B2 | 8/2022 | Shelton, IV et al. |
| 11,410,259 B2 | 8/2022 | Harris et al. |
| 11,413,042 B2 | 8/2022 | Shelton, IV et al. |
| 11,413,102 B2 | 8/2022 | Shelton, IV et al. |
| 11,419,606 B2 | 8/2022 | Overmyer et al. |
| 11,419,630 B2 | 8/2022 | Yates et al. |
| 11,424,027 B2 | 8/2022 | Shelton, IV |
| 11,426,160 B2 | 8/2022 | Shelton, IV et al. |
| 11,426,167 B2 | 8/2022 | Shelton, IV et al. |
| 11,426,251 B2 | 8/2022 | Kimball et al. |
| 11,432,816 B2 | 9/2022 | Leimbach et al. |
| 11,432,885 B2 | 9/2022 | Shelton, IV et al. |
| 11,439,470 B2 | 9/2022 | Spivey et al. |
| 11,446,029 B2 | 9/2022 | Shelton, IV et al. |
| 11,446,034 B2 | 9/2022 | Shelton, IV et al. |
| 11,452,528 B2 | 9/2022 | Leimbach et al. |
| 11,457,918 B2 | 10/2022 | Shelton, IV et al. |
| 11,464,511 B2 | 10/2022 | Timm et al. |
| 11,464,512 B2 | 10/2022 | Shelton, IV et al. |
| 11,464,513 B2 | 10/2022 | Shelton, IV et al. |
| 11,464,514 B2 | 10/2022 | Yates et al. |
| 11,464,601 B2 | 10/2022 | Shelton, IV et al. |
| 11,471,155 B2 | 10/2022 | Shelton, IV et al. |
| 11,471,156 B2 | 10/2022 | Shelton, IV et al. |
| 11,471,157 B2 | 10/2022 | Baxter, III et al. |
| 11,478,241 B2 | 10/2022 | Shelton, IV et al. |
| 11,478,242 B2 | 10/2022 | Shelton, IV et al. |
| 11,478,244 B2 | 10/2022 | DiNardo et al. |
| 11,478,247 B2 | 10/2022 | Shelton, IV et al. |
| 11,484,307 B2 | 11/2022 | Hall et al. |
| 11,484,310 B2 | 11/2022 | Shelton, IV et al. |
| 11,484,311 B2 | 11/2022 | Shelton, IV et al. |
| 11,490,889 B2 | 11/2022 | Overmyer et al. |
| 11,497,488 B2 | 11/2022 | Leimbach et al. |
| 11,497,489 B2 | 11/2022 | Baxter, III et al. |
| 11,497,492 B2 | 11/2022 | Shelton, IV |
| 11,497,499 B2 | 11/2022 | Shelton, IV et al. |
| 11,504,116 B2 | 11/2022 | Schmid et al. |
| 11,504,119 B2 | 11/2022 | Shelton, IV et al. |
| 11,504,122 B2 | 11/2022 | Shelton, IV et al. |
| 11,504,192 B2 | 11/2022 | Shelton, IV et al. |
| 11,510,671 B2 | 11/2022 | Shelton, IV et al. |
| 11,510,741 B2 | 11/2022 | Shelton, IV et al. |
| 11,517,304 B2 | 12/2022 | Yates et al. |
| 11,517,306 B2 | 12/2022 | Miller et al. |
| 11,517,309 B2 | 12/2022 | Bakos et al. |
| 11,517,311 B2 | 12/2022 | Lytle, IV et al. |
| 11,517,315 B2 | 12/2022 | Huitema et al. |
| 11,517,325 B2 | 12/2022 | Shelton, IV et al. |
| 11,523,821 B2 | 12/2022 | Harris et al. |
| 11,523,822 B2 | 12/2022 | Shelton, IV et al. |
| 11,523,823 B2 | 12/2022 | Hunter et al. |
| 11,529,137 B2 | 12/2022 | Shelton, IV et al. |
| 11,529,138 B2 | 12/2022 | Jaworek et al. |
| 11,529,139 B2 | 12/2022 | Shelton, IV et al. |
| 11,529,140 B2 | 12/2022 | Shelton, IV et al. |
| 11,529,142 B2 | 12/2022 | Leimbach et al. |
| 11,534,162 B2 | 12/2022 | Shelton, IV |
| 11,540,824 B2 | 1/2023 | Shelton, IV et al. |
| 11,540,829 B2 | 1/2023 | Shelton, IV et al. |
| 11,547,403 B2 | 1/2023 | Shelton, IV et al. |
| 11,547,404 B2 | 1/2023 | Shelton, IV et al. |
| 11,553,916 B2 | 1/2023 | Vendely et al. |
| 11,553,971 B2 | 1/2023 | Shelton, IV et al. |
| 11,559,302 B2 | 1/2023 | Timm et al. |
| 11,559,303 B2 | 1/2023 | Shelton, IV et al. |
| 11,559,304 B2 | 1/2023 | Boudreaux et al. |
| 11,559,307 B2 | 1/2023 | Shelton, IV et al. |
| 11,559,308 B2 | 1/2023 | Yates et al. |
| 11,559,496 B2 | 1/2023 | Widenhouse et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2001/0034530 A1 | 10/2001 | Malackowski et al. |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0087048 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0111624 A1 | 8/2002 | Witt et al. |
| 2002/0116063 A1 | 8/2002 | Giannetti et al. |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0138086 A1 | 9/2002 | Sixto et al. |
| 2002/0143340 A1 | 10/2002 | Kaneko |
| 2002/0151770 A1 | 10/2002 | Noll et al. |
| 2002/0158593 A1 | 10/2002 | Henderson et al. |
| 2002/0177848 A1 | 11/2002 | Truckai et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0012805 A1 | 1/2003 | Chen et al. |
| 2003/0039689 A1 | 2/2003 | Chen et al. |
| 2003/0040670 A1 | 2/2003 | Govari |
| 2003/0045835 A1 | 3/2003 | Anderson et al. |
| 2003/0047230 A1 | 3/2003 | Kim |
| 2003/0050654 A1 | 3/2003 | Whitman et al. |
| 2003/0066858 A1 | 4/2003 | Holgersson |

(56) References Cited

U.S. PATENT DOCUMENTS

| | | |
|---|---|---|
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0121586 A1 | 7/2003 | Mitra et al. |
| 2003/0139741 A1 | 7/2003 | Goble et al. |
| 2003/0149406 A1 | 8/2003 | Martineau et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0164172 A1 | 9/2003 | Chumas et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034287 A1 | 2/2004 | Hickle |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0092992 A1 | 5/2004 | Adams et al. |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0239582 A1 | 12/2004 | Seymour |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0129735 A1 | 6/2005 | Cook et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0242950 A1 | 11/2005 | Lindsay et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0258963 A1 | 11/2005 | Rodriguez et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2005/0283226 A1 | 12/2005 | Haverkost |

(56) References Cited

U.S. PATENT DOCUMENTS

| | | |
|---|---|---|
| 2006/0008787 A1 | 1/2006 | Hayman et al. |
| 2006/0015009 A1 | 1/2006 | Jaffe et al. |
| 2006/0020167 A1 | 1/2006 | Sitzmann |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079874 A1 | 4/2006 | Faller et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0106369 A1 | 5/2006 | Desai et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0144898 A1 | 7/2006 | Bilotti et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0176242 A1 | 8/2006 | Jaramaz et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0226957 A1 | 10/2006 | Miller et al. |
| 2006/0235368 A1 | 10/2006 | Oz |
| 2006/0241666 A1 | 10/2006 | Briggs et al. |
| 2006/0244460 A1 | 11/2006 | Weaver |
| 2006/0252981 A1 | 11/2006 | Matsuda et al. |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0005045 A1 | 1/2007 | Mintz et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0018958 A1 | 1/2007 | Tavakoli et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0103437 A1 | 5/2007 | Rosenberg |
| 2007/0106113 A1 | 5/2007 | Ravo |
| 2007/0106317 A1 | 5/2007 | Shelton et al. |
| 2007/0118115 A1 | 5/2007 | Artale et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0152829 A1 | 7/2007 | Lindsay et al. |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0173872 A1 | 7/2007 | Neuenfeldt |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0187857 A1 | 8/2007 | Riley et al. |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0244496 A1 | 10/2007 | Hellenkamp |
| 2007/0246505 A1 | 10/2007 | Pace-Floridia et al. |
| 2007/0260132 A1 | 11/2007 | Sterling |
| 2007/0262592 A1 | 11/2007 | Hwang et al. |
| 2007/0270660 A1 | 11/2007 | Caylor et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0290027 A1 | 12/2007 | Maatta et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0039746 A1 | 2/2008 | Hissong et al. |
| 2008/0042861 A1 | 2/2008 | Dacquay et al. |
| 2008/0051833 A1 | 2/2008 | Gramuglia et al. |
| 2008/0064920 A1 | 3/2008 | Bakos et al. |
| 2008/0064921 A1 | 3/2008 | Larkin et al. |
| 2008/0065153 A1 | 3/2008 | Allard et al. |
| 2008/0069736 A1 | 3/2008 | Mingerink et al. |
| 2008/0071328 A1 | 3/2008 | Haubrich et al. |
| 2008/0077158 A1 | 3/2008 | Haider et al. |
| 2008/0078802 A1 | 4/2008 | Hess et al. |
| 2008/0081948 A1 | 4/2008 | Weisenburgh et al. |
| 2008/0082114 A1 | 4/2008 | McKenna et al. |
| 2008/0082125 A1 | 4/2008 | Murray et al. |

(56) References Cited

U.S. PATENT DOCUMENTS

| | | |
|---|---|---|
| 2008/0082126 A1 | 4/2008 | Murray et al. |
| 2008/0083807 A1 | 4/2008 | Beardsley et al. |
| 2008/0083811 A1 | 4/2008 | Marczyk |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0149682 A1 | 6/2008 | Uhm |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0177392 A1 | 7/2008 | Williams et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0206186 A1 | 8/2008 | Butler et al. |
| 2008/0208058 A1 | 8/2008 | Sabata et al. |
| 2008/0234709 A1 | 9/2008 | Houser |
| 2008/0242939 A1 | 10/2008 | Johnston |
| 2008/0243088 A1 | 10/2008 | Evans |
| 2008/0249536 A1 | 10/2008 | Stabler et al. |
| 2008/0249608 A1 | 10/2008 | Dave |
| 2008/0255413 A1 | 10/2008 | Zemlok et al. |
| 2008/0255420 A1 | 10/2008 | Lee et al. |
| 2008/0255663 A1 | 10/2008 | Akpek et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0281332 A1 | 11/2008 | Taylor |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0298784 A1 | 12/2008 | Kastner |
| 2008/0308602 A1 | 12/2008 | Timm et al. |
| 2008/0308603 A1 | 12/2008 | Shelton et al. |
| 2008/0312686 A1 | 12/2008 | Ellingwood |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0099579 A1 | 4/2009 | Nentwick et al. |
| 2009/0099876 A1 | 4/2009 | Whitman |
| 2009/0110533 A1 | 4/2009 | Jinno |
| 2009/0112234 A1 | 4/2009 | Crainich et al. |
| 2009/0118762 A1 | 5/2009 | Crainch et al. |
| 2009/0119011 A1 | 5/2009 | Kondo et al. |
| 2009/0131819 A1 | 5/2009 | Ritchie et al. |
| 2009/0132400 A1 | 5/2009 | Conway |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177218 A1 | 7/2009 | Young et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0221993 A1 | 9/2009 | Sohi et al. |
| 2009/0227834 A1 | 9/2009 | Nakamoto et al. |
| 2009/0234273 A1 | 9/2009 | Intoccia et al. |
| 2009/0242610 A1 | 10/2009 | Shelton, IV et al. |
| 2009/0246873 A1 | 10/2009 | Yamamoto et al. |
| 2009/0247368 A1 | 10/2009 | Chiang |
| 2009/0247901 A1 | 10/2009 | Zimmer |
| 2009/0248100 A1 | 10/2009 | Vaisnys et al. |
| 2009/0253959 A1 | 10/2009 | Yoshie et al. |
| 2009/0255974 A1 | 10/2009 | Viola |
| 2009/0261141 A1 | 10/2009 | Stratton et al. |
| 2009/0262078 A1 | 10/2009 | Pizzi |
| 2009/0270895 A1 | 10/2009 | Churchill et al. |
| 2009/0277288 A1 | 11/2009 | Doepker et al. |
| 2009/0278406 A1 | 11/2009 | Hoffman |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2009/0325859 A1 | 12/2009 | Ameer et al. |
| 2010/0005035 A1 | 1/2010 | Carpenter et al. |
| 2010/0012703 A1 | 1/2010 | Calabrese et al. |
| 2010/0015104 A1 | 1/2010 | Fraser et al. |
| 2010/0016853 A1 | 1/2010 | Burbank |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0030239 A1 | 2/2010 | Viola et al. |
| 2010/0032179 A1 | 2/2010 | Hanspers et al. |
| 2010/0036370 A1 | 2/2010 | Mirel et al. |
| 2010/0051668 A1 | 3/2010 | Milliman et al. |
| 2010/0057118 A1 | 3/2010 | Dietz et al. |
| 2010/0065604 A1 | 3/2010 | Weng |
| 2010/0069833 A1 | 3/2010 | Wenderow et al. |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0100123 A1 | 4/2010 | Bennett |
| 2010/0100124 A1 | 4/2010 | Calabrese et al. |
| 2010/0116519 A1 | 5/2010 | Garels |
| 2010/0122339 A1 | 5/2010 | Boccacci |
| 2010/0133317 A1 | 6/2010 | Shelton, IV et al. |
| 2010/0137990 A1 | 6/2010 | Apatsidis et al. |
| 2010/0138659 A1 | 6/2010 | Carmichael et al. |
| 2010/0145146 A1 | 6/2010 | Melder |
| 2010/0147921 A1 | 6/2010 | Olson |
| 2010/0147922 A1 | 6/2010 | Olson |
| 2010/0159435 A1 | 6/2010 | Mueller et al. |
| 2010/0179022 A1 | 7/2010 | Shirokoshi |
| 2010/0180711 A1 | 7/2010 | Kilibarda et al. |
| 2010/0191262 A1 | 7/2010 | Harris et al. |

(56) References Cited

U.S. PATENT DOCUMENTS

| | | |
|---|---|---|
| 2010/0191292 A1 | 7/2010 | DeMeo et al. |
| 2010/0193566 A1 | 8/2010 | Scheib et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0228250 A1 | 9/2010 | Brogna |
| 2010/0234687 A1 | 9/2010 | Azarbarzin et al. |
| 2010/0241137 A1 | 9/2010 | Doyle et al. |
| 2010/0245102 A1 | 9/2010 | Yokoi |
| 2010/0249497 A1 | 9/2010 | Peine et al. |
| 2010/0249947 A1 | 9/2010 | Lesh et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0301097 A1 | 12/2010 | Scirica et al. |
| 2010/0310623 A1 | 12/2010 | Laurencin et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0009694 A1 | 1/2011 | Schultz et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0029270 A1 | 2/2011 | Mueglitz |
| 2011/0036891 A1 | 2/2011 | Zemlok et al. |
| 2011/0046667 A1 | 2/2011 | Culligan et al. |
| 2011/0052660 A1 | 3/2011 | Yang et al. |
| 2011/0056717 A1 | 3/2011 | Herisse |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0095067 A1 | 4/2011 | Ohdaira |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0118708 A1 | 5/2011 | Burbank et al. |
| 2011/0125149 A1 | 5/2011 | El-Galley et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0220381 A1 | 9/2011 | Friese et al. |
| 2011/0225105 A1 | 9/2011 | Scholer et al. |
| 2011/0230713 A1 | 9/2011 | Kleemann et al. |
| 2011/0235168 A1 | 9/2011 | Sander |
| 2011/0238044 A1 | 9/2011 | Main et al. |
| 2011/0241597 A1 | 10/2011 | Zhu et al. |
| 2011/0256266 A1 | 10/2011 | Orme et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0285507 A1 | 11/2011 | Nelson |
| 2011/0290856 A1 | 12/2011 | Shelton, IV et al. |
| 2011/0290858 A1 | 12/2011 | Whitman et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0008880 A1 | 1/2012 | Toth |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078243 A1 | 3/2012 | Worrell et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0171539 A1 | 7/2012 | Rejman et al. |
| 2012/0175398 A1 | 7/2012 | Sandborn et al. |
| 2012/0190964 A1 | 7/2012 | Hyde et al. |
| 2012/0197239 A1 | 8/2012 | Smith et al. |
| 2012/0197272 A1 | 8/2012 | Oray et al. |
| 2012/0211542 A1 | 8/2012 | Racenet |
| 2012/0220990 A1 | 8/2012 | Mckenzie et al. |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0271327 A1 | 10/2012 | West et al. |
| 2012/0283707 A1 | 11/2012 | Giordano et al. |
| 2012/0289811 A1 | 11/2012 | Viola et al. |
| 2012/0289979 A1 | 11/2012 | Eskaros et al. |
| 2012/0292367 A1 | 11/2012 | Morgan et al. |
| 2012/0296342 A1 | 11/2012 | Haglund Wendelschafer |
| 2012/0298722 A1 | 11/2012 | Hess et al. |
| 2012/0301498 A1 | 11/2012 | Altreuter et al. |
| 2012/0316424 A1 | 12/2012 | Stopek |
| 2012/0330329 A1 | 12/2012 | Harris et al. |
| 2013/0006227 A1 | 1/2013 | Takashino |
| 2013/0008937 A1 | 1/2013 | Viola |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0087597 A1 | 4/2013 | Shelton, IV et al. |
| 2013/0090534 A1 | 4/2013 | Burns et al. |
| 2013/0096568 A1 | 4/2013 | Justis |

(56) References Cited

U.S. PATENT DOCUMENTS

| | | |
|---|---|---|
| 2013/0098970 A1 | 4/2013 | Racenet et al. |
| 2013/0106352 A1 | 5/2013 | Nagamine |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0169217 A1 | 7/2013 | Watanabe et al. |
| 2013/0172713 A1 | 7/2013 | Kirschenman |
| 2013/0172878 A1 | 7/2013 | Smith |
| 2013/0175317 A1 | 7/2013 | Yates et al. |
| 2013/0183769 A1 | 7/2013 | Tajima |
| 2013/0211244 A1 | 8/2013 | Nathaniel |
| 2013/0214025 A1 | 8/2013 | Zemlok et al. |
| 2013/0215449 A1 | 8/2013 | Yamasaki |
| 2013/0231681 A1 | 9/2013 | Robinson et al. |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256380 A1 | 10/2013 | Schmid et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0293353 A1 | 11/2013 | McPherson et al. |
| 2013/0306704 A1 | 11/2013 | Balbierz et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0008289 A1 | 1/2014 | Williams et al. |
| 2014/0014704 A1 | 1/2014 | Onukuri et al. |
| 2014/0014705 A1 | 1/2014 | Baxter, III |
| 2014/0014707 A1 | 1/2014 | Onukuri et al. |
| 2014/0018832 A1 | 1/2014 | Shelton, IV |
| 2014/0022283 A1 | 1/2014 | Chan et al. |
| 2014/0039549 A1 | 2/2014 | Belsky et al. |
| 2014/0041191 A1 | 2/2014 | Knodel |
| 2014/0048580 A1 | 2/2014 | Merchant et al. |
| 2014/0081176 A1 | 3/2014 | Hassan |
| 2014/0094681 A1 | 4/2014 | Valentine et al. |
| 2014/0100558 A1 | 4/2014 | Schmitz et al. |
| 2014/0107697 A1 | 4/2014 | Patani et al. |
| 2014/0115229 A1 | 4/2014 | Kothamasu et al. |
| 2014/0131418 A1 | 5/2014 | Kostrzewski |
| 2014/0135832 A1 | 5/2014 | Park et al. |
| 2014/0151433 A1 | 6/2014 | Shelton, IV et al. |
| 2014/0155916 A1 | 6/2014 | Hodgkinson et al. |
| 2014/0158747 A1 | 6/2014 | Measamer et al. |
| 2014/0166723 A1 | 6/2014 | Beardsley et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0183244 A1 | 7/2014 | Duque et al. |
| 2014/0188091 A1 | 7/2014 | Vidal et al. |
| 2014/0188159 A1 | 7/2014 | Steege |
| 2014/0207124 A1 | 7/2014 | Aldridge et al. |
| 2014/0209658 A1 | 7/2014 | Skalla et al. |
| 2014/0224857 A1 | 8/2014 | Schmid |
| 2014/0228632 A1 | 8/2014 | Sholev et al. |
| 2014/0228867 A1 | 8/2014 | Thomas et al. |
| 2014/0239047 A1 | 8/2014 | Hodgkinson et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0249573 A1 | 9/2014 | Arav |
| 2014/0262408 A1 | 9/2014 | Woodard |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0358163 A1 | 12/2014 | Farin et al. |
| 2014/0367445 A1 | 12/2014 | Ingmanson et al. |
| 2014/0374130 A1 | 12/2014 | Nakamura et al. |
| 2014/0378950 A1 | 12/2014 | Chiu |
| 2015/0001272 A1 | 1/2015 | Sniffin et al. |
| 2015/0002089 A1 | 1/2015 | Rejman et al. |
| 2015/0025549 A1 | 1/2015 | Kilroy et al. |
| 2015/0025571 A1 | 1/2015 | Suzuki et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076211 A1 | 3/2015 | Irka et al. |
| 2015/0082624 A1 | 3/2015 | Craig et al. |
| 2015/0083781 A1 | 3/2015 | Giordano et al. |
| 2015/0087952 A1 | 3/2015 | Albert et al. |
| 2015/0088127 A1 | 3/2015 | Craig et al. |
| 2015/0088547 A1 | 3/2015 | Balram et al. |
| 2015/0090759 A1* | 4/2015 | Spivey ............ A61B 1/00042 227/175.1 |
| 2015/0090760 A1 | 4/2015 | Giordano et al. |
| 2015/0090762 A1 | 4/2015 | Giordano et al. |
| 2015/0127021 A1 | 5/2015 | Harris et al. |
| 2015/0134077 A1 | 5/2015 | Shelton, IV et al. |
| 2015/0150620 A1 | 6/2015 | Miyamoto et al. |
| 2015/0173749 A1 | 6/2015 | Shelton, IV et al. |
| 2015/0173756 A1 | 6/2015 | Baxter, III |
| 2015/0173789 A1 | 6/2015 | Baxter, III et al. |
| 2015/0196295 A1 | 7/2015 | Shelton, IV et al. |
| 2015/0196299 A1 | 7/2015 | Swayze et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209045 A1 | 7/2015 | Hodgkinson et al. |
| 2015/0222212 A1 | 8/2015 | Iwata |
| 2015/0223868 A1 | 8/2015 | Brandt et al. |
| 2015/0230697 A1 | 8/2015 | Phee et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |

(56) References Cited

U.S. PATENT DOCUMENTS

| | | |
|---|---|---|
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297824 A1 | 10/2015 | Cabiri et al. |
| 2015/0303417 A1 | 10/2015 | Koeder et al. |
| 2015/0313594 A1 | 11/2015 | Shelton, IV et al. |
| 2015/0324317 A1 | 11/2015 | Collins et al. |
| 2015/0352699 A1 | 12/2015 | Sakai et al. |
| 2015/0366585 A1 | 12/2015 | Lemay et al. |
| 2015/0367497 A1 | 12/2015 | Ito et al. |
| 2015/0372265 A1 | 12/2015 | Morisaku et al. |
| 2015/0374372 A1 | 12/2015 | Zergiebel et al. |
| 2015/0374378 A1 | 12/2015 | Giordano et al. |
| 2016/0000437 A1 | 1/2016 | Giordano et al. |
| 2016/0000452 A1 | 1/2016 | Yates et al. |
| 2016/0000453 A1 | 1/2016 | Yates et al. |
| 2016/0015390 A1* | 1/2016 | Timm ............. A61B 17/00234 227/176.1 |
| 2016/0030042 A1 | 2/2016 | Heinrich et al. |
| 2016/0030043 A1 | 2/2016 | Fanelli et al. |
| 2016/0051316 A1 | 2/2016 | Boudreaux |
| 2016/0066913 A1 | 3/2016 | Swayze et al. |
| 2016/0069449 A1 | 3/2016 | Kanai et al. |
| 2016/0074035 A1 | 3/2016 | Whitman et al. |
| 2016/0074040 A1 | 3/2016 | Widenhouse et al. |
| 2016/0082161 A1 | 3/2016 | Zilberman et al. |
| 2016/0135835 A1 | 5/2016 | Onuma |
| 2016/0135895 A1 | 5/2016 | Faasse et al. |
| 2016/0139666 A1 | 5/2016 | Rubin et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192960 A1 | 7/2016 | Bueno et al. |
| 2016/0199063 A1 | 7/2016 | Mandakolathur Vasudevan et al. |
| 2016/0199956 A1 | 7/2016 | Shelton, IV et al. |
| 2016/0235494 A1 | 8/2016 | Shelton, IV et al. |
| 2016/0242783 A1 | 8/2016 | Shelton, IV et al. |
| 2016/0249910 A1 | 9/2016 | Shelton, IV et al. |
| 2016/0249922 A1 | 9/2016 | Morgan et al. |
| 2016/0256159 A1 | 9/2016 | Pinjala et al. |
| 2016/0256221 A1 | 9/2016 | Smith |
| 2016/0256229 A1 | 9/2016 | Morgan et al. |
| 2016/0262745 A1 | 9/2016 | Morgan et al. |
| 2016/0262921 A1 | 9/2016 | Balbierz et al. |
| 2016/0270781 A1 | 9/2016 | Scirica |
| 2016/0287265 A1 | 10/2016 | Macdonald et al. |
| 2016/0287279 A1 | 10/2016 | Bovay et al. |
| 2016/0302820 A1 | 10/2016 | Hibner et al. |
| 2016/0310143 A1 | 10/2016 | Bettuchi |
| 2016/0314716 A1 | 10/2016 | Grubbs |
| 2016/0314717 A1 | 10/2016 | Grubbs |
| 2016/0367122 A1 | 12/2016 | Ichimura et al. |
| 2016/0374716 A1 | 12/2016 | Kessler |
| 2017/0007234 A1 | 1/2017 | Chin et al. |
| 2017/0007244 A1 | 1/2017 | Shelton, IV et al. |
| 2017/0007245 A1 | 1/2017 | Shelton, IV et al. |
| 2017/0007347 A1 | 1/2017 | Jaworek et al. |
| 2017/0055819 A1 | 3/2017 | Hansen et al. |
| 2017/0066054 A1 | 3/2017 | Birky |
| 2017/0079642 A1 | 3/2017 | Overmyer et al. |
| 2017/0086829 A1 | 3/2017 | Vendely et al. |
| 2017/0086830 A1 | 3/2017 | Yates et al. |
| 2017/0086842 A1 | 3/2017 | Shelton, IV et al. |
| 2017/0086930 A1 | 3/2017 | Thompson et al. |
| 2017/0105733 A1 | 4/2017 | Scheib et al. |
| 2017/0135711 A1 | 5/2017 | Overmyer et al. |
| 2017/0135717 A1 | 5/2017 | Boudreaux et al. |
| 2017/0135747 A1 | 5/2017 | Broderick et al. |
| 2017/0172382 A1 | 6/2017 | Nir et al. |
| 2017/0172549 A1 | 6/2017 | Smaby et al. |
| 2017/0172662 A1 | 6/2017 | Panescu et al. |
| 2017/0182195 A1 | 6/2017 | Wagner |
| 2017/0182211 A1 | 6/2017 | Raxworthy et al. |
| 2017/0196558 A1 | 7/2017 | Morgan et al. |
| 2017/0196649 A1 | 7/2017 | Yates et al. |
| 2017/0202770 A1 | 7/2017 | Friedrich et al. |
| 2017/0224332 A1 | 8/2017 | Hunter et al. |
| 2017/0231628 A1 | 8/2017 | Shelton, IV et al. |
| 2017/0231629 A1 | 8/2017 | Stopek et al. |
| 2017/0238962 A1 | 8/2017 | Hansen et al. |
| 2017/0242455 A1 | 8/2017 | Dickens |
| 2017/0249431 A1 | 8/2017 | Shelton, IV et al. |
| 2017/0255799 A1 | 9/2017 | Zhao et al. |
| 2017/0262110 A1 | 9/2017 | Polishchuk et al. |
| 2017/0265774 A1 | 9/2017 | Johnson et al. |
| 2017/0281186 A1 | 10/2017 | Shelton, IV et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0312042 A1 | 11/2017 | Giordano et al. |
| 2017/0319201 A1 | 11/2017 | Morgan et al. |
| 2017/0333034 A1 | 11/2017 | Morgan et al. |
| 2017/0333035 A1 | 11/2017 | Morgan et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0358052 A1 | 12/2017 | Yuan |
| 2017/0360441 A1 | 12/2017 | Sgroi |
| 2018/0049794 A1 | 2/2018 | Swayze et al. |
| 2018/0051780 A1 | 2/2018 | Shelton, IV et al. |
| 2018/0055501 A1 | 3/2018 | Zemlok et al. |
| 2018/0085117 A1 | 3/2018 | Shelton, IV et al. |
| 2018/0092710 A1 | 4/2018 | Bosisio et al. |
| 2018/0114591 A1 | 4/2018 | Pribanic et al. |
| 2018/0116658 A1 | 5/2018 | Aronhalt, IV et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125594 A1 | 5/2018 | Beardsley |
| 2018/0132849 A1 | 5/2018 | Miller et al. |
| 2018/0132850 A1 | 5/2018 | Leimbach et al. |
| 2018/0132926 A1 | 5/2018 | Asher et al. |
| 2018/0132952 A1 | 5/2018 | Spivey et al. |
| 2018/0133521 A1 | 5/2018 | Frushour et al. |
| 2018/0140299 A1 | 5/2018 | Weaner et al. |
| 2018/0146960 A1 | 5/2018 | Shelton, IV et al. |
| 2018/0153542 A1 | 6/2018 | Shelton, IV et al. |
| 2018/0153634 A1 | 6/2018 | Zemlok et al. |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1* | 6/2018 | Shelton, IV ..... A61B 17/07207 |
| 2018/0168650 A1 | 6/2018 | Shelton, IV et al. |
| 2018/0168651 A1* | 6/2018 | Shelton, IV ..... A61B 17/07292 |
| 2018/0168754 A1 | 6/2018 | Overmyer |
| 2018/0228490 A1 | 8/2018 | Richard et al. |
| 2018/0235609 A1 | 8/2018 | Harris et al. |
| 2018/0236181 A1 | 8/2018 | Marlin et al. |
| 2018/0242970 A1 | 8/2018 | Mozdzierz |
| 2018/0271604 A1 | 9/2018 | Grout et al. |
| 2018/0273597 A1 | 9/2018 | Stimson |
| 2018/0289371 A1 | 10/2018 | Wang et al. |
| 2018/0296216 A1 | 10/2018 | Shelton, IV et al. |
| 2018/0333169 A1 | 11/2018 | Leimbach et al. |
| 2018/0360446 A1 | 12/2018 | Shelton, IV et al. |
| 2018/0360456 A1 | 12/2018 | Shelton, IV et al. |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0000470 A1 | 1/2019 | Yates et al. |

(56) References Cited

U.S. PATENT DOCUMENTS

| | | |
|---|---|---|
| 2019/0000475 A1 | 1/2019 | Shelton, IV et al. |
| 2019/0000477 A1 | 1/2019 | Shelton, IV et al. |
| 2019/0000481 A1 | 1/2019 | Harris et al. |
| 2019/0015102 A1 | 1/2019 | Baber et al. |
| 2019/0015165 A1 | 1/2019 | Giordano et al. |
| 2019/0029682 A1 | 1/2019 | Huitema et al. |
| 2019/0029701 A1 | 1/2019 | Shelton, IV et al. |
| 2019/0038281 A1 | 2/2019 | Shelton, IV et al. |
| 2019/0038283 A1 | 2/2019 | Shelton, IV et al. |
| 2019/0038285 A1 | 2/2019 | Mozdzierz |
| 2019/0059986 A1 | 2/2019 | Shelton, IV et al. |
| 2019/0076143 A1 | 3/2019 | Smith |
| 2019/0090871 A1 | 3/2019 | Shelton, IV et al. |
| 2019/0091183 A1 | 3/2019 | Tomat et al. |
| 2019/0104919 A1 | 4/2019 | Shelton, IV et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105039 A1 | 4/2019 | Morgan et al. |
| 2019/0105044 A1 | 4/2019 | Shelton, IV et al. |
| 2019/0110779 A1 | 4/2019 | Gardner et al. |
| 2019/0110791 A1 | 4/2019 | Shelton, IV et al. |
| 2019/0117224 A1 | 4/2019 | Setser et al. |
| 2019/0125320 A1 | 5/2019 | Shelton, IV et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125342 A1 | 5/2019 | Beardsley et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125476 A1 | 5/2019 | Shelton, IV et al. |
| 2019/0133422 A1 | 5/2019 | Nakamura |
| 2019/0138770 A1 | 5/2019 | Compaijen et al. |
| 2019/0150925 A1 | 5/2019 | Marczyk et al. |
| 2019/0151029 A1 | 5/2019 | Robinson |
| 2019/0183502 A1 | 6/2019 | Shelton, IV et al. |
| 2019/0192141 A1 | 6/2019 | Shelton, IV et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192151 A1 | 6/2019 | Shelton, IV et al. |
| 2019/0192153 A1 | 6/2019 | Shelton, IV et al. |
| 2019/0192155 A1 | 6/2019 | Shelton, IV et al. |
| 2019/0192157 A1 | 6/2019 | Scott et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201034 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |
| 2019/0201136 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201594 A1 | 7/2019 | Shelton, IV et al. |
| 2019/0205001 A1 | 7/2019 | Messerly et al. |
| 2019/0205567 A1 | 7/2019 | Shelton, IV et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |
| 2019/0216558 A1 | 7/2019 | Giordano et al. |
| 2019/0261983 A1 | 8/2019 | Granger et al. |
| 2019/0261984 A1 | 8/2019 | Nelson et al. |
| 2019/0261987 A1 | 8/2019 | Viola et al. |
| 2019/0269400 A1 | 9/2019 | Mandakolathur Vasudevan et al. |
| 2019/0269402 A1 | 9/2019 | Murray et al. |
| 2019/0269428 A1 | 9/2019 | Allen et al. |
| 2019/0274685 A1 | 9/2019 | Olson et al. |
| 2019/0282233 A1 | 9/2019 | Burbank et al. |
| 2019/0290264 A1 | 9/2019 | Morgan et al. |
| 2019/0290266 A1 | 9/2019 | Scheib et al. |
| 2019/0290267 A1 | 9/2019 | Baxter, III et al. |
| 2019/0290297 A1 | 9/2019 | Haider et al. |
| 2019/0298350 A1 | 10/2019 | Shelton, IV et al. |
| 2019/0298353 A1 | 10/2019 | Shelton, IV et al. |
| 2019/0298360 A1 | 10/2019 | Shelton, IV et al. |
| 2019/0298361 A1 | 10/2019 | Shelton, IV et al. |
| 2019/0298362 A1 | 10/2019 | Shelton, IV et al. |
| 2019/0307452 A1 | 10/2019 | Shelton, IV et al. |
| 2019/0307453 A1 | 10/2019 | Shelton, IV et al. |
| 2019/0307454 A1 | 10/2019 | Shelton, IV et al. |
| 2019/0307456 A1 | 10/2019 | Shelton, IV et al. |
| 2019/0321040 A1 | 10/2019 | Shelton, IV |
| 2019/0328387 A1 | 10/2019 | Overmyer et al. |
| 2019/0343515 A1 | 11/2019 | Morgan et al. |
| 2019/0357909 A1 | 11/2019 | Huitema et al. |
| 2020/0000531 A1 | 1/2020 | Giordano et al. |
| 2020/0008802 A1 | 1/2020 | Aronhalt et al. |
| 2020/0008809 A1 | 1/2020 | Shelton, IV et al. |
| 2020/0015915 A1 | 1/2020 | Swayze et al. |
| 2020/0038016 A1 | 2/2020 | Shelton, IV et al. |
| 2020/0038018 A1 | 2/2020 | Shelton, IV et al. |
| 2020/0038020 A1 | 2/2020 | Yates et al. |
| 2020/0054321 A1 | 2/2020 | Harris et al. |
| 2020/0054332 A1 | 2/2020 | Shelton, IV et al. |
| 2020/0054333 A1 | 2/2020 | Shelton, IV et al. |
| 2020/0054334 A1 | 2/2020 | Shelton, IV et al. |
| 2020/0054355 A1 | 2/2020 | Laurent et al. |
| 2020/0060523 A1 | 2/2020 | Matsuda et al. |
| 2020/0060713 A1 | 2/2020 | Leimbach et al. |
| 2020/0085431 A1 | 3/2020 | Swayze et al. |
| 2020/0085435 A1 | 3/2020 | Shelton, IV et al. |
| 2020/0085518 A1 | 3/2020 | Giordano et al. |
| 2020/0093484 A1 | 3/2020 | Shelton, IV et al. |
| 2020/0093506 A1 | 3/2020 | Leimbach et al. |
| 2020/0093550 A1 | 3/2020 | Spivey et al. |
| 2020/0100783 A1 | 4/2020 | Yates et al. |
| 2020/0107829 A1 | 4/2020 | Shelton, IV et al. |
| 2020/0138436 A1 | 5/2020 | Yates et al. |
| 2020/0138534 A1 | 5/2020 | Garcia Kilroy et al. |
| 2020/0146741 A1 | 5/2020 | Long et al. |
| 2020/0187943 A1 | 6/2020 | Shelton, IV et al. |
| 2020/0197027 A1 | 6/2020 | Hershberger et al. |
| 2020/0214706 A1 | 7/2020 | Vendely et al. |
| 2020/0214731 A1 | 7/2020 | Shelton, IV et al. |
| 2020/0237371 A1 | 7/2020 | Huitema et al. |
| 2020/0253605 A1 | 8/2020 | Swayze et al. |
| 2020/0261086 A1 | 8/2020 | Zeiner et al. |
| 2020/0261106 A1 | 8/2020 | Hess et al. |
| 2020/0268377 A1 | 8/2020 | Schmid et al. |
| 2020/0275927 A1 | 9/2020 | Shelton, IV et al. |
| 2020/0275930 A1 | 9/2020 | Harris et al. |
| 2020/0289112 A1 | 9/2020 | Whitfield et al. |
| 2020/0297341 A1 | 9/2020 | Yates et al. |
| 2020/0297346 A1 | 9/2020 | Shelton, IV et al. |
| 2020/0305862 A1 | 10/2020 | Yates et al. |

(56) References Cited

U.S. PATENT DOCUMENTS

| | | |
|---|---|---|
| 2020/0305863 A1 | 10/2020 | Yates et al. |
| 2020/0305864 A1 | 10/2020 | Yates et al. |
| 2020/0305868 A1* | 10/2020 | Shelton, IV ........... A61B 34/37 |
| 2020/0305870 A1 | 10/2020 | Shelton, IV |
| 2020/0305872 A1 | 10/2020 | Weidner et al. |
| 2020/0305874 A1 | 10/2020 | Huitema et al. |
| 2020/0315612 A1 | 10/2020 | Shelton, IV et al. |
| 2020/0323526 A1 | 10/2020 | Huang et al. |
| 2020/0330092 A1 | 10/2020 | Shelton, IV et al. |
| 2020/0330093 A1 | 10/2020 | Shelton, IV et al. |
| 2020/0330096 A1 | 10/2020 | Shelton, IV et al. |
| 2020/0337693 A1 | 10/2020 | Shelton, IV et al. |
| 2020/0337791 A1 | 10/2020 | Shelton, IV et al. |
| 2020/0345346 A1 | 11/2020 | Shelton, IV et al. |
| 2020/0345352 A1 | 11/2020 | Shelton, IV et al. |
| 2020/0345353 A1 | 11/2020 | Leimbach et al. |
| 2020/0345356 A1 | 11/2020 | Leimbach et al. |
| 2020/0345357 A1 | 11/2020 | Leimbach et al. |
| 2020/0345358 A1 | 11/2020 | Jenkins |
| 2020/0345359 A1 | 11/2020 | Baxter, III et al. |
| 2020/0345435 A1 | 11/2020 | Traina |
| 2020/0352562 A1 | 11/2020 | Timm et al. |
| 2020/0367886 A1 | 11/2020 | Shelton, IV et al. |
| 2020/0375585 A1 | 12/2020 | Swayze et al. |
| 2020/0375597 A1 | 12/2020 | Shelton, IV et al. |
| 2020/0390444 A1 | 12/2020 | Harris et al. |
| 2020/0405292 A1 | 12/2020 | Shelton, IV et al. |
| 2020/0405293 A1 | 12/2020 | Shelton, IV et al. |
| 2020/0405296 A1 | 12/2020 | Shelton, IV et al. |
| 2020/0405302 A1 | 12/2020 | Shelton, IV et al. |
| 2020/0405306 A1 | 12/2020 | Shelton, IV et al. |
| 2020/0405307 A1 | 12/2020 | Shelton, IV et al. |
| 2020/0405308 A1 | 12/2020 | Shelton, IV |
| 2020/0405316 A1 | 12/2020 | Shelton, IV et al. |
| 2020/0405341 A1 | 12/2020 | Hess et al. |
| 2020/0405410 A1 | 12/2020 | Shelton, IV |
| 2020/0405439 A1 | 12/2020 | Shelton, IV et al. |
| 2020/0410177 A1 | 12/2020 | Shelton, IV |
| 2021/0000466 A1 | 1/2021 | Leimbach et al. |
| 2021/0000467 A1 | 1/2021 | Shelton, IV et al. |
| 2021/0015480 A1 | 1/2021 | Shelton, IV et al. |
| 2021/0030416 A1 | 2/2021 | Shelton, IV et al. |
| 2021/0045742 A1 | 2/2021 | Shelton, IV et al. |
| 2021/0052271 A1 | 2/2021 | Harris et al. |
| 2021/0059661 A1 | 3/2021 | Schmid et al. |
| 2021/0059662 A1 | 3/2021 | Shelton, IV |
| 2021/0059664 A1 | 3/2021 | Hensel et al. |
| 2021/0059670 A1 | 3/2021 | Overmyer et al. |
| 2021/0059672 A1 | 3/2021 | Giordano et al. |
| 2021/0059673 A1 | 3/2021 | Shelton, IV et al. |
| 2021/0068820 A1 | 3/2021 | Parihar et al. |
| 2021/0068832 A1 | 3/2021 | Yates et al. |
| 2021/0068835 A1 | 3/2021 | Shelton, IV et al. |
| 2021/0077099 A1 | 3/2021 | Shelton, IV et al. |
| 2021/0077100 A1 | 3/2021 | Shelton, IV et al. |
| 2021/0077109 A1 | 3/2021 | Harris et al. |
| 2021/0085313 A1 | 3/2021 | Morgan et al. |
| 2021/0085314 A1 | 3/2021 | Schmid et al. |
| 2021/0085315 A1 | 3/2021 | Aronhalt et al. |
| 2021/0085316 A1 | 3/2021 | Harris et al. |
| 2021/0085318 A1 | 3/2021 | Swayze et al. |
| 2021/0085320 A1 | 3/2021 | Leimbach et al. |
| 2021/0085321 A1 | 3/2021 | Shelton, IV et al. |
| 2021/0085325 A1 | 3/2021 | Shelton, IV et al. |
| 2021/0093321 A1 | 4/2021 | Auld et al. |
| 2021/0093323 A1 | 4/2021 | Scirica et al. |
| 2021/0100541 A1 | 4/2021 | Shelton, IV et al. |
| 2021/0100982 A1 | 4/2021 | Laby et al. |
| 2021/0106333 A1 | 4/2021 | Shelton, IV et al. |
| 2021/0107031 A1 | 4/2021 | Bales, Jr. et al. |
| 2021/0121175 A1 | 4/2021 | Yates et al. |
| 2021/0128146 A1 | 5/2021 | Shelton, IV et al. |
| 2021/0137522 A1 | 5/2021 | Shelton, IV et al. |
| 2021/0186492 A1 | 6/2021 | Shelton, IV et al. |
| 2021/0186493 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186499 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0204941 A1 | 7/2021 | Dewaele et al. |
| 2021/0212691 A1 | 7/2021 | Smith et al. |
| 2021/0228209 A1 | 7/2021 | Shelton, IV et al. |
| 2021/0236117 A1 | 8/2021 | Morgan et al. |
| 2021/0236124 A1 | 8/2021 | Shelton, IV et al. |
| 2021/0244406 A1 | 8/2021 | Kerr et al. |
| 2021/0244407 A1 | 8/2021 | Shelton, IV et al. |
| 2021/0244410 A1 | 8/2021 | Swayze et al. |
| 2021/0244412 A1 | 8/2021 | Vendely et al. |
| 2021/0259681 A1 | 8/2021 | Shelton, IV et al. |
| 2021/0259687 A1 | 8/2021 | Gonzalez et al. |
| 2021/0259986 A1 | 8/2021 | Widenhouse et al. |
| 2021/0259987 A1 | 8/2021 | Widenhouse et al. |
| 2021/0267589 A1 | 9/2021 | Swayze et al. |
| 2021/0267594 A1 | 9/2021 | Morgan et al. |
| 2021/0267595 A1 | 9/2021 | Posada et al. |
| 2021/0267596 A1 | 9/2021 | Fanelli et al. |
| 2021/0275053 A1 | 9/2021 | Shelton, IV et al. |
| 2021/0275172 A1 | 9/2021 | Harris et al. |
| 2021/0275173 A1 | 9/2021 | Shelton, IV et al. |
| 2021/0275176 A1 | 9/2021 | Beckman et al. |
| 2021/0282767 A1 | 9/2021 | Shelton, IV et al. |
| 2021/0282769 A1 | 9/2021 | Baxter, III et al. |
| 2021/0282776 A1 | 9/2021 | Overmyer et al. |
| 2021/0290226 A1 | 9/2021 | Mandakolathur Vasudevan et al. |
| 2021/0290231 A1 | 9/2021 | Baxter, III et al. |
| 2021/0290232 A1 | 9/2021 | Harris et al. |
| 2021/0290233 A1 | 9/2021 | Shelton, IV et al. |
| 2021/0290236 A1 | 9/2021 | Moore et al. |
| 2021/0290322 A1 | 9/2021 | Traina |
| 2021/0353284 A1 | 11/2021 | Yang et al. |
| 2022/0031313 A1 | 2/2022 | Bakos et al. |
| 2022/0031314 A1 | 2/2022 | Bakos et al. |
| 2022/0031319 A1 | 2/2022 | Witte et al. |
| 2022/0031320 A1 | 2/2022 | Hall et al. |
| 2022/0031322 A1 | 2/2022 | Parks |
| 2022/0031323 A1 | 2/2022 | Witte |
| 2022/0031324 A1 | 2/2022 | Hall et al. |
| 2022/0031345 A1 | 2/2022 | Witte |
| 2022/0031346 A1 | 2/2022 | Parks |
| 2022/0031350 A1 | 2/2022 | Witte |
| 2022/0031351 A1 | 2/2022 | Moubarak et al. |
| 2022/0071632 A1 | 3/2022 | Patel et al. |

FOREIGN PATENT DOCUMENTS

| | | |
|---|---|---|
| AU | 2012268848 A1 | 1/2013 |
| AU | 2011218702 B2 | 6/2013 |
| AU | 2012200178 B2 | 7/2013 |
| BR | 112013027777 A2 | 1/2017 |
| CA | 1015829 A | 8/1977 |
| CA | 1125615 A | 6/1982 |
| CA | 2520413 A1 | 3/2007 |
| CA | 2725181 A1 | 11/2007 |
| CA | 2851239 A1 | 11/2007 |
| CA | 2664874 A1 | 11/2009 |
| CA | 2813230 A1 | 4/2012 |
| CA | 2940510 A1 | 8/2015 |
| CA | 2698728 C | 8/2016 |
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 1777406 A | 5/2006 |
| CN | 2796654 Y | 7/2006 |
| CN | 2868212 Y | 2/2007 |
| CN | 200942099 Y | 9/2007 |
| CN | 200984209 Y | 12/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101188900 A | 5/2008 |

(56) References Cited

FOREIGN PATENT DOCUMENTS

| | | | |
|---|---|---|---|
| CN | 101203085 A | 6/2008 |
| CN | 101273908 A | 10/2008 |
| CN | 101378791 A | 3/2009 |
| CN | 101507635 A | 8/2009 |
| CN | 101522120 A | 9/2009 |
| CN | 101669833 A | 3/2010 |
| CN | 101721236 A | 6/2010 |
| CN | 101756727 A | 6/2010 |
| CN | 101828940 A | 9/2010 |
| CN | 101873834 A | 10/2010 |
| CN | 201719298 U | 1/2011 |
| CN | 102038532 A | 5/2011 |
| CN | 201879759 U | 6/2011 |
| CN | 201949071 U | 8/2011 |
| CN | 102217961 A | 10/2011 |
| CN | 102217963 A | 10/2011 |
| CN | 102243850 A | 11/2011 |
| CN | 102247183 A | 11/2011 |
| CN | 101779977 B | 12/2011 |
| CN | 101912284 B | 7/2012 |
| CN | 102125450 B | 7/2012 |
| CN | 202313537 U | 7/2012 |
| CN | 202397539 U | 8/2012 |
| CN | 202426586 U | 9/2012 |
| CN | 102743201 A | 10/2012 |
| CN | 202489990 U | 10/2012 |
| CN | 102228387 B | 11/2012 |
| CN | 102835977 A | 12/2012 |
| CN | 202568350 U | 12/2012 |
| CN | 103037781 A | 4/2013 |
| CN | 103083053 A | 5/2013 |
| CN | 103391037 A | 11/2013 |
| CN | 203328751 U | 12/2013 |
| CN | 103505264 A | 1/2014 |
| CN | 103584893 A | 2/2014 |
| CN | 103635150 A | 3/2014 |
| CN | 103690212 A | 4/2014 |
| CN | 203564285 U | 4/2014 |
| CN | 203564287 U | 4/2014 |
| CN | 203597997 U | 5/2014 |
| CN | 103829981 A | 6/2014 |
| CN | 103829983 A | 6/2014 |
| CN | 103860221 A | 6/2014 |
| CN | 103908313 A | 7/2014 |
| CN | 203693685 U | 7/2014 |
| CN | 203736251 U | 7/2014 |
| CN | 103981635 A | 8/2014 |
| CN | 104027145 A | 9/2014 |
| CN | 203815517 U | 9/2014 |
| CN | 102783741 B | 10/2014 |
| CN | 102973300 B | 10/2014 |
| CN | 204092074 U | 1/2015 |
| CN | 104337556 A | 2/2015 |
| CN | 204158440 U | 2/2015 |
| CN | 204158441 U | 2/2015 |
| CN | 102469995 B | 3/2015 |
| CN | 104422849 A | 3/2015 |
| CN | 104586463 A | 5/2015 |
| CN | 204520822 U | 8/2015 |
| CN | 204636451 U | 9/2015 |
| CN | 103860225 B | 3/2016 |
| CN | 103750872 B | 5/2016 |
| CN | 105919642 A | 9/2016 |
| CN | 103648410 B | 10/2016 |
| CN | 105997173 A | 10/2016 |
| CN | 106344091 A | 1/2017 |
| CN | 104349800 B | 11/2017 |
| CN | 107635483 A | 1/2018 |
| CN | 208625784 U | 3/2019 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004041871 A1 | 3/2006 |
| DE | 102004063606 A1 | 7/2006 |
| DE | 202007003114 U1 | 6/2007 |
| DE | 102010013150 A1 | 9/2011 |
| DE | 102012213322 A1 | 1/2014 |
| DE | 102013101158 A1 | 8/2014 |
| EM | 002220467-0008 | 4/2013 |
| EP | 0000756 A1 | 2/1979 |
| EP | 0122046 A1 | 10/1984 |
| EP | 0129442 B1 | 11/1987 |
| EP | 0255631 A1 | 2/1988 |
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1064882 A1 | 1/2001 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1558161 A1 | 8/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |

(56) References Cited

FOREIGN PATENT DOCUMENTS

| | | |
|---|---|---|
| EP | 2606812 A1 | 6/2013 |
| EP | 2649948 A1 | 10/2013 |
| EP | 2649949 A1 | 10/2013 |
| EP | 2668910 A2 | 12/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2789299 A1 | 10/2014 |
| EP | 2842500 A1 | 3/2015 |
| EP | 2853220 A1 | 4/2015 |
| EP | 2298220 B1 | 6/2016 |
| EP | 2510891 B1 | 6/2016 |
| EP | 3031404 A1 | 6/2016 |
| EP | 3047806 A1 | 7/2016 |
| EP | 3078334 A1 | 10/2016 |
| EP | 2364651 B1 | 11/2016 |
| EP | 2747235 B1 | 11/2016 |
| EP | 3095399 A2 | 11/2016 |
| EP | 3120781 A2 | 1/2017 |
| EP | 3135225 A2 | 3/2017 |
| EP | 2789299 B1 | 5/2017 |
| EP | 3178413 A1 | 6/2017 |
| EP | 3225190 A2 | 10/2017 |
| EP | 3326548 A1 | 5/2018 |
| EP | 3363378 A1 | 8/2018 |
| EP | 3476334 A1 | 5/2019 |
| EP | 3275378 B1 | 7/2019 |
| ES | 1070456 U | 9/2009 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S5367286 A | 6/1978 |
| JP | S56112235 A | 9/1981 |
| JP | S60113007 A | 6/1985 |
| JP | S62170011 U | 10/1987 |
| JP | S63270040 A | 11/1988 |
| JP | S63318824 A | 12/1988 |
| JP | H0129503 B2 | 6/1989 |
| JP | H02106189 A | 4/1990 |
| JP | H0378514 U | 8/1991 |
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H05226945 A | 9/1993 |
| JP | H0630945 A | 2/1994 |
| JP | H06237937 A | 8/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H09-323068 A | 12/1997 |
| JP | H10118090 A | 5/1998 |
| JP | H10-200699 A | 7/1998 |
| JP | H10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000210299 A | 8/2000 |
| JP | 2000271141 A | 10/2000 |
| JP | 2000287987 A | 10/2000 |
| JP | 2000325303 A | 11/2000 |
| JP | 2001-69758 A | 3/2001 |
| JP | 2001087272 A | 4/2001 |
| JP | 2001208655 A | 8/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002153481 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005211455 A | 8/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006291180 A | 10/2006 |
| JP | 2006346445 A | 12/2006 |
| JP | 2007-97252 A | 4/2007 |
| JP | 2007289715 A | 11/2007 |
| JP | 2007304057 A | 11/2007 |
| JP | 2007306710 A | 11/2007 |
| JP | D1322057 | 2/2008 |
| JP | 2008154804 A | 7/2008 |
| JP | 2008220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | D1383743 | 2/2010 |
| JP | 2010065594 A | 3/2010 |
| JP | 2010069307 A | 4/2010 |
| JP | 2010069310 A | 4/2010 |
| JP | 2010098844 A | 4/2010 |
| JP | 2010214128 A | 9/2010 |
| JP | 2011072574 A | 4/2011 |
| JP | 4722849 B2 | 7/2011 |
| JP | 4728996 B2 | 7/2011 |
| JP | 2011524199 A | 9/2011 |

(56) References Cited

FOREIGN PATENT DOCUMENTS

| | | |
|---|---|---|
| JP | 2011200665 A | 10/2011 |
| JP | D1432094 | 12/2011 |
| JP | 2012115542 A | 6/2012 |
| JP | 2012143283 A | 8/2012 |
| JP | 5154710 B1 | 2/2013 |
| JP | 2013099551 A | 5/2013 |
| JP | 2013126430 A | 6/2013 |
| JP | D1481426 | 9/2013 |
| JP | 2013541982 A | 11/2013 |
| JP | 2013541983 A | 11/2013 |
| JP | 2013541997 A | 11/2013 |
| JP | D1492363 | 2/2014 |
| JP | 2014121599 A | 7/2014 |
| JP | 2014171879 A | 9/2014 |
| JP | 1517663 S | 2/2015 |
| JP | 2015512725 A | 4/2015 |
| JP | 2015513956 A | 5/2015 |
| JP | 2015513958 A | 5/2015 |
| JP | 2015514471 A | 5/2015 |
| JP | 2015516838 A | 6/2015 |
| JP | 2015521524 A | 7/2015 |
| JP | 2015521525 A | 7/2015 |
| JP | 2016007800 A | 1/2016 |
| JP | 2016512057 A | 4/2016 |
| JP | 2016530949 A | 10/2016 |
| JP | 2017513563 A | 6/2017 |
| JP | 1601498 S | 4/2018 |
| JP | 2019513530 A | 5/2019 |
| KR | 20100110134 A | 10/2010 |
| KR | 20110003229 A | 1/2011 |
| KR | 300631507 | 3/2012 |
| KR | 300747646 | 6/2014 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |
| RU | 2104671 C1 | 2/1998 |
| RU | 2110965 C1 | 5/1998 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2430692 C2 | 10/2011 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9308754 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9827870 A1 | 7/1998 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0024448 A2 | 10/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A2 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006073581 A2 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012013577 A1 | 2/2012 |
| WO | WO-2012044606 A2 | 4/2012 |
| WO | WO-2012061725 A1 | 5/2012 |
| WO | WO-2012072133 A1 | 6/2012 |
| WO | WO-2012166503 A1 | 12/2012 |
| WO | WO-2013087092 A1 | 6/2013 |
| WO | WO-2013151888 A1 | 10/2013 |
| WO | WO-2014004209 A2 | 1/2014 |
| WO | WO-2014113438 A1 | 7/2014 |
| WO | WO-2014175894 A1 | 10/2014 |
| WO | WO-2015032797 A1 | 3/2015 |
| WO | WO-2015076780 A1 | 5/2015 |
| WO | WO-2015137040 A1 | 9/2015 |
| WO | WO-2015138760 A1 | 9/2015 |
| WO | WO-2015187107 A1 | 12/2015 |
| WO | WO-2016100682 A1 | 6/2016 |

(56) References Cited

FOREIGN PATENT DOCUMENTS

| WO | WO-2016107448 A1 | 7/2016 |
|---|---|---|
| WO | WO-2019036490 A1 | 2/2019 |

OTHER PUBLICATIONS

ASTM procedure D2240-05, "Standard Test Method for Rubber Property-Durometer Hardness," (Published Apr. 2010).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.eom/journal/119040681/abstract?CRETRY=1&SRETRY=0; [online] accessed: Sep. 22, 2008 (2 pages).
D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. Wit Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d9395 03e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP055246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP055246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.

(56) References Cited

OTHER PUBLICATIONS

Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11 ?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Meeh. Behavior of Biomed. Mater. 7(2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B-Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00740C, Microchip Technology Inc., Available: http://ww1.microchip.com/downloads/en/AppNotes/00710c.pdf.
Kawamura, Atsuo, et al. "Wireless Transmission of Power and Information T High-Frequency Resonant AC Link Inverter for Robot Manipulator Applications,". May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-207700303?irgwc=1 &utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite](Year: 2016).
Tutorial overview of inductively coupled RFID Systems, UPM, May 2003, pp. 1-4, UPM Rafsec,<http://cdn.mobiusconsulting.com/papers/rfidsystems.pdf>.
Schroeter, John, "*Demystifying UHF Gen 2 RFID, HF RFID*," Online Article, Jun. 2, 2008, pp. 1-3, <https://www.edn.com/desiqn/industrial-control/4019123/Demystifying-UHF-Gen-2-RFID-HF-RFID>.
Adeeb, et al., "*An Inductive Link-Based Wireless Power Transfer System for Biomedical Applications*," Research Article, Nov. 14, 2011, pp. 1-12, vol. 2012, Article ID 879294, Hindawi Publishing Corporation.
Pushing Pixels (GIF), published on dribble,com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
International Search Report and Written Opinion dated Jan. 11, 2022 for Application No. PCT/IB2021/056742, 18 pgs.

\* cited by examiner

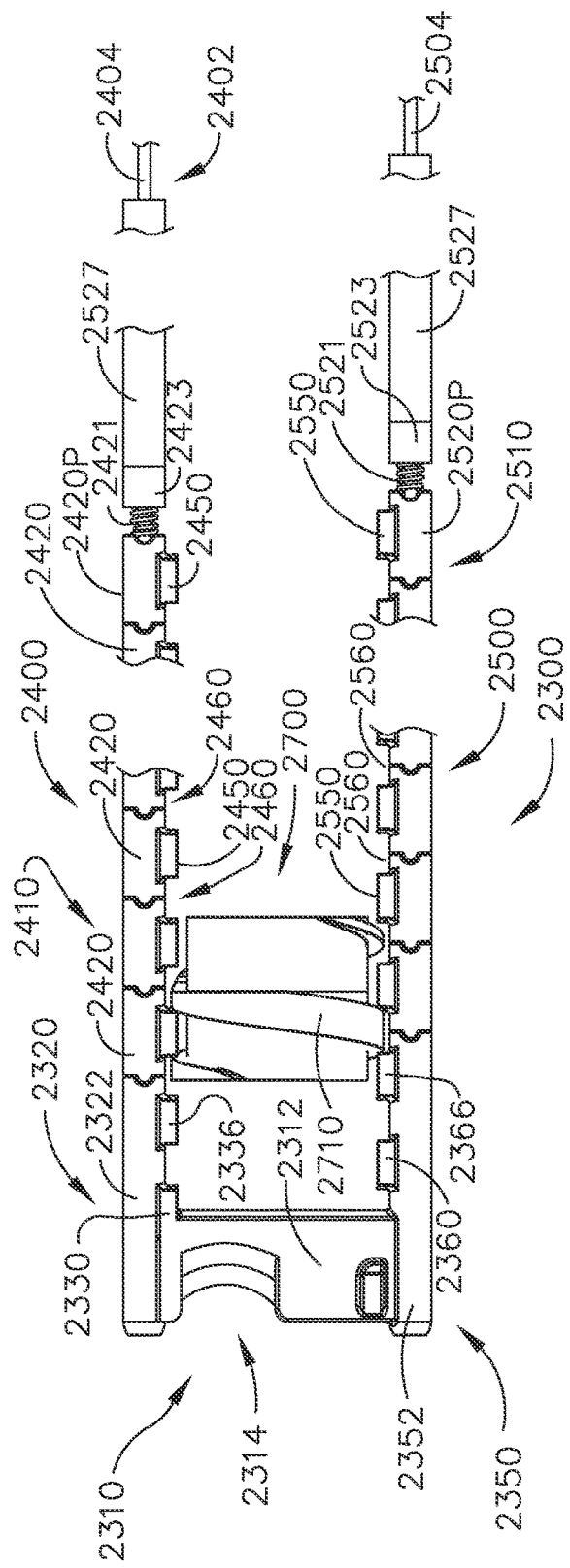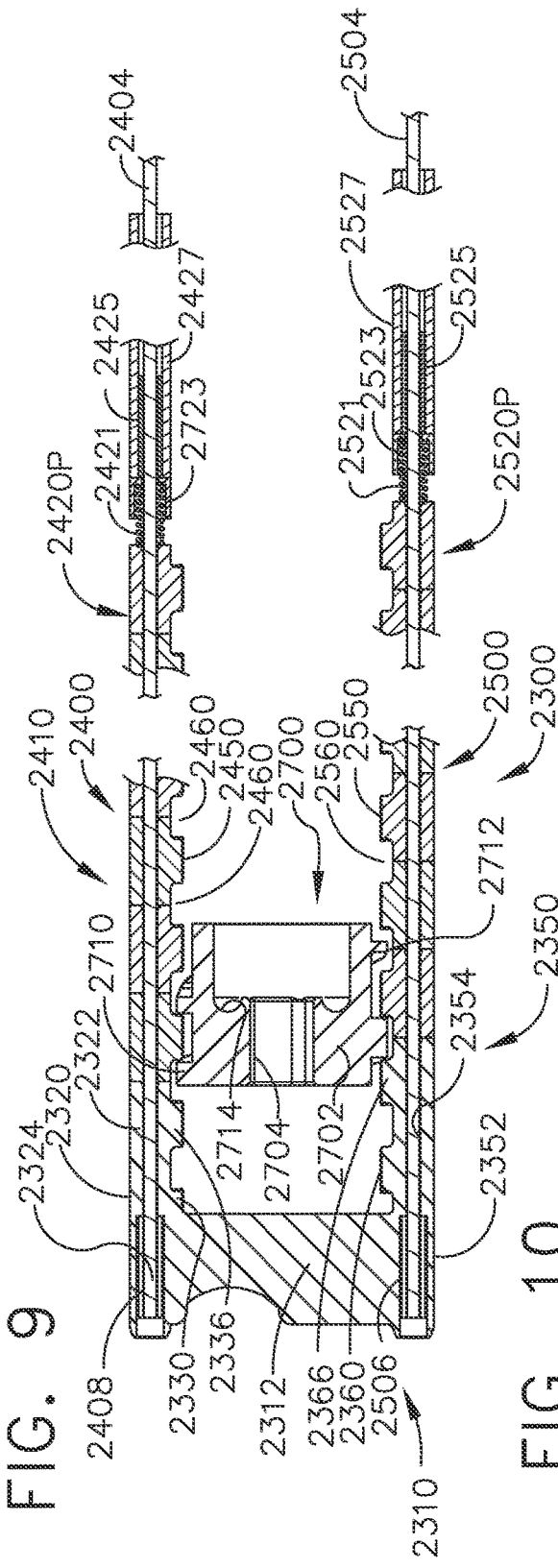

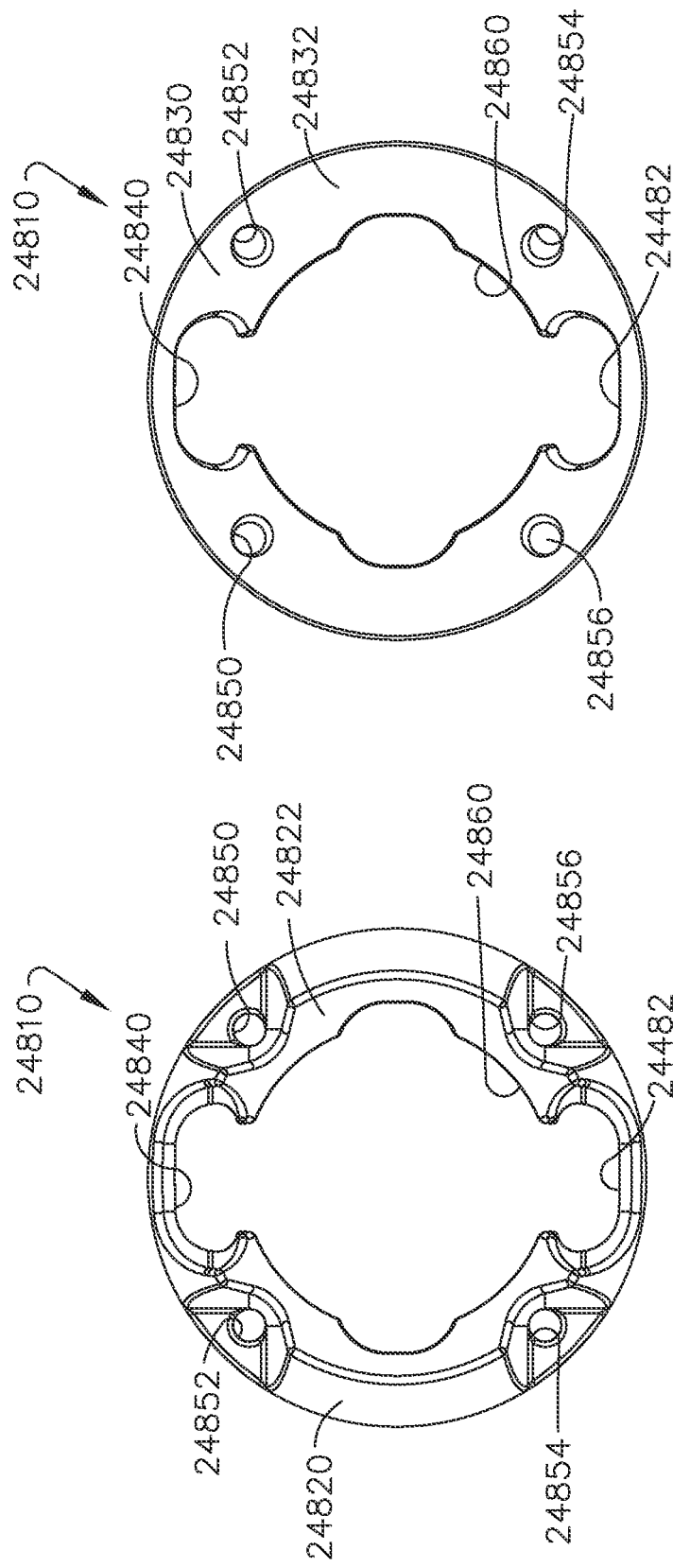

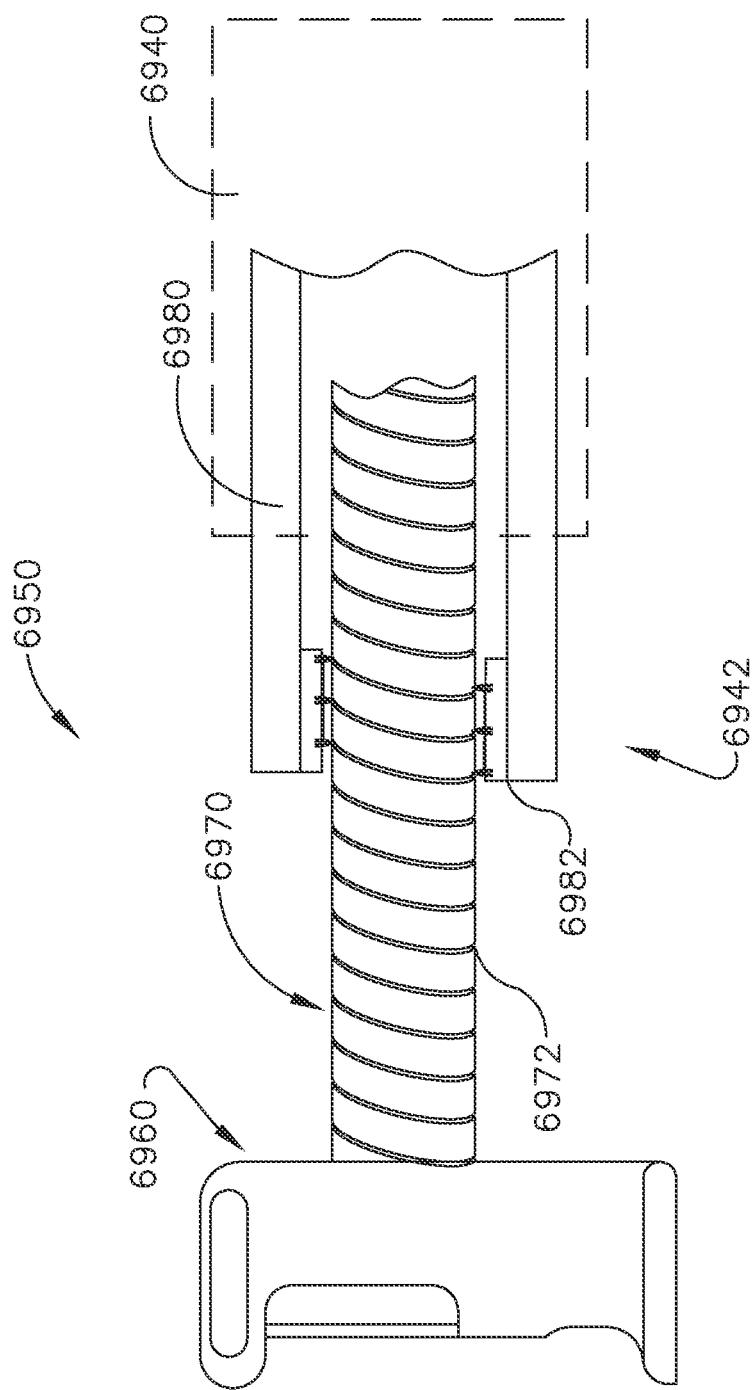

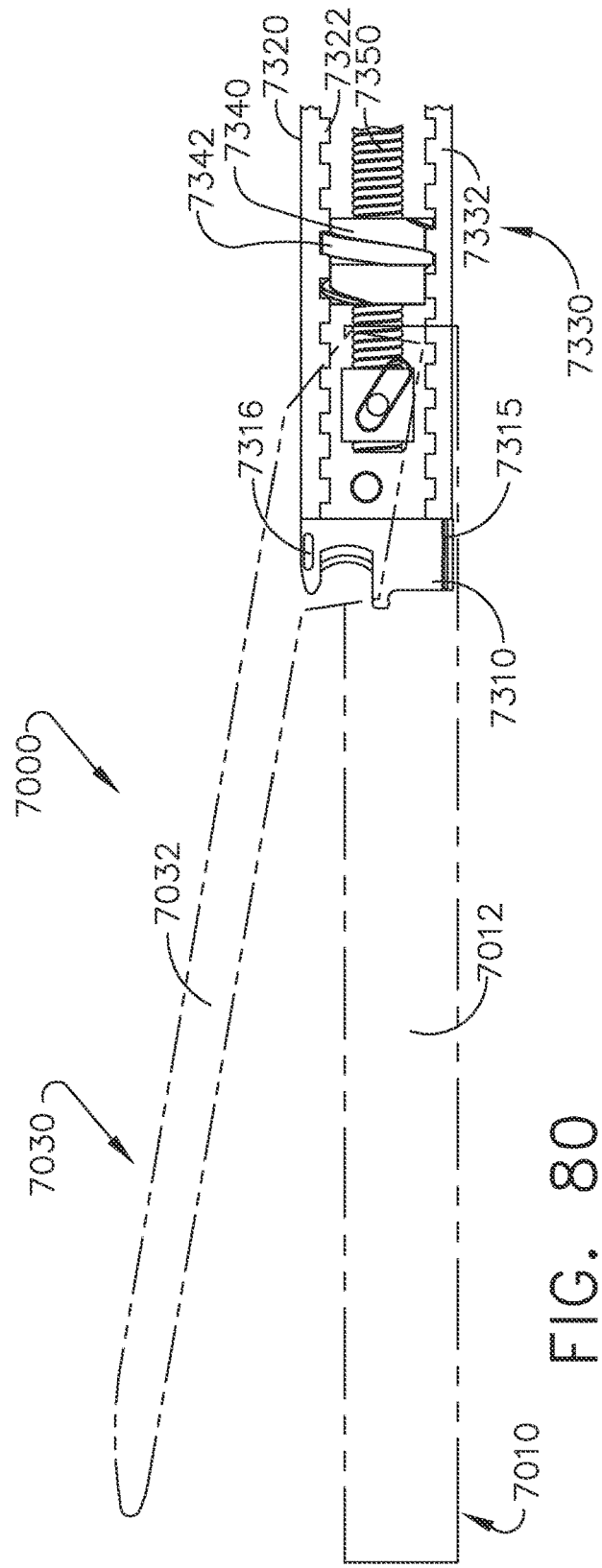
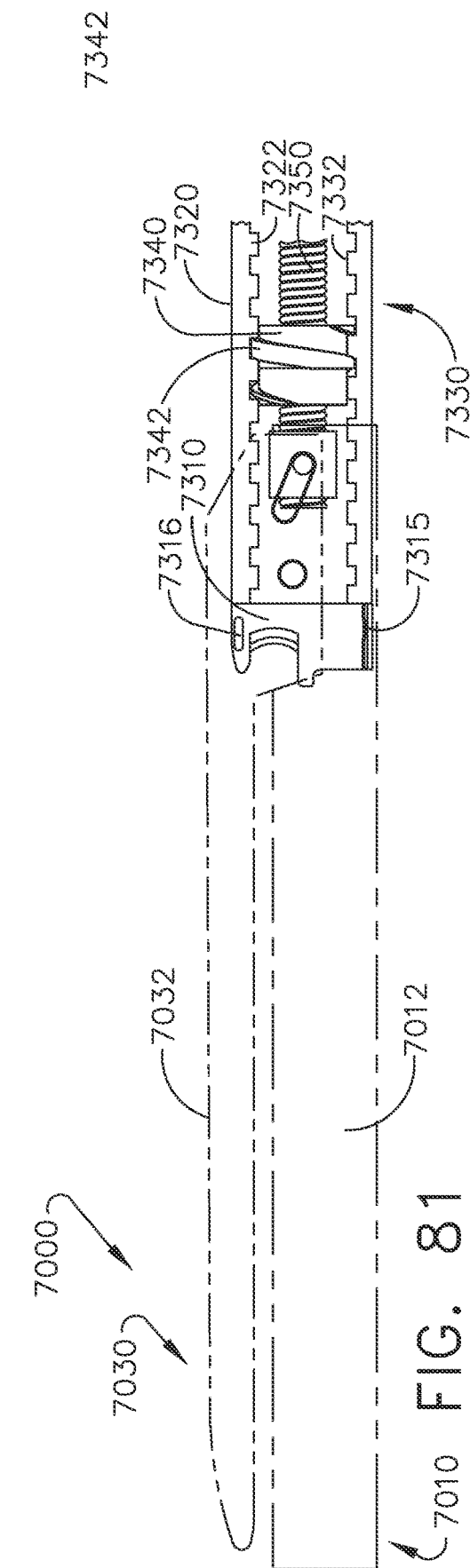

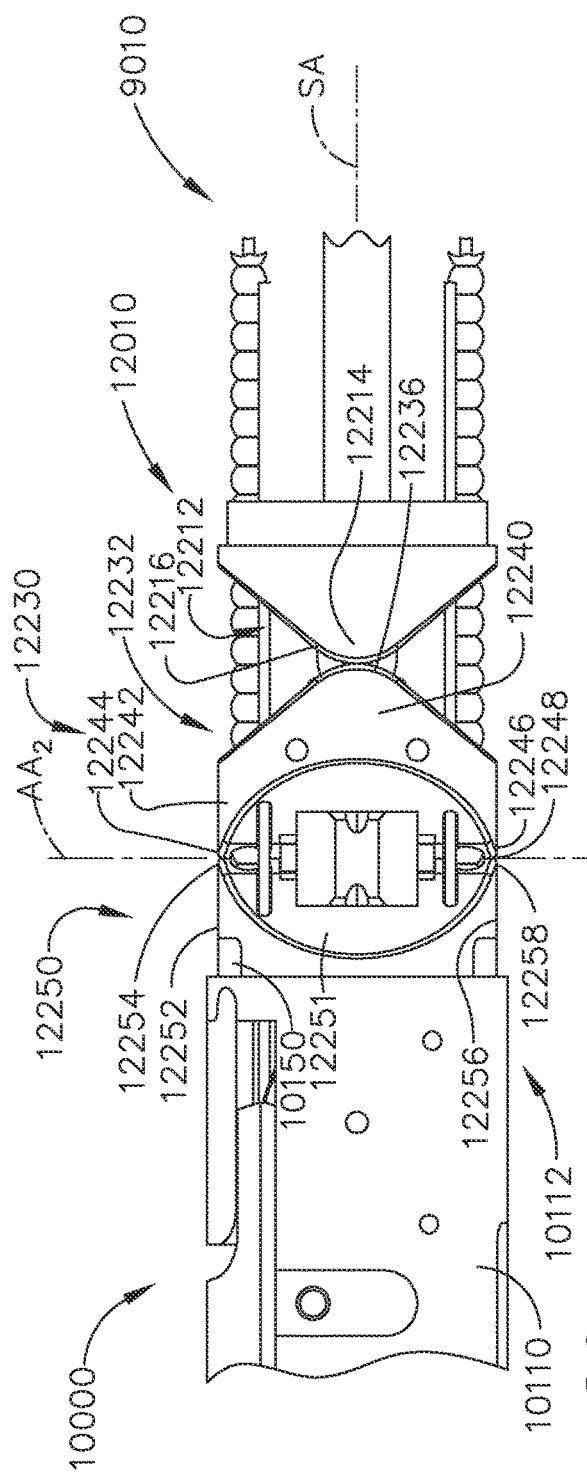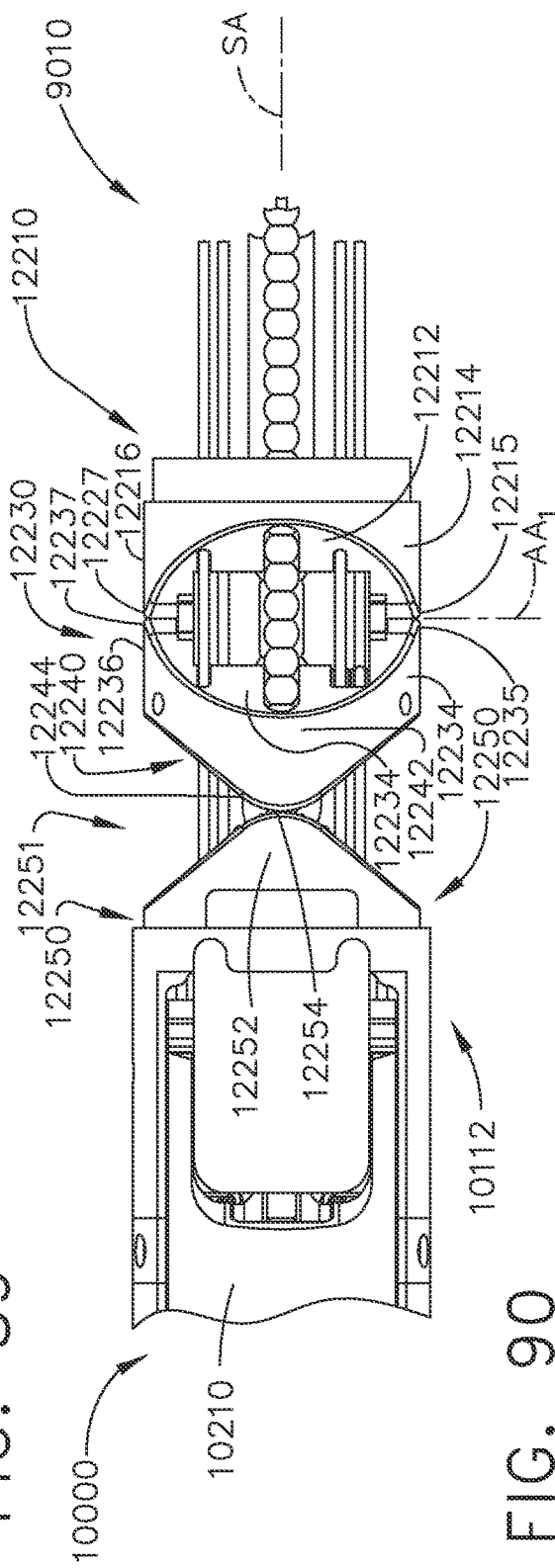

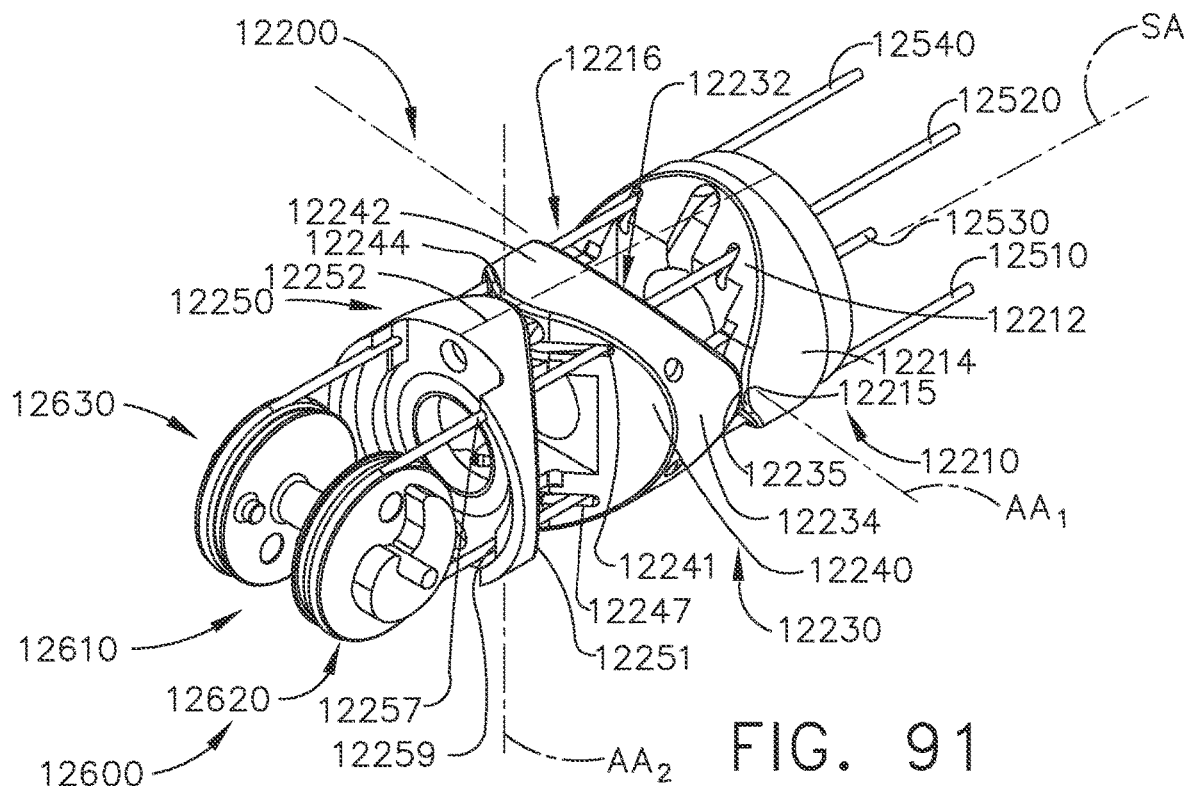
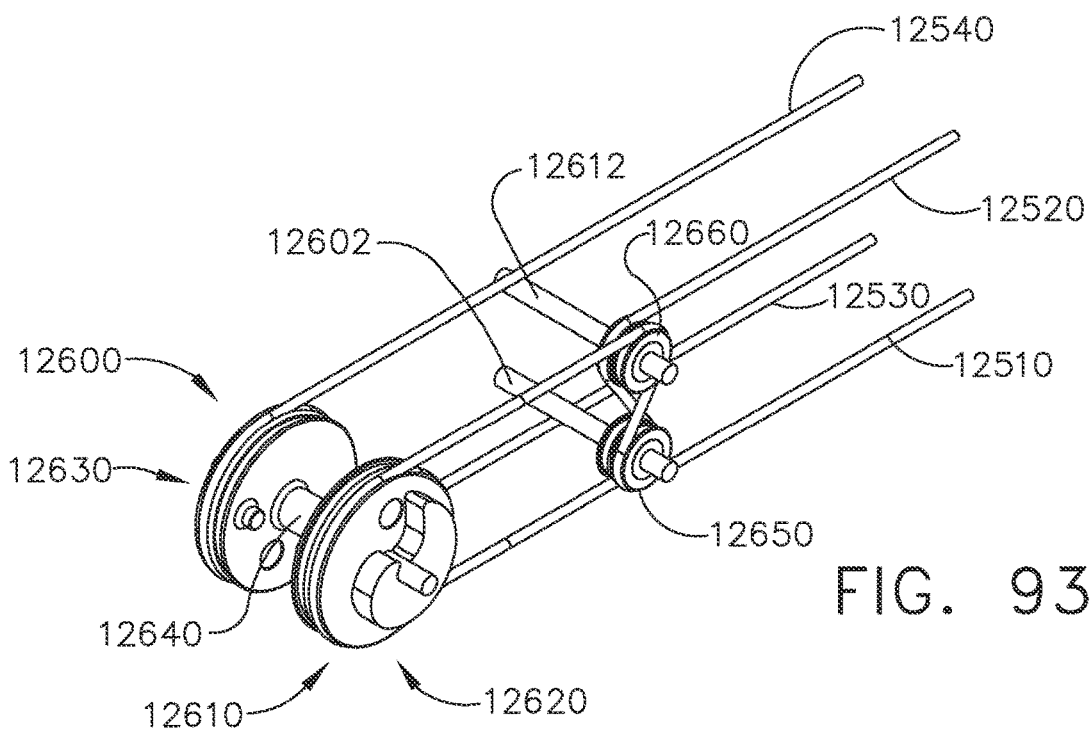

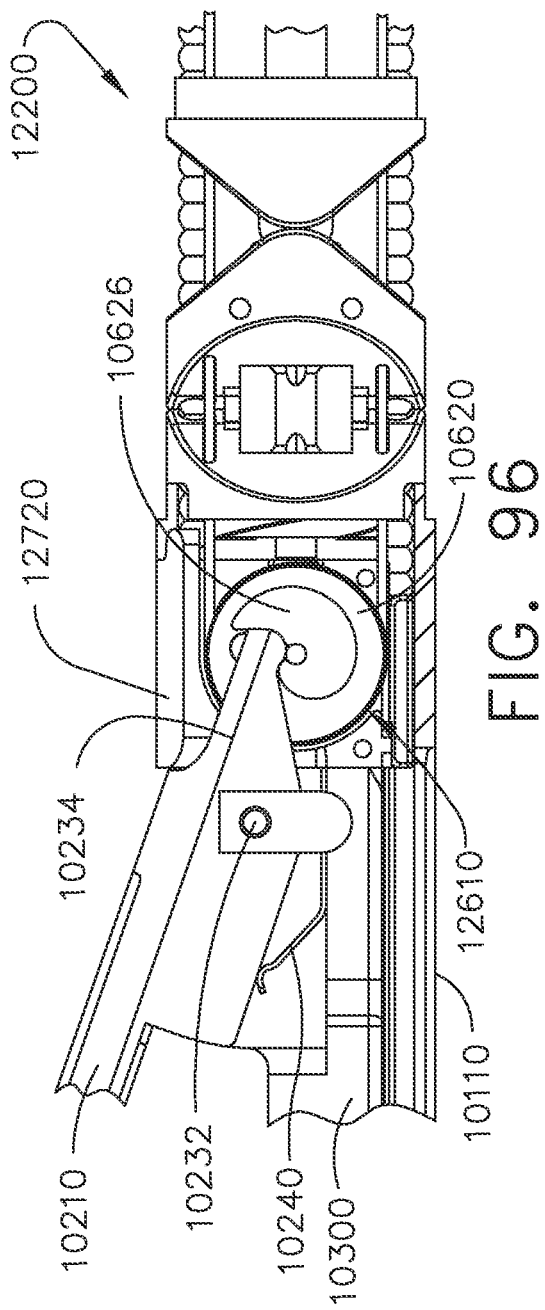
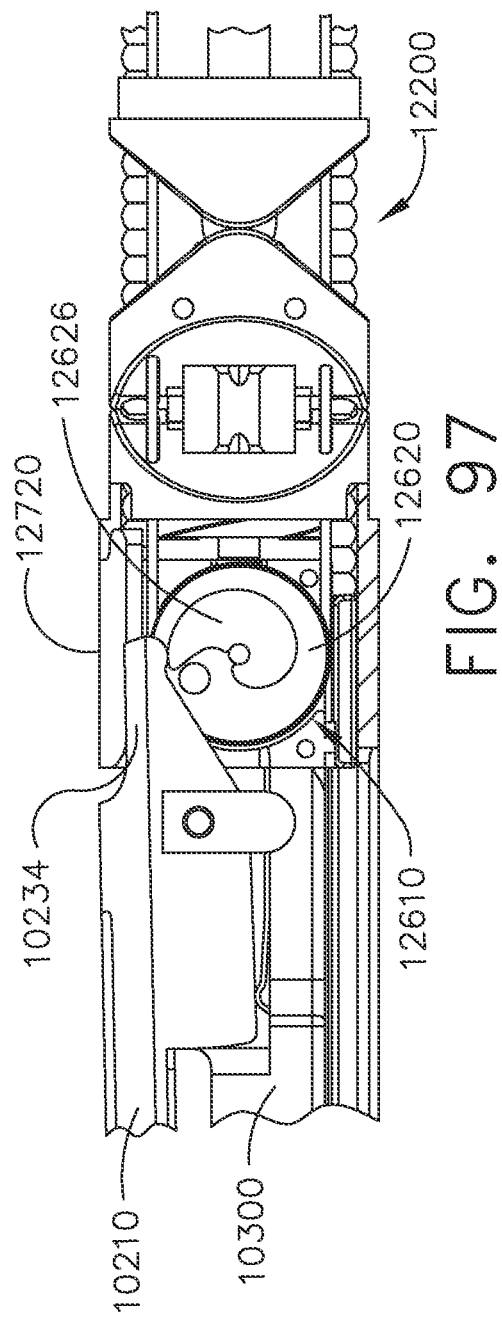

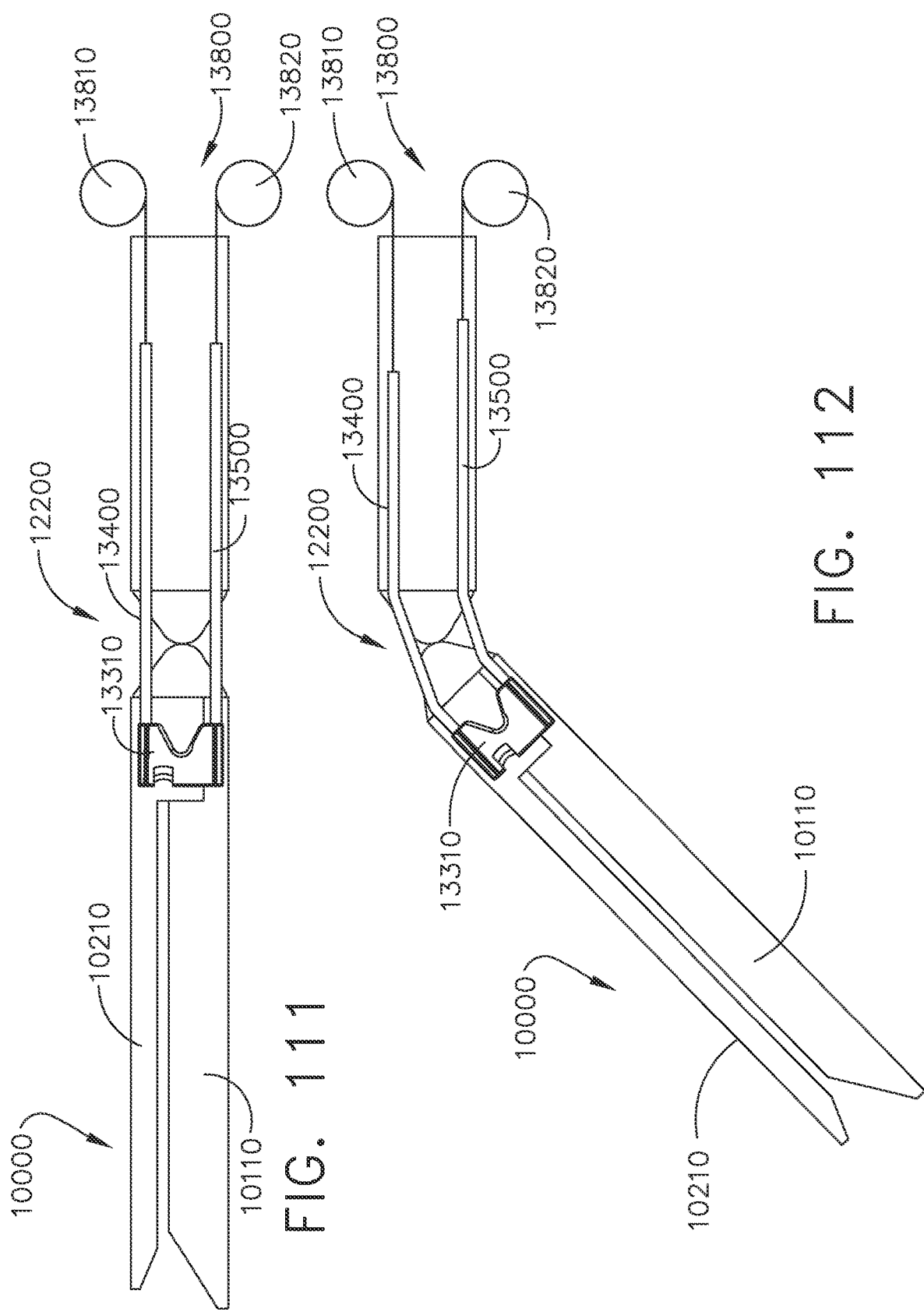

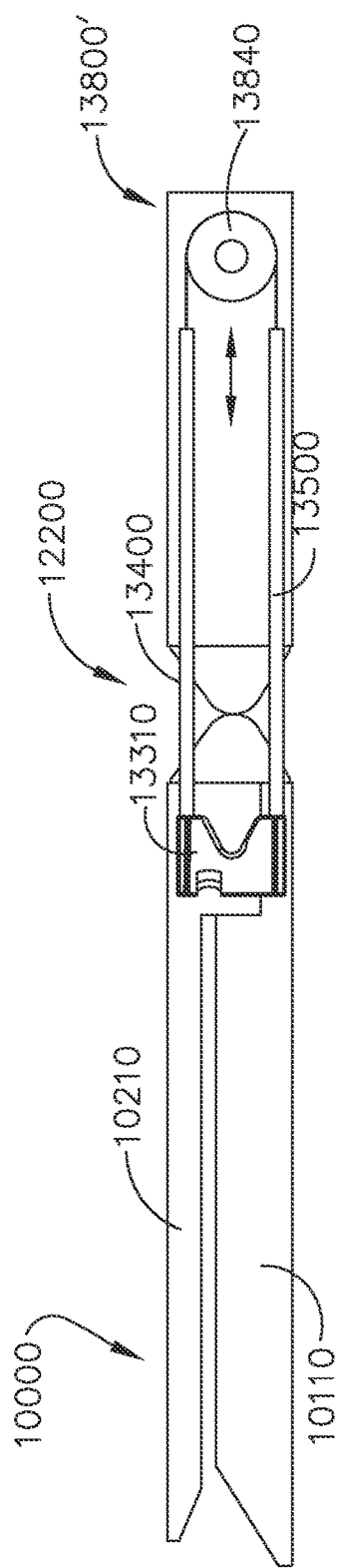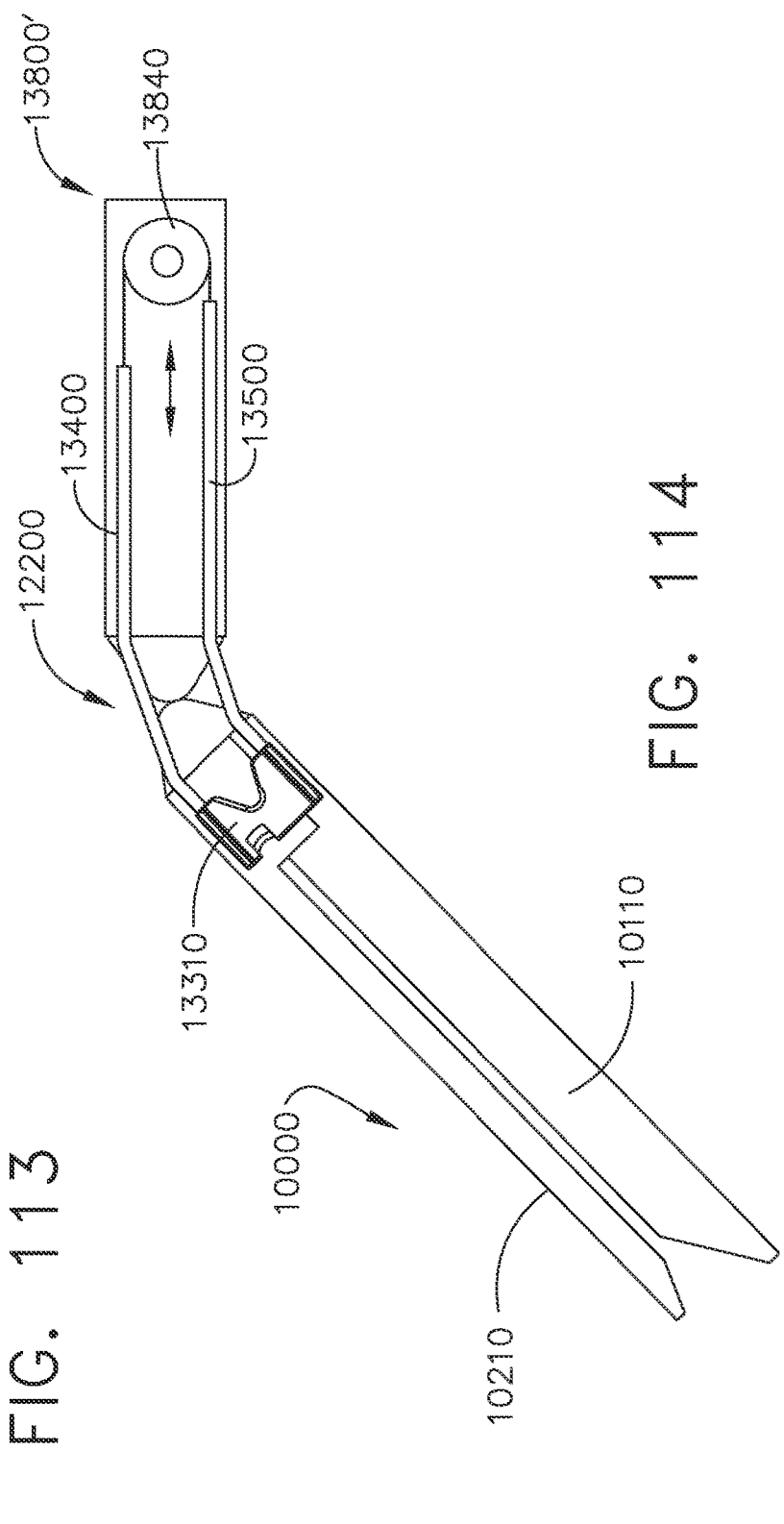

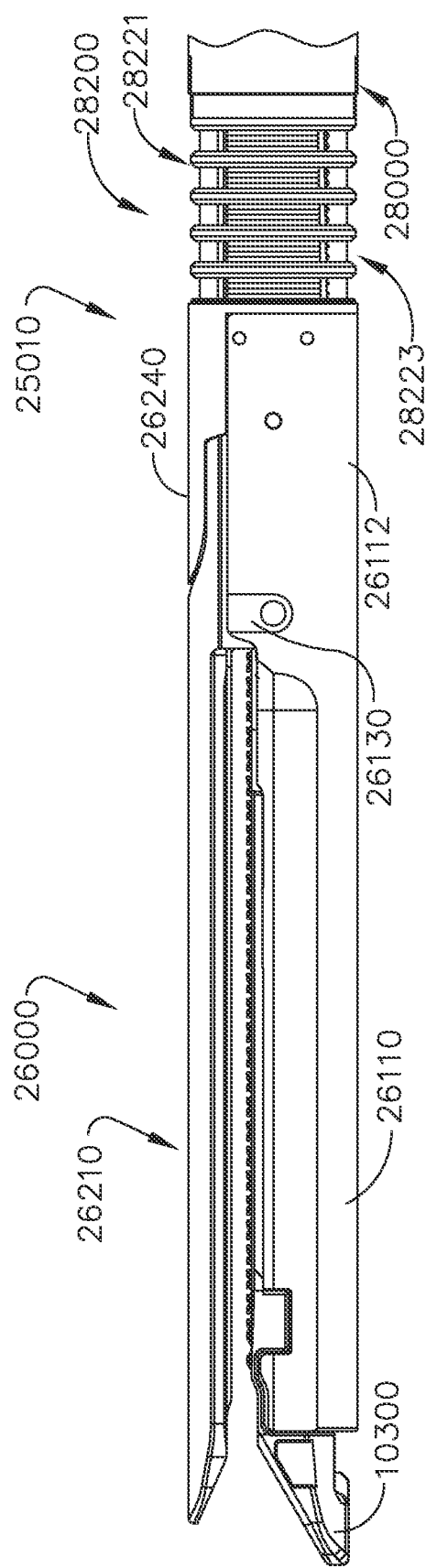
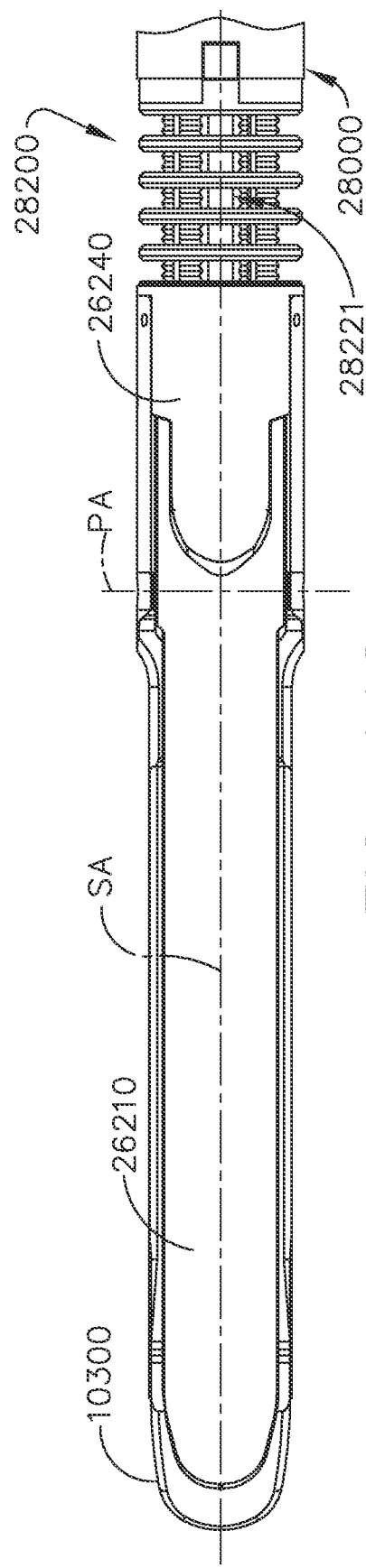
FIG. 117
FIG. 118

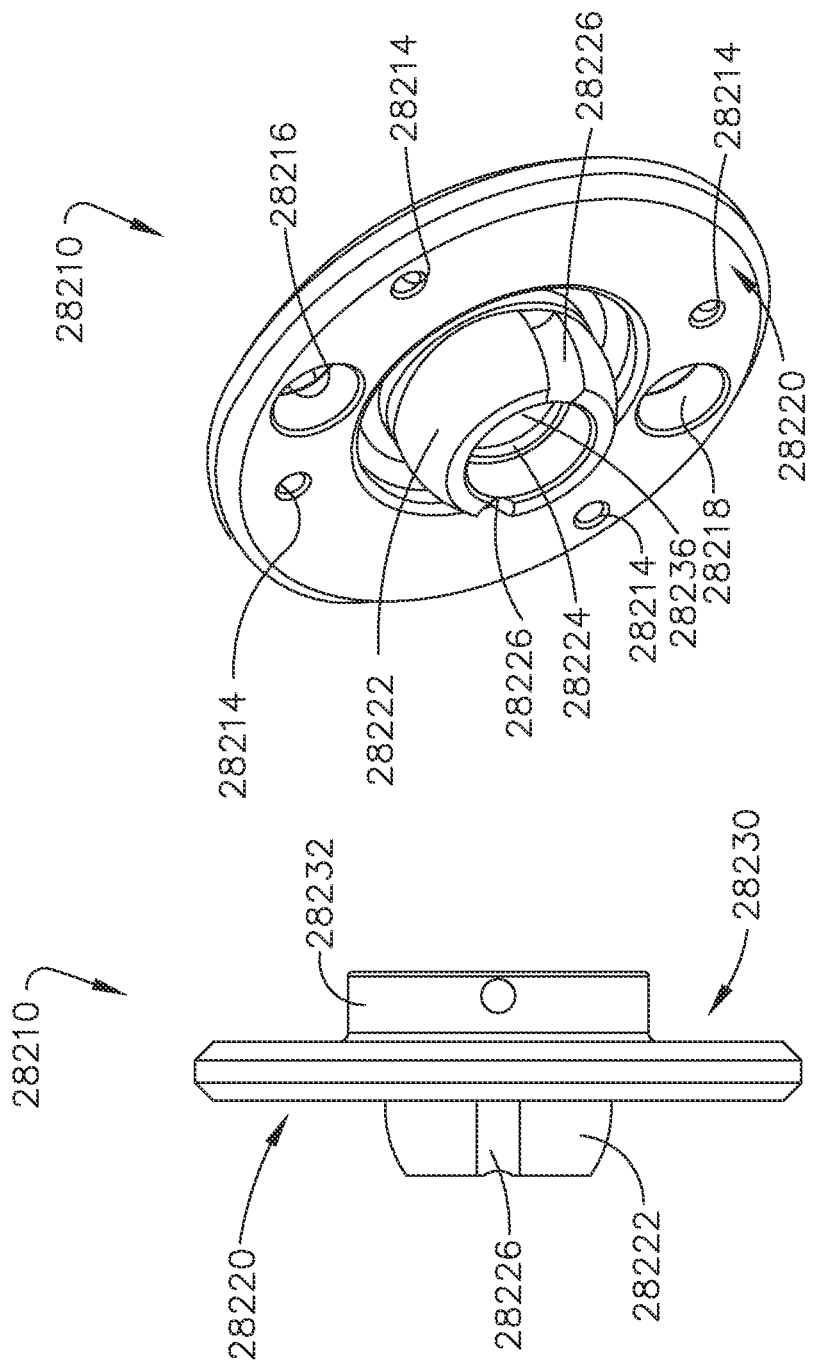

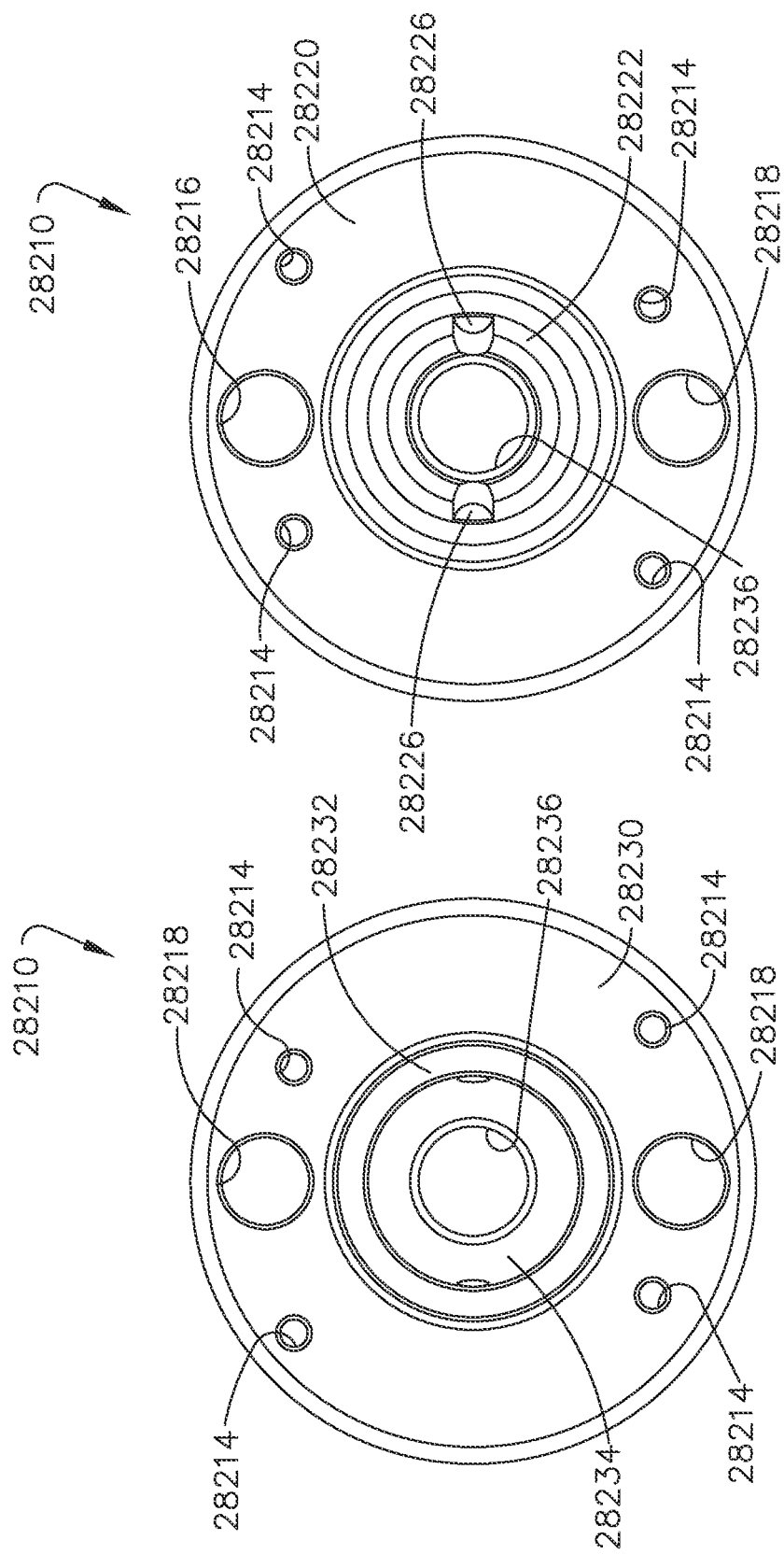

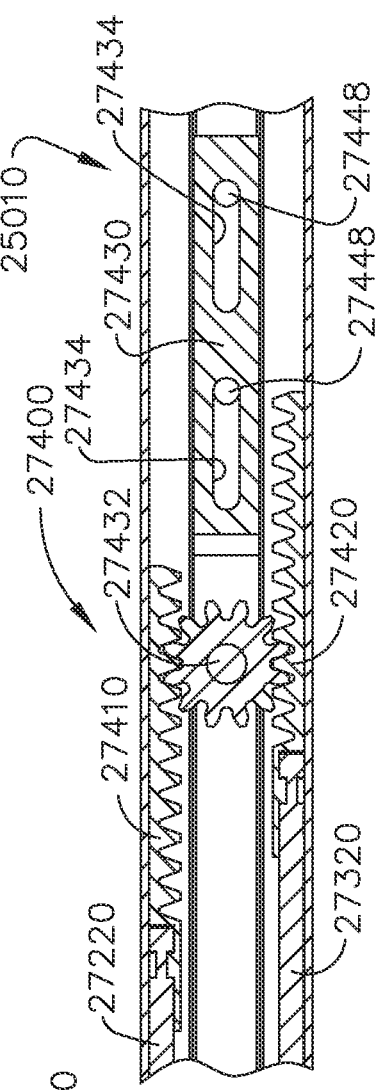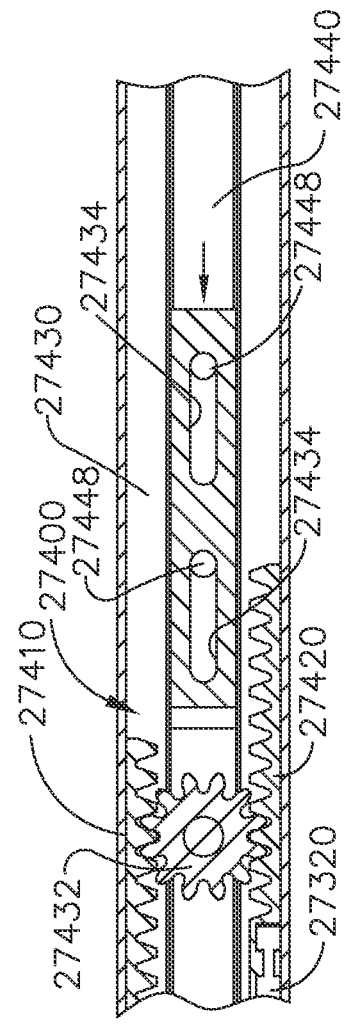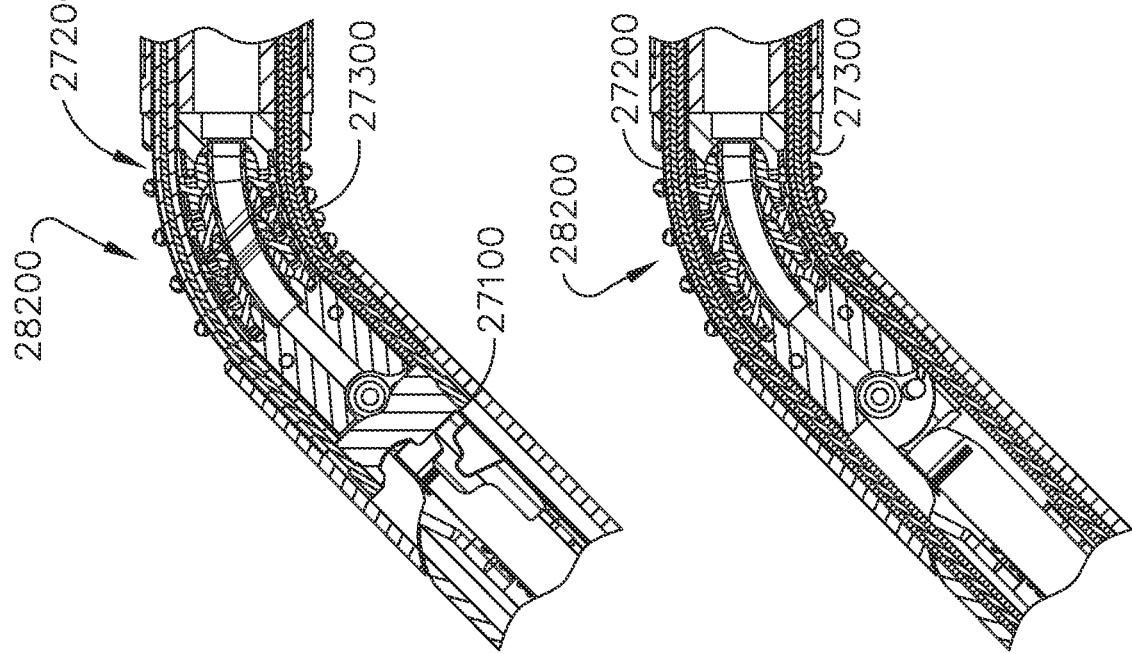

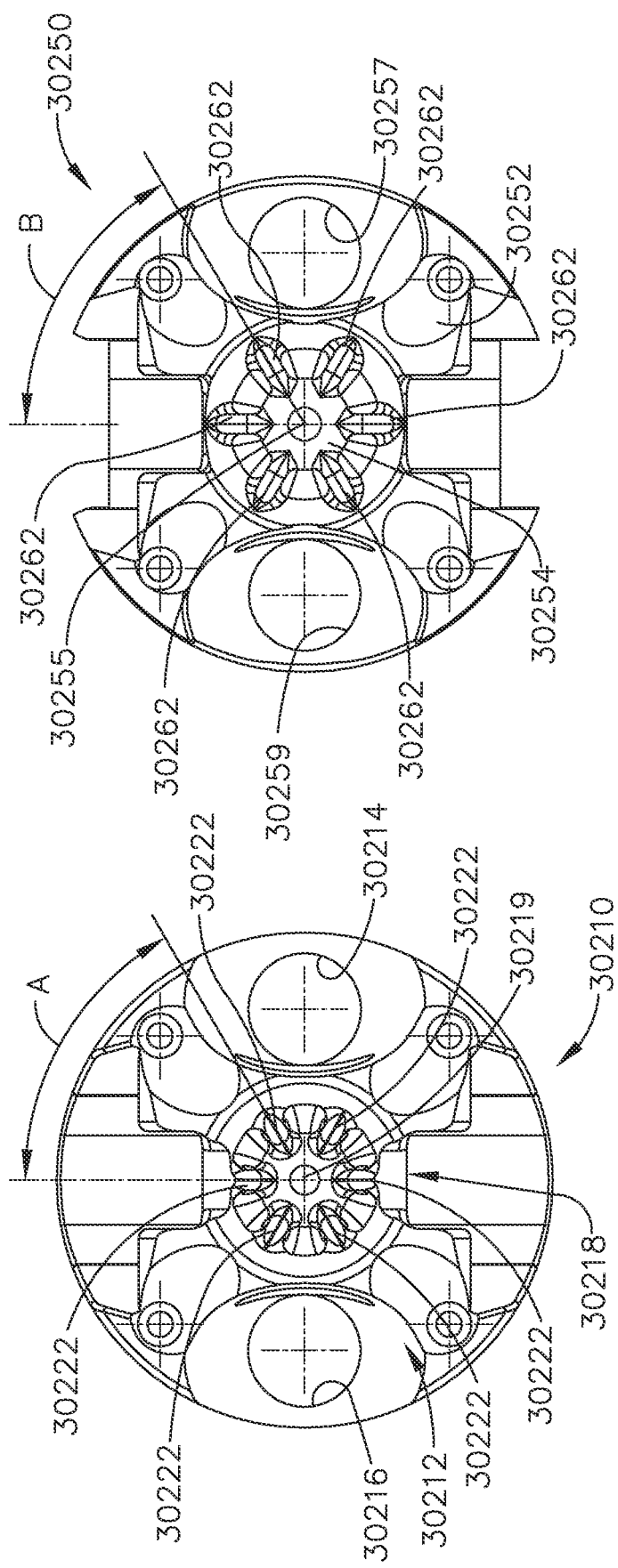

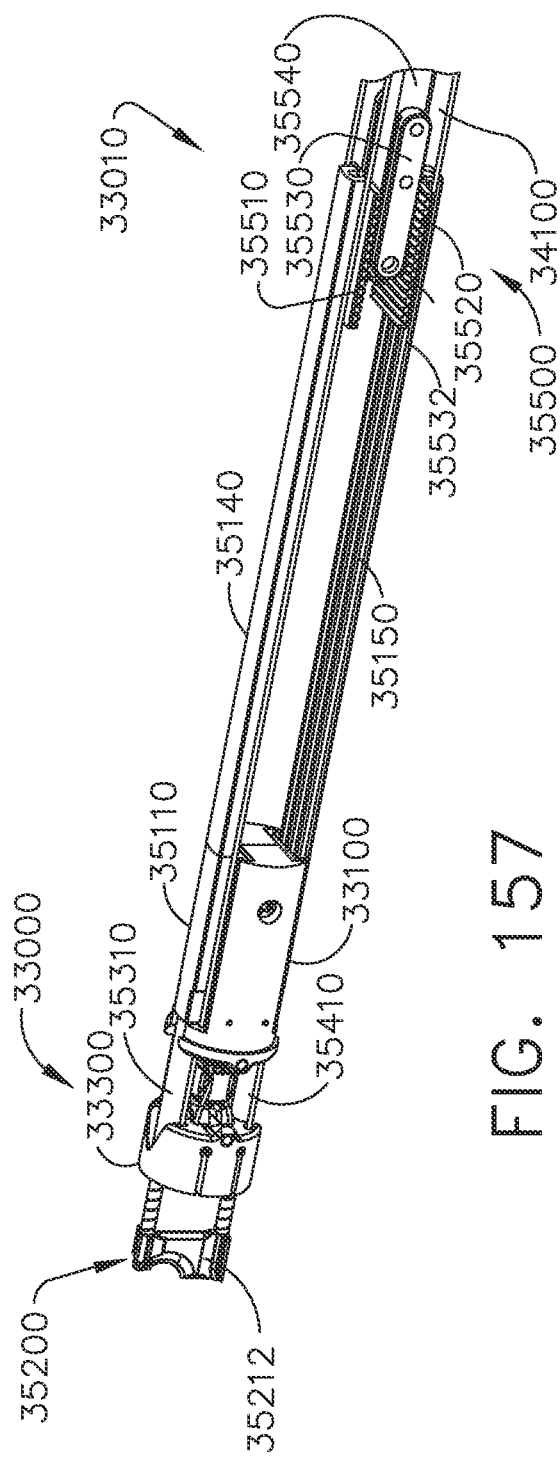
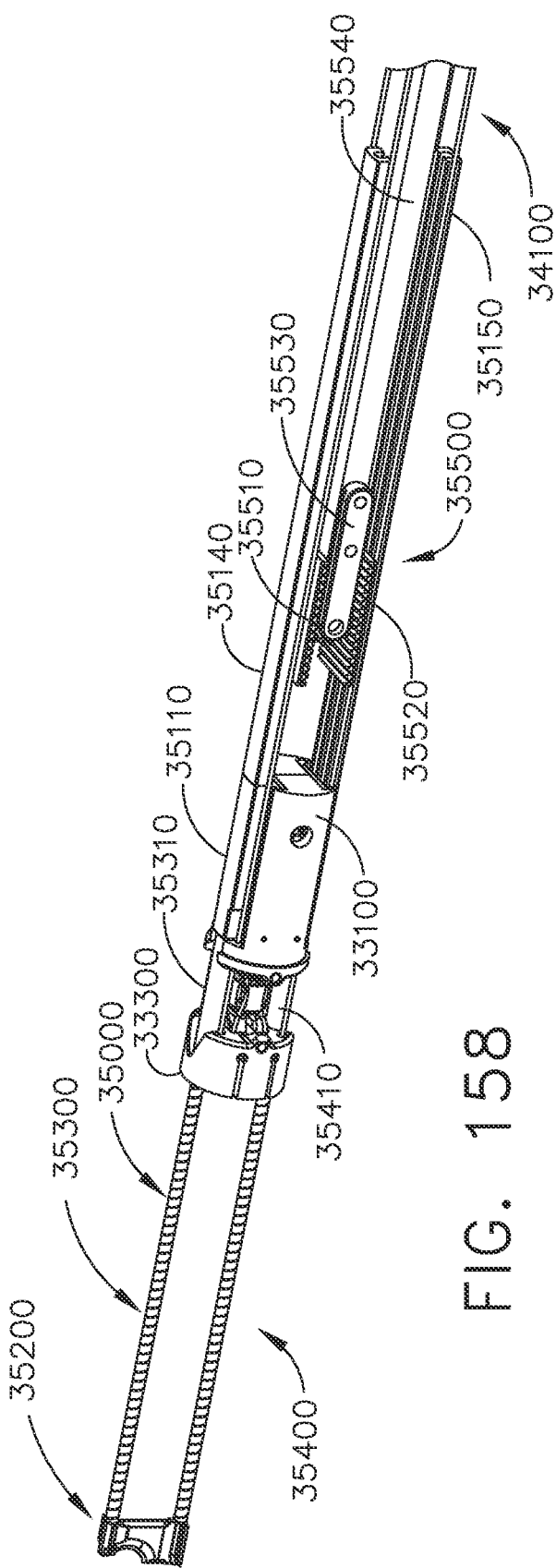
FIG. 157
FIG. 158

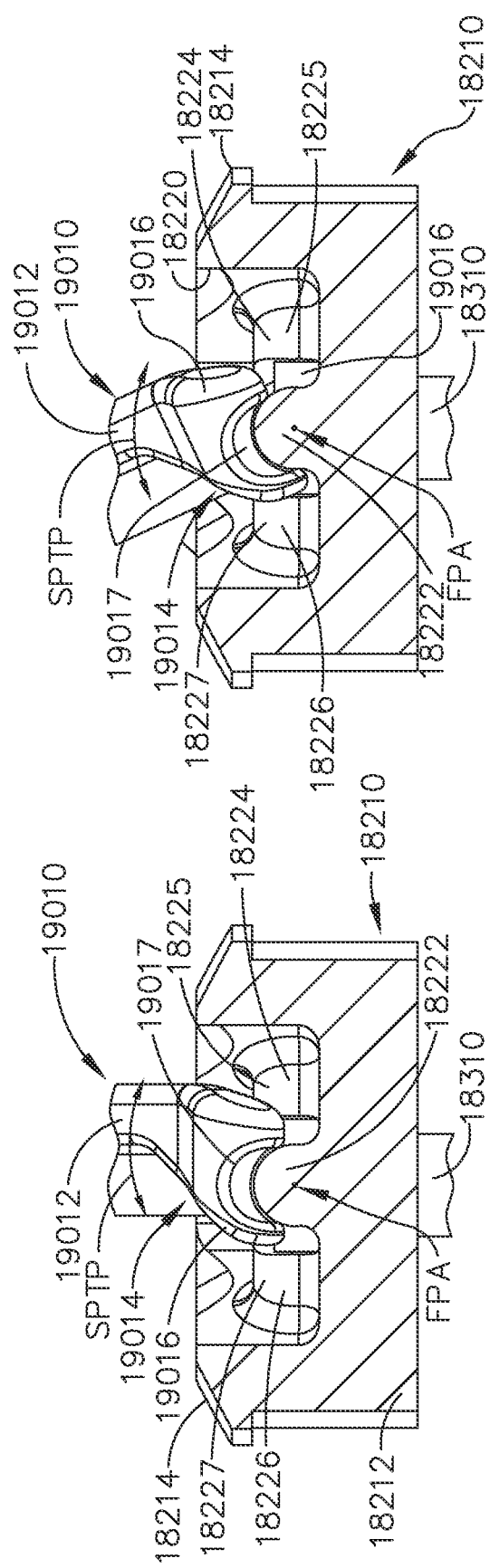

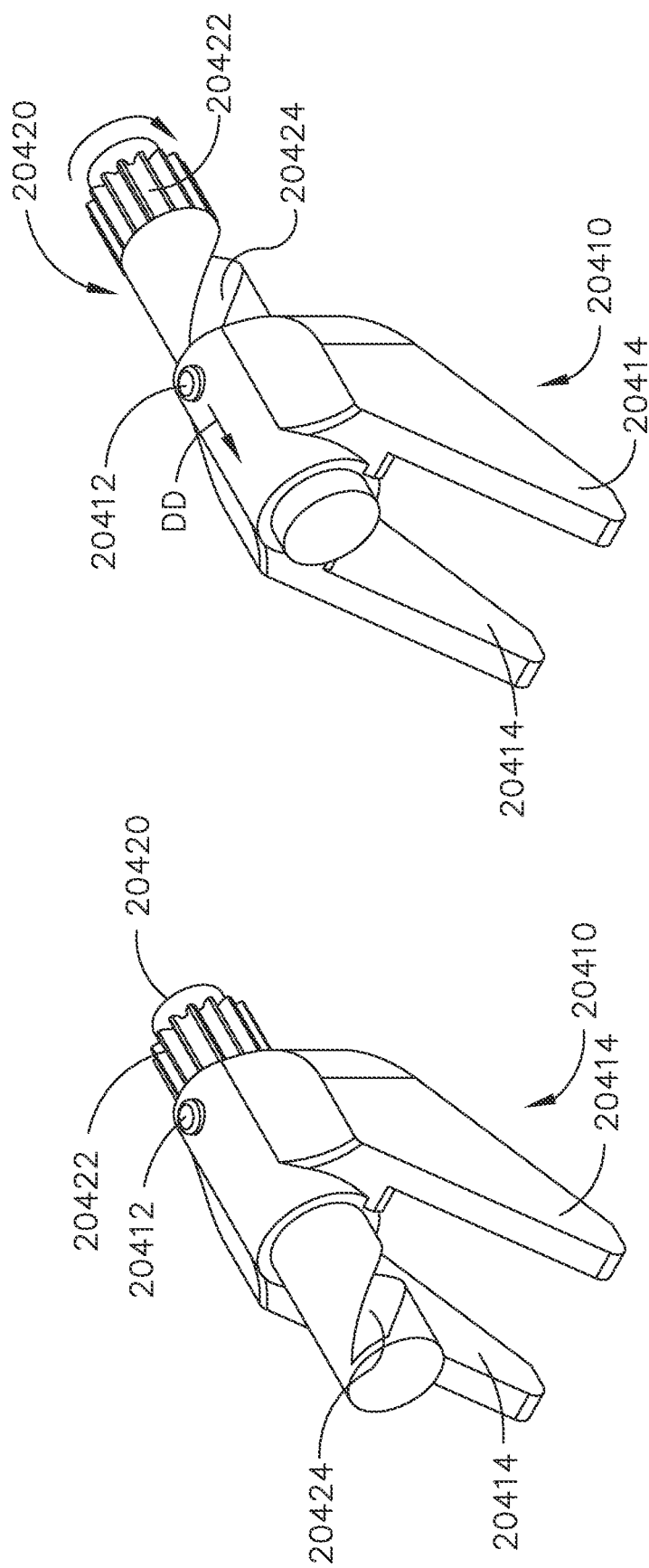

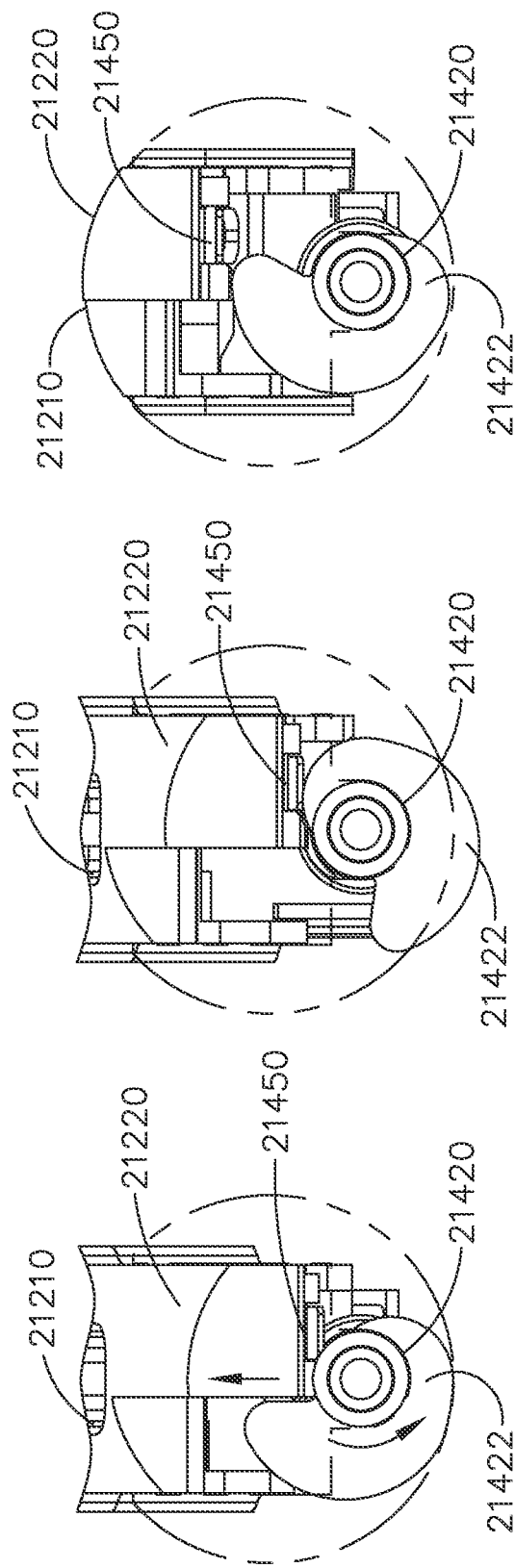

METHOD OF OPERATING A SURGICAL INSTRUMENT

CROSS-REFERENCE TO RELATED APPLICATIONS

This non-provisional application claims the benefit under 35 U.S.C. § 119(e) of U.S. Provisional Patent Application Ser. No. 63/057,430, entitled SURGICAL INSTRUMENTS WITH TORSION SPINE DRIVE ARRANGEMENTS, filed Jul. 28, 2020, of U.S. Provisional Patent Application Ser. No. 63/057,432, entitled ARTICULATION JOINT ARRANGEMENTS FOR SURGICAL INSTRUMENTS, filed Jul. 28, 2020, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue. The surgical instruments may be configured for use in open surgical procedures, but have applications in other types of surgery, such as laparoscopic, endoscopic, and robotic-assisted procedures and may include end effectors that are articulatable relative to a shaft portion of the instrument to facilitate precise positioning within a patient.

BRIEF DESCRIPTION OF THE DRAWINGS

The novel features of the various aspects are set forth with particularity in the appended claims. The described aspects, however, both as to organization and methods of operation, may be best understood by reference to the following description, taken in conjunction with the accompanying drawings in which:

FIG. 9 is a side view of a firing member and upper and lower flexible spine assemblies of the firing system in engagement with a rotary drive screw of the rotary drive system of FIG. 8;

FIG. 10 is a cross-sectional view of the firing member and upper and lower flexible spine assemblies of FIG. 9;

FIG. 55 is a view of a proximal face of an annular rib member of a movable exoskeleton assembly of the surgical instrument of FIG. 46;

FIG. 56 is a view of a distal face of the annular rib member of FIG. 55;

FIG. 79 is a side view of a portion of a rotary firing system and firing member of another surgical instrument;

FIG. 80 is a partial view of another surgical instrument that employs a rotary driven firing system to drive a firing member through a surgical end effector with an anvil of the surgical end effector in an open position;

FIG. 81 is another partial side view of the surgical instrument and end effector of FIG. 80 with the anvil thereof in a closed position;

FIG. 89 is a side elevational view of an articulation joint of the surgical instrument of FIG. 87;

FIG. 90 is a top view of the articulation joint of FIG. 89;

FIG. 91 is a perspective view of the articulation joint of FIG. 89 and a cable-controlled closure pulley system for applying closing motions to the anvil of the surgical end effector of FIG. 89;

FIG. 93 is another perspective view of the cable-controlled closure pulley system of FIG. 91;

FIG. 96 is a side cross-sectional view of a portion of the surgical end effector of FIG. 89 with the anvil of the surgical end effector in an open position;

FIG. 97 is another side elevational view of the surgical end effector of FIG. 96 with the anvil in a closed position;

FIG. 111 is a partial side elevational view of the surgical instrument of FIG. 87 illustrating one form of a cable tensioning system with the surgical end effector in an unarticulated orientation;

FIG. 112 is another partial side view of the surgical instrument and cable tensioning system of FIG. 111 with the surgical end effector in an articulated orientation;

FIG. 113 is a partial side elevational view of the surgical instrument of FIG. 87 illustrating another form of a cable tensioning system with the surgical end effector in an unarticulated orientation;

FIG. 114 is another partial side view of the surgical instrument and cable tensioning system of FIG. 113 with the surgical end effector in an articulated orientation;

FIG. 117 is a side elevational view of the surgical end effector of FIG. 116, with an anvil thereof in a closed position;

FIG. 118 is a top view of the surgical end effector of FIG. 117;

FIG. 119 is an exploded assembly perspective view of a portion of the surgical instrument of FIG. 115;

FIG. 120 is a bottom cross sectional view of an articulation joint and portions of the anvil of the surgical instrument of FIG. 115;

FIG. 121 is an exploded assembly view of the articulation joint of FIG. 120;

FIG. 122 is a side view of an annular disc member of the articulation joint of FIG. 121;

FIG. 123 is a perspective view of the annular disc member of FIG. 122;

FIG. 124 is a view of a distal face of the annular disc member of FIG. 122;

FIG. 125 is a view of a proximal face of the annular disc member of FIG. 122;

FIG. 126 is a top view of a pulley unit of the surgical instrument of FIG. 115;

FIG. 127 is a perspective view of a portion of the articulation joint and elongate shaft assembly of the surgical instrument of FIG. 115, with an outer shaft tube omitted for clarity;

FIG. 128 is a side elevational view of the pulley unit of FIG. 126;

FIG. 129 is another side elevational view of the pulley unit of FIG. 126;

FIG. 130 is a perspective view of the pulley unit of FIG. 126 and a continuum shaft of the articulation joint of the surgical instrument of FIG. 115;

Figure 115:
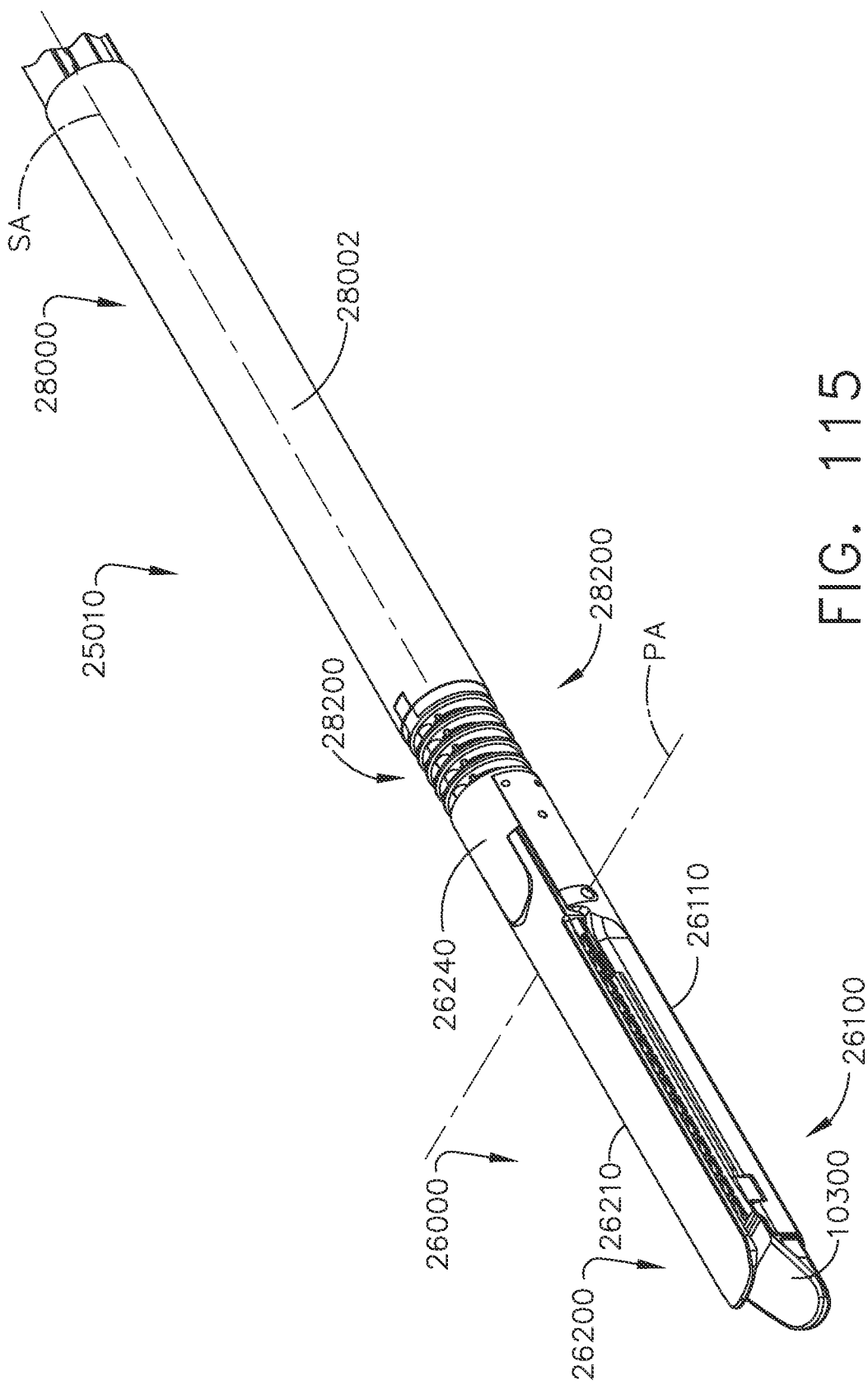
FIG. 115 is a perspective view of a portion of another surgical instrument embodiment.
Figure 116:
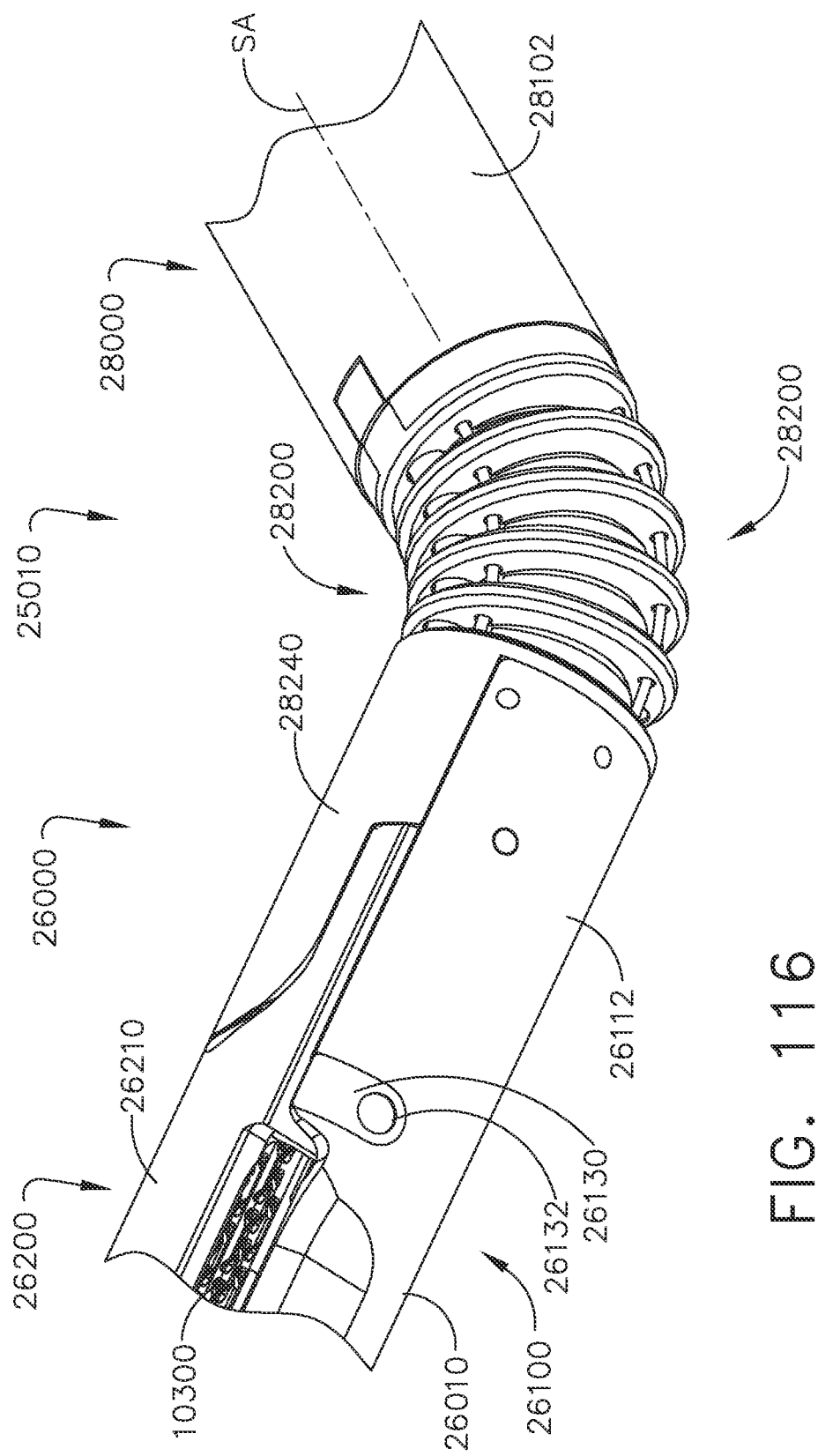
FIG. 116 is a perspective view of a portion of the surgical instrument of FIG. 115 with a surgical end effector portion thereof in an articulated position relative to an elongate shaft portion thereof.
Figure 126:
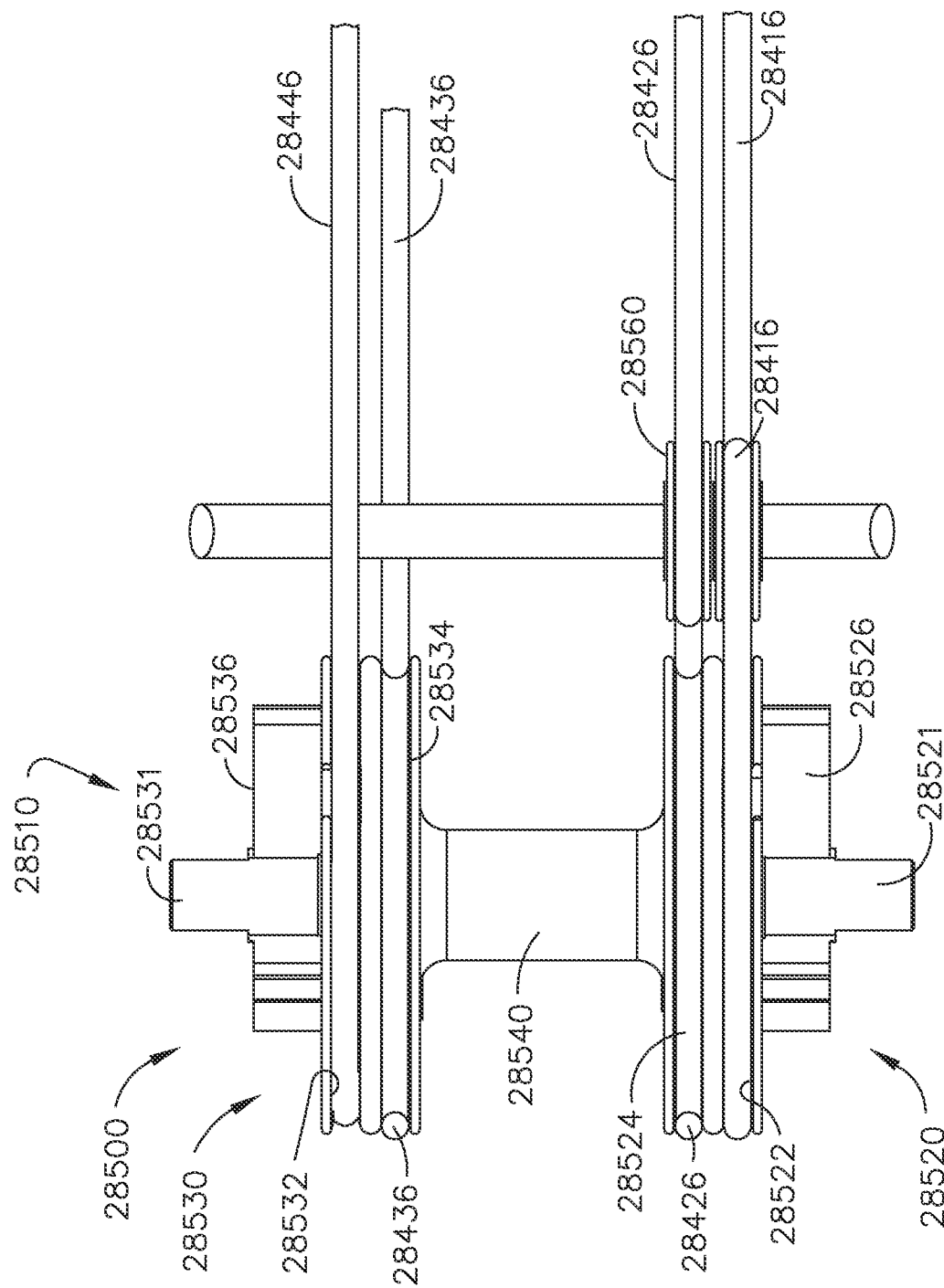
Figure 131:
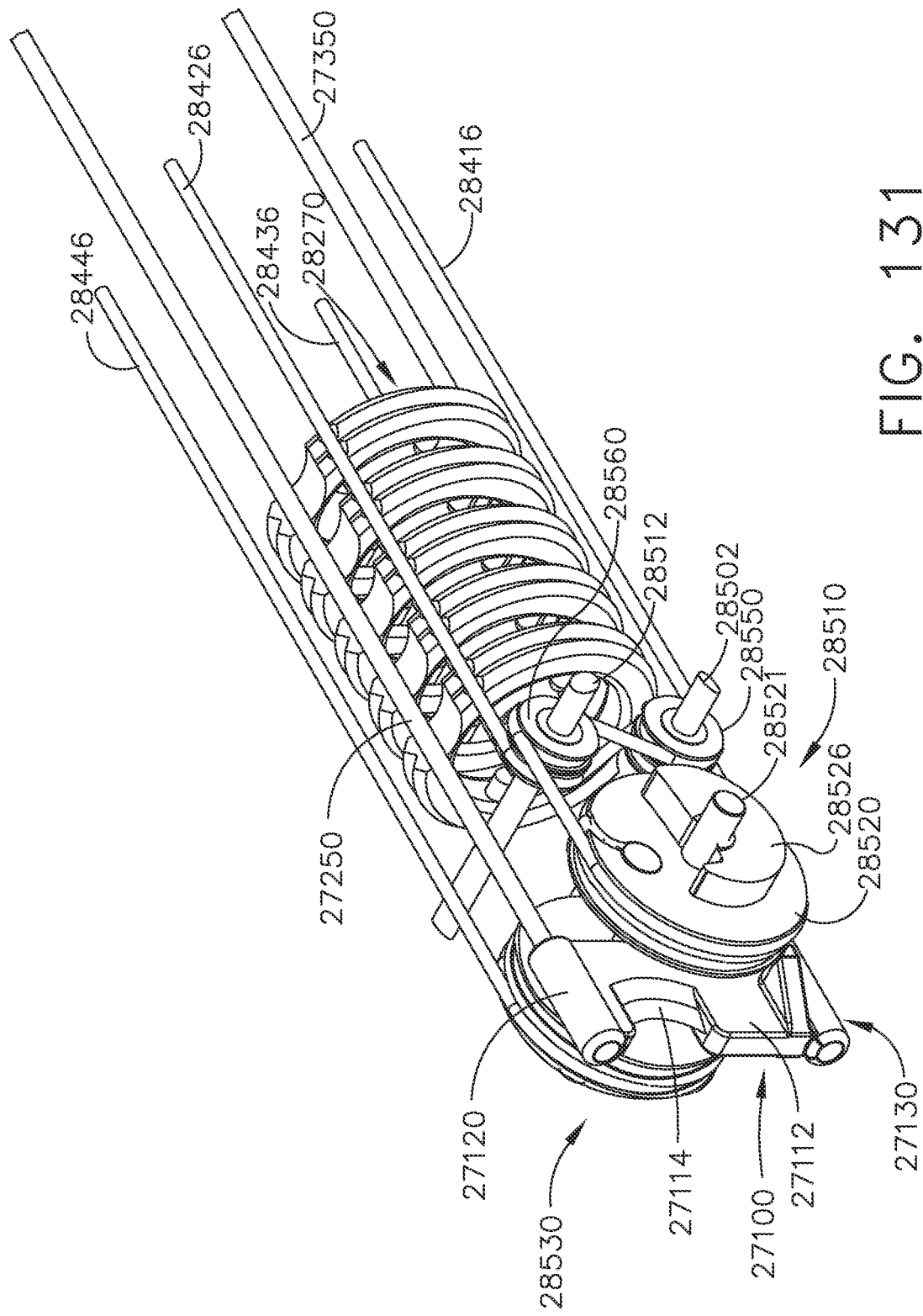
Figure 132:
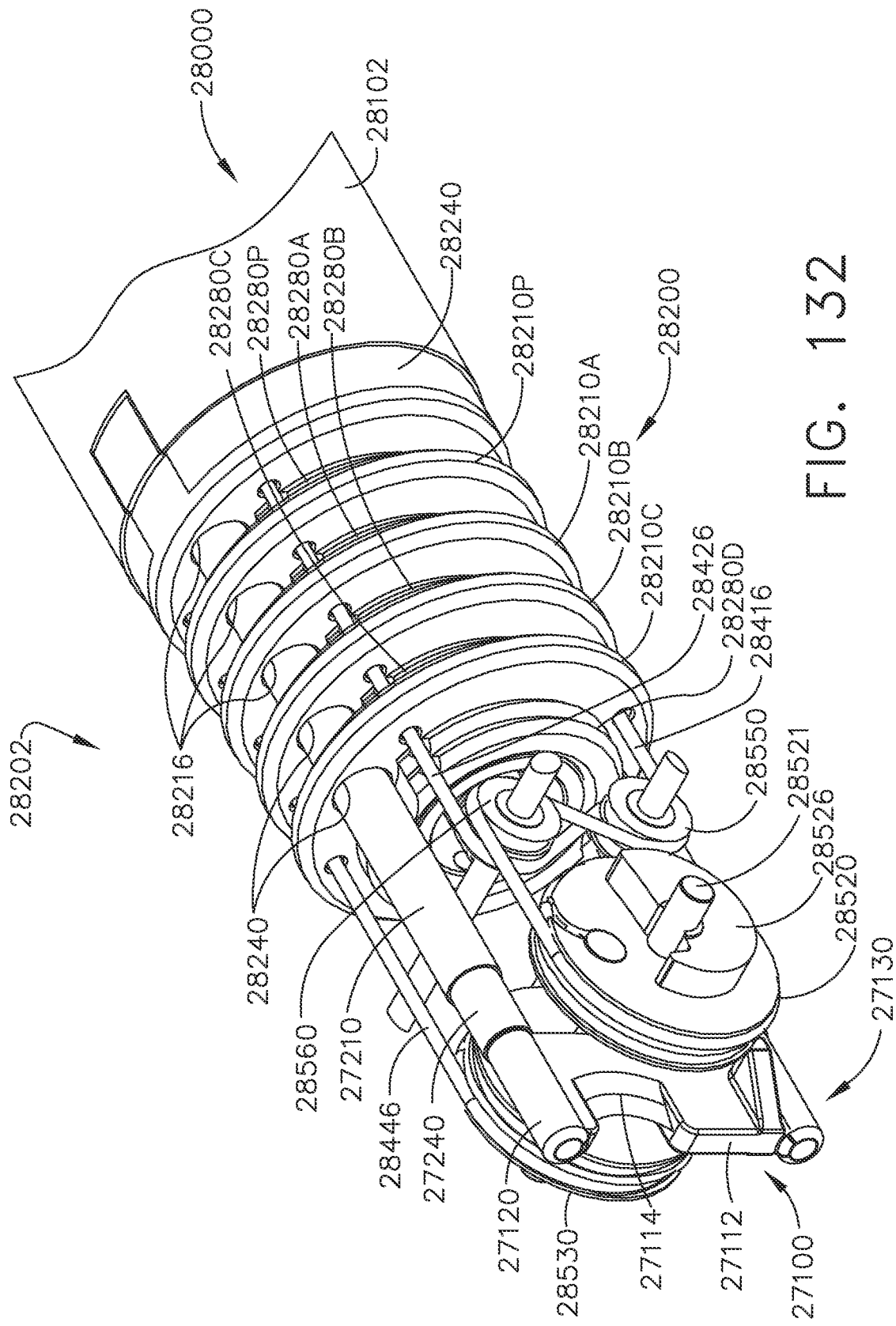
Figure 133:
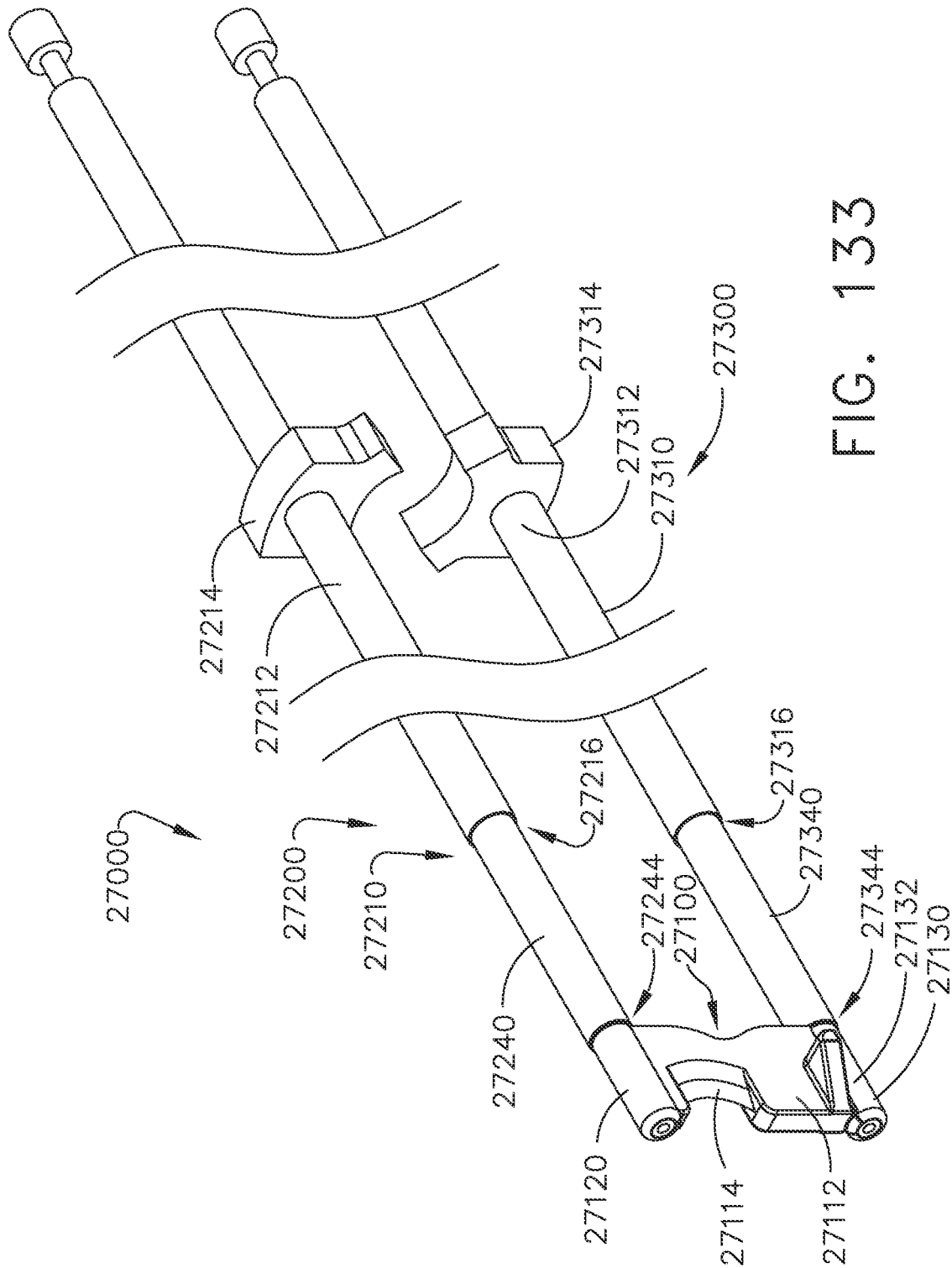
Figure 134:
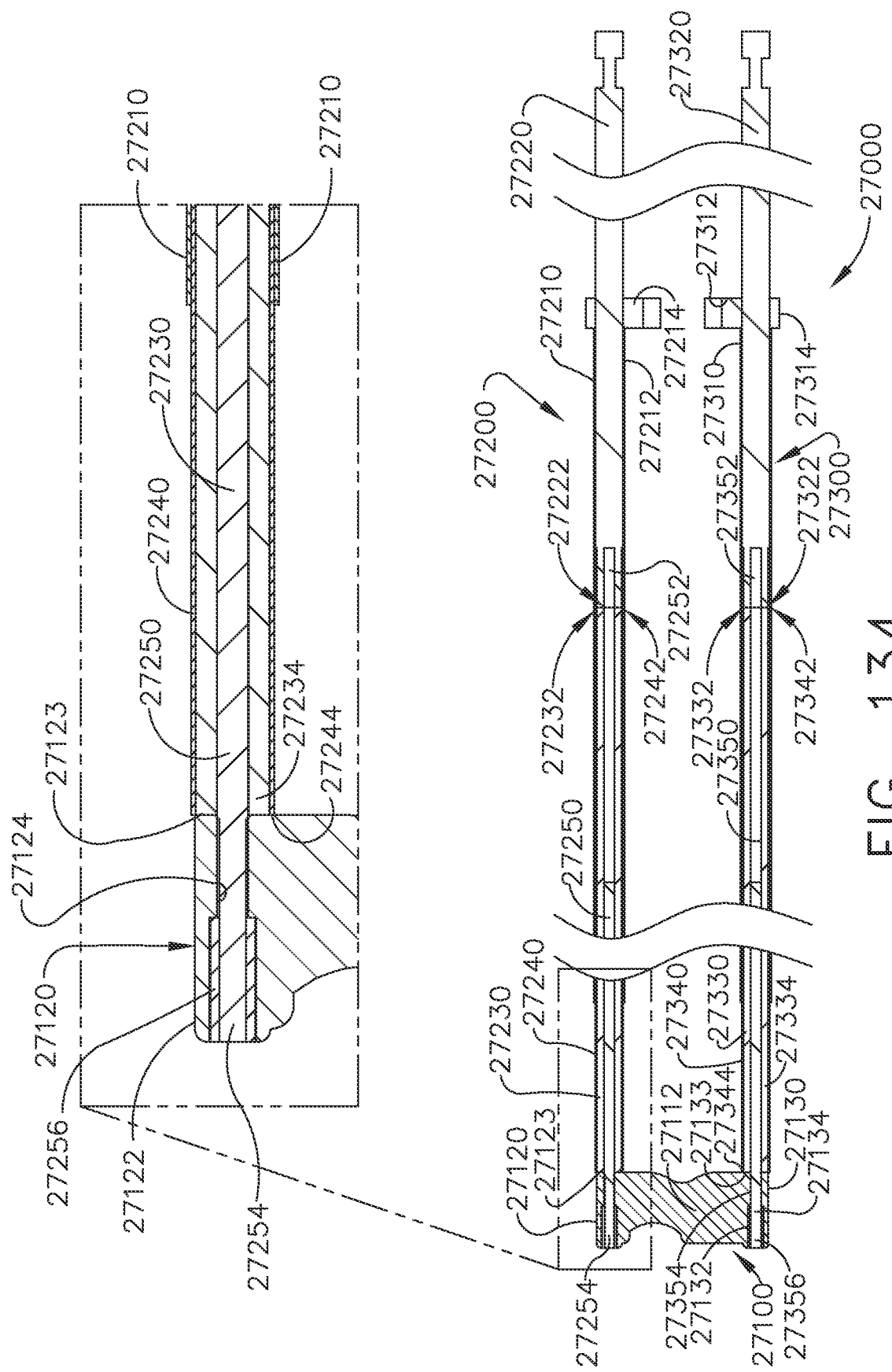
Figure 135:
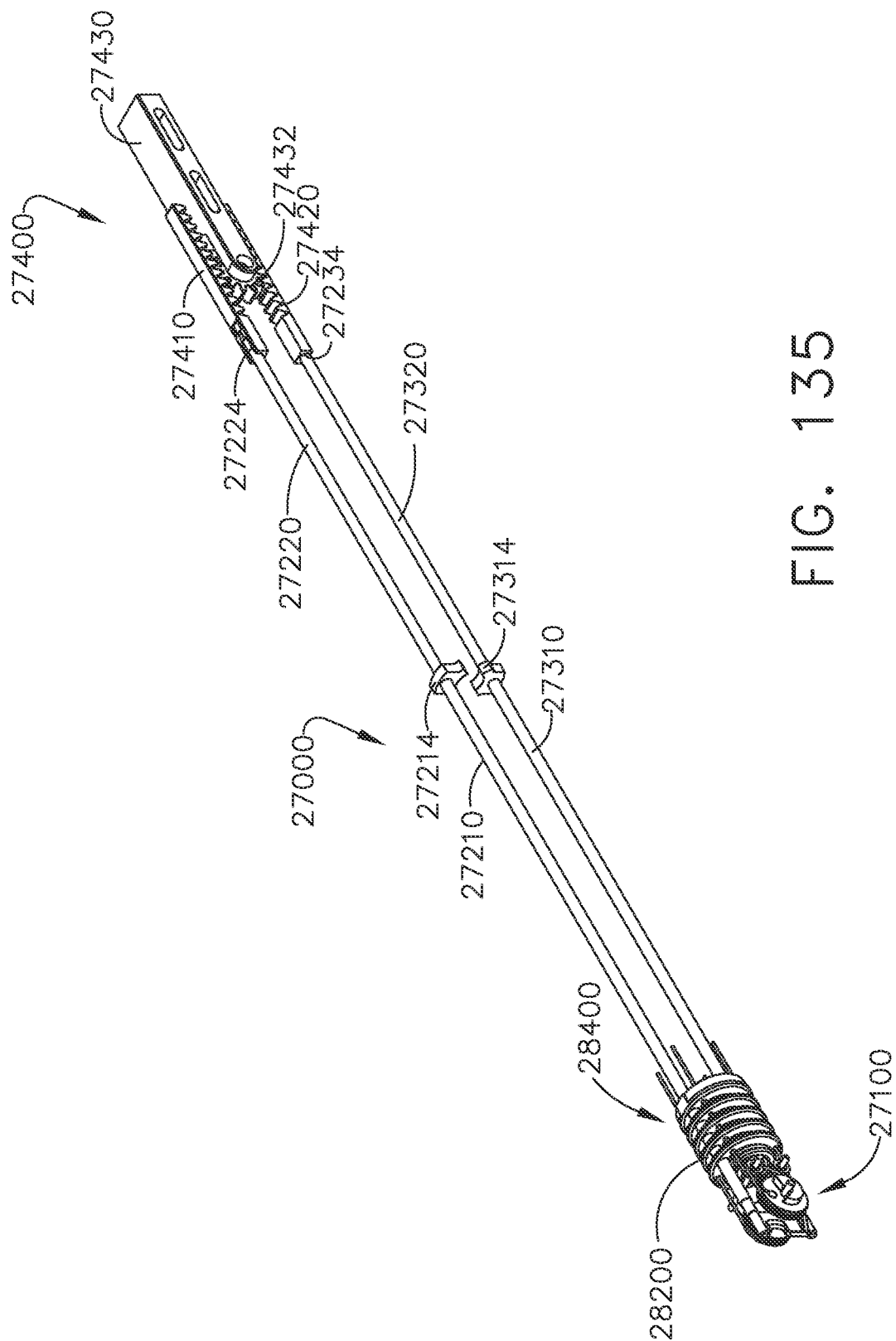
Figure 136:
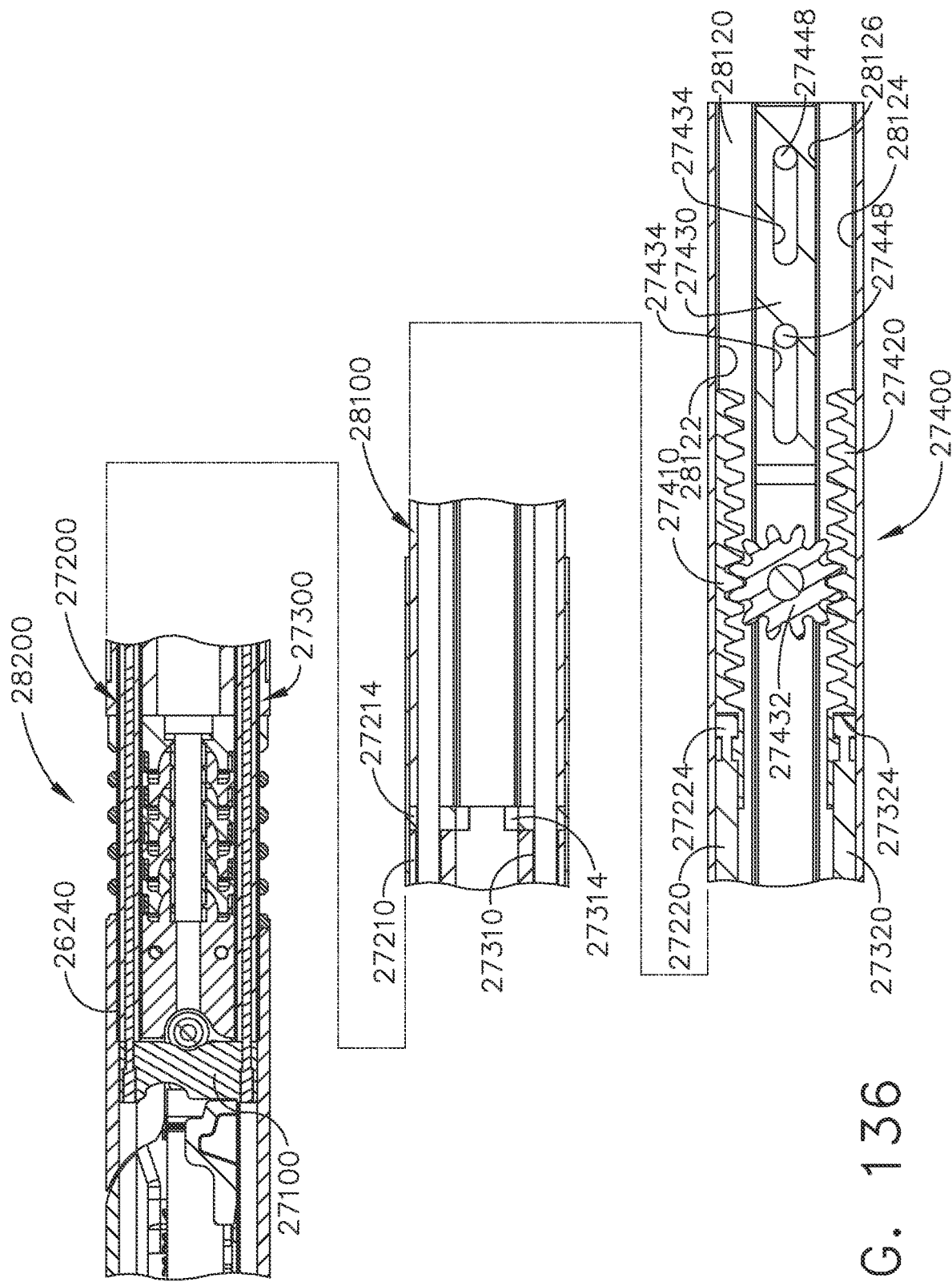
Figure 137:
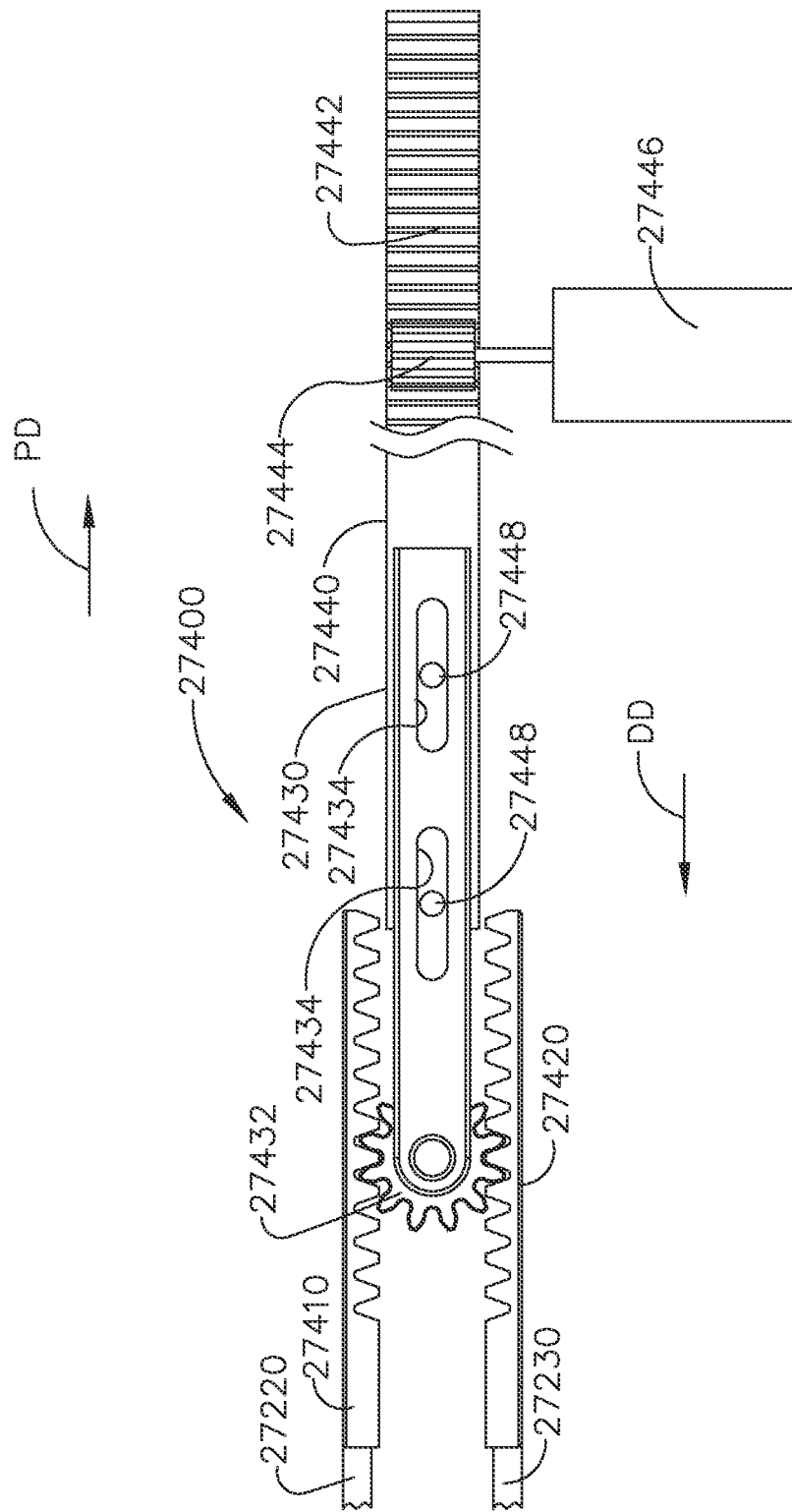
Figure 140:
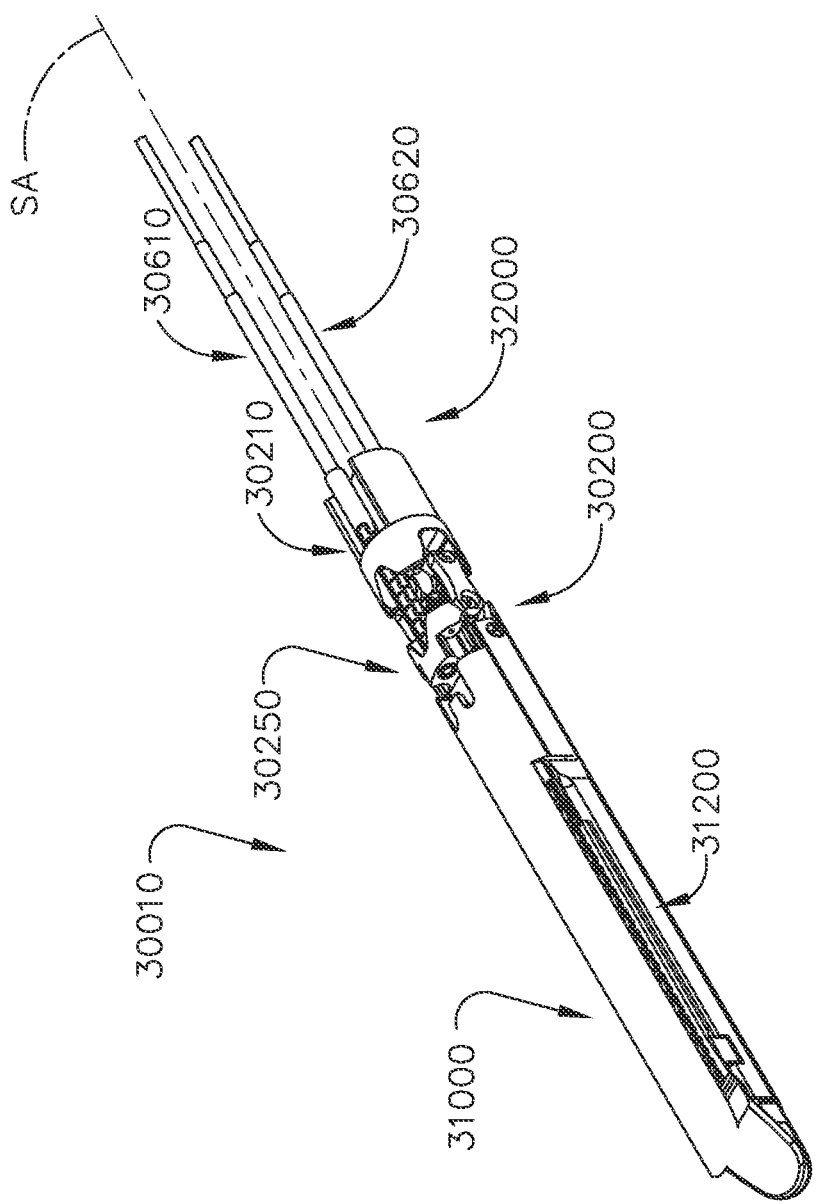
Figure 141:
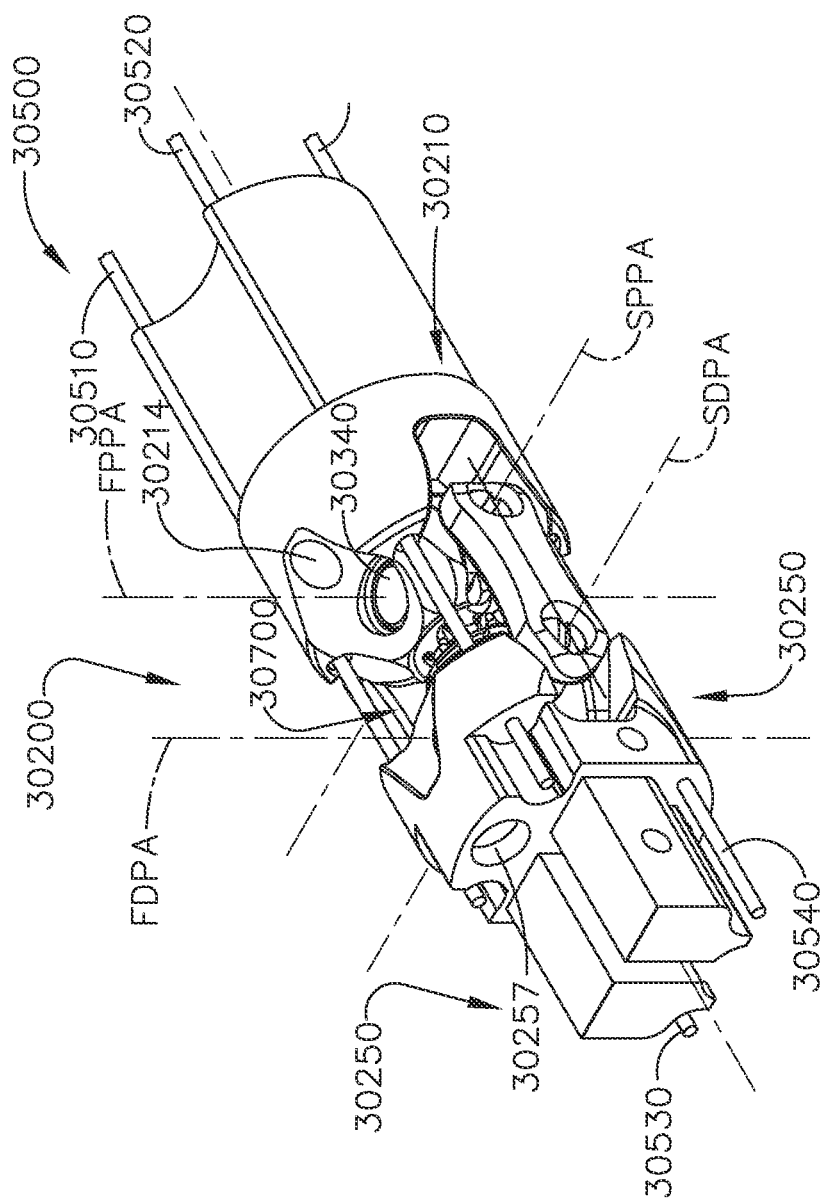
Figure 142:
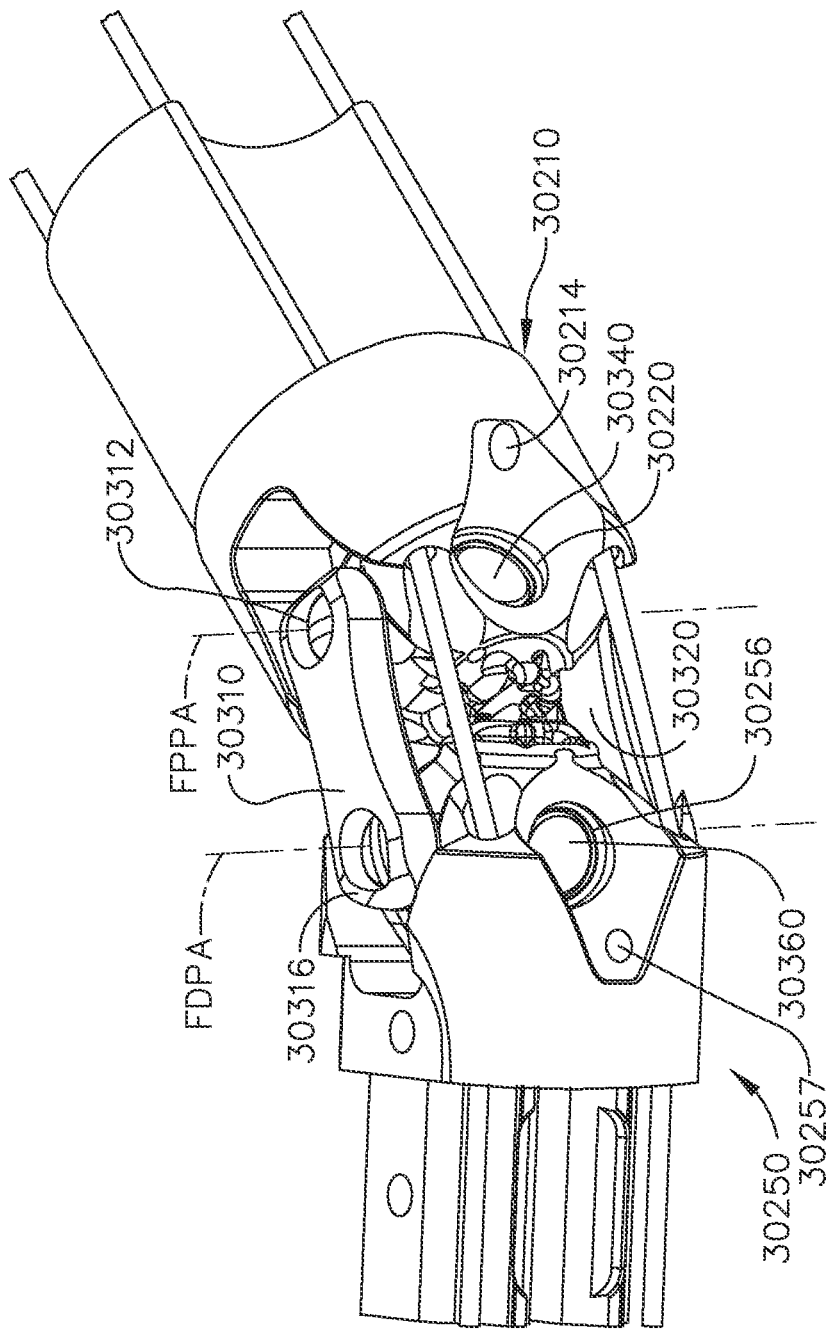
Figure 143:
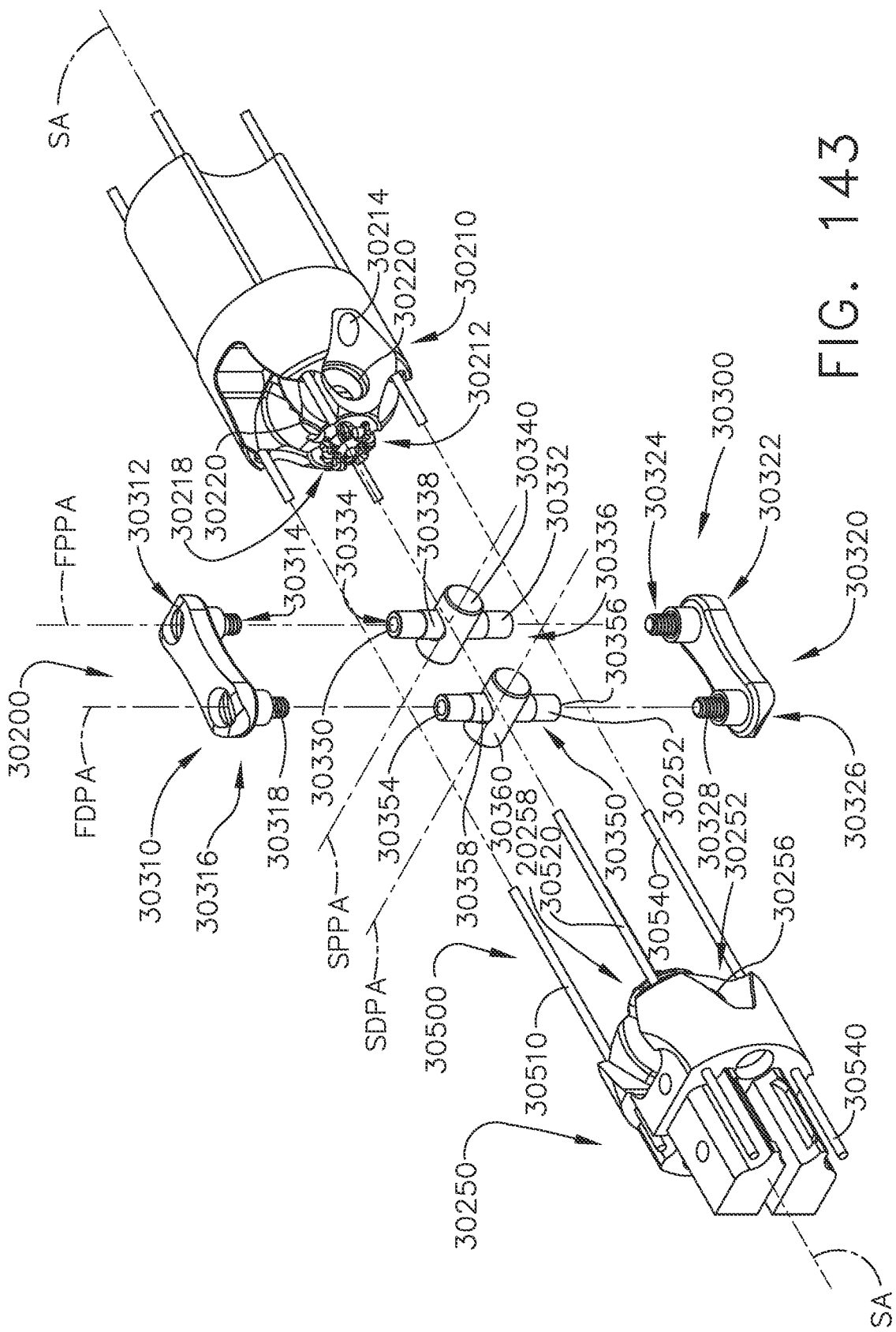
Figure 144:
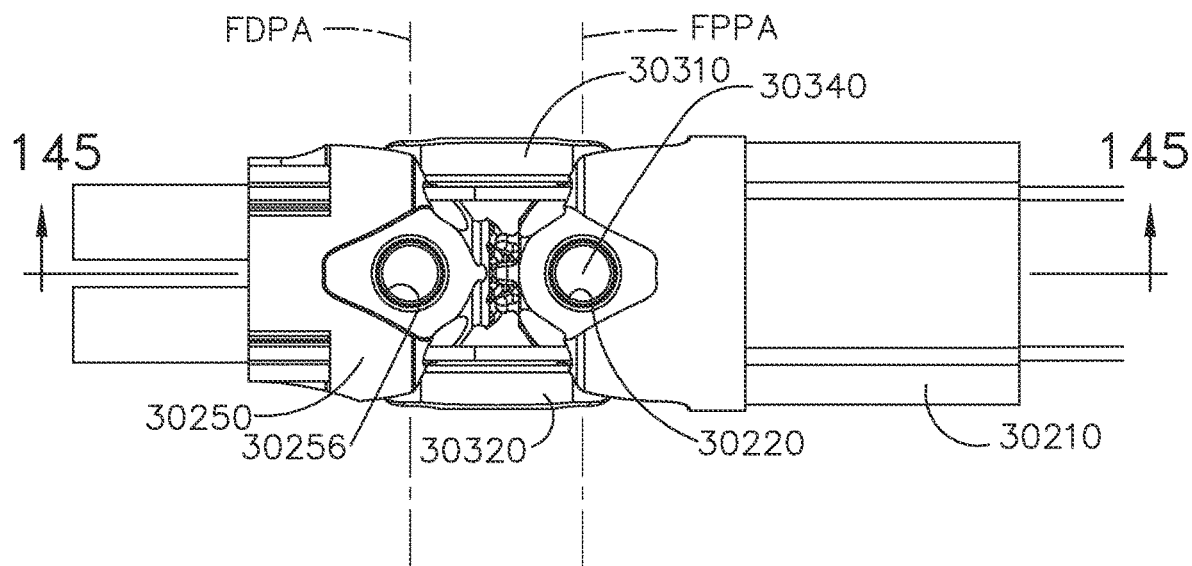
Figure 145:
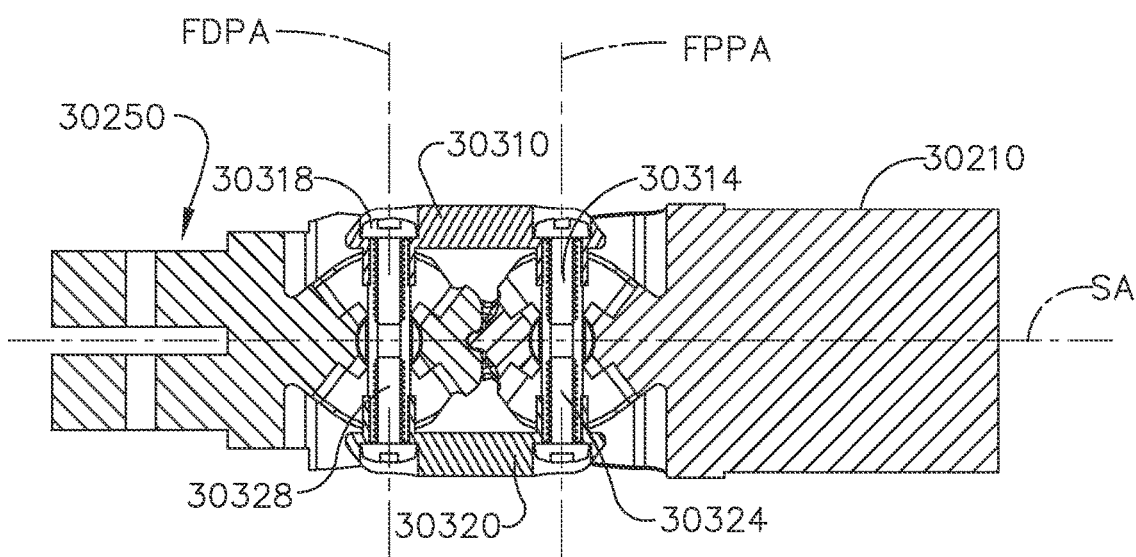
Figure 146:
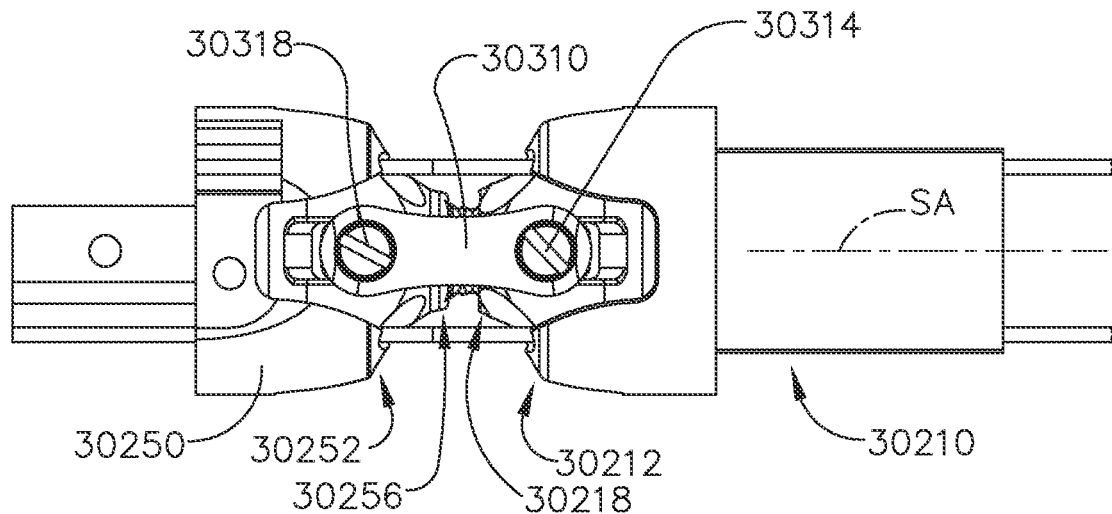
Figure 147:
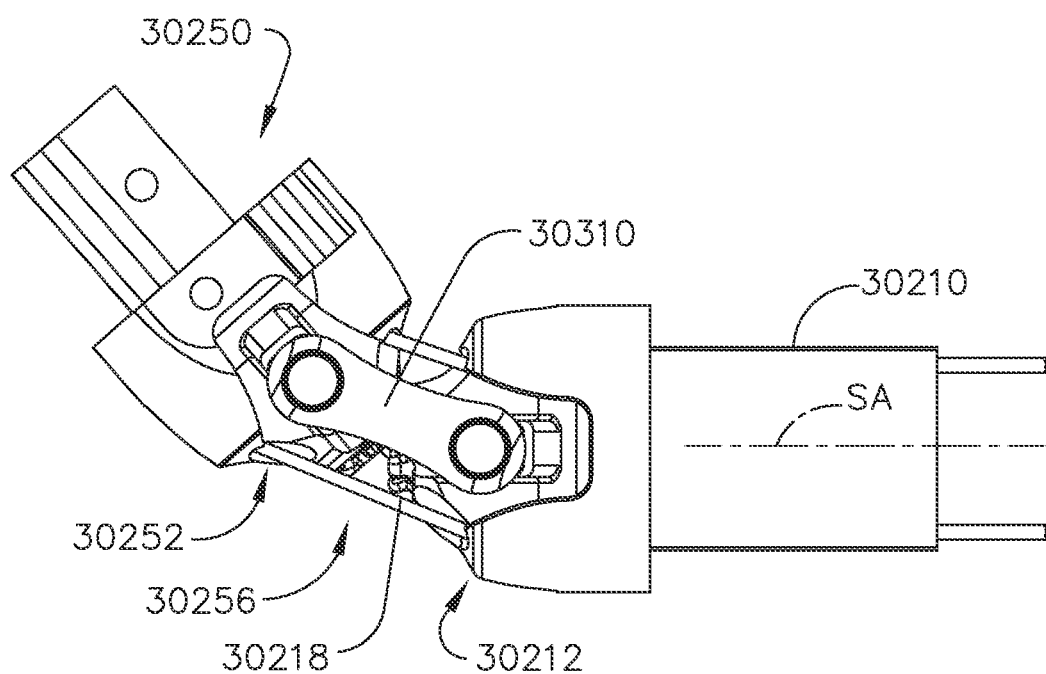
Figure 148:
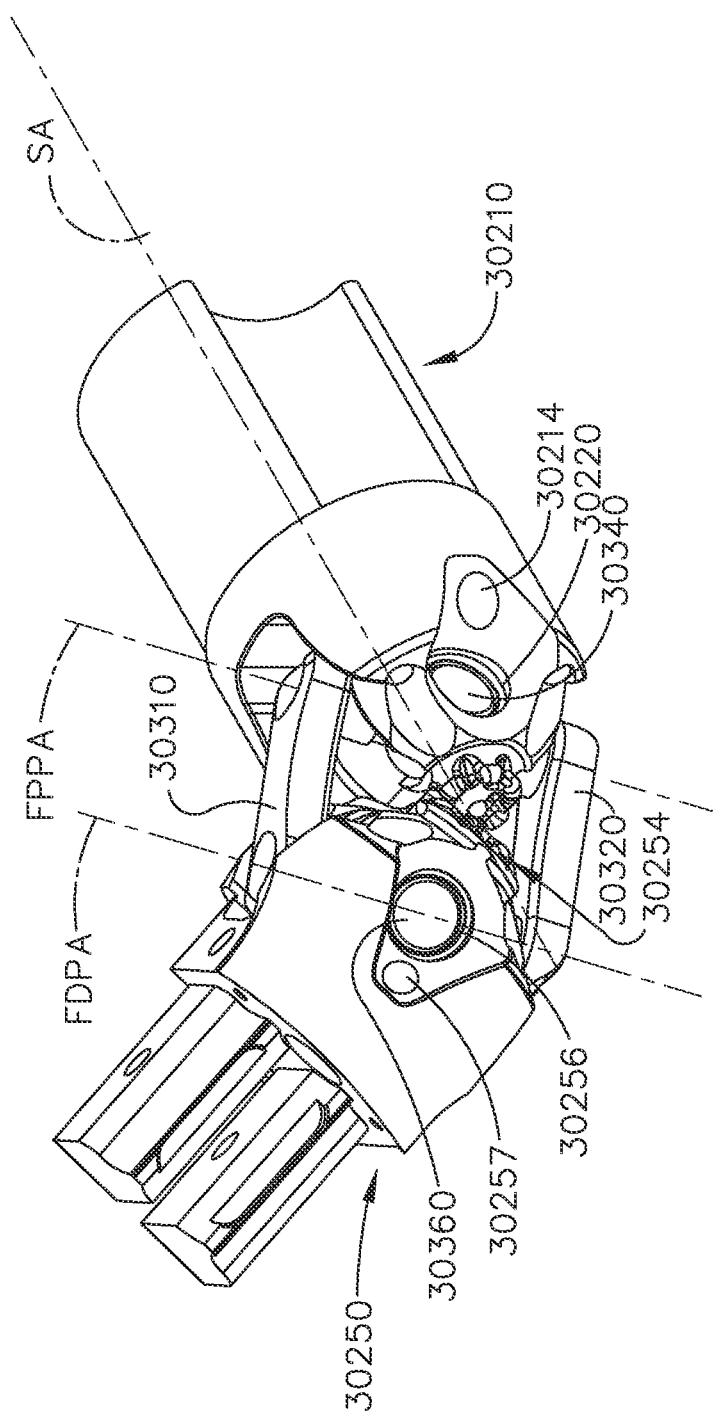
Figure 149:
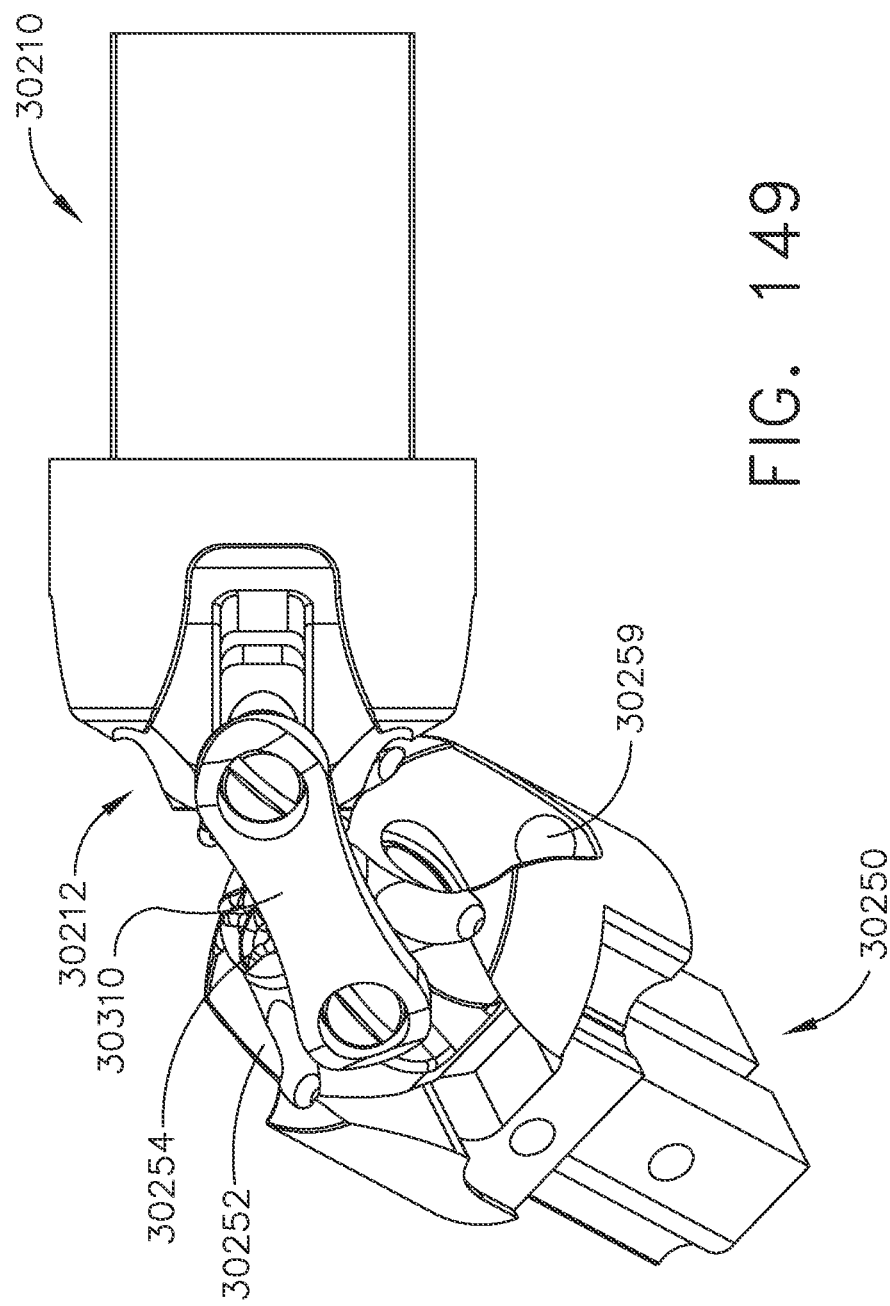
Figure 152:
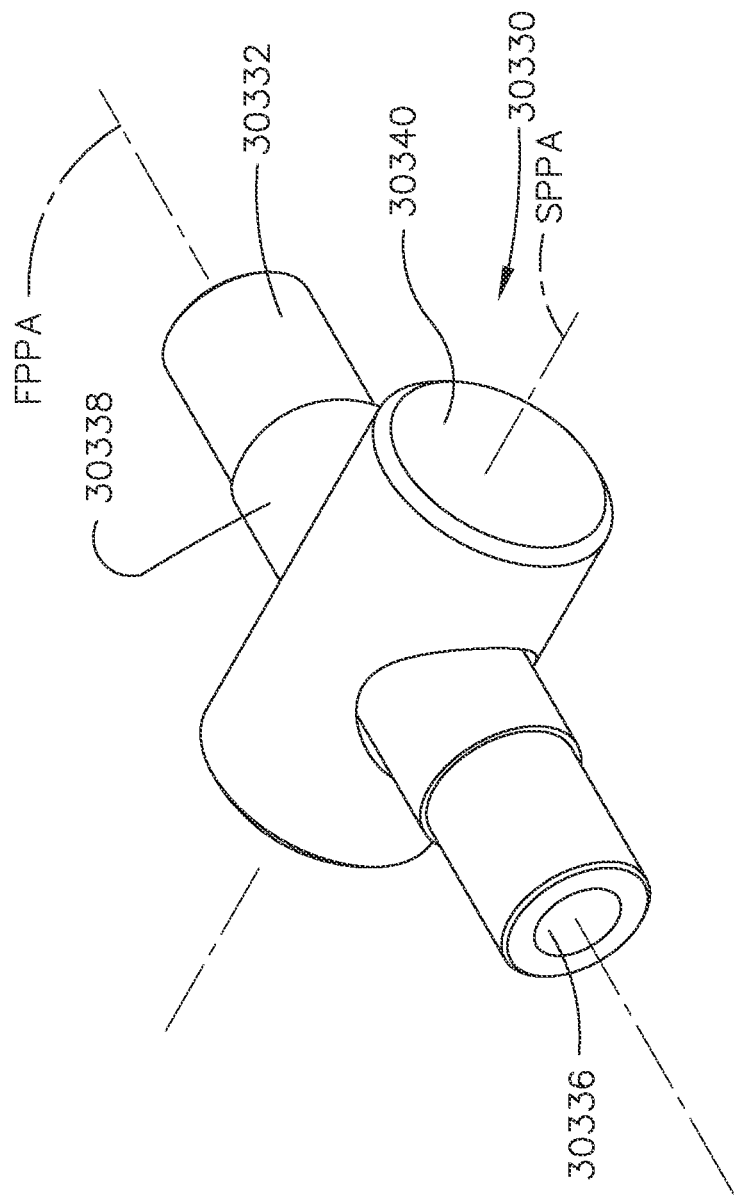
Figure 153:
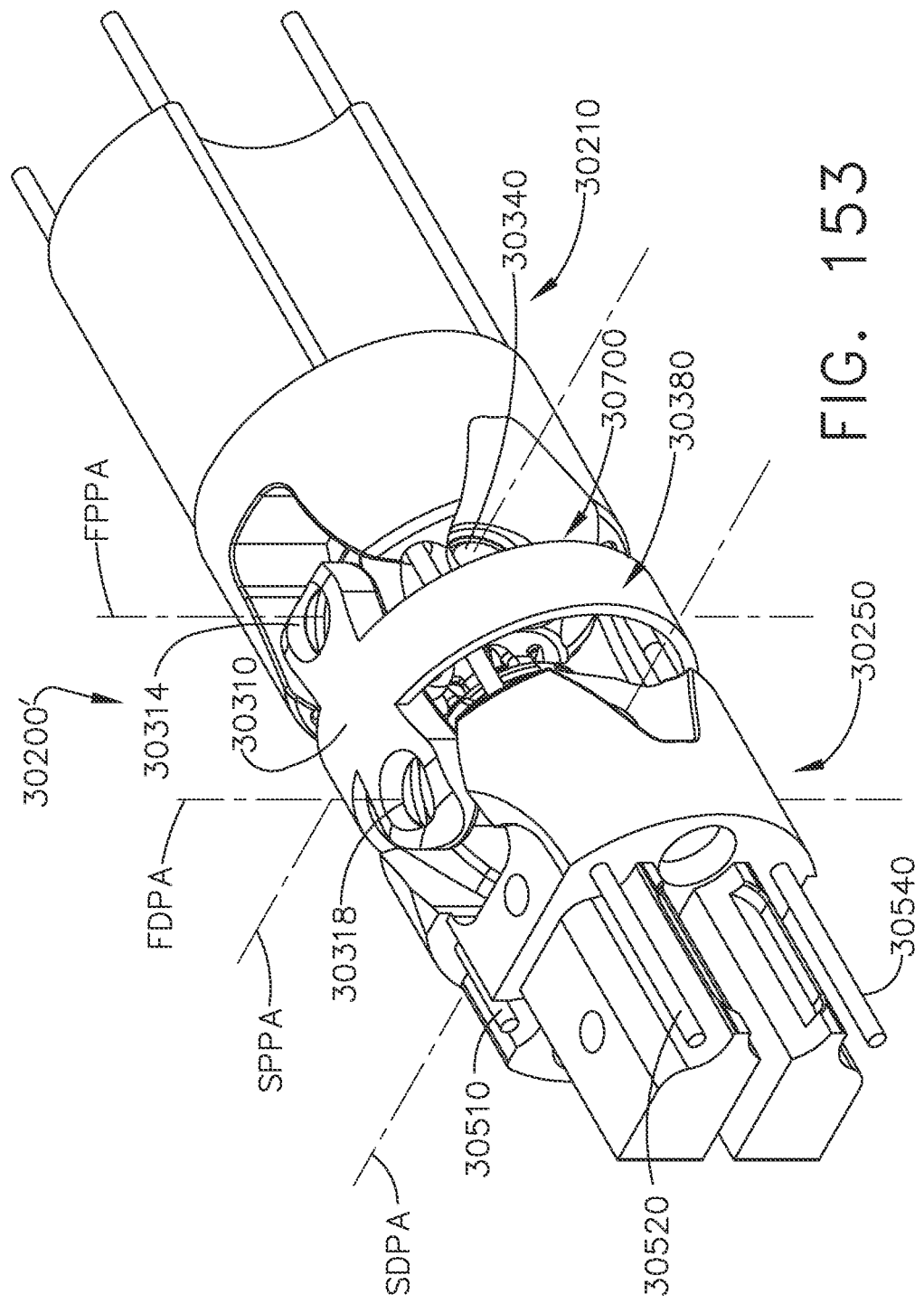
Figure 154:
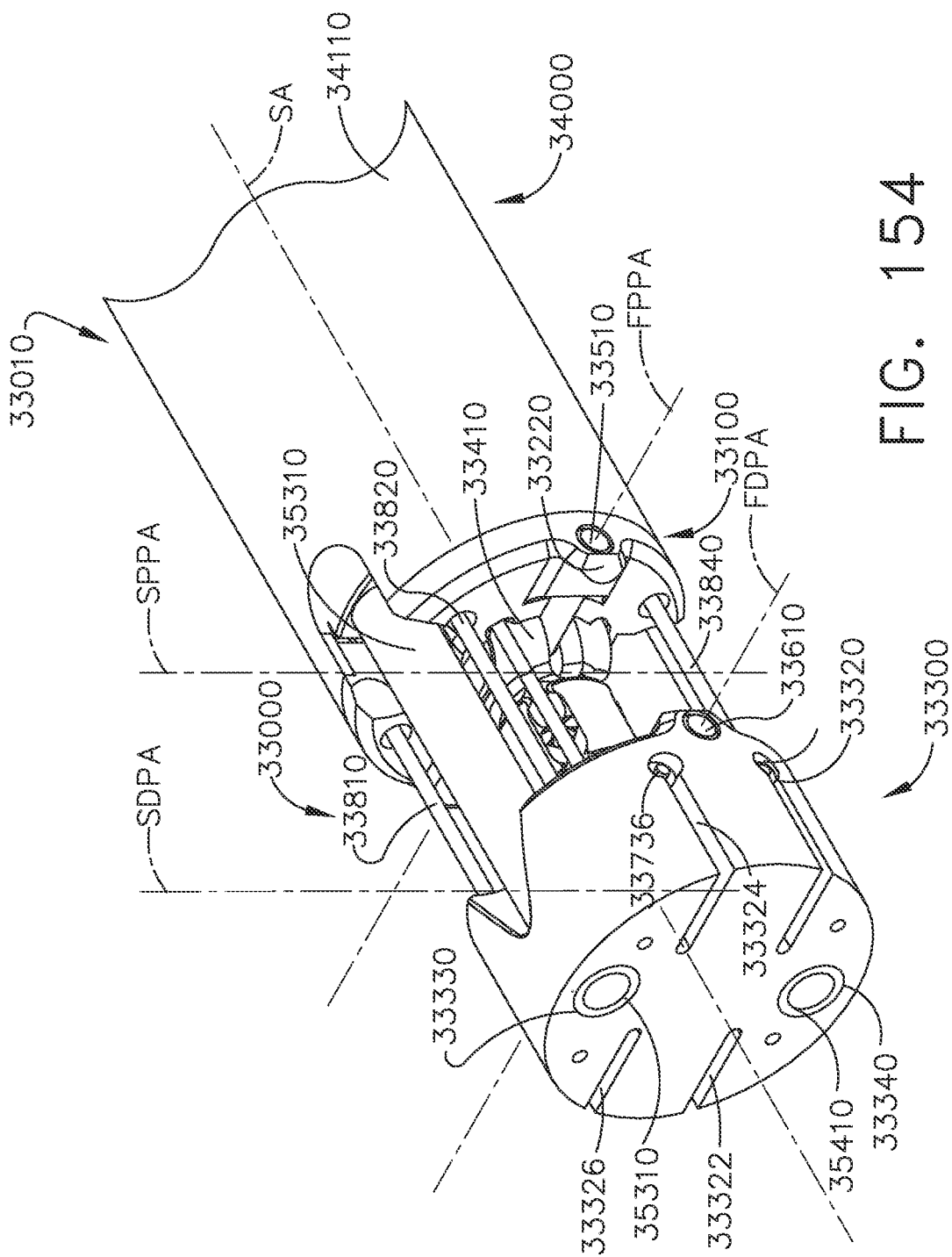
Figure 155:
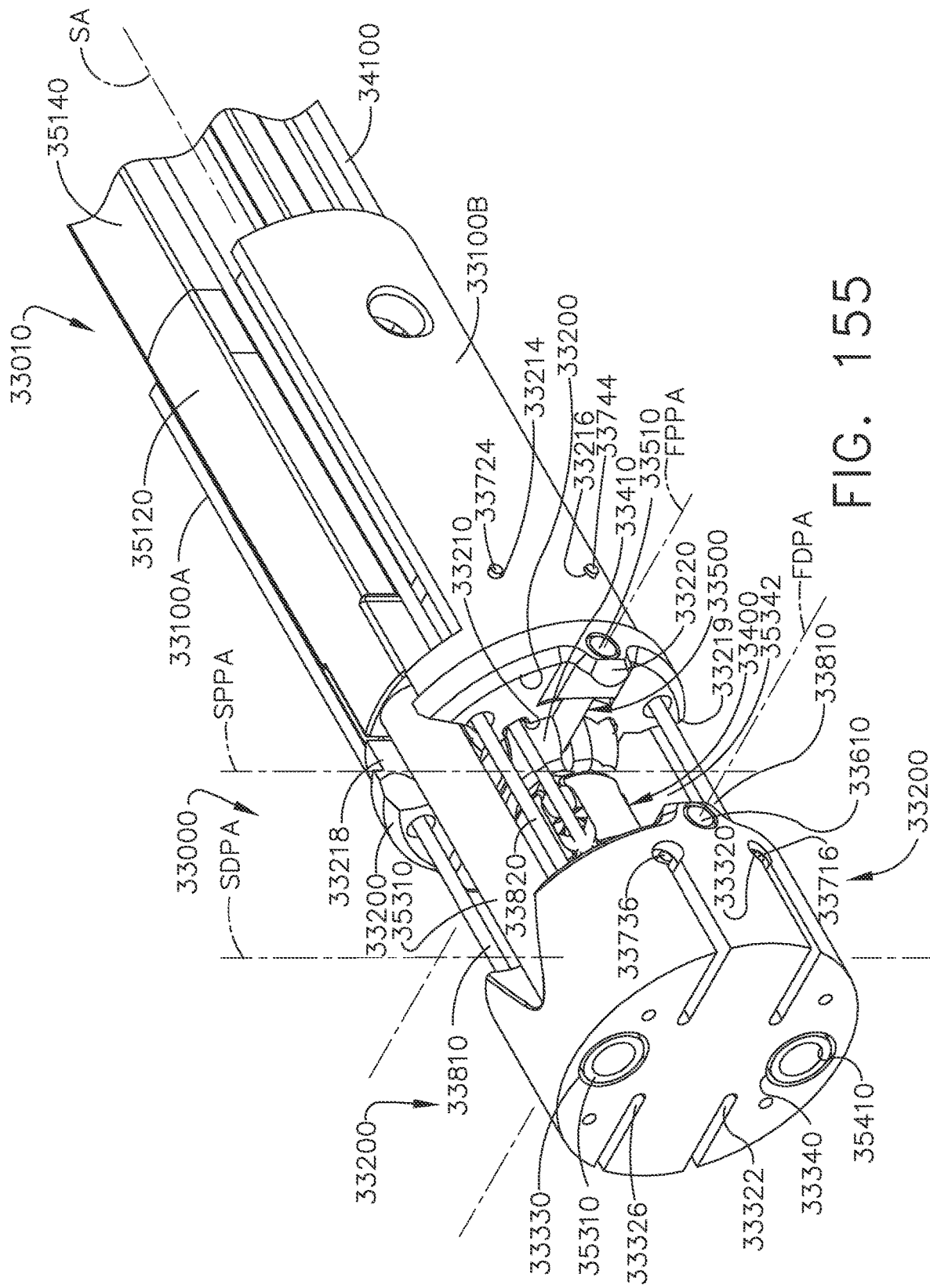
Figure 156:
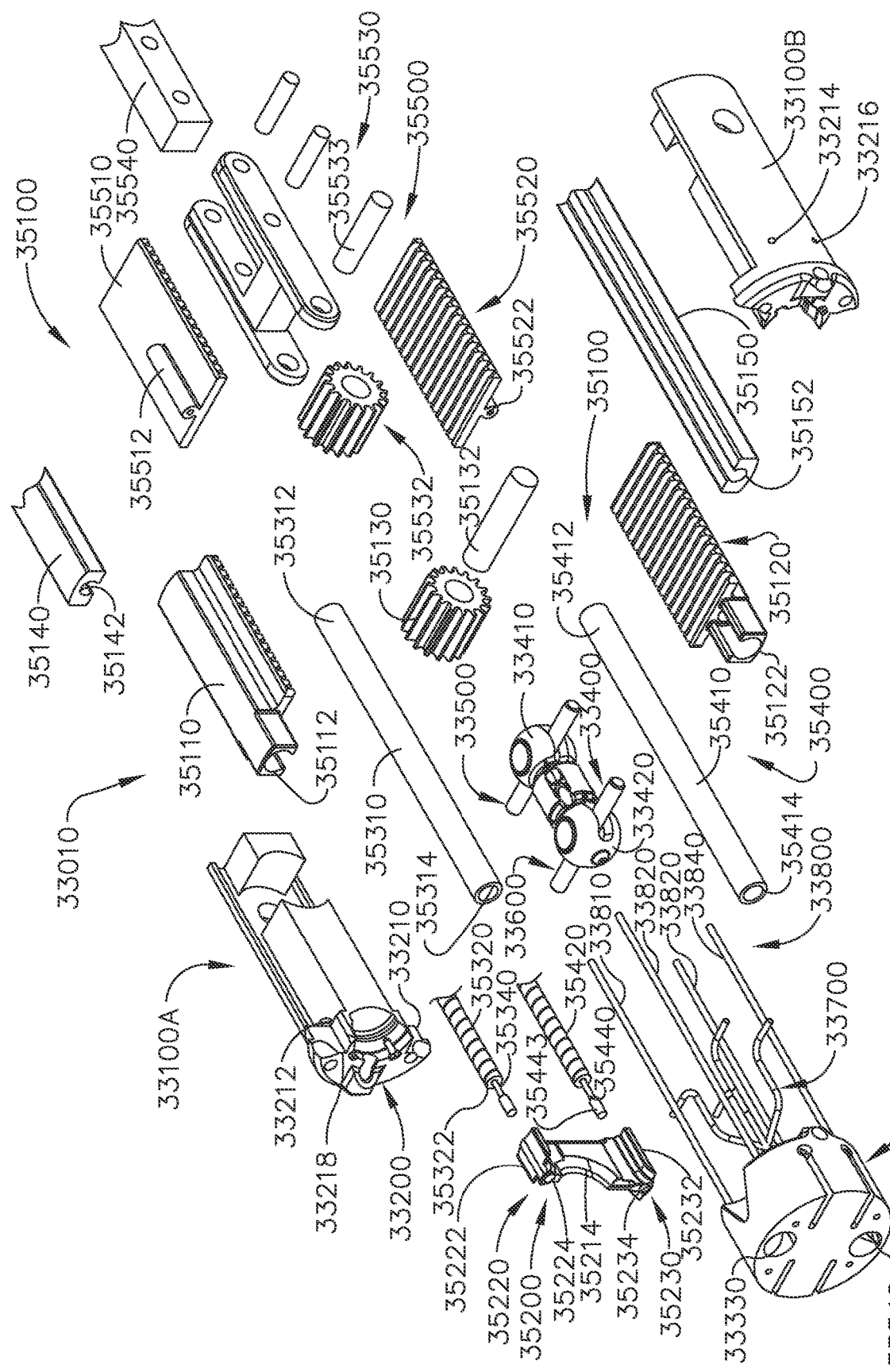
Figure 159:
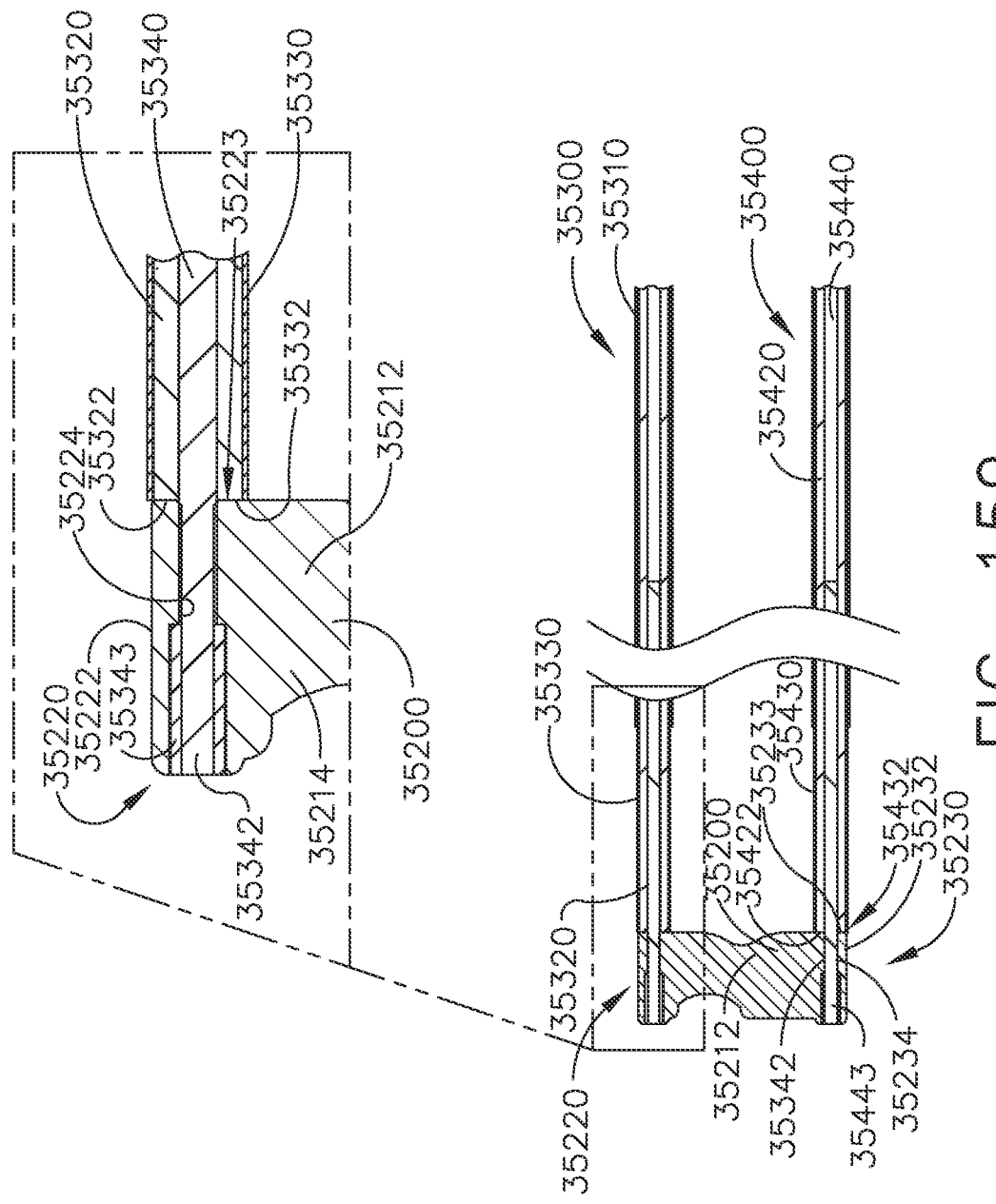
Figure 160:
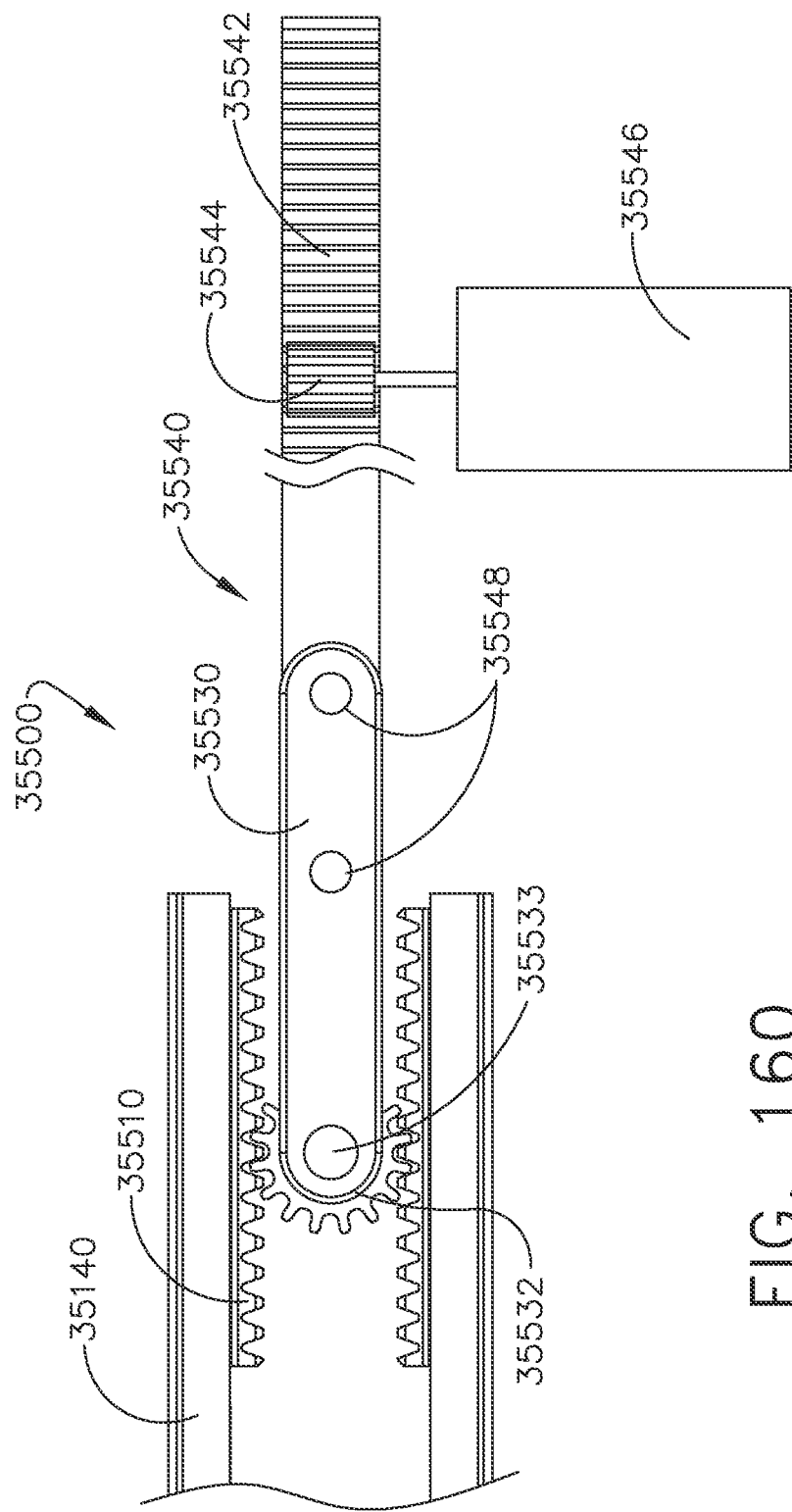
Figure 161:
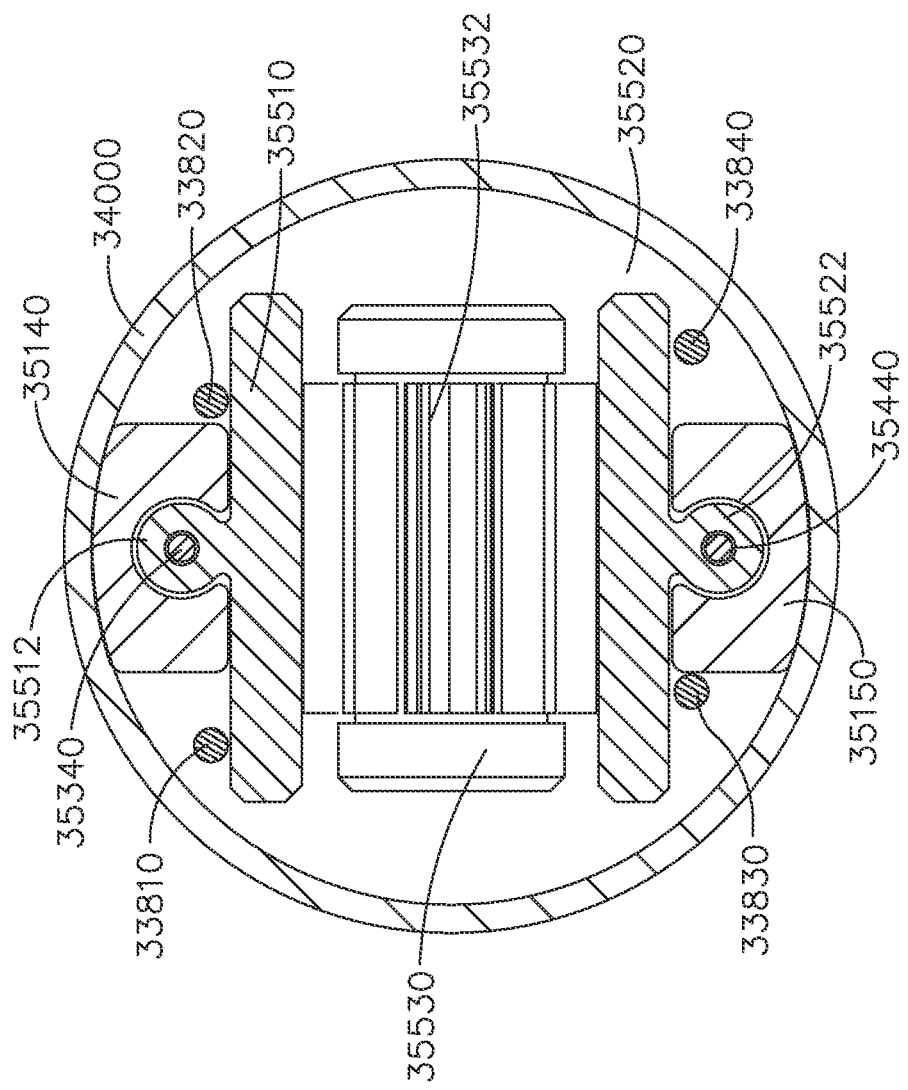
Figure 162:
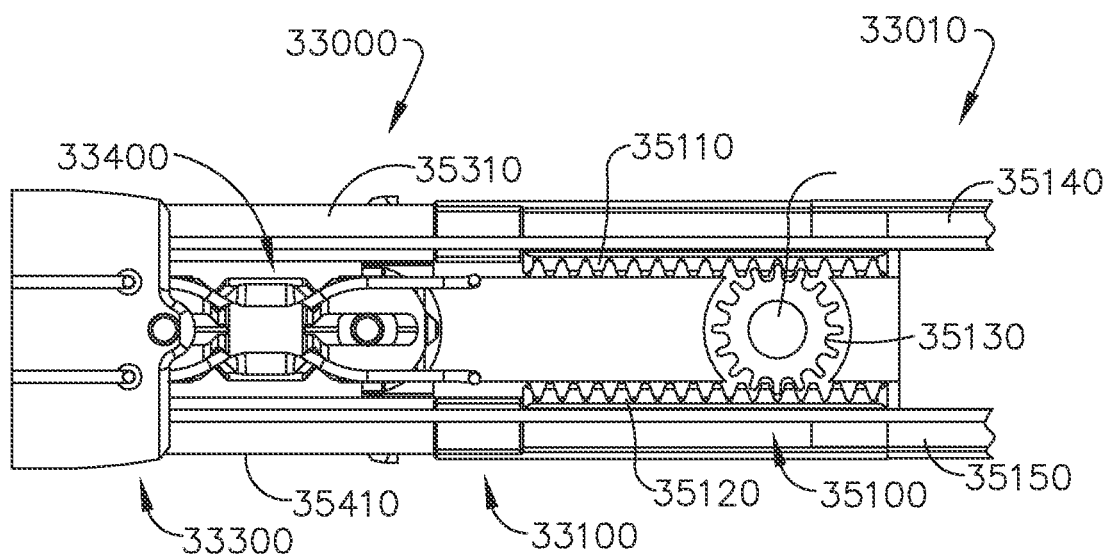
Figure 163:
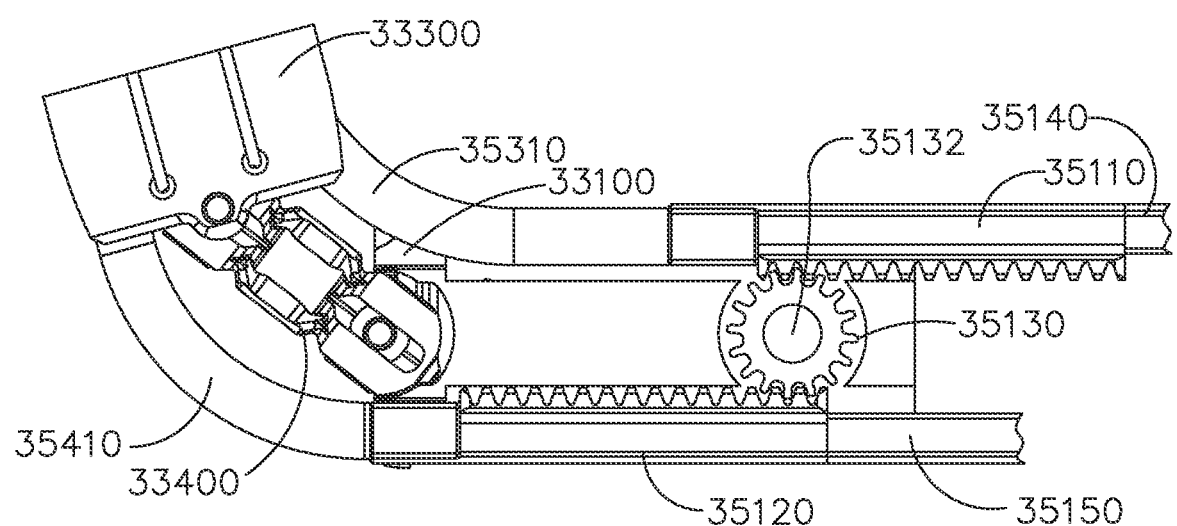
Figure 165:
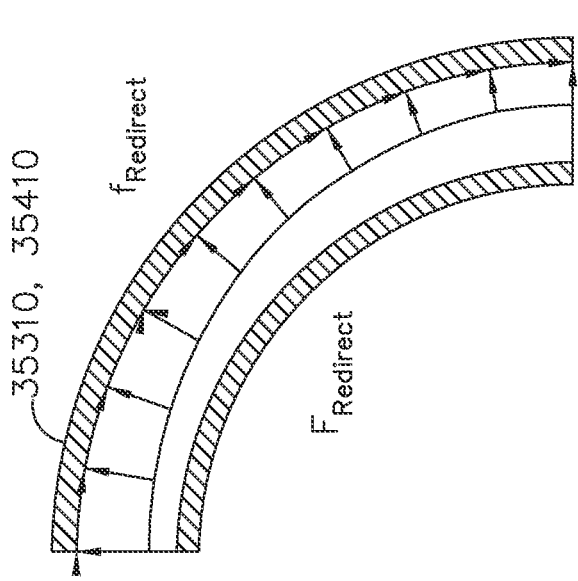
Figure 164:
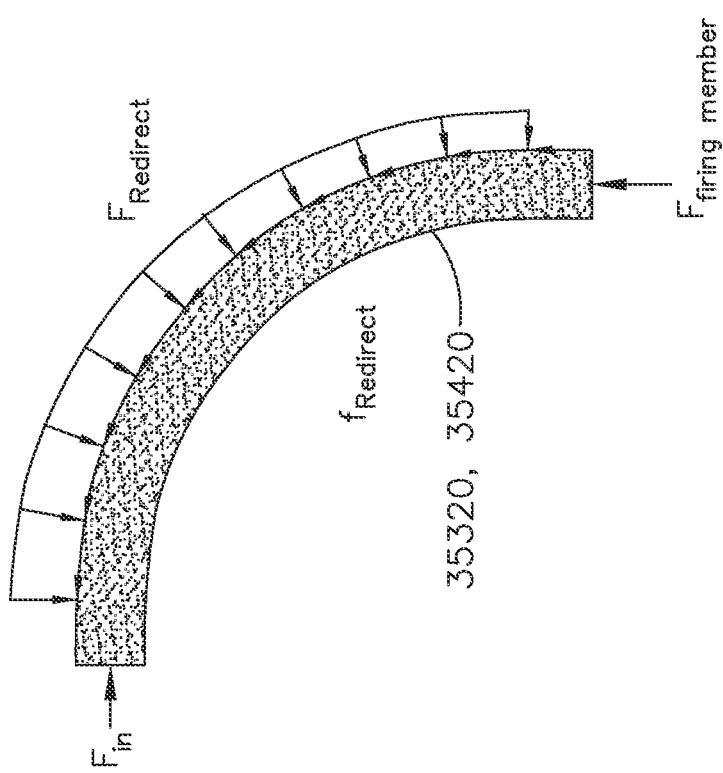
Figure 166:
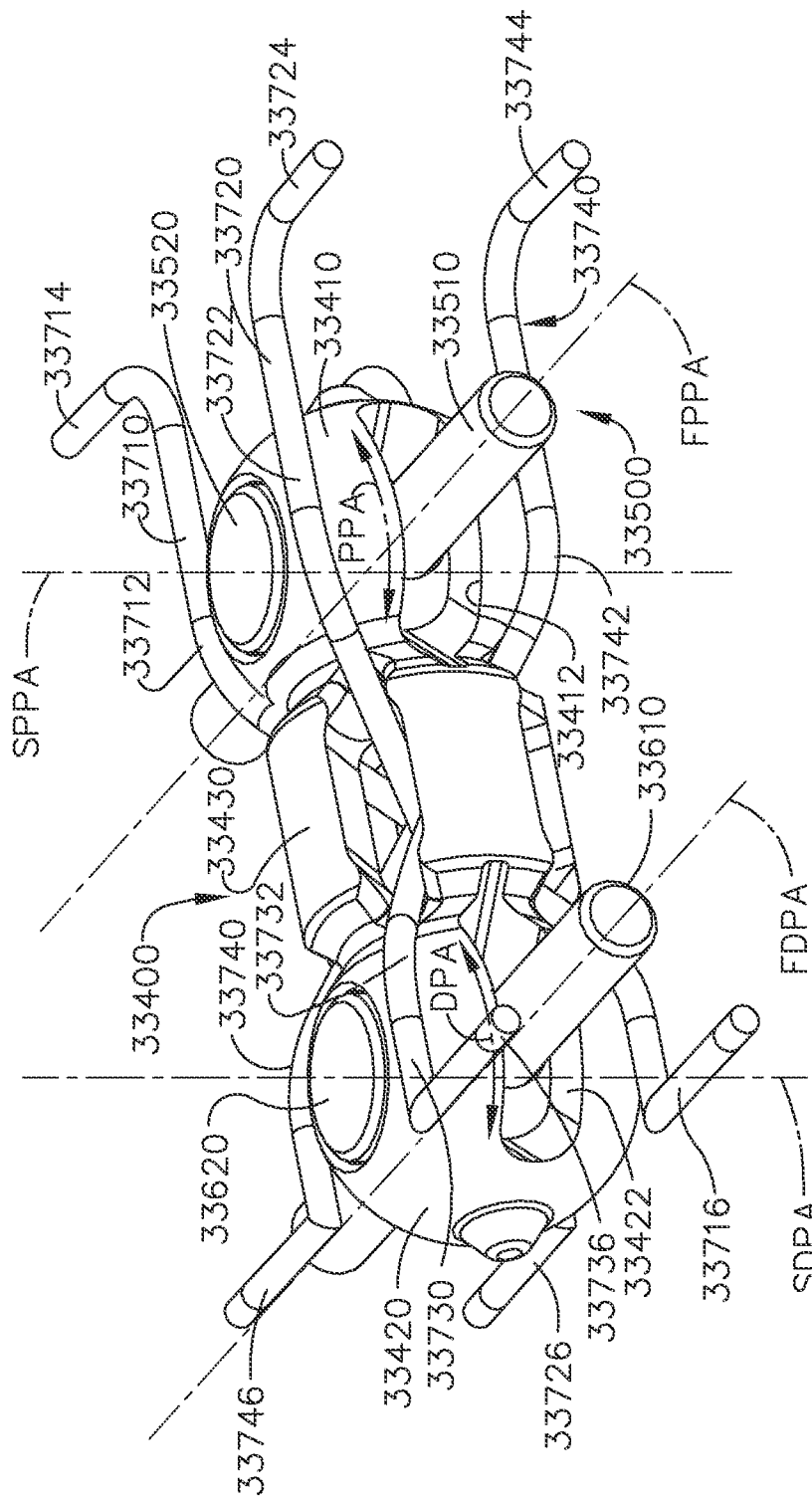
Figure 167:
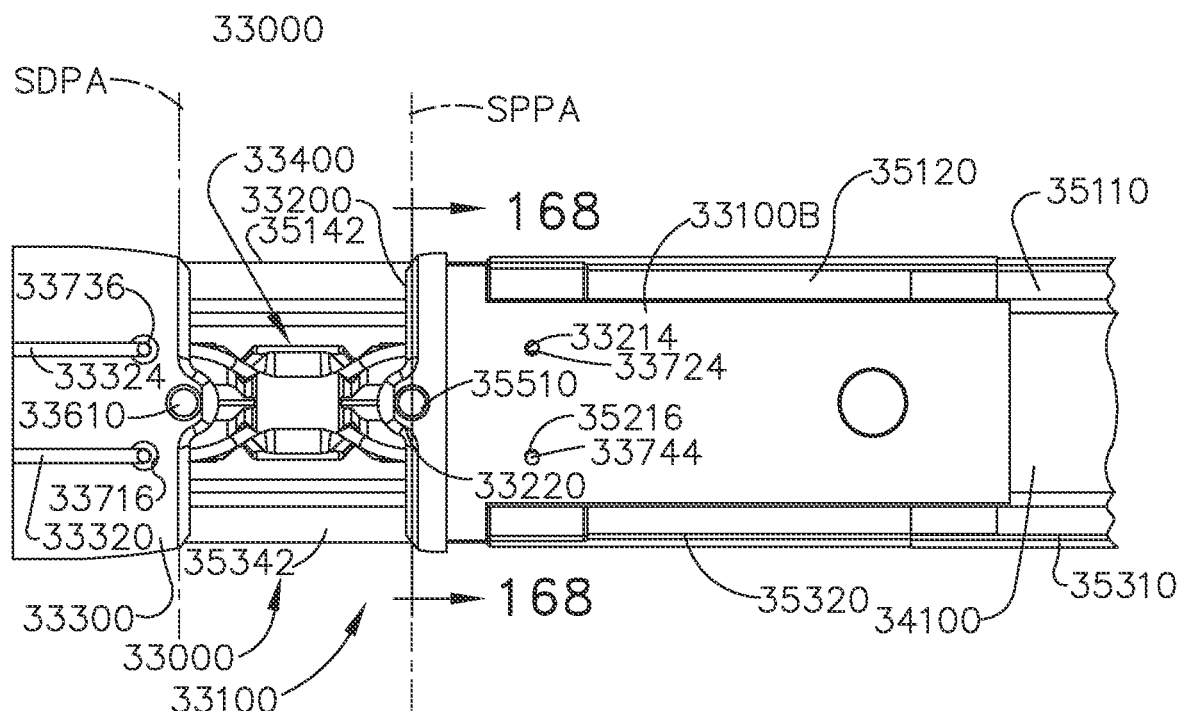
Figure 168:
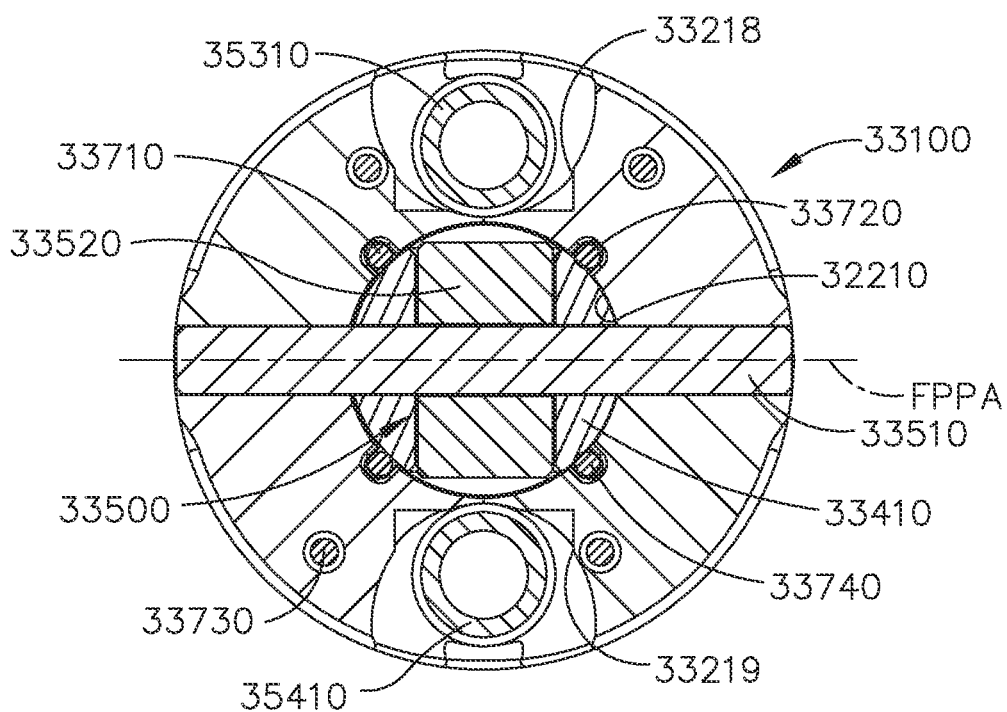
Figure 169:
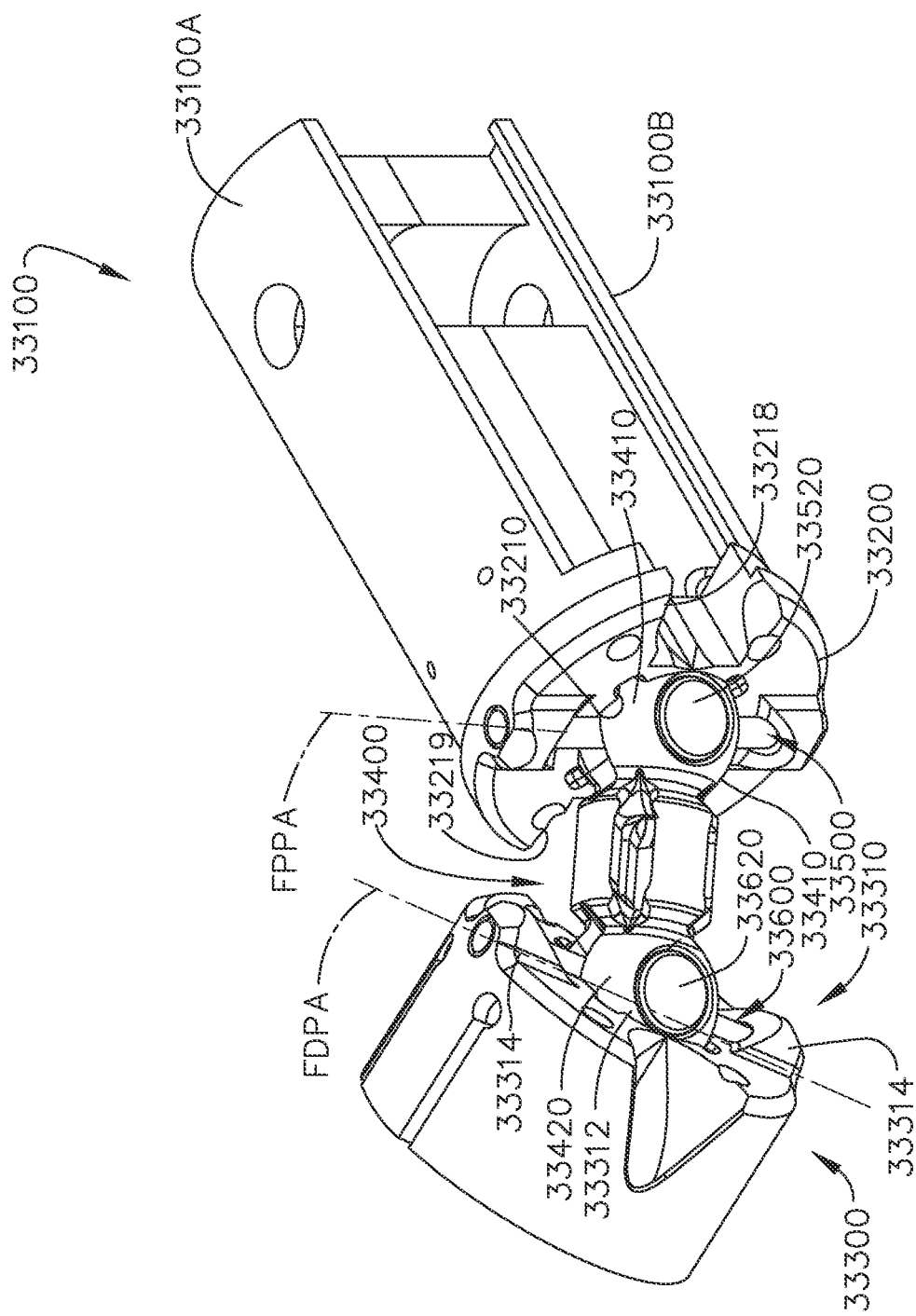
Figure 170:
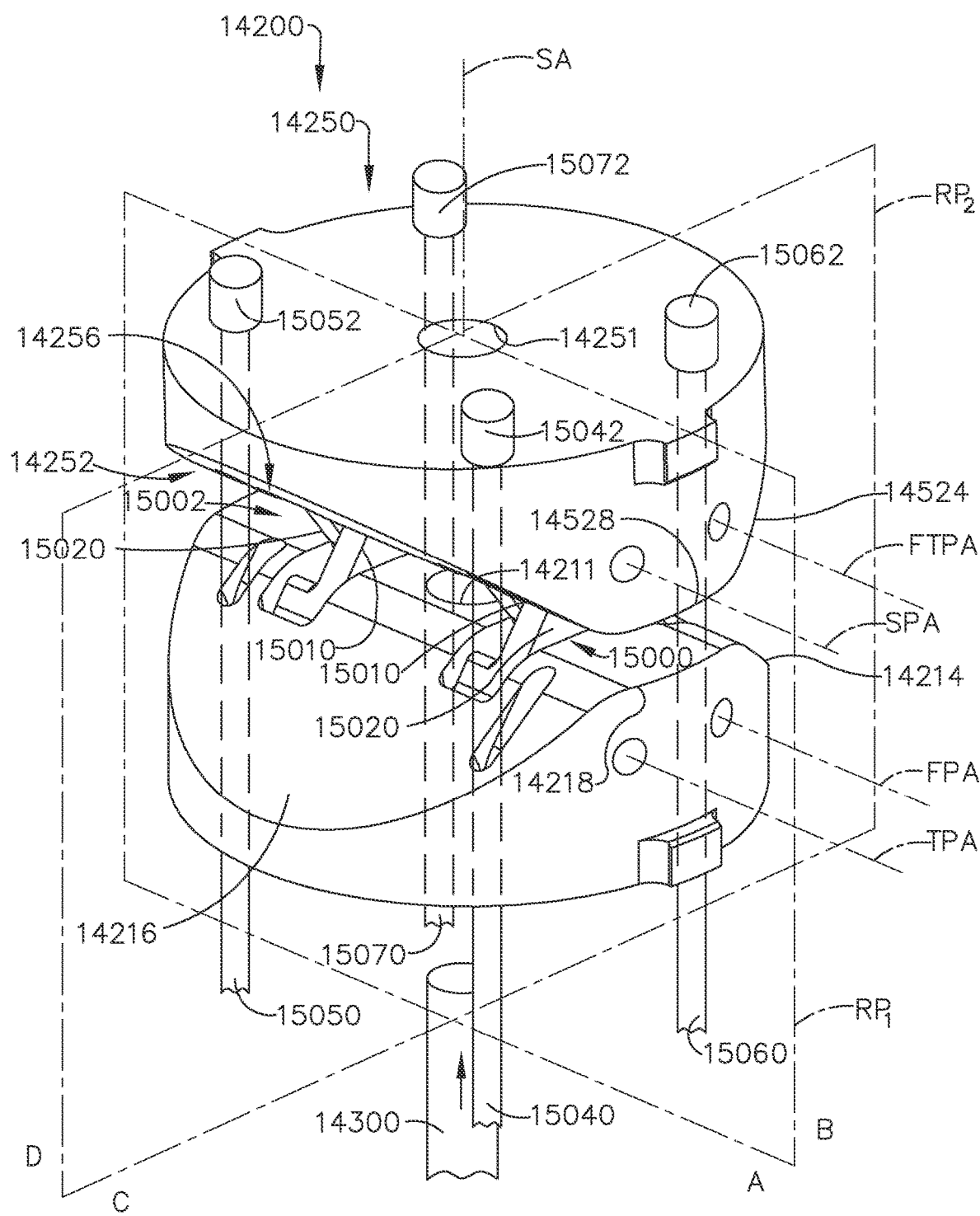
Figure 173:
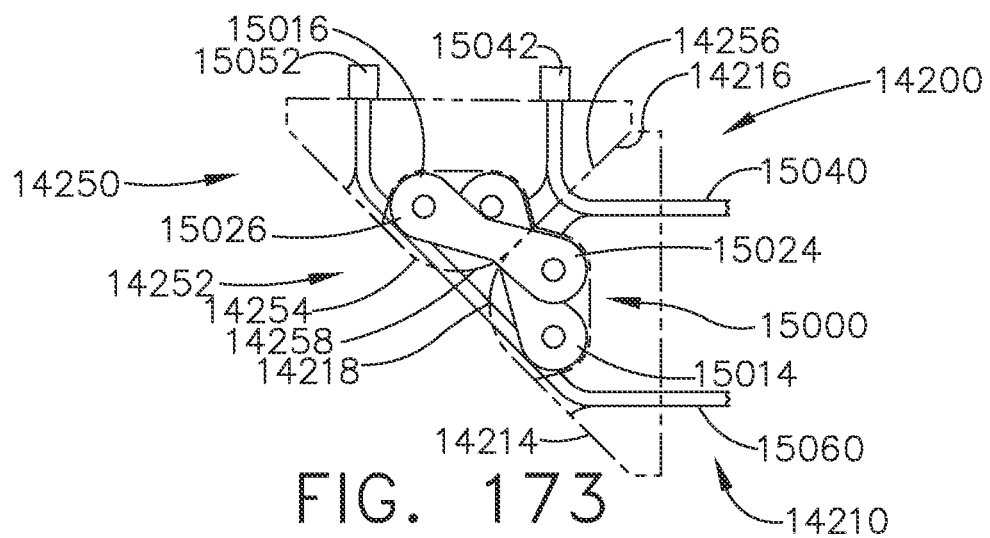
Figure 172:
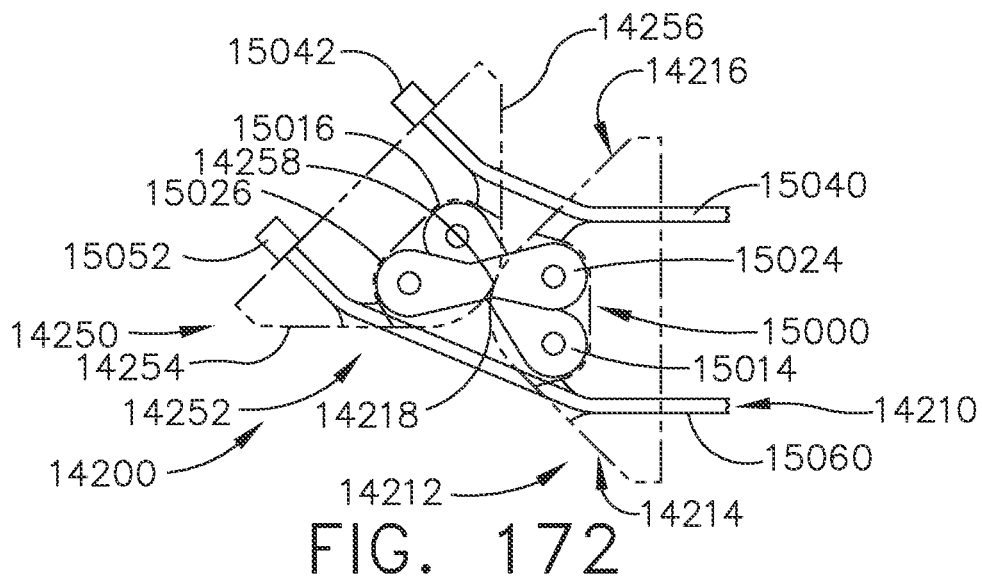
Figure 171:
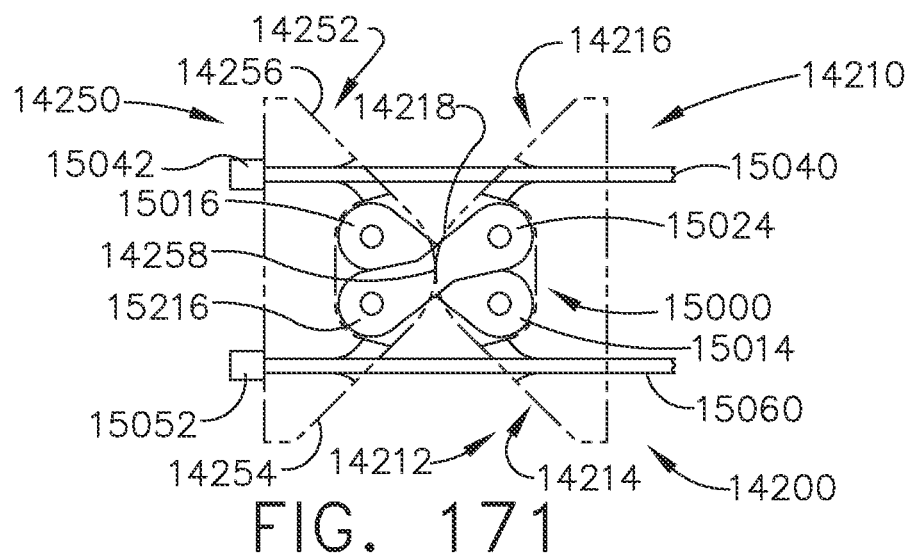
Figure 175:
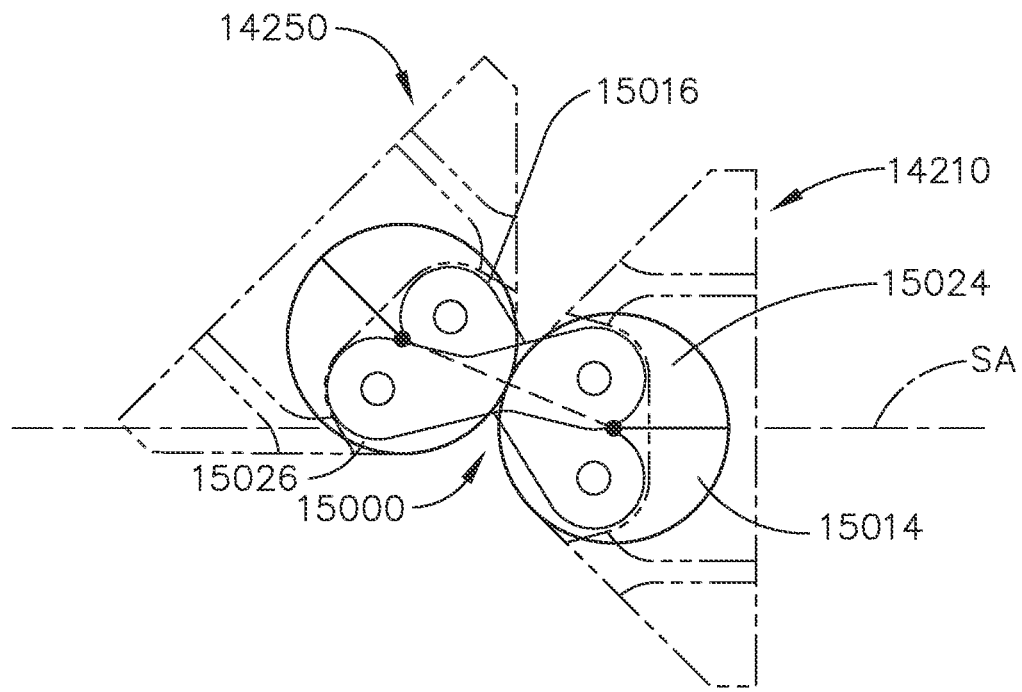
Figure 174:
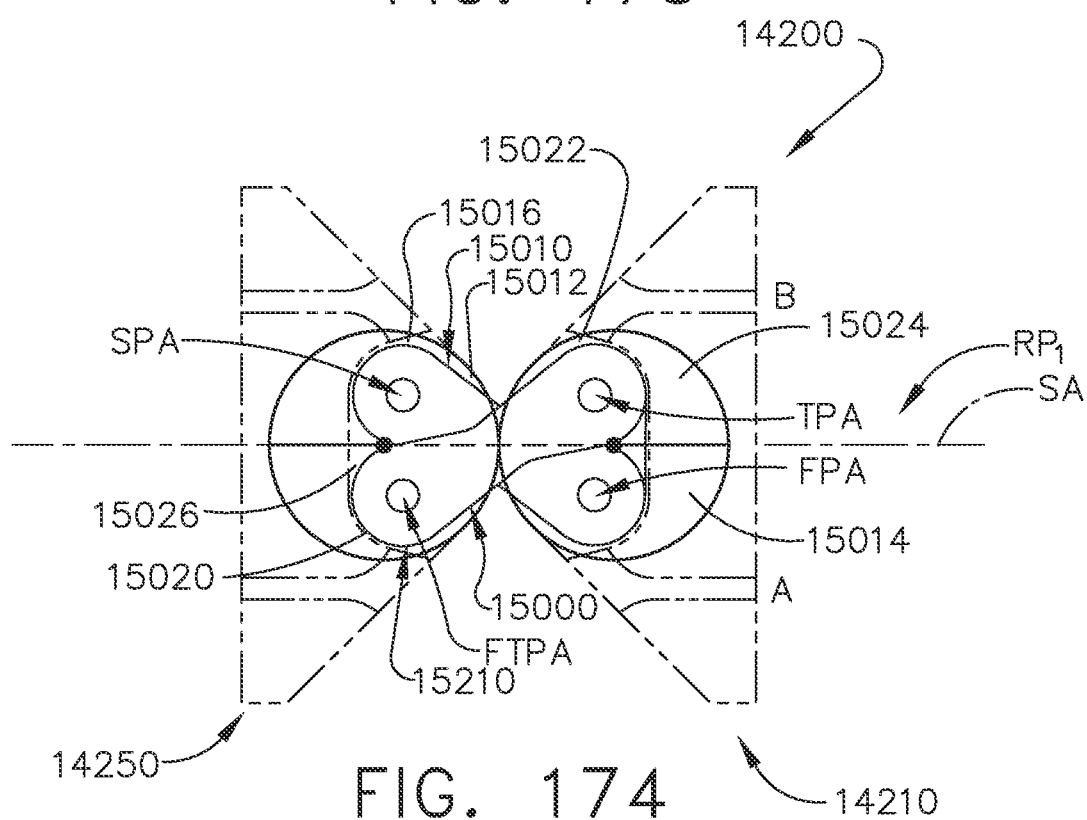
Figure 177:
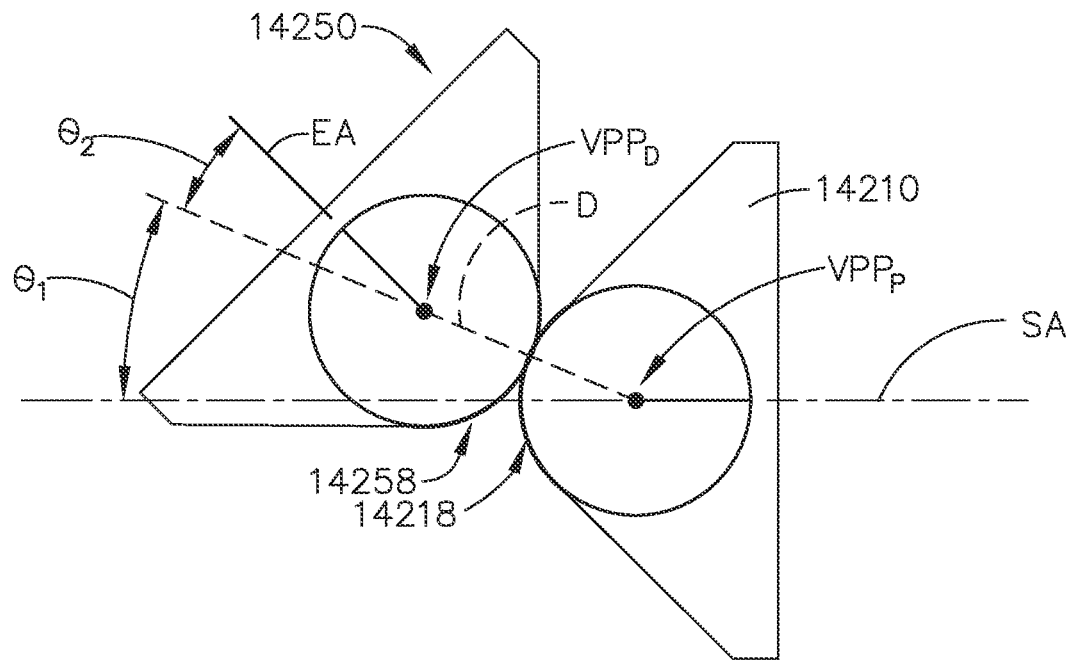
Figure 176:
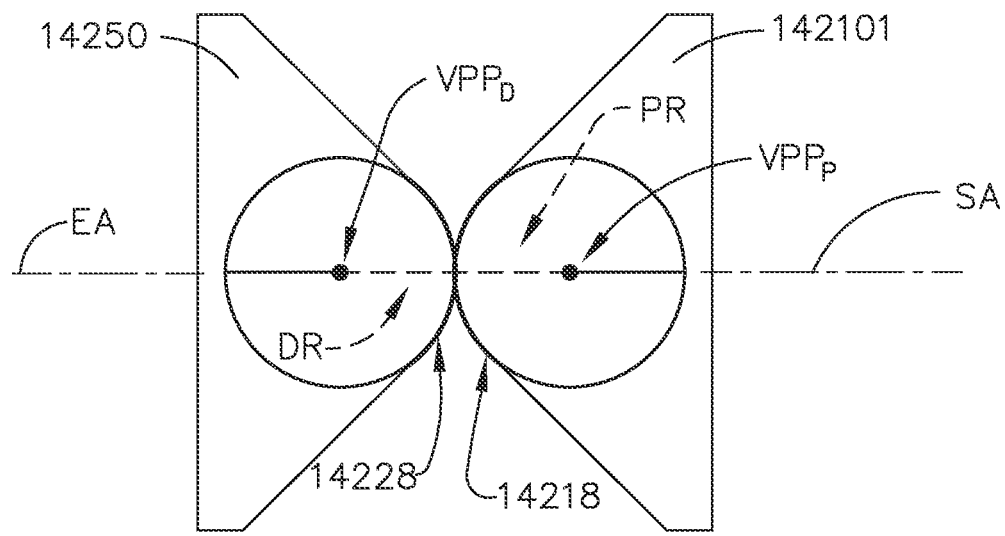
Figure 178:
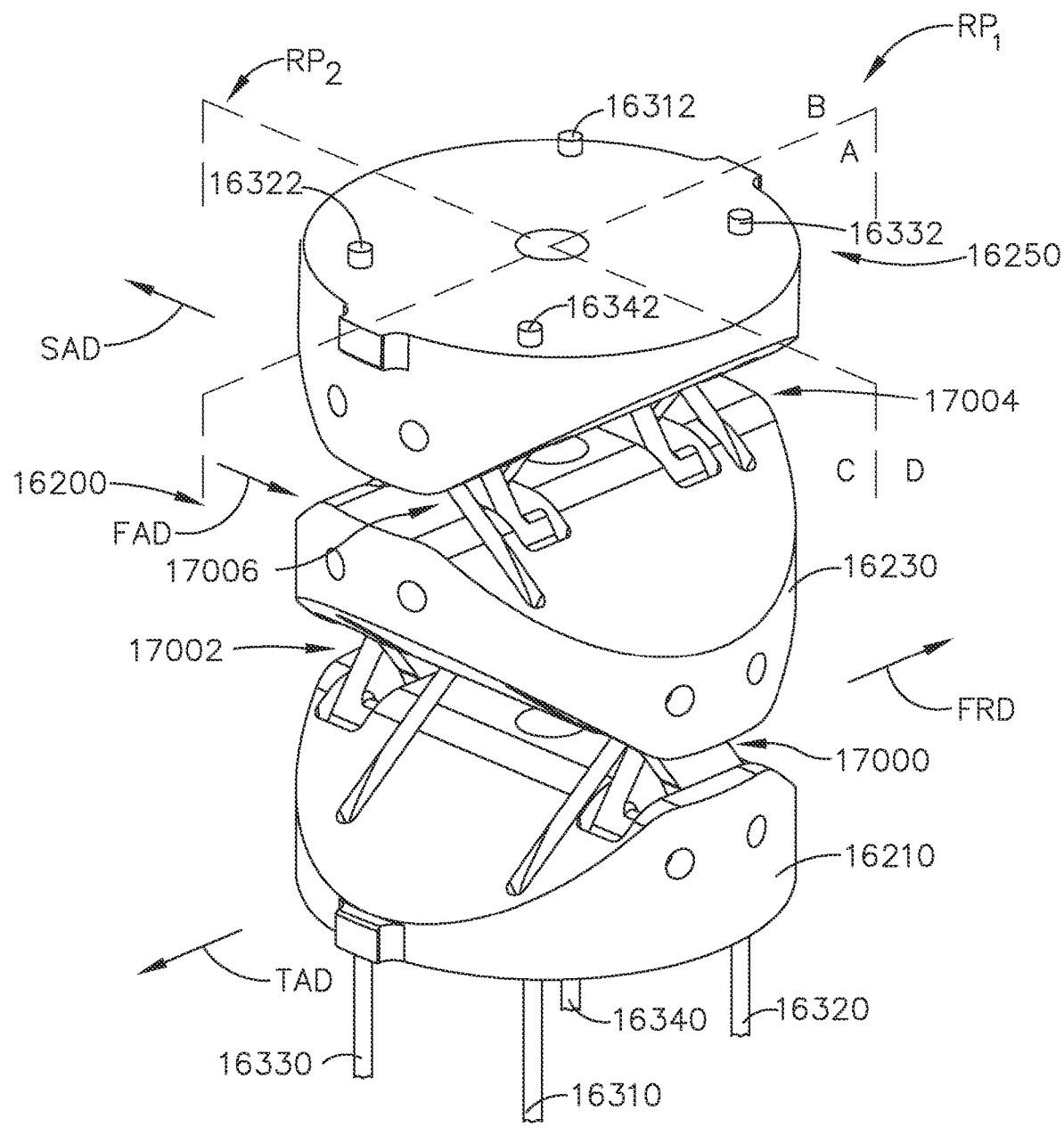
Figure 179:
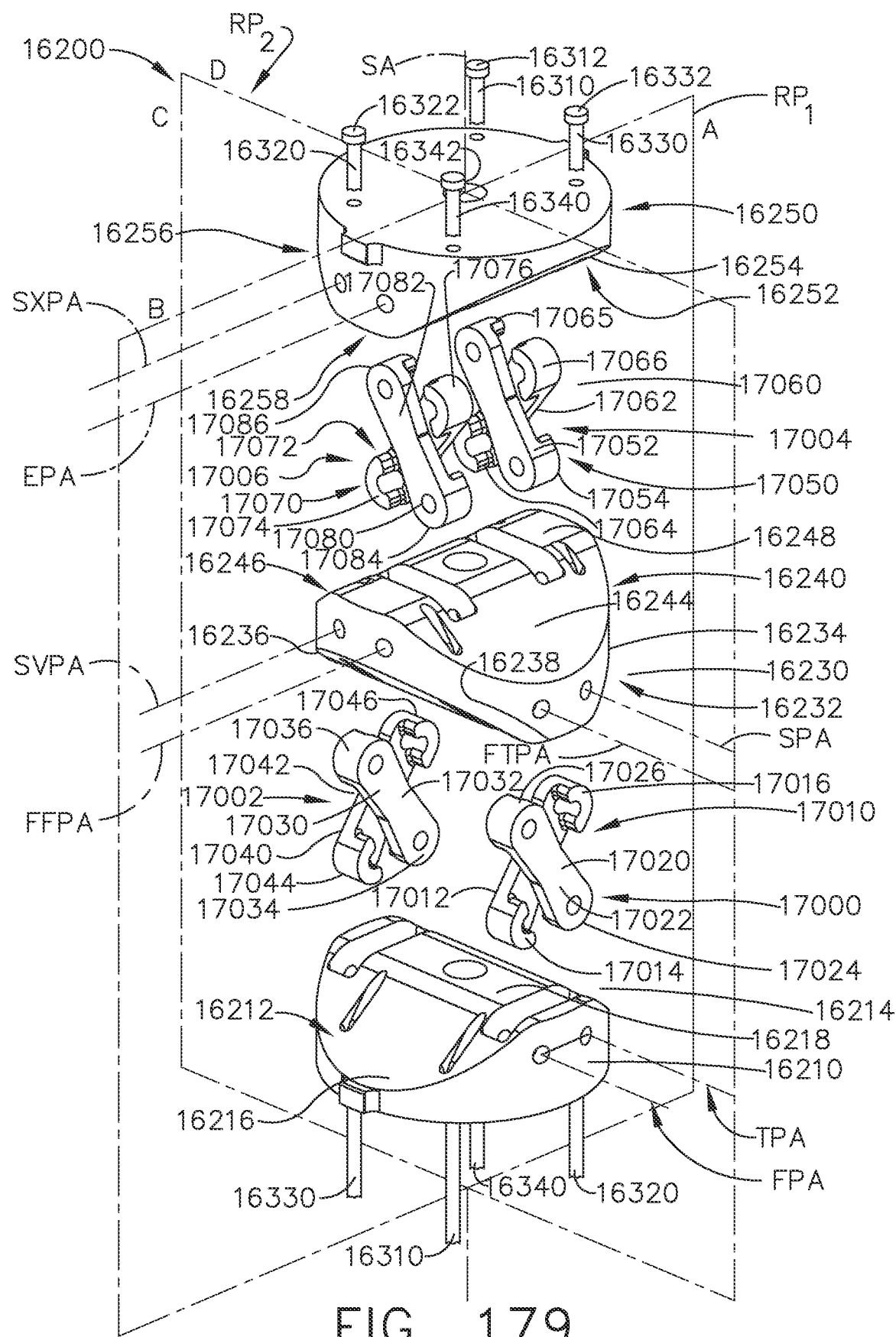
Figure 180:
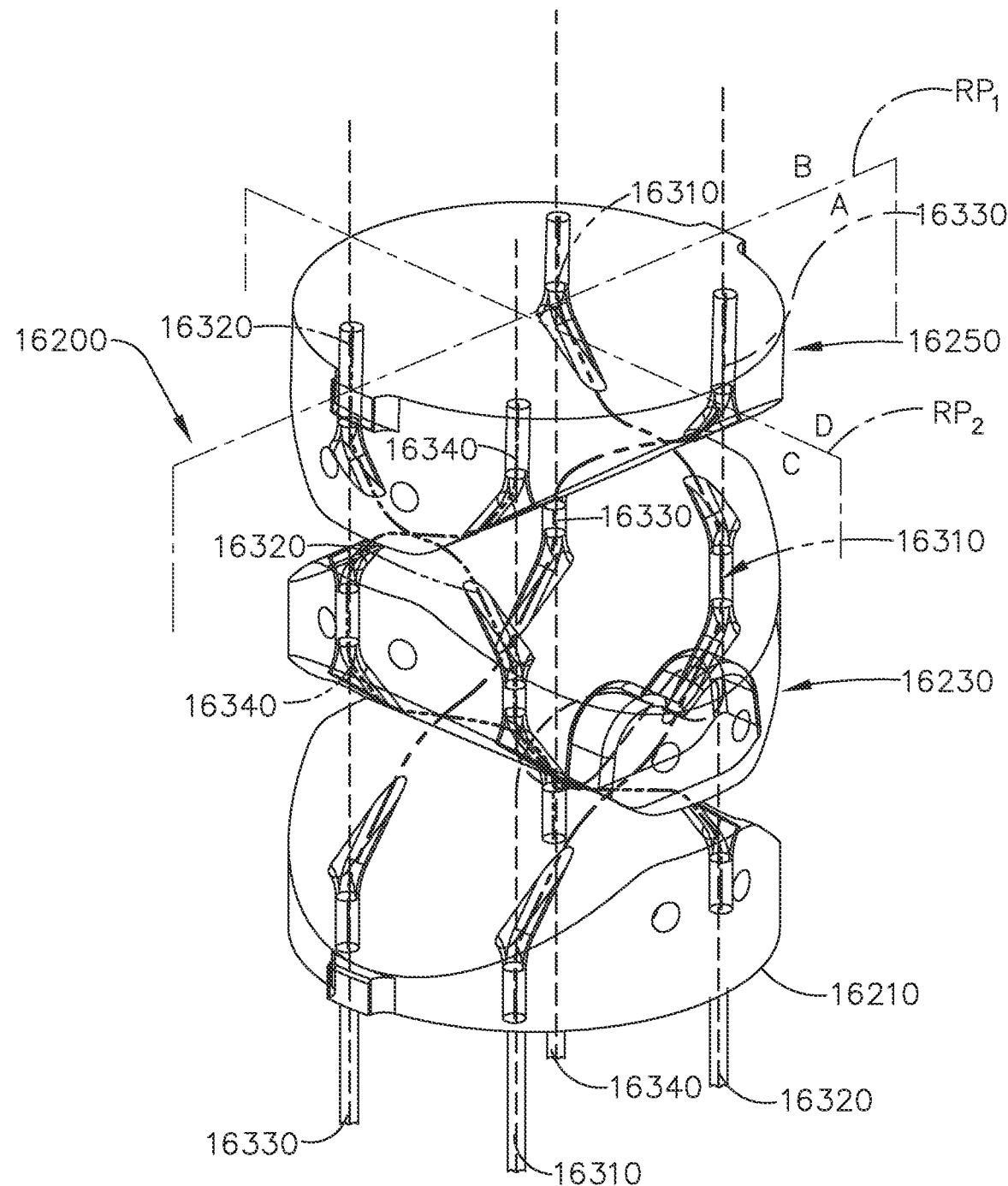
Figure 181:
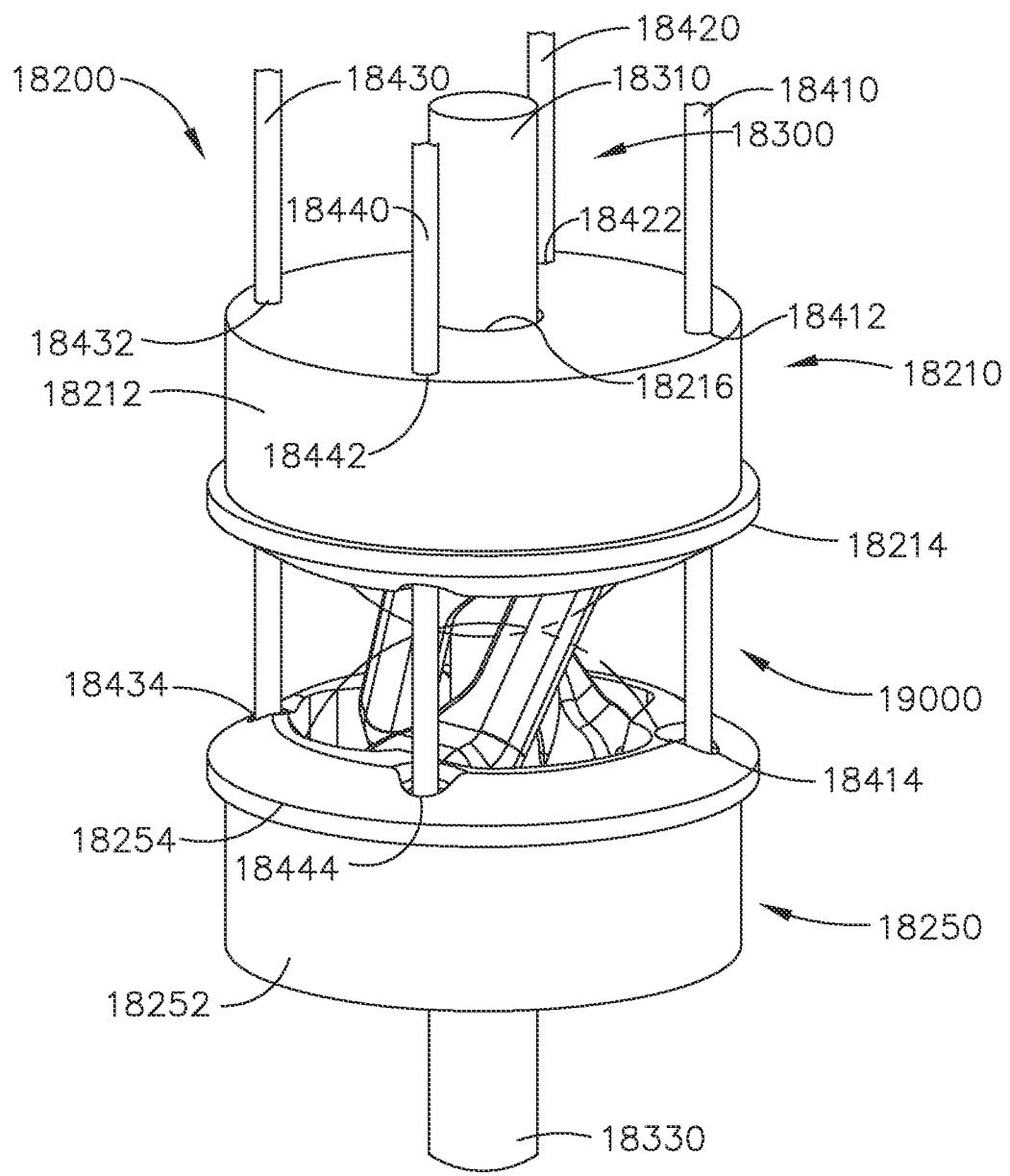
Figure 182:
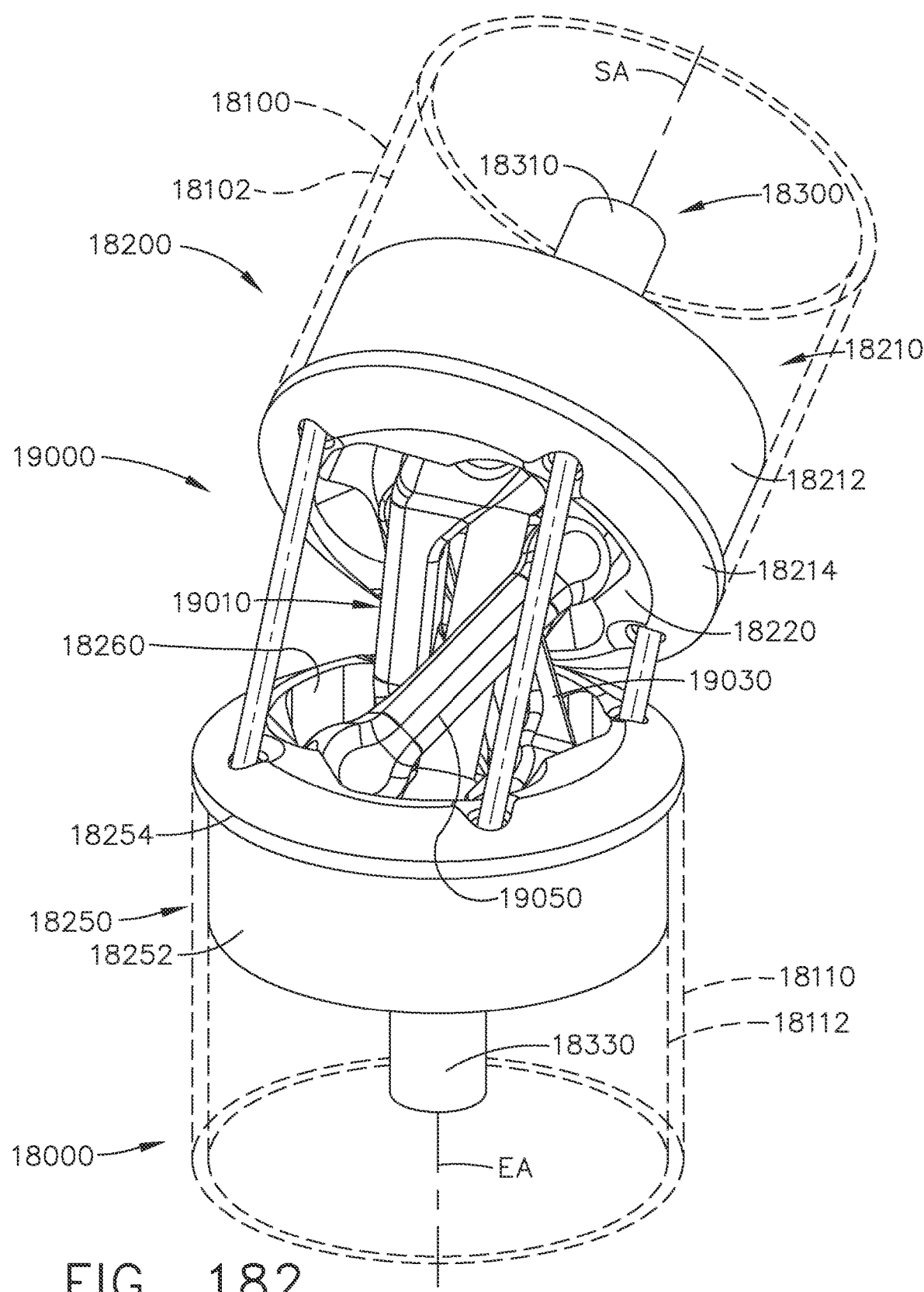
Figure 183:
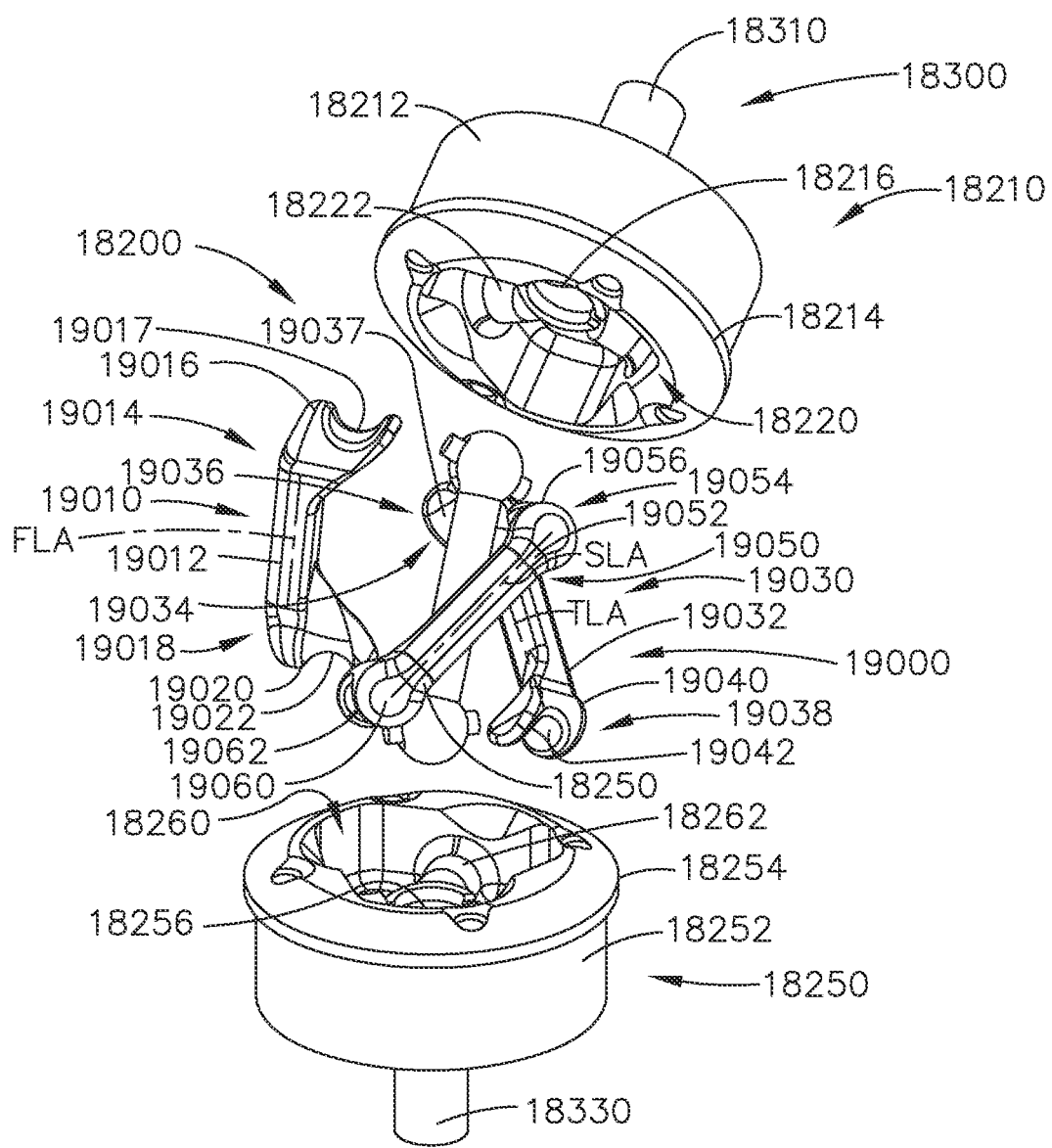
Figure 184:
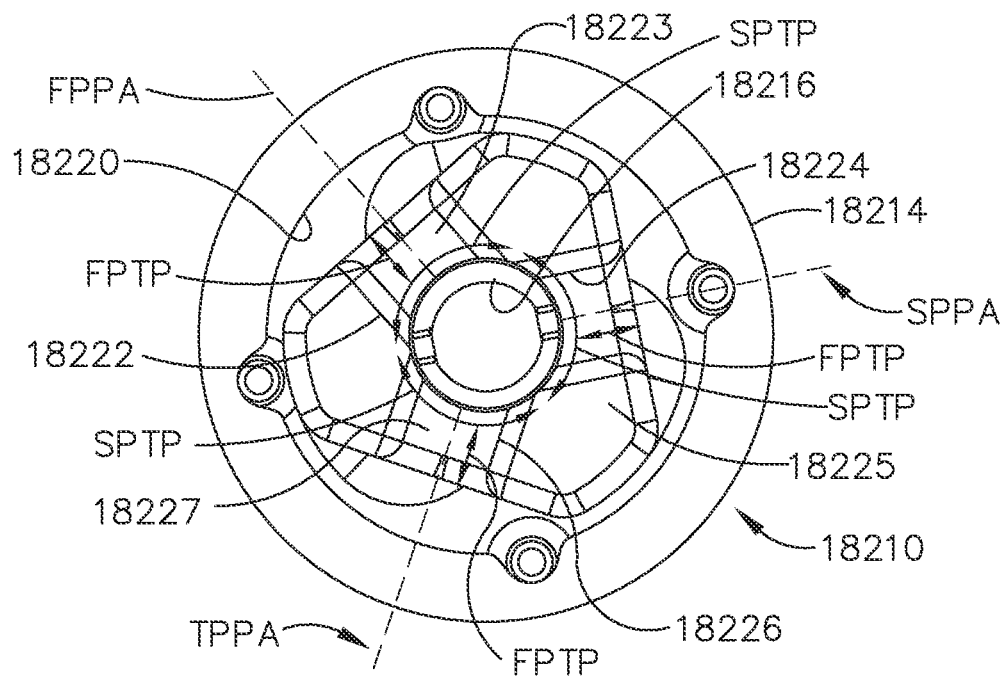
Figure 185:
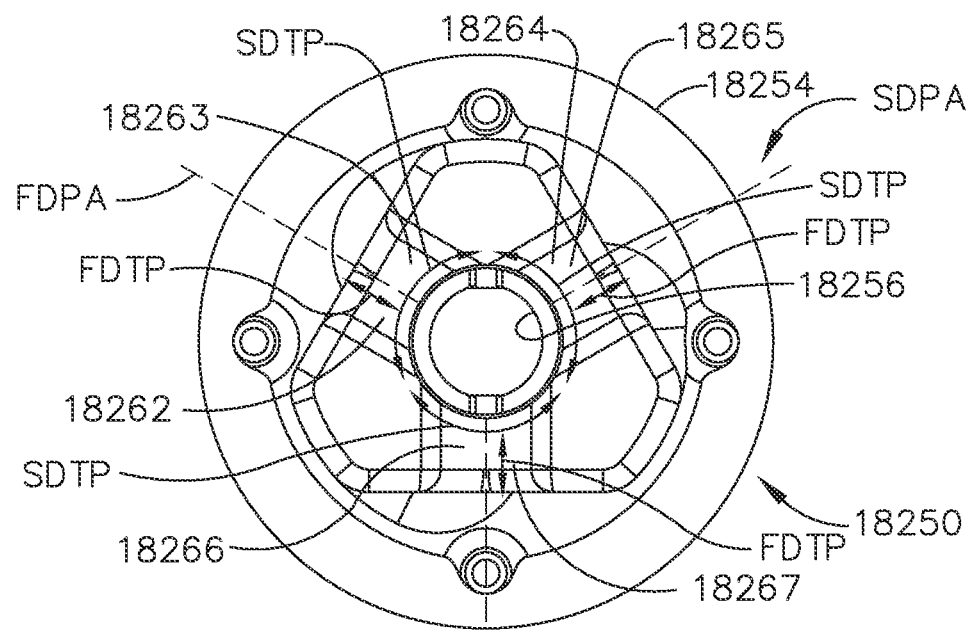
Figures 188, 189:
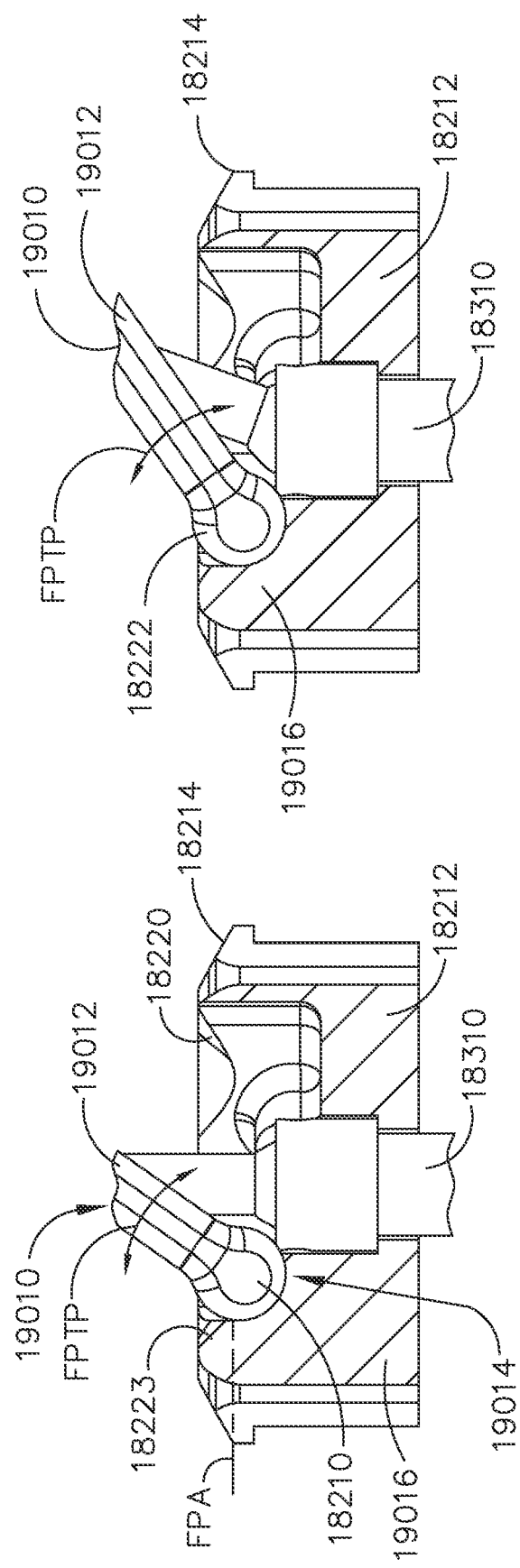
Figure 190:
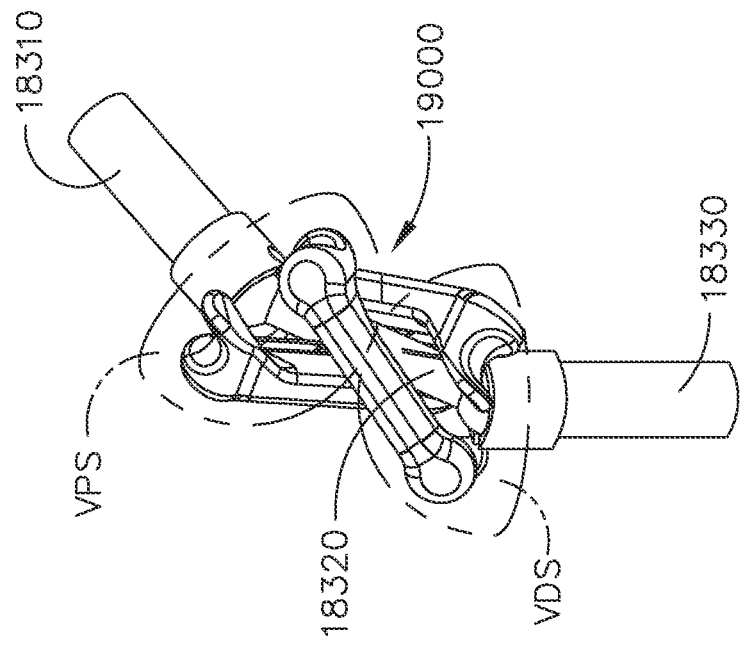
Figure 191:
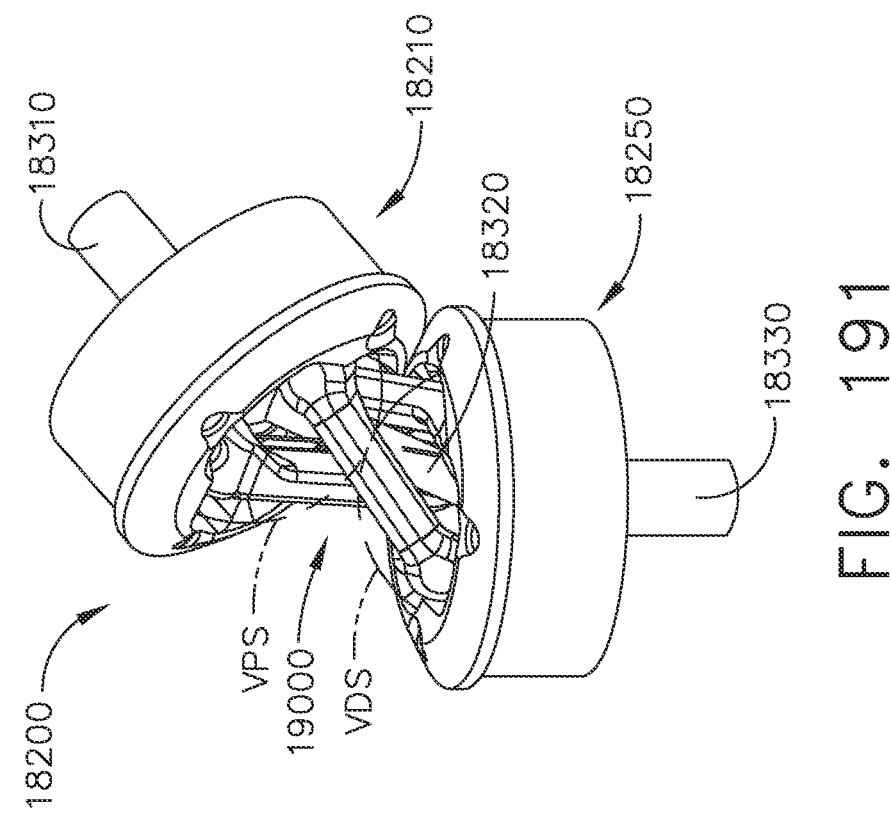
Figure 192:
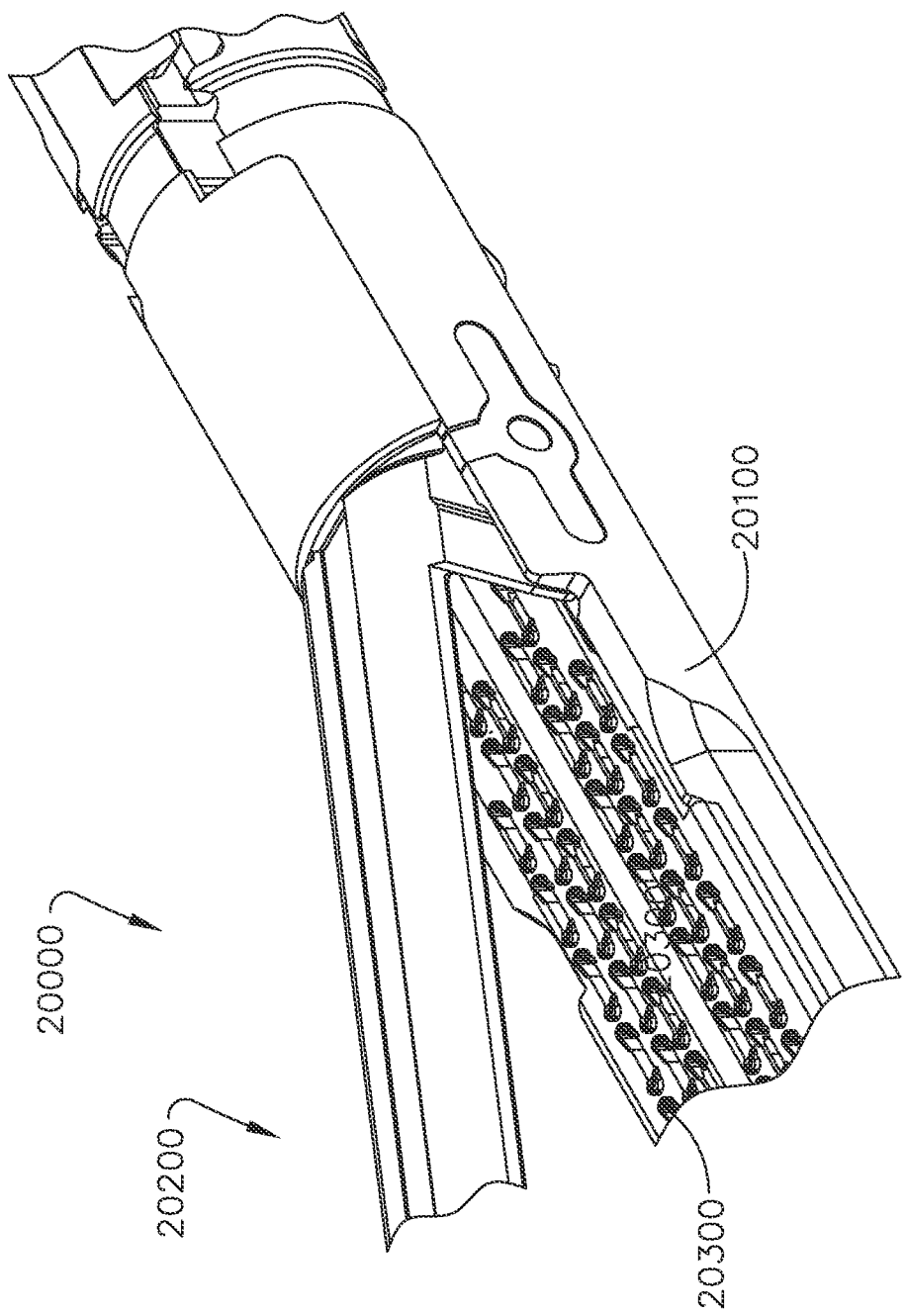
Figure 193:
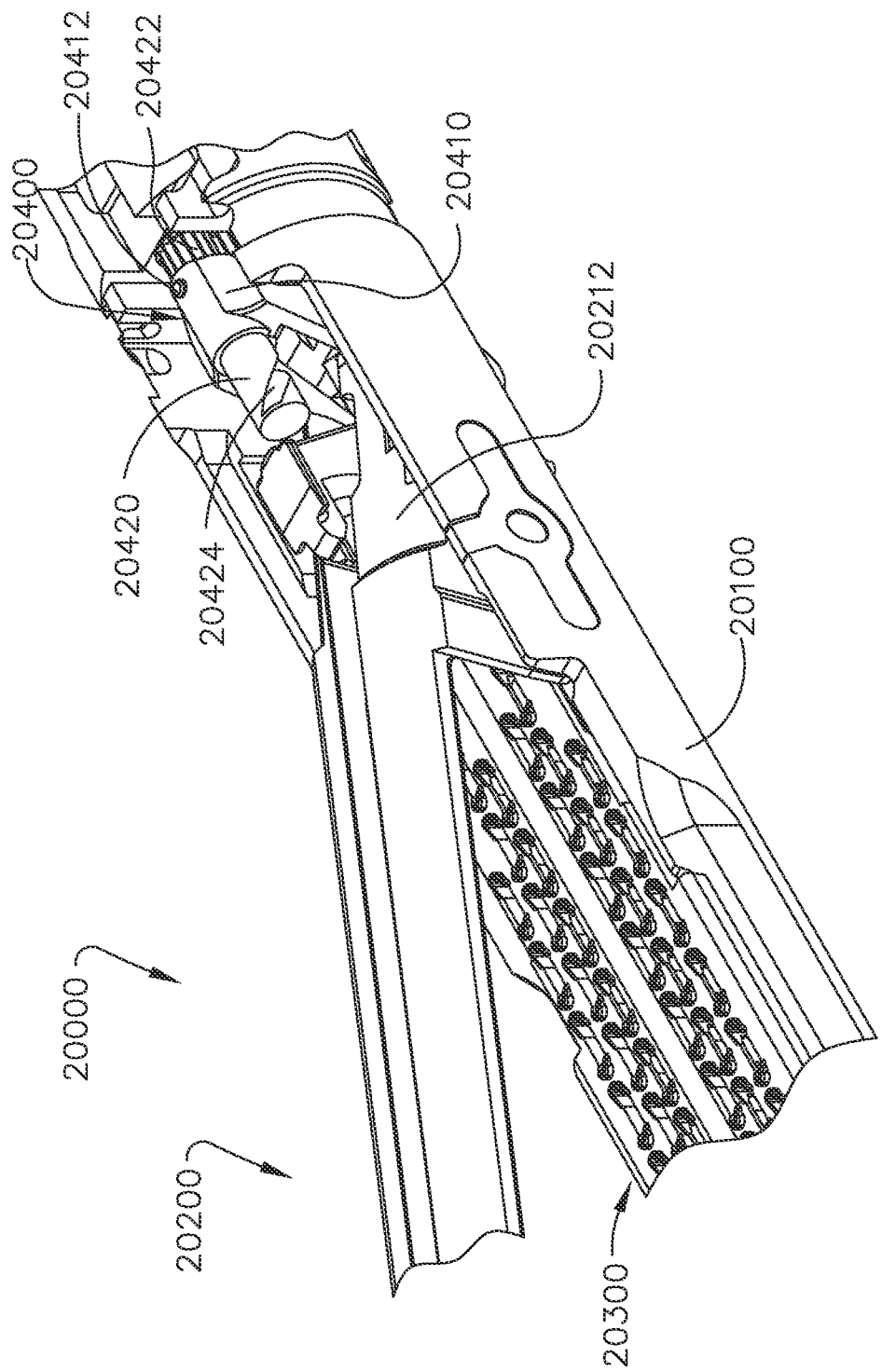
Figure 195:
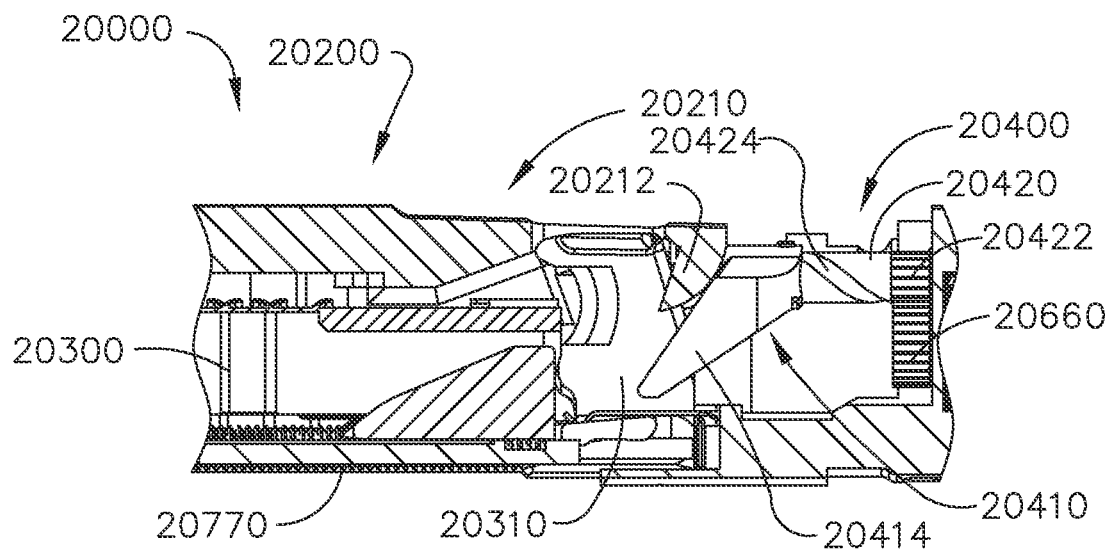
Figure 194:
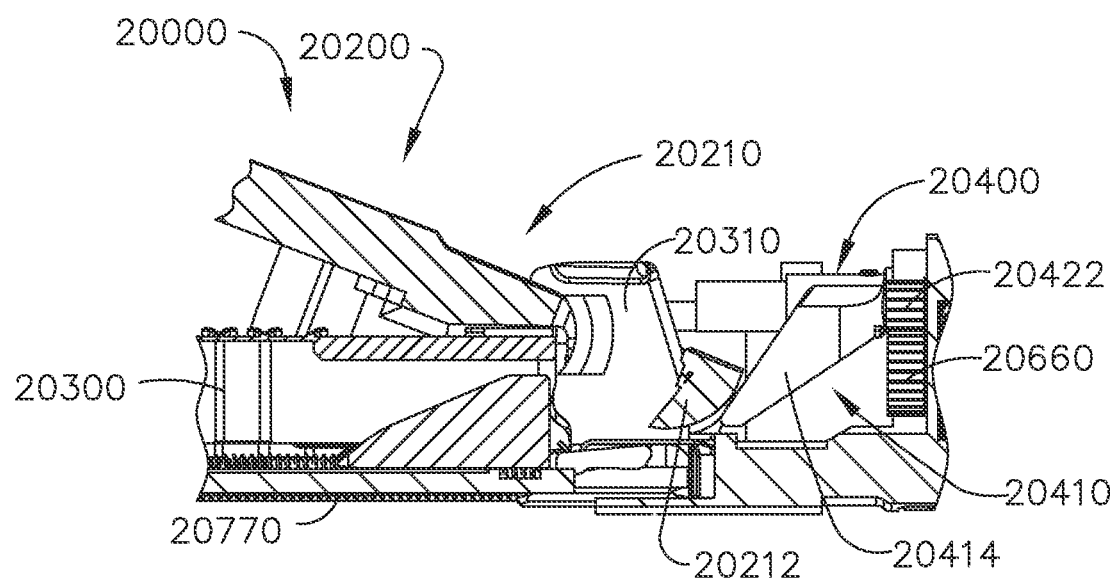
Figure 198:
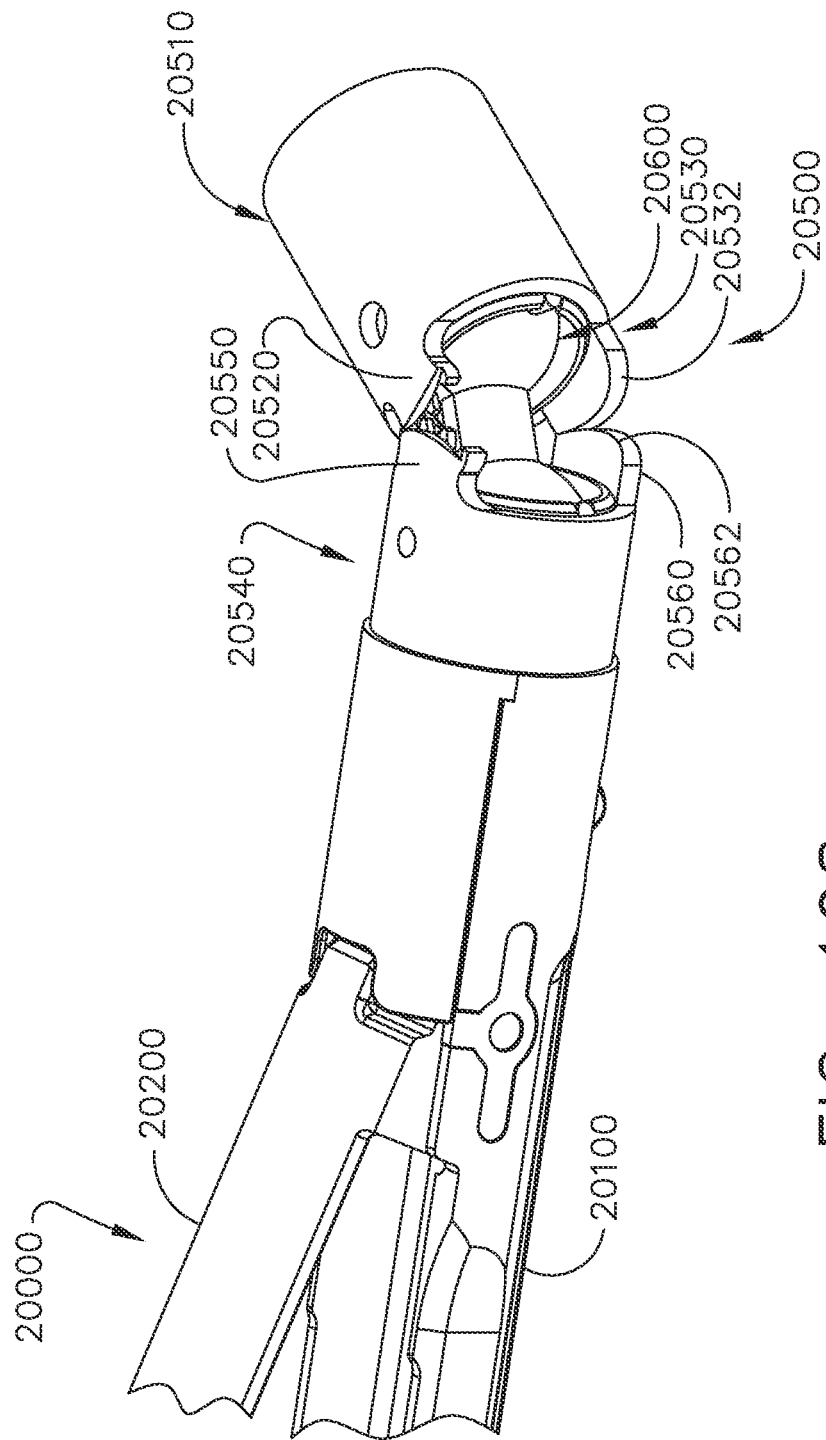
Figure 199:
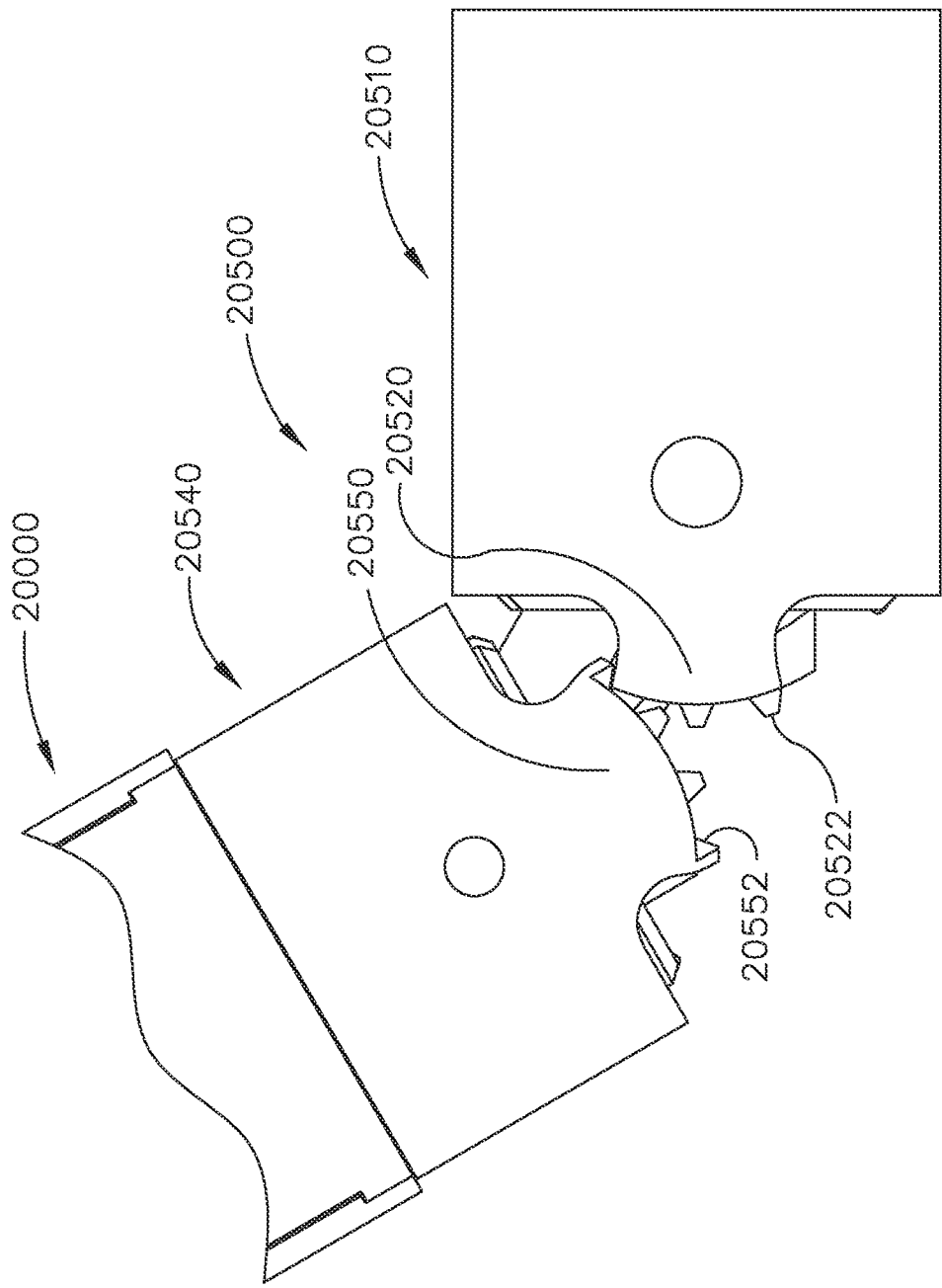
Figure 200:
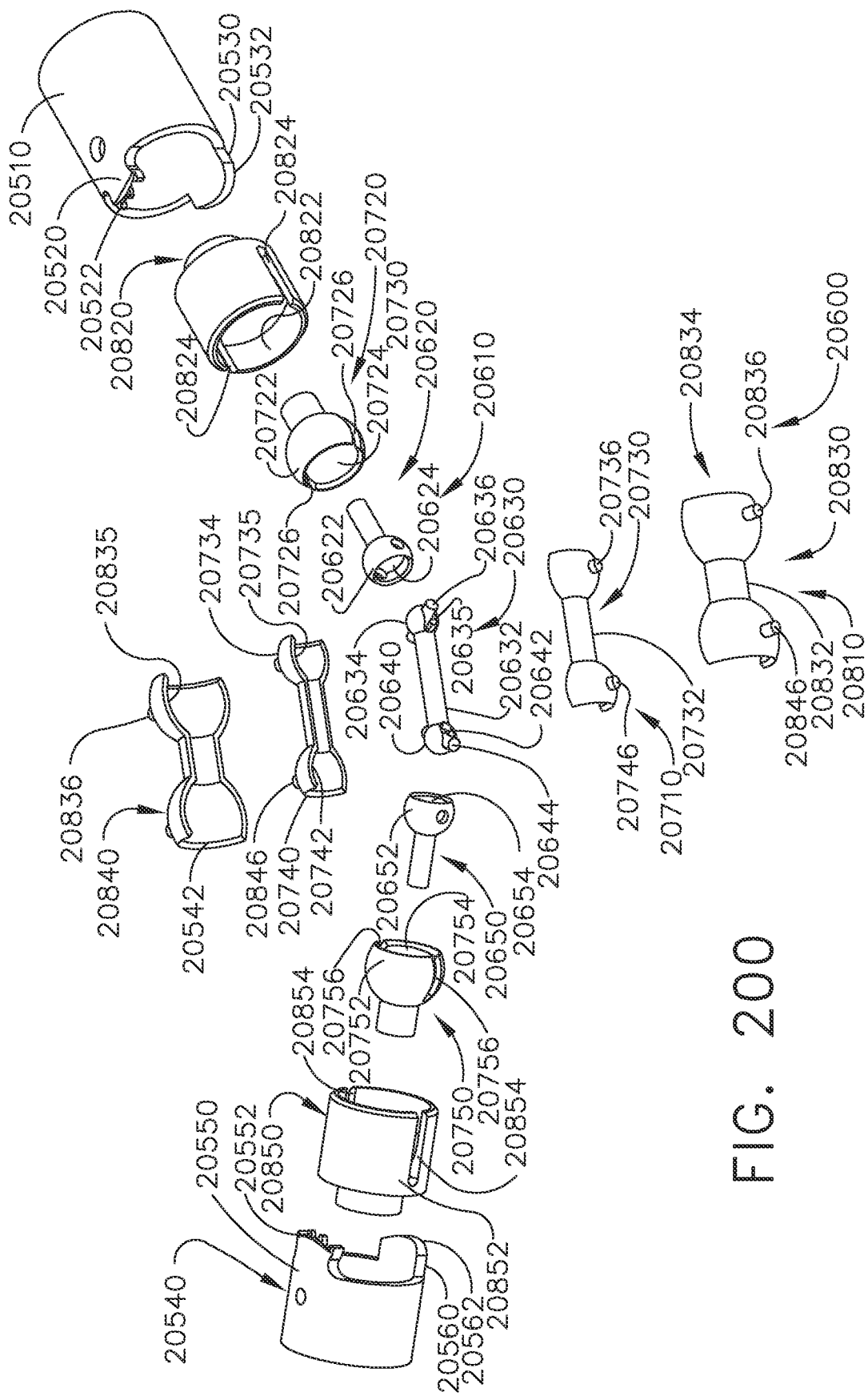
Figure 201:
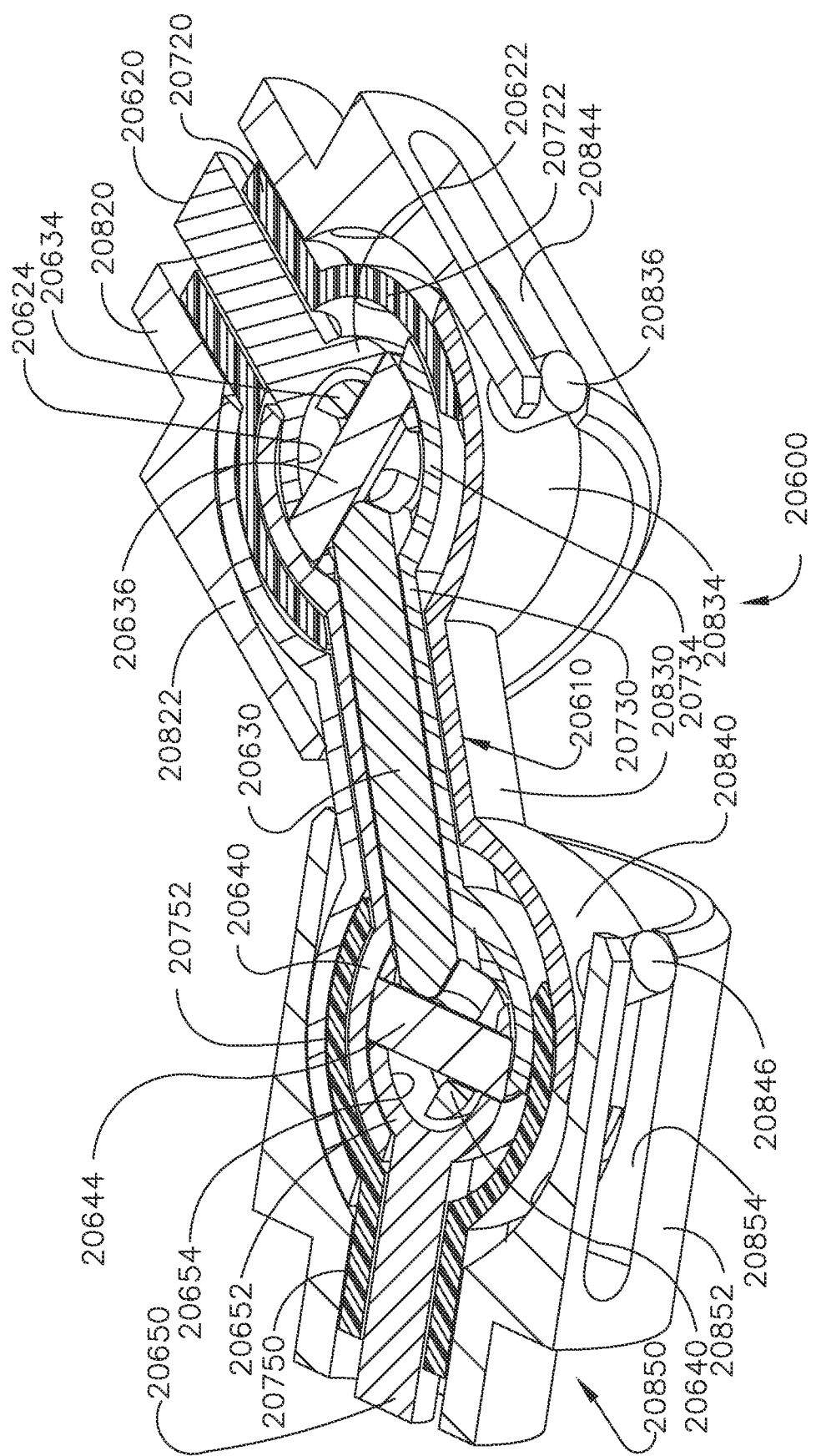
Figure 202:
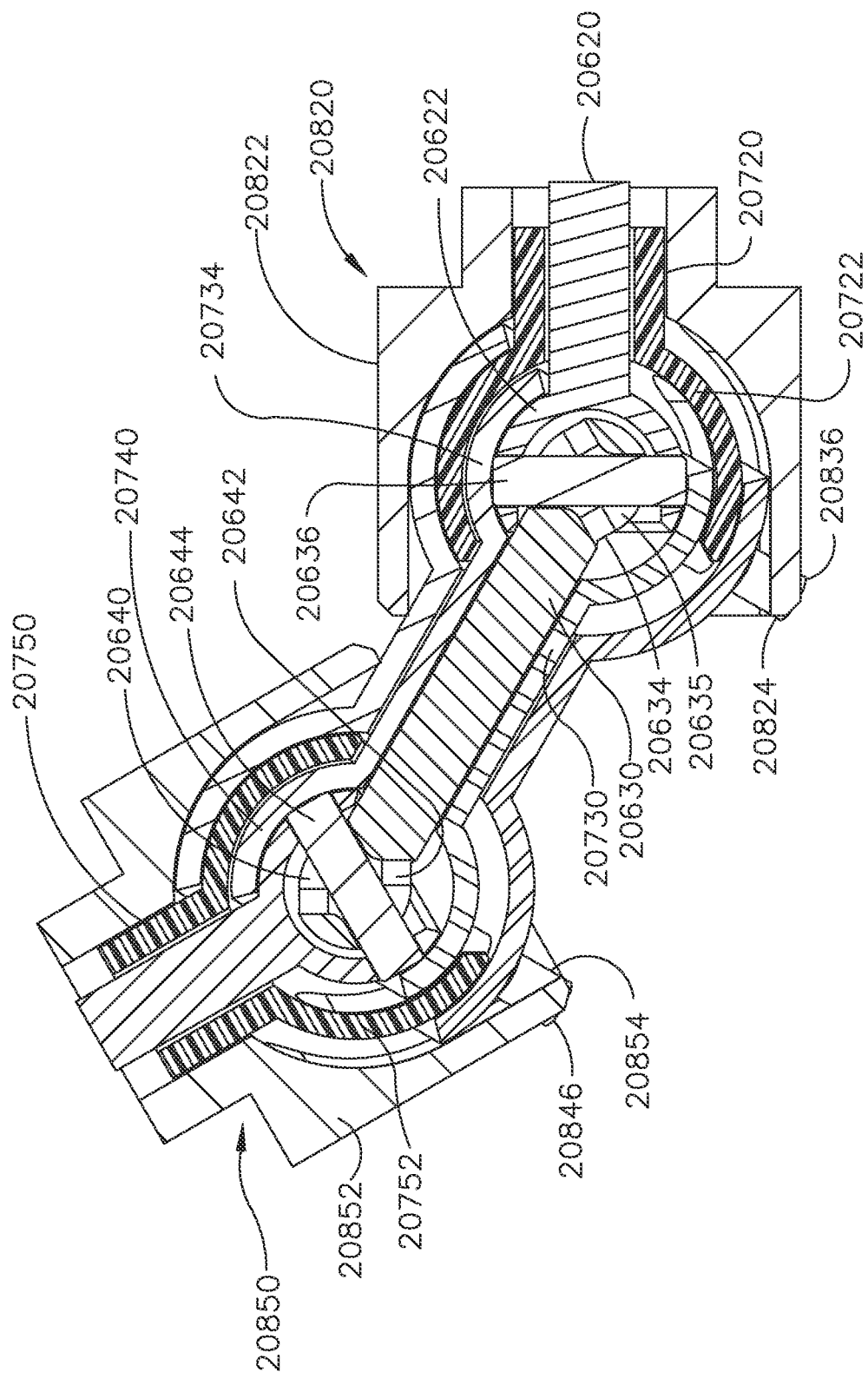
Figure 203:
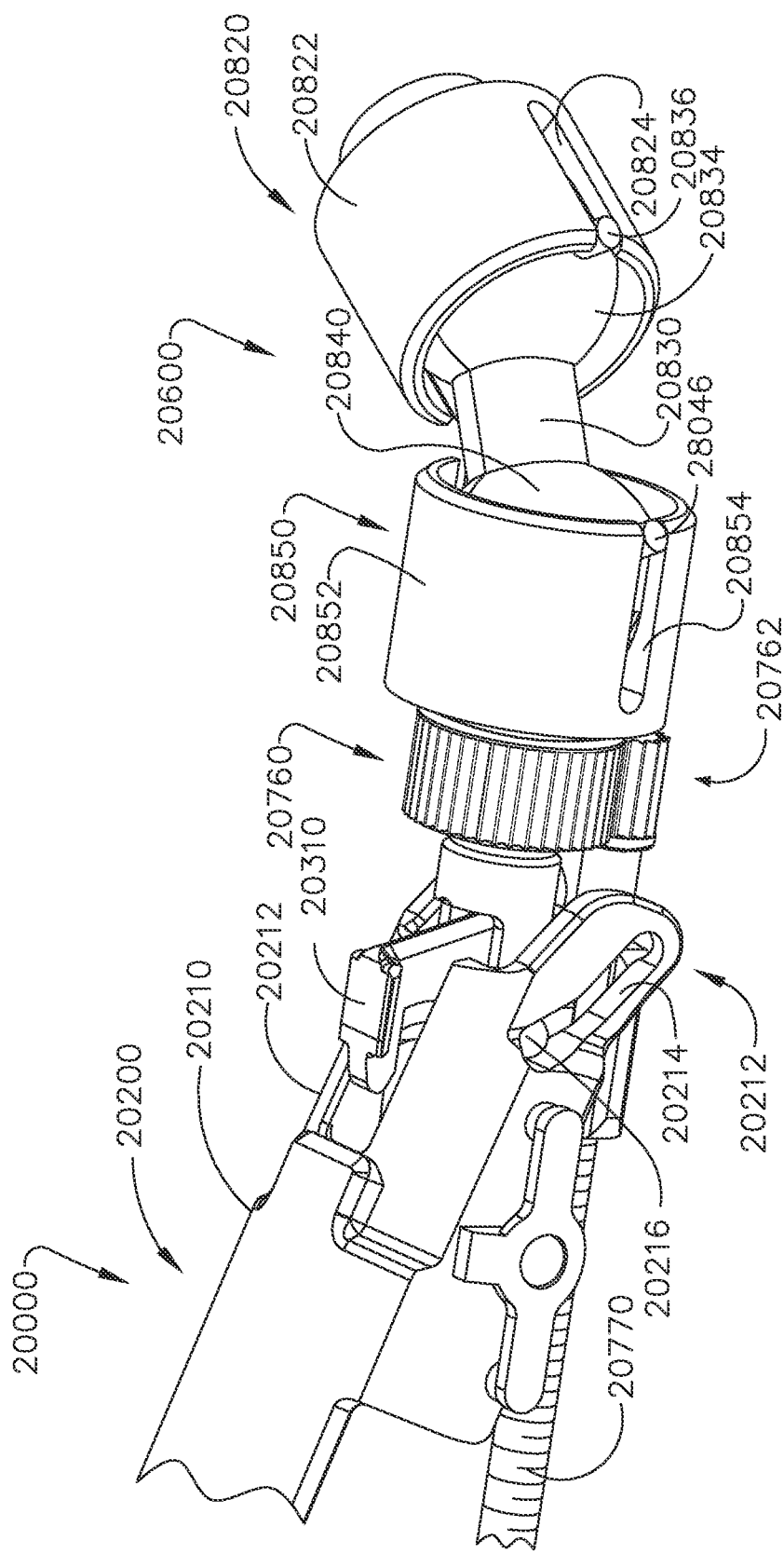
Figure 204:
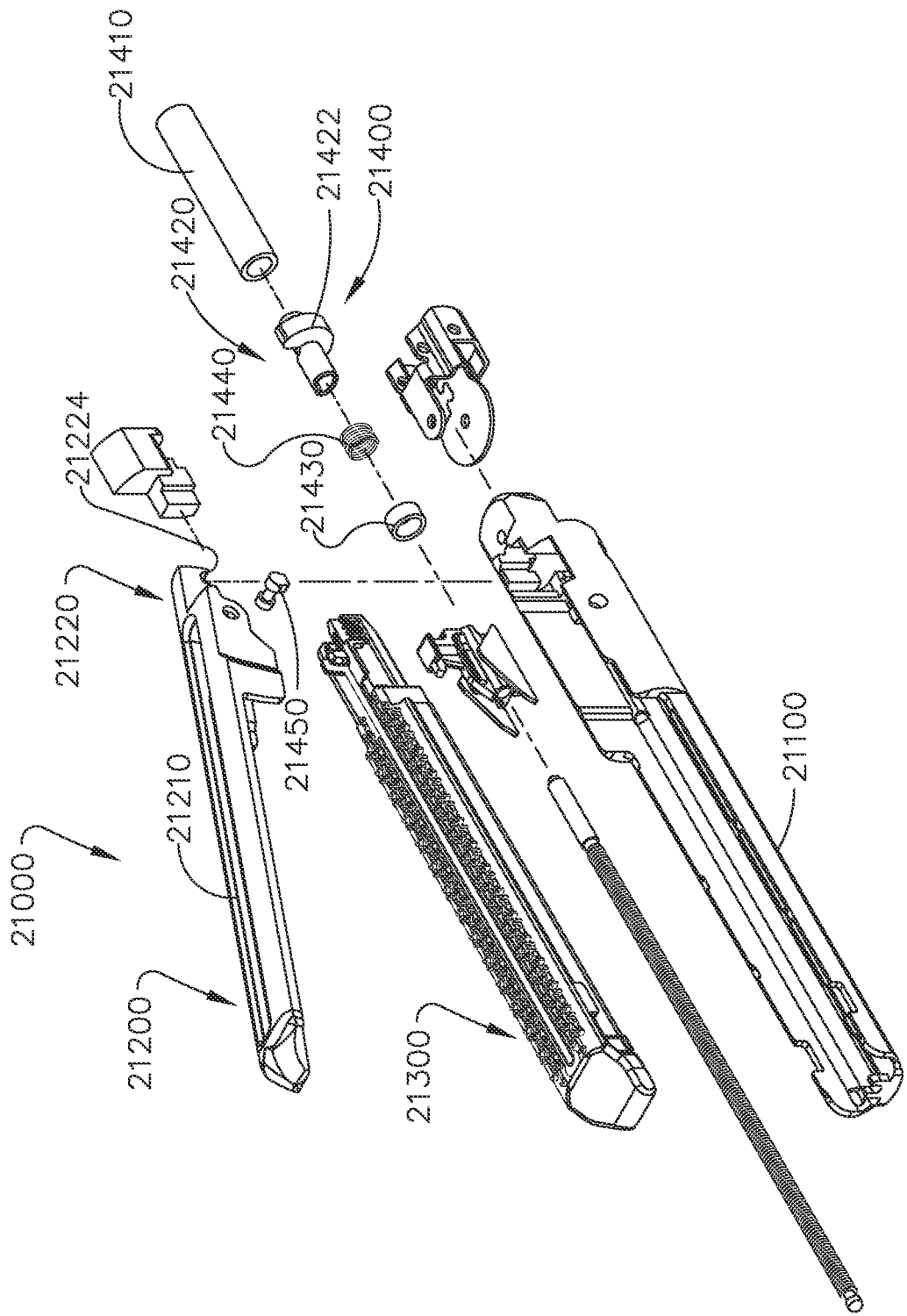
Figure 205:
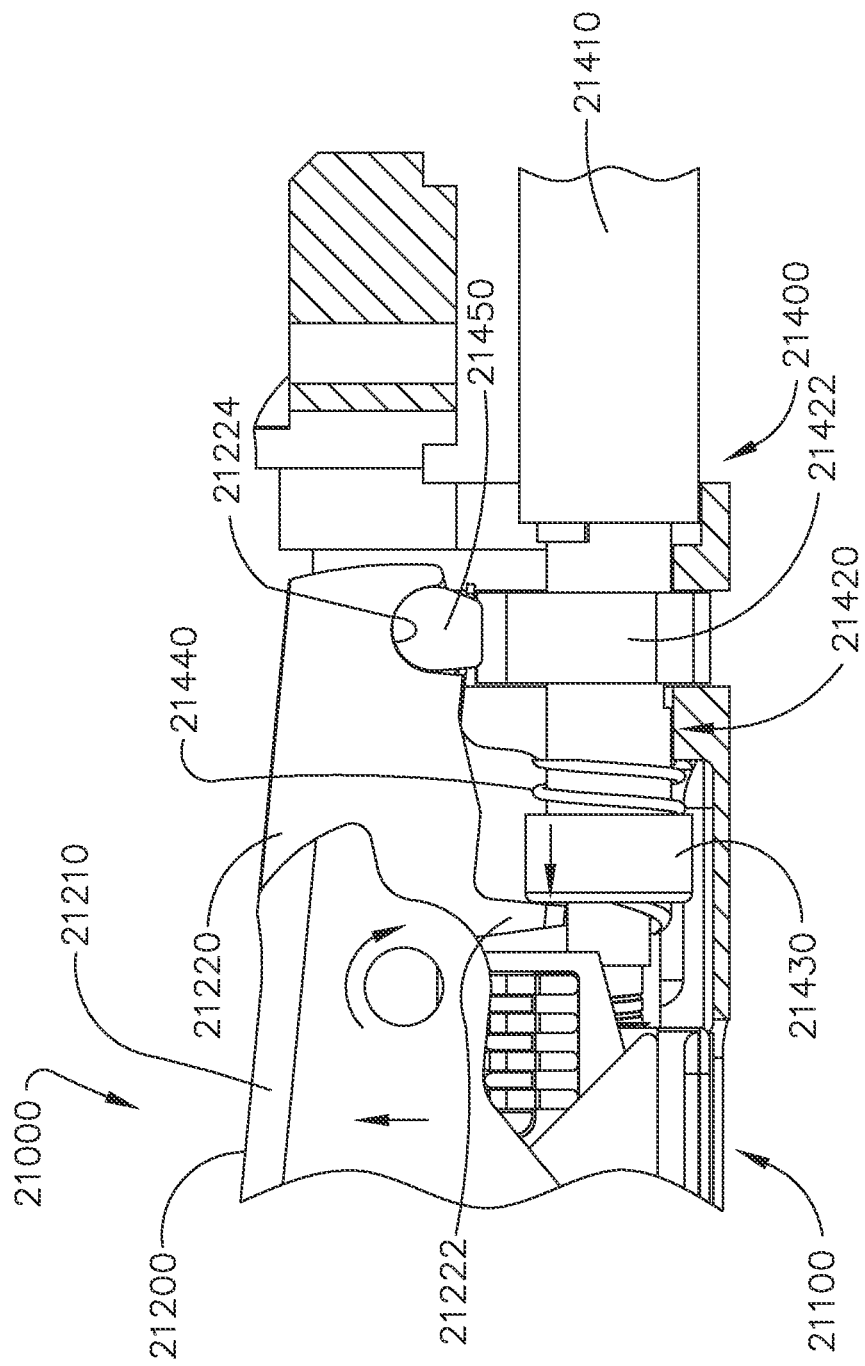
Figure 206:
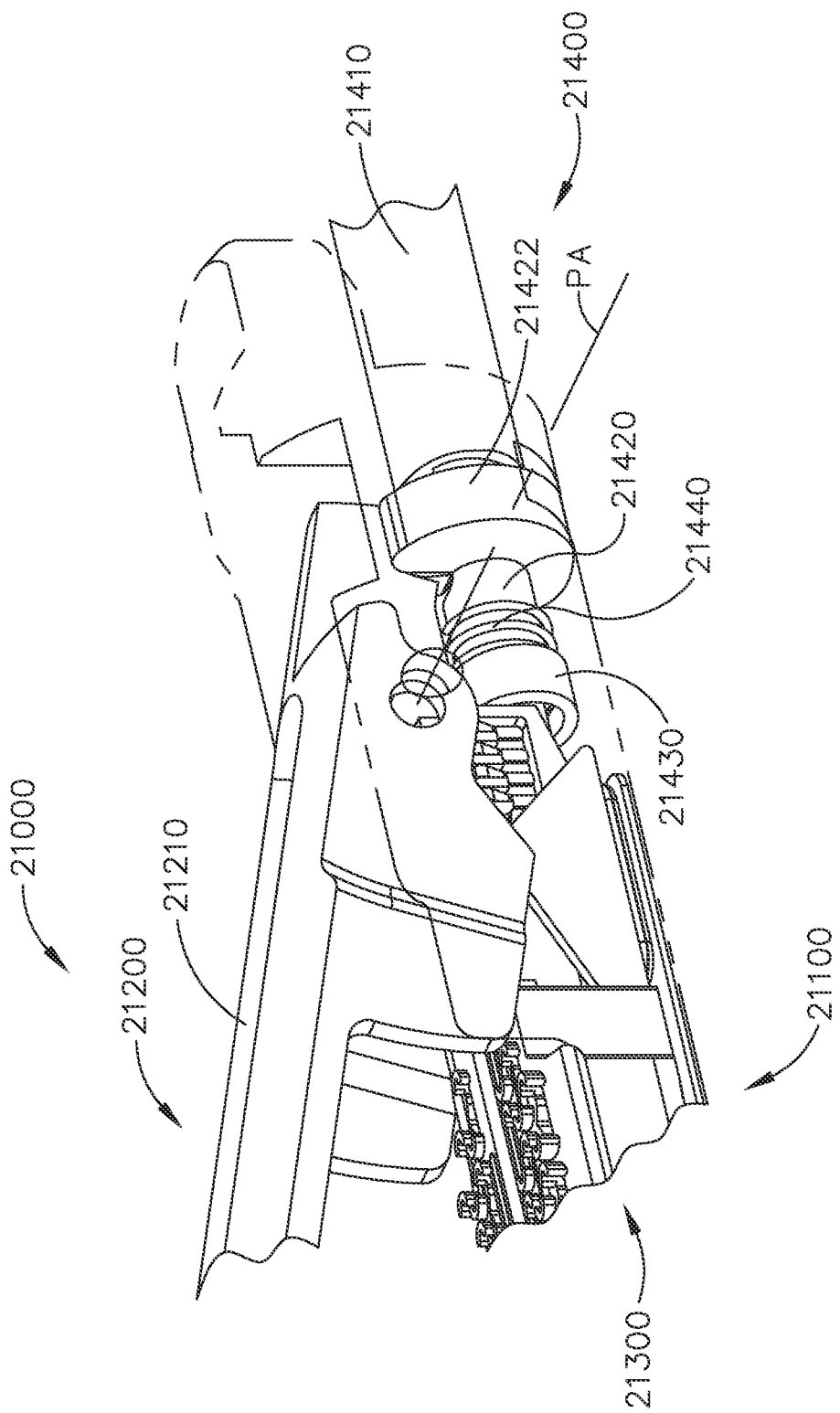
Figure 210:
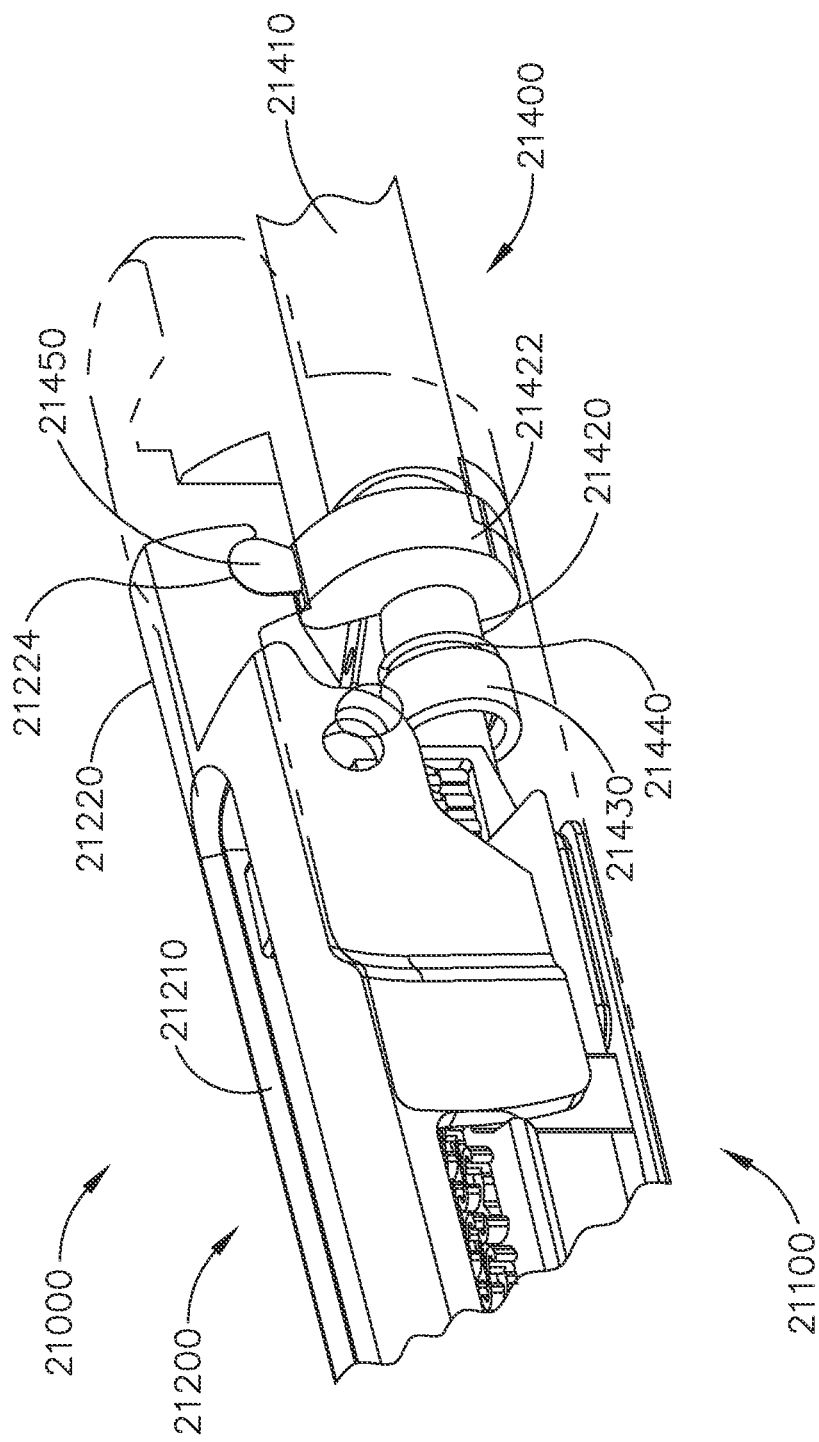
Figure 211:
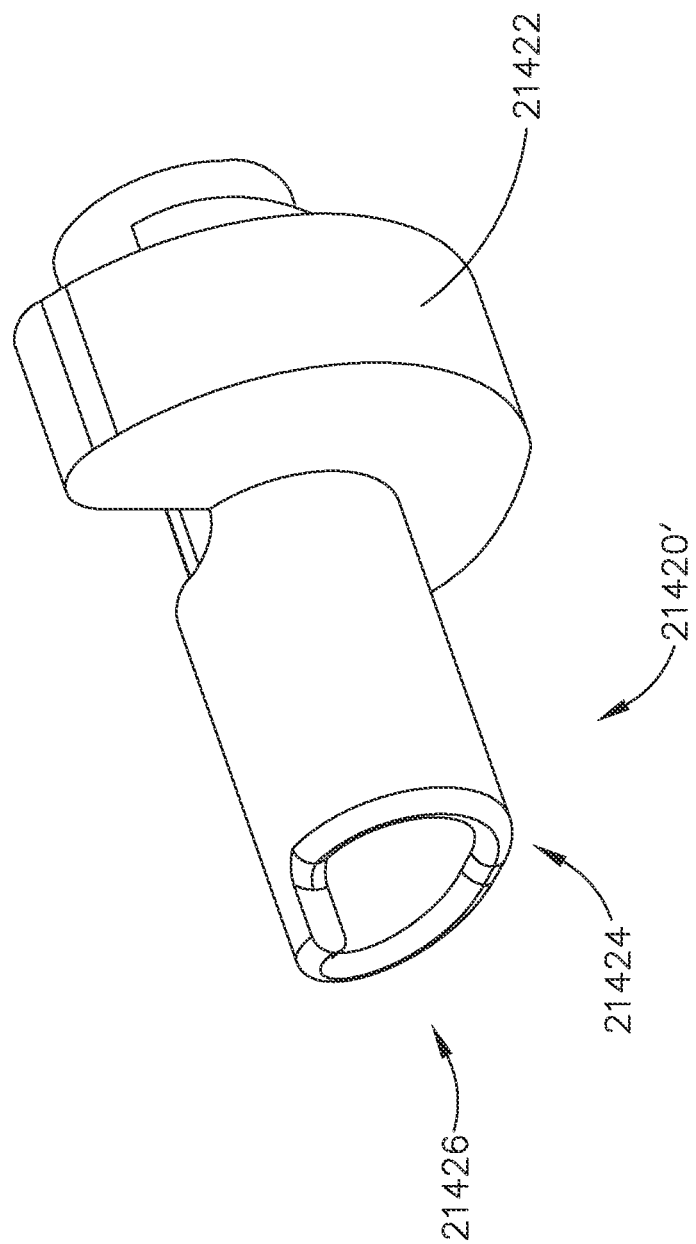

FIG. 131 is another perspective view of the pulley unit of FIG. 126 and a series of elastomeric annular spacer members of the articulation joint of the surgical instrument of FIG. 115;

FIG. 132 is another perspective view of the pulley unit, portions of a firing system and the articulation joint of the surgical instrument of FIG. 115;

FIG. 133 is a perspective view of a portion of a firing system of the surgical instrument of FIG. 115;

FIG. 134 is a partial cross-sectional view of the firing system of FIG. 133;

FIG. 135 is a perspective view of the firing system, articulation joint, and a closure system of the surgical instrument of FIG. 115;

FIG. 136 is a partial cross sectional view of the surgical instrument of FIG. 115 with the surgical end effector thereof in an unarticulated position;

FIG. 137 is a partial view of a differential drive assembly embodiment of the firing system of the surgical instrument of FIG. 115;

FIG. 138 is another partial cross sectional view of the surgical instrument of FIG. 115 with the surgical end effector thereof in an articulated position;

FIG. 139 is another partial cross sectional view of the surgical instrument of FIG. 115 with the surgical end effector thereof in an articulated position;

FIG. 140 is a perspective of a portion of another surgical instrument embodiment;

FIG. 141 is a perspective view of an articulation joint of the surgical instrument of FIG. 140 in an unarticulated orientation;

FIG. 142 is another perspective view of the articulation joint of FIG. 141 in another articulated orientation;

FIG. 143 is an exploded perspective view of the articulation joint of FIG. 141;

FIG. 144 is a top view of the articulation joint of FIG. 141;

FIG. 145 is a cross-sectional view of the articulation joint of FIG. 144 taken along line 145-145 in FIG. 144;

FIG. 146 is a side elevational view of the articulation joint of FIG. 144;

FIG. 147 is another side elevation al view of the articulation joint of FIG. 146 in an articulated orientation;

FIG. 148 is a perspective view of the articulation join of FIG. 141 in another articulated orientation;

FIG. 149 is another perspective view of the articulation join of FIG. 141 in another articulated orientation;

FIG. 150 is an end view of the proximal joint member of the articulation joint of FIG. 141;

FIG. 151 is an end view of the distal joint member of the articulation joint of FIG. 141;

FIG. 152 is a perspective view of a proximal cross pin assembly of the articulation joint of FIG. 141;

FIG. 153 is a perspective view of another articulation joint embodiment;

FIG. 154 is a perspective view of an articulation joint portion of another surgical instrument embodiment;

FIG. 155 is another perspective view of the articulation joint arrangement of FIG. 154 with an outer shaft tube omitted for clarity;

FIG. 156 is an exploded perspective assembly view of the articulation joint arrangement and firing drive system of the surgical instrument of FIG. 154;

FIG. 157 is a perspective view of the articulation joint and firing system arrangement of FIG. 156 with an outer shaft tube omitted for clarity and wherein a firing member is in a starting position;

FIG. 158 is another perspective view of the articulation joint and firing system of FIG. 157 after the firing member has been advanced to a distal position;

FIG. 159 is a partial cross-sectional view of a portion of the firing system of the surgical instrument of FIG. 154;

FIG. 160 is a partial view of a proximal differential drive assembly of the surgical instrument embodiment of FIG. 154;

FIG. 161 is a cross sectional end view through the proximal differential drive assembly of FIG. 160;

FIG. 162 is a side elevational view of the articulation joint and distal differential drive assembly of the surgical instrument of FIG. 154;

FIG. 163 is another side elevational view of the articulation joint and distal differential drive assembly of FIG. 162 in an articulated orientation;

FIG. 164 is a partial graphical depiction of reactive forces acting on push coils of the surgical instrument of FIG. 154 when the articulation joint thereof is in an articulated orientation and the firing member is being distally advanced;

FIG. 165 is another partial graphical depiction of reactive forces acting on flexible outer tubes of the surgical instrument of FIG. 154 when the articulation joint thereof is in an articulated orientation;

FIG. 166 is a perspective view of a central link member and flexible joint support assembly of the surgical instrument of FIG. 154;

FIG. 167 is a side elevational view of the articulation joint of the surgical instrument of FIG. 154 in an unarticulated orientation;

FIG. 168 is a cross-sectional view of the articulation joint of FIG. 167 taken along line 168-168 in FIG. 167;

FIG. 169 is a partial perspective view of the articulation joint of the surgical instrument of FIG. 154 in an articulated orientation with the flexible joint support assembly omitted for clarity;

FIG. 170 is a perspective view of another articulation joint embodiment for a surgical instrument;

FIG. 171 is a side view of the articulation joint of FIG. 170 in an unarticulated orientation;

FIG. 172 is another side view of the articulation joint of FIG. 170 partially articulated in a first articulation direction;

FIG. 173 is another side view of the articulation joint of FIG. 170 fully articulated in the first articulation direction;

FIG. 174 is another side view of the articulation joint of FIG. 170 illustrating virtual pivot points and a position of a first pair of links when the articulation joint is in an unarticulated orientation;

FIG. 175 is another side view of the articulation joint and links of FIG. 170 partially articulated in the first articulation direction;

FIG. 176 is another side view of the articulation joint of FIG. 174 illustrating the virtual pivot points and with the links omitted for clarity;

FIG. 177 is another side view of the articulation joint of FIG. 174 partially articulated in a first articulation direction;

FIG. 178 is a perspective view of another articulation joint embodiment for a surgical instrument;

FIG. 179 is an exploded assembly view of the articulation joint of FIG. 178;

FIG. 180 is a perspective view of the articulation joint of FIG. 178 illustrating cable control paths;

FIG. 181 is a perspective view of another articulation joint embodiment for a surgical instrument with the joint in an unarticulated orientation;

FIG. 182 is another perspective view of the articulation joint of FIG. 181 in an articulated orientation;

FIG. 183 is an exploded assembly view of the articulation joint of FIG. 181;

FIG. 184 is an end view of a proximal joint member of the articulation joint of FIG. 181;

FIG. 185 is an end view of a distal joint member of the articulation joint of FIG. 181;

FIG. 186 is a cross-sectional view of the proximal joint member of FIG. 184 and a portion of a first link of the articulation joint in a first position;

FIG. 187 is another cross-sectional view of the proximal joint member of FIG. 184 with the first link in another position;

FIG. 188 is another cross-sectional view of the proximal joint member and the first link of FIG. 186;

FIG. 189 is another cross-sectional view of the proximal joint member and first link of FIG. 187;

FIG. 190 is another perspective view of the articulation joint of FIG. 181 depicting virtual spheres for illustrating the articulation travel between a proximal portion of the articulation joint relative to a distal portion of the articulation joint;

FIG. 191 is another perspective view of the articulation joint of FIG. 190 depicting the virtual spheres in relation to the proximal joint member and distal joint member of the articulation joint of FIG. 181;

FIG. 192 is a perspective view of a portion of a surgical end effector of a surgical instrument with an anvil thereof in an open position;

FIG. 193 is another perspective view of the surgical end effector of FIG. 192 with a portion of the surgical end effector omitted to illustrate positions of various closure system components of the surgical instrument;

FIG. 194 is a cross-sectional view of the surgical end effector and closure system components of FIG. 193 with the anvil in an open position;

FIG. 195 is another cross-sectional view of the surgical end effector and closure system components of FIG. 193 with the anvil in a closed position;

FIG. 196 is a perspective view of a closure cam member in a starting position on a rotatable cam shaft corresponding to an open position of the anvil of the surgical end effector of FIG. 194;

FIG. 197 is another perspective view of the closure cam member in an ending position on the rotatable cam shaft that corresponds to the closed position of the anvil as shown in FIG. 195;

FIG. 198 is another perspective view of the surgical end effector of FIG. 192 oriented in an articulated orientation about an articulation joint that is attached thereto;

FIG. 199 is a top view of a distal joint portion of the articulation joint of FIG. 198 articulated relative to a proximal articulation joint portion of the articulation joint of FIG. 198;

FIG. 200 is an exploded assembly view of the articulation joint of FIG. 192 and a rotary drive assembly;

FIG. 201 is a cross-sectional view of the rotary drive assembly of FIG. 200;

FIG. 202 is another cross-sectional view of the rotary drive assembly of FIG. 201;

FIG. 203 is another perspective view of the surgical end effector and articulation joint of FIG. 198 with portions thereof omitted for clarity;

FIG. 204 is an exploded assembly view of another surgical end effector and rotary driven closure system;

FIG. 205 is a partial side view of a portion of the surgical end effector and rotary drive closure system of FIG. 204 with the anvil in a closed orientation;

FIG. 206 is a partial perspective view of a portion of the surgical end effector and rotary drive system of FIG. 204 with the anvil in an open orientation;

FIG. 207 is a partial end view of a portion of a rotary cam shaft and cam follower of the rotary drive system of FIG. 204 in a position when the anvil is in the open position;

FIG. 208 is another partial end view of the rotary cam shaft and cam follower of FIG. 207 after the closure process has started;

FIG. 209 is another partial end view of the rotary cam shaft and cam follower of FIG. 207 after a cam lobe on the rotary cam shaft has cammed the cam follower into a position wherein the anvil is pivoted to an open position;

FIG. 210 is another perspective view of a portion of the surgical end effector and rotary drive system of FIG. 204 with the anvil in a closed position;

FIG. 211 is a perspective view of another rotary cam shaft; and

Figure 212:
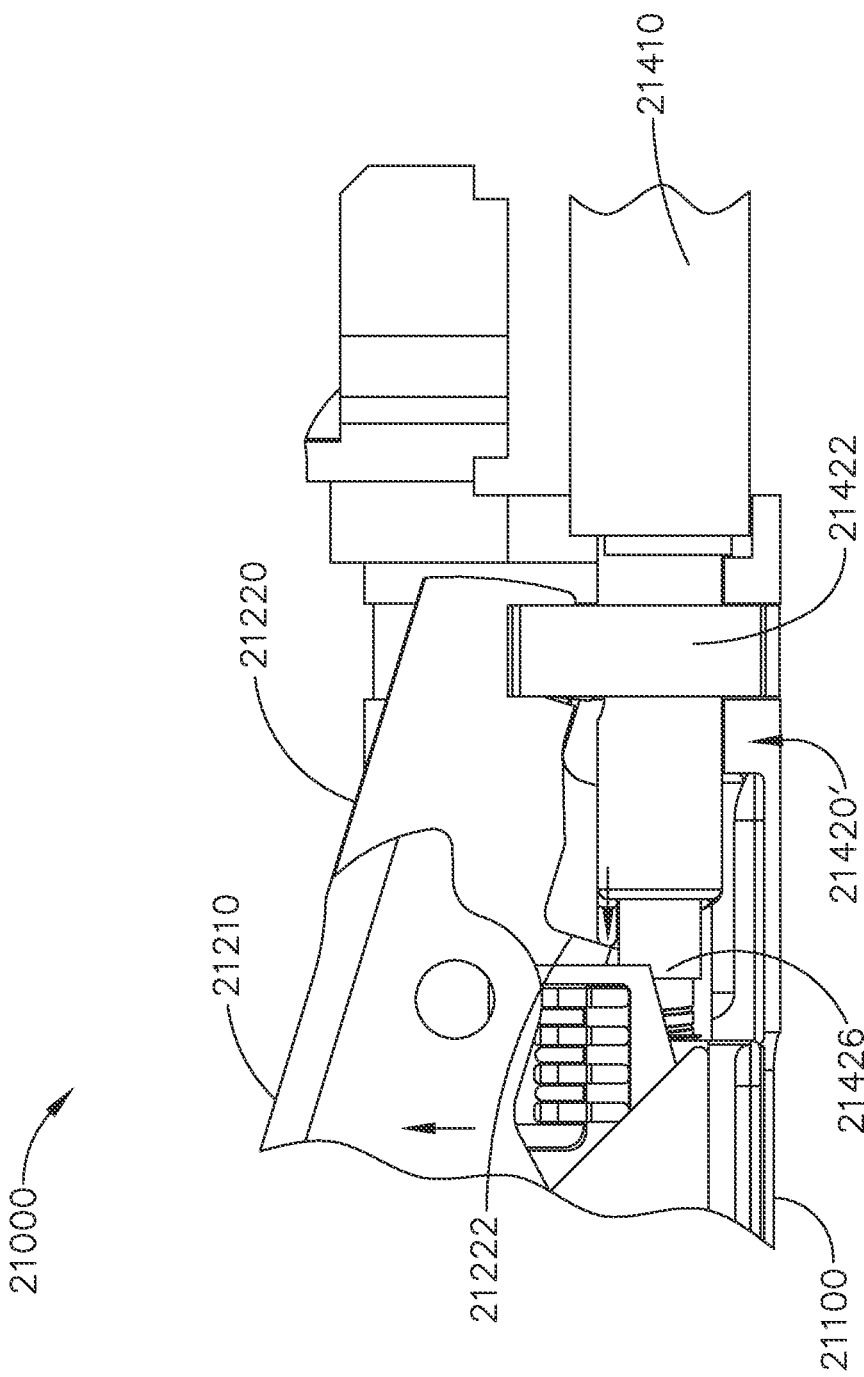

FIG. 212 is a partial side elevational view of a portion of the surgical end effector and rotary drive system of FIG. 204 employing the rotary cam shaft of FIG. 211 and with the anvil in an open position.

DETAILED DESCRIPTION

Applicant of the present application owns the following U.S. Patent Applications that were filed on Jun. 28, 2021 and which are each herein incorporated by reference in their respective entireties:

U.S. patent application Ser. No. 17/360,133, entitled SURGICAL INSTRUMENTS WITH TORSION SPINE DRIVE ARRANGEMENTS, now U.S. Patent Application Publication No. 2022-0031313;

U.S. patent application Ser. No. 17/360,139, entitled SURGICAL INSTRUMENTS WITH FIRING MEMBER CLOSURE FEATURES, now U.S. Patent Application Publication No. 2022-0031322;

U.S. patent application Ser. No. 17/360,149, entitled SURGICAL INSTRUMENTS WITH SEGMENTED FLEXIBLE DRIVE ARRANGEMENTS, now U.S. Patent Application Publication No. 2022-0031314;

U.S. patent application Ser. No. 17/360,162, entitled SURGICAL INSTRUMENTS WITH FLEXIBLE BALL CHAIN DRIVE ARRANGEMENTS, now U.S. Patent Application Publication No. 2022-0031319;

U.S. patent application Ser. No. 17/360,176, entitled SURGICAL INSTRUMENTS WITH DOUBLE SPHERICAL ARTICULATION JOINTS WITH PIVOTABLE LINKS, now U.S. Patent Application Publication No. 2022-0031345;

U.S. patent application Ser. No. 17/360,192 entitled SURGICAL INSTRUMENTS WITH DOUBLE PIVOT ARTICULATION JOINT ARRANGEMENTS, now U.S. Patent Application Publication No. 2022-0031350;

U.S. patent application Ser. No. 17/360,197, entitled SURGICAL INSTRUMENTS WITH COMBINATION FUNCTION ARTICULATION JOINT ARRANGEMENTS, now U.S. Patent Application Publication No. 2022-0031323;

U.S. patent application Ser. No. 17/360,211, entitled SURGICAL INSTRUMENTS WITH DUAL SPHERICAL ARTICULATION JOINT ARRANGEMENTS, now U.S. Patent Application Publication No. 2022-0031324;

U.S. patent application Ser. No. 17/360,220, entitled SURGICAL INSTRUMENTS WITH FLEXIBLE FIRING MEMBER ACTUATOR CONSTRAINT ARRANGEMENTS, now U.S. Patent Application Publication No. 2022-0031320;

U.S. patent application Ser. No. 17/360,244, entitled ARTICULATABLE SURGICAL INSTRUMENTS WITH ARTICULATION JOINTS COMPRISING FLEXIBLE EXOSKELETON ARRANGEMENTS, now U.S. Patent Application Publication No. 2022-0031346; and U.S. patent application Ser. No. 17/360,249, entitled SURGICAL INSTRUMENTS WITH DIFFERENTIAL ARTICULATION JOINT ARRANGEMENTS FOR ACCOMMODATING FLEXIBLE ACTUATORS, now U.S. Patent Application Publication No. 2022-0031351.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or", etc.

Recitation of ranges of values herein are not intended to be limiting, referring instead individually to any and all values falling within the range, unless otherwise indicated herein, and each separate value within such a range is incorporated into the disclosure as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be construed to contemplate a range of deviations that would be appreciated by one of ordinary skill in the art to operate satisfactorily for a corresponding use, function, purpose or the like.

The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that locked position during the actuation of the end effector and completion of the surgical procedure. Such articulation joint arrangements must also be able to withstand external forces that are experienced by the end effector during use.

A variety of surgical end effectors exist that are configured to cut and staple tissue. Such surgical end effectors commonly include a first jaw feature that supports a surgical staple cartridge and a second jaw that comprises an anvil. The jaws are supported relative to each other such that they can move between an open position and a closed position to position and clamp target tissue therebetween. Many of these surgical end effectors employ an axially moving firing member. In some end effector designs, the firing member is configured to engage the first and second jaws such that as the firing member is initially advanced distally, the firing member moves the jaws to the closed position. Other end effector designs employ a separate closure system that is independent and distinct from the system that operates the firing member.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, in these surgical end effectors, the sled is moved distally by the firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Many surgical end effectors employ an axially movable firing beam that is attached to the firing member and is used to apply axial firing and retraction motions to the firing member. Many of such firing beams comprise a laminated construction that affords the firing beam with some degree of flexure about the articulation joint. As the firing beam traverses the articulation joint, the firing beam can apply de-articulation forces to the joint and can cause the beam to buckle. To prevent the firing beam from buckling under pressure, the articulation joint is commonly provided with lateral supports or "blow-out" plate features to support the portion of the beam that traverses the articulation joint. To advance the firing beam through an angle of greater than sixty degrees, for example, a lot of axial force is required. This axial force must be applied to the firing member in a balanced manner to avoid the firing member from binding with the jaws as the firing member moves distally. Any binding of the firing member with the jaws can lead to component damage and wear as well as require an increased amount of axial drive force to drive the firing member through the clamped tissue.

Other end effector designs employ a firing member that is rotary powered. In many of such designs, a rotary drive shaft extends through the articulation joint and interfaces with a rotatable firing member drive shaft that is rotatably supported within one of the jaws. The firing member threadably engages the rotatable firing member drive shaft and, as the rotatable firing member drive shaft is rotated, the firing member is driven through the end effector. Such arrangements require the supporting jaw to be larger to accommodate the firing member drive shaft. In such devices, a lower end of the firing member commonly operably interfaces with the drive shaft which can also result in an application of forces that tend to unbalance the firing member as it is driven distally.

FIGS. 1-4 illustrate one form of a surgical instrument 10 that may address many of the challenges facing surgical instruments with articulatable end effectors that are configured to cut and fasten tissue. In various embodiments, the surgical instrument 10 may comprise a handheld device. In other embodiments, the surgical instrument 10 may comprises an automated system sometimes referred to as a robotically-controlled system, for example. In various forms, the surgical instrument 10 comprises a surgical end effector 1000 that is operably coupled to an elongate shaft assembly 2000. The elongate shaft assembly 2000 may be operably attached to a housing 2002. In one embodiment, the housing 2002 may comprise a handle that is configured to be grasped, manipulated, and actuated by the clinician. In other embodiments, the housing 2002 may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

In one form, the surgical end effector 1000 comprises a first jaw 1100 and a second jaw 1200. In the illustrated arrangement, the first jaw 1100 comprises an elongate channel 1110 that comprises a proximal end 1112 and a distal end 1114 and is configured to operably support a surgical staple cartridge 1300 therein. The surgical staple cartridge 1300 comprises a cartridge body 1302 that has an elongate slot 1304 therein. A plurality of surgical staples or fasteners (not shown) are stored therein on drivers (not shown) that are arranged in rows on each side of the elongate slot 1304. The drivers are each associated with corresponding staple cavities 1308 that open through a cartridge deck surface 1306. The surgical staple cartridge 1300 may be replaced after the staples/fasteners have been discharged therefrom. Other embodiments are contemplated wherein the elongate channel 1110 and/or the entire surgical end effector 1000 may be discarded after the surgical staple cartridge 1300 has been used. Such end effector arrangements may be referred to as "disposable loading units", for example.

In the illustrated arrangement, the second jaw 1200 comprises an anvil 1210 that comprises an elongate anvil body 1212 that comprises a proximal end 1214 and a distal end 1216. In one arrangement, a pair of stiffening rods or members 1213 may be supported in the anvil body 1212 to provide the anvil body 1212 with added stiffness and rigidity. The anvil body 1212 comprises a staple-forming undersurface 1218 that faces the first jaw 1100 and may include a series of staple-forming pockets (not shown) that corresponds to each of the staples or fasteners in the surgical staple cartridge 1300. The anvil body 1212 may further include a pair of downwardly extending tissue stop features 1220 that are formed adjacent the proximal end 1214 of the anvil body 1212. One tissue stop feature 1220 extends from each side of the anvil body 1212 such that a distal end 1222 on each tissue stop corresponds to the proximal-most staples/fasteners in the surgical staple cartridge 1300. When the anvil 1210 is moved to a closed position onto tissue positioned between the staple-forming undersurface 1218 of the anvil 1210 and the cartridge deck surface 1306 of the surgical staple cartridge 1300, the tissue contacts the distal ends 1222 of the tissue stop features 1220 to prevent the tissue from migrating proximally past the proximal-most staples/fasteners to thereby ensure that the tissue that is cut is also stapled. When the surgical staple cartridge is "fired" as will be discussed in further detail below, the staples/fasteners supported within each staple cavity are driven out of the staple cavity 1308 through the clamped tissue and into forming contact with the staple-forming undersurface 1218 of the anvil 1210.

Figure 1:
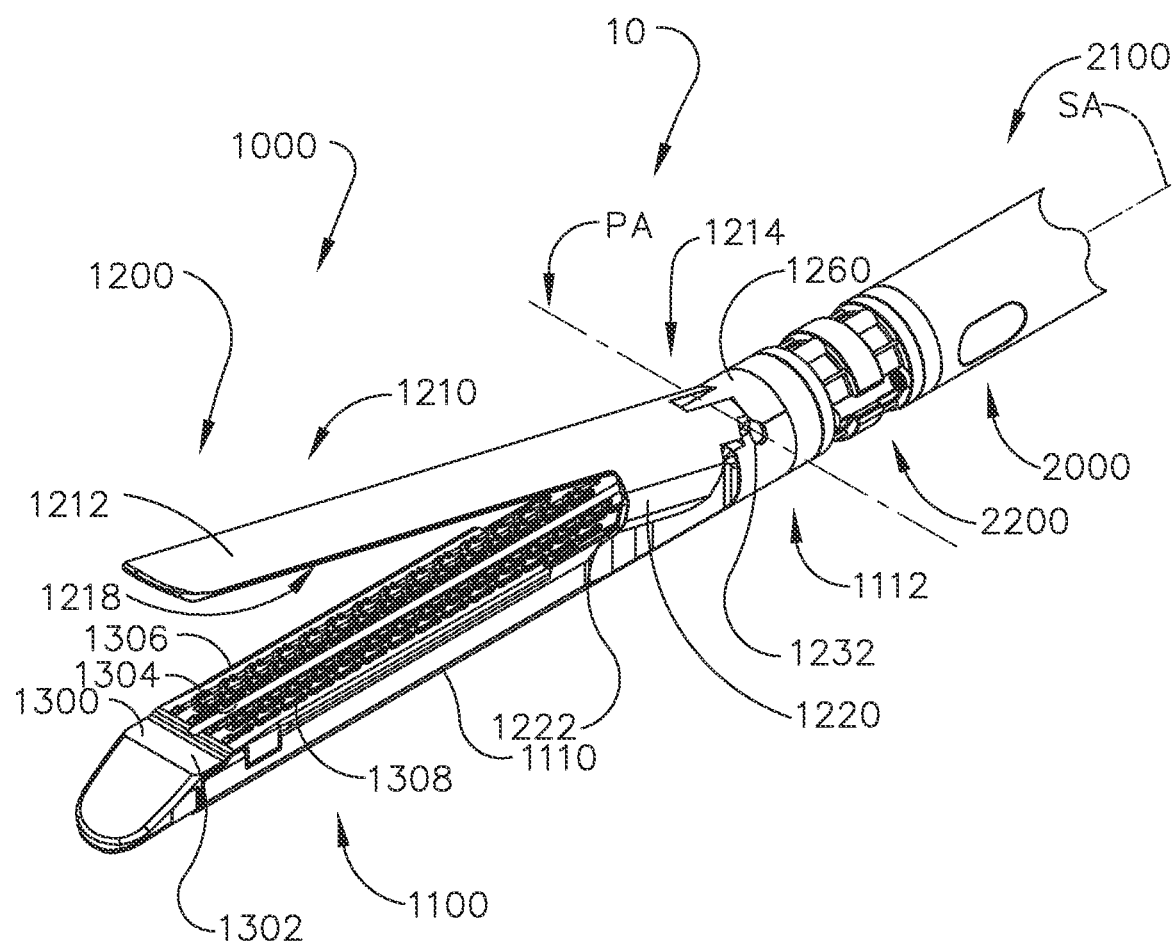
FIG. 1 is a perspective view of a surgical end effector portion of a surgical instrument in accordance with at least one aspect of the present disclosure.
Figure 2:
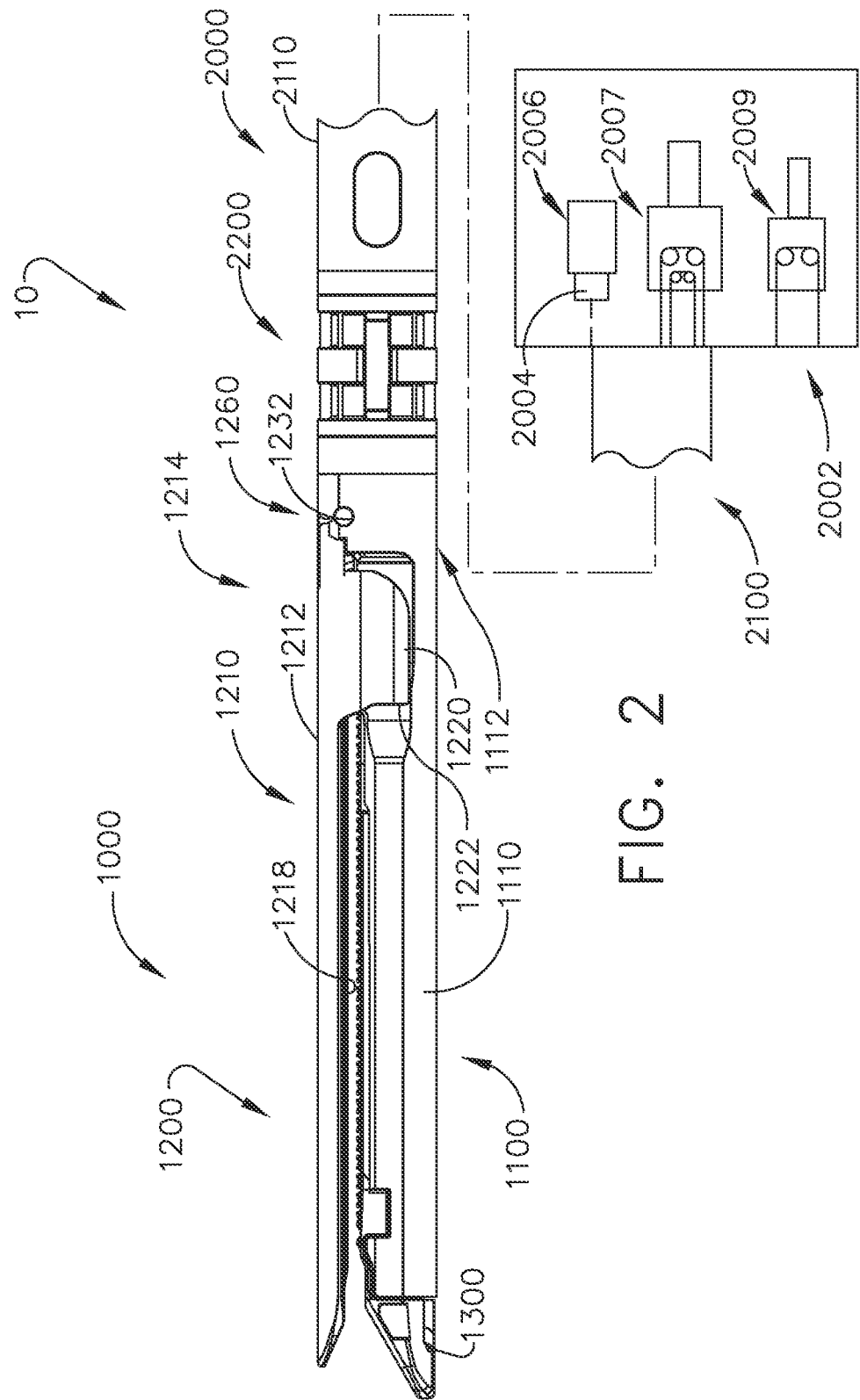
FIG. 2 is a side view of the surgical end effector portion instrument of FIG. 1 in a closed orientation.
Figure 3:
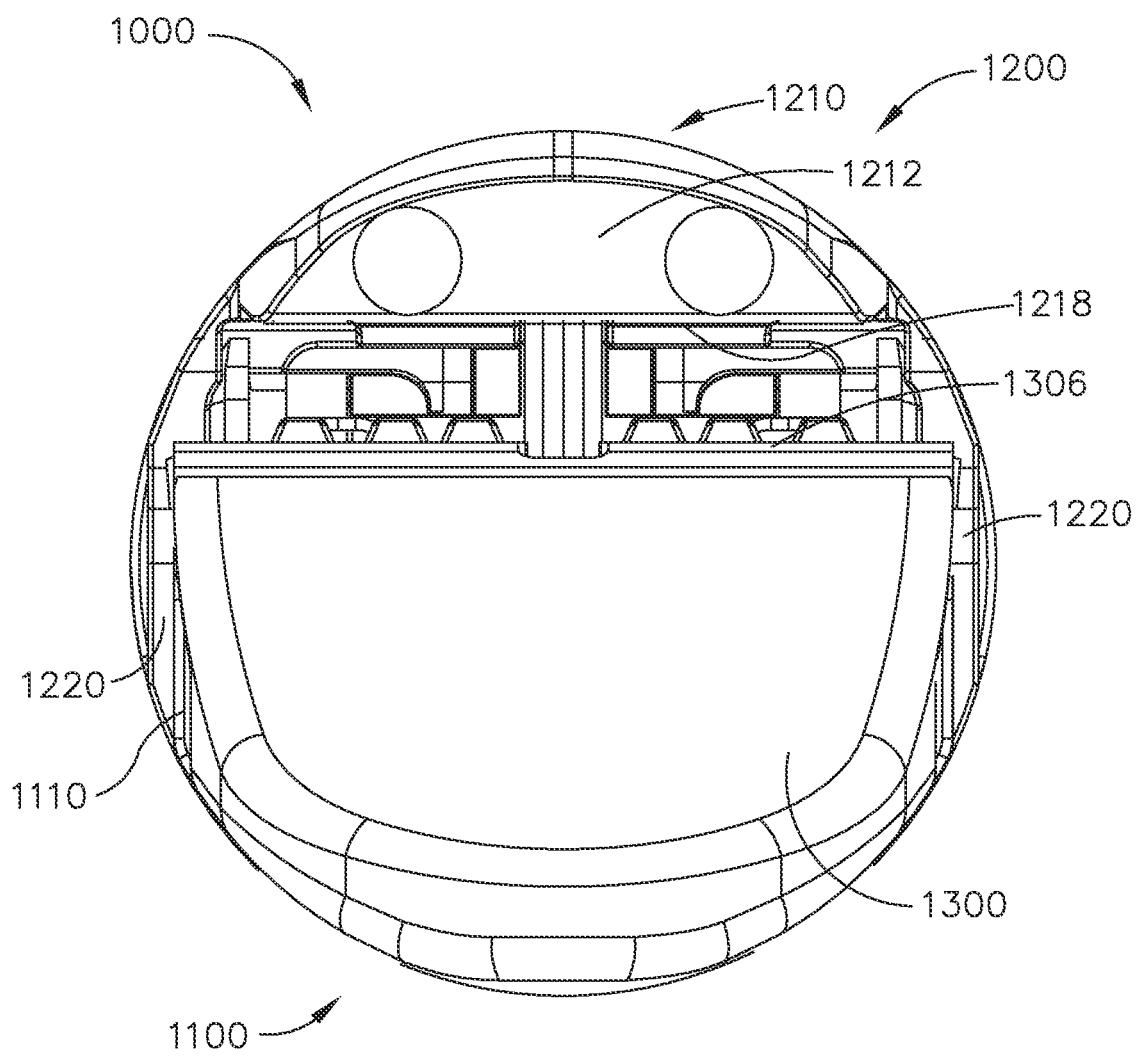
FIG. 3 is an end view of the surgical end effector of FIG. 2.
Figure 4:
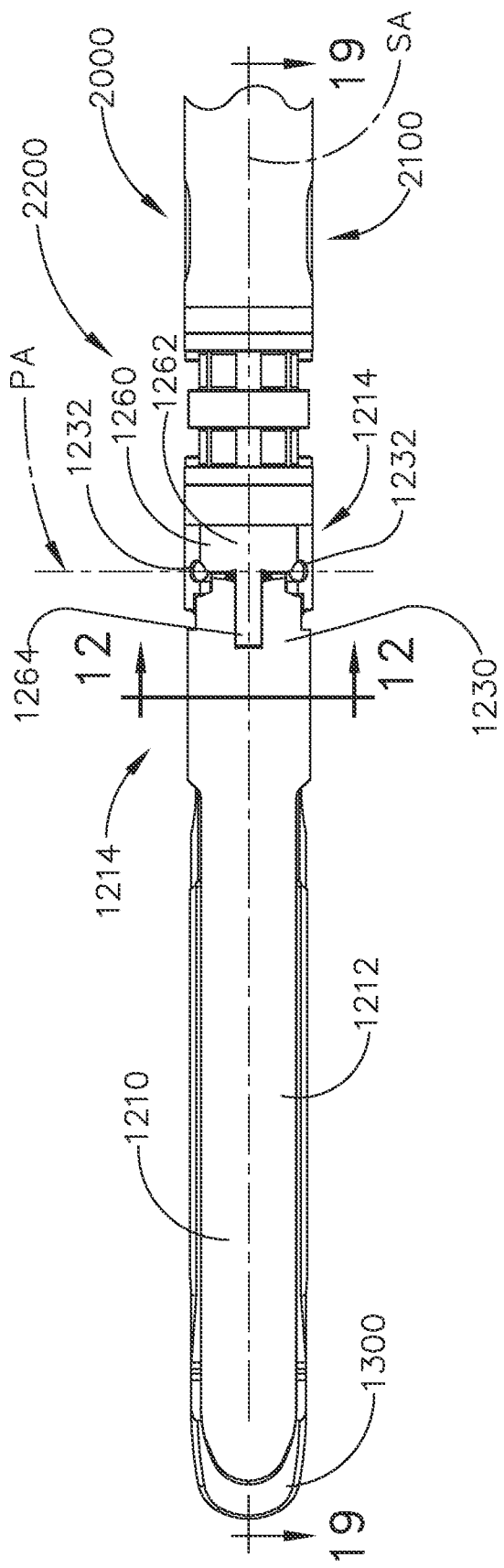
FIG. 4 is a top view of the surgical end effector of FIG. 2.
Figure 5:
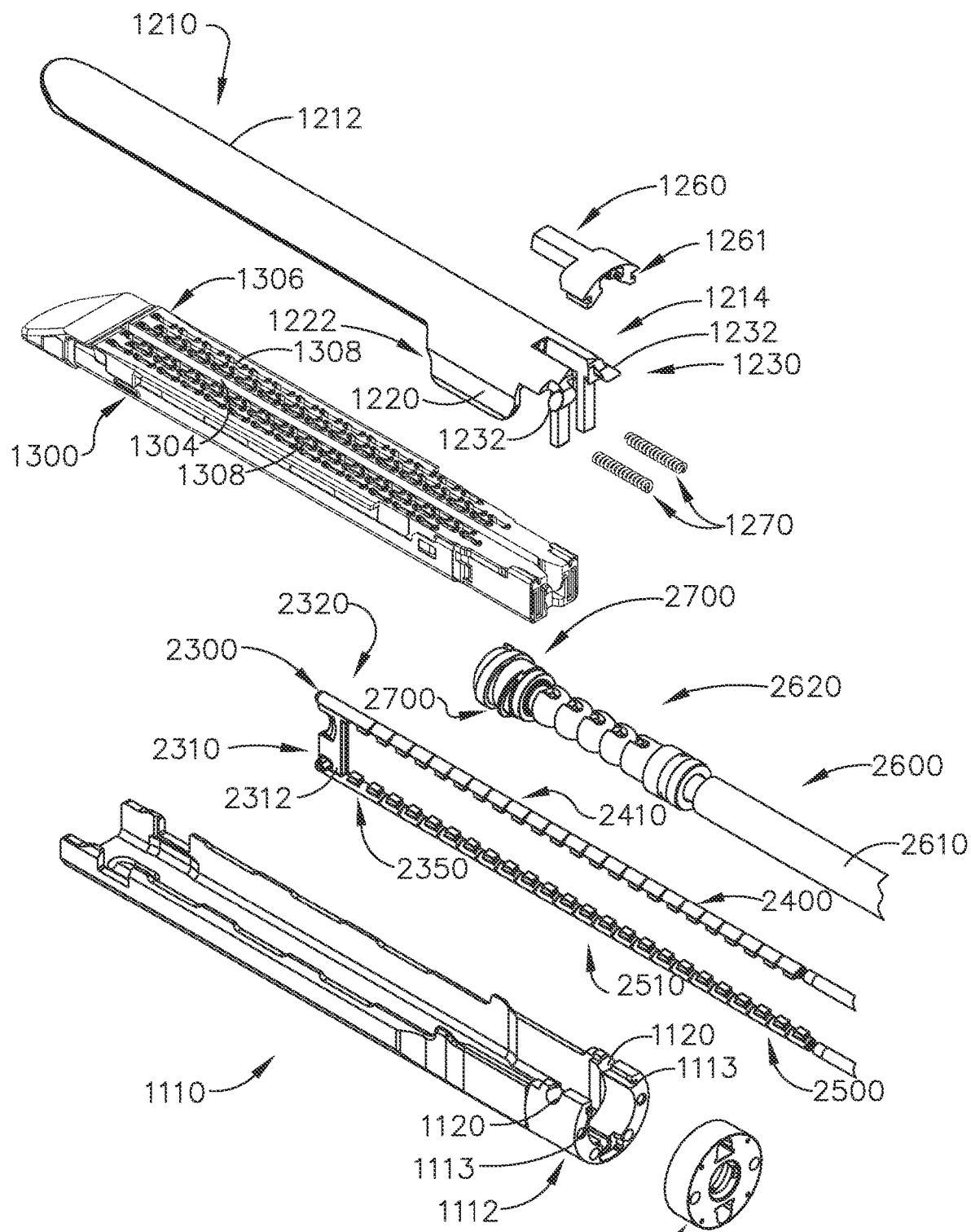
FIG. 5 is an exploded assembly view of a portion of the surgical instrument of FIG. 1.
Figure 6:
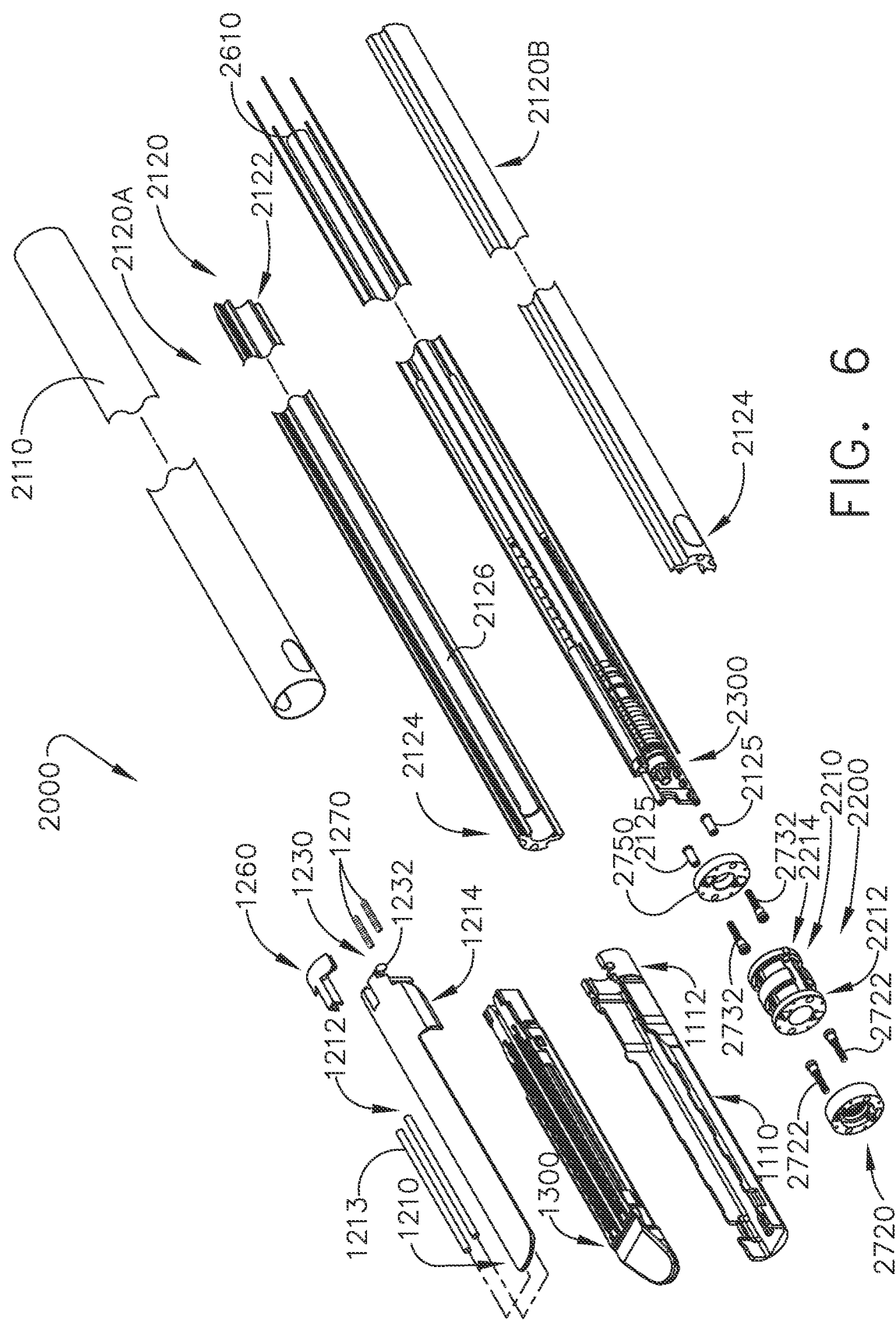
FIG. 6 is an exploded assembly view of an elongate shaft assembly of the surgical instrument of FIG. 1.

As can be seen in FIGS. 5 and 6, the proximal end 1214 of the anvil body 1212 comprises an anvil mounting portion 1230 that includes a pair of laterally extending mounting pins 1232 that are configured to be received in corresponding mounting cradles or pivot cradles 1120 formed in the proximal end 1112 of the elongate channel 1110. The mounting pins 1232 are pivotally retained within the mounting cradles 1120 by an anvil cap 1260 that may be attached to the proximal end 1112 of the elongate channel 1110 by mechanical snap features 1261 that are configured to engage retention formations 1113 on the elongate channel 1110. See FIG. 5. In other arrangements, the anvil cap 1260 may be attached to the elongate channel 1110 by welding, adhesive, etc. Such arrangement facilitates pivotal travel of the anvil 1210 relative to the surgical staple cartridge 1300 mounted in the elongate channel 1110 about a pivot axis PA between an open position (FIG. 1) and a closed position (FIGS. 2-5). Such pivot axis PA may be referred to herein as being "fixed" in that the pivot axis does not translate or otherwise move as the anvil 1200 is pivoted from an open position to a closed position.

In the illustrated arrangement, the elongate shaft assembly 2000 defines a shaft axis SA and comprises a proximal shaft portion 2100 that may operably interface with a housing of the control portion (e.g., handheld unit, robotic tool driver, etc.) of the surgical instrument 10. The elongate shaft assembly 2000 further comprises an articulation joint 2200 that is attached to the proximal shaft portion 2100 and the surgical end effector 1000. In various instances, the proximal shaft portion 2100 comprises a hollow outer tube 2110 that may be operably coupled to a housing 2002. See FIG. 2. As can be seen in FIG. 6, the proximal shaft portion 2100 may further comprise a rigid proximal support shaft 2120 that is supported within the hollow outer tube 2110 and extends from the housing to the articulation joint 2200. The proximal support shaft 2120 may comprise a first half 2120A and a second half 2120B that may be coupled together by, for example, welding, adhesive, etc. The proximal support member 2120 comprises a proximal end 2122 and a distal end 2124 and includes an axial passage 2126 that extends therethrough from the proximal end 2122 to the distal end 2124.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 10 employs a firing system 2300 that may address many if not all of these issues as well as others.

As can be seen in FIGS. 5-11, in at least one embodiment, the firing system 2300 comprises a firing member 2310 that includes a vertically-extending firing member body 2312 that comprises a top firing member feature 2320 and a bottom firing member feature 2350. A tissue cutting blade 2314 is attached to or formed in the vertically-extending firing member body 2312. See FIGS. 9 and 11. In at least one arrangement, it is desirable for the firing member 2310 to pass through the anvil body 1212 with low friction, high strength and high stiffness. In the illustrated arrangement, the top firing member feature 2320 comprises a top tubular body 2322 that has a top axial passage 2324 extending therethrough. See FIG. 10. The bottom firing member feature 2350 comprises a bottom tubular body 2352 that has a bottom axial passage 2354 extending therethrough. In at least one arrangement, the top firing member feature 2320 and the bottom firing member feature 2350 are integrally formed with the vertically-extending firing member body 2312. As can be seen in FIG. 12, the anvil body 1212 comprises an axially extending anvil slot 1240 that has a cross-sectional shape that resembles a "keyhole". Similarly, the elongate channel 1110 comprises an axially extending channel slot 1140 that also has a keyhole cross-sectional shape.

Traditional firing member arrangements employ long flexible cantilever wings that extend from a top portion and a bottom portion of the firing member. These cantilever wings slidably pass through slots in the anvil and channel that are commonly cut with a rectangular t-cutter which tended to produce higher friction surfaces. Such long cantilever wings have minimum surface area contact with the anvil and channel and can result in galling of those components. The keyhole-shaped channel slot 1140 and keyhole-shaped anvil slot 1240 may be cut with a round t-cutter and may be finished with a reamer/borer which will result in the creation of a lower friction surface. In addition, the top tubular body 2322 and the bottom tubular body 2352 tend to be stiffer than the prior cantilever wing arrangements and have increased surface area contact with the anvil and channel, respectively which can reduce galling and lead to a stronger sliding connection. Stated another way, because the anvil slot 1240 and the channel slot 1140 are keyhole-shaped and have less material removed than a traditional rectangular slot, the geometry and increased material may result in a stiffer anvil and channel when compared to prior arrangements.

Figure 11:
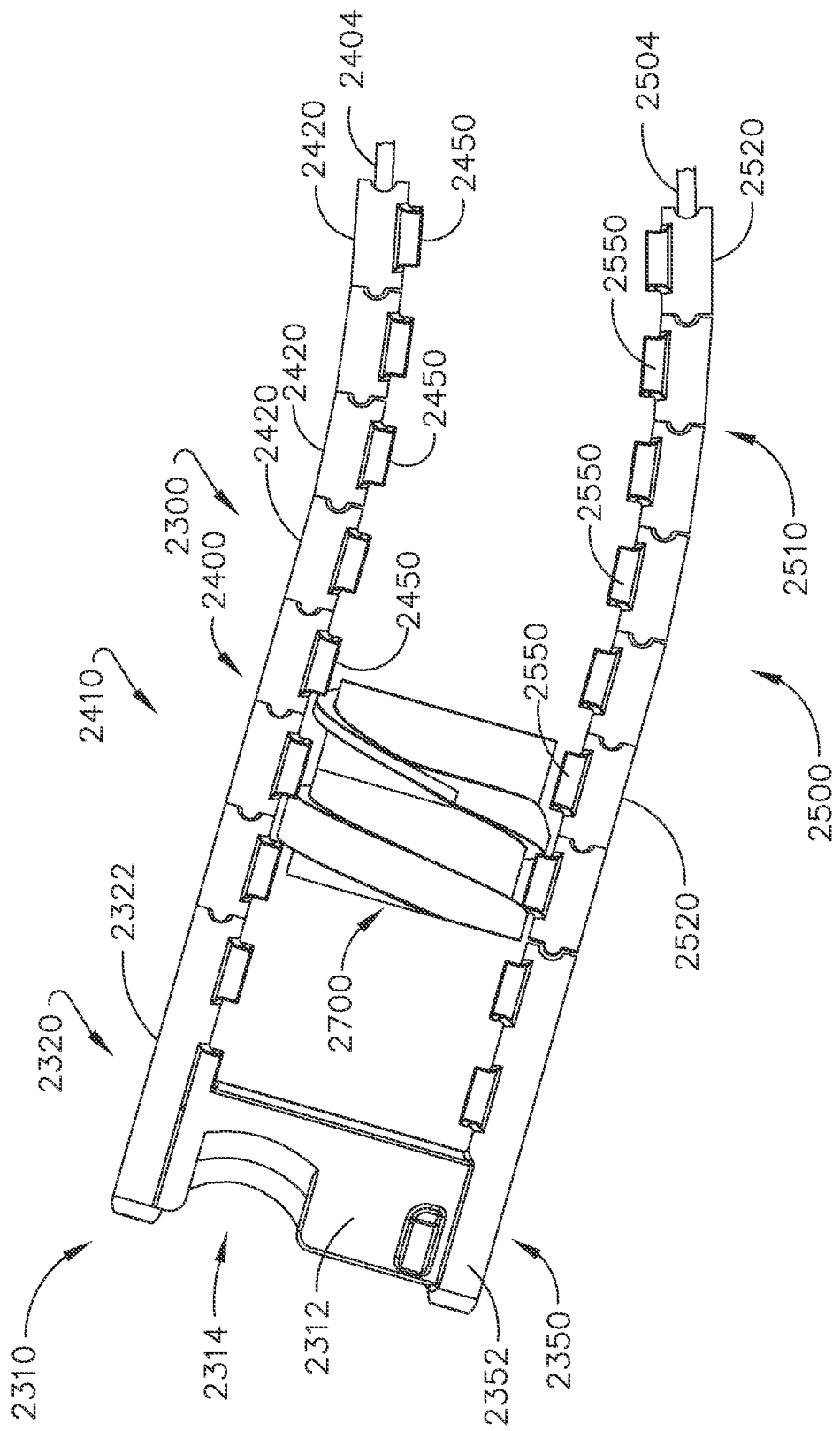
FIG. 11 is a side elevational view of the firing member and upper and lower flexible spine assemblies in engagement with the rotary drive screw of FIG. 9.
Figure 12:
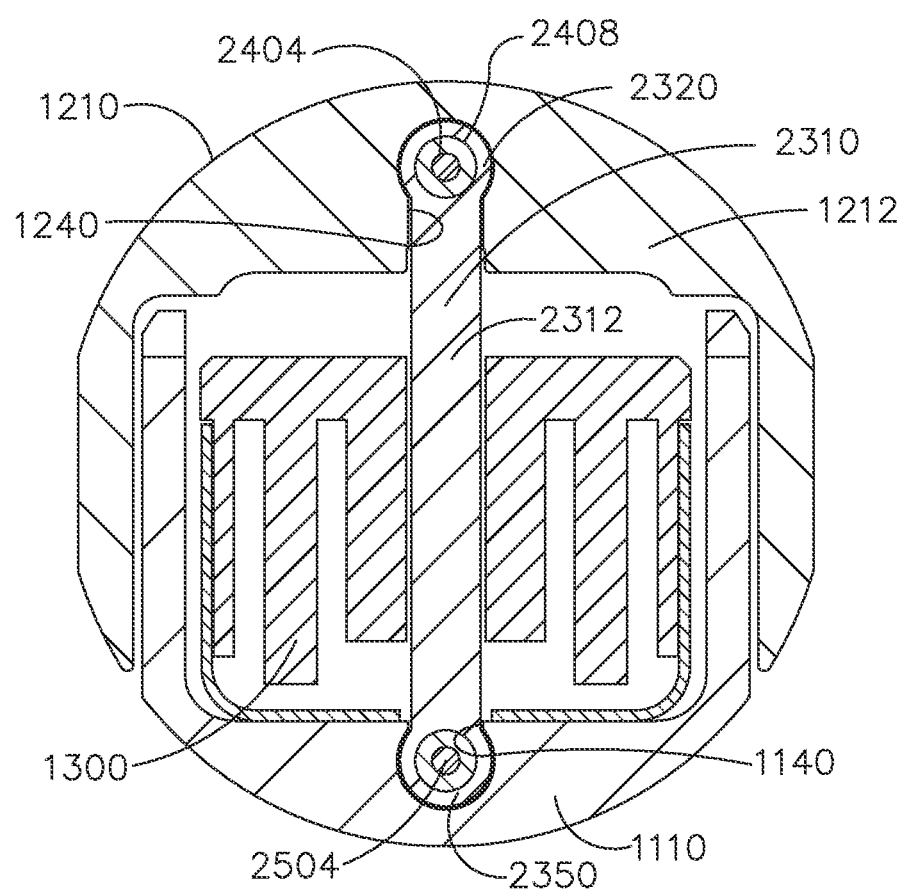
FIG. 12 is a cross-sectional end view of the surgical end effector of FIG. 4 taken along line 12-12 in FIG. 4.

Turning to FIGS. 9-11, in one arrangement, the firing system 2300 further comprises an upper flexible spine assembly 2400 that is operably coupled to the top firing member feature 2320 and a lower flexible spine assembly 2500 that is operably coupled to the bottom firing member feature 2350. In at least one embodiment, the upper flexible spine assembly 2400 comprises an upper series 2410 of upper vertebra members 2420 that are loosely coupled together by an upper flexible coupler member 2402 that is attached to the top firing member feature 2320. The upper flexible coupler member 2402 may comprises a top cable 2404 that extends through the top axial passage 2324 in the top firing member feature 2320 and a distal end 2406 of the top cable 2404 is attached to a retainer ferrule 2408 that is secured with the top axial passage 2324.

Figure 13:
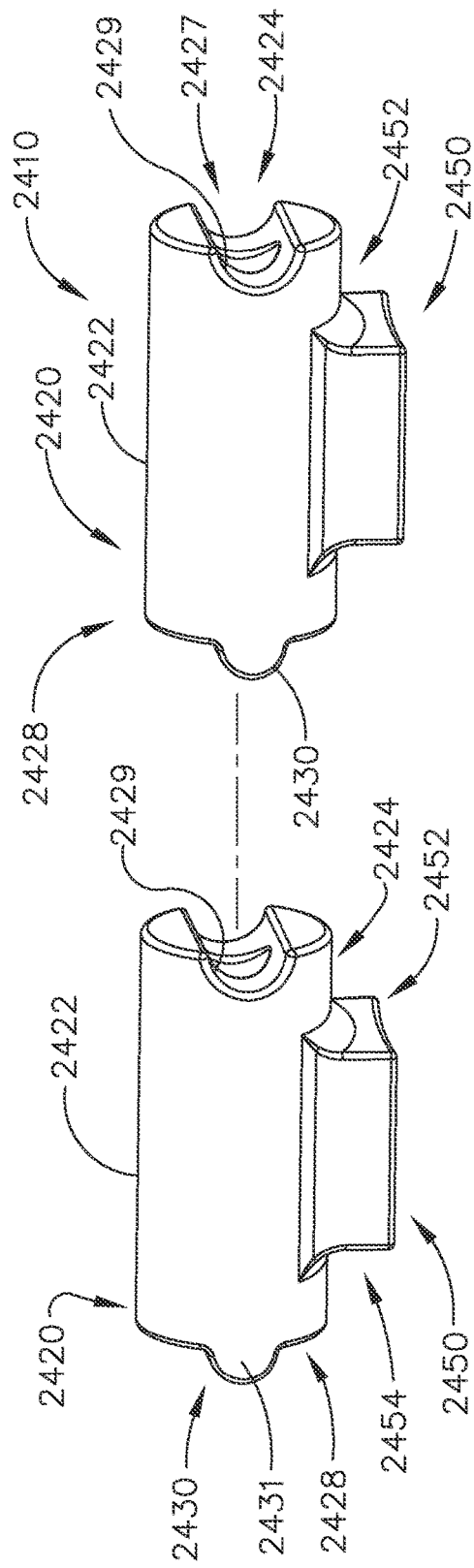
FIG. 13 is an exploded perspective view of two adjacent upper vertebra members of the upper flexible spine assembly of FIG. 10.

As can be seen in FIG. 13, each upper vertebra member 2420 comprises an upper vertebra body portion 2422 that has a proximal end 2424 and a distal end 2428. An upper hollow passage 2429 extends through the upper vertebra body portion 2422 to accommodate passage of the upper flexible coupler member 2402 therethrough. Each upper vertebra member 2420 further comprises a downwardly extending upper drive feature or upper vertebra member tooth 2450 that protrudes from the upper vertebra body portion 2422. Each upper vertebra member tooth 2450 has a helix-shaped proximal upper face portion 2452 and a helix-shaped distal upper face portion 2454. Each proximal end 2424 of the upper vertebra body portions 2422 has an upper proximal mating feature 2426 therein and each distal end 2428 has an upper distal mating feature 2430 formed therein. In at least one embodiment, the upper proximal mating feature 2426 comprises a concave recess 2427 and each upper distal mating feature 2430 comprises a convex mound 2431. When arranged in the upper series 2410, the convex mound 2431 on one upper vertebra member 2420 contacts and mates with the concave recess 2427 on an adjacent upper vertebra member 2420 in the upper series 2410 to maintain the upper vertebra members 2420 roughly in alignment so that the helix-shaped proximal upper face portion 2452 and a helix-shaped distal upper face portion 2454 on each respective upper tooth 2450 can be drivingly engaged by a rotary drive screw 2700 as will be discussed in further detail below.

Similarly, in at least one embodiment, the lower flexible spine assembly 2500 comprises a lower series 2510 of lower vertebra members 2520 that are loosely coupled together by a lower flexible coupler member 2502 that is attached to the bottom firing member feature 2350. The lower flexible coupler member 2502 may comprises a lower cable 2504 that extends through the bottom axial passage 2354 in the bottom firing member feature 2350 and a distal end 2506 of the bottom cable 2504 is attached to a retainer ferrule 2508 that is secured with the bottom axial passage 2354.

Figure 14:
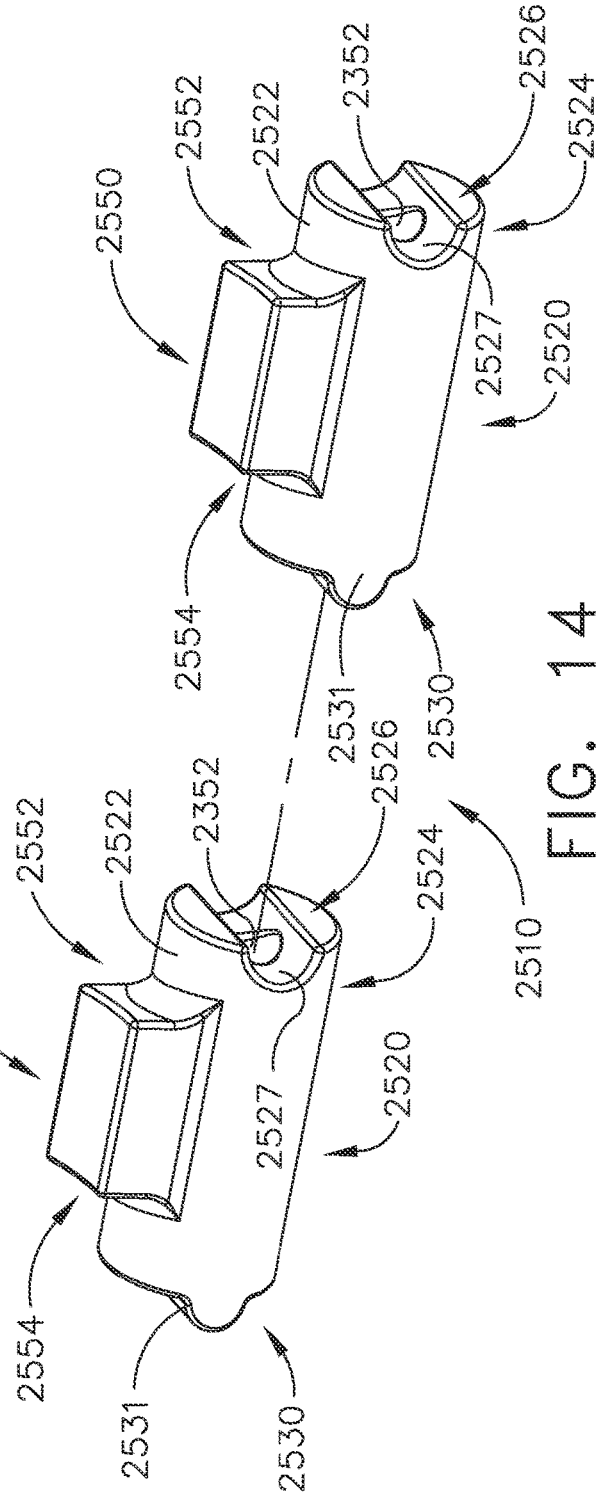
FIG. 14 is an exploded perspective view of two adjacent lower vertebra members of the lower flexible spine assembly of FIG. 10.

As can be seen in FIG. 14, each lower vertebra member 2520 comprises a lower vertebra body portion 2522 that has a proximal end 2524 and a distal end 2528. A lower hollow passage 2529 extends through the lower vertebra body portion 2522 to accommodate passage of the lower flexible coupler member 2502 therethrough. Each lower vertebra member 2520 further comprises an upwardly extending lower drive feature or lower vertebra member tooth 2550 that protrudes upward from the lower vertebra body portion 2522. Each lower vertebra member tooth 2550 has a helix-shaped proximal lower face portion 2552 and a helix-shaped distal lower face portion 2554. Each proximal end 2524 of the lower vertebra body portions 2522 has a lower proximal mating feature 2526 therein and each distal end 2528 has a lower distal mating feature 2530 formed therein. In at least one embodiment, the lower proximal mating feature 2526 comprises a concave recess 2527 and each lower distal mating feature 2530 comprises a convex mound 2531. When arranged in the lower series 2510, the convex mound 2531 on one lower vertebra member 2520 contacts and mates with the concave recess 2527 on an adjacent lower vertebra member 2520 in the lower series 2510 to maintain the lower vertebra members 2520 roughly in alignment so that the helix-shaped proximal lower face portion 2552 and a helix-shaped distal lower face portion 2554 on each respective lower vertebra member tooth 2550 can be drivingly engaged by a rotary drive screw 2700 as will be discussed in further detail below.

Figure 7:
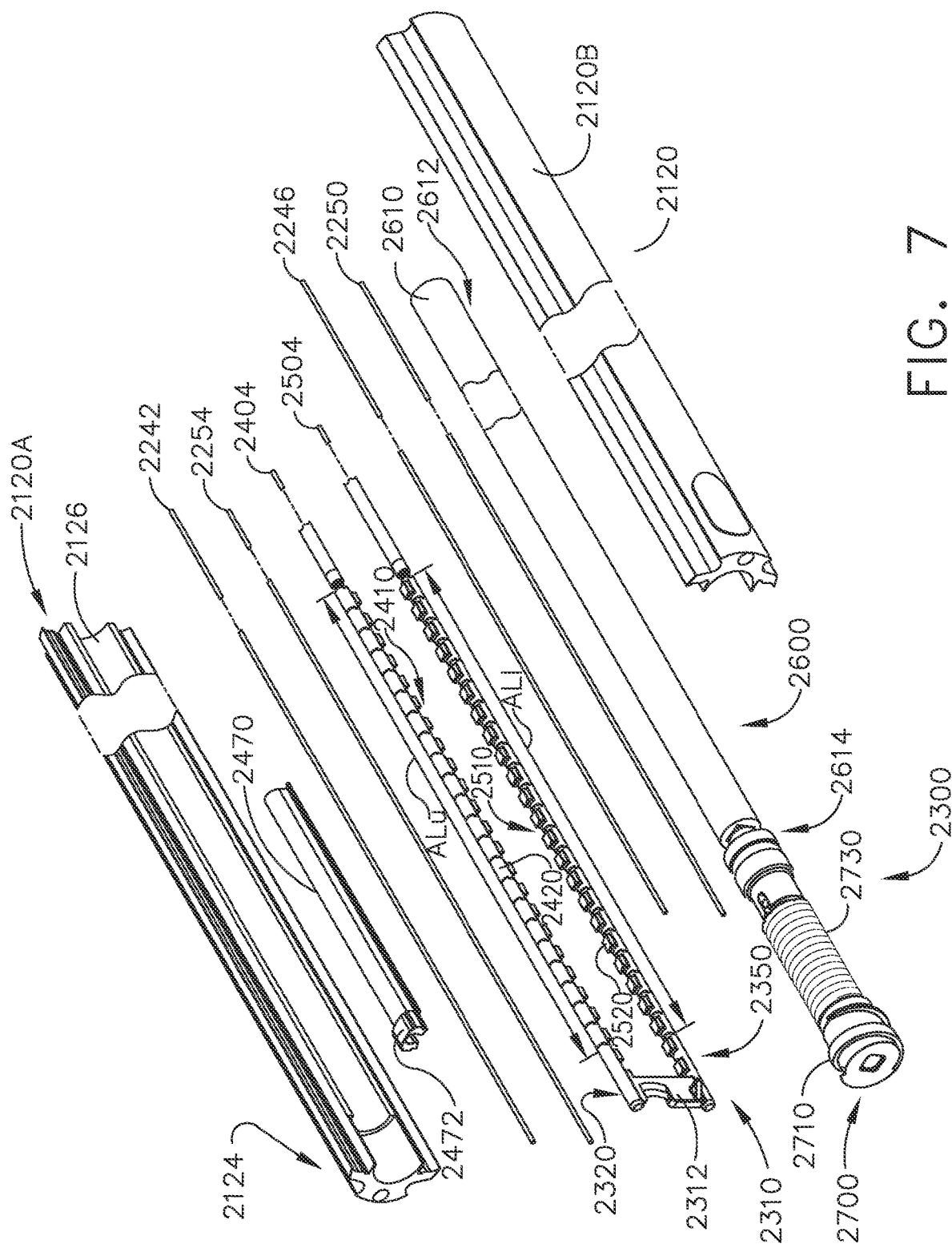
FIG. 7 is another exploded assembly view of the elongate shaft assembly of FIG. 6.
Figure 8:
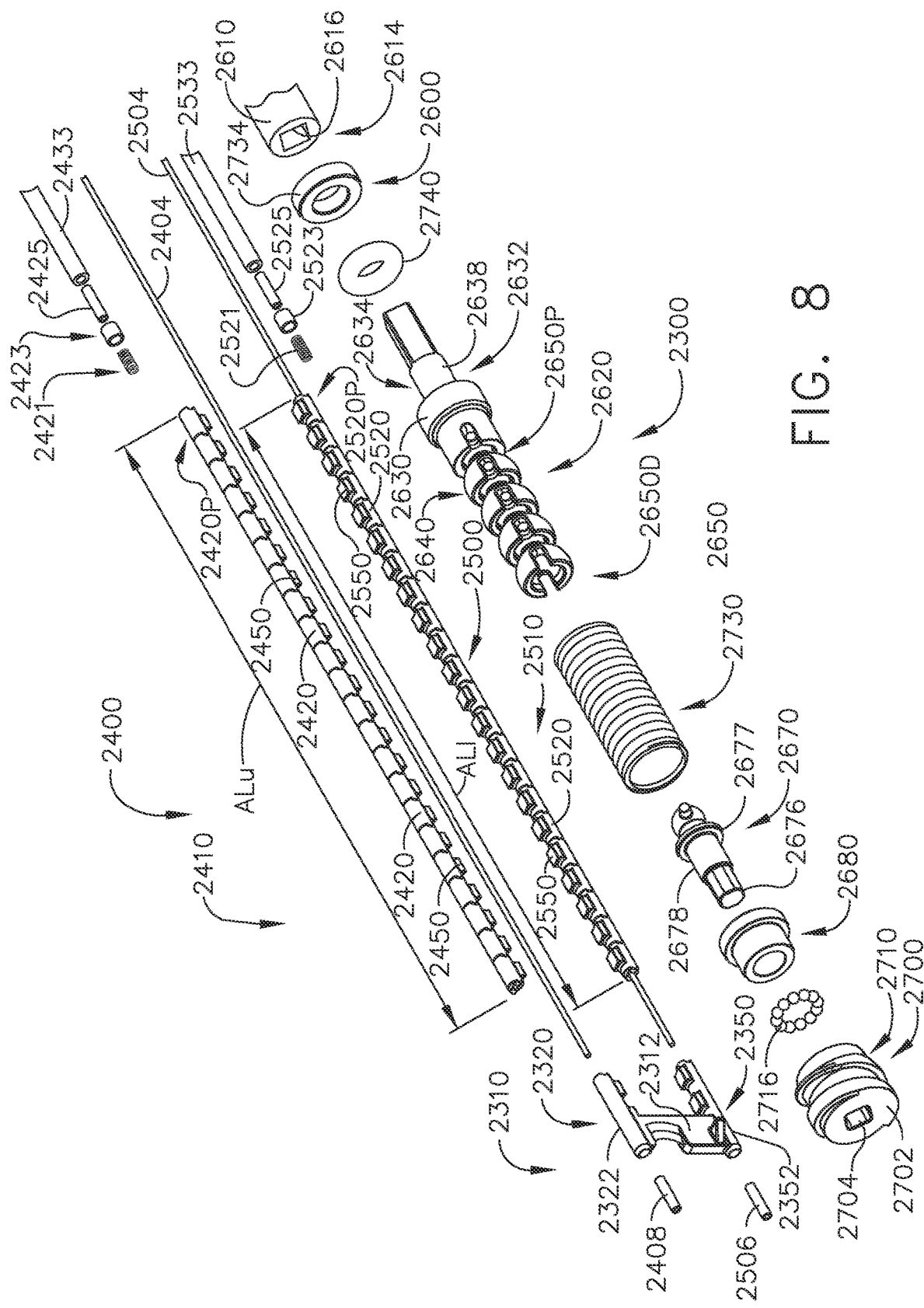
FIG. 8 is an exploded assembly view of a firing system and a rotary drive system according to at least one aspect of the present disclosure.

Now turning to FIGS. 5, 7, and 8, in at least one arrangement, the firing drive system 2300 further comprises a rotary drive screw 2700 that is configured to drivingly interface with the upper series 2410 of upper vertebra members 2420 and the lower series 2510 of lower vertebra members 2520. In the illustrated arrangement, the rotary drive screw 2700 is driven by a rotary drive system 2600 that comprises a proximal rotary drive shaft 2610 that is rotatably supported within the axial passage 2126 within the proximal support shaft 2120. See FIG. 7. The proximal rotary drive shaft 2610 comprises a proximal end 2612 and a distal end 2614. The proximal end 2612 may interface with a gear box 2004 or other arrangement that is driven by a motor 2006 or other source of rotary motion housed in the housing of the surgical instrument. See FIG. 2. Such source of rotary motion causes the proximal rotary drive shaft to rotate about the shaft axis SA within the axial passage 2126 in the proximal support shaft 2120.

Figure 16:
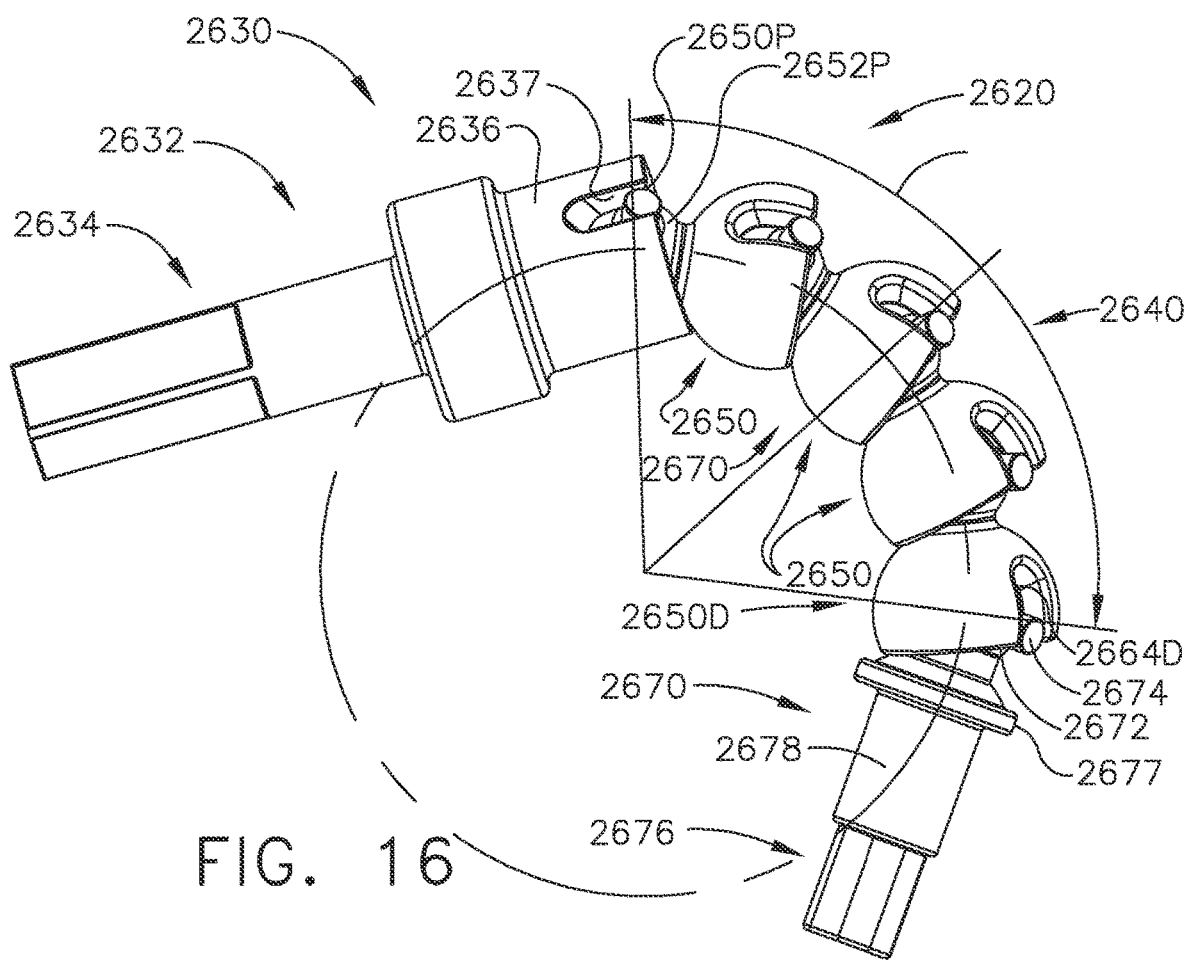
FIG. 16 is a perspective view of a CV drive shaft assembly of the rotary drive system of FIG. 8 in an articulated orientation.
Figure 17:
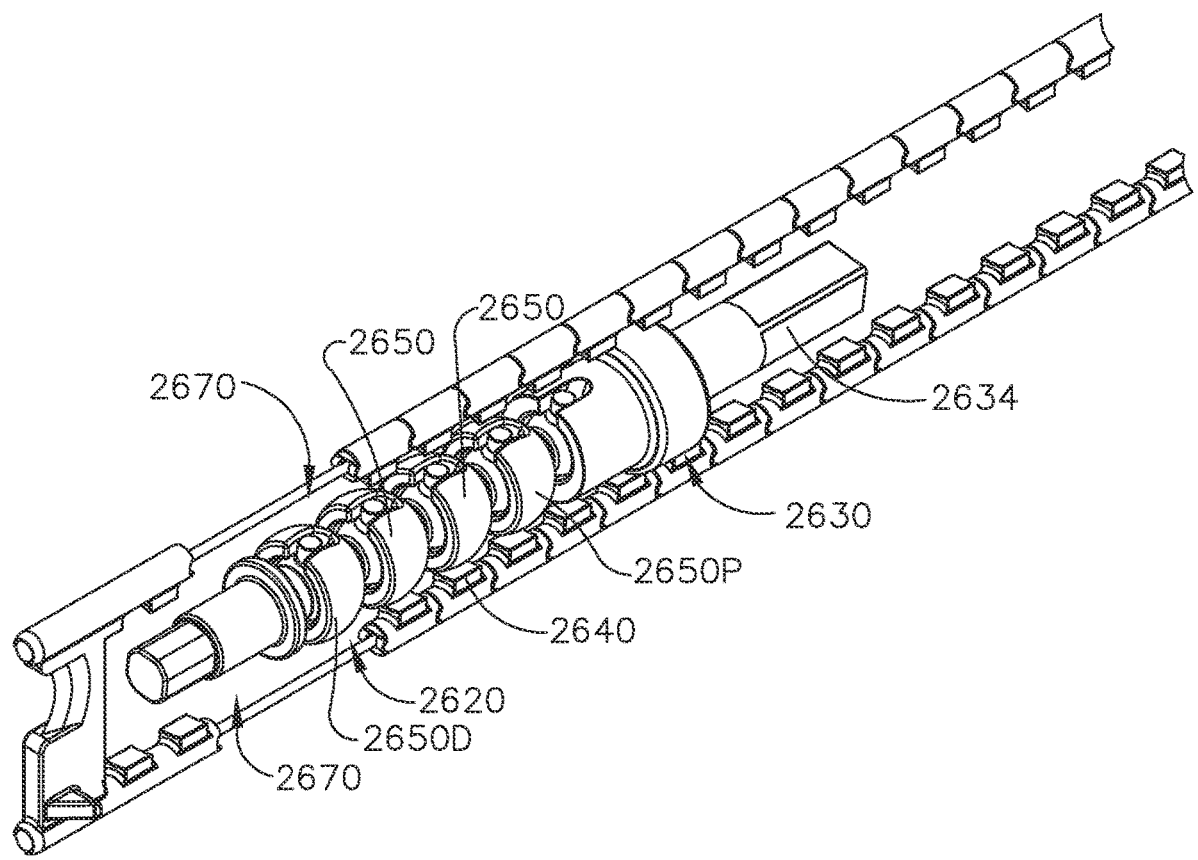
FIG. 17 is a perspective view of the firing system of FIG. 8 in driving engagement with the CV drive shaft assembly of FIG. 16 in accordance with at least one aspect of the present disclosure.

The proximal rotary drive shaft 2610 is operably supported within the elongate shaft assembly 2000 in a location that is proximal to the articulation joint 2200 and operably interfaces with a constant velocity (CV) drive shaft assembly 2620 that "spans" or extends axially through the articulation joint 2200. As can be seen in FIGS. 8, 16, and 17, in at least one arrangement, the CV drive shaft assembly 2620 comprises a proximal CV drive assembly 2630 and a distal CV drive shaft 2670. The proximal CV drive assembly 2630 comprises a proximal shaft segment 2632 that consists of an attachment shaft 2634 that is configured to be non-rotatably received within a similarly-shaped coupler cavity 2616 in the distal end 2614 of the proximal rotary drive shaft 2610. The proximal shaft segment 2632 operably interfaces with a series 2640 of movably coupled drive joints 2650.

Figure 18:
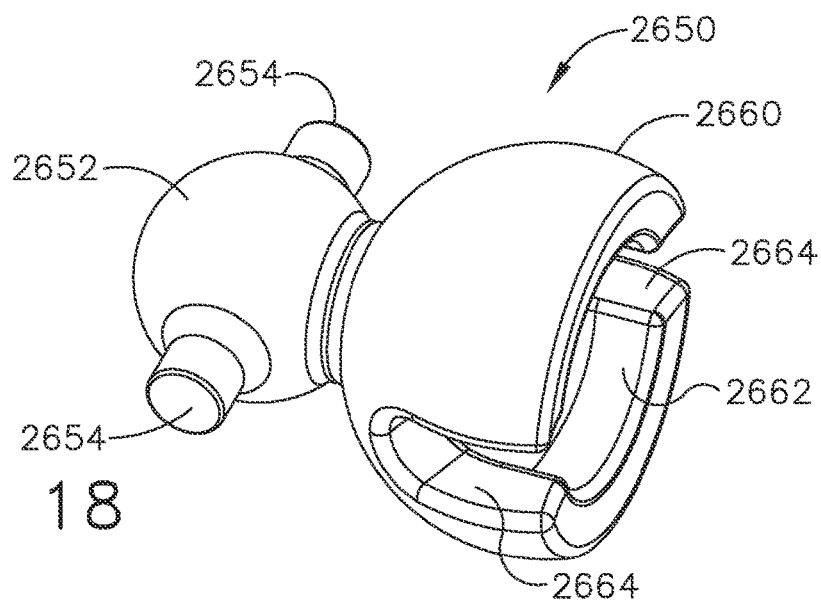
FIG. 18 is a perspective view of a drive joint of the CV drive shaft assembly of FIG. 16.

As can be seen in FIG. 18, in at least one arrangement, each drive joint 2650 comprises a first or distal sphere portion 2660 and a second or proximal sphere portion 2652. The distal sphere portion 2660 is larger than the proximal sphere portion 2652. The distal sphere portion 2660 comprises a socket cavity 2662 that is configured to rotatably receive a proximal sphere portion 2652 of an adjacent drive joint 2650 therein. Each proximal sphere portion 2652 comprises a pair of diametrically opposed joint pins 2654 that are configured to be movably received in corresponding pin slots 2664 in the distal sphere portion 2660 of an adjacent drive joint 2650 as can be seen in FIG. 16. A proximal sphere portion 2652P of a proximal-most drive joint 2650P is rotatably received in a distal socket portion 2636 of the proximal shaft segment 2632 as shown in FIG. 16. The joint pins 2654P are received within corresponding pin slots 2637 in the distal socket portion 2636. As can be further seen in FIG. 16, a distal-most drive joint 2650D in the series 2640 of movably coupled drive joints 2650 is movably coupled to a distal CV drive shaft 2670.

In at least one arrangement, the distal CV drive shaft 2670 comprises a proximal sphere portion 2672 that is sized to be movably received in the socket cavity 2662D in the distal-most drive joint 2650D. The proximal sphere portion 2672 includes joint pins 2674 that are movably received in the pin slots 2664D in the distal-most drive joint 2650D. The distal CV drive shaft 2670 further comprises a distally extending shaft stem 2676 that is configured to be non-rotatably coupled to the rotary drive screw 2700 that is positioned distal to the articulation joint 2200. The distal CV drive shaft 2670 includes a flange 2677 and a mounting barrel portion 2678 for receiving a thrust bearing housing 2680 thereon.

In the illustrated arrangement, when the series 2640 of movably coupled drive joints 2650 articulates, the joint pins 2674 remain in the corresponding pin slots 2664 of an adjacent drive joint 2650. In the example illustrated in FIG. 18, each drive joint may be capable of approximately eighteen degrees of articulation in the pitch and yaw directions. FIG. 16 illustrates an angle of the series of 2640 of drive joints 2650 when each drive joint 2650 in the series are fully articulated ninety degrees in pitch and yaw which yields an angle α of approximately 100.9 degrees. In such arrangement, the outer surface of each distal sphere portion 2660 clears the outer surface of the adjacent or adjoining proximal sphere portion 2652 allowing for unrestricted motion until the eighteen degree limit is reached. The rigid design and limited small angles allow the series 2640 of movably coupled drive joints 2650 to carry high loads torsionally at an overall large angle.

In the illustrated arrangement, the articulation joint 2200 comprises an articulation joint spring 2230 that is supported within an outer elastomeric joint assembly 2210. The outer elastomeric joint assembly 2210 comprises a distal end 2212 that is attached to the proximal end 1112 of the elongate channel 1110. For example, as can be seen in FIG. 6, the distal end 2212 of the outer elastomeric joint assembly 2210 is attached to the proximal end 1112 of the elongate channel 1110 by a pair of cap screws 2722 that extend through a distal mounting bushing 2720 to be threadably received in the proximal end 1112 of the elongate channel 1110. A proximal end 2214 of the elastomeric joint assembly 2210 is attached to the distal end 2124 of the proximal support shaft 2120. The proximal end 2214 of the elastomeric joint assembly 2210 is attached to the distal end 2124 of the proximal support member 2120 by a pair of cap screws 2732 that extend through a proximal mounting bushing 2750 to be threadably received in threaded inserts 2125 mounted within the distal end 2124 of the proximal support shaft 2120.

To prevent the drive joints 2650 from buckling during articulation, the series 2640 of movably coupled drive joints 2650 extend through at least one low friction articulation joint spring 2730 that is supported within the outer elastomeric joint assembly 2210. See FIG. 19. The articulation joint spring 2730 is sized relative to the drive joints 2650 such that a slight radial clearance is provided between the articulation joint spring 2730 and the drive joints 2650. The articulation joint spring 2730 is designed to carry articulation loads axially which may be significantly lower than the torsional firing loads. The joint spring(s) is longer than the series 2640 of drive joints 2650 such that the drive joints are axially loose. If the "hard stack" of the series 2640 of drive joints 2650 is longer than the articulation joint spring(s) 2730 hard stack, then the drive joints 2650 may serve as an articulation compression limiter causing firing loads and articulation loads to resolve axially through the series 2640 of the drive joints 2650. When the firing loads resolve axially through the series 2640 of the drive joints 2650, the loads may try to straighten the articulation joint 2200 or in other words cause de-articulation. If the hard stack of the articulation joint spring(s) 2730 is longer than the hard stack of the series 2640 of the drive joints 2650, the firing loads will then be contained within the end effector and no firing loads will resolve through the drive joints 2650 or through the springs(s) 2730.

Figure 19:
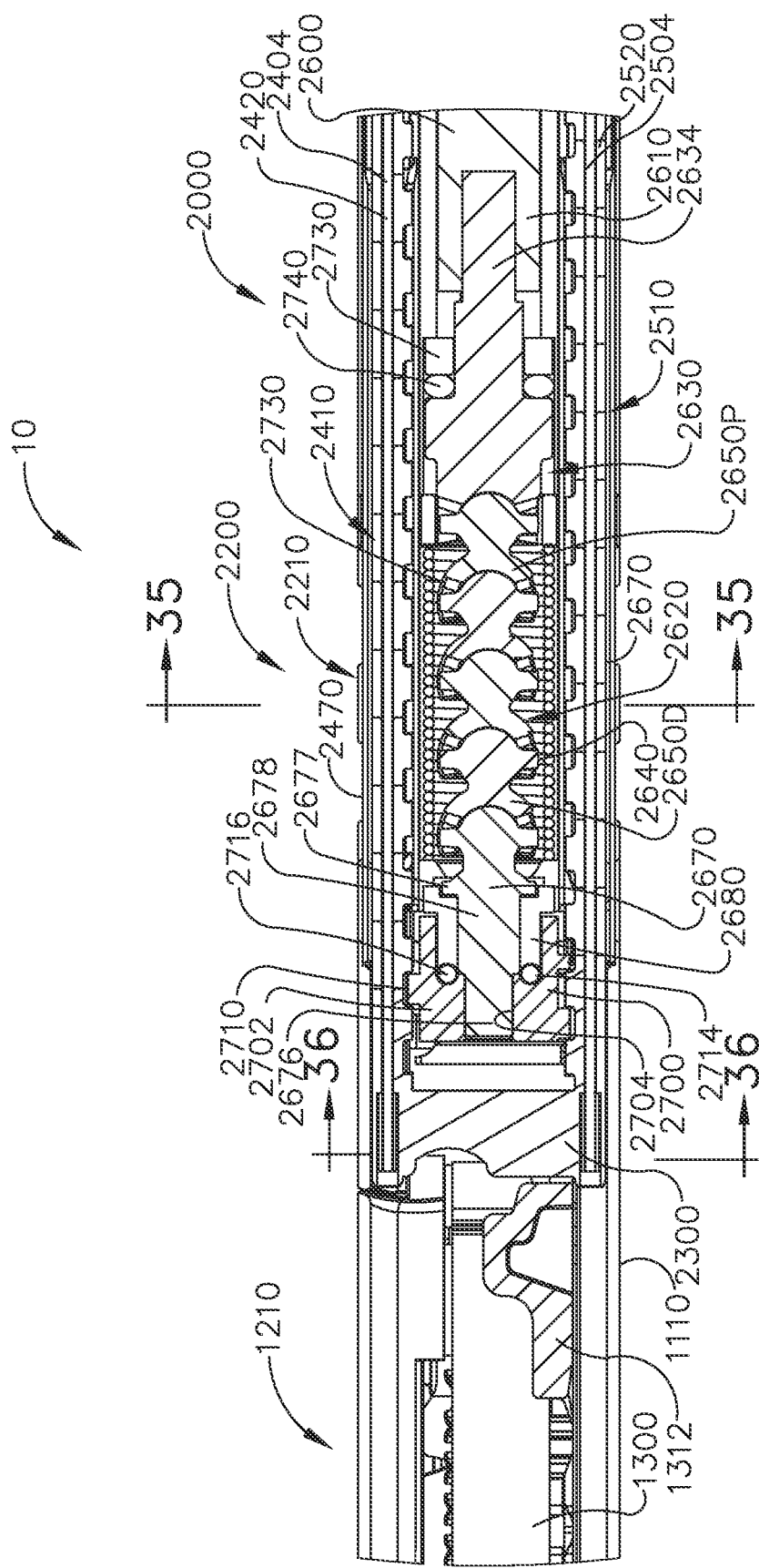
FIG. 19 is a cross-sectional view of a portion of the surgical instrument of FIG. 4 taken along line 19-19 in FIG. 4.
Figure 20:
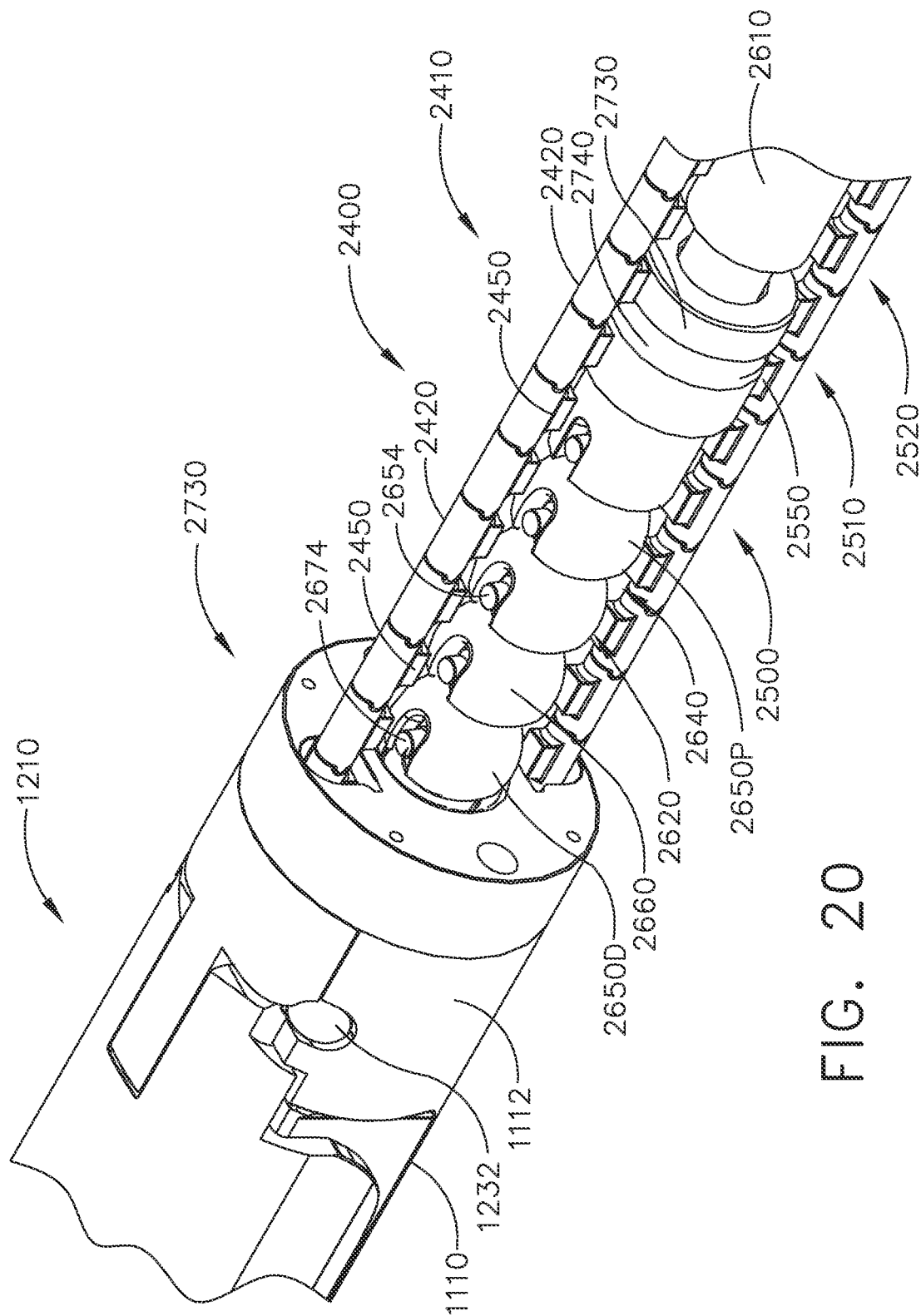
FIG. 20 is a partial perspective view of a proximal end portion of the surgical end effector and portions of the firing system and the rotary drive system of the surgical instrument of FIG. 1.
Figure 21:
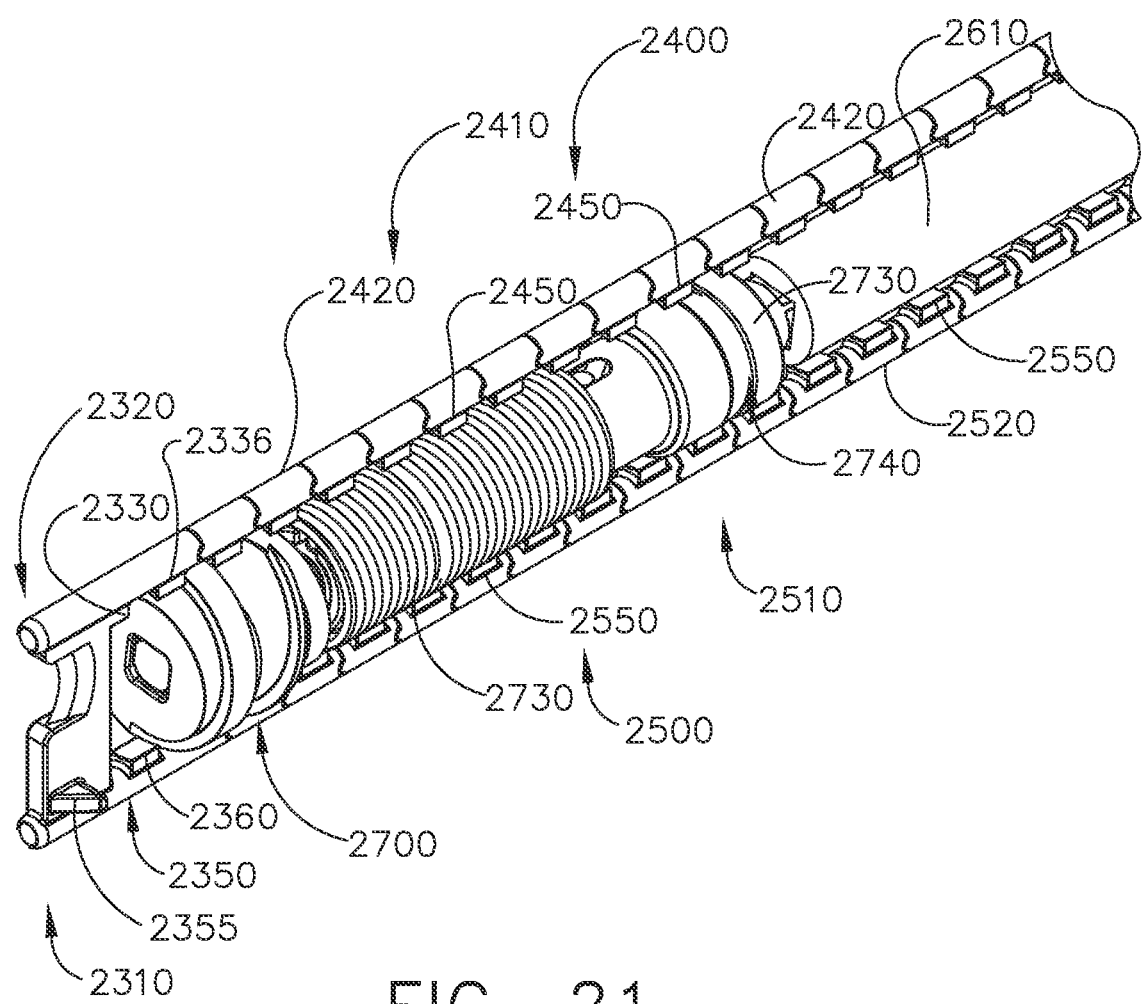
FIG. 21 is a perspective view of the rotary drive system of the surgical instrument of FIG. 1 in driving engagement with the firing system thereof in accordance with at least one aspect of the present disclosure.

To further ensure that the drive joints 2650 are always engaged with each other, a proximal drive spring 2740 is employed to apply an axial biasing force to the series 2640 of drive joints 2650. For example, as can be seen in FIGS. 8, 19, and 20, the proximal drive spring 2740 is positioned between the proximal mounting bushing 2734 and a support flange that is formed between the distal socket portion 2636 and a proximal barrel portion 2638 of the proximal shaft segment 2632. In one arrangement, the proximal drive spring 2740 may comprise an elastomeric O-ring/bushing received on the proximal barrel portion 2638 of the proximal shaft segment 2632. The proximal drive spring 2740 lightly biases the drive joints 2650 together to decrease any gaps that may occur during articulation. This ensures that the drive joints 2650 transfer loads torsionally. It will be appreciated, however, that in at least one arrangement, the proximal drive spring 2740 does not apply a high enough axial load to cause firing loads to translate through the articulation joint 2200.

As can be seen in FIGS. 9 and 10, the top firing member feature 2320 on the firing member 2310 comprises a distal upper firing member tooth segment 2330 that is equivalent to one half of an upper tooth 2450 on each upper vertebra member 2420. In addition, a proximal upper firing member tooth 2336 that is identical to an upper tooth 2450 on each upper vertebra member 2420 is spaced from the distal upper firing member tooth segment 2330. The distal upper firing member tooth segment 2330 and the proximal upper firing member tooth 2336 may be integrally formed with the top firing member feature 2320 of the firing member 2310. Likewise, the bottom firing member feature 2350 of the firing member 2310 comprises a distal lower firing member tooth 2360 and a proximal lower firing member tooth 2366 that are integrally formed on the bottom firing member feature 2350. For example, in at least one arrangement, the firing member 2310 with the rigidly attached teeth 2330, 2336, 2360, and 2366 may be fabricated at one time as one unitary component using conventional metal injection molding techniques.

As indicated above, each of the upper vertebra members 2520 is movably received on an upper flexible coupler member 2402 in the form of a top cable 2404. As was described above, the distal end 2406 of the top cable 2404 is secured to the top firing member feature 2320 of the firing member 2310. Similarly, each of the lower vertebra members 2520 is movably received on a lower flexible coupler member 2502 in the form of a lower cable 2504. A distal end 2506 of the lower cable 2504 is secured to the bottom firing member feature 2350 of the firing member 2310. In at least one arrangement, the top cable 2404 and the bottom cable 2504 extend through the proximal shaft portion 2100 and, as will be discussed in further detail below, may interface with a bailout arrangement supported in the housing for retracting the firing member 2310 back to its home or starting position should the firing member drive system fail.

Turning again to FIG. 8, the axial length $AL_u$ of the upper series 2410 of upper vertebra members 2420 and the axial length $AL_l$ of the lower series 2510 of lower vertebra members 2520 are equal and must be sufficiently long enough to facilitate the complete distal advancement of the firing member 2310 from the home or starting position to a distal-most ending position within the staple cartridge while the proximal-most upper vertebra members 2420 in the upper series 2410 of upper vertebra members 2420 and the proximal-most lower vertebra members 2520 in the lower series 2510 of lower vertebra members 2520 remain in driving engagement with the rotary drive screw 2700. As can be seen in FIG. 8, an upper compression limiting spring 2421 is configured to interface with a proximal-most upper vertebra member 2420P in the upper series 2410 of upper vertebra members 2420. The upper compression limiting spring 2421 is journaled on the top cable 2404 and is retained in biasing engagement with the proximal-most upper vertebra member 2420P by an upper spring holder 2423 that is retained in position by an upper ferrule 2425 that is crimped onto the top cable 2404. The top cable 2404 extends through an upper hypotube 2433 that is supported in the proximal support shaft. Likewise, a lower compression limiting spring 2521 is configured to interface with a proximal-most, lower vertebra member 2520P in the lower series 2510 of lower vertebra members 2520. The lower compression spring 2521 is journaled on the lower cable 2504 and is retained in biasing engagement with the proximal-most, lower vertebra member 2520P by a lower spring holder 2523 that is retained in position by a lower ferrule 2525 that is crimped onto the lower cable 2504. The lower cable 2504 extends through a lower hypotube 2533 that is supported in the proximal support shaft.

When the upper vertebra members 2420 and the lower vertebra members 2520 angle through the articulation joint (after the end effector has been positioned in an articulated position), the gaps between the respective vertebra members 2420, 2520 increase in each series 2410, 2510 which causes the springs 2421, 2521 to become tighter. The compression limiting springs 2421, 2521 provide enough slack in the cables 2404, 2504, respectively to enable the vertebra members 2420, 2520 angle through the most extreme articulation angles. If the cables 2404, 2504 are pulled too tight, the spring holders 2423, 2523 will contact their respective proximal-most vertebra members 2420P, 2520P. Such compression limiting arrangements ensure that the vertebra members 2420, 2520 in their respective series 2410, 2510 always remain close enough together so that the rotary drive screw 2700 will always drivingly engage them in the manner discussed in further detail below. When the vertebra members 2420, 2520 are aligned straight again, the compression limiting springs 2421, 2521 may partially relax while still maintaining some compression between the vertebra members.

As indicated above, when the upper vertebra members 2420 are arranged in the upper series 2410 and lower vertebra members 2520 are arranged in the lower series 2510, the convex mounds and concave recesses in each vertebra member as well as the compression limiter springs serve to maintain the upper and lower vertebra members in relatively linear alignment for driving engagement by the rotary drive screw 2700. As can be seen in FIGS. 9 and 10, when the upper vertebra members 2420 are in linear alignment, the upper teeth 2450 are spaced from each other by an opening space generally designated as 2460 that facilitates driving engagement with the helical drive thread 2170 on the rotary drive screw. Similarly, when the lower vertebra members 2520 are in linear alignment, the lower vertebra member teeth 2550 are spaced from each other by an opening space generally designated as 2560 that facilitates driving engagement with the helical drive thread 2170 of the rotary drive screw 2700.

Figure 22:
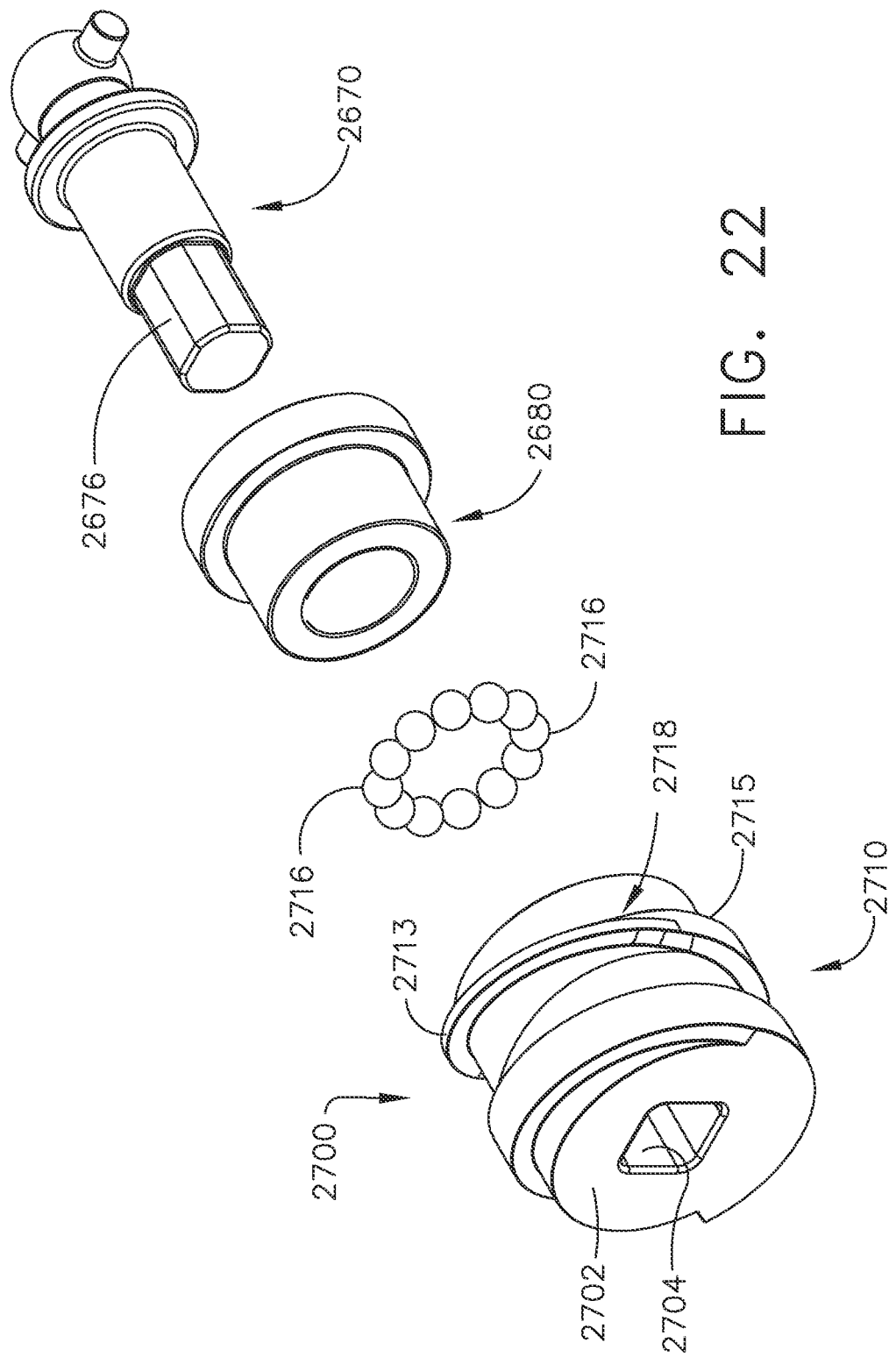
FIG. 22 is an exploded perspective view of the rotary drive screw and thrust bearing arrangement of the firing system of FIG. 21.

Turning to FIGS. 8 and 22, the rotary drive screw 2700 comprises a screw body 2702 that has a socket 2704 therein for receiving the distally extending shaft stem 2676 of the distal CV drive shaft 2670. An internal radial groove 2714 (FIG. 10) is formed in the screw body 2702 for supporting a plurality of ball bearings 2716 therein. In one arrangement, for example, 12 ball bearings 2716 are employed. The radial groove 2714 supports the ball bearings 2716 between the screw body 2702 and a distal end of the thrust bearing housing 2680. The ball bearings 2716 serve to distribute the axial load of the rotary drive screw 2700 and significantly reduce friction through the balls' rolling motion.

Figure 24:
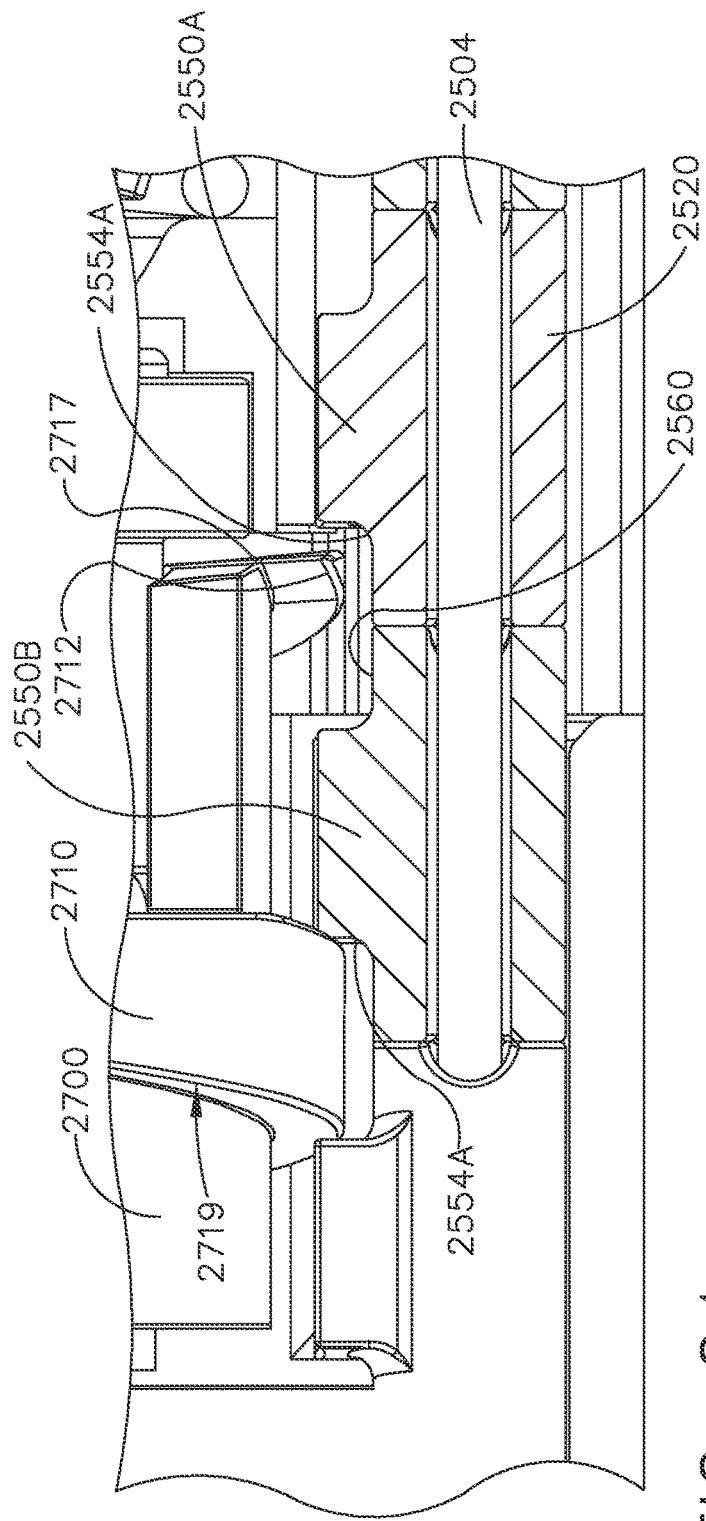
FIG. 24 is a partial cross-sectional side view of a portion of the lower flexible spine assembly and a portion of the firing member of FIG. 21 in driving engagement with a portion of the rotary drive screw.
Figure 23:
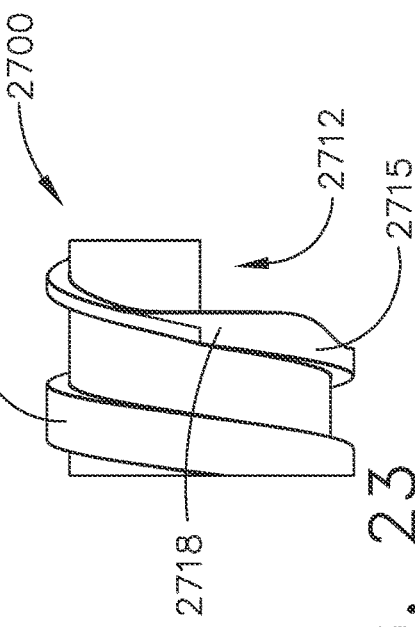
FIG. 23 is a side view of the rotary drive screw of FIG. 22.

As can be seen in FIG. 23, a helical drive thread 2710 is provided around the screw body 2702 and serves to form a proximal thread scoop feature 2712. The proximal thread scoop feature 2712 is formed with a first pitch 2713 and the remaining portion of the helical drive thread 2710 is formed with a second pitch 2715 that differs from the first pitch 2713. In FIGS. 22 and 23, area 2718 illustrates where the first pitch 2713 and the second pitch 2715 converge. In at least one embodiment, the first pitch 2713 is larger than the second pitch 2715 to ensure that the rotary drive screw 2700 captures and "scoops up" or drivingly engages every upper vertebra member 2420 and every lower vertebra member 2520. As can be seen in FIG. 24, a proximal end 2717 of the helical drive thread 2710 that has the first pitch 2713 has scooped into the into the opening space 2560 between two adjacent lower vertebra member teeth 2550A and 2550B while the center portion 2719 of the helical drive thread 2710 that has the second pitch 2715 is in driving engagement with the helix-shaped distal lower face portion 2554 on the lower vertebra member tooth 2550B and the helix-shaped proximal lower face portion 2552 on the proximal lower firing member tooth 2366. As can also be appreciated, the scoop feature 2712 may not contact the helix-shaped distal lower face portion 2554A of the lower vertebra member tooth 2550A as it scoops up the lower vertebra member tooth 2550B when driving the firing member 2310 distally. The helical drive thread 2710 interacts with the teeth 2450 of the upper vertebra members 2420 in a similar manner.

A power screw is a threaded rod with a full three hundred sixty degree nut around it. Rotation of the power screw causes the nut to advance or move longitudinally. In the present arrangements, however, due to space constraints, a full three hundred sixty degree nut cannot fit inside the end effector. In a general sense, the upper flexible spine assembly 2400 and the lower flexible spine assembly 2500 comprise a radially/longitudinally segmented "power screw nut" that is rotatably driven by the rotary drive screw 2700. When the rotary drive screw is rotated in a first rotary direction, the rotary drive screw 2700 drives one or more vertebra members in each of the upper series and lower series of vertebra members longitudinally while the vertebra members 2420, 2520 stay in the same locations radially. The upper series 2410 and lower series 2510 are constrained from rotating around the rotary drive screw 2700 and can only move longitudinally. In one arrangement, the upper vertebra members 2420 in the upper series 2410 and the lower vertebra members 2520 in the lower series 2510 only surround the rotary drive screw 2700 with less than ten degrees each.

Figure 25:
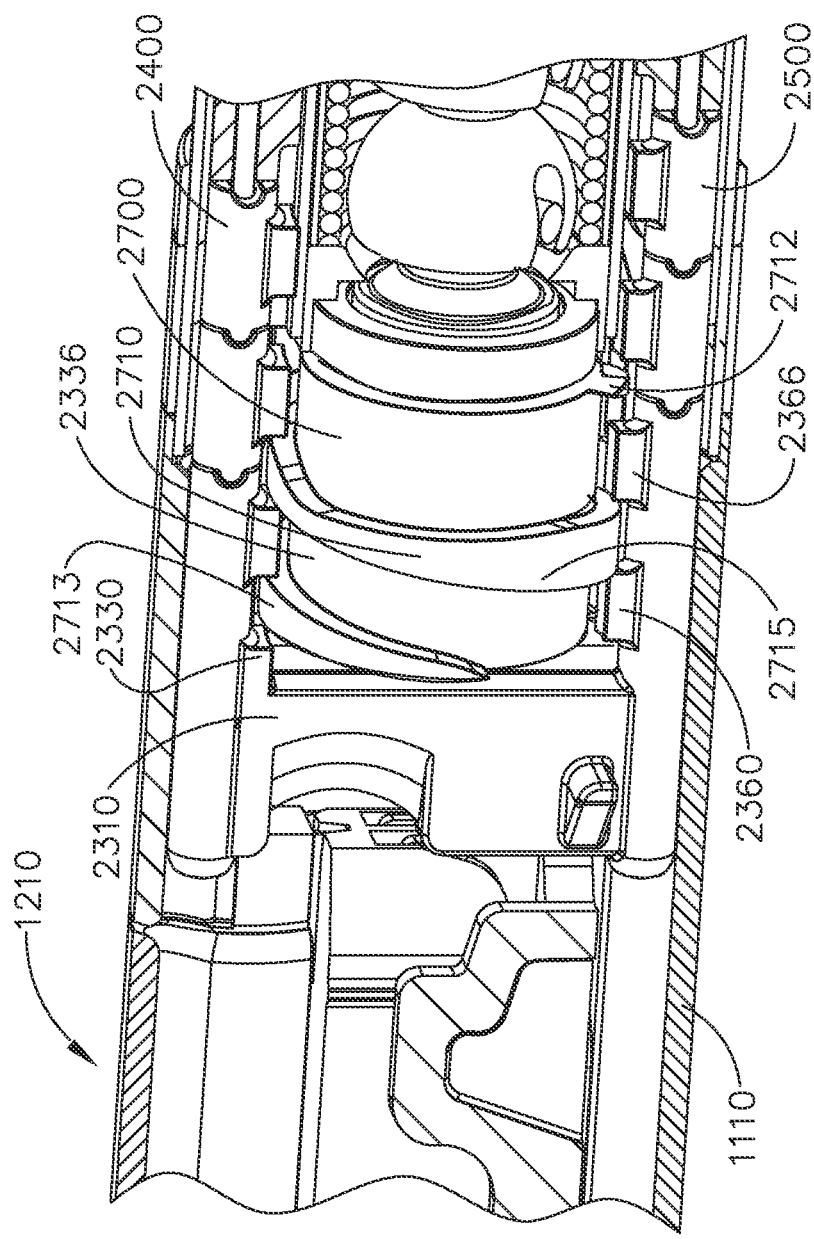
FIG. 25 is a perspective view of the firing member in a home or starting position within the surgical end effector of the surgical instrument of FIG. 1.
Figure 26:
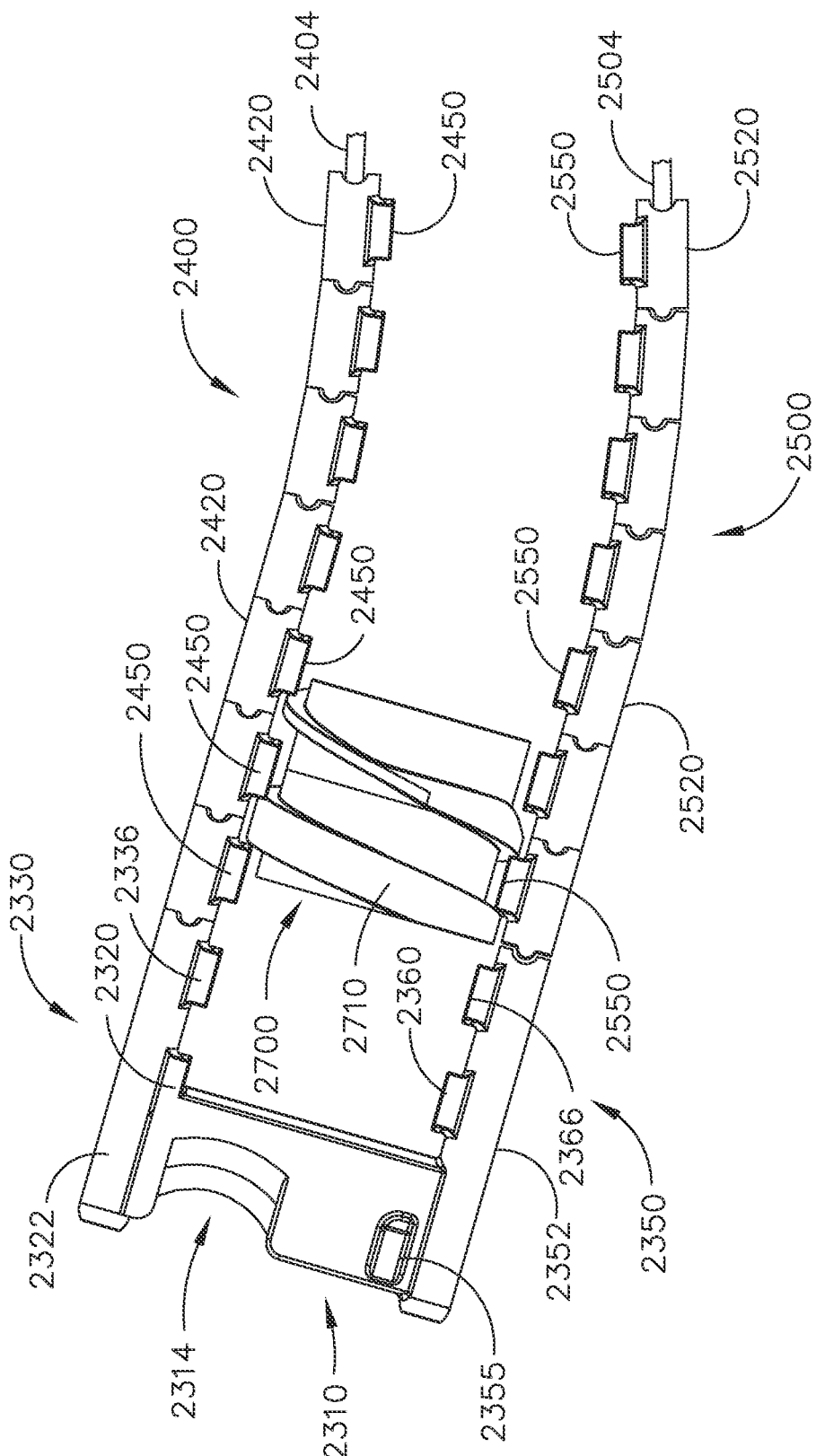
FIG. 26 is a side view illustrating the upper flexible spine assembly and the lower flexible spine assembly of FIG. 21 in driving engagement with the rotary drive screw after the firing member has been driven distally from a home or starting position.

FIG. 25 illustrates the firing member 2310 in the home or starting position. As can be seen in FIG. 25, a portion of the helical drive thread 2710 on the rotary drive screw 2700 is engaged between the distal upper firing member tooth segment 2330 and the proximal upper firing member tooth 2336 and another portion of the helical drive thread 2710 is engaged between the distal lower firing member tooth 2360 and a proximal lower firing member tooth 2366 on the firing member 2310. Such arrangement enables the rotary drive screw 2700 to precisely control the distal and proximal movement of the firing member 2310 which, as will be discussed in further detail below, can result in the precise movement of the anvil 1210. Once the firing member 2310 has been sufficiently distally advanced during a firing stroke, the helical drive thread 2710 operably engages the teeth on the upper and lower vertebras. See FIG. 26.

Figure 27:
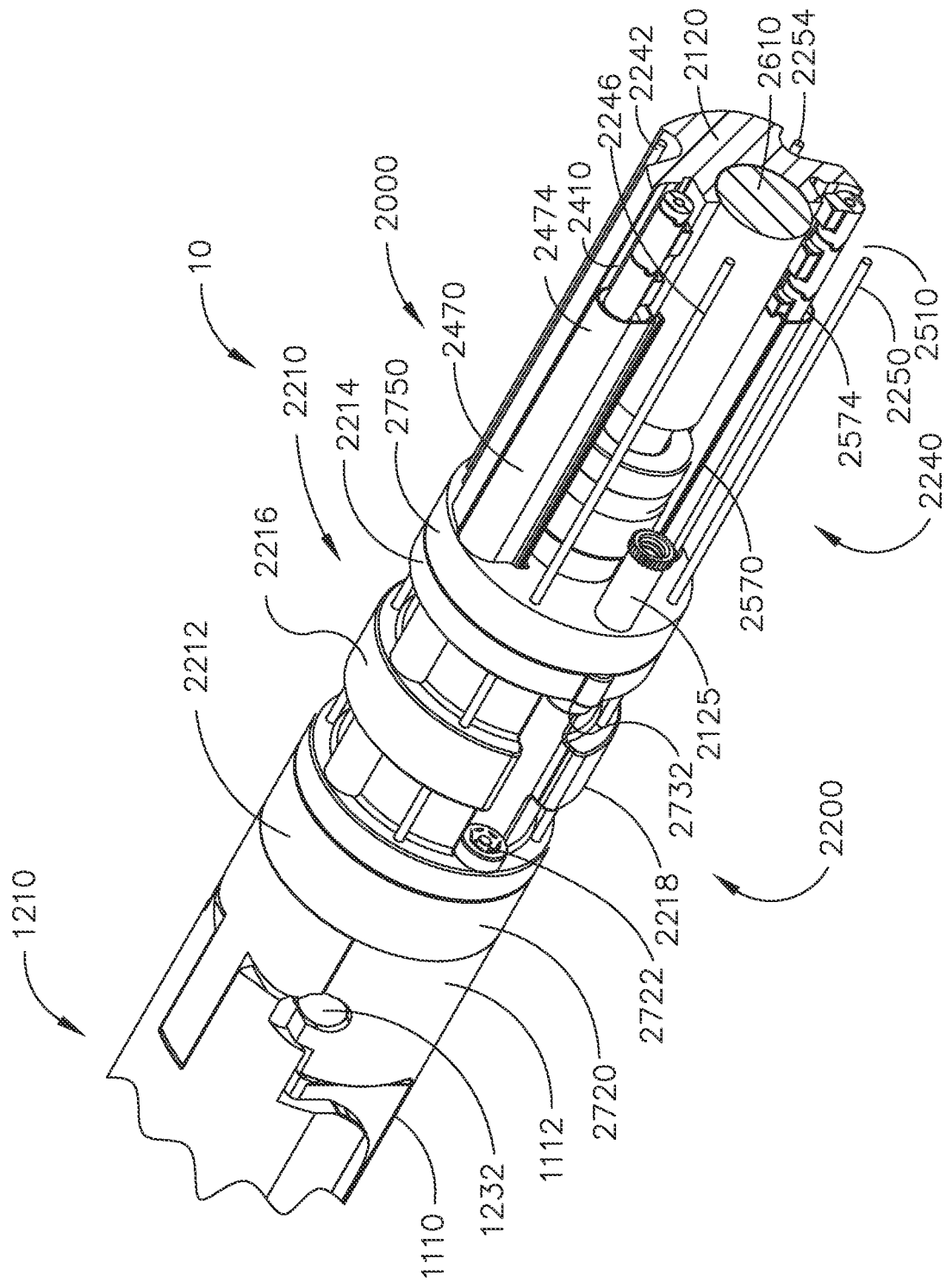
FIG. 27 is a partial cross-sectional perspective view of a portion of the surgical end effector, firing system and rotary drive system of the surgical instrument of FIG. 1 according to at least one aspect of the present disclosure with an outer elastomeric joint assembly of an articulation joint omitted for clarity.
Figure 29:
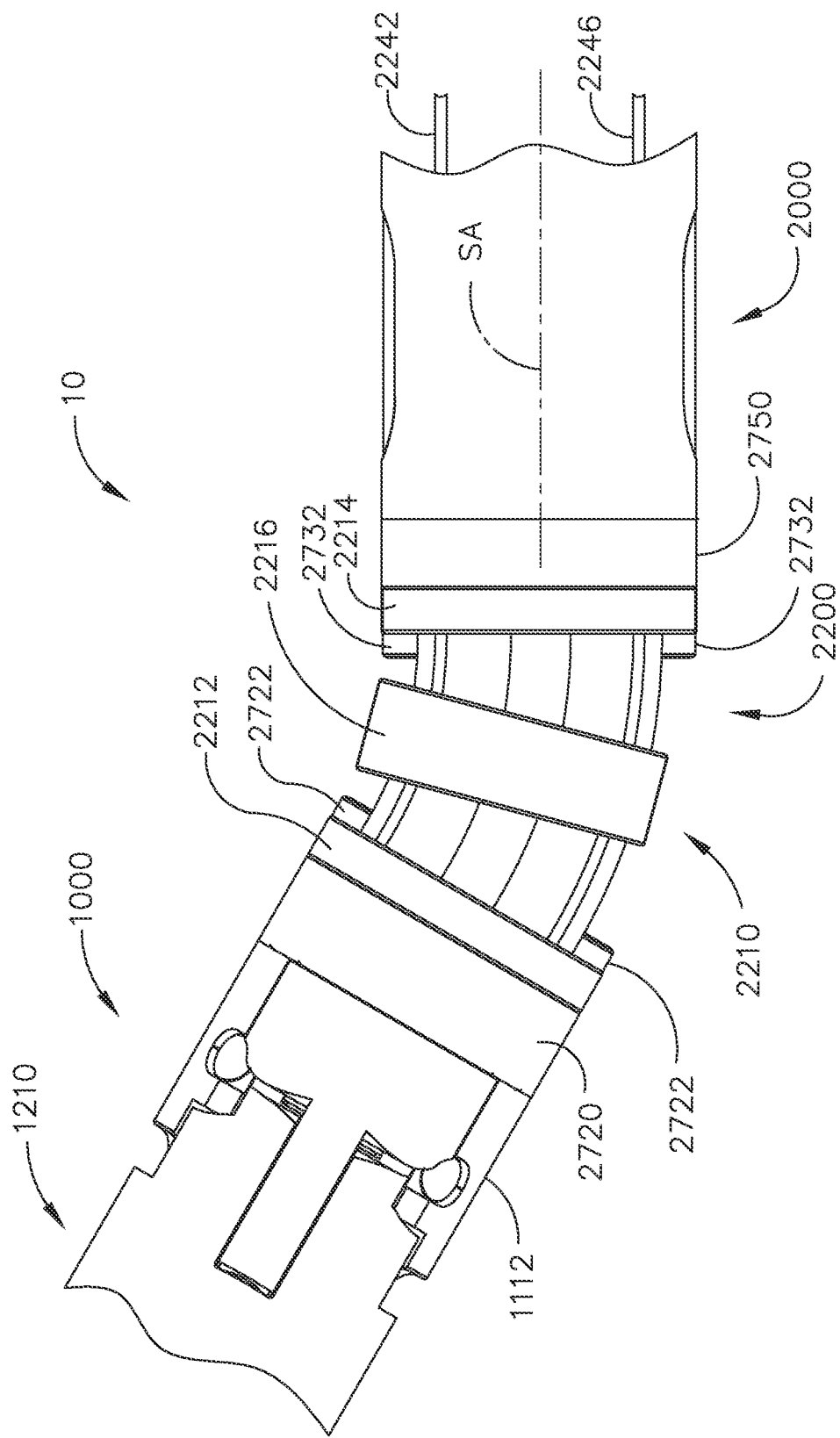
FIG. 29 is a top view of the surgical end effector of FIG. 27 articulated in a first direction relative to a portion of the elongate shaft assembly in accordance with at least one aspect of the present disclosure.
Figure 30:
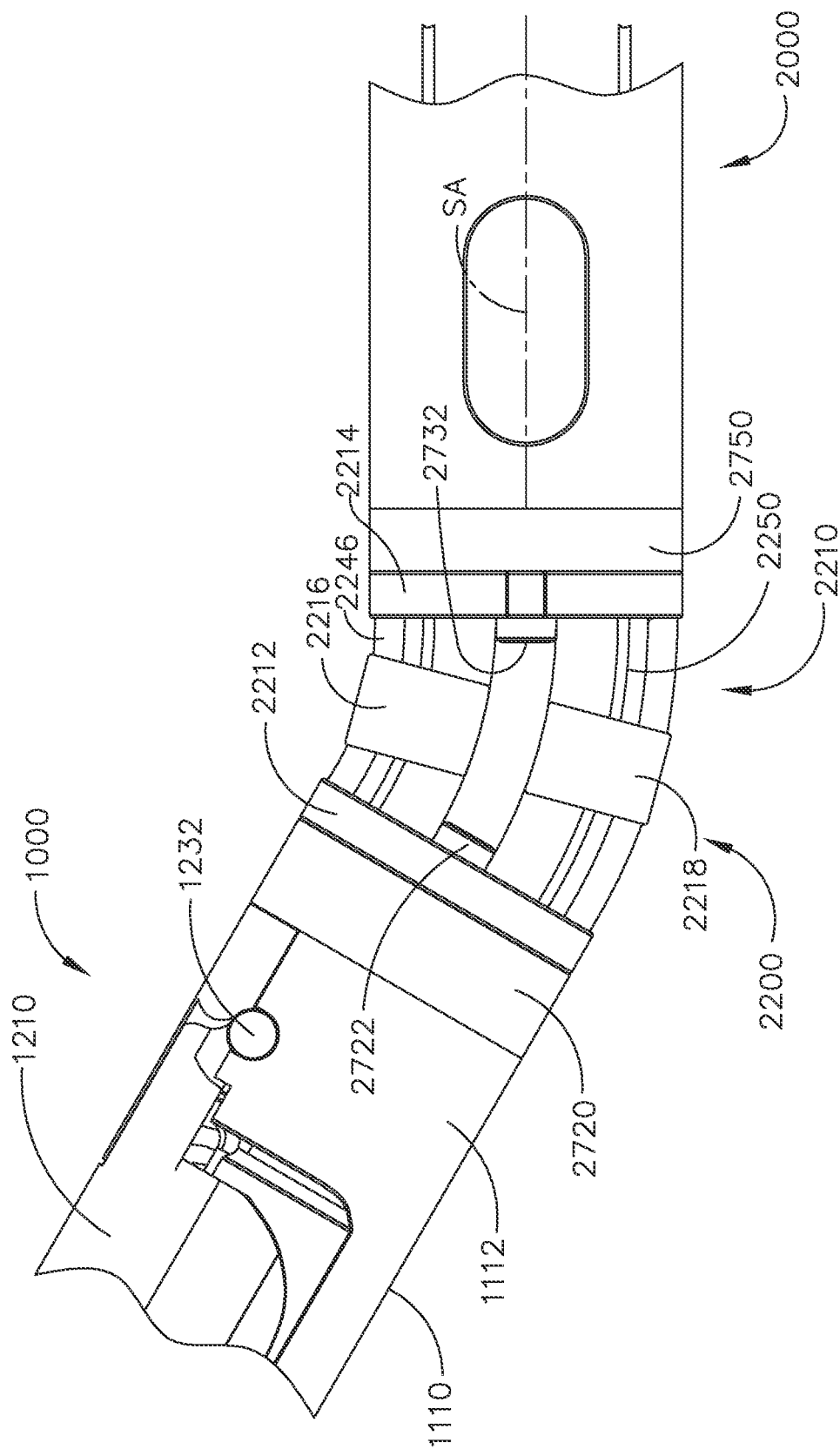
FIG. 30 is a side view of the surgical end effector of FIG. 29 articulated in another direction relative to a portion of the elongate shaft assembly in accordance with at least one aspect of the present disclosure.
Figure 31:
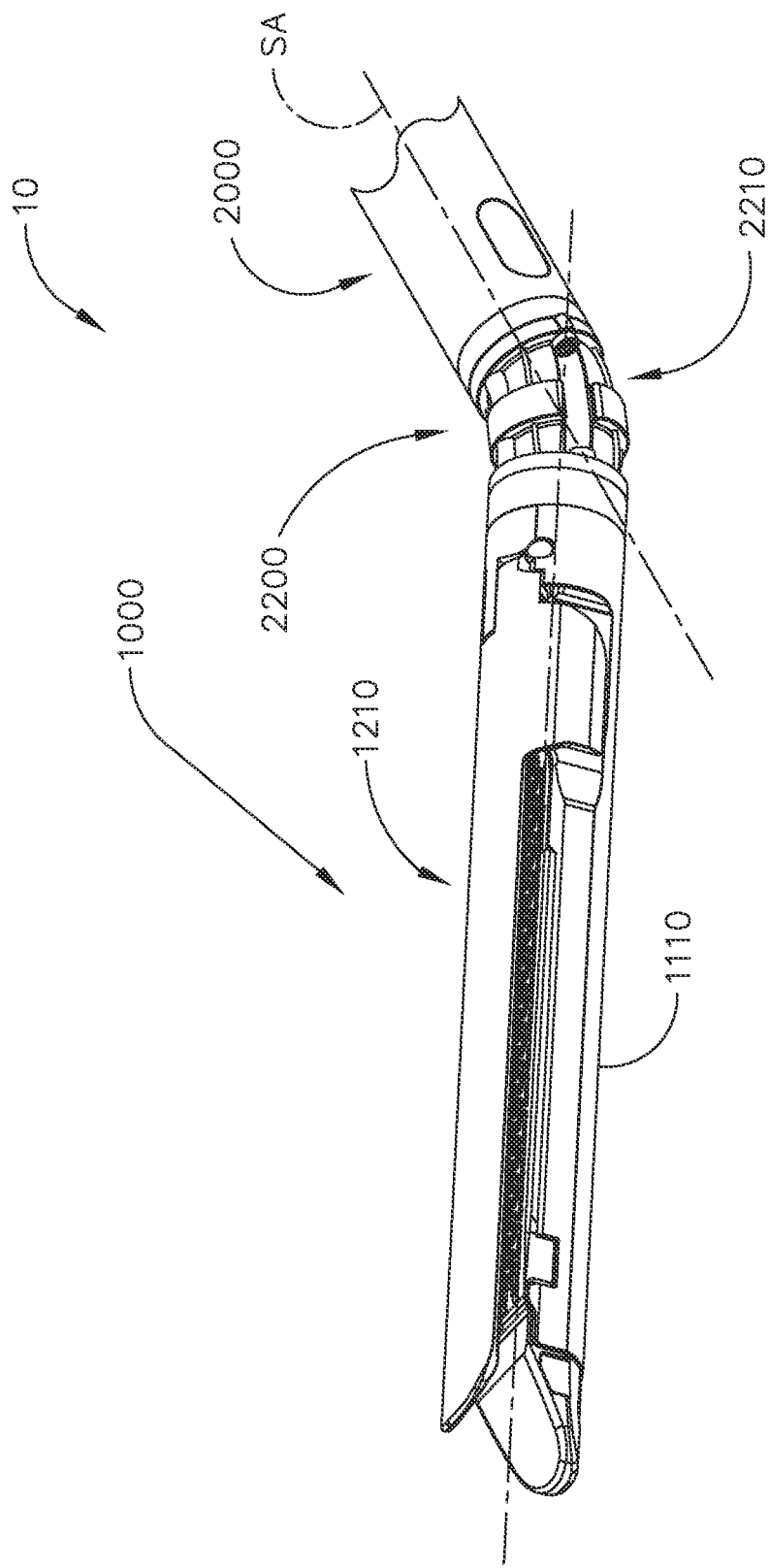
FIG. 31 is a perspective view of the surgical end effector of FIG. 29 articulated in multiple planes with respect to a portion of the elongate shaft assembly in accordance with at least one aspect of the present disclosure.

The surgical instrument 10 also comprises an articulation system 2240 that is configured to apply articulation motions to the surgical end effector 1000 to articulate the surgical end effector relative to the elongate shaft assembly 2000. In at least one arrangement, for example, the articulation system comprises four articulation cables 2242, 2246, 2250, and 2254 that extend through the elongate shaft assembly 2000. See FIG. 27. In the illustrated arrangement, the articulation cables 2242, 2246 pass through the proximal mounting bushing 2750, the proximal end 2214 of the elastomeric joint assembly 2210, as well as a central rib segment 2216 to be secured to the distal end 2212 of the elastomeric joint assembly 2210 or other portion of the surgical instrument. Likewise, the articulation cables 2250 and 2254 extend through the proximal mounting bushing 2750, the proximal end 2214 of the elastomeric joint assembly 2210, as well as a central rib segment 2218 to be secured to the distal end 2212 of the elastomeric joint assembly 2210 or other portion of the surgical end effector. The cables 2242, 2246, 2250, and 2254 operably interface with an articulation control system that is supported in the housing of the surgical instrument 10. For example, a proximal portion of each cable 2242, 2246, 2250, and 2254 may be spooled on a corresponding rotary spool or cable-management system 2007 (FIG. 2) in the housing portion of the surgical instrument 10 that is configured to payout and retract each cable 2242, 2246, 2250, and 2254 in desired manners. The spools/cable management system may be motor powered or manually powered (ratchet arrangement, etc.). FIG. 29 illustrates articulation of the surgical end effector 1000 through a first articulation plane relative to the elongate shaft assembly 2000. FIG. 30 illustrates articulation of the surgical end effector 1000 through a second articulation plane relative to the elongate shaft assembly 2000. FIG. 31 illustrates articulation of the surgical end effector 1000 through multiple articulation planes relative to the elongate shaft assembly 2000.

Figure 32:
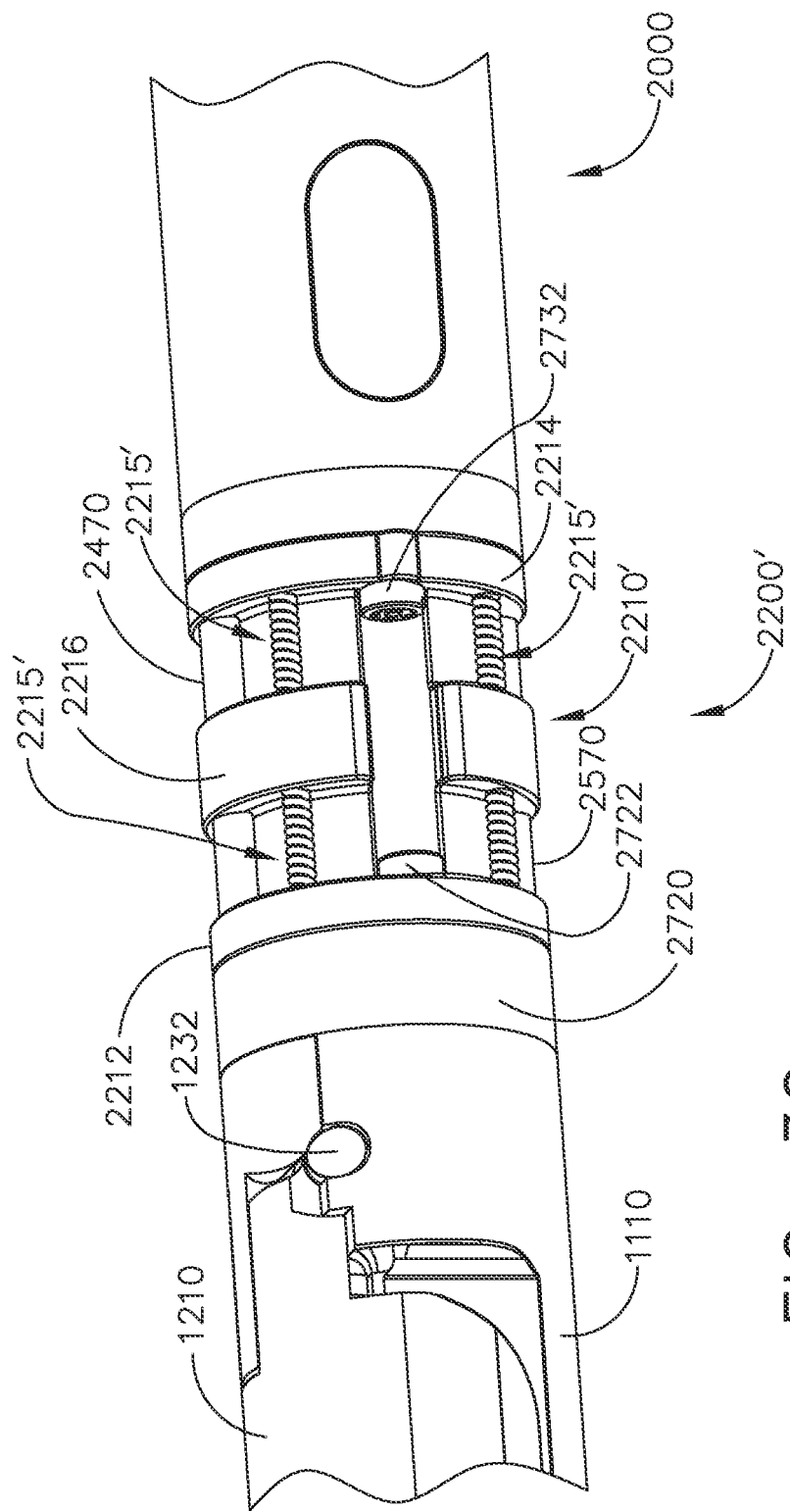
FIG. 32 is a side elevational view of a portion of another surgical instrument that employs another outer elastomeric joint assembly in accordance with at least one aspect of the present disclosure.
Figure 33:
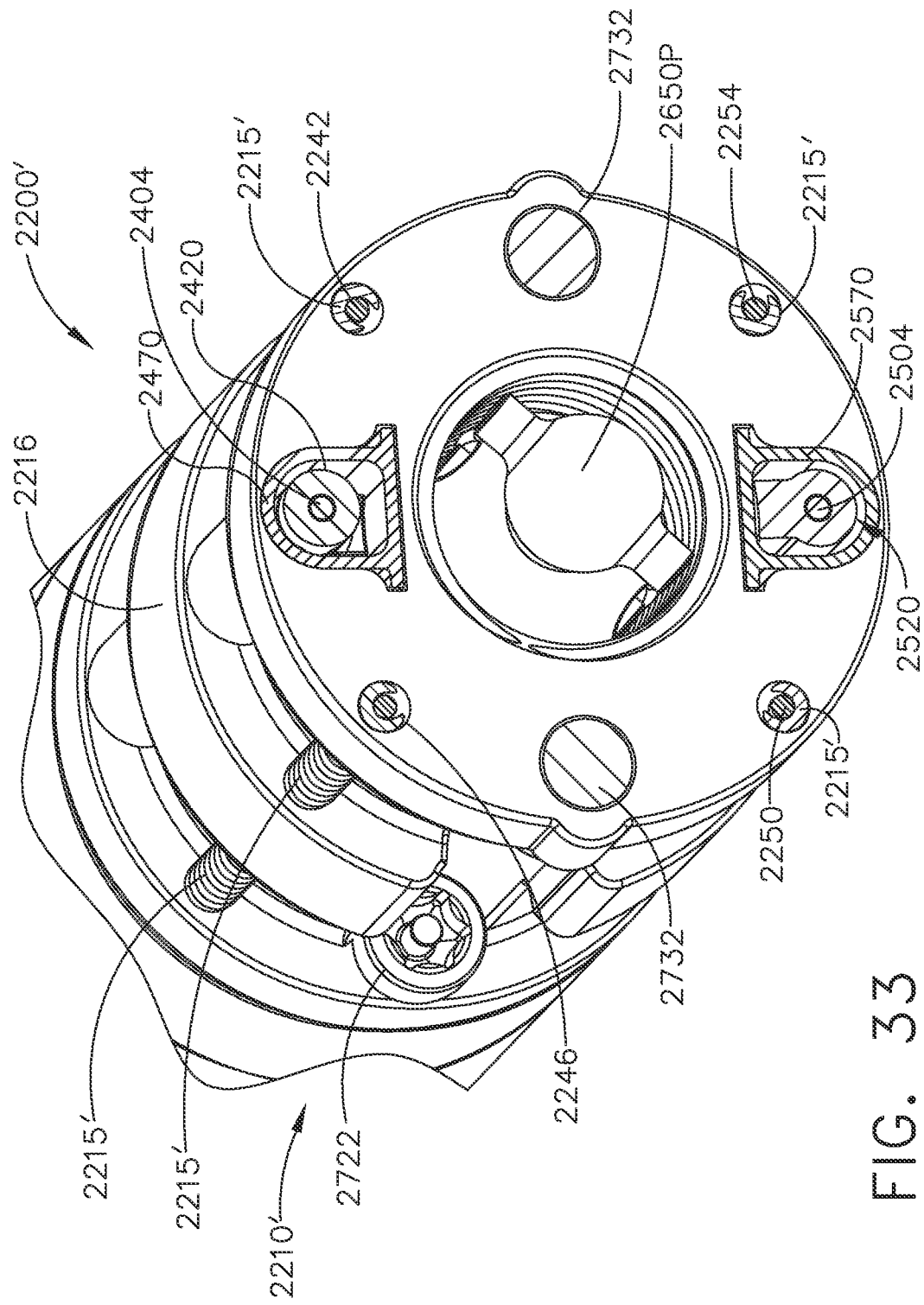
FIG. 33 is a partial cross-sectional perspective view of the surgical instrument of FIG. 32.
Figure 34:
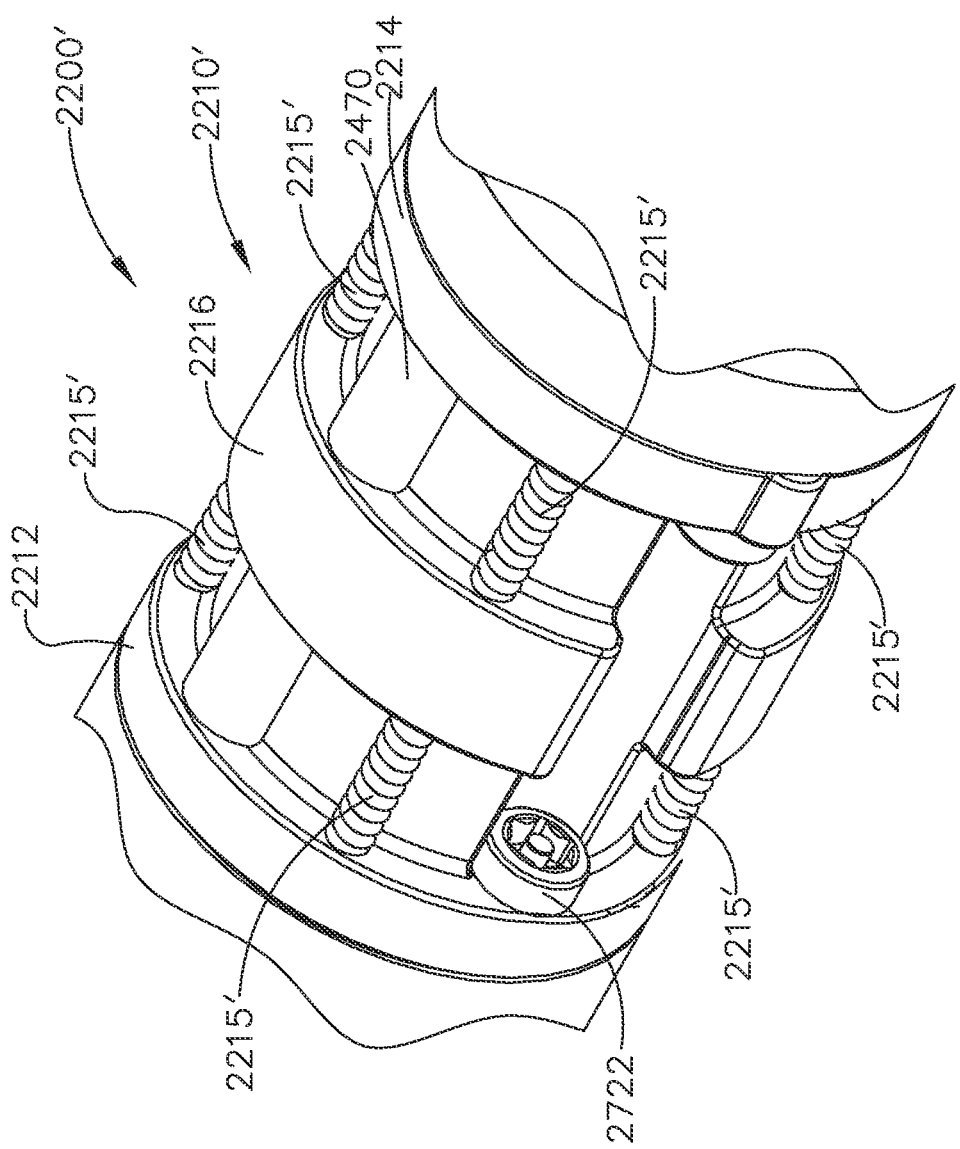
FIG. 34 is a perspective view of a portion of the outer elastomeric joint assembly of FIG. 32.

FIGS. 32-34 illustrate an alternative articulation joint 2200' in the form of an elastomeric joint assembly 2210'. As can be seen in FIG. 33, each articulation cable passes through a corresponding spring 2215' that is mounted in the ribs 2216' of the elastomeric joint assembly 2210'. For example, cable 2242 extends through spring 2244. Cable 2246 extends through spring 2248. Cable 2250 extends through spring 2252 and cable 2254 extends through spring 2256. As indicated above, the end effector is articulated by pulling on and relaxing the appropriate cables 2242, 2246, 2250 and 2254. To achieve higher articulation angles with greater joint stability, each of the springs 2244, 2248, 2252, and 2256 can slide through the ribs of the elastomeric joint to push the end effector and pull on the cables extending therethrough. The springs 2244, 2248, 2252, and 2256 will also retract into the ribs when the cables 2242, 2246, 2250, and 2254 are pulled tight. Each of the springs 2244, 2248, 2252, and 2256 loosely seat over the particular cable that passes therethrough. Each cable and corresponding spring may terminate or otherwise be coupled to a corresponding solid rod that is supported in the elongate shaft assembly 2000 and may be pushed and pulled from its proximal end. When the cable is pulled, the corresponding spring would carry little to no load. When the spring is pushed, the cable would carry little load, but will help limit the end effector movement. This interaction between the cable and spring may facilitate higher articulation angles that may approach ninety degrees, for example.

Figure 28:
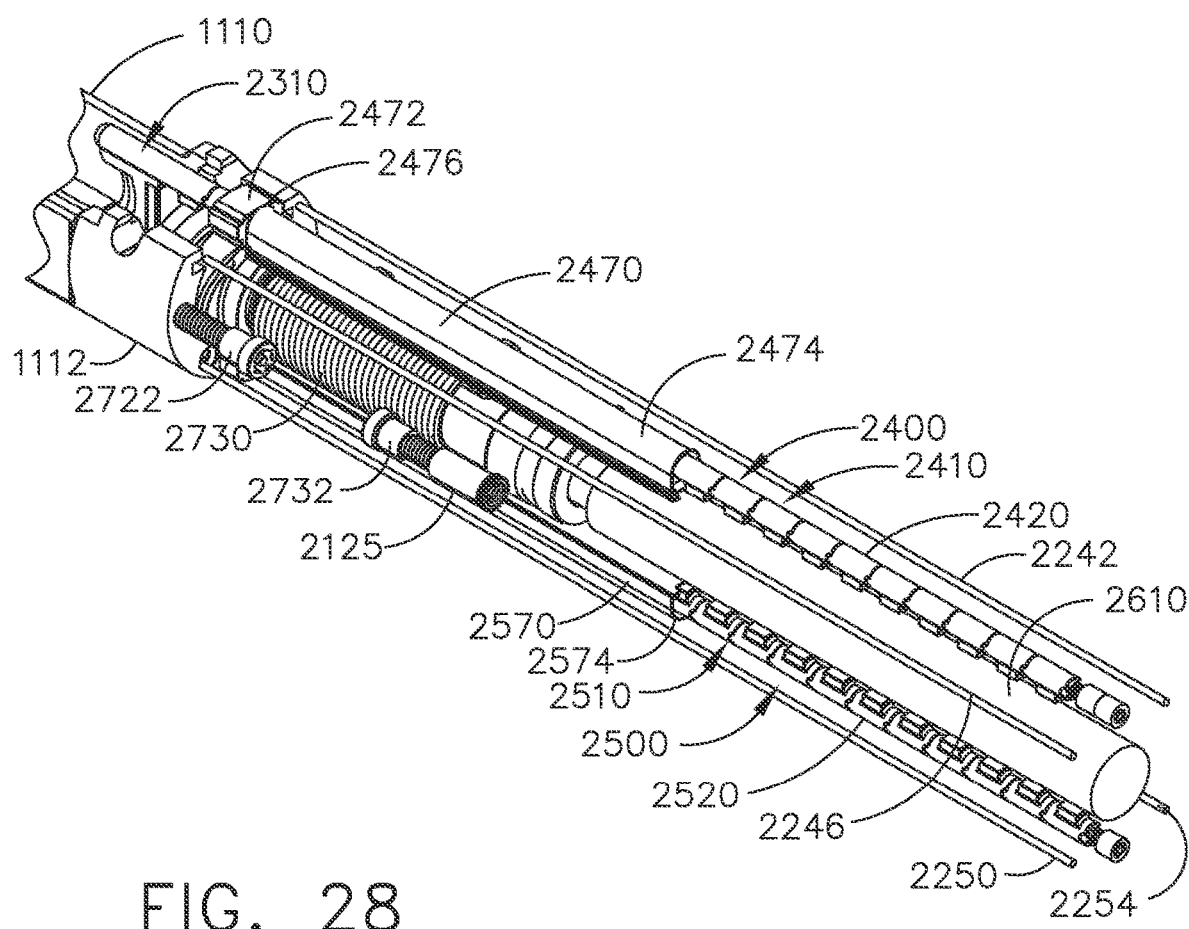
FIG. 28 is another partial perspective view of a portion of the surgical end effector, firing system and rotary drive system of FIG. 27 with an outer elastomeric joint assembly of an articulation joint and portions of the elongate shaft assembly omitted for clarity.
Figure 35:
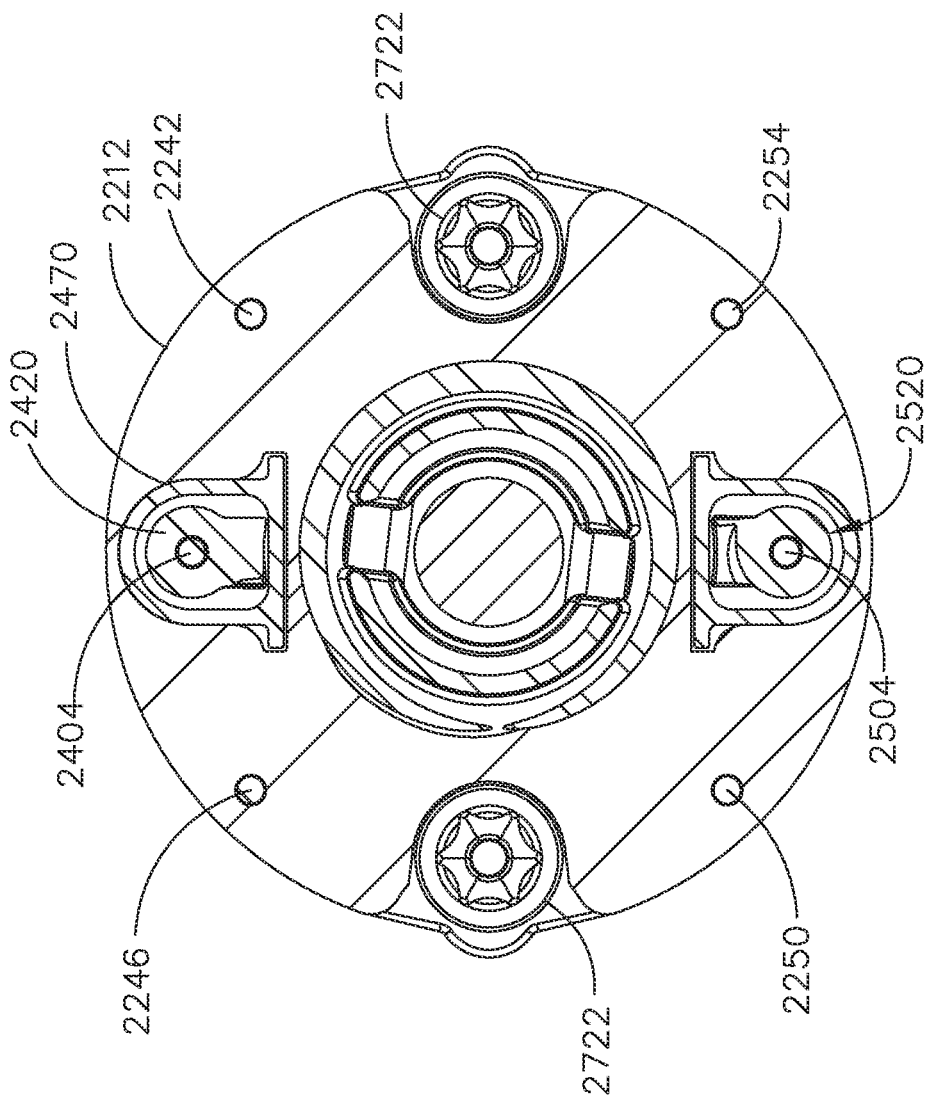
FIG. 35 is a cross-sectional end view of a portion of the surgical instrument of FIG. 19 taken along lines 35-35 in FIG. 19.

Because the radially/longitudinally segmented power screw nut arrangement disclosed herein does not have the same constraints as a three hundred sixty degree nut, the upper vertebra members 2420 in the upper series 2410 and the lower vertebra members 2520 in the lower series 2510 are constrained to ensure that their loads are transferred to the firing member in a longitudinal direction. To maintain each of the upper vertebra members 2420 in the desired orientation and to prevent the upper vertebra members 2420 from becoming snagged or disoriented when traversing through the articulation joint 2200, the upper vertebra members 2420 are aligned to pass through an upper sleeve 2470 that extends through an upper portion of the outer elastomeric joint assembly 2210 of the articulation joint 2200. See FIGS. 27, 28, and 35. A distal end 2472 of the upper sleeve 2470 is supported in the proximal end 1112 of the elongate channel 1110 and a proximal end 2474 of the upper sleeve 2470 is supported in the distal end of the proximal support shaft 2120. The upper sleeve 2470 is fabricated from a polymer or plastic material that has a low coefficient of friction and is flexible to enable the upper sleeve 2470 to flex with the outer elastomeric joint assembly 2210. The upper sleeve 2470 protects the upper vertebra members 2420 from contacting the outer elastomeric joint assembly 2210 that is fabricated from an elastomeric material that may have a higher coefficient of friction than the coefficient of friction of the material of the upper sleeve 2470. Stated another way, the upper sleeve 2470 forms a low friction, flexible, continuous, uninterrupted, and fully encapsulating path for the upper vertebra members 2420 as they traverse the articulation joint 2200.

Similarly, a lower sleeve 2570 is employed to support the lower vertebra members 2520 as they pass through the articulation joint 2200. A distal end 2572 of the lower sleeve 2570 is supported in the proximal end of the elongate channel and a proximal end of the lower sleeve 2570 is supported in the distal end of the proximal support shaft 2120. Like the upper sleeve 2470, the lower sleeve 2570 is fabricated from a polymer or plastic material that has a low coefficient of friction and is flexible to enable the lower sleeve 2570 to flex with the outer elastomeric joint assembly 2210. The lower sleeve 2570 protects the lower vertebra members 2520 from contacting the outer elastomeric joint assembly 2210 as they pass through the articulation joint 2200. Stated another way, the lower sleeve 2570 forms a low friction, flexible, continuous, uninterrupted, and fully encapsulating path for the lower vertebra members 2520 as they traverse the articulation joint 2200. In various embodiments, the upper sleeve 2470 and the lower sleeve 2570 are configured to bend freely without creating a kink. To prevent the formation of kinks in the sleeves, in at least one arrangement, the sleeves 2470, 2570 are supported within the outer elastomeric joint assembly 2210 such that the sleeves may move axially. For example, when the articulation joint angles up, the lower sleeve 2570 may slide distally and have a large bend radius; the upper sleeve 2470 in the same example, may slide proximally and have a tighter bend radius. By moving axially, the amount of material exposed outside of the joint assembly 2210 which might otherwise be susceptible to kinking under a tight bend radius is reduced. In at least one arrangement, the distal end 2472 of the upper sleeve 2470 is formed with an upper scoop 2476 that is configured to funnel the upper vertebra members 2420 into the anvil cap 1260. Similarly, the distal end of the lower sleeve 2570 may be formed with a lower scoop that is configured to funnel the lower vertebra members 2520 into the channel slot 1140 in the elongate channel 1110.

Figure 36:
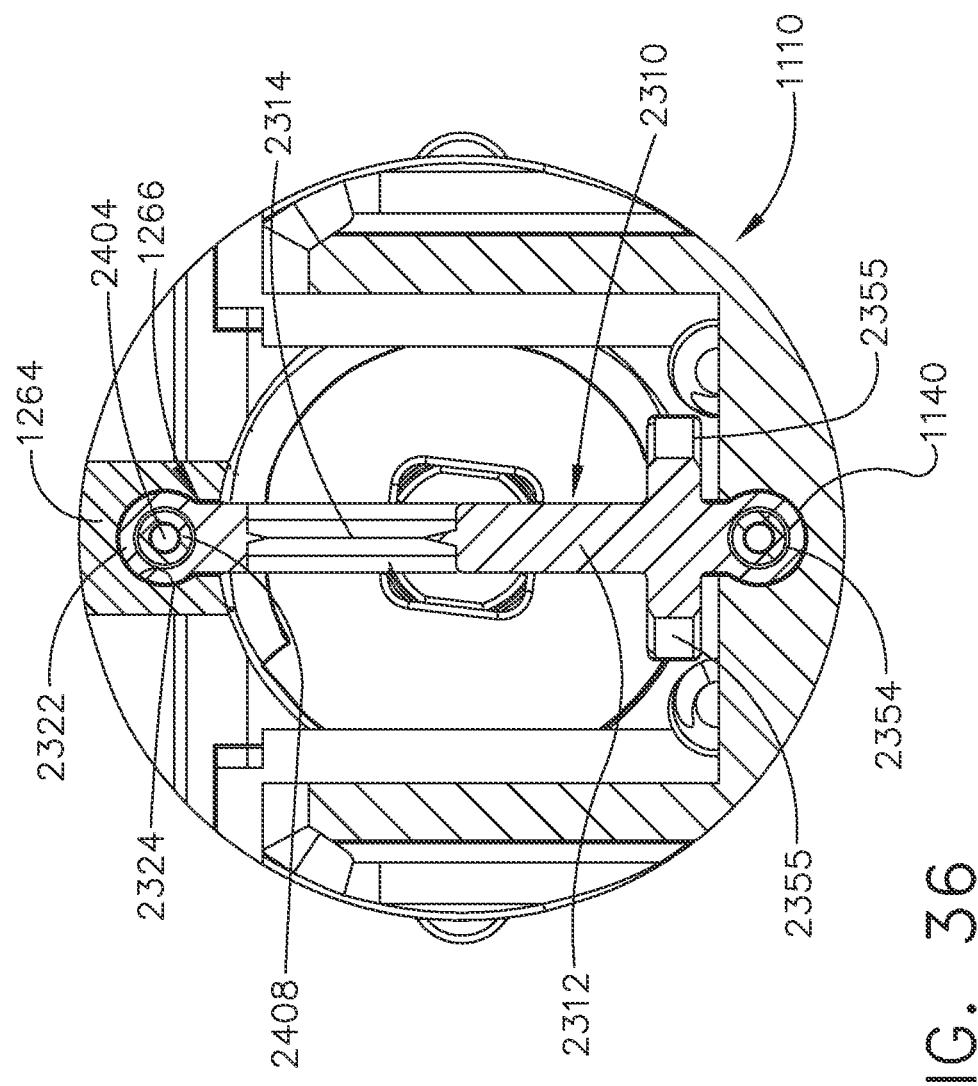
FIG. 36 is a cross-sectional end view of a portion of the surgical instrument of FIG. 19 taken along lines 36-36 in FIG. 19.
Figure 37:
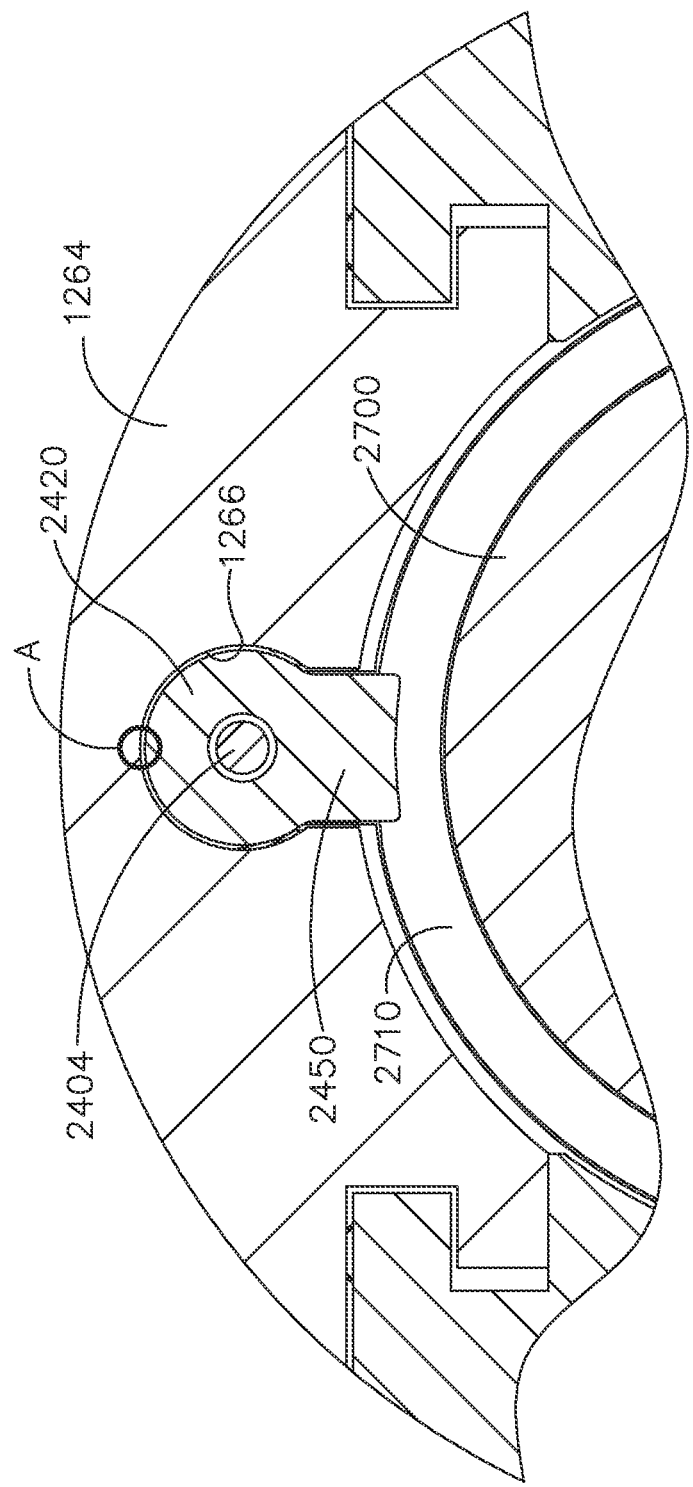
FIG. 37 is a partial cross-sectional view of a portion of an anvil cap and an upper vertebra member of the surgical instrument of FIG. 19 in accordance with at least one aspect of the present disclosure.

As indicated above, the anvil mounting portion 1230 comprises a pair of laterally extending mounting pins 1232 that are configured to be received in corresponding mounting cradles or pivot cradles 1120 that are formed in the proximal end 1112 of the elongate channel 1110. The mounting pins 1232 are pivotally retained within the mounting cradles 1120 by an anvil cap 1260 that is attached to the proximal end 1112 of the elongate channel 1110 in the above-described manners. The anvil cap 1260 comprises a proximal end 1262 and a distal end 1264 and has a keyhole-shaped vertebra passage 1266 extending therethrough to accommodate passage of the top firing member feature 2320 and upper vertebra members 2420 therethrough. FIG. 36 illustrates the vertebra passage 1266 in the anvil cap 1260. When the rotary drive screw 2700 applies load to the upper vertebra members 2420, the vertebra members 2420 will tend to tilt about the area A in FIG. 37, so the upper vertebra member tooth 2450 is no longer square with the rotary drive screw 2700 and may instead experience a higher-pressure line contact. Areas B in FIG. 37 show where the upper vertebra member 2420 stops tilting. To ensure that most of the loads stay in the longitudinal direction to perform useful work, the upper vertebra member tooth 2450 must be angled the same amount as the upper vertebra member 2420 tilts. Thus, when the upper vertebra member 2420 tilts, the upper vertebra member tooth 2450 will still maintain surface contact with the helical drive member 2710 on the rotary drive screw 2700 and all loads will be directed longitudinally and not vertically. The slightly angled upper vertebra member tooth 2450 may behave like a square thread when the vertebra member 2420 is tilted and better distributes loads to lower the pressure contact. By directing most of the loads in the longitudinal direction, vertical loads are avoided which could result in the establishment of friction that would counter the longitudinal loads. The upper vertebra members 2420 react similarly as they pass down the keyhole-shaped anvil slot 1240. Likewise, the lower vertebra members 2520 react similarly as they pass through the keyhole-shaped axially extending channel slot 1140 in the elongate channel 1110.

Figure 38:
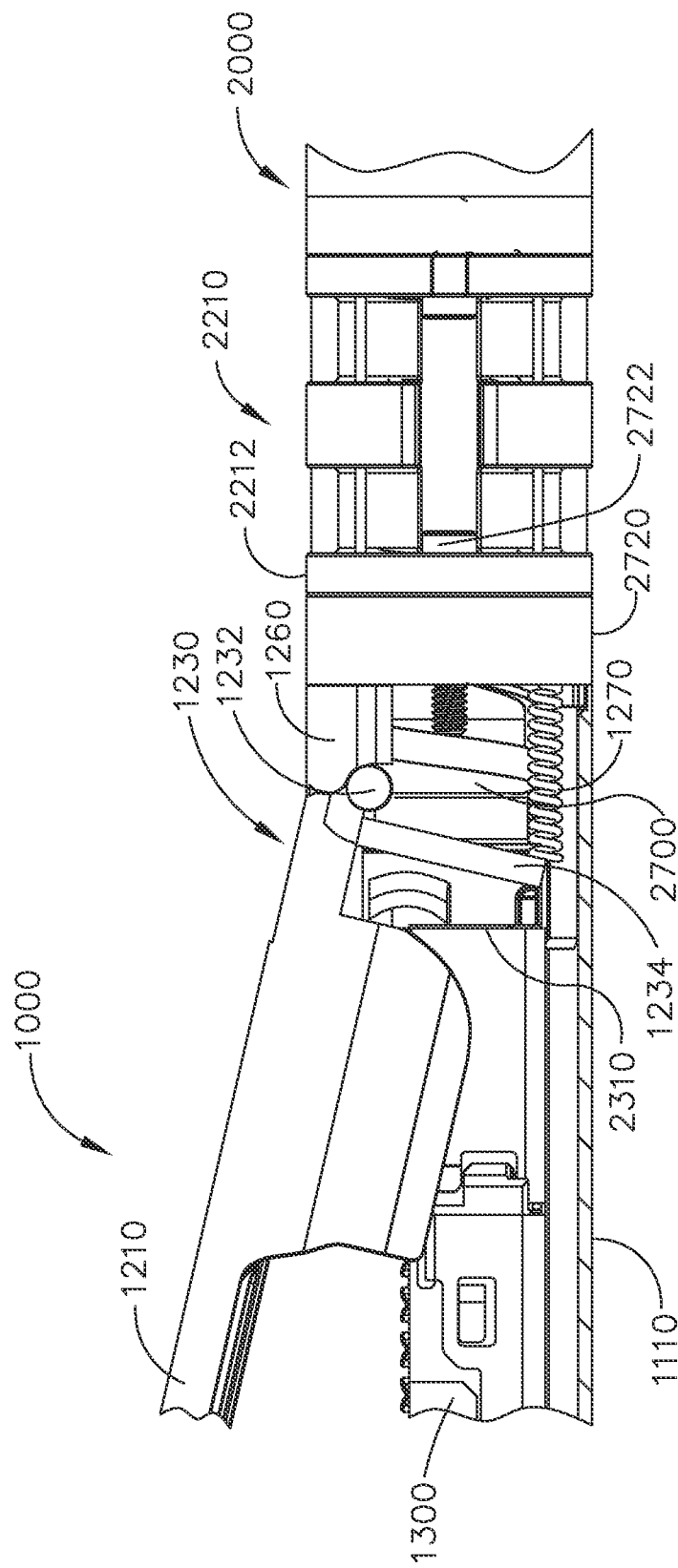
FIG. 38 is a side view of a portion of the surgical end effector of the surgical instrument of FIG. 19 with an anvil thereof in an open position in accordance with at least one aspect of the present disclosure and with portions of the surgical end effector omitted for clarity.

In the illustrated arrangement, the anvil 1210 is moved to the open position by a pair of anvil springs 1270 that are supported within the proximal end of the elongate channel. See FIGS. 38, 42, and 43. The springs 1270 are positioned to apply a pivotal biasing force to corresponding anvil control arms 1234 that may be integrally formed with anvil mounting portion 1230 and extend downwardly therefrom. See FIG. 38.

Figure 39:
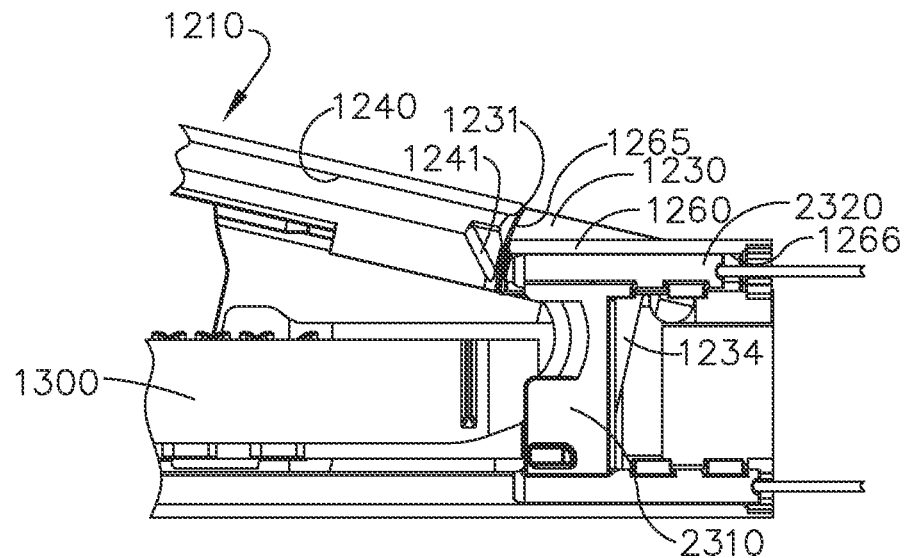
FIG. 39 is a partial cross-sectional side view of the surgical end effector of FIG. 38 with the anvil in an open position and the firing member in the home or starting position in accordance with at least one aspect of the present disclosure.
Figure 40:
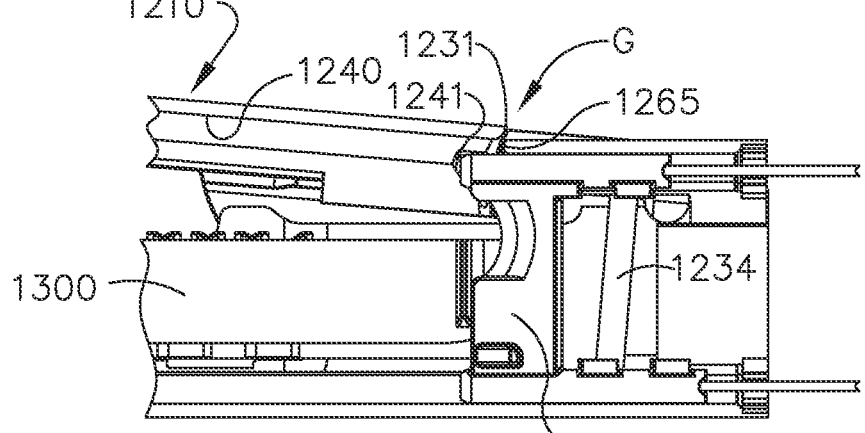
FIG. 40 is another partial cross-sectional side view of the surgical end effector of FIG. 39 with the anvil in a partially closed position.
Figure 41:
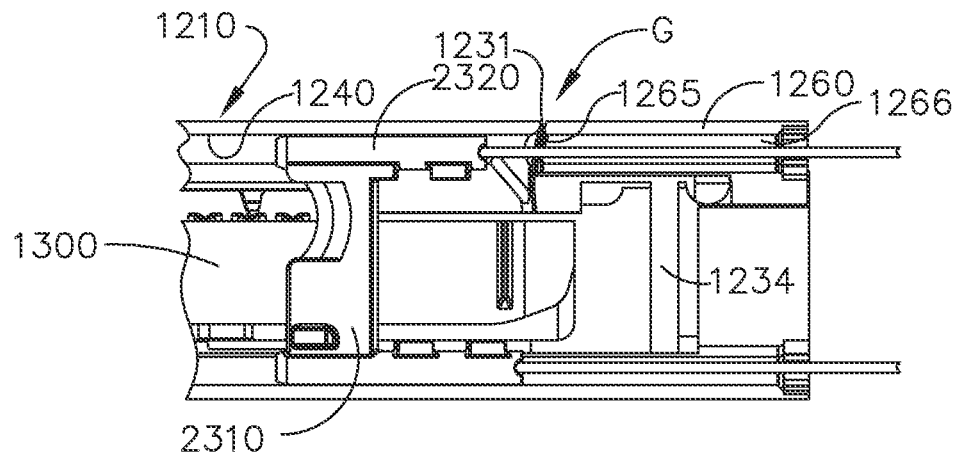
FIG. 41 is another partial cross-sectional side view of the surgical end effector of FIG. 39 with the anvil in a fully closed position and the firing member distally advancing through the surgical end effector.

FIGS. 39-41 illustrate portions of the anvil 1210, the firing member 2310, and the anvil cap 1260 when the anvil 1210 is open (FIG. 39), when the anvil 1210 is partially closed (FIG. 40) and after the firing member has been advanced distally from the home or starting position (FIG. 41). As can be seen in FIG. 39, when the firing member 2310 is in the home or starting position, the top firing member feature 2320 is completely received within the vertebra passage 1266 in the anvil cap 1260. During a firing stroke, the top firing member feature 2320 and the upper vertebra members 2420 in the upper series 2410 must transition from the vertebra passage 1266 in the anvil cap 1260 to the keyhole-shaped anvil slot 1240. Thus, it is desirable to minimize any gap "G" between the anvil mounting portion 1230 and a distal end 1264 of the anvil cap 1260. To minimize this gap G while facilitate unimpeded pivotal travel of the anvil 1210, the distal end 1264 of the anvil cap 1260 is formed with a curved cap surface 1265 that matches a curved mating surface 1231 on the anvil mounting portion 1230. Both surfaces 1265, 1231 are curved and concentric about the pivot axis PA or some other reference point. Such arrangement allows the anvil 1210 to move radially and not interfere with the anvil cap 1260 while maintaining a minimal gap G therebetween. The gap G between the anvil mounting portion 1230 and the distal end 1264 of the anvil cap 1260 is significantly shorter than a length of an upper vertebra member 2420 which facilitates easy transition of each upper vertebra member 2420 from the vertebra passage 1266 in the anvil cap 1260 to the keyhole-shaped anvil slot 1240. In addition, to further assist with the transition of the top firing member feature 2320 into the keyhole-shaped anvil slot 1240, a ramped surface 1241 is formed adjacent the curved mating surface 1231 on the anvil mounting portion 1230. As the firing member 2310 is initially advanced distally from the home or starting position, a distal end of the top firing member feature 2320 contacts the ramped surface 1241 and begins to apply a closing motion to the anvil 1210 as can be seen in FIG. 40. Further distal advancement of the firing member 2310 during the firing stroke or firing sequence causes the top firing member feature to enter the keyhole shaped anvil slot 1240 to completely close the anvil 1210 and retain the anvil 1210 in the closed position during the firing sequence. See FIG. 41.

Figure 15:
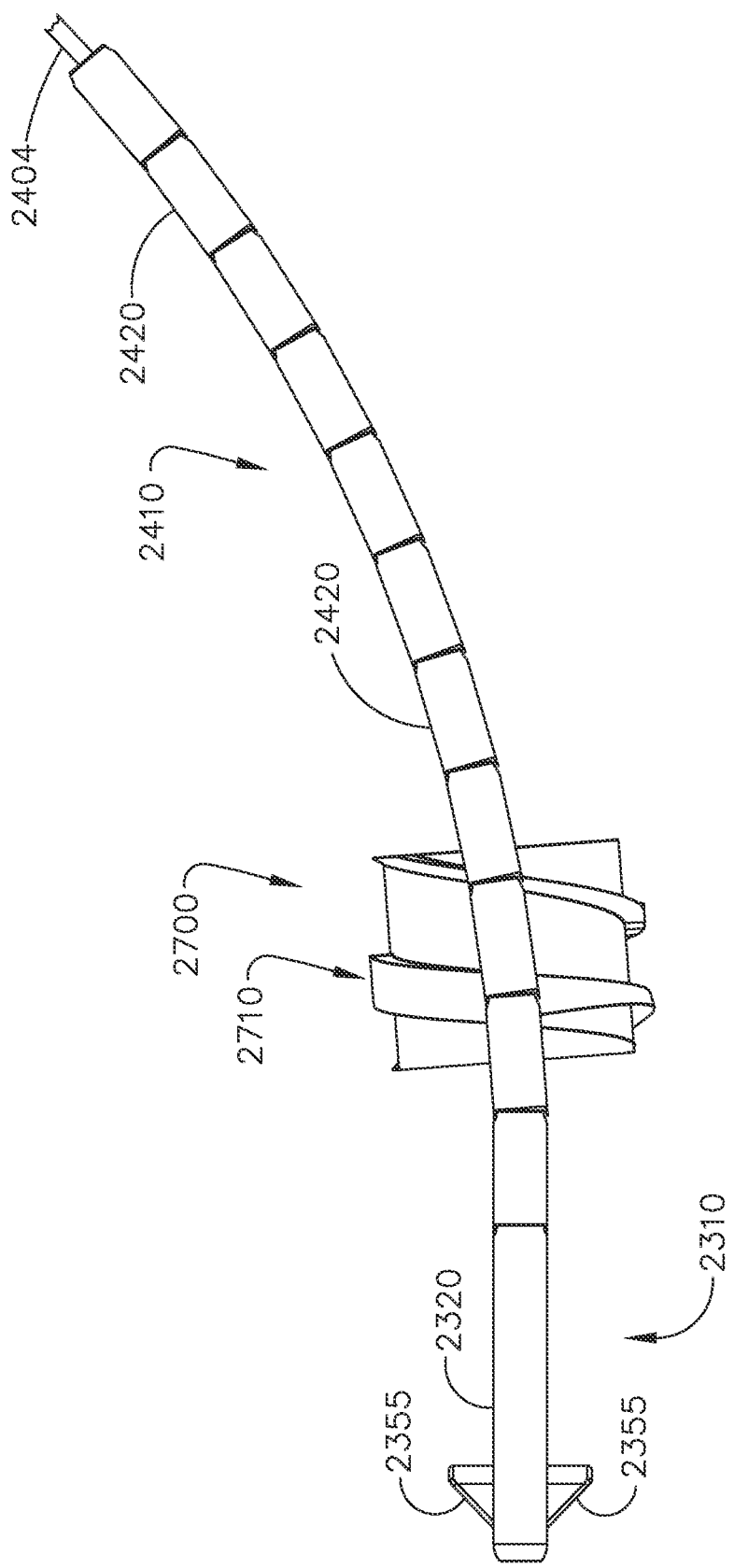
FIG. 15 is a top view of a firing member and upper and lower flexible spine assemblies in engagement with the rotary drive screw of FIG. 9.
Figure 42:
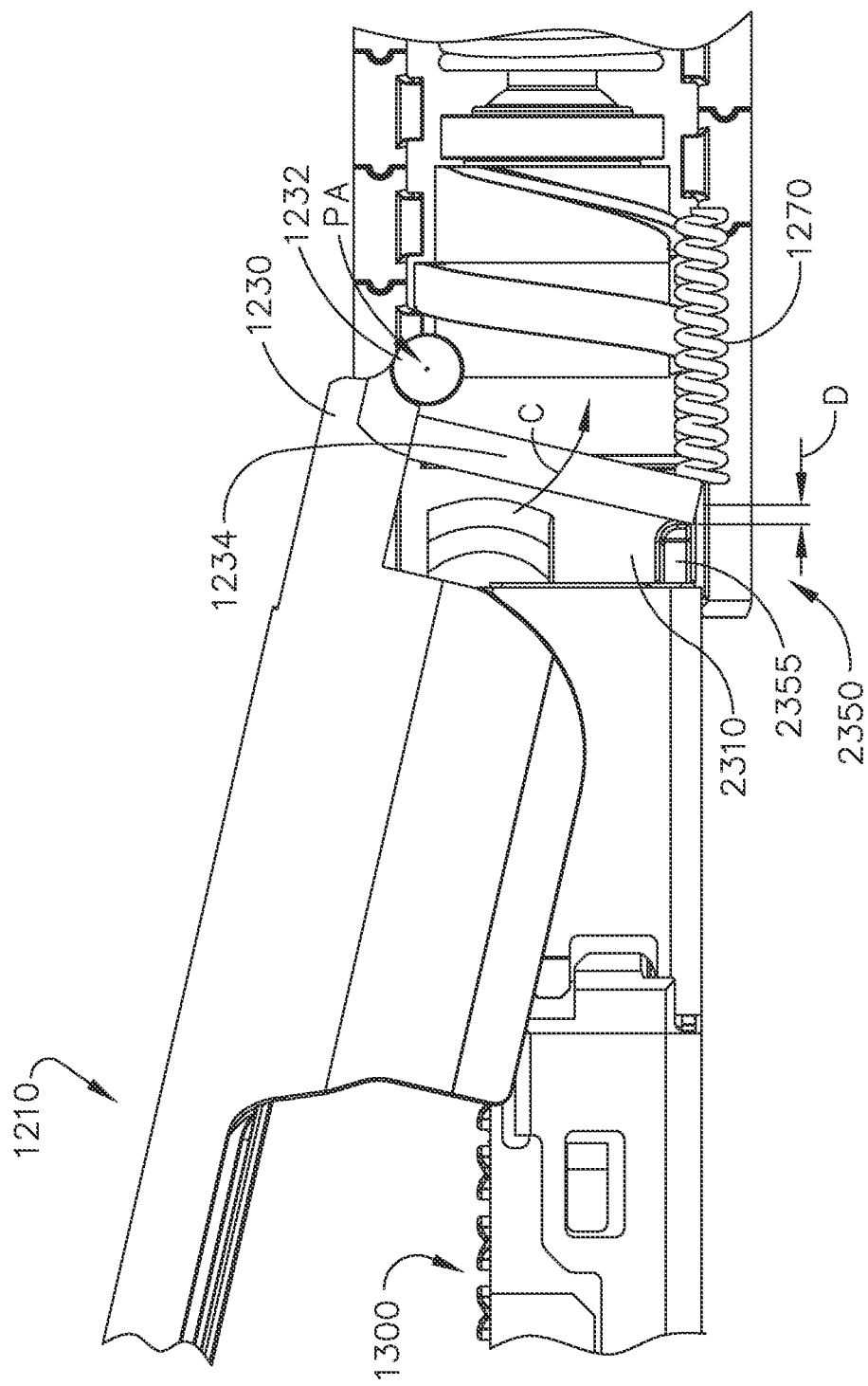
FIG. 42 is a partial side elevational view of the surgical end effector of FIG. 19 with portions thereof omitted for clarity to illustrate the anvil opening springs applying an opening motion to the anvil and with the firing member in a home or starting position.
Figure 43:
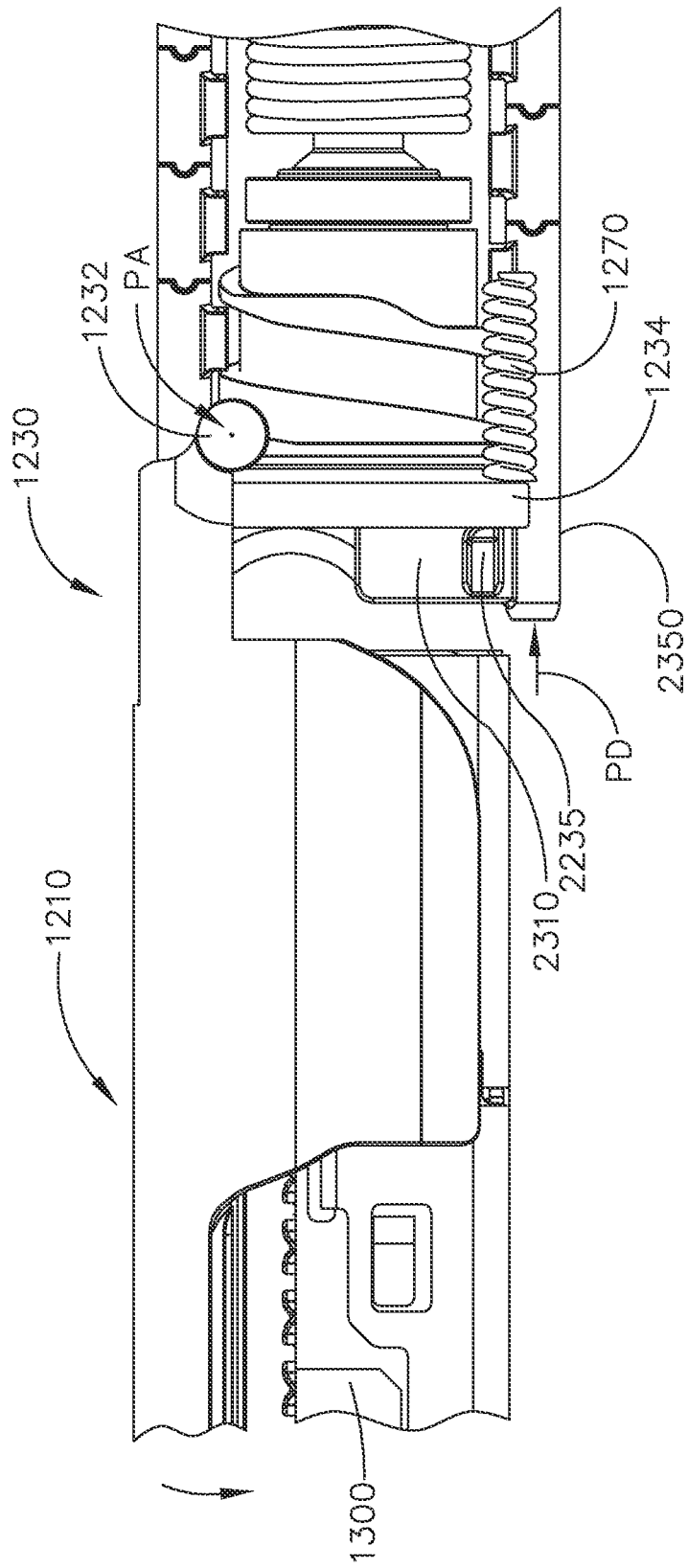
FIG. 43 is another partial side view of the surgical end effector of FIG. 42, after the firing member has moved proximally a short distance to apply a quick closure motion to the anvil for grasping purposes.

In general, the highest firing forces established in an endocutter are associated with cutting and stapling tissue. If those same forces can be used to close the anvil, then the forces generated during pre-clamping and grasping of tissue can be high as well. In at least one arrangement, the firing member body 2312 further comprises a firing member wing or tab 2355 that extends laterally from each lateral side of the firing member body 2312. See FIGS. 15 and 36. The firing member wings 2355 are positioned to contact the corresponding anvil control arms 1234 when the firing member 2310 is driven in the proximal direction PD from the home or starting position to quickly close the anvil 1210 for grasping purposes. In at least one arrangement, when the firing member 2310 is in the home or starting position, the firing member wings 2355 are located distal to the anvil control arms 1234 as shown in FIG. 42. When the firing member 3210 is moved proximally, the firing member wings 2355 push the anvil control arms 1234 (pivotal direction C) against the bias of the anvil springs 1270. See FIG. 42. In one arrangement, the firing member 2310 only has to move a short distance D to pivot the anvil 1210 to a closed position. In one embodiment, distance D may be approximately 0.070 inches long, for example. This short movement allows for a quick response. Because the anvil pivot point or pivot axis PA is relatively far from the firing member wings 2355 which creates a substantial moment arm, the proximal movement of the firing member 2310 (and firing member wings 2355) results in an application of high pre-compression torque to the anvil 1210 to move the anvil 1210 to a closed position. Thus, the firing member wings 2355 may be referred to herein as "pre-compression features". See FIG. 43. Thus, the clinician may use the surgical end effector 1000 to grasp and manipulate tissue between the anvil 1210 and the surgical staple cartridge 1300 without cutting the tissue and forming the staples, by advancing the firing member 2310 proximally the short distance D to cause the anvil 1210 to quickly pivot to a closed position.

The firing member 2310 may be moved in the proximal direction PD by rotating the rotary drive screw 2700 in a second rotary direction. Thus, when the firing member 2310 is in the "home" or starting position, the anvil 1210 may be biased into the fully open position by the anvil springs 1270. Activation of the rotary drive system 2600 to apply a rotary motion to the rotary drive screw 2700 in a first rotary direction will cause the firing member 2310 to be advanced distally from the home or starting position to apply an anvil closure motion to the anvil 1210 to move the anvil closed to clamp the target tissue between the anvil 1210 and the surgical staple cartridge 1300. Continued rotation of the rotary drive screw in the first rotary direction will cause the firing member 2310 to continue to distally advance through the surgical end effector 1000. As the firing member 2310 moves distally, the firing member 2310 contacts a sled 1312 (FIG. 19) that is supported in the surgical staple cartridge 1300 and drives the sled 1312 distally through the staple cartridge body 1302. When the firing member 2310 is in the home or starting position, the surgeon may wish to use the surgical end effector to grasp and manipulate tissue. To do so, the rotary drive system is actuated to apply a second rotary drive motion to the rotary drive screw 2700 in a second rotary direction that is opposite to the first rotary direction. Such rotary movement of the rotary drive screw 2700 in the second rotary direction will drive the firing member 2310 proximally from the starting position and cause the anvil 1210 to quickly pivot to the closed position. Thus, in accordance with at least one embodiment, the "home or starting position" of the firing member 2310 is not its proximal-most position.

If during the firing process, the rotary drive system 2600 quits rotating, the firing member 2310 may become stuck within the surgical end effector. In such instance, the top firing member feature 2320 may remain engaged with the anvil 1210 and the bottom firing member feature 2350 may remain engaged with the elongate channel 1110 and thereby prevent the surgeon from moving the anvil 1210 to an open position to release the tissue clamped between anvil 1210 and surgical staple cartridge 1300. This could occur, for example, if the motor or other control arrangement supplying the rotary drive motions to the rotary drive shaft 2610 fails or otherwise becomes inoperative. In such instances, the firing member 2310 may be retracted back to the home or starting position within the surgical end effector 1000 by pulling the top cable 2404 and the lower cable 2504 in a proximal direction. For example, a proximal portion of the top cable 2404 and a proximal portion of the lower cable 2505 may be spooled on a rotary spool or cable-management system 2009 (FIG. 2) in the housing portion of the surgical instrument 10 that is configured to payout the top cable 2404 and lower cable 2504 during the firing stroke and also retract the cables 2404, 2504 in a proximal direction should the firing member 2310 need to be retracted. The cable management system 2009 may be motor powered or manually powered (ratchet arrangement, etc.) to apply retraction motions to the cables 2404, 2504. When the cables 2404, 2504 are retracted, the upper vertebra members 2420 and lower vertebra members 2520 will cause the rotary drive screw 2700 to spin in reverse.

The following equation may be used to determine whether the rotary drive screw 2700 will spin in reverse depending upon the lead (L), pitch diameter ($d_p$), tooth angle ($\alpha$) and friction ($\mu$):

$$\mu \geq \frac{L \cos \alpha}{\pi d_p}$$

The rotary drive screw 2700 may self-lock if the above equation is true. For the most part, in many instances, the pitch diameter is mostly fixed for an endocutter, but the lead and tooth angle are variable. Because the upper vertebra member teeth 2450 and lower vertebra member teeth 2550 are mostly square, the rotary drive screw 2700 is more likely to be back drivable (cos (90)=1). The leads of the upper vertebra member teeth 2450 and lower vertebra member teeth 2550 may also be advantageous in that the rolling friction between the vertebra members 2420, 2520 and the rotary drive screw 2700 is more likely to enable the rotary drive screw 2700 to be back driven. Thus, in the event of an emergency, the surgeon can pull on the upper and lower cables 2404, 2504 in the proximal direction to cause the firing member 2310 to fully retract for a quick "bailout".

As indicated above, the relative control motions for the rotary drive system 2600, as well as the various cable-management systems employed in connection with the firing system 2300 and the articulation control system 2240, may be supported within a housing 2002 which may be handheld or comprise a portion of a larger automated surgical system. The firing system 2300, articulation control system 2240, and the rotary drive system 2600 may, for example, be motor-controlled and operated by one or more control circuits.

Figure 44:
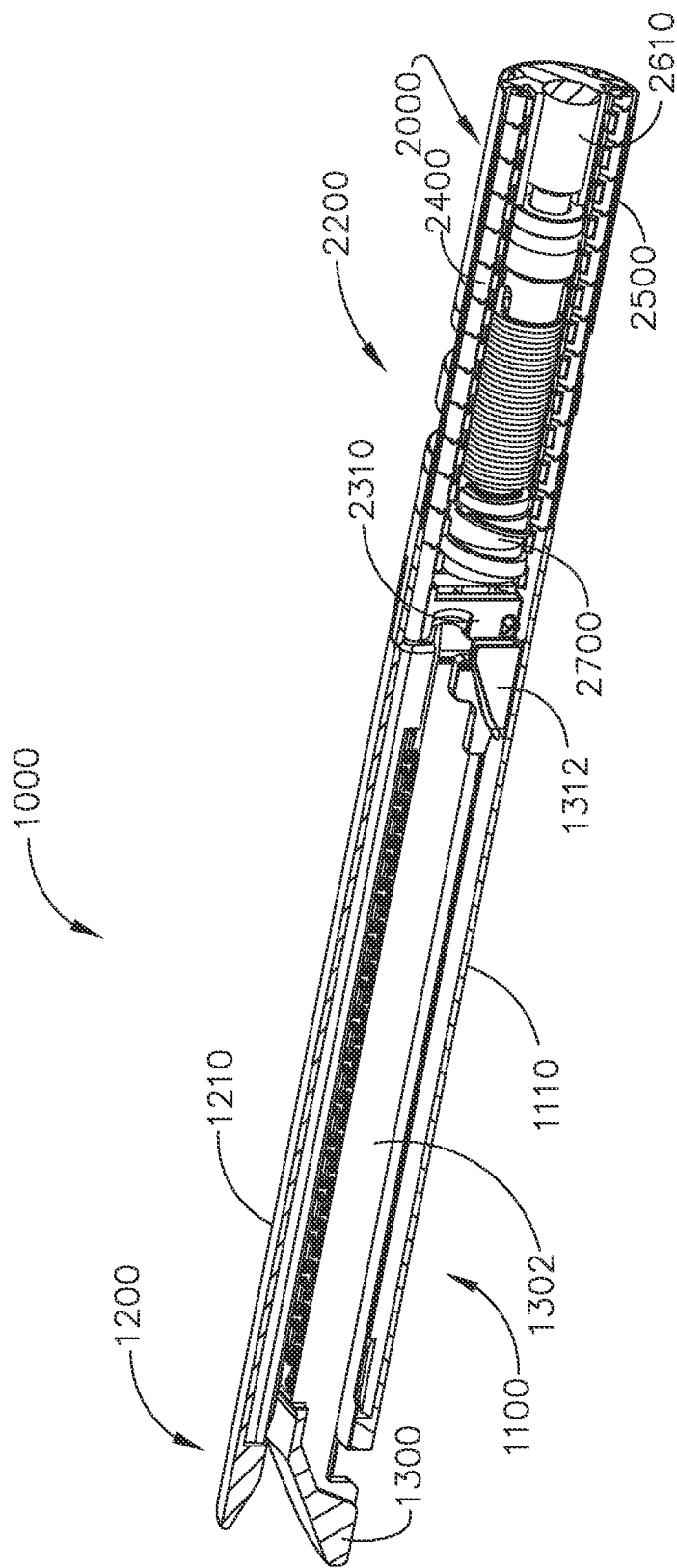
FIG. 44 is a cross-sectional view of the surgical end effector of FIG. 19 with the jaws thereof in a closed position and the firing member thereof in a proximal-most position.

One method of using the surgical instrument 10 may involve the use of the surgical instrument 10 to cut and staple target tissue within a patient using laparoscopic techniques. For example, one or more trocars may have been placed through the abdominal wall of a patient to provide access to a target tissue within the patient. The surgical end effector 1000 may be inserted through one trocar and one or more cameras or other surgical instruments may be inserted through the other trocar(s). To enable the surgical end effector 1000 to pass through the trocar cannula, the surgical end effector 1000 is positioned in an unarticulated orientation and the jaws 1100 and 1200 must be closed. To retain the jaws 1100 and 1200 in the closed position for insertion purposes, for example, the rotary drive system 2600 may be actuated to apply the second rotary motion to the rotary drive screw 2700 to cause the firing member 2310 to move proximally from the starting position to move the anvil 1210 (jaw 1200) to the closed position. See FIG. 44. The rotary drive system 2600 is deactivated to retain the firing member 2310 in that position. Once the surgical end effector has passed into the abdomen through the trocar, the rotary drive system 2600 may be activated to cause the rotary drive screw 2700 to drive the firing member 2310 distally back to the starting position wherein the anvil springs 1270 will pivot the anvil 1210 to the open position. See FIG. 38.

Once inside the abdomen and before engaging the target tissue, the surgeon may need to articulate the surgical end effector 1000 into an advantageous position. The articulation control system 2240 is then actuated to articulate the surgical end effector in one or more planes relative to a portion of the elongate shaft assembly 2000 that is received within the cannula of the trocar. Once the surgeon has oriented the surgical end effector 1000 in a desirable position, the articulation control system 2240 is deactivated to retain the surgical end effector 1000 in the articulated orientation. The surgeon may then use the surgical end effector to grasp the target tissue or adjacent tissue by activating the rotary drive system to rotate the rotary drive screw in the second rotary direction to move the firing member proximally to cause the anvil 1210 to rapidly close to grasp the tissue between the anvil 1210 and the surgical staple cartridge 1300. The anvil 1210 may be opened by reversing the rotation of the rotary drive screw 2700. This process may be repeated as necessary until the target tissue has be properly positioned between the anvil 1210 and the surgical staple cartridge 1300.

Once the target tissue has been positioned between the anvil 1210 and the surgical staple cartridge, the surgeon may commence the closing and firing process by activating the rotary drive system 2600 to drive the firing member 2310 distally from the starting position. As the firing member 2310 moves distally from the starting position, the firing member 2310 applies a closure motion to the anvil 1210 and moves the anvil 1210 from the open position to the closed position in the manners discussed above. As the firing member 2310 moves distally, the firing member 2310 retains the anvil 1210 in the closed position thereby clamping the target tissue between the anvil 1210 and the surgical staple cartridge 1300. As the firing member 2310 moves distally, the firing member 2310 contacts a sled 1312 supported in the surgical staple cartridge 1300 and also drives the sled 1312 distally through the staple cartridge body 1302. The sled 1312 serially drives rows of drivers supported in the staple cartridge toward the clamped target tissue. Each driver has supported thereon one or more surgical staples or fasteners which are then driven through the target tissue and into forming contact with the underside of the anvil 1210. As the firing member 2310 moves distally, the tissue cutting edge 2314 thereon cuts through the stapled tissue.

Figure 45:
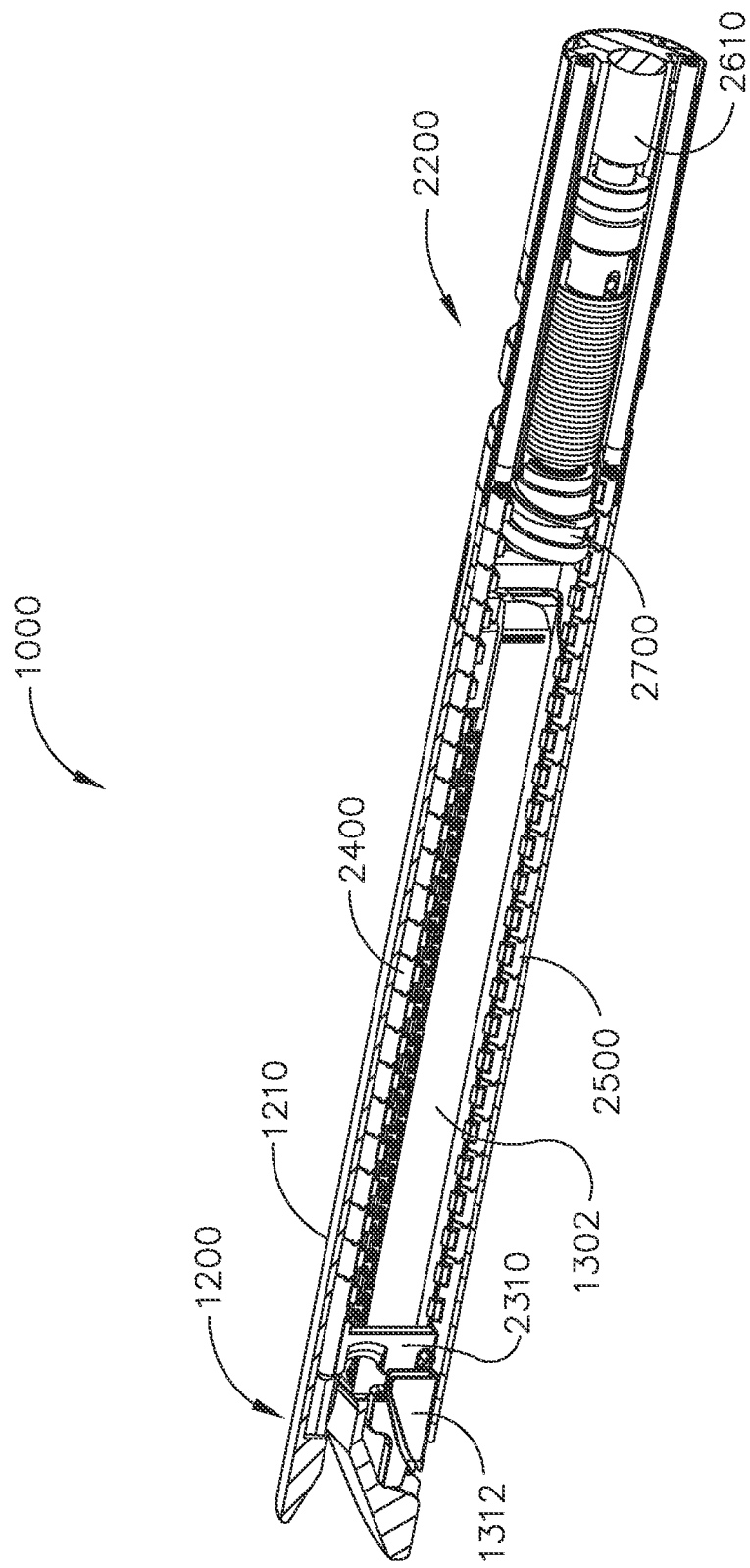
FIG. 45 is another cross-sectional view of the surgical end effector of FIG. 44, after the firing member has been distally advanced to the ending position within the surgical end effector.
Figure 46:
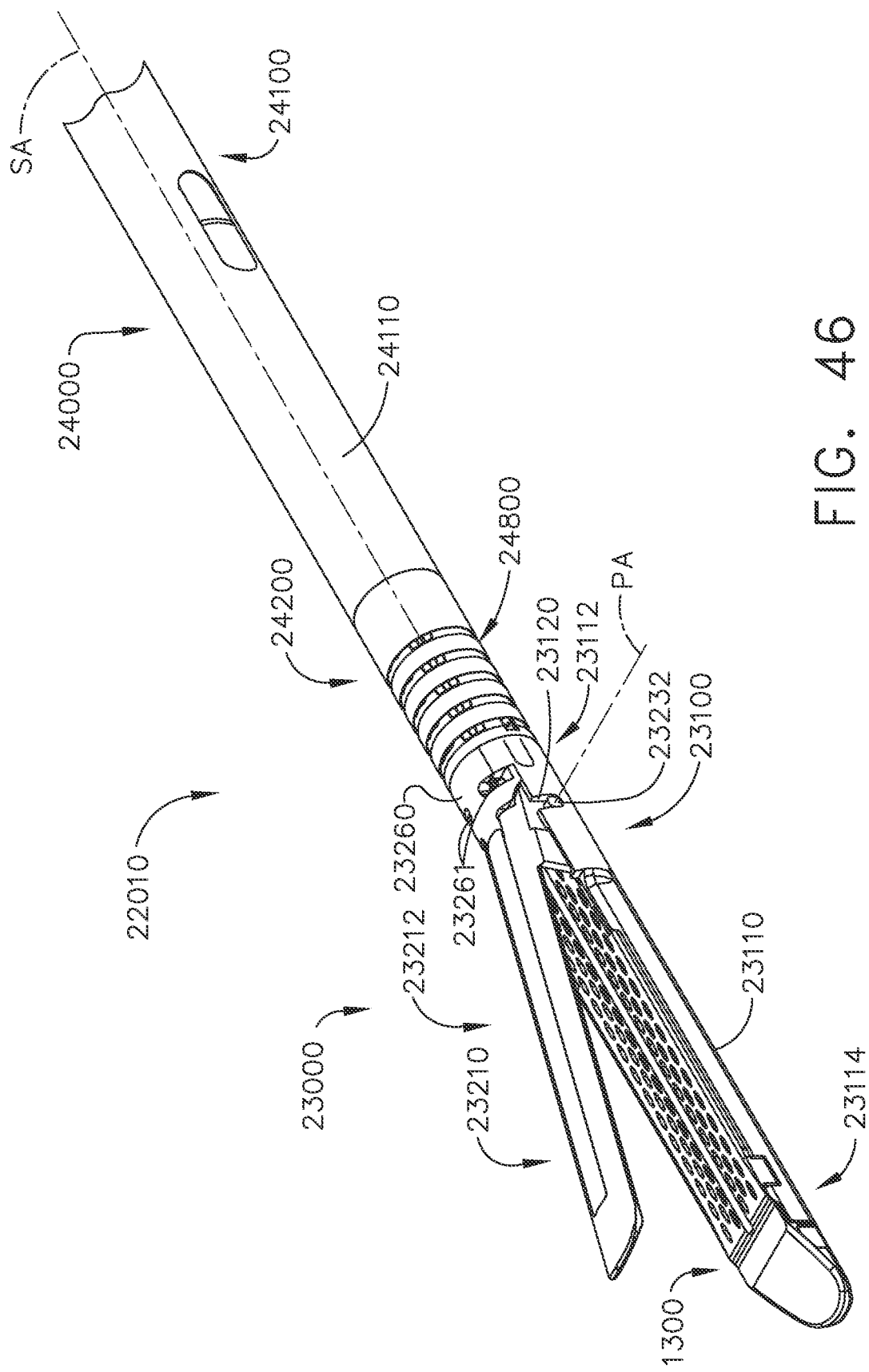
FIG. 46 is a perspective view of a portion of another surgical instrument.
Figure 47:
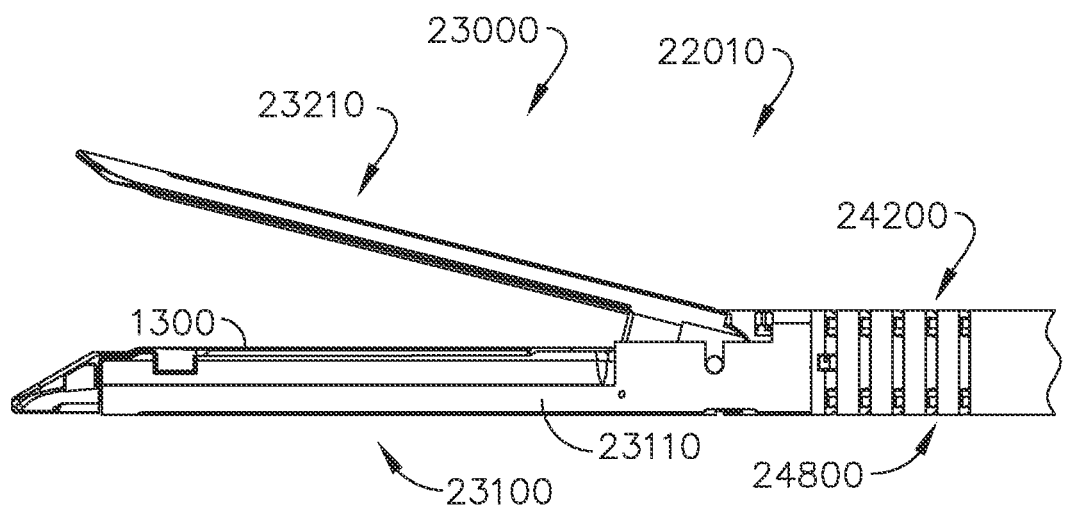
FIG. 47 is a side elevational view of a surgical end effector of the surgical instrument of FIG. 46, with the jaws thereof in an open position.

After the firing member 2310 has been driven distally to the ending position within the surgical end effector 1000 (FIG. 45), the rotary drive system 2600 is reversed which causes the firing member 2310 to retract proximally back to the home or starting position. Once the firing member 2310 has returned to the starting position, the anvil springs 1270 will pivot the anvil 1210 to the open position to enable the surgeon to release the stapled tissue from the surgical end effector 1000. Once the stapled tissue has been released, the surgical end effector may be withdrawn out of the patient through the trocar cannula. To do so, the surgeon must first actuate the articulation control system 2240 to return the surgical end effector 1000 to an unarticulated position and actuate the rotary drive system to drive the firing member 2310 proximally from the home or starting position to close the jaws. Thereafter, the surgical end effector 1000 may be withdrawn through the trocar cannula. If during the firing process or during the retraction process, the firing system becomes inoperative, the surgeon may retract the firing member 2310 back to the starting position by applying a pulling motion to the cables 2404, 2505 in the proximal direction in the various manners described herein.

FIGS. 46-68 illustrate another surgical instrument 22010 that in many aspects is identical or very similar to the surgical instrument 10 described above, except for the various differences discussed below. Like surgical instrument 10, surgical instrument 22010 may address many of the challenges facing surgical instruments with articulatable end effectors that are configured to cut and fasten tissue. In various embodiments, the surgical instrument 22010 may comprise a handheld device. In other embodiments, the surgical instrument 22010 may comprises an automated system sometimes referred to as a robotically-controlled system, for example. In various forms, the surgical instrument 22010 comprises a surgical end effector 23000 that is operably coupled to an elongate shaft assembly 24000. The elongate shaft assembly 24000 may be operably attached to a housing that is handheld or otherwise comprises a portion of a robotic system as was discussed above.

Figure 48:
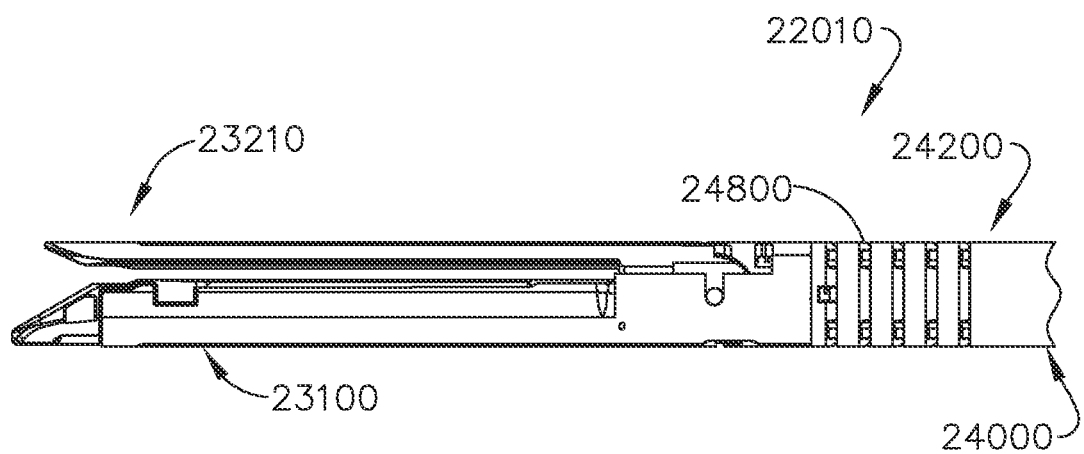
FIG. 48 is another side view of the surgical end effector of FIG. 48 with the jaws thereof in a closed position.
Figure 49:
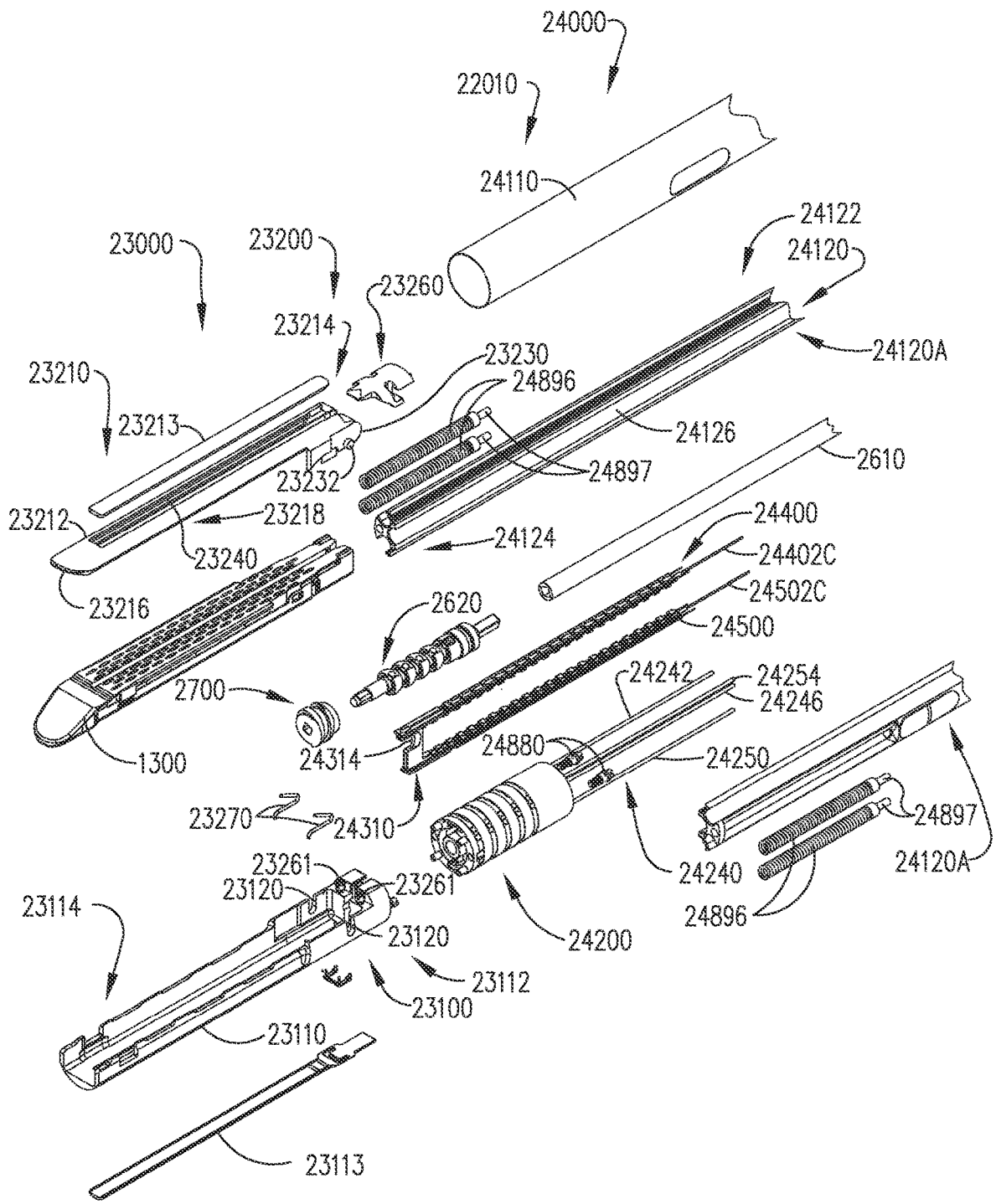
FIG. 49 is an exploded assembly view of a portion of the surgical instrument of FIG. 46.
Figure 50:
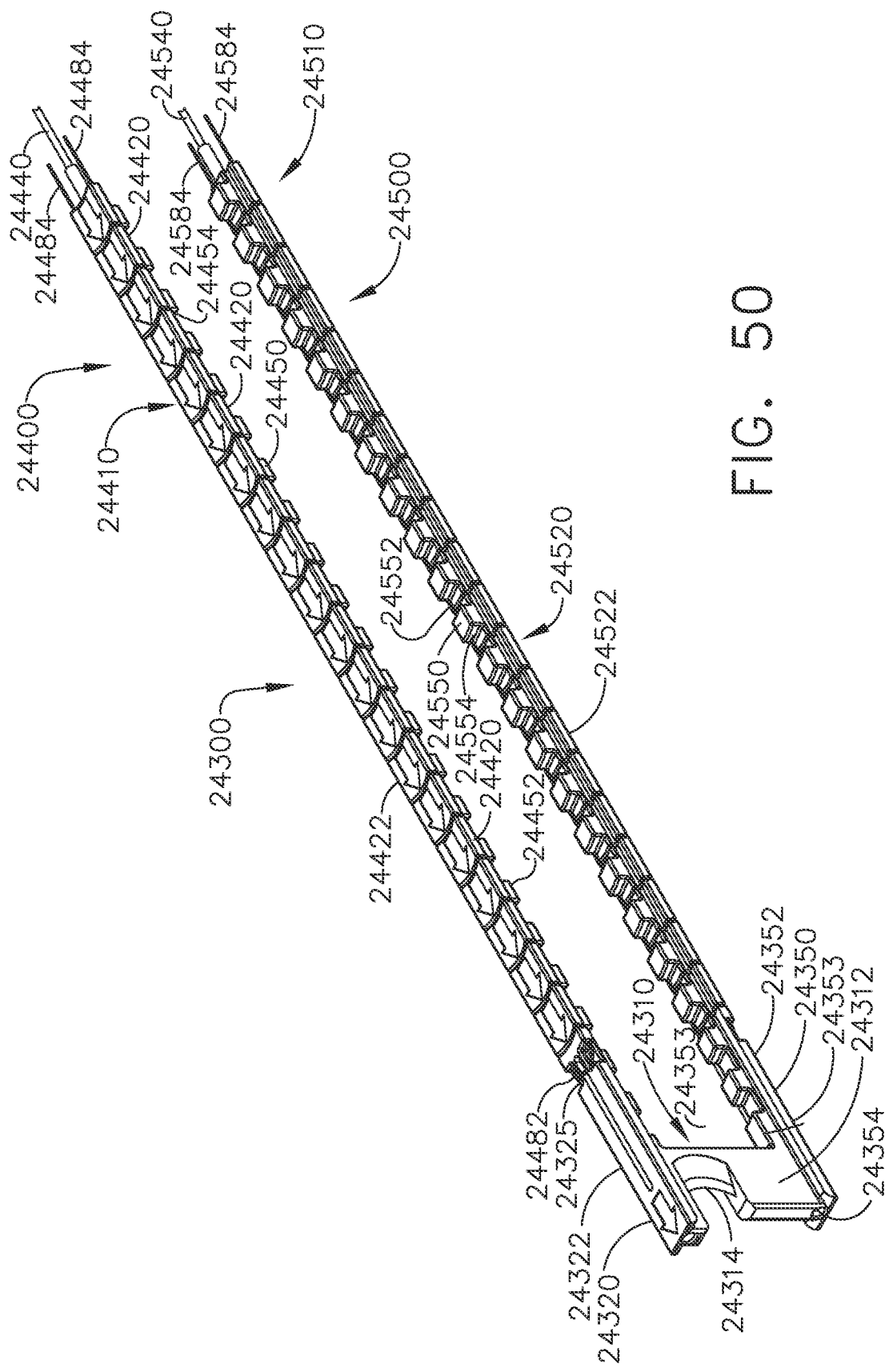
FIG. 50 is a perspective view of a firing member and portions of an upper flexible spine assembly and a lower flexible spine assembly of a firing system of the surgical instrument of FIG. 46.

As can be seen in FIG. 49, in one form, the surgical end effector 23000 comprises a first jaw 23100 and a second jaw 23200. In the illustrated arrangement, the first jaw 23100 comprises an elongate channel 23110 that comprises a proximal end 23112 and a distal end 23114 and is configured to operably support a surgical staple cartridge 1300 therein. The elongate channel 23110 has an open bottom to facilitate ease of assembly and has a channel cover 23113 that is configured to be attached thereto (welded, etc.) to cover the opening and add rigidity to the elongate channel 23110. In the illustrated arrangement, the second jaw 23200 comprises an anvil 23210 that comprises an elongate anvil body 23212 that comprises a proximal end 23214 and a distal end 23216. In one arrangement, an anvil cover 23213 is provided to facilitate assembly of the device and add rigidity to the anvil 23210 when it is attached (welded, etc.) to the anvil body 23212. The anvil body 23212 comprises a staple-forming undersurface 23218 that faces the first jaw 23100 and may include a series of staple-forming pockets (not shown) that corresponds to each of the staples or fasteners in the surgical staple cartridge 1300. The proximal end 23214 of the anvil body 23212 comprises an anvil mounting portion 23230 that includes a pair of laterally extending mounting pins 23232 that are configured to be received in corresponding mounting cradles or pivot cradles 23120 formed in the proximal end 23112 of the elongate channel 23110. The mounting pins 23232 are pivotally retained within the mounting cradles 23120 by an anvil cap 23260 that may be attached to the proximal end 23112 of the elongate channel 23110 by screws 23261. In other arrangements, the anvil cap 23260 may be attached to the elongate channel 23110 by welding, adhesive, etc. Such arrangement facilitates pivotal travel of the anvil 23210 relative to the surgical staple cartridge 1300 mounted in the elongate channel 23110 about a pivot axis PA between an open position (FIG. 47) and a closed position (FIG. 48). Such pivot axis PA may be referred to herein as being "fixed" in that the pivot axis does not translate or otherwise move as the anvil 23210 is pivoted from an open position to a closed position.

In the illustrated arrangement, the anvil 23210 is moved to the open position by a pair of anvil springs 23270 that are supported within the proximal end 23112 of the elongate channel 23110. See FIGS. 49 and 62. The springs 23270 are positioned to apply a pivotal biasing force to corresponding portions of the anvil 23210 to apply opening forces thereto. See FIG. 47.

In the illustrated arrangement, the elongate shaft assembly 24000 defines a shaft axis SA and comprises a proximal shaft portion 24100 that may operably interface with a housing of the control portion (e.g., handheld unit, robotic tool driver, etc.) of the surgical instrument 22010. The elongate shaft assembly 24000 further comprises an articulation joint 24200 that is attached to the proximal shaft portion 24100 and the surgical end effector 23000. In various instances, the proximal shaft portion 24100 comprises a hollow outer tube 24110 that may be operably coupled to a housing in the various manners discussed above. As can be seen in FIG. 49, the proximal shaft portion 24100 may further comprise a rigid proximal support shaft 24120 that is supported within the hollow outer tube 24110 and extends from the housing to the articulation joint 24200. The rigid proximal support shaft 24120 may comprise a first half 24120A and a second half 24120B that may be coupled together by, for example, welding, adhesive, etc. The rigid proximal support shaft 24120 comprises a proximal end 24122 and a distal end 24124 and includes an axial passage 24126 that extends therethrough from the proximal end 24122 to the distal end 24124.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 22010 employs a firing system 24300 that is identical to or very similar in many aspects as firing system 2300 described above. As such, only those aspects of the firing system 24300 needed to understand the operation of the surgical instrument 22010 will be discussed below.

Figure 54:
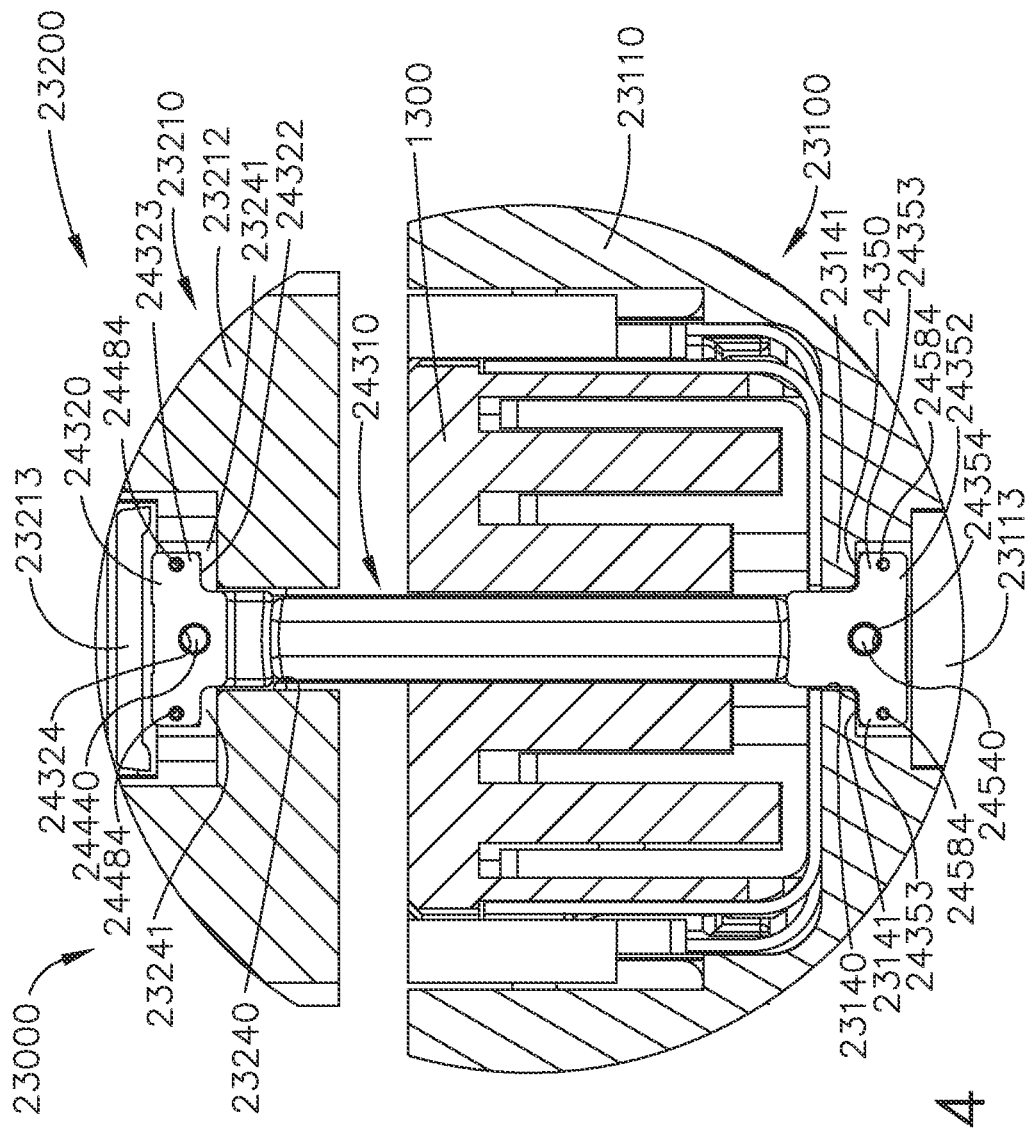
FIG. 54 is a cross-sectional end view of the surgical end effector of the surgical instrument of FIG. 46, with the jaws thereof in a closed position.

As can be seen in FIGS. 50-54, in at least one embodiment, the firing system 24300 comprises a firing member 24310 that includes a vertically-extending firing member body 24312 that comprises a top firing member feature 24320 and a bottom firing member feature 24350. A tissue cutting blade 24314 is attached to or formed in the vertically-extending firing member body 24312. See FIGS. 50 and 51. In at least one arrangement, it is desirable for the firing member 24310 to pass through the anvil body 23212 with low friction, high strength and high stiffness. In the illustrated arrangement, the top firing member feature 24320 comprises a T-shaped body 24322 that has two laterally extending tabs 24323 protruding therefrom and a top axial passage 24324 extending therethrough. See FIG. 53. The bottom firing member feature 24350 comprises a T-shaped body 24352 that has two laterally extending tabs 24353 protruding therefrom and a bottom axial passage 24354 extending therethrough. See FIG. 50. In at least one arrangement, the top firing member feature 24320 and the bottom firing member feature 24350 are integrally formed with the vertically-extending firing member body 24312. As can be seen in FIG. 54, the anvil body 23212 comprises an axially extending anvil slot 23240 that defines two opposed ledges 23241 for slidably receiving the laterally extending tabs 24323 thereon. Similarly, the elongate channel 23110 comprises an axially extending channel slot 23140 that defines axially extending channel ledges 23141 that are configured to slidably receive the laterally extending tabs 24353 thereon.

In the illustrated arrangement, the firing system 24300 comprises an upper flexible spine assembly 24400 that is operably coupled to the top firing member feature 24320 of the firing member 24310. In at least one embodiment, the upper flexible spine assembly 24400 comprises an upper series 24410 of upper vertebra members 24420 that are loosely coupled together by an upper flexible coupler member 24440 that extends through each of the upper vertebra members 24420 and is attached to the top firing member feature 24320.

Figure 52:
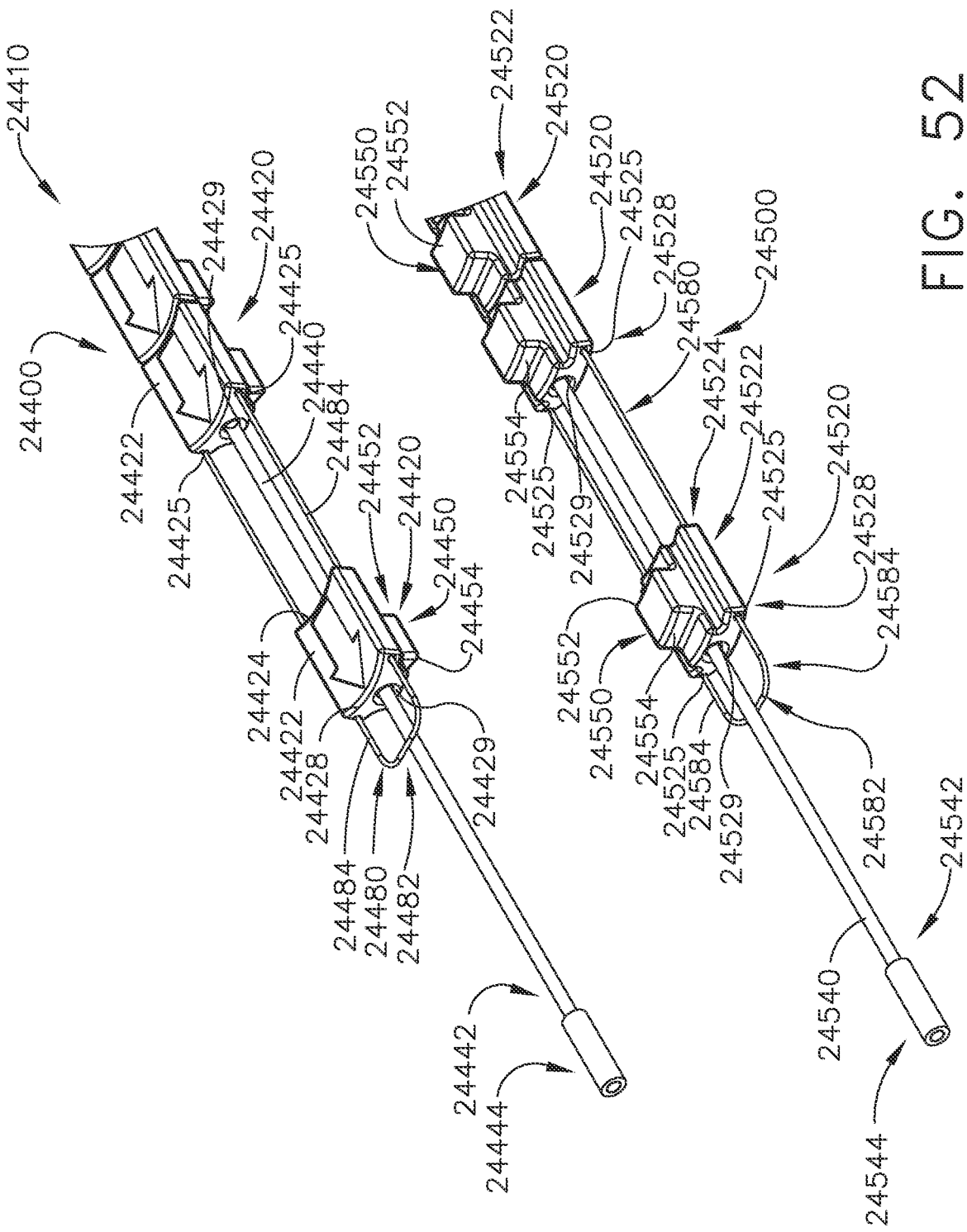
FIG. 52 is a partial exploded assembly view of the upper flexible spine assembly and lower flexible spine assembly depicted in FIG. 51.
Figure 53:
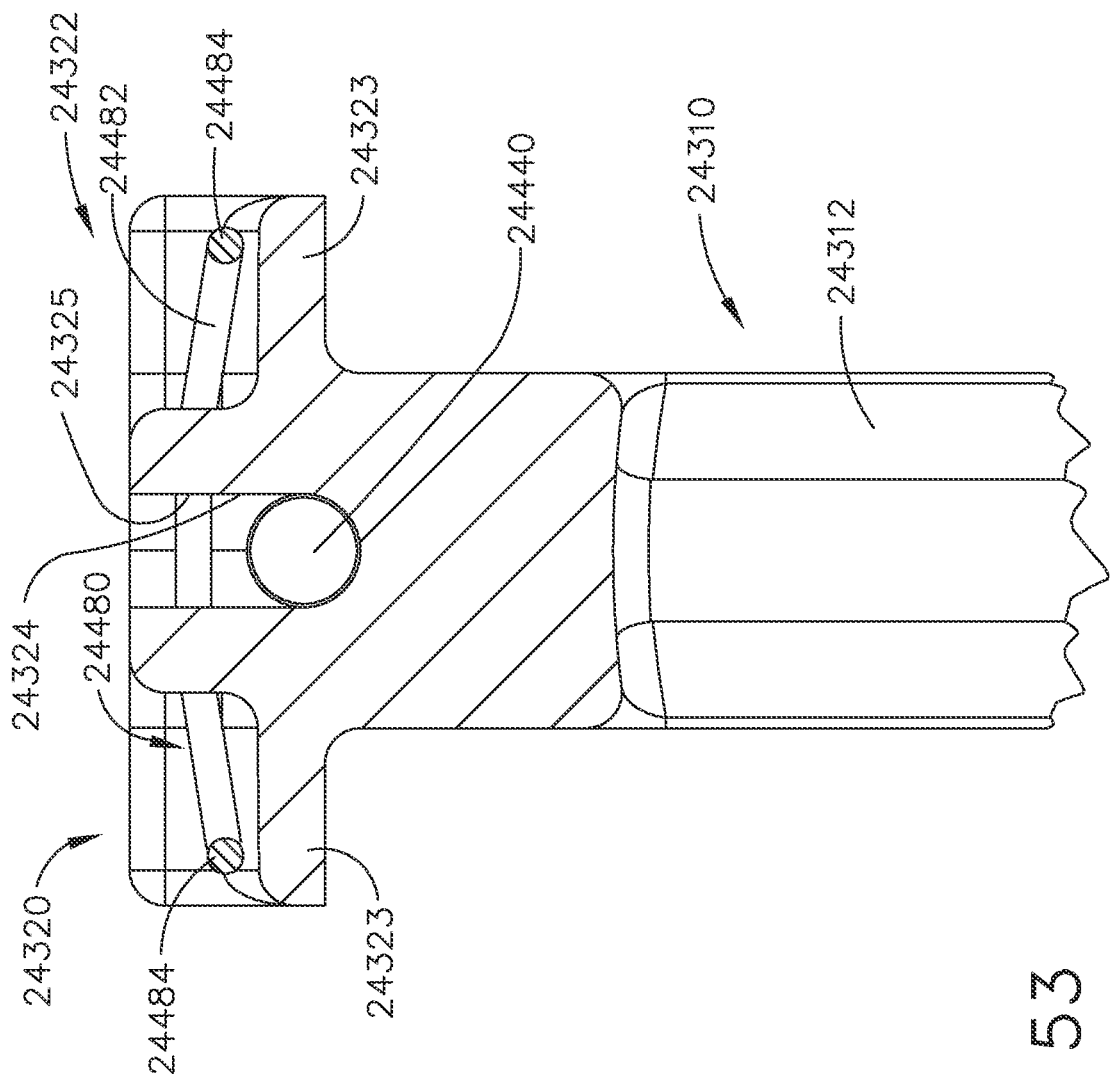
FIG. 53 is a partial cross-sectional end view of an upper portion of the firing member depicted in FIG. 50.

As can be seen in FIG. 52, each upper vertebra member 24420 is substantially T-shaped when viewed from an end thereof. In one aspect, each upper vertebra member 24420 comprises an upper vertebra body portion 24422 that has a proximal end 24424 and a distal end 24428. Each upper vertebra member 24420 further comprises a downwardly extending upper drive feature or upper vertebra member tooth 24450 that protrudes from the upper vertebra body portion 24422. Each upper vertebra member tooth 24450 has a helix-shaped proximal upper face portion 24452 and a helix-shaped distal upper face portion 24454. Each proximal end 24424 of the upper vertebra body portions 24422 has an arcuate or slightly concave curved shape and each distal end 24428 has an arcuate or slightly convex curved shape. When arranged in the upper series 24410, the convex distal end 24428 on one upper vertebra member 24420 contacts and mates with the concave proximal end 24424 on an adjacent upper vertebra member 24420 in the upper series 24410 to maintain the upper vertebra members 24420 roughly in alignment so that the helix-shaped proximal upper face portion 24452 and a helix-shaped distal upper face portion 24454 on each respective upper vertebra member tooth 24450 can be drivingly engaged by a rotary drive screw 2700 in the various manners disclosed herein. These curved mating surfaces on the upper vertebra members 24420 allow the upper vertebras members 24420 to better transfer loads between themselves even when they tilt.

In at least one embodiment, an upper alignment member 24480 is employed to assist with the alignment of the upper vertebra members 24420 in the upper series 24410. In one arrangement, the alignment member 24480 comprises a spring member or metal cable which may be fabricated from Nitinol wire, spring steel, etc., and be formed with a distal upper looped end 24482 and two upper leg portions 24484 that extend through corresponding upper passages 24425 in each upper vertebra body portion 24422. The upper flexible coupler member 24440 extends through an upper passage 24429 in each of the upper vertebra members 24420 to be attached to the firing member 24310. In particular, a distal end portion 24442 extends through the top axial passage 24324 in the top firing member feature 24320 and is secured therein by an upper retention lug 24444. A proximal portion of the upper flexible coupler member 24440 may interface with a corresponding rotary spool or cable-management system of the various types and designs disclosed herein that serve to payout and take up the upper flexible coupler member 24440 to maintain a desired amount of tension therein during operation and articulation of the surgical end effector 23000. The cable management system may be motor powered or manually powered (ratchet arrangement, etc.) to maintain a desired amount of tension in the upper flexible coupler member 24440. The amount of tension in each flexible coupler member may vary depending upon the relative positioning of the surgical end effector 23000 to the elongate shaft assembly 24000.

The firing system 24300 further comprises a lower flexible spine assembly 24500 that is operably coupled to the bottom firing member feature 24350. The lower flexible spine assembly 24500 comprises a lower series 24510 of lower vertebra members 24520 that are loosely coupled together by a lower flexible coupler member 24540 that extends through each of the lower vertebra members 24520 and is attached to the bottom firing member feature 24350. As can be seen in FIG. 52, each lower vertebra member 24520 is substantially T-shaped when viewed from an end thereof. In one aspect, each lower vertebra member 24520 comprises a lower vertebra body portion 24522 that has a proximal end 24524 and a distal end 24528. Each lower vertebra member 24520 further comprises an upwardly extending lower drive feature or lower vertebra member tooth 24550 that protrudes from the lower vertebra body portion 24522. Each lower vertebra member tooth 24550 has a helix-shaped proximal lower face portion 24552 and a helix-shaped distal lower face portion 24554. The proximal end 24524 of each lower vertebra body portions 24522 has an arcuate or slightly concave curved shape and each distal end 24528 has an arcuate or slightly convex curved shape. When arranged in the lower series 24510, the convex distal end 24528 on one lower vertebra member 24520 contacts and mates with the concave proximal end 24524 on an adjacent lower vertebra member 24520 in the lower series 24510 to maintain the lower vertebra members 24520 roughly in alignment so that the helix-shaped proximal lower face portion 24552 and a helix-shaped distal lower face portion 24554 on each respective lower vertebra member tooth 24550 can be drivingly engaged by the rotary drive screw 2700 in the various manners disclosed herein. These curved mating surfaces on the lower vertebra members 24520 allow the lower vertebra members 24520 to better transfer loads between themselves even when they tilt.

In at least one embodiment, a lower alignment member 24580 is employed to assist with the alignment of the lower vertebra members 24520 in the lower series 24510. In one arrangement, the lower alignment member 24580 comprises a spring member or metal cable which may be fabricated from Nitinol wire, spring steel, etc., and be formed with a distal lower looped end 24582 and two lower leg portions 24584 that extend through corresponding lower passages 24525 in each lower vertebra body portion 24522. The lower flexible coupler member 24540 extends through the bottom axial passage 24529 in each of the lower vertebra members 24520 to be attached to the firing member 24310. In particular, a distal end portion 24542 of the lower flexible coupler member 24540 extends through the bottom axial passage 24354 in the bottom firing member feature 24350 and is secured therein by a lower retention lug 24544. A proximal portion of the lower flexible coupler member 24540 may interface with a corresponding rotary spool or cable-management system of the various types and designs disclosed herein that serve to payout and take up the lower flexible coupler member 24540 to maintain a desired amount of tension therein during operation and articulation of the surgical end effector 23000. The cable management system may be motor powered or manually powered (ratchet arrangement, etc.) to maintain a desired amount of tension in the lower flexible coupler member 24540. The amount of tension in each flexible coupler member may vary depending upon the relative positioning of the surgical end effector 23000 to the elongate shaft assembly 24000.

In accordance with at least one aspect, a large surface area is advantageous for distributing the force between the vertebra members when they push so that the vertebra members cannot twist relative to each other. The available area in the anvil and channel is limited and the anvil and channel must remain stiff. The T-shaped upper vertebra members 24420 and the T-shaped lower vertebra members 24520 are designed to fit in the limited spaces available in the anvil 23210 and the elongate channel 23110 while ensuring that there is a large amount of area to distribute the firing loads.

The curved surfaces on each upper vertebra member 24420 and each lower vertebra member 24520 allow each of those vertebras to better transfer loads between themselves even when they tilt. The upper alignment member 24480 and the lower alignment member 24580 may also serve to prevent the upper vertebra members 24420 and the lower vertebra members 24520 from twisting relative to each other. The large surface area may also help to prevent galling of the vertebra members and/or the anvil and channel. The upper flexible spine assembly 24400 and the lower flexible spine assembly 24500 otherwise operably interface with the rotary drive screw 2700 arrangements as disclosed herein. The upper flexible coupler member 24440 and the lower flexible coupler member 24540 may also be used in the manners discussed above to retract the firing member 24310 back to its starting position if, during a firing stroke, the firing drive system 24300 fails.

Figure 51:
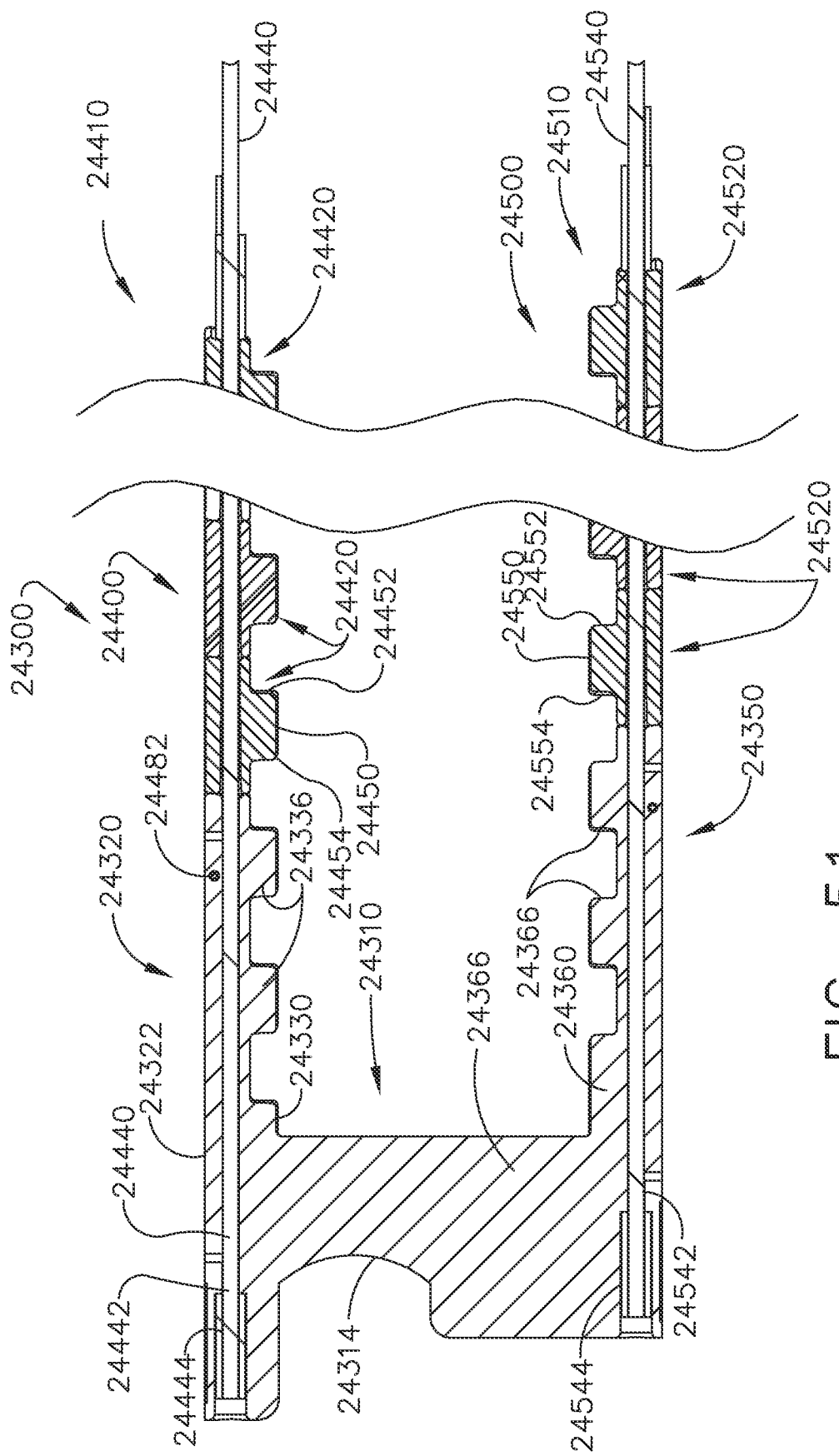
FIG. 51 is a cross-sectional side view of portions of the firing system depicted in FIG. 50.

As can be seen in FIG. 51, the top firing member feature 24320 on the firing member 24310 comprises a distal upper firing member tooth segment 24330 that is equivalent to one half of an upper vertebra member tooth 24450 on each upper vertebra member 24420. In addition, two proximal upper firing member teeth 24336 that are identical to an upper vertebra member tooth 24450 on each upper vertebra member 24420 are spaced from the distal upper firing member tooth segment 24330. The distal upper firing member tooth segment 24330 and the proximal upper firing member teeth 24336 may each be integrally formed with the top firing member feature 24320 of the firing member 24310. Likewise, the bottom firing member feature 24350 of the firing member 24310 comprises a distal lower firing member tooth 24360 and two proximal lower firing member teeth 24366 that are integrally formed on the bottom firing member feature 24350. For example, in at least one arrangement, the firing member 24310 with the rigidly attached teeth 24330, 24336, 24360, and 24366 may be fabricated at one time as one unitary component using conventional metal injection molding techniques. The person of ordinary skill in the art will recognize that the firing member 24310 operates in essentially the same manner as the firing member 2310 as was described in detail herein.

Figure 57:
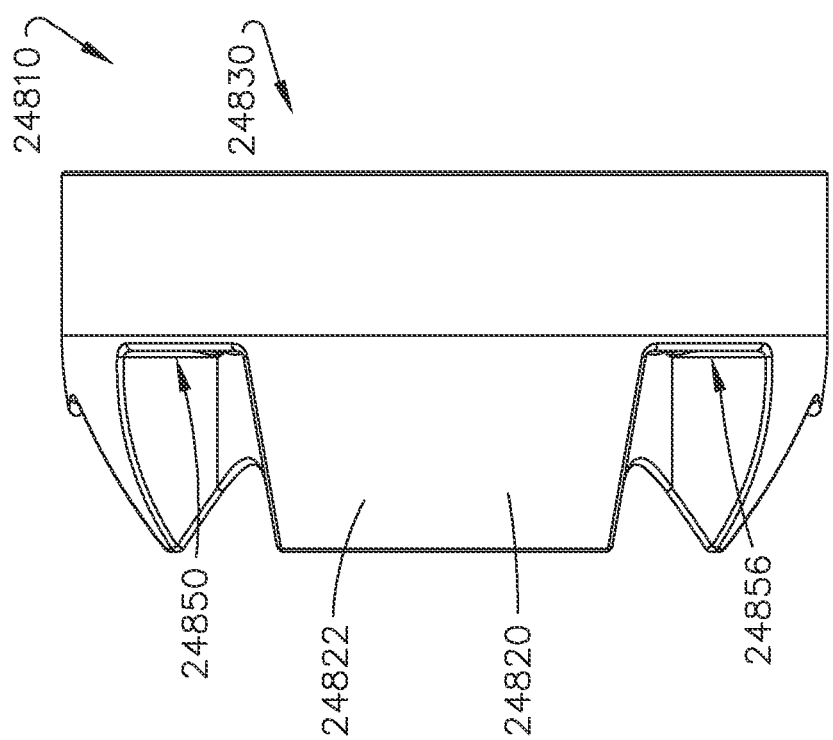
FIG. 57 is a side view of the annular rib member of FIGS. 55 and 56.

Turning now to FIGS. 55-58, in accordance with at least one aspect, the articulation joint 24200 comprises a movable exoskeleton assembly 24800. In one form, the movable exoskeleton assembly 24800 comprises a series 24802 of movably interfacing annular rib members 24810. As can be seen in FIGS. 55-57, each annular rib member 24810 comprises a first or proximal face 24820 that comprises a convex or domed portion 24822. Each annular rib member 24810 further comprises a second or distal face 24830 that is concave or dished. Each annular rib member 24810 further comprises an upper spine passage 24840 that is configured to accommodate passage of the upper flexible spine assembly 24400 therethrough and a lower spine passage 24842 that is configured to accommodate passage of the lower flexible spine assembly 24500 therethrough. In addition, each annular rib member 24810 further comprises four articulation passages 24850, 24852, 24854, and 24856 to accommodate passage of articulation actuators in the form of articulation cables 24242, 22446, 24250, and 24254 therethrough. See FIG. 49. Each annular rib member 24810 further comprises a central drive passage 24860 that is configured to accommodate passage of the constant velocity (CV) drive shaft assembly 2620 therethrough.

Figure 58:
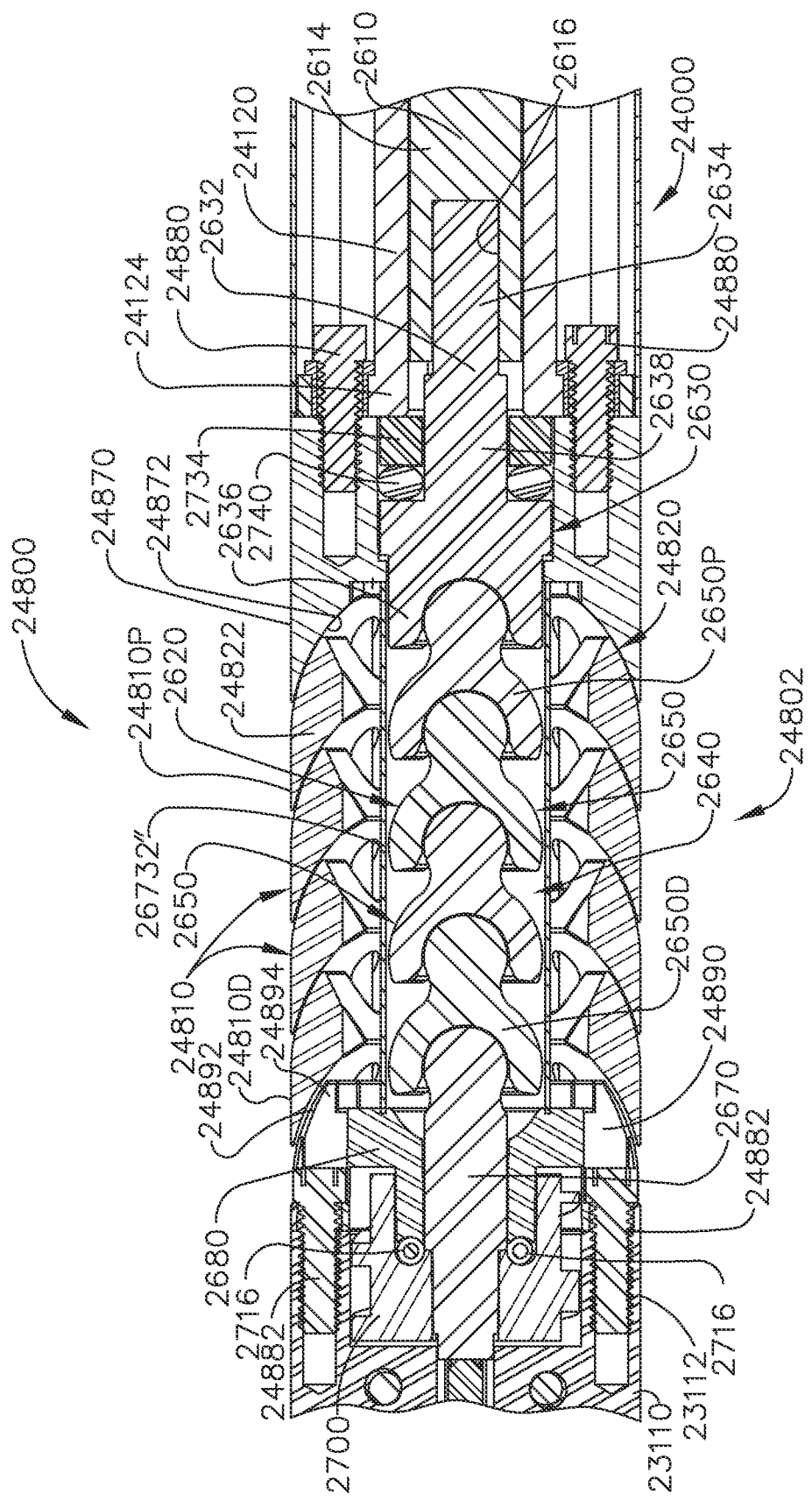
FIG. 58 is a partial cross-sectional view of a portion of the surgical instrument of FIG. 46.

As can be seen in FIG. 58, the movable exoskeleton assembly 24800 comprises a proximal attachment rib 24870 that is configured to attach the movable exoskeleton assembly 24800 to the distal end 24124 of the proximal support shaft 24120 by cap screws 24880 or other suitable fastener arrangements. The proximal attachment rib 24870 comprises a first or distal face 24872 that is concave or dished to receive or movably interface with the convex or domed portion 24822 of the proximal face 24820 of a proximal-most annular rib member 24810P. Similarly, the movable exoskeleton assembly 24800 comprises a distal attachment rib 24890 that is configured to attach the movable exoskeleton assembly 24800 to the proximal end 23112 of the elongate channel 23110 by cap screws 24882 or other suitable fasteners. The distal attachment rib 24890 comprises a first or proximal face 24892 that comprises a convex or domed portion 24894 that configured to be received in or movably interface with the concave or dished distal face 24832 of a distal-most annular rib member 24810D. In various embodiments, the annular rib members 24810, 24810P, and 24810D may be fabricated from any suitable metal (e.g., stainless steel, titanium, etc.) or other suitable material. The annular rib members 24810, 24810P, and 24810D may be formed by suitable drawing or forming operations, by machining or casting. The proximal faces 24820 and the distal faces 24830 may be polished or otherwise finished to a desirable smooth finish to reduce friction and facilitate movement between the annular rib members 24810, 24810P, and 24810D. In accordance with one aspect, all edges on each annular rib member 24810, 24810P, 24810D are rounded to facilitate relative movement between the annular rib members. The proximal attachment rib 24870 and the distal attachment rib 24890 may be formed with similar attributes.

The surgical instrument 22010 also comprises an articulation system 24240 that is configured to apply articulation motions to the surgical end effector 23000 to articulate the surgical end effector 23000 relative to the elongate shaft assembly 24000. In at least one arrangement, for example, as mentioned above, the articulation system 24240 comprises four articulation cables 24242, 24246, 24250, and 24254 that extend through the elongate shaft assembly 2400. See FIG. 49. In the illustrated arrangement, the articulation cables 24242, 24246 pass through the proximal attachment rib 24870 and through each of the annular rib members 24810P, 24810, and 24810D to be secured to the distal attachment rib 24890. In one arrangement for example, each of the articulation cables 24242, 24246 are secured to the distal attachment rib 24890 by corresponding attachment lugs 24243. See FIGS. 61 and 63. Likewise, the articulation cables 24250 and 24254 extend through the proximal attachment rib 24870 and through each of the annular rib members 24810P, 24810, and 24810D to be secured to the distal attachment rib 24890 by corresponding attachment lugs 24243.

Figure 59:
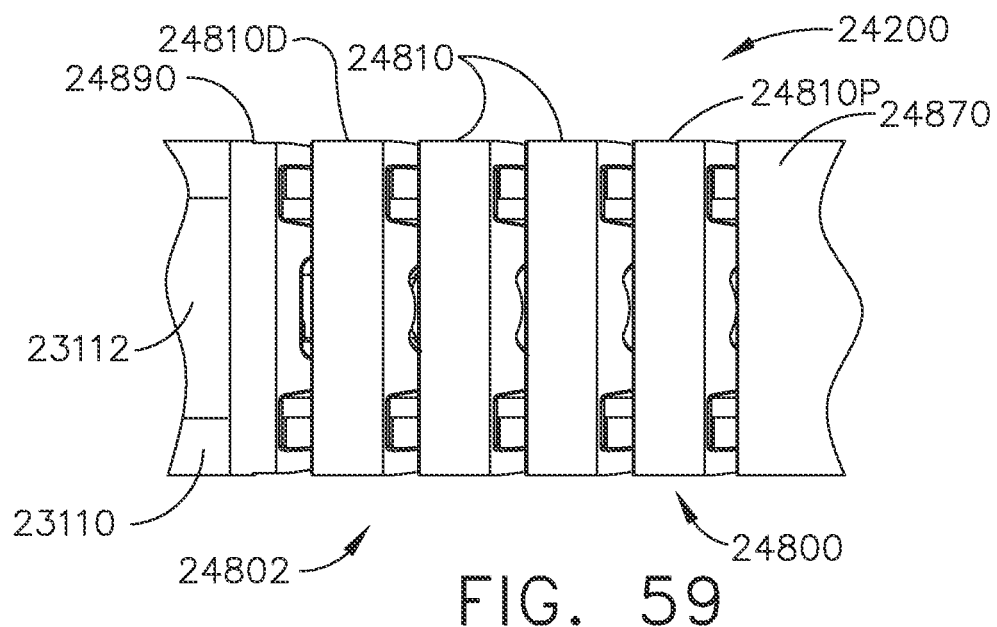
FIG. 59 is a side view of an articulation joint of the surgical instrument of FIG. 46 when the surgical end effector thereof is in an unarticulated position.
Figure 60:
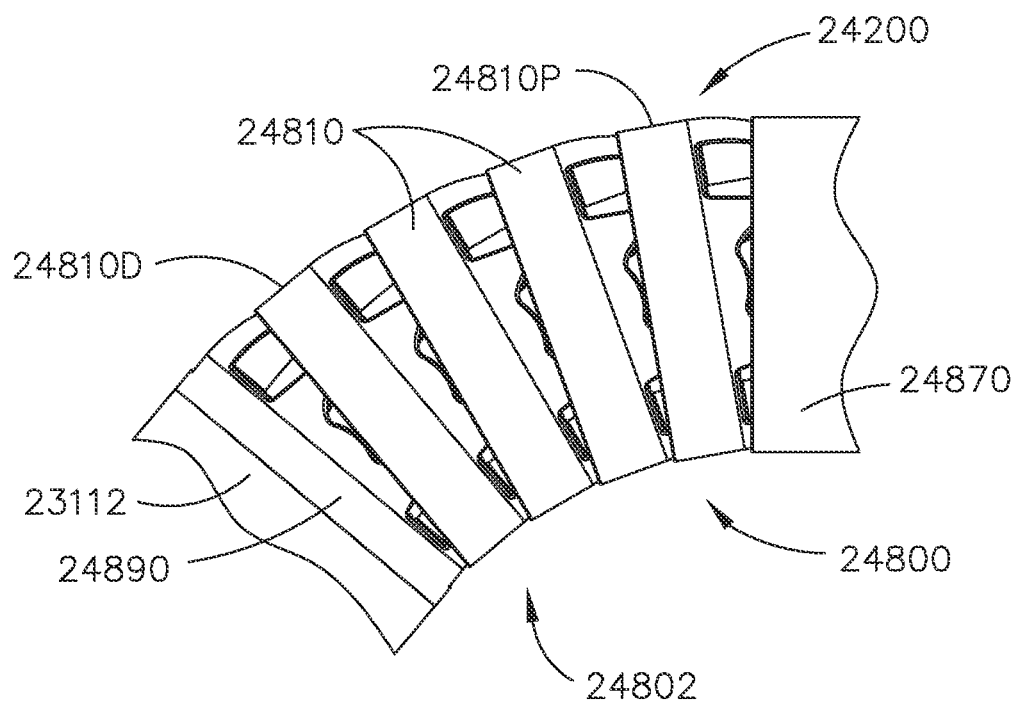
FIG. 60 is another side view of the articulation joint of FIG. 59 when the surgical end effector is in an articulated position.
Figure 61:
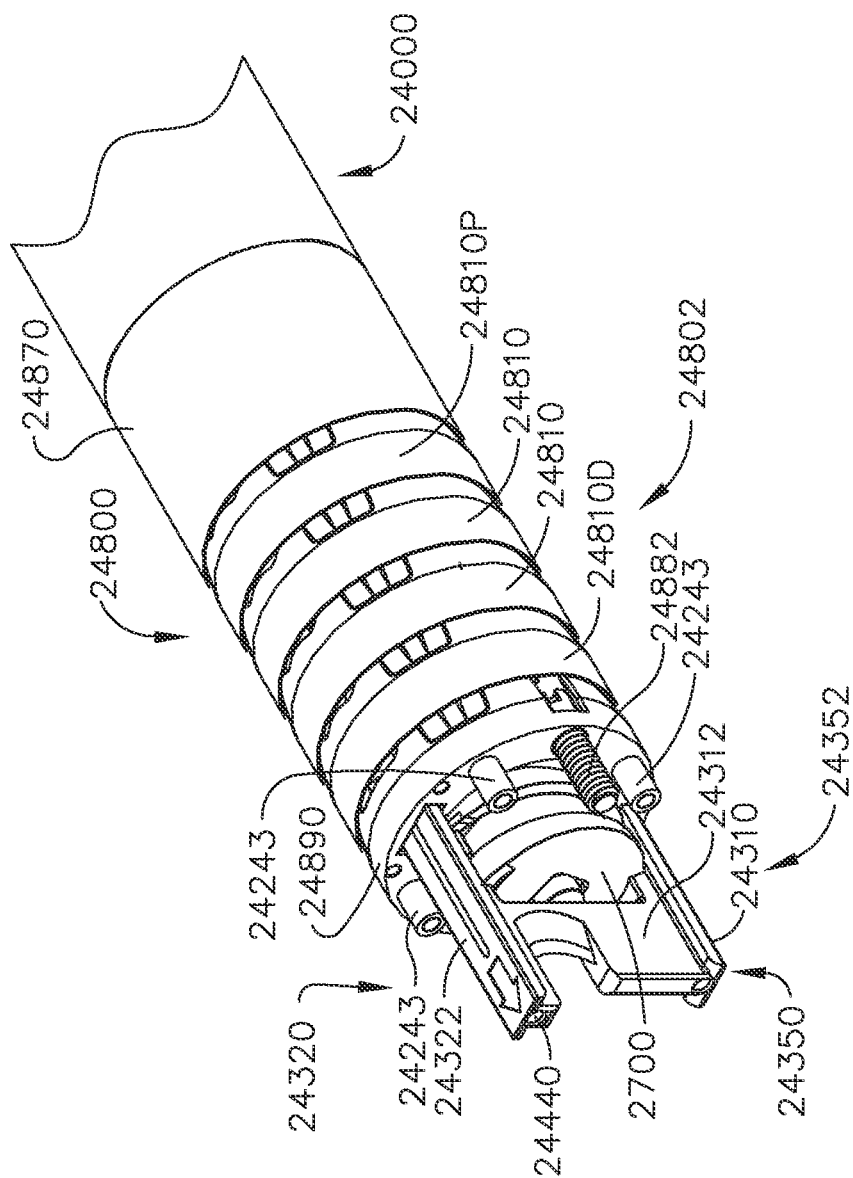
FIG. 61 is partial perspective view of a portion of the surgical instrument of FIG. 46 with the surgical end effector omitted for clarity.
Figure 62:
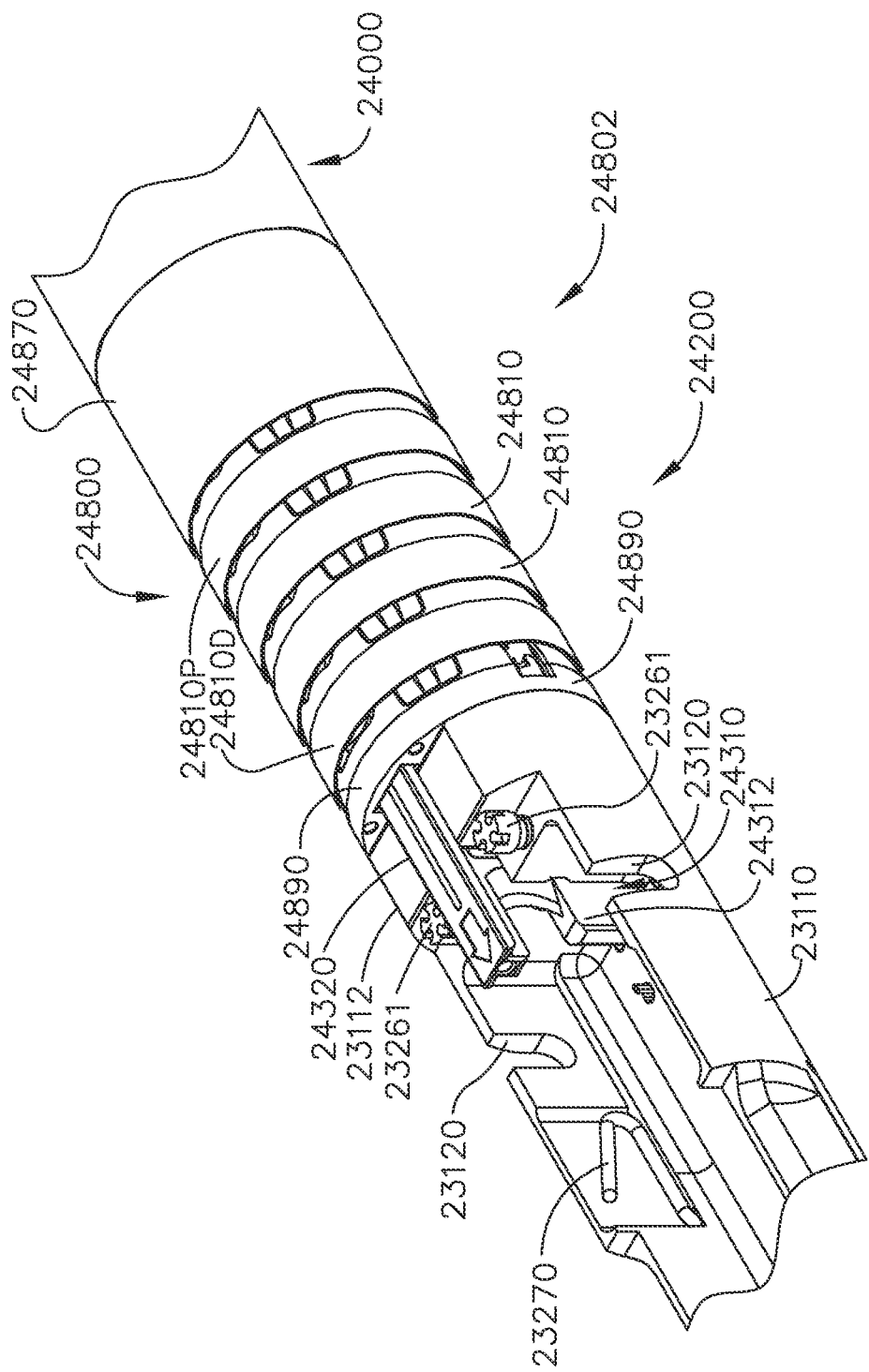
FIG. 62 is another partial perspective view of a portion of the surgical instrument of FIG. 46.
Figure 63:
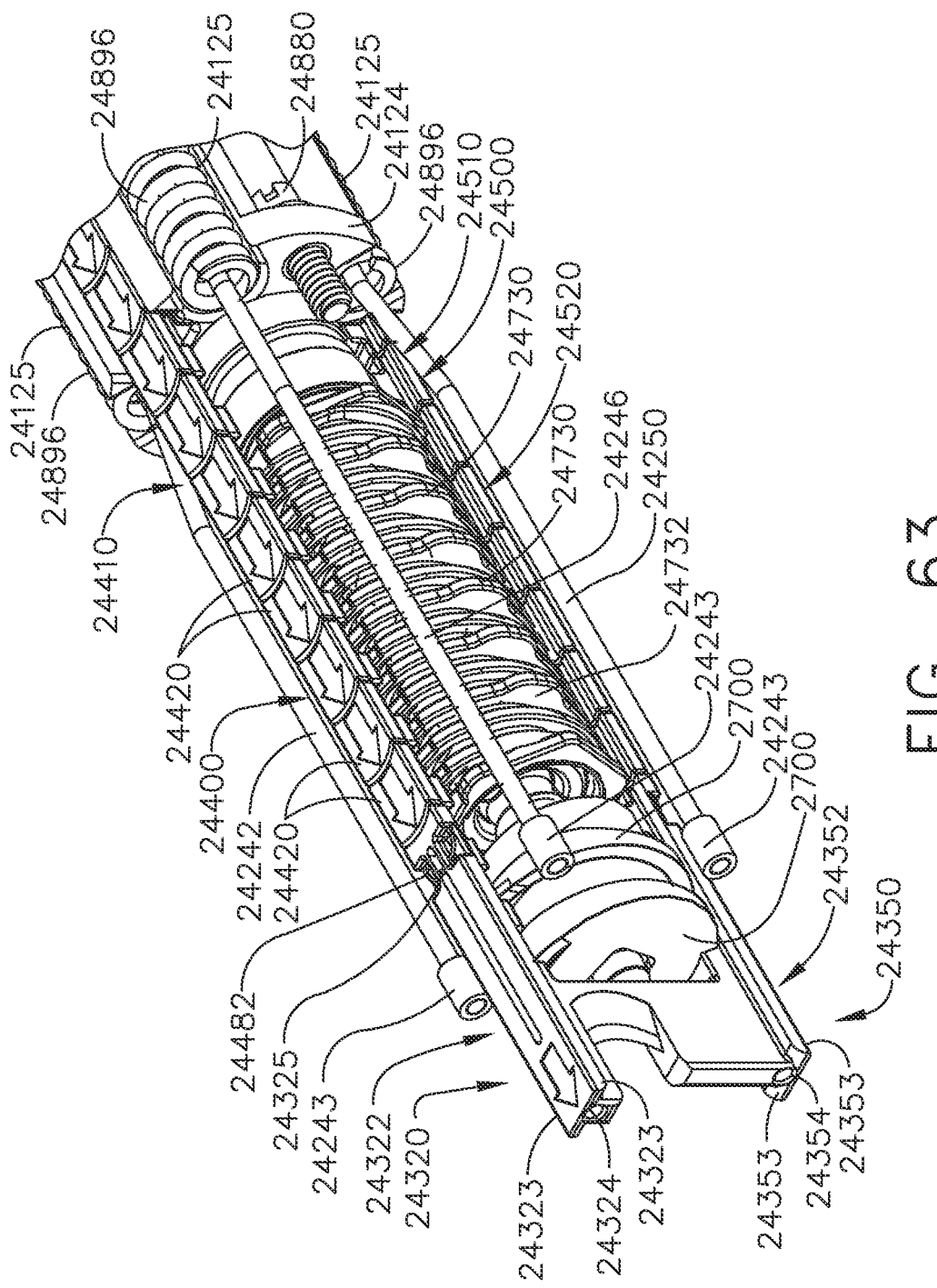
FIG. 63 is another partial perspective view of a portion of the surgical instrument of FIG. 46.

In one arrangement, each of the articulation cables 24242, 24246, 24250, and 24254 extend through corresponding coil springs 24896 that are supported in cavities 24125 in the distal end 24124 of the rigid proximal support shaft 24120. In addition, each coil spring 24896 is associated with a tensioning lug 24897 that is also journaled onto each respective articulation cable 24242, 24246, 24250, and 24524 and is secured thereon to attain a desired amount of compression in each spring 24896 which serves to retain the annular rib members 24810P, 24810, and 24810D in movable engagement with each other and with the proximal attachment rib 24870 and the distal attachment rib 24890. The cables 24242, 24246, 24250, and 24254 operably interface with an articulation control system that is supported in the housing of the surgical instrument 22010. For example, as was discussed above, a proximal portion of each cable 24242, 24246, 24250, and 24254 may be spooled on a corresponding rotary spool or cable-management system 2007 (FIG. 2) in the housing portion of the surgical instrument 22010 that is configured to payout and retract each cable 24242, 24246, 24250, and 24254 in desired manners. The spools/cable management system may be motor powered or manually powered (ratchet arrangement, etc.). FIG. 59 illustrates the articulation joint 24200 in an unarticulated position and FIG. 60 illustrates the articulation joint in one articulated configuration. Such arrangement permits the surgical end effector 23000 to be articulated through multiple articulation planes relative to the elongate shaft assembly 24000.

Figure 64:
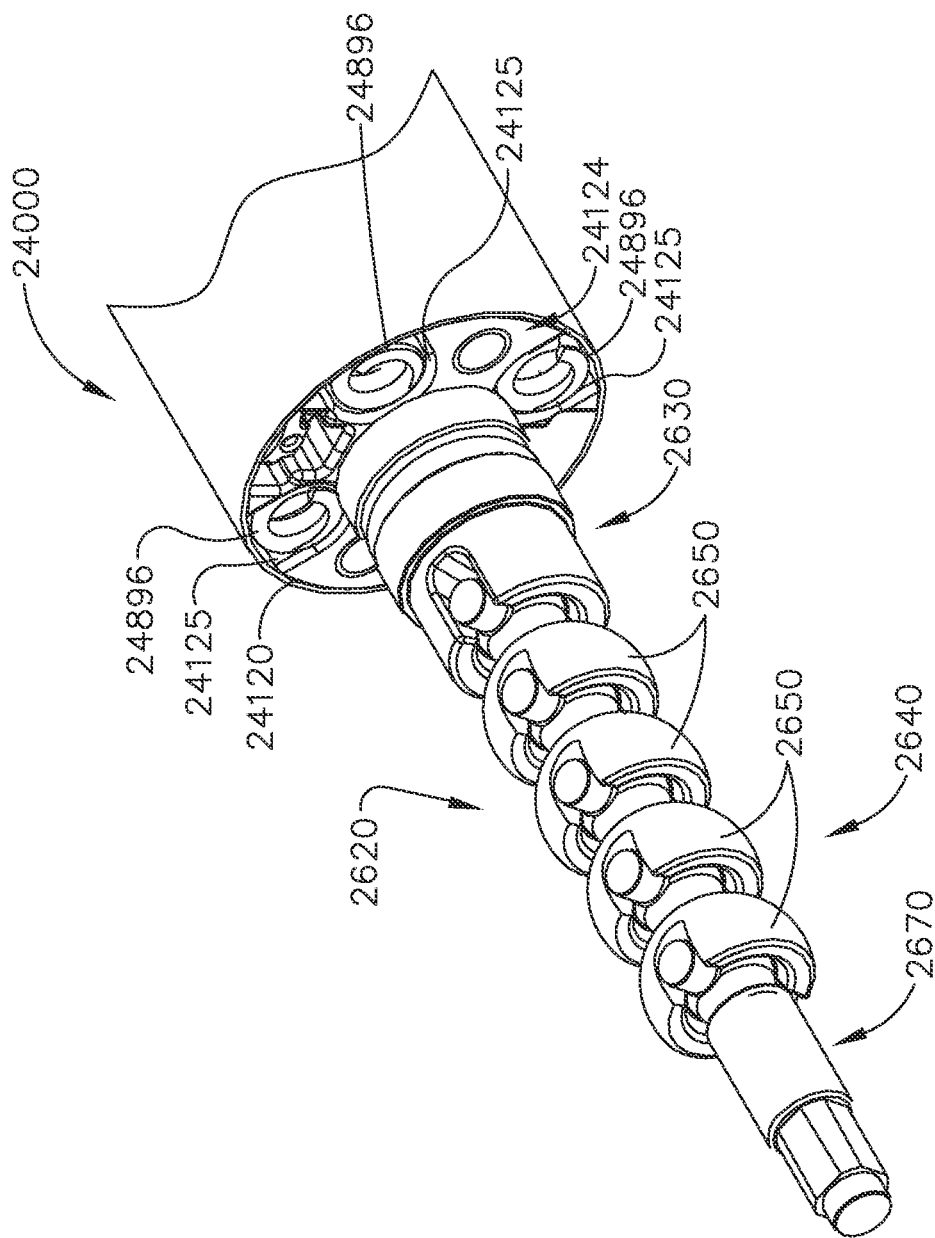
FIG. 64 is a perspective view of a CV drive shaft assembly and a portion of the elongate shaft assembly of the surgical instrument of FIG. 46.
Figure 65:
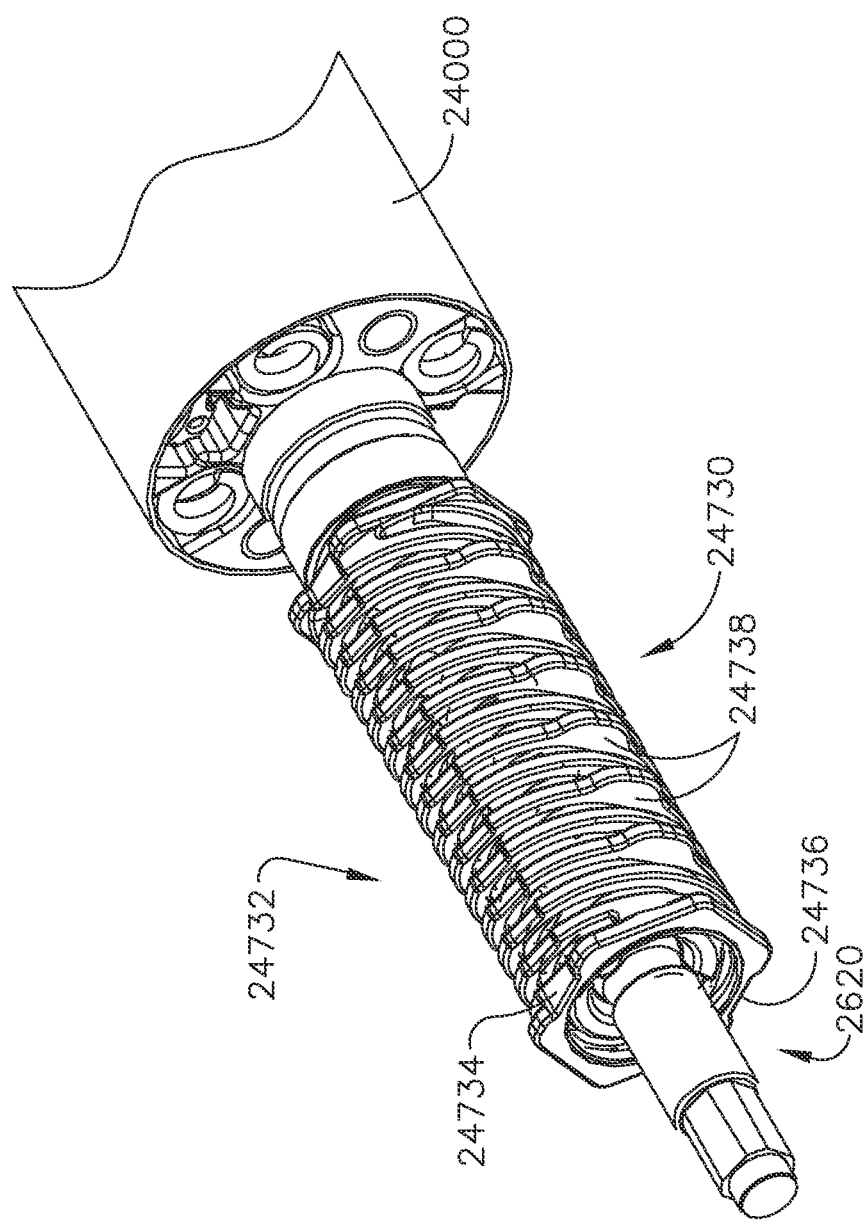
FIG. 65 is another perspective view of the CV drive shaft assembly and elongated shaft assembly of FIG. 64 with a drive cover embodiment installed around the CV drive shaft assembly.

As can be seen in FIGS. 49, 58, and 64, the surgical instrument 22010 employs a constant velocity (CV) drive shaft assembly 2620 that spans or extends axially through the articulation joint 24200. The operation and construction of the CV drive shaft assembly 2620 was described in detail above and will not be repeated here beyond what is necessary to understand the operation of the surgical instrument 22010. Briefly as described above, the CV drive shaft assembly 2620 comprises a proximal CV drive assembly 2630 and a distal CV drive shaft 2670. The proximal CV drive assembly 2630 comprises a proximal shaft segment 2632 that consists of an attachment shaft 2634 that is configured to be non-rotatably received within a similarly-shaped coupler cavity 2616 in the distal end 2614 of the proximal rotary drive shaft 2610. The proximal shaft segment 2632 operably interfaces with a series 2640 of movably coupled drive joints 2650. As can be seen in FIG. 58 as was also described previously, to ensure that the drive joints 2650 are engaged with each other, a proximal drive spring 2740 is employed to apply an axial biasing force to the series 2640 of drive joints 2650. For example, as can be seen in FIG. 58, proximal drive spring 2740 is positioned between the proximal mounting bushing 2734 and a support flange that is formed between the distal socket portion 2636 and a proximal barrel portion 2638 of the proximal shaft segment 2632. In one arrangement, the proximal drive spring 2740 may comprise an elastomeric O-ring received on the proximal barrel portion 2638 of the proximal shaft segment 2632. The proximal drive spring 2740 lightly biases the drive joints 2650 together to decrease any gaps that occur during articulation. This ensures that the drive joints 2650 transfer loads torsionally. It will be appreciated, however, that in at least one arrangement, the proximal drive spring 2740 does not apply a high enough axial load to cause firing loads to translate through the articulation joint 2200.

Figure 66:
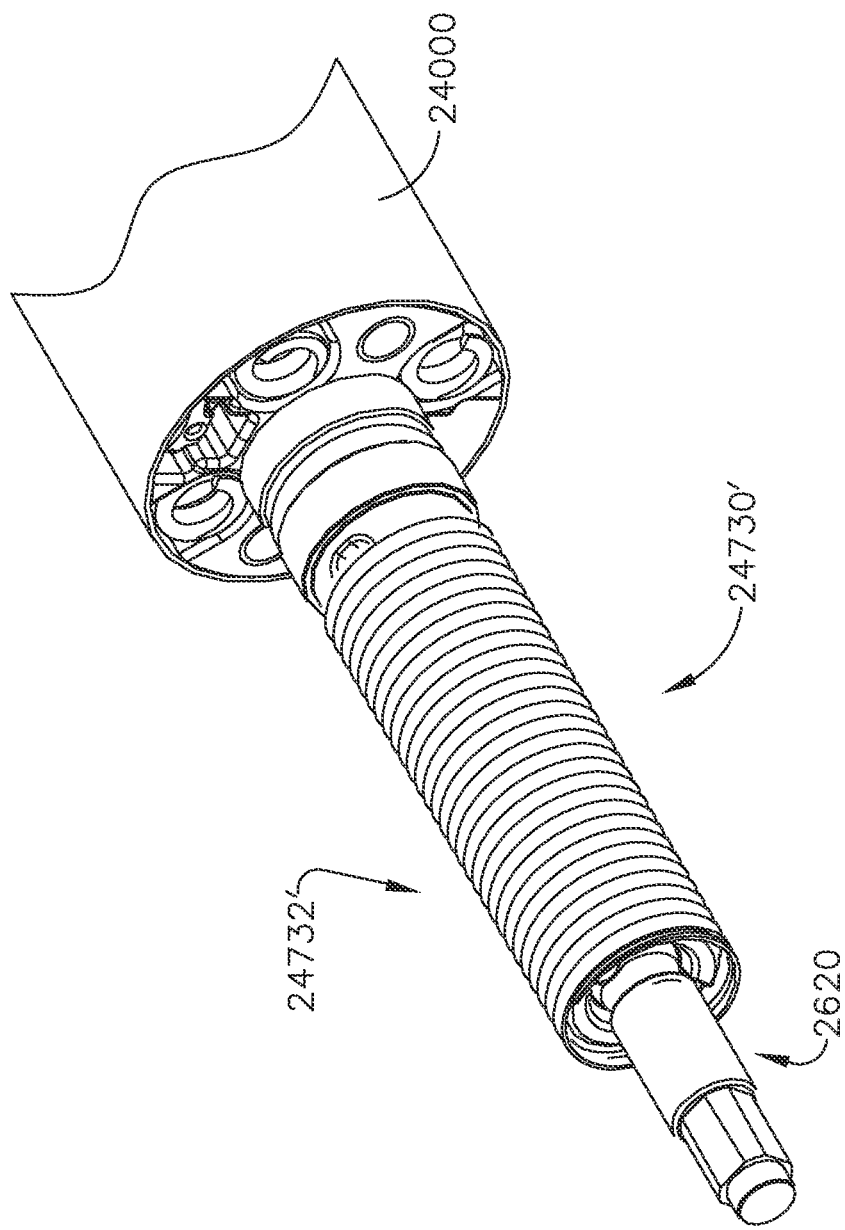
FIG. 66 is another perspective view of the CV drive shaft assembly and elongated shaft assembly of FIG. 64 with another drive cover embodiment installed around the CV drive shaft assembly.
Figure 67:
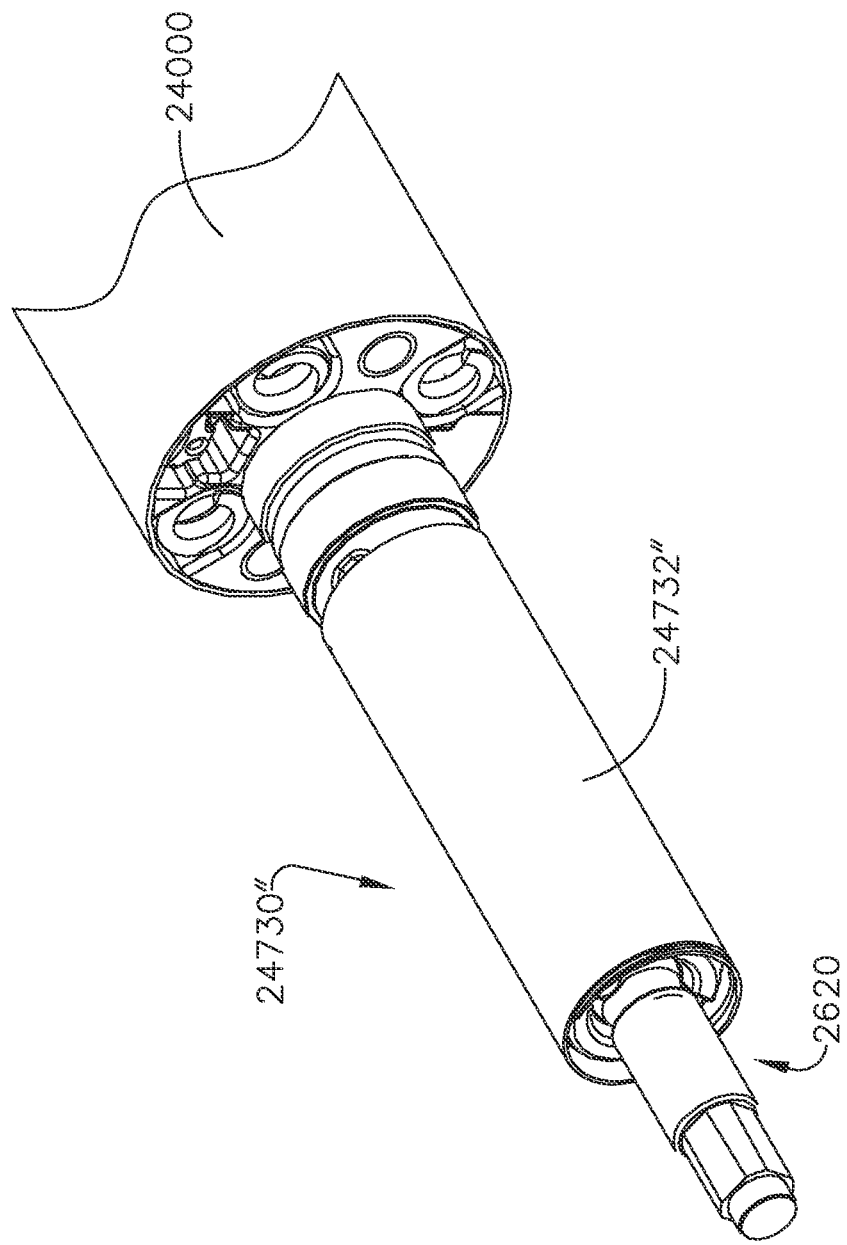
FIG. 67 is another perspective view of the CV drive shaft assembly and elongated shaft assembly of FIG. 64 with another drive cover embodiment installed around the CV drive shaft assembly.
Figure 68:
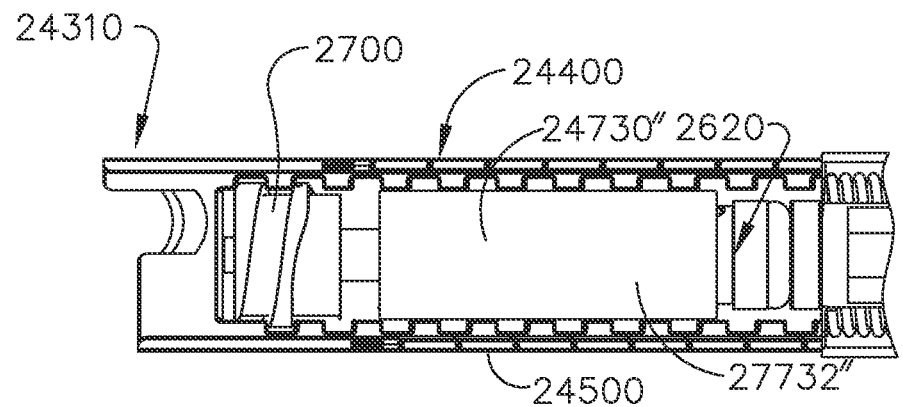
FIG. 68 is a side view of a portion of the firing system of the surgical instrument of FIG. 46 with the drive cover of FIG. 67 installed around the CV drive shaft assembly.
Figure 69:
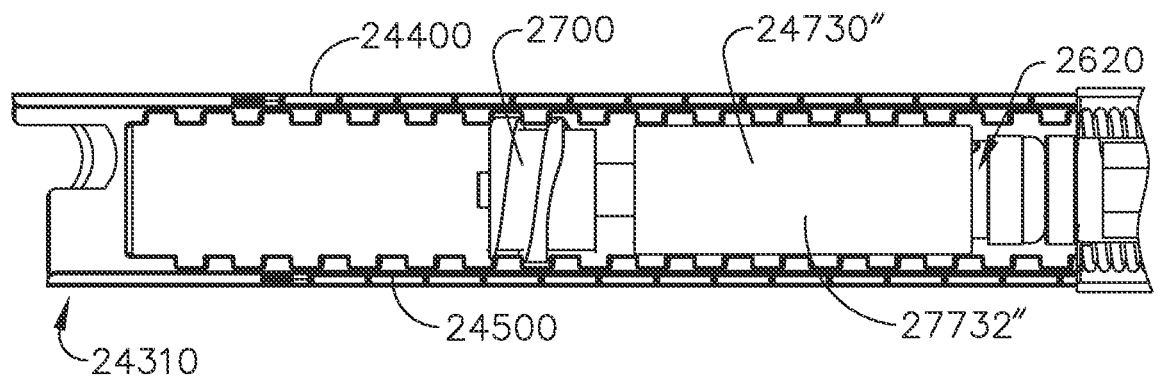
FIG. 69 is another side view of the portion of the firing system and drive cover of FIG. 68.
Figure 70:
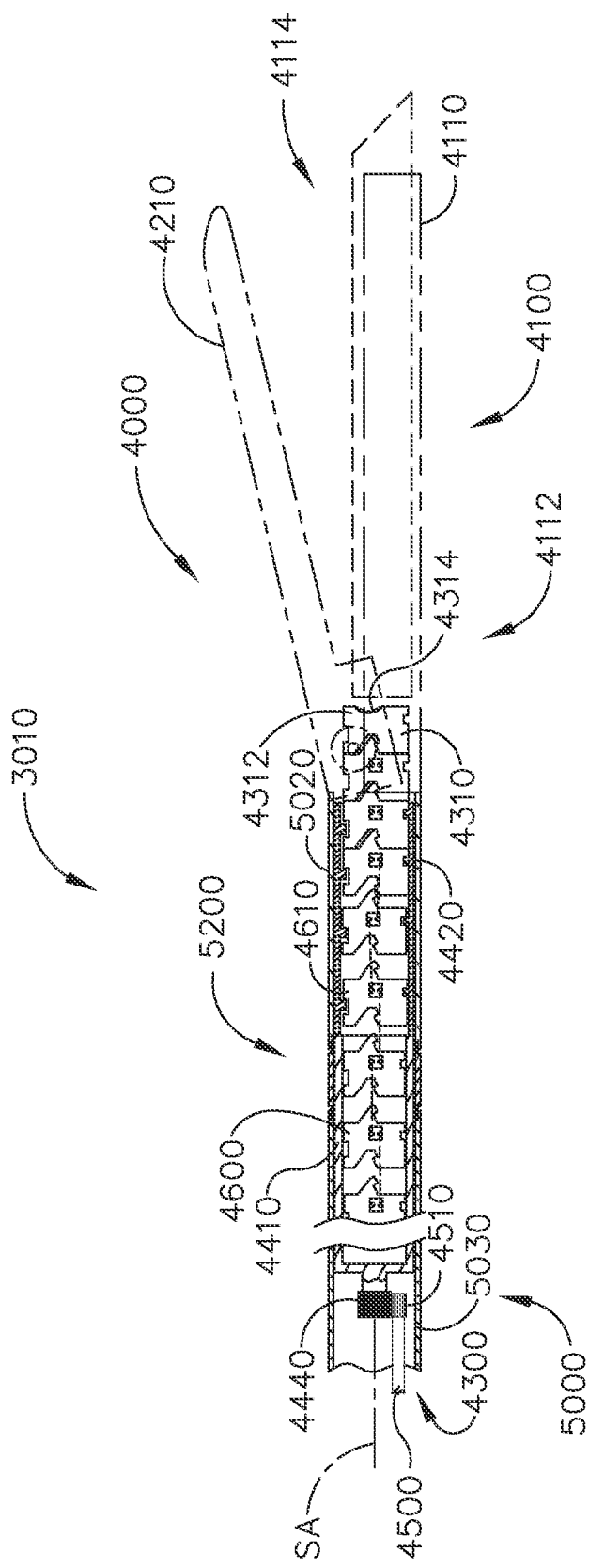
FIG. 70 is a cross-sectional view of a portion of another surgical instrument.
Figure 71:
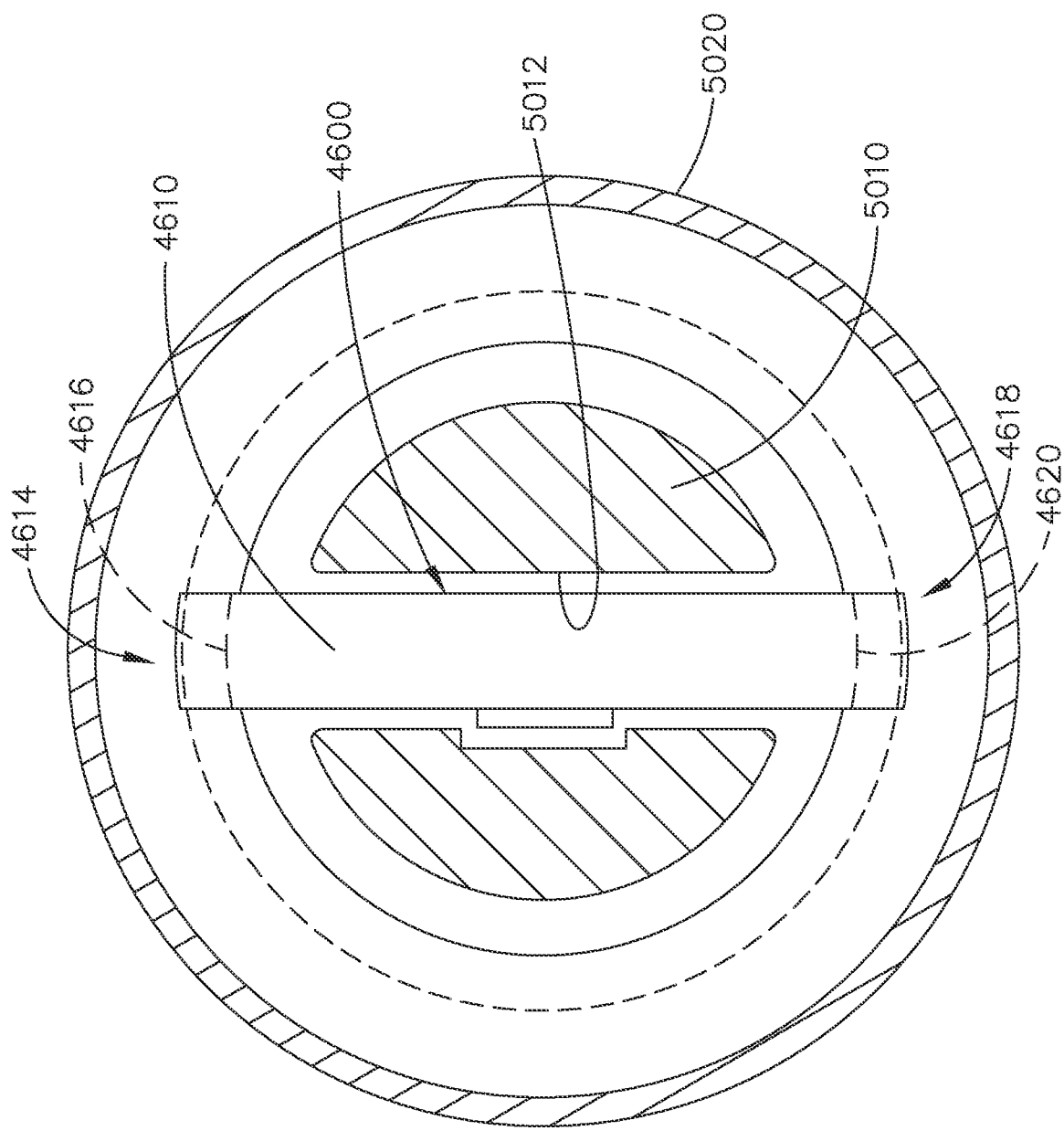
FIG. 71 is a cross-sectional end view of a surgical end effector of the surgical instrument of FIG. 70.

To further prevent the drive joints 2650 from buckling during articulation, the series 2640 of movably coupled drive joints 2650 extend through at least one low friction drive cover 24730 that extends through the central drive passage 24860 in each of the annular rib members 24810. In the arrangement depicted in FIGS. 63 and 65, the drive cover 24730 comprises an outer and inner cut hypotube 24732. Such hypotube 24732 may be fashioned from metal (e.g., stainless steel, etc.) and have multiple series of cuts or slits therein that may be made using laser cutter arrangements. In the illustrated arrangement, the hypotube 24732 may be fabricated with an upper relief passage 24734 that provides clearance for the upper flexible spine assembly 24400 to pass thereover during operation while the surgical end effector 23000 is in an articulated position and articulated positions. In addition, the hypotube 24732 may have a lower relief passage 24736 to provide similar clearance for the lower flexible spine assembly 24500. As can also be seen in FIG. 65, the hypotube 24732 may be shaped with diametrically opposed lateral tab portions 24738 to provide lateral stability during articulation. FIG. 66 illustrates an alternative drive cover 24730' that comprises an inner cut hypotube 24732'. FIGS. 58, 67, 68, and 69 illustrate an alternative drive cover 24730" that comprises flexible heat shrink tubing 24732" that is applied over the constant velocity (CV) drive shaft assembly 2620. In still other arrangements, the drive cover may comprise a coiled spring or coiled member as well.

Various embodiments of the present disclosure provide advantages over previous surgical endocutter configurations that are capable of articulation. For example, pushing a firing member forward in an articulating end effector generally requires a lot of force and that force must be balanced. For example, when firing the firing member at an angle of greater than sixty degrees, it becomes very difficult to push a beam through the articulation joint. The joint also experiences significant loads which may cause the articulation joint to de-articulate. By employing an upper flexible drive arrangement and a lower flexible drive arrangement that are each flexible through the articulation joint, but then become rigid when they are distal to the articulation joint can allow for a large degree of articulation (e.g., articulation angles over seventy degrees) while applying balanced loads to the firing member that are constrained to the firing member and not to the articulation joint. Stated another way, torsional loads are applied proximal to the articulation joint instead of longitudinal loads which could lead to de-articulation of the end effector. The torsional loads are converted to longitudinal loads at a position that is distal to the articulation joint. Thus, the rotary drive screw serves to actually convert torsional motion or loads to longitudinal loads that are applied to the firing member at a location that is distal to the articulation joint.

Further, by longitudinally breaking up the threaded drive arrangements, the threaded drive arrangements pass through the articulation joint while also effectively decreasing the length of the surgical end effector. For example, each single vertebra tooth is significantly shorter than multiple pitches rigidly connected. The vertebra can angle as they pass through the articulation joint. This flexible interconnection enables the rotary drive screw to be closely positioned to the articulation joint as compared to being significantly spaced therefrom if all of the pitches were rigidly connected.

FIGS. 70-73 illustrate another surgical end effector 4000 that may be employed with a surgical instrument 3010 that may be similar to the surgical instrument 10 in many aspects. The surgical end effector 4000 may be similar to the surgical end effector 1000 except for the differences discussed below. The surgical end effector 4000 is operably coupled to an elongate shaft assembly 5000. The elongate shaft assembly 5000 may be operably attached to a housing portion of the surgical instrument 3010. The housing may comprise a handle that is configured to be grasped, manipulated and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents.

In at least one form, the surgical end effector 4000 comprises a first jaw 4100 and a second jaw 4200. In the illustrated arrangement, the first jaw 4100 comprises an elongate channel 4110 that comprises a proximal end 4112 and a distal end 4114 and is configured to operably support a surgical staple cartridge 1300 therein. In the illustrated arrangement, the second jaw 4200 comprises an anvil 4210 that may be similar to anvil 1210 described above. In the illustrated arrangement, the elongate shaft assembly 5000 defines a shaft axis SA and comprises a proximal shaft segment that operably interfaces with a housing of the control portion (e.g., handheld unit, robotic tool driver, etc.) of the surgical instrument 3010. The elongate shaft assembly 5000 further comprises an articulation joint 5200 that is attached to a proximal shaft portion and the surgical end effector 4000.

The elongate shaft assembly 5000 may comprise a distal spine assembly 5010 that is attached to the proximal end 4112 of the elongate channel 4110 and the articulation joint 5200. See FIG. 70. The distal spine assembly 5010 is non-movably supported in a distal outer tube segment 5020 that operably interfaces with the surgical end effector 4000. The elongate shaft assembly 5000 further includes a proximal spine member (not shown) that operably interfaces with a proximal end of the articulation joint 5200 and may be attached to or otherwise operably interface with the housing of the surgical instrument 3010. A proximal outer tube segment 5030 extends from the articulation joint 5200 back to the housing to operably interface therewith.

The surgical instrument 3010 employs a firing drive system 4300 that comprises a firing member 4310 that includes a vertically-extending firing member body 4312 that comprises a top firing member feature and a bottom firing member feature. A tissue cutting blade 4314 is attached to or formed in the vertically-extending firing member body 4312. The firing drive system 4300 comprises a rotary drive nut 4400 that is configured to rotatably drive a series 4600 of drive components 4610 that operably interface with the firing member 4310. The rotary drive nut 4400 comprises a flexible proximal segment 4410 that spans the articulation joint 5200 and a threaded distal segment 4420 that is distal to the articulation joint 5200. The threaded distal segment 4420 comprises a series of variable pitched threads 4430, with coarse spacing 4432 at the proximal end, and tighter spacing 4434 at the distal or exit end. See FIG. 72. The threaded rotary drive nut 4400 comprises a proximal drive gear 4440 that meshingly interfaces with a distal drive gear 4510 that is attached to a rotary drive shaft 4500. See FIG. 70. The rotary drive shaft 4500 may interface with a gearbox/motor arrangement supported in the housing of the surgical instrument 3010. Rotation of the rotary drive shaft 4500 causes the drive nut 4400 to rotate about the shaft axis SA.

The rotary drive nut 4400 comprises a proximal segment 4410 and a threaded distal segment 4420. The threaded distal segment 4420 is located distal to the articulation joint 5200 and is configured to threadably engage a series 4600 of drive components 4610 that are loosely linked together by flexible tethers 4640. In at least one arrangement, for example, each drive component 4610 comprises a vertically extending plate member 4612 that each includes a top end 4614 and a bottom end 4618. The top end 4614 includes a top thread segment 4616 and the bottom end 4418 includes a bottom thread segment 4620. The top thread segment 4616 and the bottom thread segment 4620 are configured to threadably engage the threads 4430 of the rotary drive nut 4400. The series 4600 of drive components 4610 is configured to flexibly pass through the articulation joint 5200 and into a vertical passage 5012 in the distal spine assembly 5010. Rotation of the rotary drive nut 4400 in a first rotary direction causes the series 4600 of drive components 4610 to move axially in the distal direction and rotation of the rotary drive nut 4400 in a second rotary direction will cause the series 4600 of drive components 4610 to move axially in the proximal direction.

Figure 72:
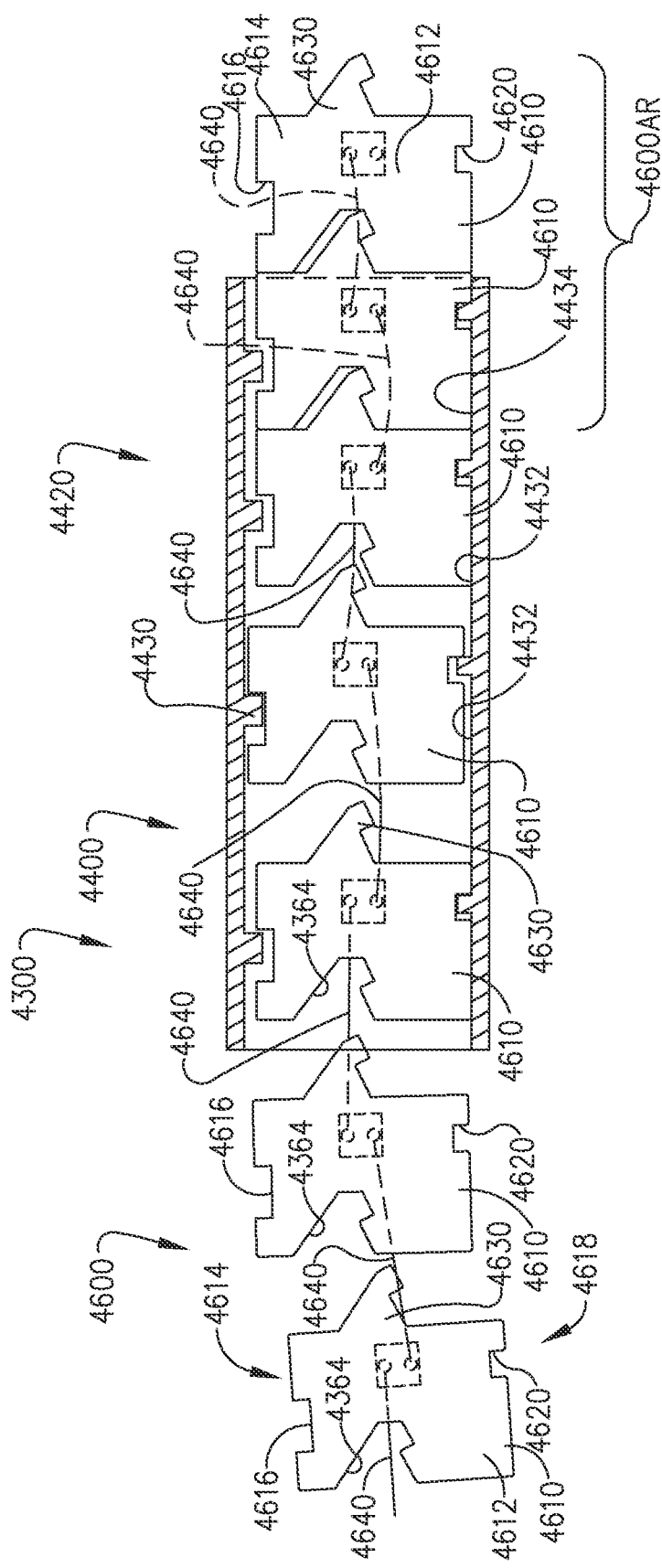
FIG. 72 is a cross-sectional side view of a rotary drive nut in engagement with drive components of the surgical instrument of FIG. 70.

Turning to FIG. 72, in at least one arrangement, each drive component 4610 further comprises a distally protruding latch feature 4630. Each latch feature 4360 is configured to be releasably received in latching engagement within a latch cavity 4364 that is formed in the adjacent drive component 4610 that is immediately distal thereto. When the drive components 4610 are latched together, they form an axially rigid series 4600AR of drive components for applying an axial drive motion to the firing member 5310 to drive the firing member 5310 through the surgical end effector 4000 from a starting to an ending position and then from the ending position back to the starting position. As can be seen in FIG. 72, as the drive components 4610 enter the threaded distal segment 4420 of the rotary drive nut 4400, they are loosely linked together. As the drive components 4610 threadably engage the finely pitched threads 4430 in the threaded distal segment 4420 of the rotary drive nut 4400, the latch features 4630 are latchingly received within the corresponding latch cavity 4364 in the distally adjacent drive component 4610 to form the axially rigid series 4600AR of drive components 4610. In one arrangement, a distal-most drive component 4610 may be configured to latchingly engage the firing member 4310 in a similar manner or in alternative arrangements, the distal-most drive component may be non-removably attached to the firing member 4310.

In the illustrated example, the drive components 4610 in the series 4600 of drive components are flexibly linked together such that they can move relative to each other to accommodate the articulation joint and without the need for reinforcing and support plates that are commonly required when pushing a firing beam through an articulated joint. As the series of drive components 4610 enters and is drivingly engaged by the threaded distal segment 4420 which is distal to the articulation joint, the drive components 4610 form the axially rigid series of drive components for driving the firing member 4310 through the surgical end effector 4000. The anvil 4210 may be pivoted into an open position by a spring or other arrangement in the various manners disclosed herein and then closed by the firing member 4310 as the firing member 4310 is driven distally from a starting position to an ending position in the various manners discussed herein. Other jaw control arrangements may also be employed to control the opening and closing of the jaws.

FIGS. 73-76 illustrate another surgical end effector 6000 that employs a drive system 6300 that comprises a series 6600 of flexibly linked drive components 6610 that can be used to traverse an articulation joint 6200 and rigidly advance a firing member 6130 through the surgical end effector 6000. The surgical end effector 6000 may comprise a channel 6010 that is configured to operably support a surgical staple cartridge (not shown) therein. An anvil 6020 may be pivotally coupled to the channel 6010 and is movable between an open position and a closed position by the firing member 6130 or other closure system arrangement. The anvil 6020 may be moved to an open position by a spring or other arrangement in the various manners disclosed herein.

Figure 74:
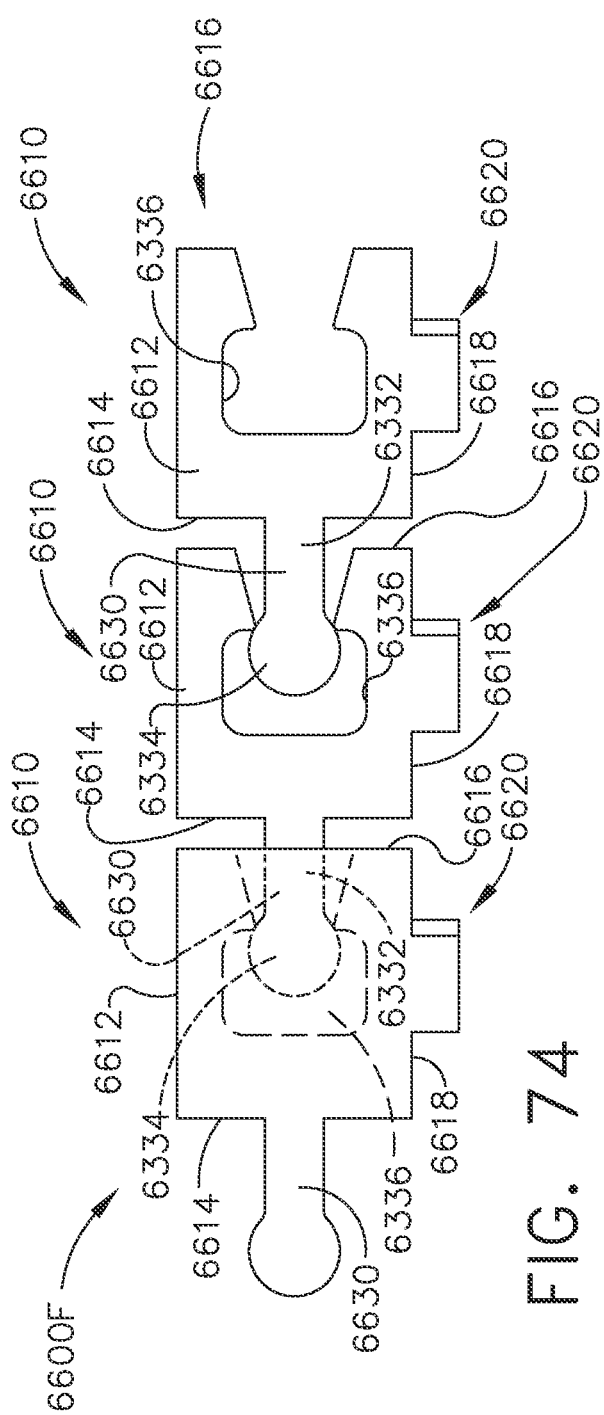
FIG. 74 is a side view of a portion of the series of flexibly linked drive components of the surgical instrument of FIG. 73 prior to engagement with a rotary drive gear in the surgical end effector.
Figure 75:
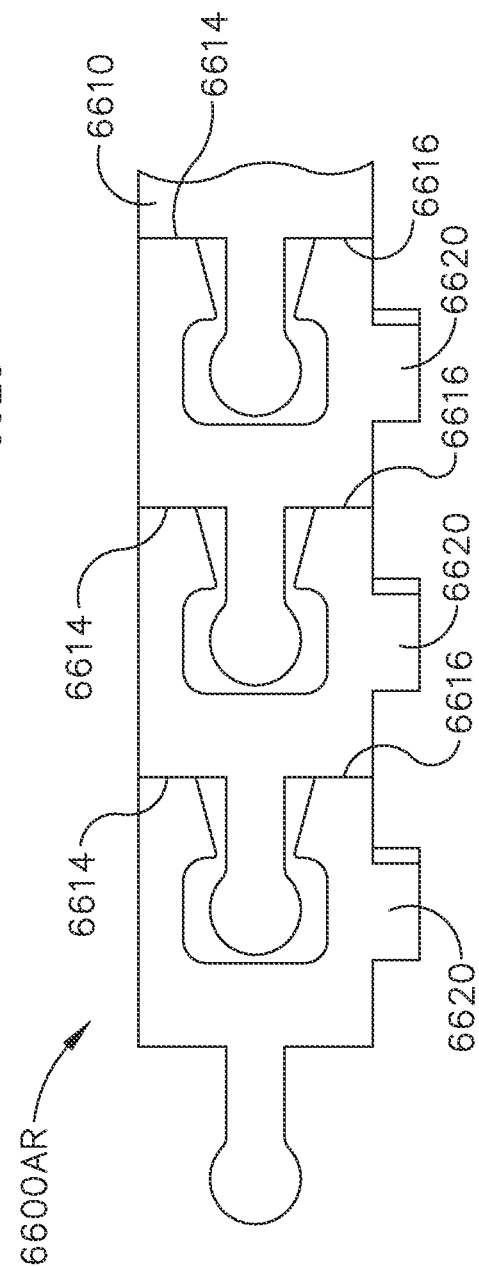
FIG. 75 is another side view of the portion of drive components of FIG. 74 after being engaged with the rotary drive gear to form a rigid series of drive components.
Figure 76:
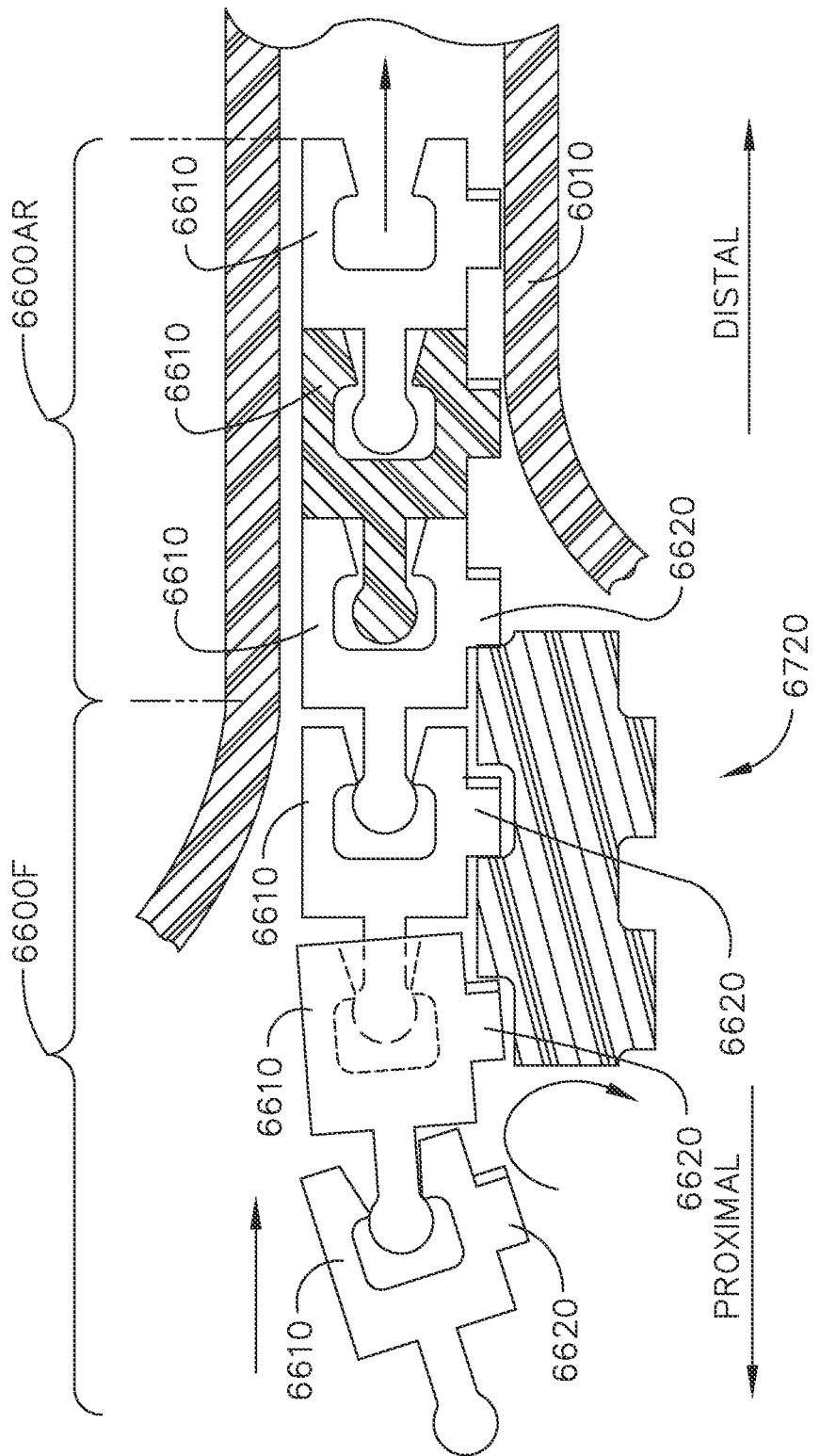
FIG. 76 is a partial cross-sectional view of the rotary drive system of the surgical instrument of FIG. 74 with components in the series of flexible drive components in driving engagement with the rotary drive gear thereof.

Turning to FIG. 74, in at least one arrangement, each drive component 6610 comprises a drive component body 6612 that has a proximal face 6614, a distal face 6616, and thread segment 6620 that is formed on a bottom surface 6618. Each drive component 6610 further comprises a proximally protruding latch feature 6630. Each latch feature 6630 comprises a neck feature 6632 that has a spherical latch head 6634 formed on an end thereof. The latch feature 6630 is configured to be movably received within a latch cavity 6336 that is formed in the adjacent drive component 6610 that is immediately distal thereto. To facilitate movable attachment of the drive components 6610 in movable serial arrangement, the spherical latch head 6634 is inserted through a tapered passage 6338 in the drive component body 6612 and into the latch cavity 6636. The spherical latch head 6634 is sized and shaped relative to the latch cavity 6636 to permit relative movement between the drive components 6610 when arranged as shown in FIG. 74. However, when the drive components are axially aligned such that the distal face 6616 of one drive component 6610 is in abutting engagement with the proximal face 6614 of the drive component that is immediately distal thereto, the drive components 6610 form an axially rigid series 6600AR of drive components that can drive the firing member 6130 through the surgical end effector 6000.

Figure 73:
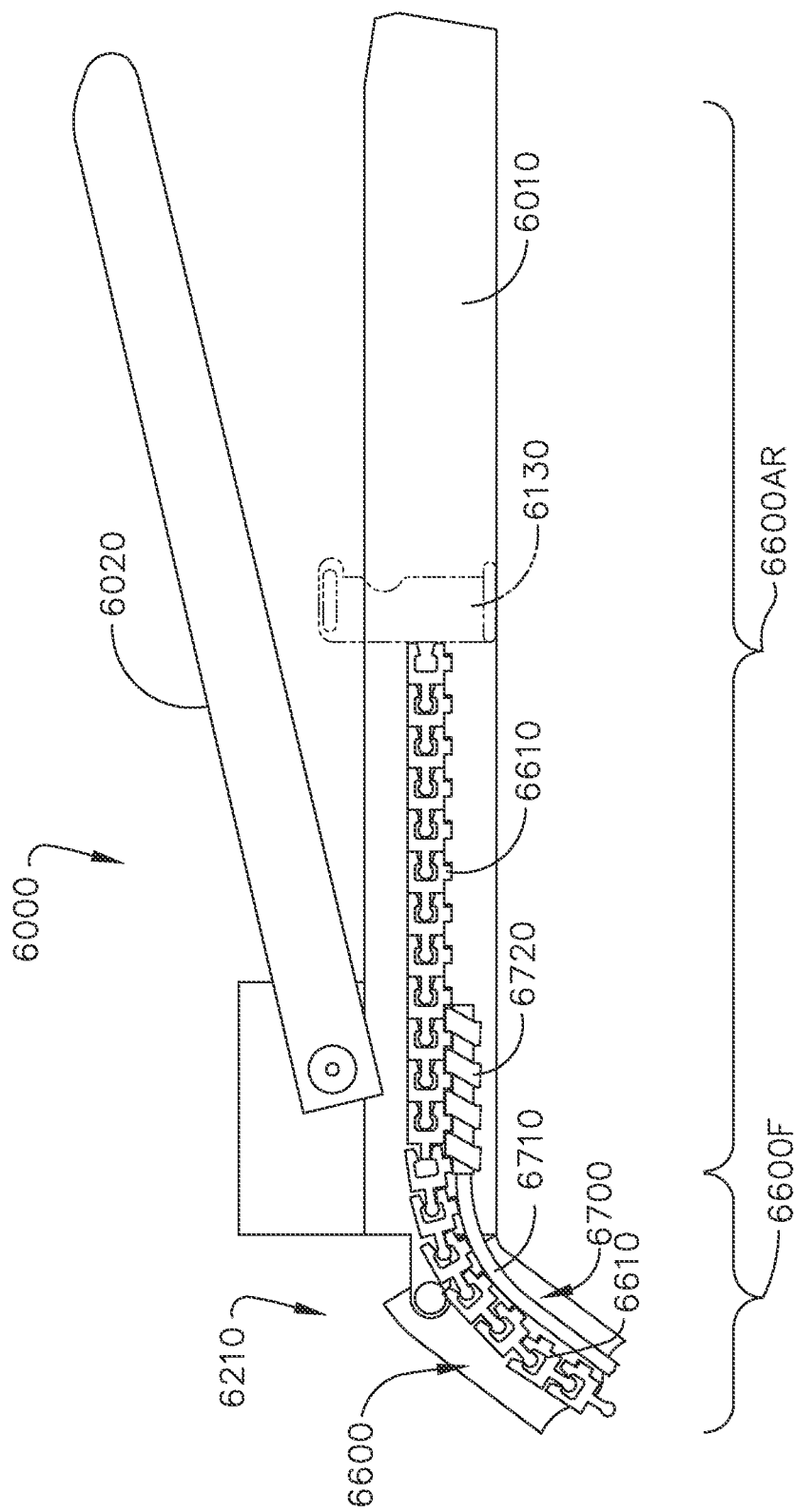
FIG. 73 is a partial side view of a surgical end effector of another surgical instrument that employs a series of flexibly linked drive components to drive a firing member through the surgical end effector.

As can be seen in FIG. 73, a flexible rotary drive system 6700 is employed to drive the series of 6600 drive components 6610. In one arrangement, the flexible rotary drive system 6700 comprises a flexible rotary drive shaft 6710 that can pass through the articulation joint 6210 and includes a rotary drive gear 6720 that is configured to threadably engage the thread segments 6620 on each drive component 6610. The flexible rotary drive shaft 6710 may be rotated by a motor/gear arrangement supported in a housing of a surgical instrument. The portion 6600F of the series 6600 of drive components 6610 that is proximal to the rotary drive gear 6720, remains flexibly linked or "floppy". As the drive components 6610 are threadably engaged by the rotary drive gear 6720 they are driven through a passage in the channel 6010 that causes the drive components to form the axially rigid series 6600AR for driving the firing member 6130 through the surgical end effector 6000.

Figure 77:
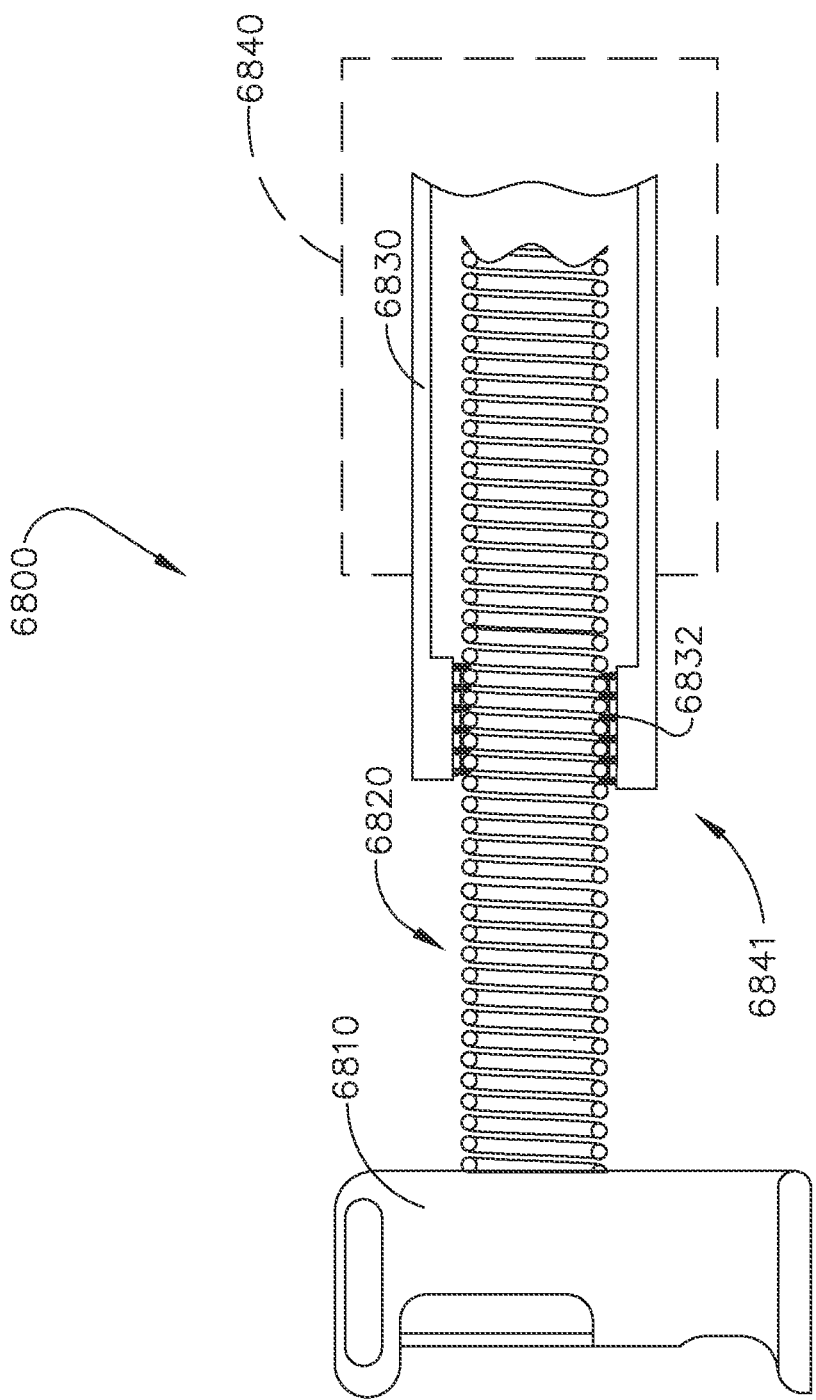
FIG. 77 is a side view of a portion of rotary firing system and firing member of another surgical instrument.

Torsional loads that are applied to firing system components as they traverse the articulation joint are less likely to de-articulate the articulation joint than axial loads. Various embodiments disclosed herein transfer torsional loads to longitudinal loads in a location that is distal of the articulation joint. Because the longitudinal loads are contained in the end effector, de-articulation is prevented. FIG. 77 illustrates one firing system 6800 example that can provide such advantages. The firing system 6800 comprises a firing member 6810 that is configured to be operably supported in a surgical end effector in the various manners described herein. A flexible spring-like driven member 6820 is attached to the firing member 6810. Such flexible, spring-like driven member 6820 can span an articulation joint area 6840 that can attain relatively large ranges of articulation. The flexible, spring-like driven member 6820 is configured to be driven axially by a flexible, spring-like torsion drive member 6830 that is rotatably supported to span the articulation joint area 6840. The flexible, spring-like torsion drive member 6830 includes a threaded insert 6832 that is configured to threadably engage the spring-like driven member 6820 at a location 6841 that is distal to the articulation joint area 6840. The flexible, spring-like torsion drive member 6830 may be rotated by a motor/gear arrangement supported in a housing of a surgical instrument. As the flexible, spring-like torsion drive member 6830 rotates in a first direction, the flexible, spring-like driven member 6820 translates longitudinally to drive the firing member 6810. Rotation of the flexible torsion drive member 6830 in a second direction will cause the flexible, spring-like driven member to move proximally.

Figure 78:
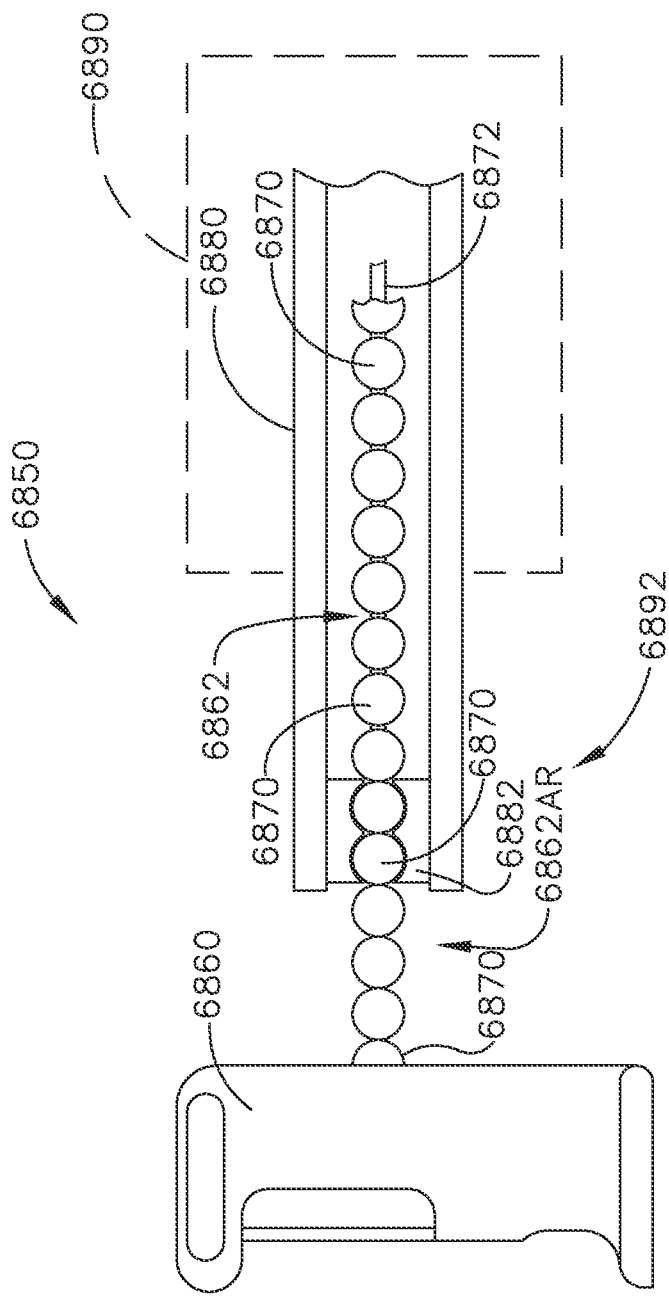
FIG. 78 is a side view of a portion of a rotary firing system and firing member of another surgical instrument.

FIG. 78 illustrates another firing system 6850 that comprises a firing member 6860 that is configured to be operably supported in a surgical end effector in the various manners described herein. The firing member 6860 is driven by firing member drive assembly 6861 which comprises a series 6862 of spherical ball members 6870 that are coupled together by a flexible cable 6872. Such series 6862 of flexible spherical ball members 6870 can span an articulation joint area 6840 that can attain relatively large ranges of articulation. The series 6862 of flexible spherical ball members 6870 is configured to be driven axially by a flexible torsion drive member 6880 that is rotatably supported to span an articulation joint area 6890. The flexible torsion drive member 6880 includes an insert 6882 that is configured to drivingly engage the spherical ball members 6870 at a location 6892 that is distal to the articulation joint area 6890. The flexible torsion drive member 6880 may be rotated by a motor/gear arrangement supported in a housing of a surgical instrument. As the flexible torsion drive member 6880 rotates in a first direction, the spherical ball members 6870 are driven distally into contact with each other to form an axially rigid series 6862AR that translates longitudinally to drive the firing member 6860 distally. Rotation of the flexible torsion drive member 6880 in a second direction will cause the series of spherical ball members 6870 to move proximally.

FIG. 79 illustrates another firing system 6950 that comprises a firing member 6960 that is configured to be operably supported in a surgical end effector in the various manners described herein. A laser cut, hypotube driven member 6970 is attached to the firing member 6960. Such flexible driven member 6970 can span an articulation joint area 6940 that can attain relatively large ranges of articulation. The flexible driven member 6970 is configured to be driven axially by a flexible torsion drive member 6980 that is rotatably supported to span the articulation joint area 6940. The flexible torsion drive member 6980 includes a threaded insert 6982 that is configured to threadably engage the laser cuts 6972 on the flexible driven member 6970 at a location 6942 that is distal to the articulation joint area 6940. The flexible torsion drive member 6980 may be rotated by a motor/gear arrangement supported in a housing of a surgical instrument. As the flexible torsion drive member 6980 rotates in a first direction, the flexible driven member 6970 translates longitudinally to drive the firing member 6960. Rotation of the flexible torsion drive member 6980 in a second direction will cause the flexible driven member 6970 to move proximally.

Figure 82:
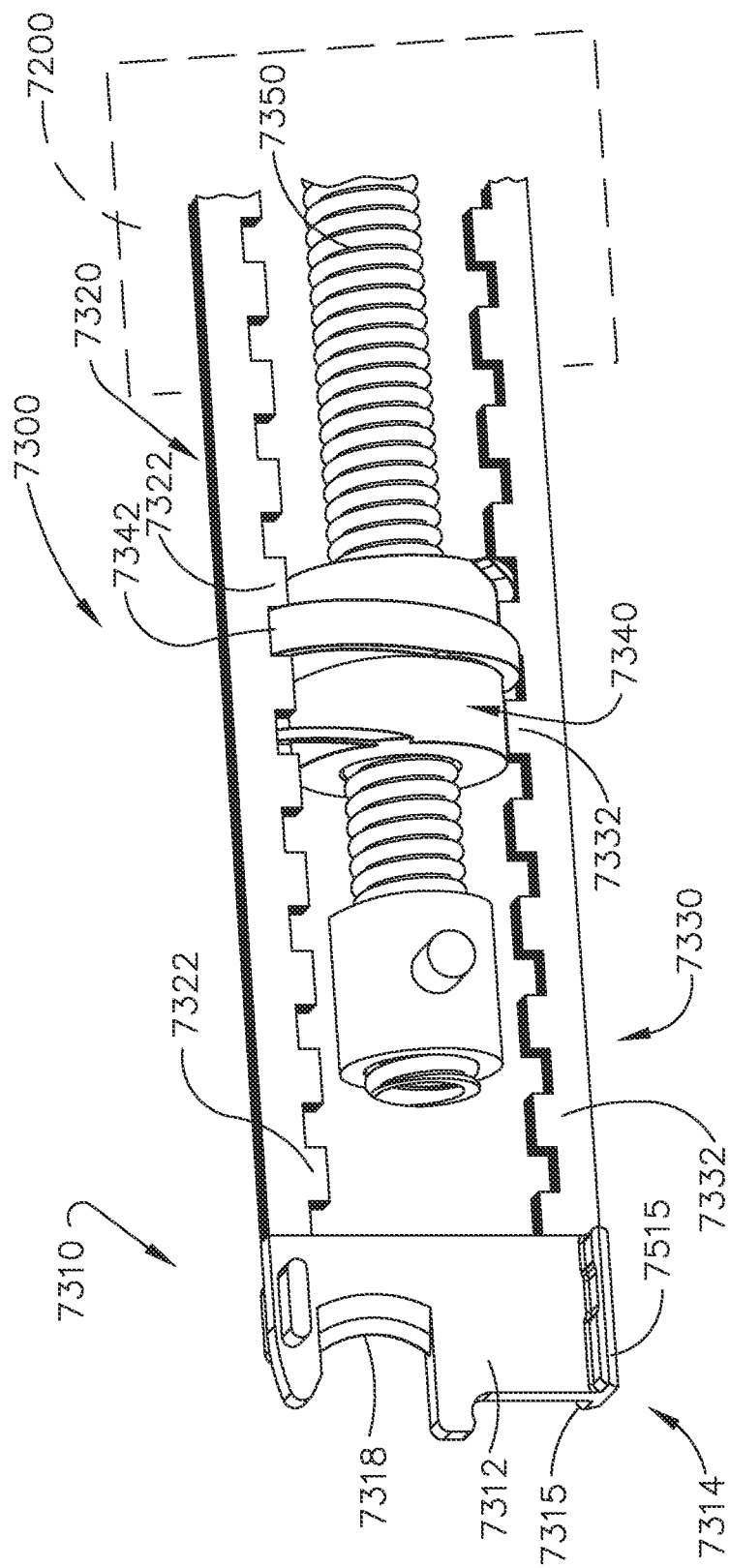
FIG. 82 is a perspective view of portions of the rotary driven firing system of the surgical instrument of FIG. 80.
Figure 83:
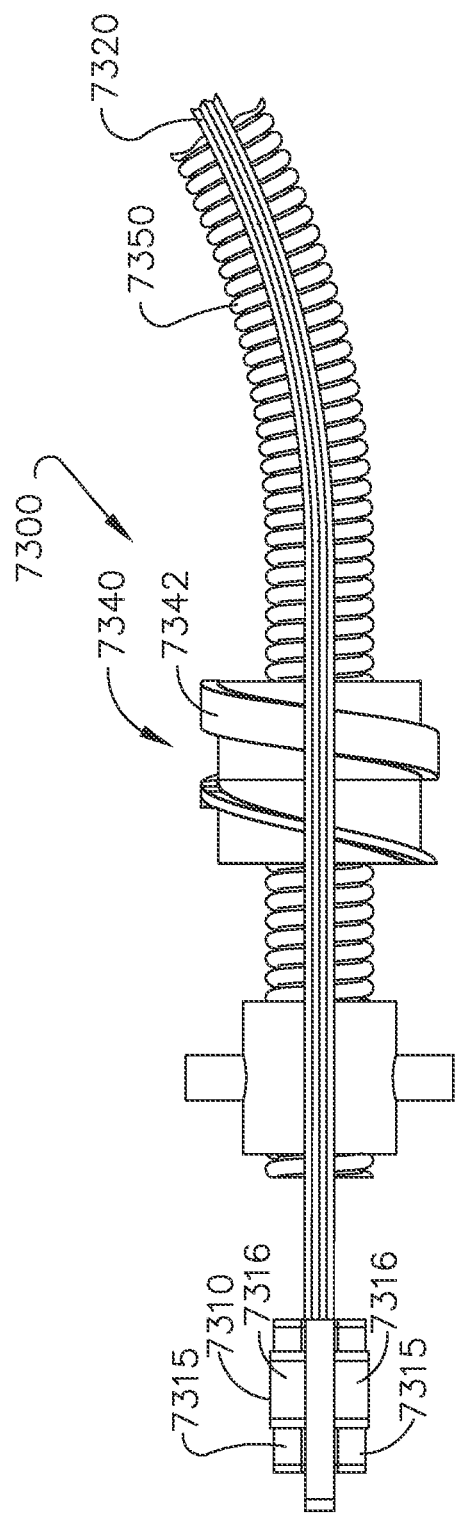
FIG. 83 is a top view of a portion of the rotary driven firing system depicted in FIG. 82.
Figure 84:
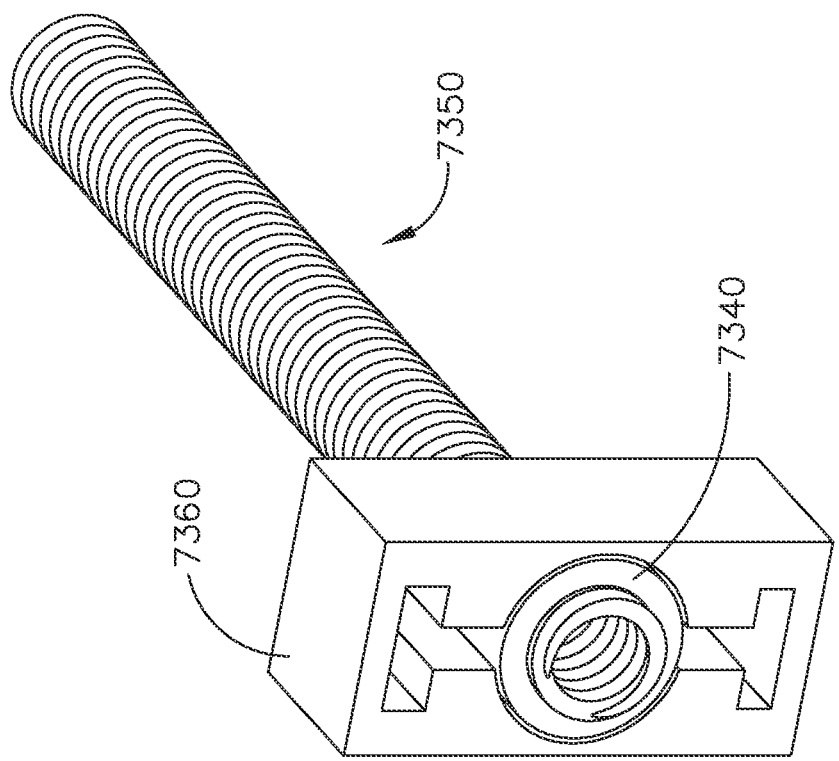
FIG. 84 is a perspective view of a guide member and rotary drive shaft of the rotary driven firing system of FIG. 83.

Pushing a firing beam forward in an articulating end effector generally requires a lot of force and such force needs to be balanced. For example, it is generally difficult to push a firing beam through an articulation joint that has been articulated to angles of greater than sixty degrees. As the firing beam traverses through the articulation joint, the firing beam can apply significant loads onto the articulation joint components which can cause the articulation joint to de-articulate. FIGS. 80-84 illustrate a firing drive system 7300 that comprises a flexible upper drive band 7320 and a flexible lower drive band 7330 that are attached to a firing member 7310 that is configured to move within a surgical end effector 7000 between a starting and ending position. As can be seen in FIGS. 80-82, the flexible upper drive band 7320 comprises a plurality of spaced upper drive teeth 7322 that are configured to threadably engage a helical thread 7342 on a rotary drive nut 7340. Similarly, the flexible lower drive band 7330 comprises a plurality of spaced lower drive teeth 7332 that are configured to threadably engage the helical thread 7342 on the rotary drive nut 7340. In at least one arrangement, the flexible upper drive band 7320 and the flexible lower drive band 7330 are formed from a metal material and are welded to or otherwise attached to the firing member 7310. Such arrangement serves to balance the firing loads that are applied to the firing member 7310.

The rotary drive nut 7340 is received on a flexible rotary drive shaft 7350 that is centrally disposed between the flexible upper drive band 7320 and the flexible lower drive band 7330 and traverses through the articulation joint area generally designated as 7200. The flexible rotary drive shaft 7350 may be rotated by a motor/gear arrangement supported in a housing of a surgical instrument. As the flexible rotary drive shaft 7350 rotates in a first direction, the flexible upper drive band 7320 and the flexible lower drive band 7330 will drive the firing member 7310 distally. Rotation of the flexible rotary drive shaft 7350 in a second direction will cause the flexible upper drive band 7320 and the flexible lower drive band 7330 to pull the firing member 7310 proximally. In at least one arrangement, flexible upper drive band 7320 and the flexible lower drive band 7330 pass through a guide member 7360 that surrounds the rotary drive nut 7340 to prevent the flexible upper drive band 7320 and the flexible lower drive band 7330 from bypassing the rotary drive nut 7340 during actuation of the flexible rotary drive shaft 7350. See FIG. 84.

In the illustrated arrangement, the firing member 7310 is configured to move through the surgical end effector 7000 that comprises a first jaw 7010 and a second jaw 7030 that is configured to move relative to the first jaw 7010. In one embodiment, the first jaw 7010 comprises an elongate channel 7012 that is configured to operably support a surgical staple cartridge therein. See FIGS. 80 and 81. The second jaw 7030 comprises an anvil 7032 that is pivotally supported on the elongate channel 7012 and is movable between an open position and a closed position relative to the elongate channel 7012. As can be seen in FIG. 82, in at least one form, the firing member 7310 comprises a shape that is commonly referred to as an "E-beam". The firing member 7310 comprises a vertically extending firing member body 7312 that has a lower foot feature 7314 that comprises two laterally extending tabs 7315 that are configured to be slidably engage the elongate channel 7012 as the firing member is driven axially therein. In addition, a pair of upper tabs 7316 protrude from the upper portion of the firing member body 7312 to engage the anvil 7032 as the firing member 7310 is driven distally through the closed anvil 7032. During the firing stroke, the tabs 7315 and 7316 may serve to space the anvil 7032 relative to the surgical staple cartridge supported in the elongate channel 7012. The firing member body 7312 also comprises a tissue cutting feature 7318. The tabs 7316 may also serve to apply a closing motion to the anvil 7032 as the firing member 7310 is moved distally from the starting position.

In the illustrated example, the firing drive system 7300 may also be employed to apply opening and closing motions to the anvil 7032. As can be seen in FIGS. 80-83, a closure nut 7370 is threadably received on the flexible rotary drive shaft 7350. The closure nut 7370 comprises a cam pin 7372 that extends laterally from each side of the closure nut 7370 to be received in corresponding cam slots 7036 in an anvil mounting portion 7034 of the anvil 7032. See FIGS. 80 and 81. Such cam pins 7372 prevent the closure nut 7370 from rotating with the flexible rotary drive shaft 7350 such that rotation of the flexible rotary drive shaft 7350 causes the closure nut 7370 to move axially. Thus, rotation of the flexible rotary drive shaft 7350 in a first direction causes the closure nut 7370 to move distally and cam the anvil 7032 from the open position to the closed position. Rotation of the flexible rotary drive shaft 7350 in the second rotary direction will cause the closure nut 7370 to move proximally and cam the anvil 7032 back to the open position. Thus, alternating the rotation of the flexible rotary drive shaft 7350 may allow the surgeon to quickly open and close the anvil 7032 for grasping purposes, for example.

Figure 85:
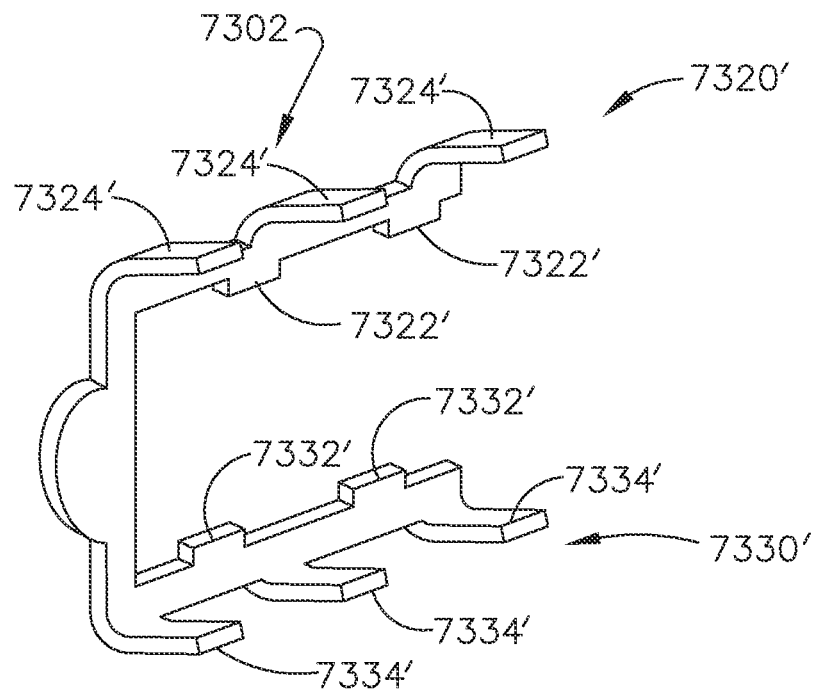
FIG. 85 is a perspective view of a portion of another flexible firing drive assembly that may be employed with the firing drive system of FIG. 83.
Figure 86:
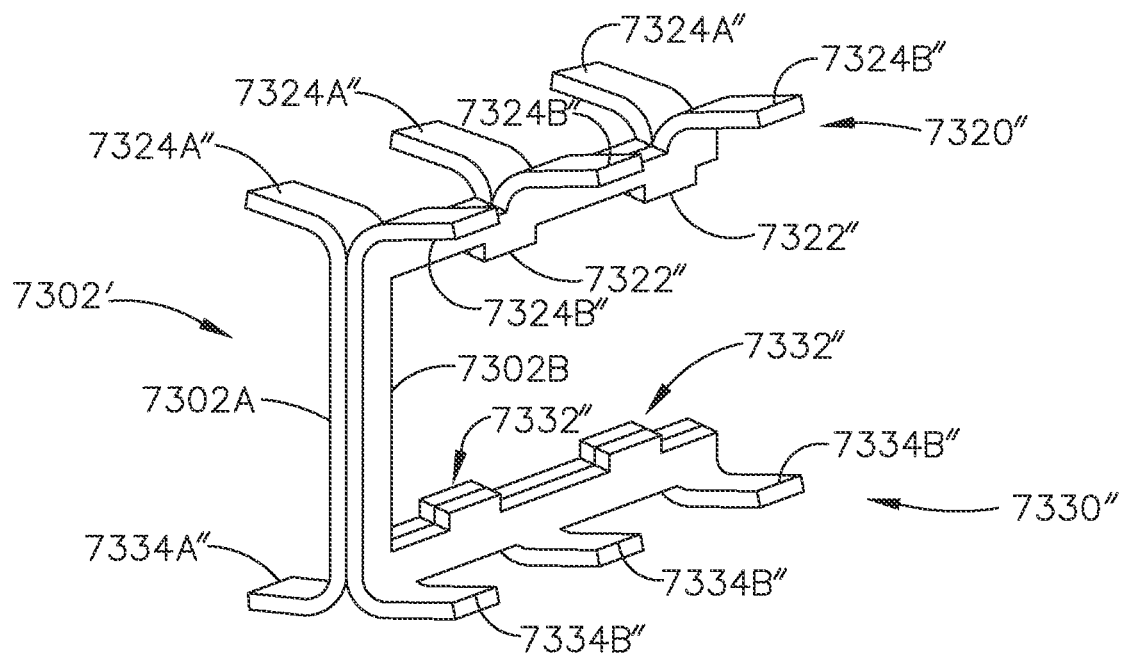
FIG. 86 is another perspective view of a portion of another flexible firing drive assembly embodiment that may be employed with the firing drive system of FIG. 83.

FIG. 85 illustrates an alternative firing drive assembly 7302 that comprises the flexible upper drive band 7320' that has upper drive teeth 7322' and a flexible lower drive band 7330' that has lower drive teeth 7332' that is formed out of one piece of material such as metal. The flexible upper drive band 7320' also includes upper strength tabs 7324' that are provided to pass through the anvil 7032 similar to the upper tabs 7316 on the firing member 7310 as well as lower strength tabs 7334 that are provided to pass through the channel 7012 similar to the tabs 7315 on the firing member 7310. FIG. 86 illustrates an alternative firing drive assembly 7302' that is fabricated from two band assemblies 7302A and 7302B that are laminated together to form the flexible upper drive band 7320" that has the upper drive teeth 7322" and a flexible lower drive band 7330" that has the lower drive teeth 7332". Each band assembly 7302A, 7302B also comprise upper strength tabs 7324A", 7324B" and lower strength tabs 7334A", 7334B" that are provided to pass through the anvil 7032 and the elongate channel 7012, respectively.

The firing drive system 7300 serves to apply a uniform drive motion to the firing member 7310 and can accommodate articulation angles that may be greater than seventy degrees, for example. In addition, because the rotary drive nut 7340 engages the flexible upper drive band 7320 and flexible lower drive band 7330 at a location that is distal to the articulation joint area 7200, the linear firing loads are confined to the end effector and do not go through the articulation joint.

Figure 87:
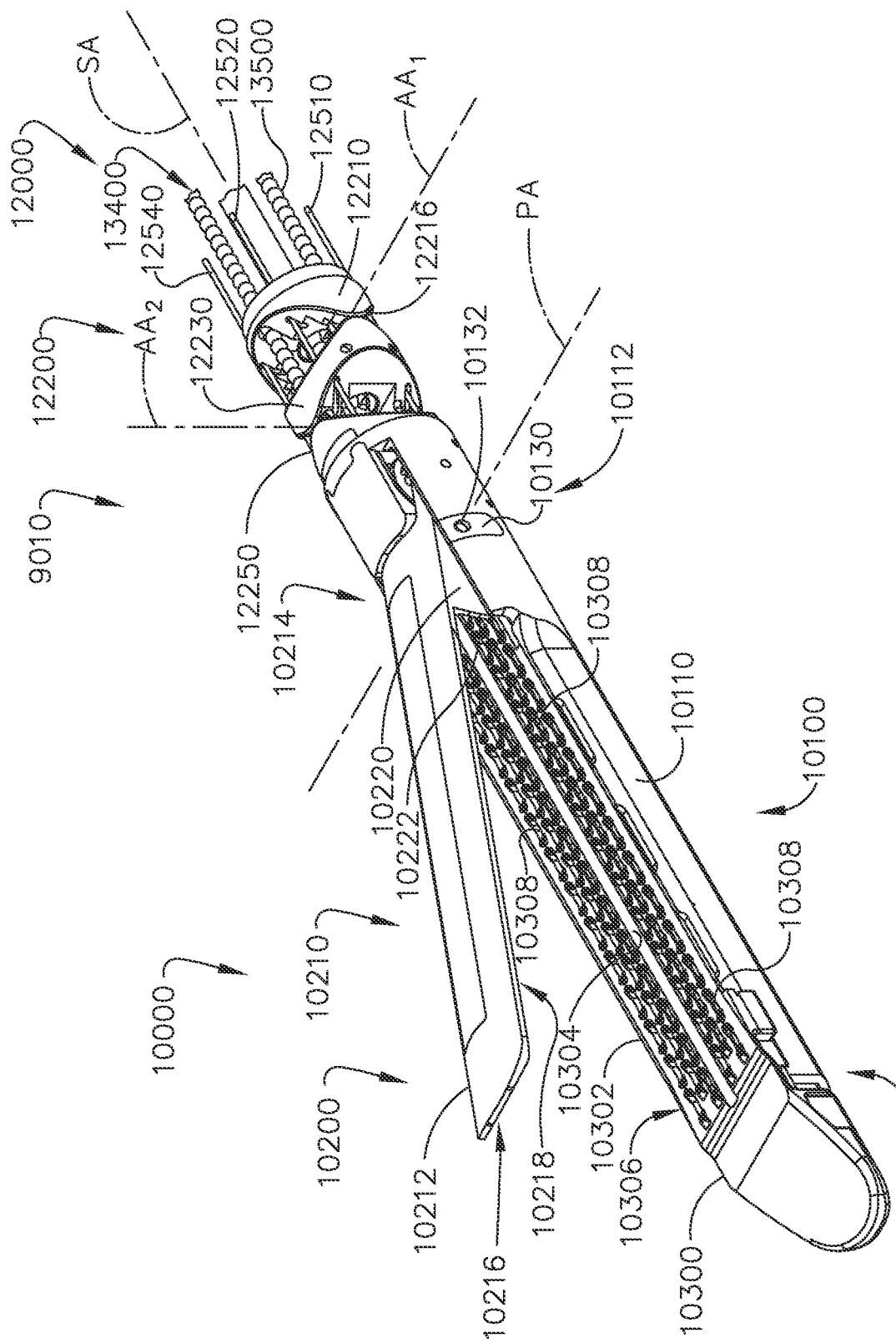
FIG. 87 is a perspective view of a surgical end effector of another surgical instrument with an anvil thereof in an open position and the surgical end effector in an unarticulated orientation.
Figure 88:
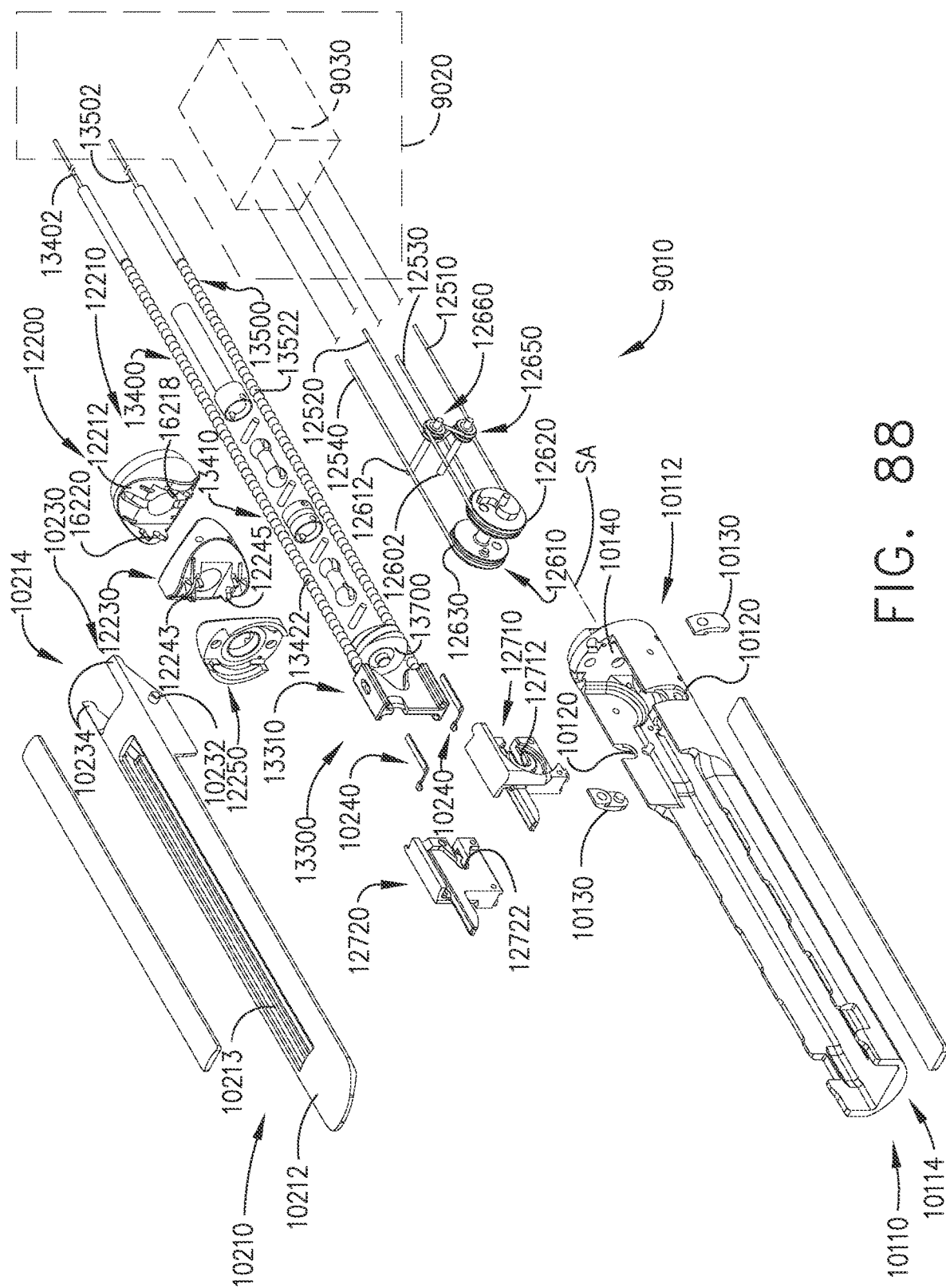
FIG. 88 is an exploded assembly view of the surgical end effector and surgical instrument of FIG. 87.

FIGS. 87-89 illustrate another form of surgical instrument 9010 that may address many of the challenges facing surgical instruments with end effectors that are articulatable to large articulation angles and that are configured to cut and fasten tissue. In various embodiments, the surgical instrument 9010 may comprise a handheld device. In other embodiments, the surgical instrument 9010 may comprise an automated system sometimes referred to as a robotically-controlled system, for example. In various forms, the surgical instrument 9010 comprises a surgical end effector 10000 that is operably coupled to an elongate shaft assembly 12000. The elongate shaft assembly 12000 may be operably attached to a housing. In one embodiment, the housing may comprise a handle that is configured to be grasped, manipulated and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

In one form, the surgical end effector 10000 comprises a first jaw 10100 and a second jaw 10200. In the illustrated arrangement, the first jaw 10100 comprises an elongate channel 10110 that comprises a proximal end 10112 and a distal end 10114 and is configured to operably support a surgical staple cartridge 10300 therein. The surgical staple cartridge 10300 comprises a cartridge body 10302 that has an elongate slot 10304 therein. A plurality of surgical staples or fasteners (not shown) are stored therein on drivers (not shown) that are arranged in rows on each side of the elongate slot 10304. The drivers are each associated with corresponding staple cavities 10308 that open through a cartridge deck surface 10306. The surgical staple cartridge 10300 may be replaced after the staples/fasteners have been discharged therefrom. Other embodiments are contemplated wherein the elongate channel 10110 and/or the entire surgical end effector 10000 is discarded after the surgical staple cartridge 10300 has been used.

In the illustrated arrangement, the second jaw 10200 comprises an anvil 10210 that comprises an elongate anvil body 10212 that has a proximal end 10214 and a distal end 10216. The anvil body 10212 comprises a staple-forming undersurface 10218 that faces the first jaw 10100 and may include a series of staple-forming pockets (not shown) that correspond to each of the staples or fasteners in the surgical staple cartridge 10300. The anvil body 10212 may further include a pair of downwardly extending tissue stop features 10220 that are formed adjacent the proximal end 10214 of the anvil body 10212. One tissue stop feature 10220 extends from each side of the anvil body 10212 such that a distal end 10222 on each tissue stop 10220 corresponds to the proximal-most staples/fasteners in the surgical staple cartridge 10300. When the anvil 10200 is moved to a closed position onto tissue positioned between the staple-forming undersurface 10218 of the anvil 10200 and the cartridge deck surface 10306 of the surgical staple cartridge 10300, the tissue contacts the distal ends 10222 of the tissue stops 10220 to prevent the tissue from migrating proximally past the proximal-most staples/fasteners to thereby ensure that the tissue that is cut is also stapled. When the surgical staple cartridge is "fired" as will be discussed in further detail below, the staples/fasteners supported within each staple cavity are driven out of the staple cavity 10308 through the clamped tissue and into forming contact with the staple forming undersurface 10218 of the anvil 10200.

As can be seen in FIG. 88, the proximal end 10214 of the anvil body 10212 comprises an anvil mounting portion 10230 that comprises a pair of laterally extending mounting pins 10232 that are configured to be received in corresponding mounting inserts 10130 that are configured to be retainingly received within mounting cradles 10120 formed in the proximal end 10112 of the elongate channel 10110. The mounting pins 10232 are pivotally received within pivot holes 10132 in the mounting inserts 10130 and then the mounting inserts 10130 are inserted into their corresponding cradle 10120 and affixed to the elongate channel 10110 by welding, adhesive, snap fit, etc. Such arrangement facilitates pivotal travel of the anvil 10210 relative to the elongate channel 10110 about a fixed (i.e., non-translating, non-moving) pivot axis PA. See FIG. 87.

In the illustrated arrangement, the elongate shaft assembly 12000 defines a shaft axis SA and comprises a hollow outer tube (omitted for clarity) that operably interfaces with a housing of the control portion (e.g., handheld unit, robotic tool driver, etc.) of the surgical instrument 9010. The elongate shaft assembly 12000 further comprises an articulation joint 12200 that may be attached to the hollow outer tube as well as the surgical end effector 10000 to facilitate selective articulation of the surgical end effector 10000 relative to the elongate shaft assembly 12000 about multiple articulation axes in multiple articulation planes. In at least one arrangement, for example, the articulation joint 12200 comprises a proximal joint member 12210, a central joint member 12230, and a distal joint member 12250. In one example, the central joint member 12230 operably interfaces with the proximal joint member 12210 such that the central joint member 12230 is selectively articulatable through a first or proximal articulation plane that is defined by a first or proximal articulation axis $AA_1$ that is transverse to the shaft axis SA. Also in one example, the distal joint member 12250 operably interfaces with the central joint member 12230 such that the distal joint member 12250 is selectively articulatable through a second or distal articulation plane that is defined by a second or distal articulation axis $AA_2$ that is transverse to the shaft axis SA and transverse to the first or proximal articulation axis $AA_1$.

As can be seen in FIGS. 89 and 90, the proximal joint member 12210 comprises a proximal joint distal face 12212 that defines two spaced, lateral apex portions 12214, 12216. The apex portion 12214 defines a radial surface 12215 and the apex portion 12216 defines a radial surface 12217 (FIG. 90). The central joint member 12230 comprises proximal face 12232 that defines two spaced lateral proximal apex portions 12234, 12236. The proximal apex portion 12234 defines a radial surface 12235 and the apex portion 12236 defines a radial surface 12237. As can be seen in FIG. 89, the proximal face 12232 of the central joint member 12230 confronts the proximal joint distal face 12212 of the proximal joint member 12210 such that the central joint member 12230 is articulatable through a first articulation plane defined by the first or proximal articulation axis $AA_1$ that extends between a point where the lateral apex portion 12214 on the proximal joint member contacts the proximal apex portion 12234 on the central joint member 12230 and the point where the lateral apex portion 12216 on the proximal joint member 12210 contacts the proximal apex portion 12236 on the central joint member 12230. In one arrangement, the radial surfaces 12215, 12217 on the lateral apex portions 12214, 12216, respectively, and the radial surfaces 12235 and 12237 on the proximal apex portions 12234, 12236, respectively, may act as rocker points/surfaces about which the central joint member 12230 may articulate relative to the proximal joint member 12210. Additionally, the central joint member 12230 comprises proximal first gear tooth segments that are configured to rotatably mesh with distal gear segments 12218, 12220 on the proximal joint member 12210. See FIG. 88. In various arrangements, the radial surface 12235 on the central joint member 12230 may be spaced from the radial surface 12215 on the proximal joint member 12210 and the radial surface 12237 on the central joint member 12230 may be spaced from the radial surface 12217 on the proximal joint member 12210.

Figure 92:
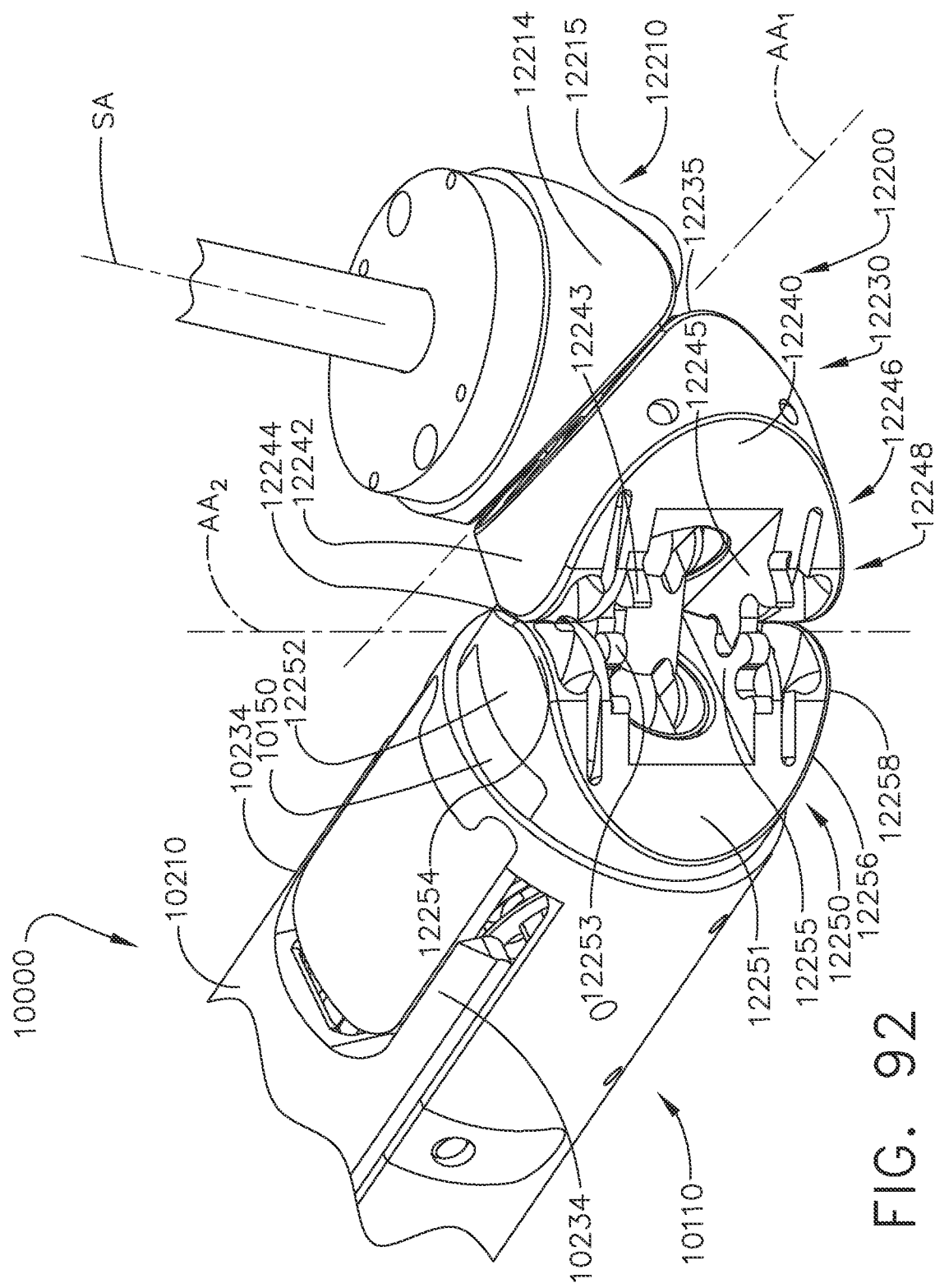
FIG. 92 is a perspective view of a portion of the surgical end effector of FIG. 89 articulated by the articulation joint of FIG. 89.
Figure 95:
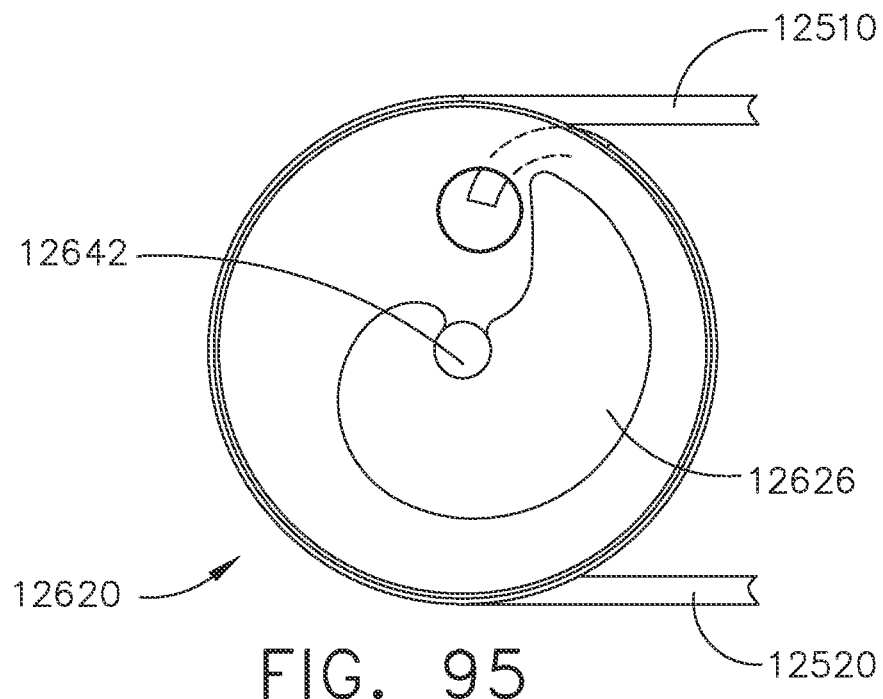
FIG. 95 is a side elevational view of a first lateral alpha wrap pulley of the pulley unit of FIG. 94.

The central joint member 12230 further comprises a central joint distal face 12240 that defines a centrally disposed upper apex portion 12242 that forms an upper radial surface 12244 and a lower apex portion 12246 that forms a lower radial surface 12248. See FIG. 89. The distal joint member 12250 is attached to the proximal end 10112 of the elongate channel 10110 by a mounting bushing 10150 and comprises a proximal face 12251 that faces or confronts the central joint distal face 12240 on the central joint member 12230. See FIGS. 89 and 92. As can be seen in FIGS. 89 and 92, the proximal face 12251 defines a centrally disposed upper apex portion 12252 that forms an upper radial surface 12254 that is configured to confront or abut the upper radial surface 12244 on the central joint member 12230. The proximal face 12251 further defines a centrally disposed lower apex portion 12256 that forms a lower radial surface 12258 that is configured to confront or abut the lower radial surface 12248 on the central joint member 12230. See FIG. 89. The distal joint member 12250 further comprises an upper gear tooth segment 12253 that is configured to rotatably mesh with an upper gear tooth segment 12243 on the central joint member 12230. In addition, the distal joint member 12250 comprises a lower gear tooth segment 12255 that is configured to rotatably mesh with a lower gear tooth segment 12245 on the central joint member 12230. See FIG. 92.

The distal joint member 12250 is configured to articulate through a second or distal articulation plane defined by the second or distal articulation axis $AA_2$ that extends between a point where the upper apex portion 12252 on the distal joint member 12250 contacts or confronts the upper apex portion 12242 on the central joint member 12230 and the point where the lower apex portion 12256 on the distal joint member 12250 contacts or confronts the lower apex portion 12246 on the central joint member 12230. See FIGS. 89 and 92. In one arrangement, the radial surfaces 12254, 12258 on the upper and lower apex portions 12252, 12256, respectively of the distal joint member 12250 and the radial surfaces 12244 and 12248 on the upper and lower apex portions 12242, 12246, respectively on the central joint member 12230 may act as rocker points/surfaces about which the distal joint member 12250 may articulate relative to the central joint member 12230. In alternative arrangements, however, the radial surface 12254 on the distal joint member 12250 is spaced from the radial surface 12244 on the central joint member 12230 and the radial surface 12258 on the distal joint member 12250 is spaced from the radial surface 12248 on the central joint member 12230.

Returning to FIG. 88, in the illustrated example, the articulation joint 12200 is operably controlled by a cable control system 9030 that comprises four cables 12510, 12520, 12530, and 12540 that extend through the elongate shaft assembly 12000. The cable control system 9030 may be supported within a housing 9020 of the surgical instrument 9010. The cable control system 9030 may comprise a plurality of cable support members/capstans, pulleys, etc. that are controlled by one or more corresponding motors that are controlled by a control circuit portion of the surgical instrument 9010. In various embodiments, the cable control system 9030 is configured to manage the tensioning (pulling) and paying out of cables at precise times during the articulation process. In addition, in at least one arrangement, the cable control system 9030 is employed to control the opening and closing of the anvil 10210 as will be discussed in further detail below.

As can be seen in FIG. 88, the cables 12510, 12520, 12530, and 12540 are configured to operably interface with a closure system 12600 that is rotatably mounted in the proximal end 10112 of the elongate channel 10110. In at least one arrangement, the closure system 12600 comprises a pulley unit 12610 that comprises a first lateral alpha wrap pulley 12620 and a second lateral alpha wrap pulley 12630 that are interconnected by a central shaft 12640. See FIGS. 93 and 94. The pulley unit 12610 is rotatably supported within the proximal end 10112 of the elongate channel 10110 by mounting brackets 12710 and 12720. See FIG. 88. More particularly, the proximal end 10112 of the elongate channel 10110 defines a firing member parking area 10140 that is proximal to the mounting cradles 10120 and is configured to operably support a firing member 12310 when in a starting position. Each mounting bracket 12710, 12720 is mounted within the firing member parking area 10140 on each side of the shaft axis SA to enable the firing member 12310 to be received in the parking area 10140 when the firing member 12310 is in a starting position. The mounting brackets 12710, 12720 may be attached to the proximal end 10112 of the elongate channel 10110 by welding, adhesive, snap features, etc. The mounting bracket 12710 comprises a first shaft cradle 12712 that is configured to rotatably support a first pivot shaft 12621 protruding from the first lateral alpha wrap pulley 12620 and the second mounting bracket 12720 comprises a second shaft cradle 12722 that is configured to rotatably support a second pivot shaft 12644 protruding from the second lateral alpha wrap pulley 12630. In addition, each mounting bracket 12710, 12720 further includes a relief area 12732 that is shaped to receive the corresponding first and second alpha wrap pulleys 12620, 12630 therein.

Figure 94:
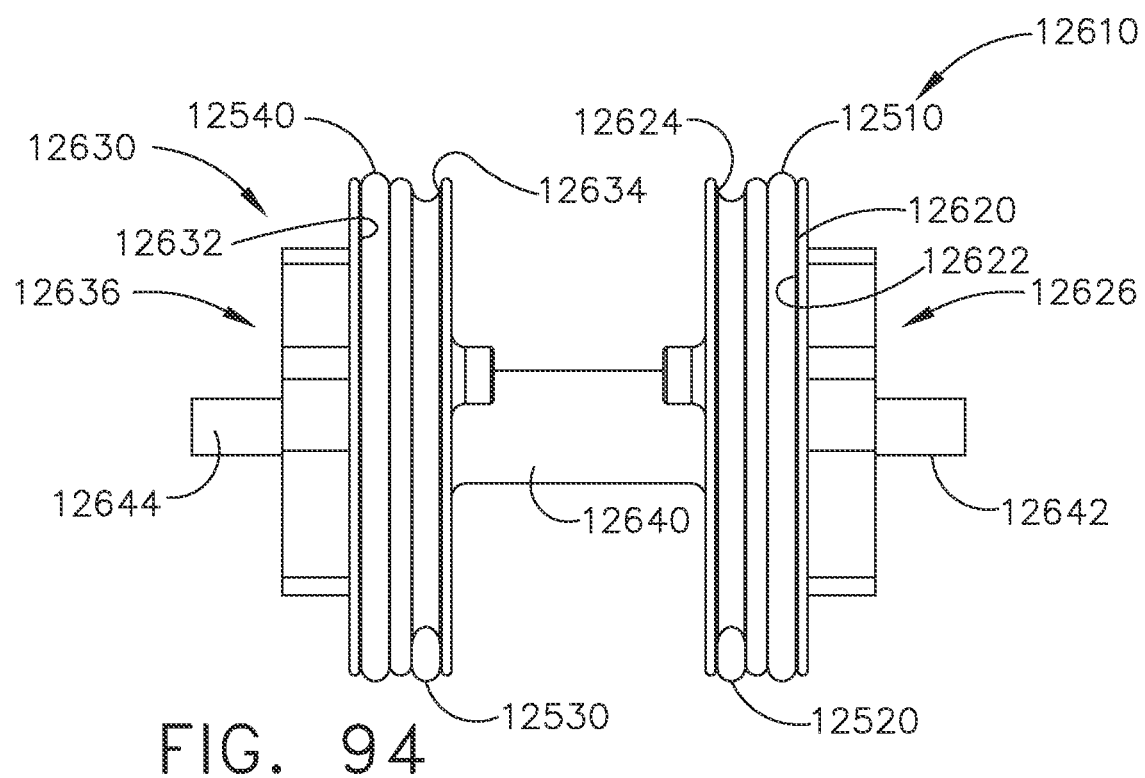
FIG. 94 is an end view of a pulley unit of the cable-controlled pulley system of FIG. 93.

As can be seen in FIG. 94, the first alpha wrap pulley 12620 comprises a first circumferential groove 12622 and a second circumferential groove 12624. In the illustrated example, the first cable 12510 is received in the first circumferential groove 12622 and is attached thereto and the second cable 12520 is received in the second circumferential groove 12624 and is attached thereto. Pulling on the first cable 12510 will result in the rotation of the first lateral alpha wrap pulley 12620 in a first direction and pulling the second cable 12520 will result in the rotation of the first lateral alpha wrap pulley 12620 in a second opposite direction. Similarly, the second lateral alpha wrap pulley 12630 comprises a first circumferential groove 12632 and a second circumferential groove 12634. In the illustrated arrangement, cable 12540 is received in the first circumferential groove 12632 and is attached thereto and the second cable 12520 is received in the second circumferential groove 12634 and is attached thereto. Pulling on the fourth cable 12540 will result in the rotation of the first second alpha wrap pulley 12630 in the first direction and pulling the third cable 12530 will result in the rotation of the second lateral alpha wrap pulley 12630 in the second opposite direction. The lateral alpha wrap pulleys 12620, 12630 can rotate approximately three hundred thirty degrees. This range of rotational travel is in contrast to a normal pulley that may have a range of rotational travel that is less than one hundred eighty degrees of rotation.

Each of the first and second lateral alpha wrap pulleys 12620, 12630 also comprises a corresponding spiral closure cam that is configured to apply closure motions to the anvil 10210. As can be seen in FIG. 94, the first lateral alpha wrap pulley 12620 includes a first spiral closure cam 12626 and the second lateral alpha wrap pulley 12630 has a second spiral closure cam 12636 thereon. The spiral closure cams 12626, 12636 are configured to cammingly interact with corresponding anvil closure arms 10234 on the anvil mounting portion 10230 of the anvil 10210 to apply closure motions thereto. FIG. 96 illustrates the position of a spiral closure cam 12626 on the first lateral alpha wrap pulley 12620 when the anvil 10210 is biased into the open position by an anvil spring 10240. Rotation of the pulley unit 12610 in a first rotary direction will cause the spiral closure cams 12626 to cam the anvil 1210 to the closed position shown in FIG. 97. To open the anvil 10210, the pulley unit 12610 is rotated in opposite direction back to the position shown in FIG. 96.

Referring now to FIGS. 91 and 93, the first cable 12510 extends from the cable control system through the elongate shaft assembly and through a passage in the proximal joint member 12210 and is looped around two redirect pulleys 12650, 12660 that are supported on shafts 12602, 12612 that are mounted in the central joint member 12230. The first cable 12510 exits the central joint member 12230 through passage 12231 and extends through passage 12257 in the distal joint member 12250 to be received within the first circumferential groove 12622 in the first lateral alpha wrap pulley 12620 where it is attached thereto. A second cable 12520 extends from the cable control system through the elongate shaft assembly and through passage 12213 in the proximal joint member 12210 to be looped around the redirect pulleys 12650, 12660 in the central joint member 12230. The second cable 12520 exits the central joint member 12230 through a corresponding passage 12241 and extends through passage 12259 in the distal joint member 12250 to be received within the second circumferential groove 12624 in the first lateral alpha wrap pulley 12620 where it is attached thereto.

In the illustrated example, the third cable 12530 extends from the cable control system 9030 through the elongate shaft assembly 12000 and through a corresponding passages in the proximal joint member 12210, the central joint member 12230, and the distal joint member 12250 to be received within a corresponding circumferential groove in the second lateral alpha wrap pulley 12630 where it is attached thereto. In addition, a fourth cable 12540 extends from the cable control system 9030 through the elongate shaft assembly 12000 and through corresponding passages in the proximal joint member 12210, the central joint member 12230, and the distal joint member 12250 to be received within a corresponding circumferential groove in the second lateral alpha wrap pulley 12630 where it is attached thereto.

Figure 98:
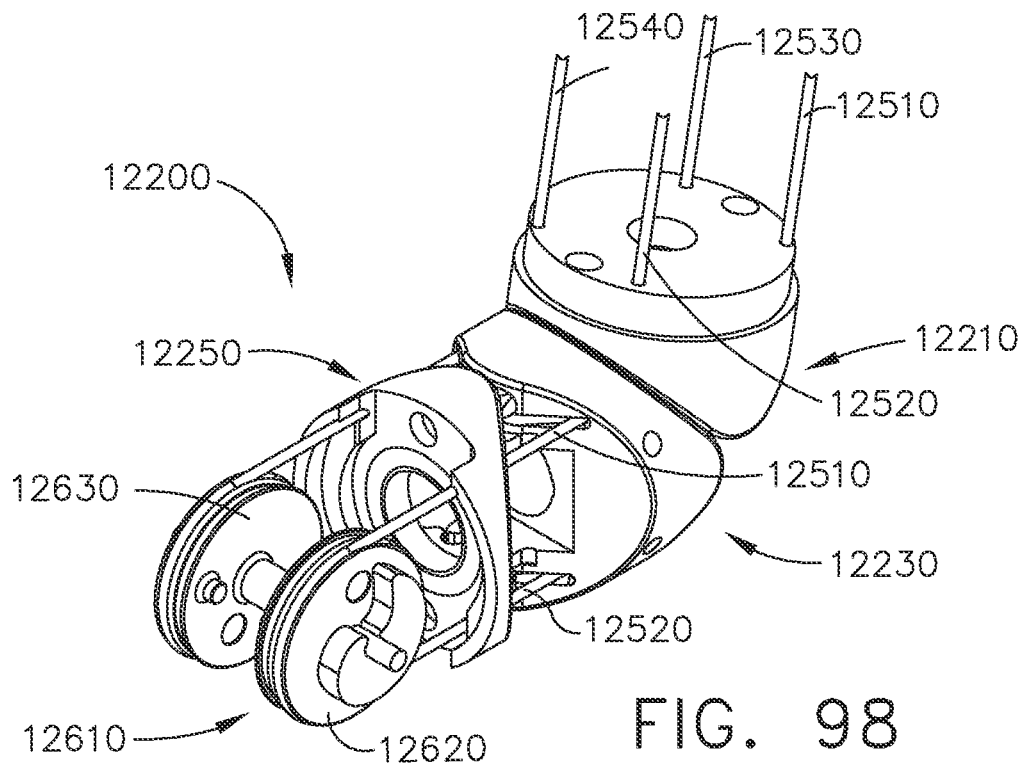
FIG. 98 is a perspective view of the articulation joint and cable-controlled closure system of the surgical instrument of FIG. 87 with a central joint member and a distal joint member articulated relative to a proximal joint member of the articulation joint.
Figure 99:
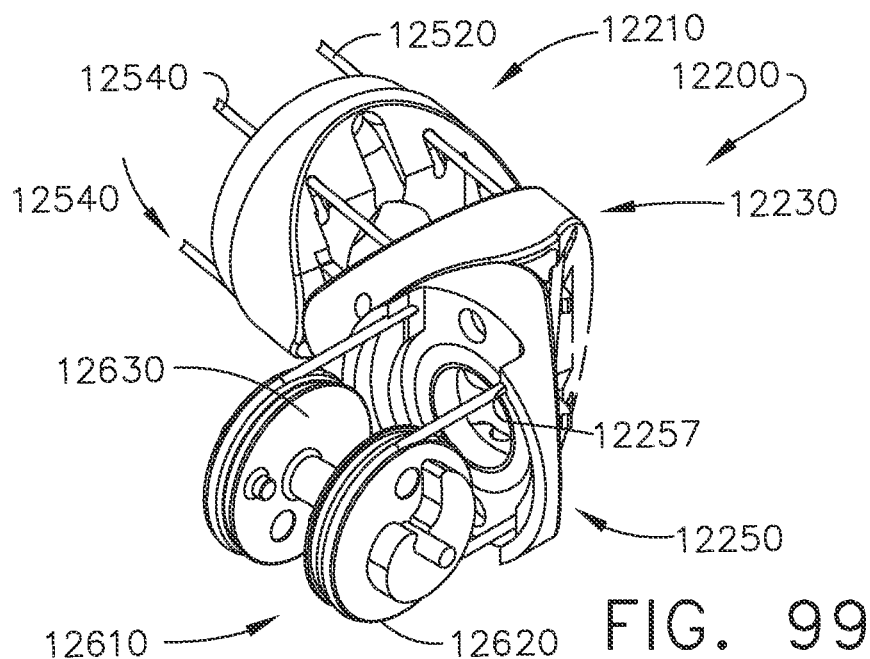
FIG. 99 is another perspective view of the articulation joint and cable-controlled closure system of the surgical instrument of FIG. 87 with the distal joint member articulated through a second articulation plane relative to a central joint member of the articulation joint.

In at least one example, to articulate the surgical end effector 10000 relative to the elongate shaft assembly 12000 through a first articulation plane that is defined by the first articulation axis $AA_1$, the cable control system 9030 is actuated to pull on the second cable 12520 and the fourth cable 12540 simultaneously with a same amount of tension being applied to each cable 12520 and 12540. Because the cables 12520, 12540 apply equal amounts of tension on both sides of the pulley unit 12610, the pulley unit 12610 does not rotate. However, the pulling action of the cables 12520 and 12540 is translated through the articulation joint 12200 to the surgical end effector 10000 which results in the articulation of the central joint member 12230 relative to the proximal joint member 12210 about the first articulation axis $AA_1$. See FIGS. 92 and 98. To articulate the surgical end effector 10000 through a second plane of articulation that is defined by the second articulation axis $AA_2$ and is transverse to the first plane of articulation, the cable control system 9030 is actuated to pull the third cable 12530 and the fourth cable 12540 simultaneously with a same amount of tension being applied to each cable 12530 and 12540. Because the cables 12530, 12540 apply equal amounts of tension on both sides of the second lateral alpha wrap pulley 12630 of the pulley unit 12610, the pulley unit 12610 does not rotate. However, the pulling action of the cables 12530 and 12540 is translated through the articulation joint 12200 to the surgical end effector 10000 which results in the articulation of the distal joint member 12250 relative to the central joint member 12230 about the second articulation axis $AA_2$. See FIGS. 92 and 99.

The cable control system 9030 may also be used to control the opening and closing of the anvil 10210 in the following manner. As indicated above, when the spiral cams 10626 on the first lateral alpha wrap pulley 10620 and the second lateral alpha wrap pulley 10630 are in the position shown in FIG. 96, the anvil 10210 is biased into the open position by the anvil spring 10240. To close the anvil 10210 from that position, the cable control system 9030 is actuated to pull the first cable 12510 and the fourth cable 12540 simultaneously with a same amount of tension being applied to each cable 12510 and 12540. These cables 12510 and 12540 will cause the pulley unit 12610 to rotate into the closure position shown in FIG. 97 which causes the closure cams 10626 to cammingly contact the anvil closure arms 10234 to pivot the anvil 10210 into the closed position. It will be appreciated that by applying equal amounts of tension into the cables 12510 and 12540, no moment is applied to the central joint member 12230 and/or distal joint member 12250 because there are equal amounts of tension being applied on each side of the articulation joint 12200. See FIG. 91. Such arrangement allows the jaw closure to be profiled as desired. This cable-controlled system 9030 allows for a faster closure when the anvil is fully open. The cable-controlled system 9030 can also function as a lower speed/higher force generating closure mechanism for clamping onto tissue. The present cable controlled system 9030 may also not produce the backlash that commonly occurs with other cable-controlled systems and thus can also be used to control the articulation position of the end effector. As will be further discussed below, this cable actuated closure and articulation system does not cross across the center axis or shaft axis of the articulation joint which provides critical space for a firing drive system 13000.

The above-described articulation joint 12200 and cable controlled system 9030 can facilitate two plane articulation while also supplying an additional actuation motion to the surgical end effector 10000 while keeping the central area of the articulation joint 12200 free for other control systems as will be discussed in further detail below. The articulation joint 12200 uses the last degree of freedom to actuate the jaw closure of the surgical end effector. In one aspect, the articulation joint 12200 comprises an N+1 joint, meaning that for N degrees of freedom, the joint requires N+1 cables to actuate it. Thus, in the above-described example, the articulation joint 12200 employs four actuation cables.

As can be seen in FIGS. 100-103, the firing drive system 13000 comprises a firing member 13310 that includes a vertically-extending firing member body 13312 that has two laterally extending tabs 13314 protruding from a bottom portion 13313 of the firing member body 13312. The tabs 13314 are configured to be slidably engage ledges 10113 in the elongate channel 10110 as the firing member 13310 is driven axially therein. In addition, a pair of upper tabs 13316 protrudes from a top portion 13315 of the firing member body 13312. The upper tabs 13316 are configured to engage ledges 10213 (FIG. 103) in the anvil body 10212 as the firing member 13310 is driven distally through the closed anvil 10210. During the firing stroke, the tabs 13314 and 13316 may serve to space the anvil 10210 relative to a surgical staple cartridge that is supported in the elongate channel 10110. The firing member body 13312 also comprises a tissue cutting feature 13318 and a proximally-facing notch 13319 that is configured to accommodate the central shaft 12640 of the pulley unit 12610 when the firing member 13310 is in its proximal-most starting position within the firing member parking area 10140 in the proximal end 10112 of the elongate channel 10110.

Figure 100:
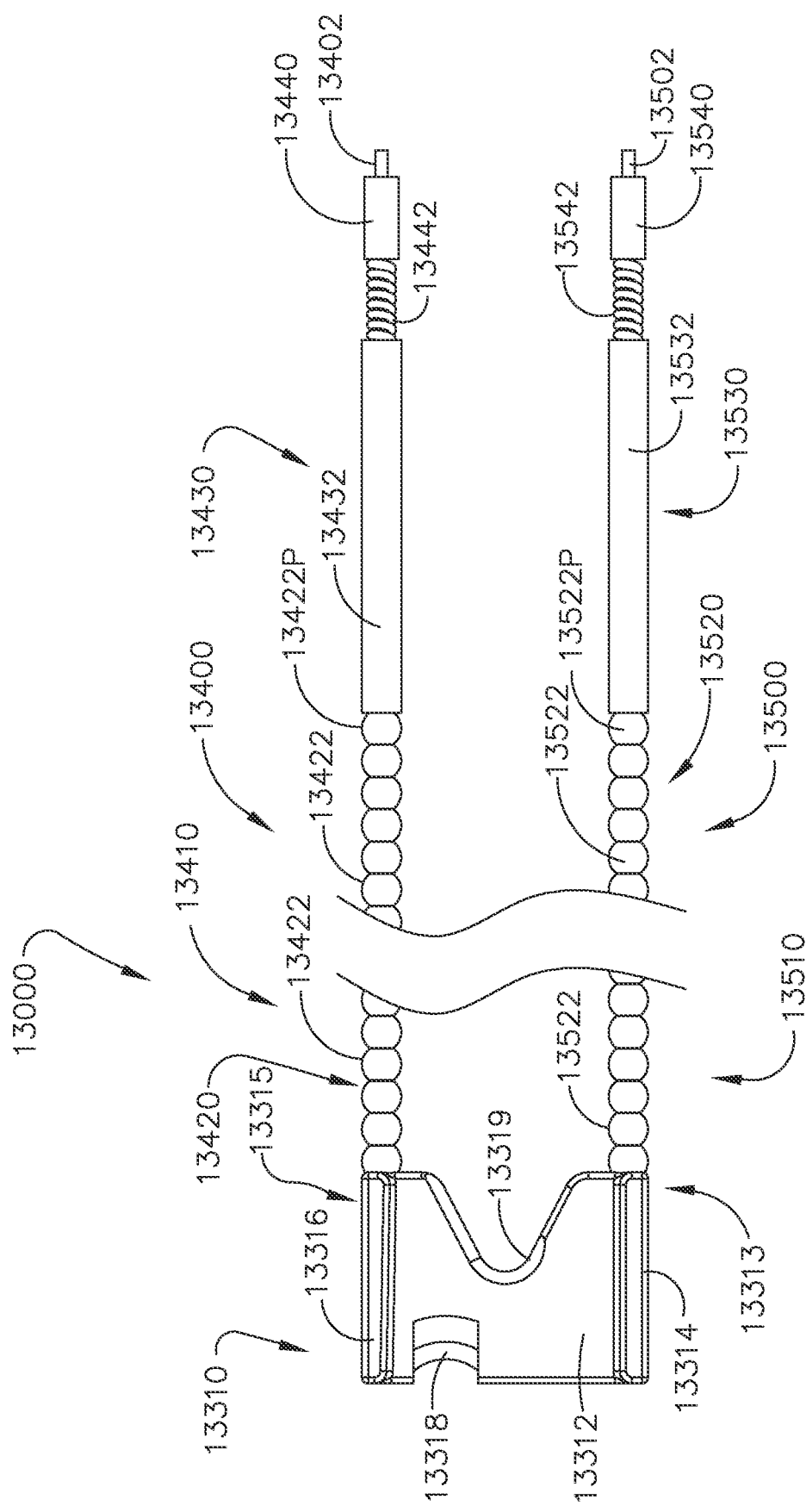
FIG. 100 is a side elevational view of portions of a firing drive system of the surgical instrument of FIG. 87.
Figure 101:
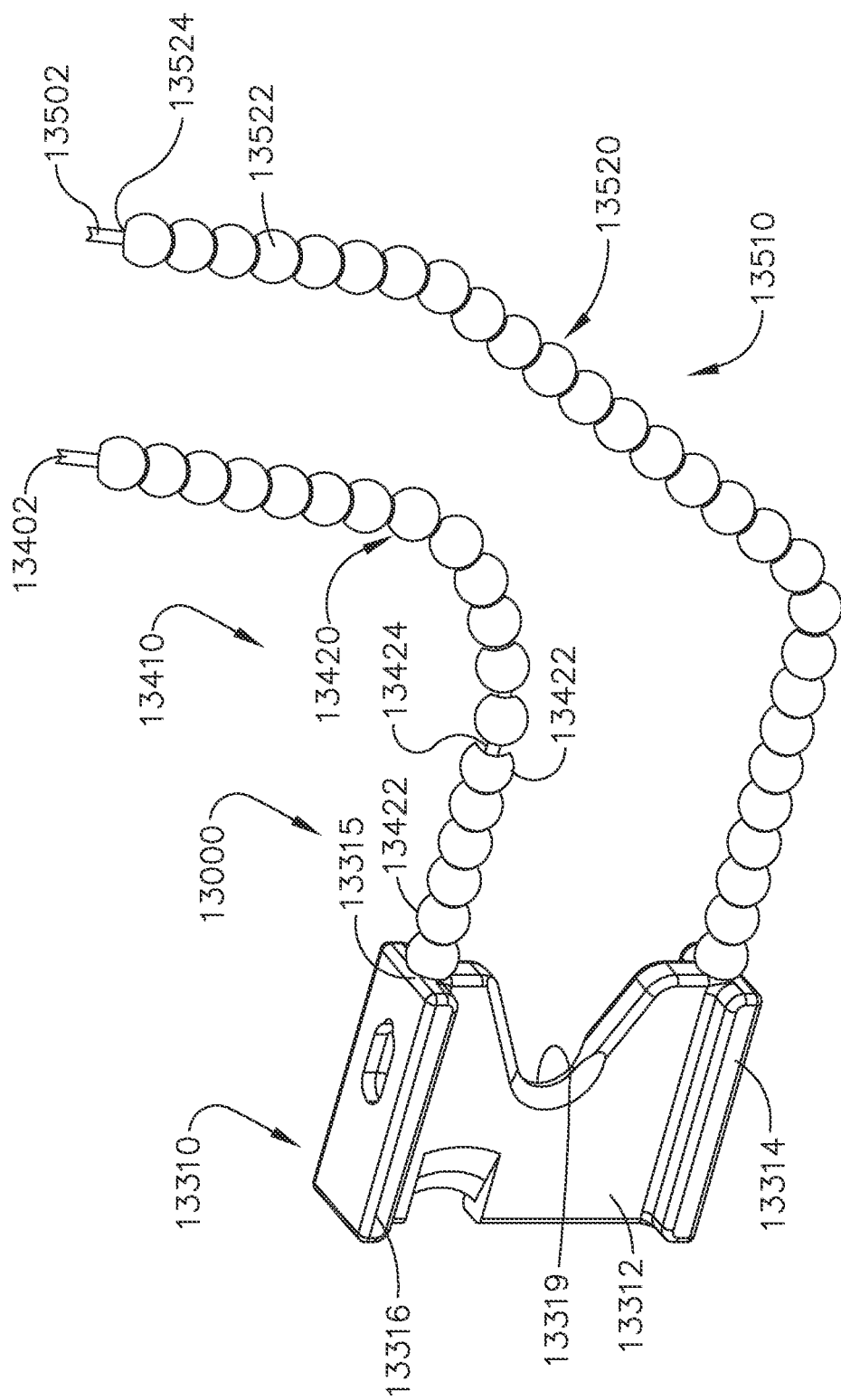
FIG. 101 is another perspective view of the firing drive system of FIG. 100 with upper chain link features and lower chain link features in articulated positions.
Figure 102:
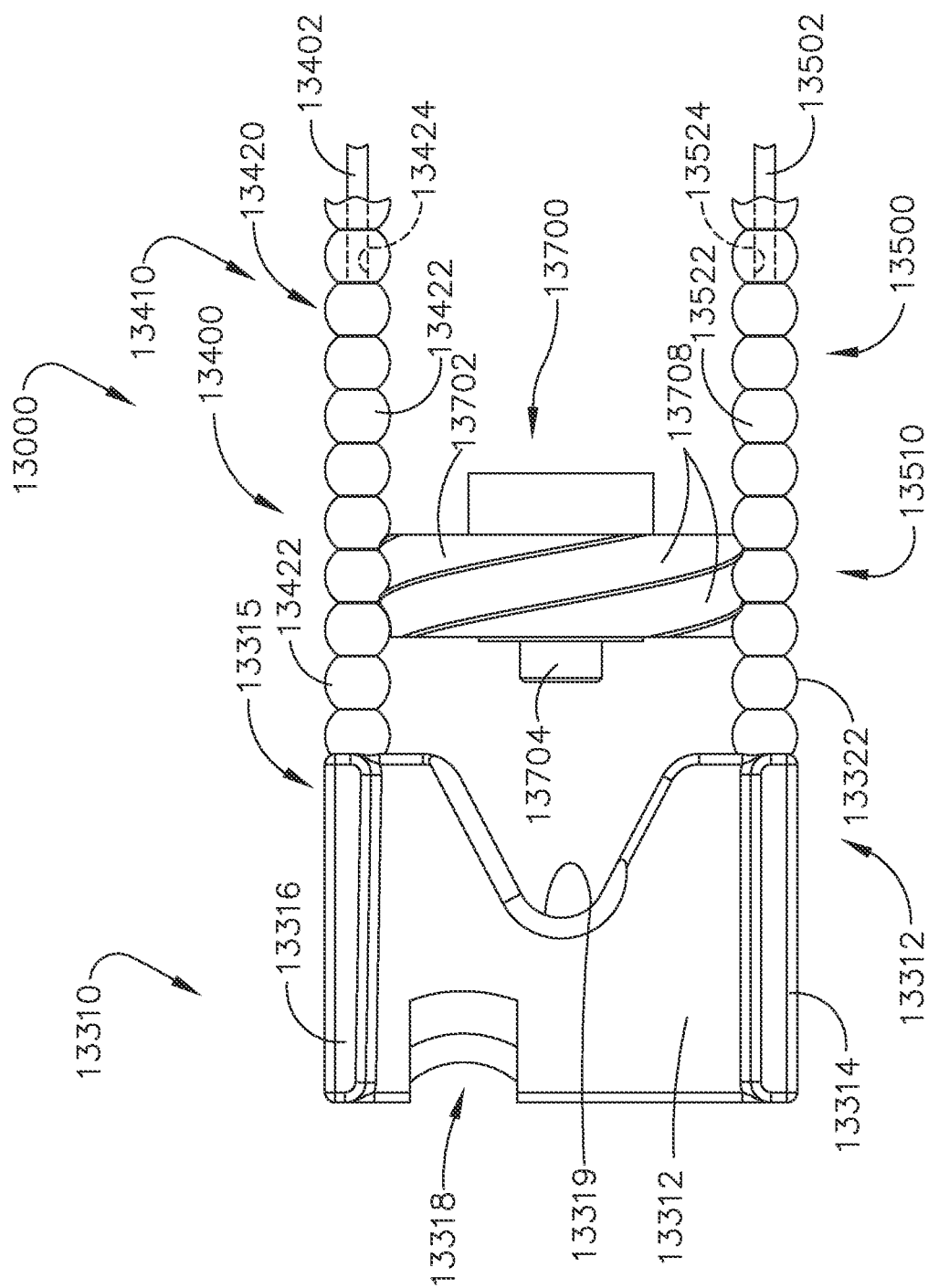
FIG. 102 is another side view of the firing drive system of FIG. 100 with the upper chain link features and lower chain link features in driving engagement with a rotary drive screw of the firing drive system.
Figure 103:
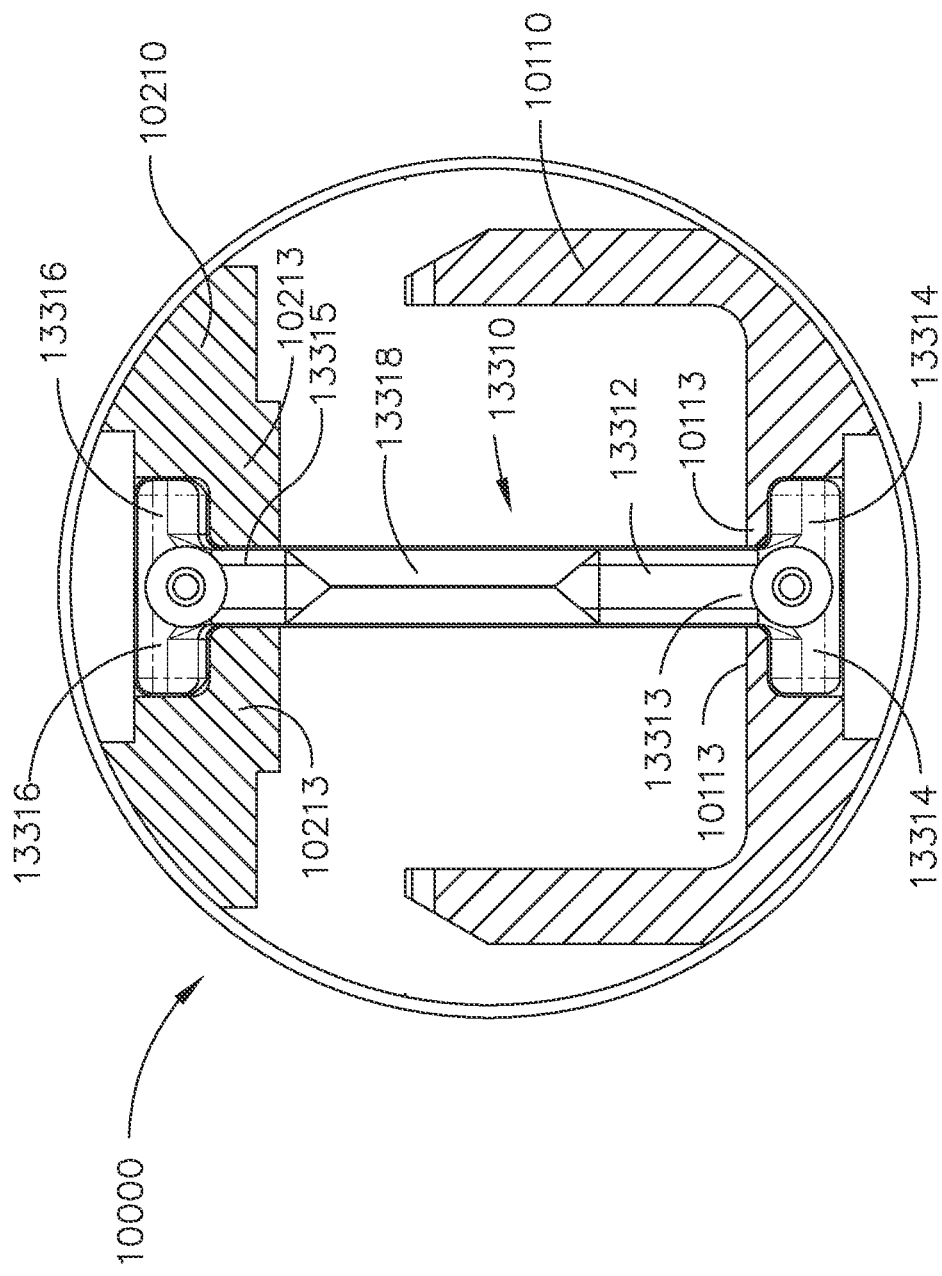
FIG. 103 is a cross-sectional end view of the surgical end effector of FIG. 87 with the anvil thereof in a closed position.

As shown in FIGS. 100-102, the firing drive system 13000 further comprises an upper flexible chain drive assembly 13400 that is operably coupled to the top portion 13315 of the firing member 13310 and a lower flexible chain drive assembly 13500 that is operably coupled to the bottom portion 13313 of the firing member 13310. In at least one embodiment, the upper flexible chain drive assembly 13400 comprises an upper series 13410 of upper chain link features 13420 that are loosely coupled together by an upper flexible coupler member 13402 that is attached to the top portion 13315 of the firing member 13310. In at least one example, each upper chain link feature 13420 comprises an upper ball or sphere 13422 that has an upper hollow passage 13424 therein that is configured to permit the upper flexible coupler member 13402 to pass therethrough. As can be seen in FIG. 100, the upper flexible chain drive assembly 13400 further comprises an upper compression assembly 13430 for compressing the upper balls 13422 in the upper series 13410 together. In one arrangement, the upper compression assembly 13430 comprises a hollow flexible compression tube 13432 that is received on the upper flexible coupler member 13402. An upper ferrule 13440 is crimped onto the upper flexible coupler member 13402 and an upper compression spring 13442 is journaled between the upper ferrule 13440 and the upper flexible compression tube 13432 to distally bias the upper flexible compression tube 13432 into contact with the proximal-most upper ball 13422P in the upper series 13410 of upper chain link features 13420.

Similarly, in at least one embodiment, the lower flexible chain drive assembly 13500 comprises a lower series 13510 of lower chain link features 13520 that are loosely coupled together by a lower flexible coupler member 13502 that is attached to the bottom portion 13313 of the firing member 13310. In at least one example, each lower chain link feature 13520 comprises a lower ball or sphere 13522 that has a lower hollow passage 13524 therein that is configured to permit the lower flexible coupler member 13502 to pass therethrough. The lower flexible chain drive assembly 13500 further comprises an upper compression assembly 13530 for compressing the lower balls 13522 in the lower series 13510 together. In one arrangement, the lower compression assembly 13530 comprises a hollow flexible compression tube 13532 that is received on the lower flexible coupler member 13502. A lower ferrule 13540 is crimped onto the lower flexible coupler member 13502 and a lower compression spring 13542 is journaled between the lower ferrule 13540 and the lower flexible compression tube 13532 to distally bias the lower flexible compression tube 13532 into contact with the proximal-most lower ball 13522P in the lower series 13510 of lower chain link features 13520.

Figure 104:
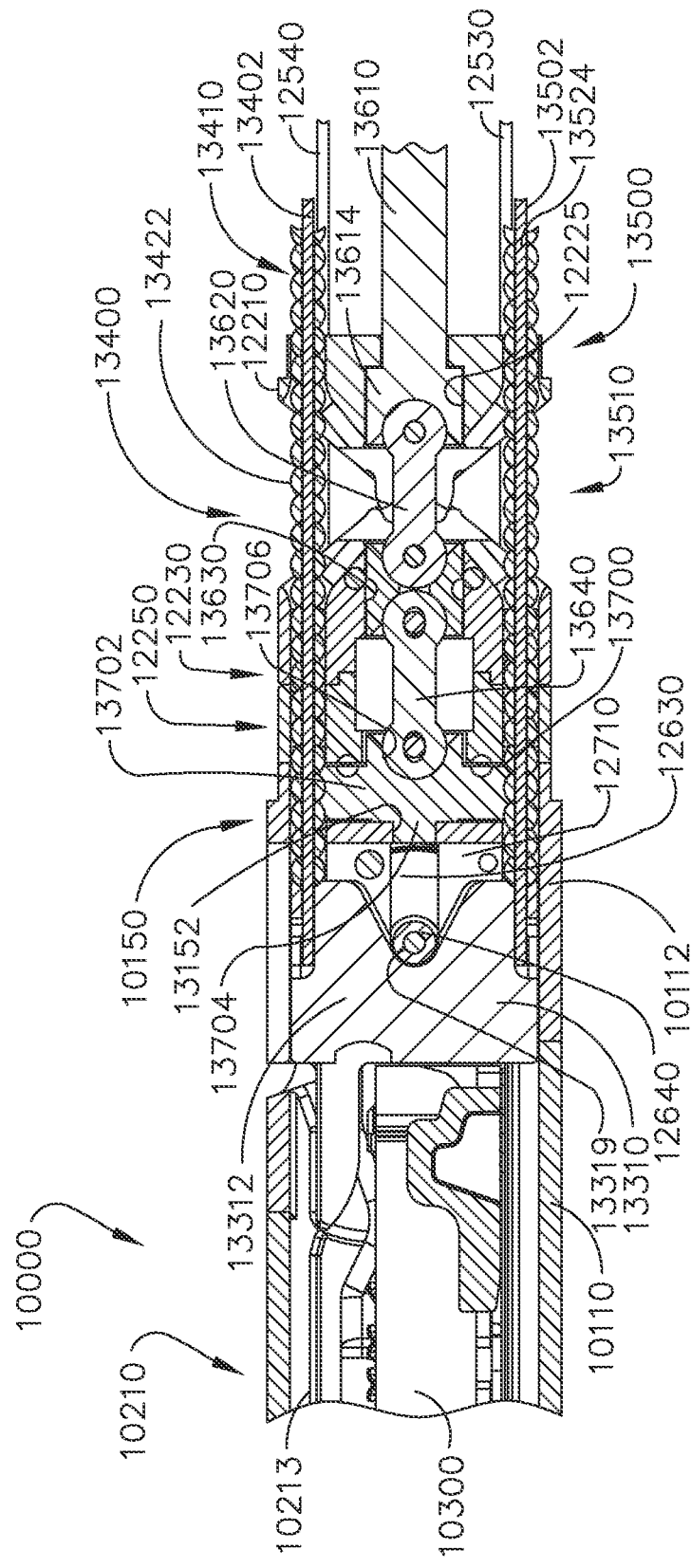
FIG. 104 is a cross-sectional side view of a portion of the surgical instrument of FIG. 87 with the firing member in a starting position and the anvil in a closed position.

Now turning to FIG. 104, in at least one arrangement, the firing drive system 13000 further comprises rotary drive screw 13700 that is configured to drivingly interface with the upper series 13410 of upper chain link features 13420 and the lower series 13510 of lower chain link features 13520. As can be seen in FIG. 104, in the illustrated arrangement, the rotary drive screw 13700 is rotatably supported in the mounting bushing 10150 that is attached to the proximal end 10112 of the elongate channel 10110. For example, the rotary drive screw 13700 comprises a body portion 13702 that has a central axle 13704 protruding therefrom that is rotatably mounted in a mounting hole 10152 in the mounting bushing 10150. Such arrangement permits the rotary drive screw 13700 to rotate about the shaft axis SA.

Figure 105:
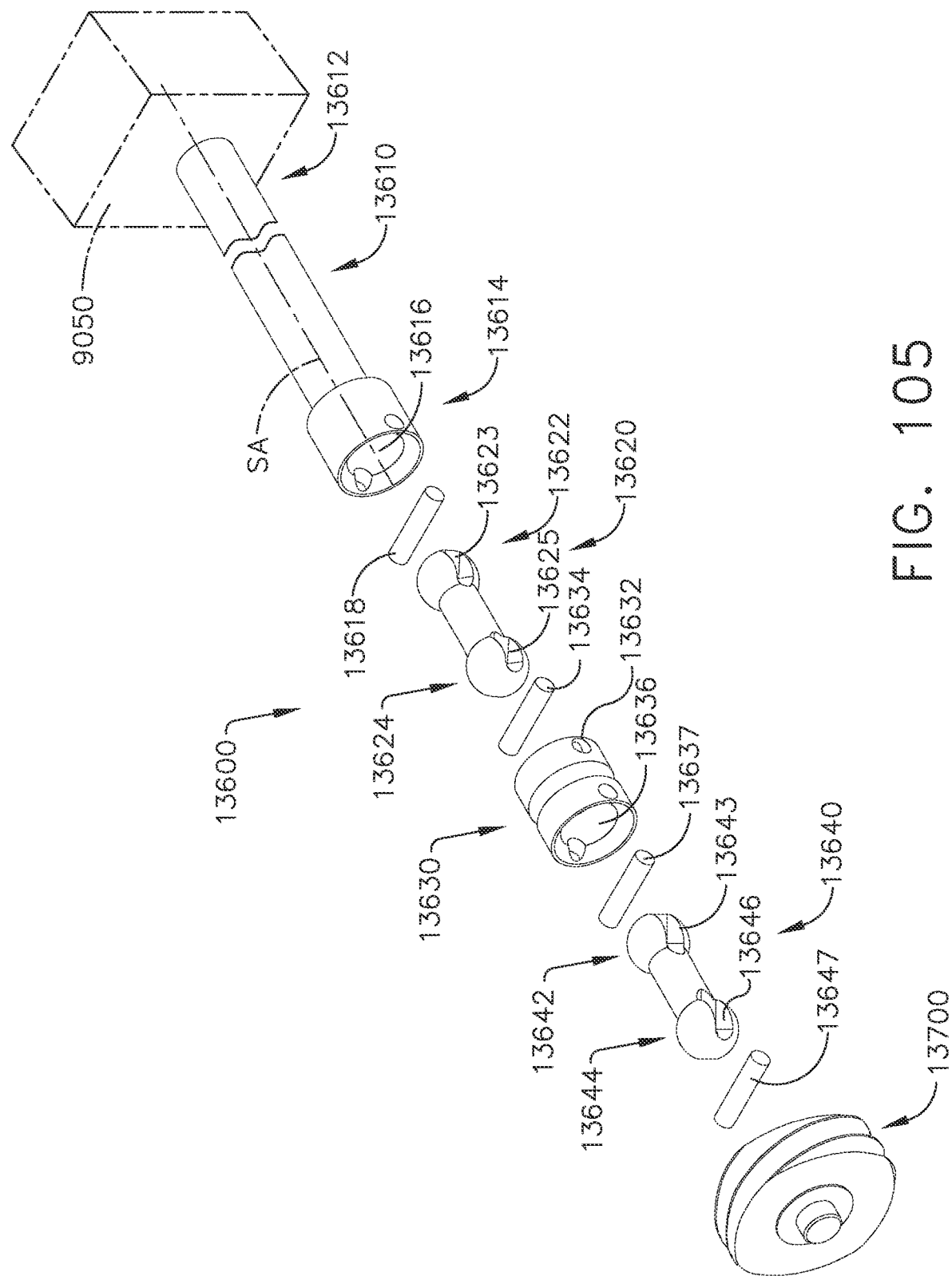
FIG. 105 is an exploded assembly view of a rotary drive system of the surgical instrument of FIG. 87.
Figure 106:
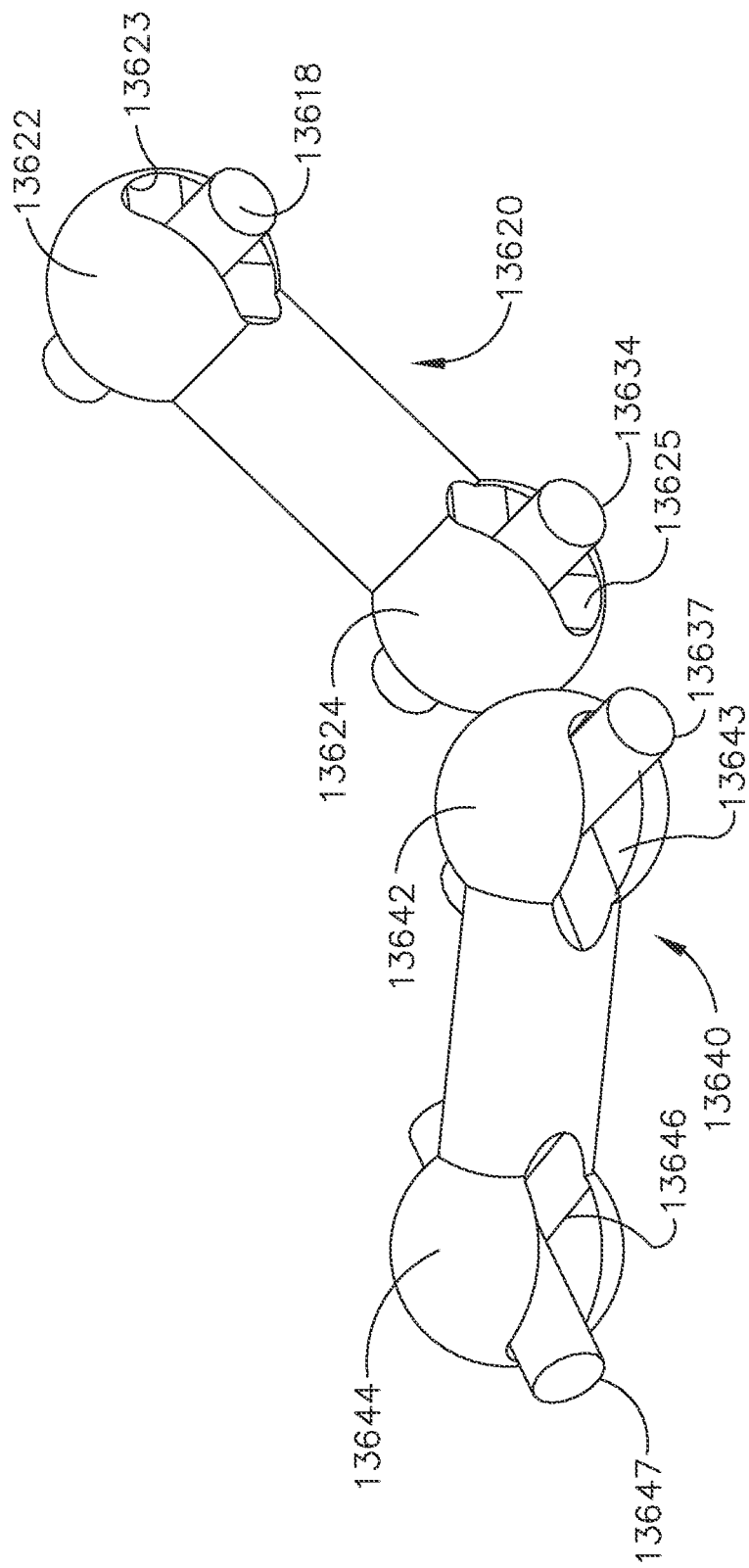
FIG. 106 is a perspective view of a first drive shaft segment and a second drive shaft segment of the rotary drive system of FIG. 105.
Figure 107:
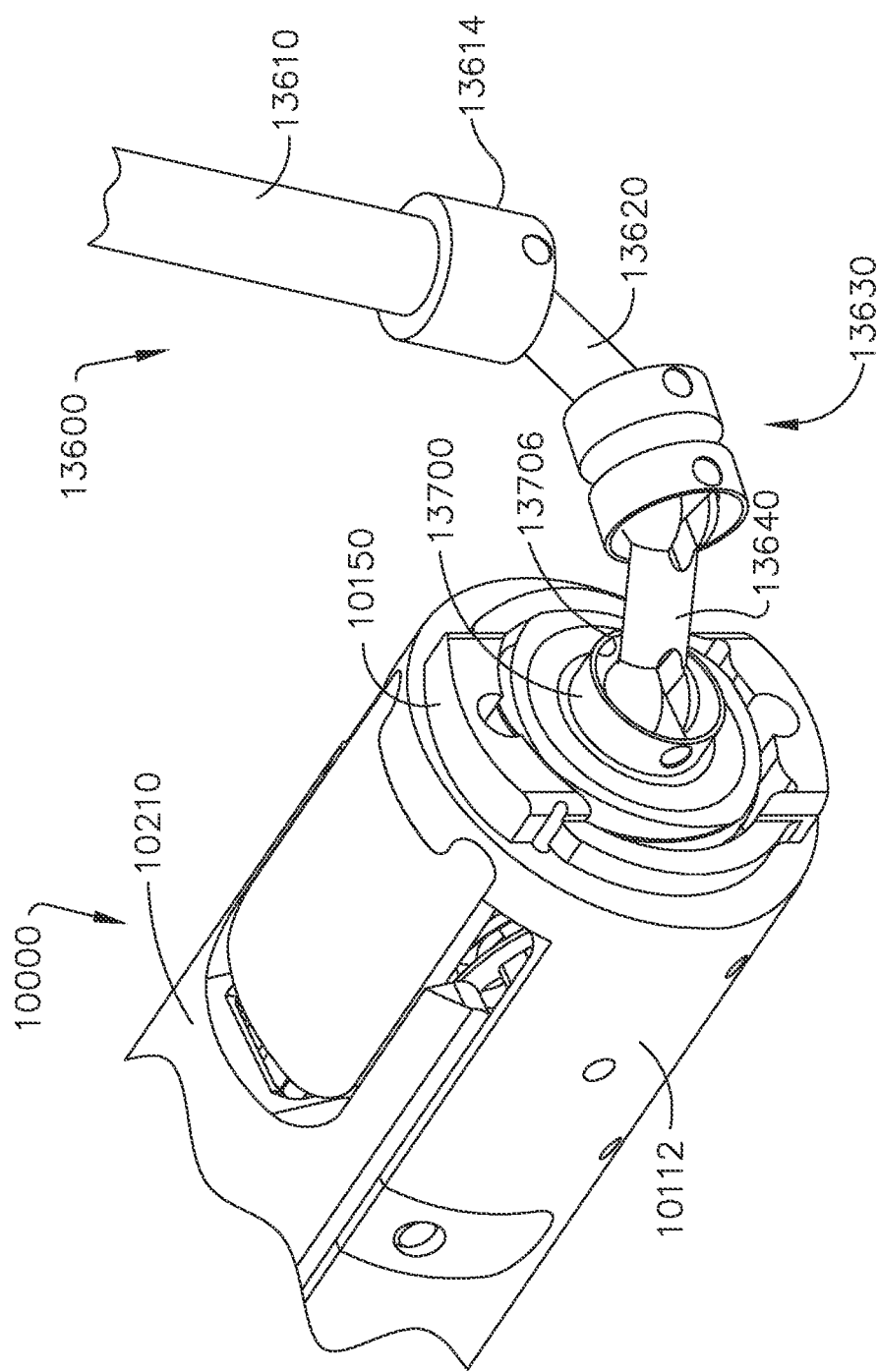
FIG. 107 is a perspective view of the surgical end effector of FIG. 87 with the rotary drive system in an articulated orientation.
Figure 108:
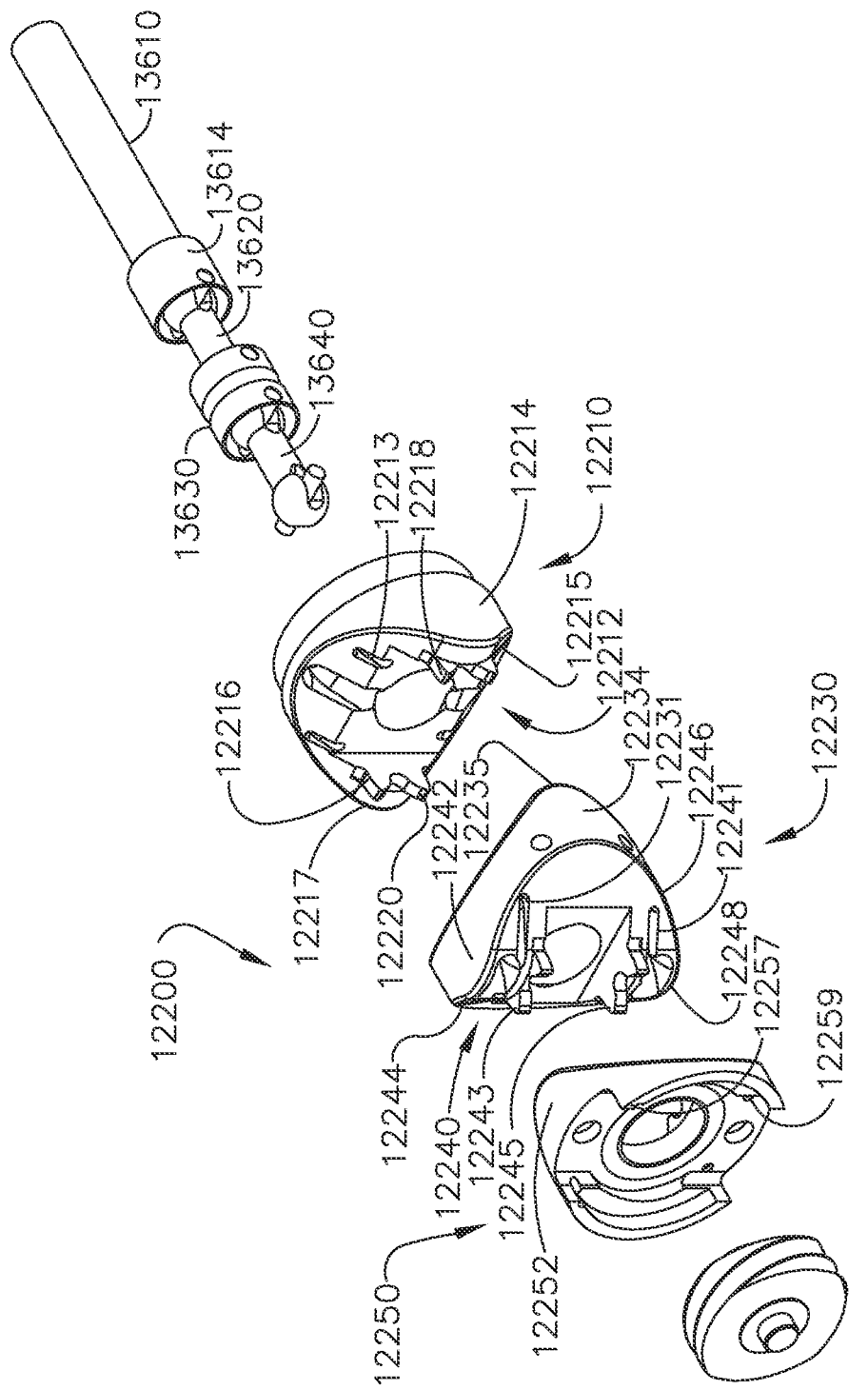
FIG. 108 is an exploded assembly view of an articulation joint and a portion of the rotary drive system of the surgical instrument of FIG. 87.
Figure 109:
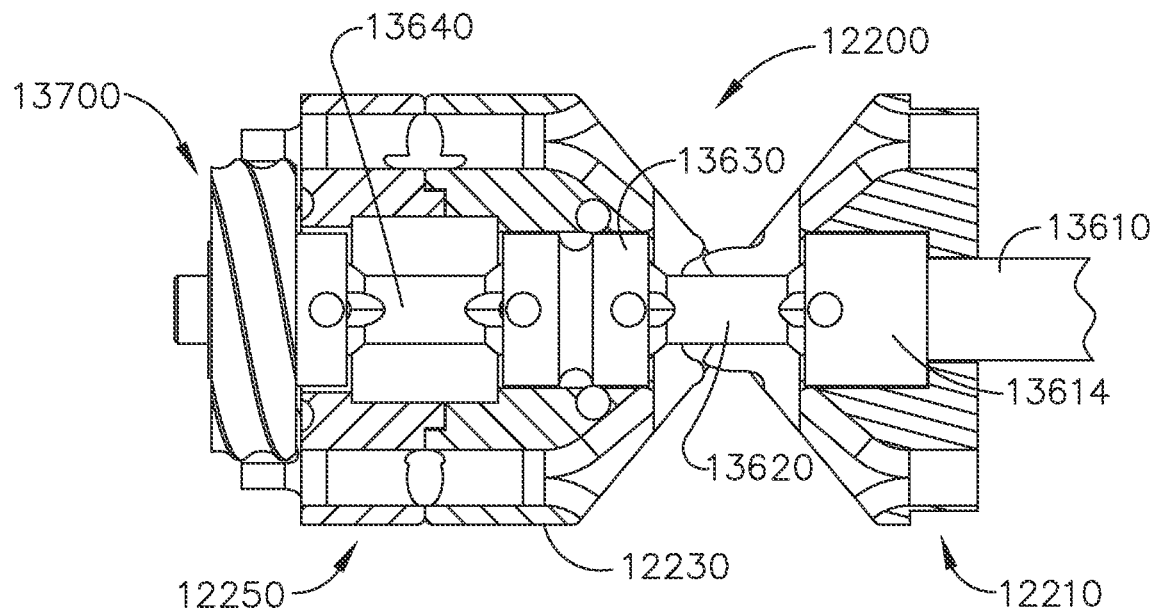
FIG. 109 is a cross-sectional view of the articulation joint and rotary drive system of FIG. 108 in an unarticulated orientation.
Figure 110:
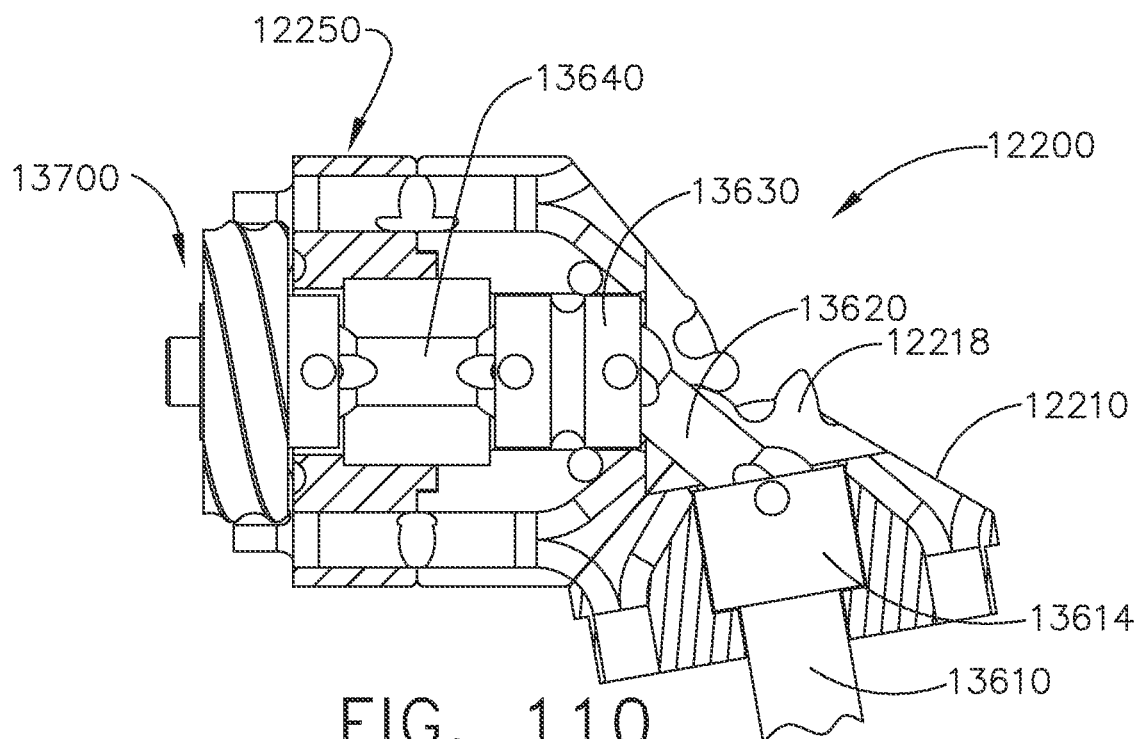
FIG. 110 is another cross-sectional view of the articulation joint and rotary drive system of FIG. 109 with a proximal joint member of the articulation joint articulated relative to a central joint member of the articulation joint.

In the illustrated example, the rotary drive screw 13700 is driven by a rotary drive system 13600 that comprises a proximal rotary drive shaft 13610 that is rotatably supported within an axial passage 12225 within the proximal joint member 12210. As can be seen in FIG. 105, the proximal rotary drive shaft 13610 comprises a proximal end 13612 and a distal end 13614. The proximal end 13612 may interface with a gear box/motor arrangement 9050 or other source of rotary motion housed in the housing 9020 of the surgical instrument 9010. Such source of rotary motion causes the proximal rotary drive shaft 13610 to rotate about the shaft axis SA within the axial passage 12225 in the proximal joint member 12210. See FIG. 104. As can be seen in FIG. 105, the distal end 13614 of the proximal rotary drive shaft 13610 is movably coupled to a first drive shaft segment 13620. In the illustrated example, the first drive shaft segment 13620 resembles a "dog bone" with a first spherical proximal end 13622 and a first spherical distal end 13624. See FIG. 106. The first spherical proximal end 13622 is movably pinned within a first distal socket 13616 formed in the distal end 13614 of the proximal rotary drive shaft 13610 by a first proximal pin 13618. The first proximal pin 13618 extends through an arcuate transverse slot 13623 in the first spherical proximal end 13622. Such arrangement permits the first spherical proximal end 13622 to move in multiple directions within the first distal socket 13616 while remaining attached thereto. The first spherical distal end 13624 is received within a first proximal socket 13632 in a central bearing housing 13630 that is mounted within the central joint member 12230. The first spherical distal end 13624 is movably pinned within the first proximal socket 13632 by a first distal pin 13634. The first distal pin 13634 extends through an arcuate transverse slot 13625 in the first spherical distal end 13624. Such arrangement permits the first spherical distal end 13624 to move in multiple directions within the first proximal socket 13632 while remaining attached to the central bearing housing 13630.

As can be seen in FIG. 105, the rotary drive system 13600 further comprises a second drive shaft segment 13640 that resembles the first drive shaft segment 13620 and includes a second spherical proximal end 13642 and a second spherical distal end 13644. The second spherical proximal end 13642 is movably pinned within a second distal socket 13636 that is formed in the central bearing housing 13630 by a second proximal pin 13637. The second proximal pin 13637 extends through an arcuate transverse slot 13643 in the second spherical proximal end 13642. Such arrangement permits the second spherical proximal end 13642 to move in multiple directions within the second distal socket 13636 while remaining attached thereto. The second spherical distal end 13644 is received within a second proximal socket 13706 in the rotary drive screw 13700 and is movably pinned within the second proximal socket 13706 by a second distal pin 13647. The second distal pin 13647 extends through a transverse slot 13646 in the second spherical distal end 13644. Such arrangement permits the second spherical distal end 13644 to move in multiple directions relative to the rotary drive screw 13700.

The double joint rotary drive maintains a linear velocity output by using the angle constraint of the joint members of the articulation joint. This universal rotary joint arrangement on its own may have a sinusoidal output based on the angle of the joint. If the angles are equal and the phases are aligned correctly, the sine output of the first universal joint will be canceled out by the second universal joint, producing a linear rotational velocity. This is an advantage to putting a constraint in the rotary drive because it decreases the complexity of the components and prevents the need to remove material from the components to attain the requisite clearance. Thus, the components of this embodiment are more robust and stronger than prior arrangements. Further, the constant velocity of the rotary drive system will allow for smoother firing and reduced wear that may be otherwise caused by vibration.

Returning to FIG. 102, the rotary drive screw 13700 comprises helical grooves or drive features 13708 formed on a circumference thereof that are configured to engage and drive the upper balls or spheres 13422 in the upper series 13410 of upper chain link features 13420 and the lower balls or spheres 13522 in the lower series 13510 of lower chain link features 13520. Thus, to drive the firing member 13310 from a starting position in the surgical end effector 10000 to an ending position within the end effector, the rotary drive system 13600 is actuated to apply a rotary drive motion to the rotary drive screw 13700. As the rotary drive screw 13700 rotates in the first rotary direction, the helical drive features 13708 engage the upper balls or spheres 13422 in the upper series 13410 of upper chain link features 13420 and the lower balls or spheres 13522 in the lower series 13510 of lower chain link features 13520 and drive the upper flexible chain drive assembly 13400 and the lower flexible chain drive assembly 13500 distally. As each upper ball 13422 and lower ball 13522 engage the rotary drive screw 13700, the upper balls 13422 in the upper series 13410 that are distal to the rotary drive screw 13700 (and the articulation joint 12200) and the lower balls 13522 in the lower series 13510 that are distal to the rotary drive screw 13700 (and the articulation joint 12200) are placed under compression to apply balanced axial drive forces to the firing member 13310. When the upper flexible chain drive assembly 13400 and the flexible lower chain drive assembly 13500 are in compression, they are constrained by the slots in the anvil 10210 and the elongate channel 10110, respectively. Such arrangement ensures that, when the upper flexible chain drive assembly 13400 and lower flexible chain drive assembly 13500 are compressed, they do not buckle.

This arrangement enables two degrees of articulation freedom for a few reasons. For example, the upper flexible chain drive assembly 13400 and lower flexible chain drive assembly 13500 can bend freely both in the pitch and yaw axes. Thus, the upper flexible chain drive assembly 13400 and lower flexible chain drive assembly 13500 can assume a variety of configurations that can accommodate various articulated positions that are attainable with the articulation joint 12200. Once the firing member 13310 has traveled through the surgical end effector 10000 distally to an ending position therein, the rotary drive system 13600 is actuated to apply a second rotary drive motion to the rotary drive screw 13700 to cause the rotary drive screw 13700 to rotate about the shaft axis in a second rotary direction. As the rotary drive screw 13700 rotates in the second rotary direction, the upper flexible chain drive assembly 13400 and the lower flexible chain drive assembly 13500 serve to retract the firing member 13310 in the proximal direction back to the starting position. As the upper flexible chain drive assembly 13400 and the lower flexible chain drive assembly 13500 retract the firing member 13310 proximally, a portion of the upper flexible chain drive assembly 13400 and the lower flexible chain drive assembly 13500 traverse back through the articulation joint 12200 and into the elongate shaft. Such arrangement allows the firing member 13310 to translate a long distance, without increasing the length of the end effector joint. Additionally, because the rotary drive screw 13700 drivingly engages the upper flexible chain drive assembly 13400 and the lower flexible chain drive assembly 13500 at a location that is distal to the articulation joint 12200, the high compressive loads are contained within the surgical end effector 10000 and do not create a moment on the articulation joint 12200. This arrangement may greatly reduce the strength requirements of the articulation joint. See FIG. 104.

In at least one arrangement, the surgical instrument 9010 may further comprise a cable tensioning system 13800 that is configured to maintain a desired amount of tension on the upper flexible chain drive assembly 13400 and the lower flexible chain drive assembly 13500 as they bend through the articulation joint 12200. Keeping the upper flexible chain drive assembly 13400 and the lower flexible chain drive assembly 13500 under a desired amount of tension as they traverse through the articulation joint 12200 may prevent slack from forming in those flexible chain drive assemblies 13400, 13500 which might otherwise cause them to undesirably bunch up in the articulation joint 12200. FIGS. 111 and 112 illustrate one form of cable tensioning system 13800 which comprises constant force spring arrangements 13810 and 13820. Such solution has the benefit of not requiring length conservation of the flexible chain drive assemblies 13400, 13500.

Another cable management system 13800' is illustrated in FIGS. 113 and 114. In this arrangement, the proximal ends of the flexible chain drive assemblies 13400, 13500 are coupled together and journaled around a cable management pulley 13840 that is configured to translate with the firing member 13310. When the firing member 13310 is distally advanced during the firing stroke, the cable management pulley 13840 also translates distally maintaining tension in the flexible chain drive assemblies 13400, 13500. During articulation, a length of one of the flexible chain drive assemblies 13400, 13500 would increase, while the other would decrease. Such arrangement serves to minimize the lengths of the flexible chain drive assemblies 13400, 13500 required to fully actuate and articulate the surgical end effector 10000.

One method of using the surgical instrument 9010 may involve the use of the surgical instrument to cut and staple target tissue within a patient using laparoscopic techniques. For example, one or more trocars may have been placed through the abdominal wall of a patient to provide access to a target tissue within the patient. The surgical end effector 10000 may be inserted through one trocar and one or more cameras or other surgical instruments may be inserted through the other trocar(s). To enable the surgical end effector 10000 to pass through the trocar cannula, the surgical end effector 10000 is positioned in an unarticulated orientation (FIG. 63) and the jaws 10100 and 10200 must be closed. To retain the jaws 10100 in the closed position for insertion purposes, for example, the cable control system 9030 is actuated to pull the first cable 12510 and the fourth cable 12540 simultaneously which causes the pulley unit 12610 to rotate and cause the closure cams 10626, 10636 to contact the anvil closure arms 10234 to pivot the anvil 10210 into the closed position. See FIG. 97. The cable control system 9030 is deactivated to retain the anvil 10210 in the closed position. Once the surgical end effector 10000 has passed into the abdomen through the trocar, the cable control system 9030 is activated to rotate the pulley unit 12610 in an opposite direction to the position shown in FIG. 96 to permit the anvil 10210 to be biased open by the anvil springs 10240.

Once inside the abdomen and before engaging the target tissue, the surgeon may need to articulate the surgical end effector 10000 into an advantageous position. The cable control system 9030 may then be actuated to articulate the surgical end effector 10000 in one or more planes relative to a portion of the elongate shaft assembly 12000 that is received within the cannula of the trocar. Once the surgeon has oriented the surgical end effector 10000 in a desirable position, the cable control system 9030 is deactivated to retain the surgical end effector 10000 in the articulated orientation. Thereafter, the surgeon may activate the cable control system 9030 in the above-described manner to cause the anvil 10210 to rapidly close to grasp the tissue between the anvil 10210 and the surgical staple cartridge 10300. This process may be repeated as necessary until the target tissue has be properly positioned between the anvil 10210 and the surgical staple cartridge 10300.

Once the target tissue has been positioned between the anvil 10210 and the surgical staple cartridge 10300, the surgeon may activate the cable control system 9030 to close the anvil 10210 to clamp the target tissue in position. Thereafter, the firing process may be commenced by activating the rotary drive system 13600 to drive the firing member 13310 distally from the starting position. As the firing member 13310 moves distally, the firing member 13310 contacts a sled that is supported in the surgical staple cartridge 10300 and also drives the sled distally through the staple cartridge body. The sled serially drives rows of drivers supported in the staple cartridge toward the clamped target tissue. Each driver has supported thereon one or more surgical staples or fasteners which are then driven through the target tissue and into forming contact with the underside of the anvil 10210. As the firing member 13310 moves distally, the tissue cutting edge 13318 thereon cuts through the stapled tissue.

After the firing member 13310 has been driven distally to the ending position within the surgical end effector 10000, the rotary drive system 13600 is reversed which causes the firing member 13310 to retract proximally back to the starting position. Once the firing member 13310 has returned to the starting position, the cable control system 9030 may be activated to rotate the pulley unit 12610 back to an open position wherein the anvil springs 10240 can pivot the anvil 10210 to the open position to enable the surgeon to release the stapled tissue from the surgical end effector 10000. Once the stapled tissue has been released, the surgical end effector 10000 may be withdrawn out of the patient through the trocar cannula. To do so, the surgeon must first actuate the cable control system 9030 to return the surgical end effector 10000 to an unarticulated position and actuate the cable control system 9030 to pivot the anvil 10210 to the closed position. Thereafter, the surgical end effector 10000 may be withdrawn through the trocar cannula.

In previous endocutter arrangements, the firing member is pushed by a flexible beam. In such arrangements, the articulation joint must redirect the linear motion of the flexible beam as it enters the articulation joint back to that linear motion as it exits the articulation joint and enters the end effector. Because of the high loads required to push the flexible beam and the firing member, the flexible beam commonly experiences high amounts of friction as it exits the articulation joint and is linearly redirected into the end effector. This added amount of friction increases the amount of driving forces that are required to drive the firing member from the starting to ending position within the end effector while the end effector is articulated. Further, as the flexible beam traverses the articulation joint, it may apply de-articulation motions to the articulation joint components. Thus, the articulation joint components must be sufficiently robust so as to resist such de-articulation motions.

Other forms of surgical endocutters employ rotary forces to drive the firing member through the end effector. Such arrangements commonly employ a rotary drive screw that is housed within the channel that supports the staple cartridge. During use, the sled and tissue place large moments on the firing member which decrease the efficiency of the system and ultimately require higher rotary forces to actuate the firing member. It is difficult to move the rotary drive screw closer to the center of such forces because of the cartridge and the location of the tissue. It is also difficult to package a screw on top and bottom of the firing member without increasing the overall diameter of the surgical end effector. The various embodiments discussed above may address many if not all of these issues and challenges.

FIGS. 115-139 illustrate another form of surgical instrument 25010 that may address many of the challenges facing surgical instruments that comprise end effectors that are articulatable to large articulation angles and that are configured to cut and fasten tissue. In various embodiments, the surgical instrument 25010 may comprise a handheld device. In other embodiments, the surgical instrument 25010 may comprises an automated system sometimes referred to as a robotically-controlled system, for example. In various forms, the surgical instrument 25010 comprises a surgical end effector 26000 that is operably coupled to an elongate shaft assembly 28000. The elongate shaft assembly 28000 may be operable attached to a housing. In one embodiment, the housing may comprise a handle that is configured to be grasped, manipulated and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

Figure 119:
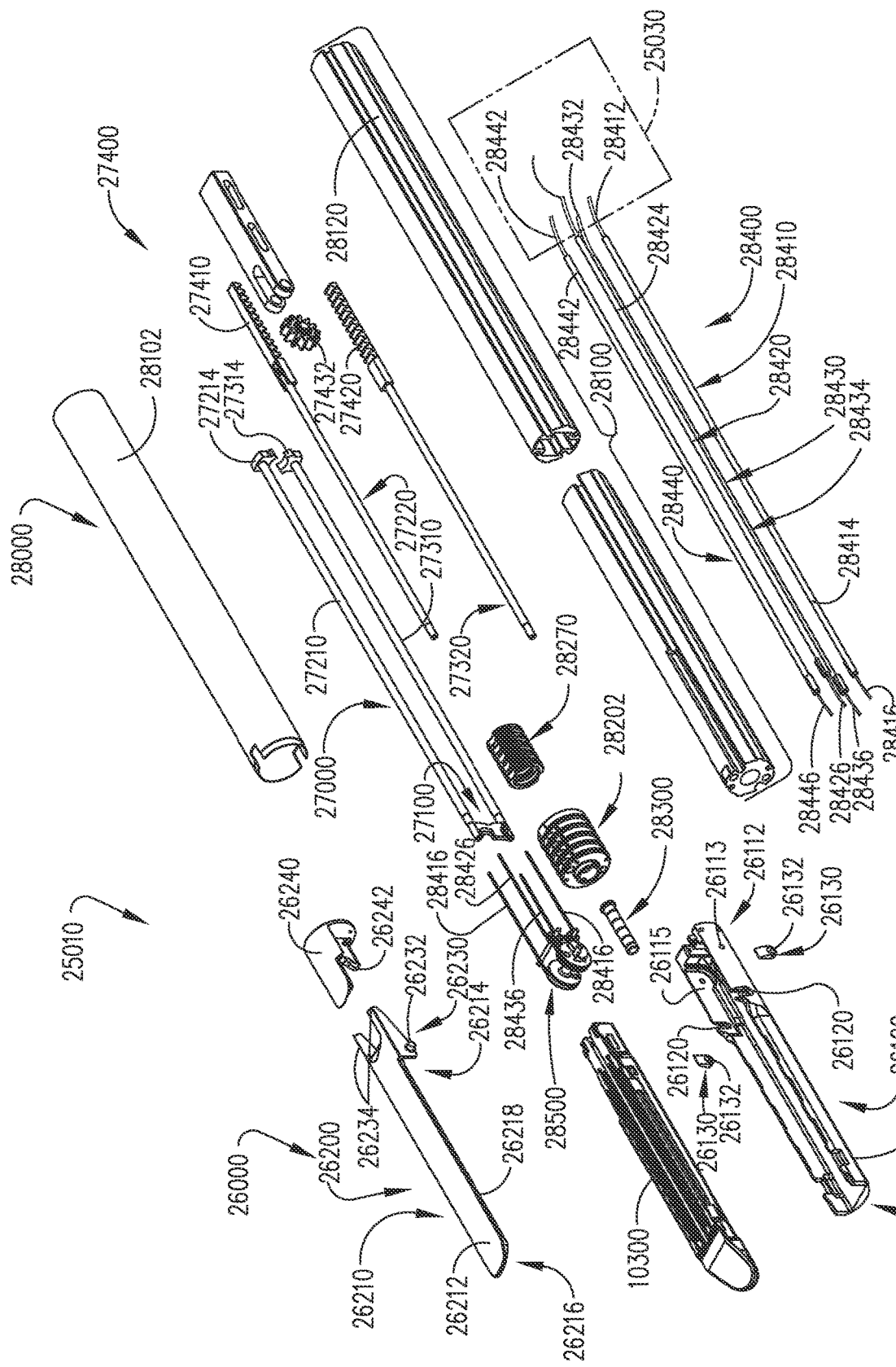

In one form, the surgical end effector 26000 comprises a first jaw 26100 and a second jaw 26200. In the illustrated arrangement, the first jaw 26100 comprises an elongate channel 26110 that comprises a proximal end 26112 and a distal end 26114 and is configured to operably support a surgical staple cartridge 10300 therein. An example of a surgical staple cartridge 10300 was described in detail above. The second jaw 26200 comprises an anvil 26210 that comprises an elongate anvil body 26212 that has a proximal end 26214 and a distal end 26216. The anvil body 26212 comprises a staple-forming undersurface 26218 that faces the first jaw 26100 and may include a series of staple-forming pockets (not shown) that corresponds to each of the staples or fasteners in the surgical staple cartridge 10300. As can be seen in FIG. 119, the proximal end 26214 of the anvil body 26212 comprises an anvil mounting portion 26230 that comprises a pair of laterally extending mounting pins 26232 that are configured to be received in corresponding mounting inserts 26130 that are configured to be retainingly received within mounting cradles 26120 formed in a proximal end 26112 of the elongate channel 26110. The mounting pins 26232 are pivotally received within pivot holes 26132 in the mounting inserts 26130 and then the mounting inserts 26130 are inserted into their corresponding cradle 26120 and affixed to the elongate channel 26110 by welding, adhesive, snap fit, etc. Such arrangement facilitates pivotal travel of the anvil 26210 relative to the elongate channel 26110 about a fixed pivot axis PA. See FIG. 115. As stated above, as used in this context, the term "fixed" means that the pivot axis PA is non-translating or non-moving relative to the elongate channel 26110.

In the illustrated arrangement, the elongate shaft assembly 28000 defines a shaft axis SA and comprises a shaft spine assembly 28100 that is received in a hollow outer shaft tube 28102. See FIG. 119. The shaft spine assembly 28100 may operably interface with a housing of the control portion (e.g., handheld unit, robotic tool driver, etc.) of the surgical instrument 25010 and in one example, comprises a proximal spine segment 28120 and a distal spine segment 28140.

Figure 120:
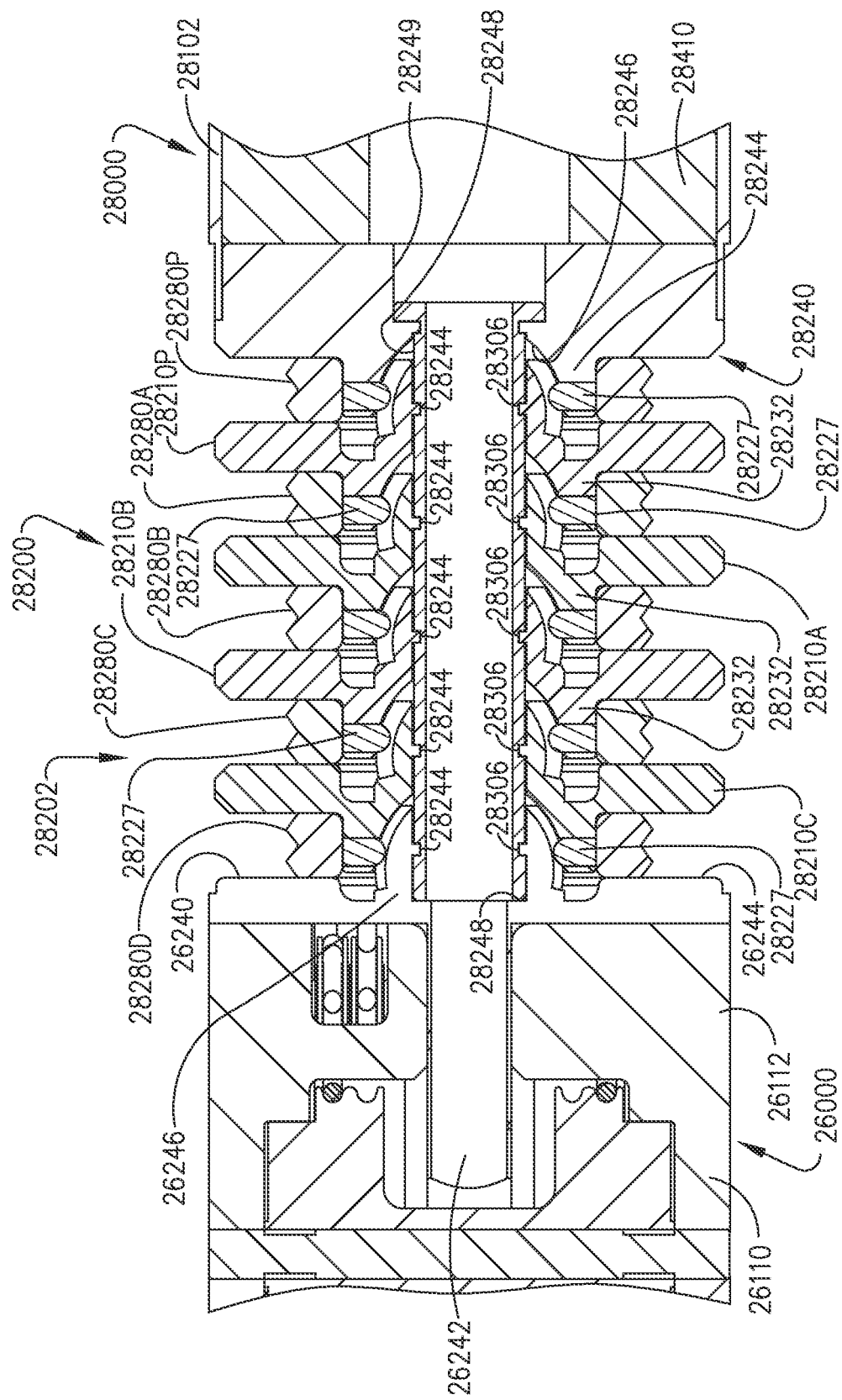
Figure 121:
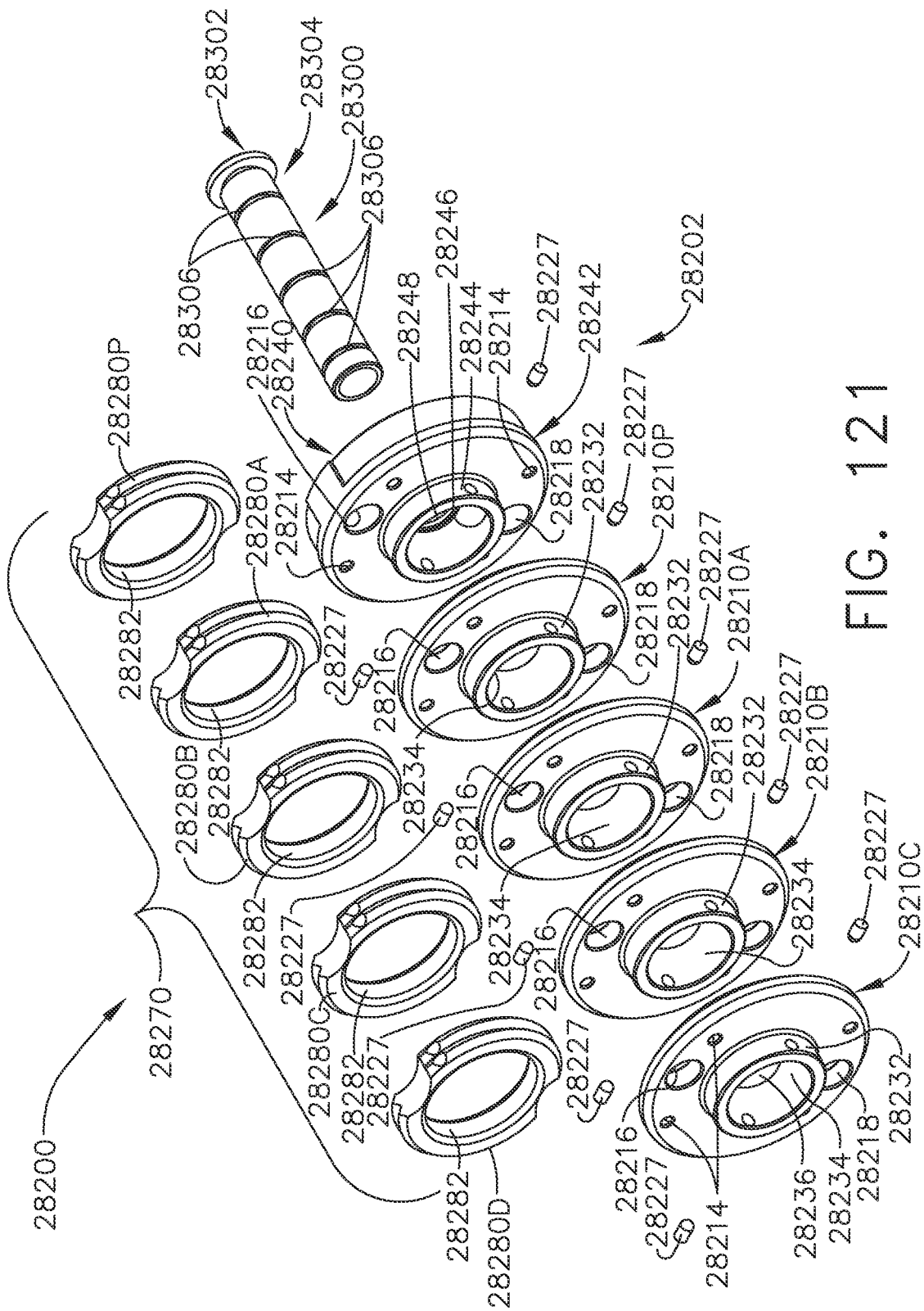

The elongate shaft assembly 28000 further comprises an articulation joint 28200 that may be attached to the distal spine segment 28140 as well as the surgical end effector 26000 to facilitate selective articulation of the surgical end effector 26000 relative to the elongate shaft assembly 28000 in multiple articulation planes. Turning now to FIGS. 120-125, the articulation joint 28200 comprises a series 28202 of movably interfacing annular disc members 28210. As can be seen in FIGS. 122, 123, and 125, each annular disc member 28210 comprises a "first" or proximal face 28220 that comprises a centrally-disposed spherical feature or protrusion 28222. Each annular disc member 28210 further comprises a second or distal face 28230 that comprises an annular hub portion 28232 that defines a concave socket 28234 therein. See FIGS. 122 and 124. Each annular disc member 28210 further has a central shaft passage 28236 therethrough. As can be seen in FIGS. 120 and 121, the articulation joint 28200 further comprises a proximal attachment disc assembly 28240 that is configured to be attached to a distal end of the distal spine segment 28140 by welding, adhesive, or other suitable fastener arrangement. The proximal attachment disc assembly 28240 comprises a distal face 28242 that includes an annular hub portion 28244 that defines a concave socket 28246 therein. The proximal attachment disc 28240 further has a central shaft passage 28248 therethrough. Also in the illustrated arrangement, the anvil mounting bracket 26240 is configured to operably interface with the articulation joint 28200. The anvil mounting bracket 26240 is attached to the proximal end 26112 of the elongate channel 26110 of the surgical end effector 26000 by welding, adhesive or other suitable fastener arrangements and comprises a proximal face 26244 that has a centrally-disposed spherical feature or protrusion 26246 protruding therefrom. See FIG. 120. The anvil mounting bracket 26240 further has a central shaft passage 26248 therethrough.

In at least one embodiment, the articulation joint further comprises a series 28270 of elastomeric annular spacer members 28280 that serve to space and provide elastic support between each annular disc member 28210. The elastomeric annular spacer members 28280 define a spacer opening 28282 such that each elastomeric spacer member 28280 may be journaled on an annular hub portion 28232 of a corresponding annular disc member 28210. Each annular disc member 28210 is journaled on a central elastomeric support or continuum shaft 28300 that is mounted to the proximal attachment disc assembly 28240 and the anvil mounting bracket 26240. In one arrangement, the central continuum shaft 28300 is fabricated from an elastomeric material (e.g., rubber, polymer, etc.) and comprises a flanged proximal end 28302 and a cylindrical body portion 28304. The cylindrical body portion 28304 comprises a series of annular grooves 28306 therein. Each annular groove 28306 corresponds to one of the annular disc members 28210. The annular disc members 28210 and annular spacer members 28280 are journaled on the central continuum shaft 28300 as shown in FIG. 120. The flanged proximal end 28302 of the central continuum shaft 28300 is supported in a proximal passage 28249 in the proximal attachment disc 28240. The cylindrical body portion 28304 of the central continuum shaft 28300 extends through the central passage 28236 in each of the annular disc members 28210 in the series 28202 of movably interfacing annular disc members 28210. Each centrally-disposed spherical feature or protrusion 28222 comprises an annular key member 28224 that is configured to be received in a corresponding annular groove 28306 in the central continuum shaft 28300. Such arrangement may serve to orient each annular disc member 28210 in a desired spacing orientation on the central continuum shaft 28300, for example.

Still referring to FIG. 120, a proximal-most elastomeric spacer member 28280P is journaled on the annular hub portion 28244 of the proximal attachment disc assembly 28240 such that it is positioned between a proximal-most annular disc member 28210P and the proximal attachment disc 28240. The annular key member 28224 of the proximal-most annular disc member 28210P is received within a corresponding annular groove 28306 in the central continuum shaft 28300 to position the centrally-disposed spherical feature or protrusion 28222 of the proximal-most annular disc member 28210P within the concave socket 28246 in the annular hub portion 28244 of the proximal attachment disc 28240. As can further be seen in FIG. 120, another elastomeric spacer member 28280A is journaled on the annular hub portion 28232 of the proximal-most annular disc member 28210P such that is positioned between the next annular disc member 28210A in the series 28202 of movably interfacing annular disc members 28202 and the proximal-most annular disc member 28210P. The annular key member 28224 of the annular disc member 28210A is received within a corresponding annular groove 28306 in the central continuum shaft 28300 to position the centrally-disposed spherical feature or protrusion 28222 of the annular disc member 28210A within the concave socket 28246 in the annular hub portion 28244 of the proximal attachment disc 28210P. Still referring to FIG. 120, another elastomeric spacer member 28280B is journaled on the annular hub portion 28232 of the annular disc member 28210A such that is positioned between the next annular disc member 28210B in the series 28202 of movably interfacing annular disc members 28210. The annular key member 28224 of the annular disc member 28210B is received within a corresponding annular groove 28306 in the central continuum shaft 28300 to position the centrally-disposed spherical feature or protrusion 28222 of the annular disc member 28210B within the concave socket 28246 in the annular hub portion 28244 of the annular disc member 28210A. Also in this arrangement, another elastomeric spacer member 28280C is journaled on the annular hub portion 28232 of the annular disc member 28210B such that is positioned between the distal-most annular disc member 28210C in the series of movably interfacing annular disc members 28202. The annular key member 28224 of the distal-most annular disc member 28210C is received within a corresponding annular groove 28306 in the central continuum shaft 28300 to position the centrally-disposed spherical feature or protrusion 28222 of the distal-most annular disc member 28210C within the concave socket 28246 in the annular hub portion 28244 of the annular disc member 28210B. Finally, another elastomeric spacer member 28280D is journaled on the annular hub portion 28232 of the distal-most annular disc member 28210C such that is positioned between the anvil mounting bracket 26240 and the distal-most annular disc member 28210C. The annular key member 28224 of the centrally-disposed spherical feature or protrusion 26246 of the anvil mounting bracket 26240 is received within a corresponding annular groove 28306 in the central continuum shaft 28300 to position the centrally-disposed spherical feature or protrusion 226246 of the anvil mounting bracket 26240 within the concave socket 28246 in the annular hub portion 28244 of the distal-most annular disc member 28210C.

In at least one arrangement, to limit pivotal travel of the annular disc members to a range of relative pivotal travel and prevent complete relative rotation of the annular disc members 28210 relative to each other, the centrally-disposed spherical feature or protrusion 28222 of each of the annular disc member 28210P, 28210A, 28210B, 28210C, as well as the distal spherical feature or protrusion 26246 of the anvil mounting bracket 26240, includes a pair of arcuate pin grooves 28226 therein. As can be seen in FIG. 120, a corresponding travel-limiting pin member 28227 is pressed into or otherwise attached to each annular hub portion 28232 and is received within the corresponding pin groove 28226 in the centrally-disposed spherical feature or protrusions 28222, 26246.

Returning to FIG. 119, in the illustrated example, the articulation joint 28200 may be operably controlled by an articulation system 28400 that comprises four cable assemblies 28410, 28420, 28430, and 28440 that extend through the elongate shaft assembly 28000. In one arrangement, the cable assembly 28410 comprises a proximal cable portion 28412 that is attached to an articulation rod 28414 that is supported in a corresponding axial groove in the shaft spine assembly 28100 for axial travel therein. A distal cable portion 28416 is attached to the articulation rod 28414. The cable assembly 28420 comprises a proximal cable portion 28422 that is attached to an articulation rod 28424 that is supported in a corresponding axial groove in the shaft spine assembly 28100 for axial travel therein. A distal cable portion 28426 is attached to the articulation rod 28414. The cable assembly 28430 comprises a proximal cable portion 28432 that is attached to an articulation rod 28434 that is supported in a corresponding axial groove in the shaft spine assembly 28100 for axial travel therein. A distal cable portion 28436 is attached to the articulation rod 28434. The cable assembly 28440 comprises a proximal cable portion 28442 that is attached to an articulation rod 28444 that is supported in a corresponding axial groove in the shaft spine assembly 28100 for axial travel therein. A distal cable portion 28446 is attached to the articulation rod 28444.

The proximal cable portions 28412, 28422, 28432, 28442 may operably interface with a portion of a cable control system 25030 that is supported within or is otherwise associated with a housing of the surgical instrument 25010. The cable control system 25030 may comprise a plurality of cable support members/capstans, pulleys, etc. that are controlled by one or more corresponding motors that are controlled by a control circuit portion of the surgical instrument 25010. In various embodiments, the cable control system 25030 is configured to manage the tensioning (pulling) and paying out of cables at precise times during the articulation process. In addition, in at least one arrangement, the cable control system 25030 may be employed to control the opening and closing of the anvil 26210 as will be discussed in further detail below.

Turning now to FIG. 126, the distal cable portions 28416, 28426, 28436, 28446 are configured to operably interface with a closure system 28500 that is rotatably mounted in the proximal end 26112 of the elongate channel 26110. As can be seen in FIG. 126, the closure system 28500 comprises a pulley unit 28510 that comprises a first lateral alpha wrap pulley 28520 and a second lateral alpha wrap pulley 28530 that are interconnected by a central shaft 28540. The pulley unit 28510 is rotatably supported within the proximal end 26112 of the elongate channel 26110 and retained therein by an anvil mounting bracket 26240 that is attached to the proximal end 26112 of the elongate channel 26112. See FIG. 119. The anvil mounting bracket 26240 may be attached to the proximal end 26112 of the elongate channel 26110 by welding, adhesive, snap features, etc. The anvil mounting bracket 26240 comprises a shaft cradle 26242 that is configured to rotatably support the central shaft 28540 within the elongate channel 26110. In the illustrated arrangement, a first pivot shaft 28521 protrudes from the first lateral alpha wrap pulley 28520 and is pivotally supported in a pivot hole 26113 in the proximal end of the elongate channel. Similarly, a second pivot shaft 28531 protrudes from the second lateral alpha wrap pulley 28530 and is pivotally supported in a pivot hole 26115 in the proximal end 26112 of the elongate channel 26110.

As can be seen in FIG. 126, the first alpha wrap pulley 28520 comprises a first circumferential groove 28522 and a second circumferential groove 28524. In the illustrated example, the first distal cable portion 28416 is received in the first circumferential groove 28522 and is attached thereto and the second distal cable portion 28426 is received in the second circumferential groove 28524 and is attached thereto. Pulling on the first distal cable portion 28416 will result in the rotation of the first lateral alpha wrap pulley 28520 in a first direction and pulling the second distal cable portion 28426 will result in the rotation of the first lateral alpha wrap pulley 28520 in a second opposite direction. Similarly, the second lateral alpha wrap pulley 28530 comprises a first circumferential groove 28532 and a second circumferential groove 28534. In the illustrated arrangement, the distal cable portion 28446 is received in the first circumferential groove 28532 and is attached thereto and the third distal cable portion 28436 is received in the second circumferential groove 28534 and is attached thereto. Pulling on the fourth distal cable portion 28446 will result in the rotation of the second alpha wrap pulley 28530 in the first direction and pulling the third distal cable portion 28436 will result in the rotation of the second lateral alpha wrap pulley 28530 in the second opposite direction. In accordance with one aspect, the lateral alpha wrap pulleys 28520, 28530 can rotate approximately three hundred thirty degrees. This range of rotational travel is in contrast to a normal pulley that may have a range of rotational travel that is less than one hundred eighty degrees of rotation.

Each of the first and second lateral alpha wrap pulleys 28520, 28530 also comprise a corresponding spiral closure cam that is configured to apply closure motions to the anvil 26210. As can be seen in FIG. 126, the first lateral alpha wrap pulley 28520 includes a first spiral closure cam 28526 and the second lateral alpha wrap pulley 28530 has a second spiral closure cam 28536 thereon. The spiral closure cams 28526, 28536 are configured to cammingly interact with corresponding anvil closure arms 26234 on the anvil mounting portion 26230 of the anvil 26210 to apply closure motions thereto. See FIG. 119. Rotation of the pulley unit 28510 in a first rotary direction will cause the spiral closure cams 28526, 28536 to cam the anvil 26210 to the closed position. To open the anvil 26210, the pulley unit 28510 is rotated in opposite direction to position the spiral closure cams 28526, 28536 in positions wherein the anvil 26210 can be pivoted open by an anvil spring (not shown).

Figure 127:
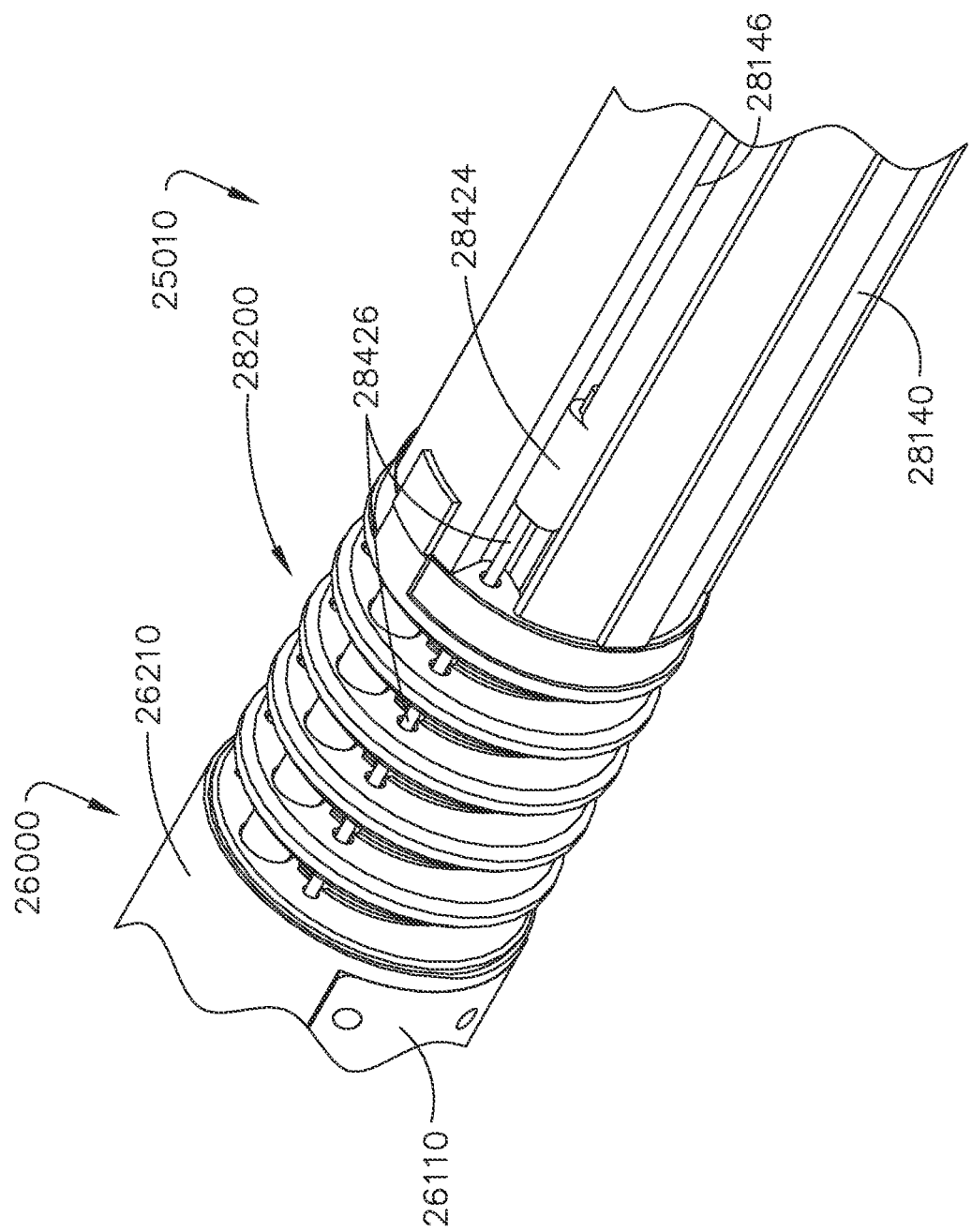
Figure 128:
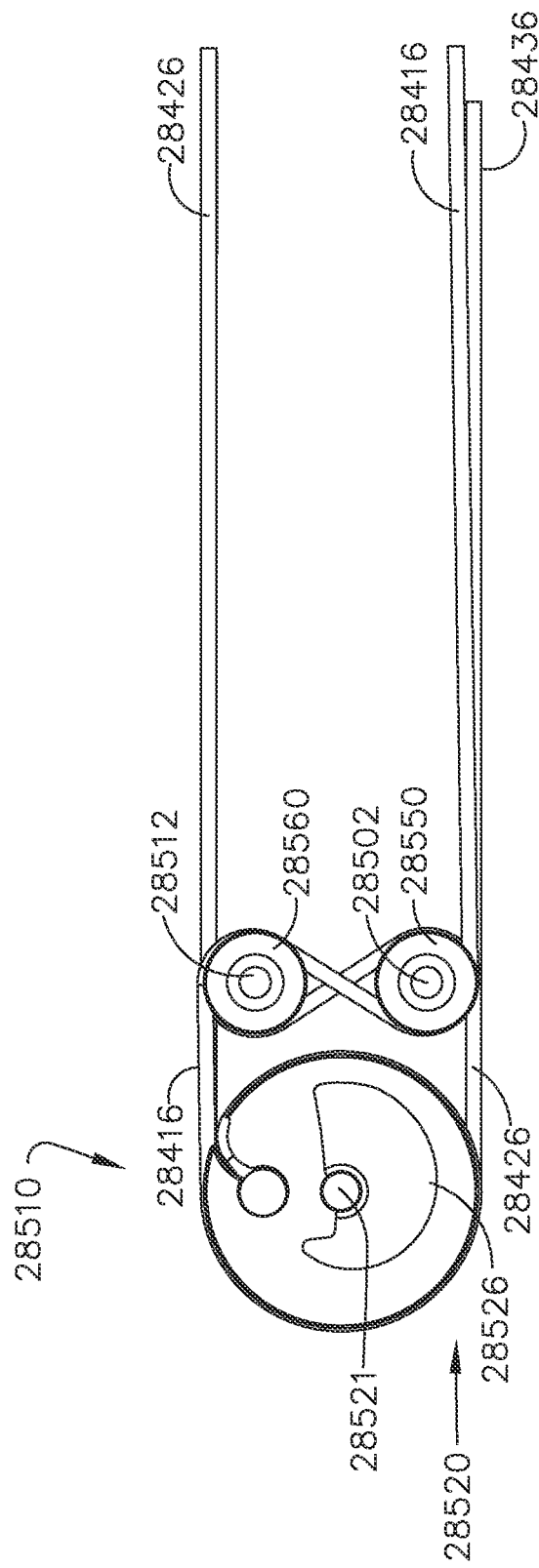
Figure 129:
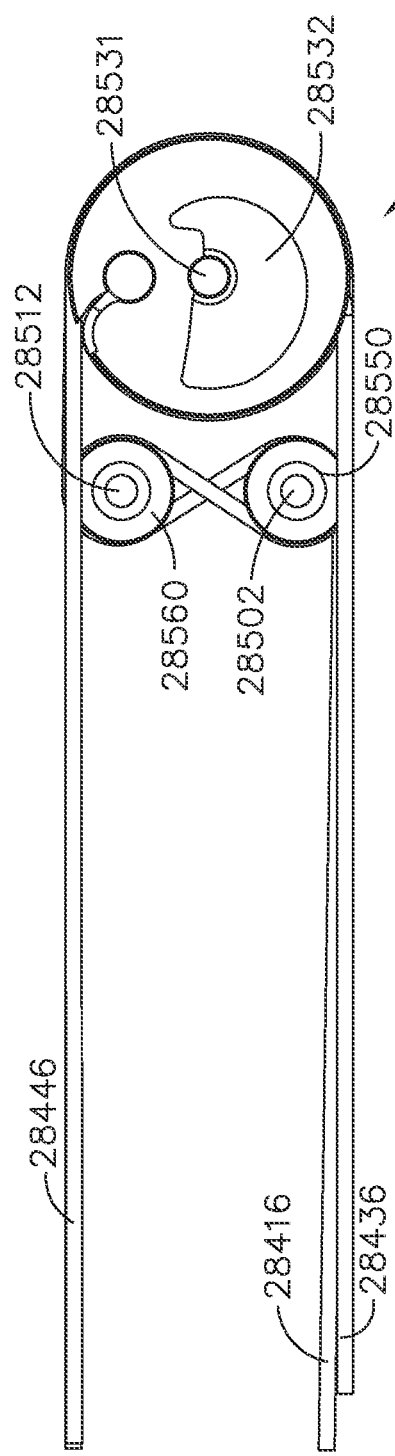
Figure 130:
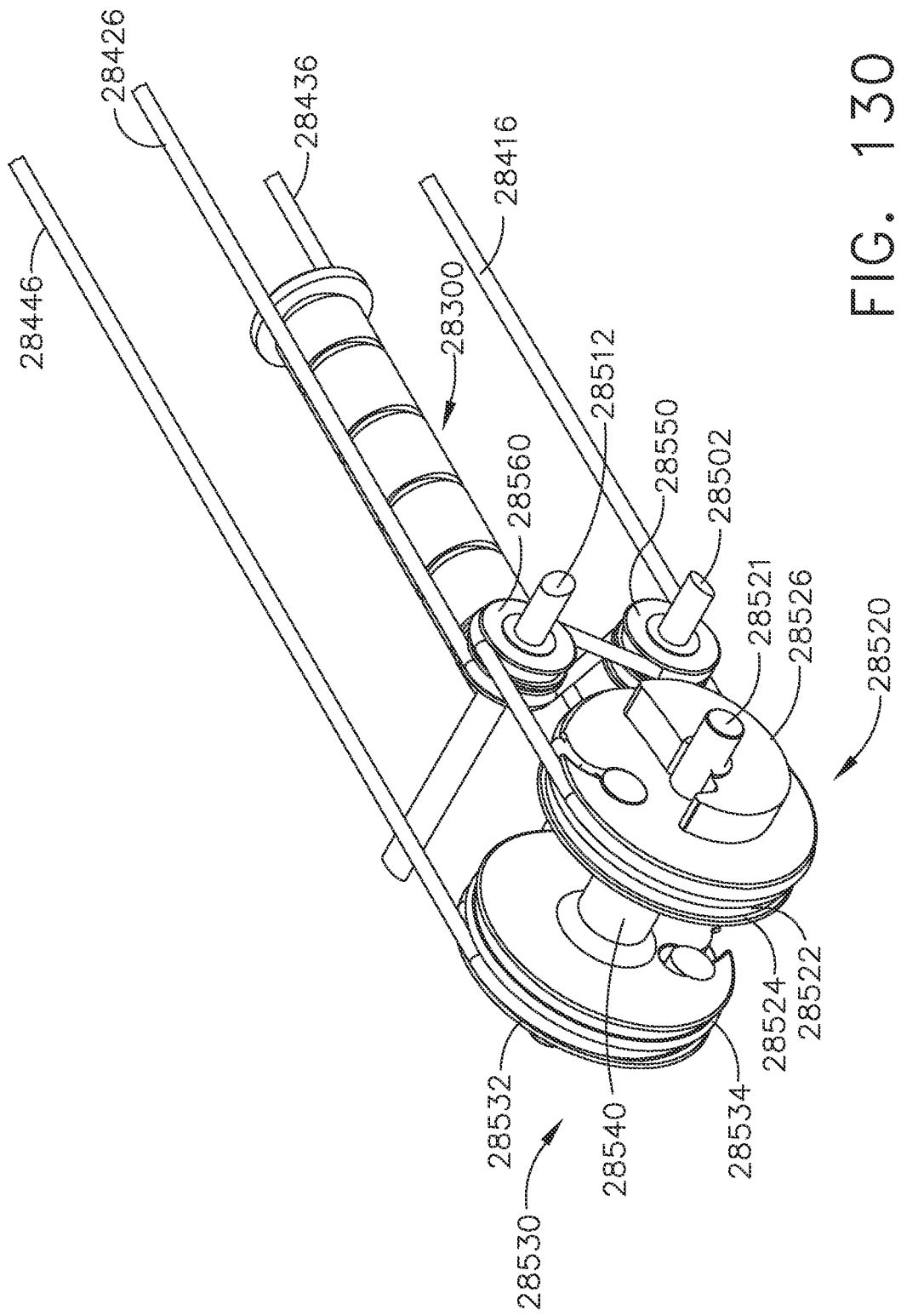

In the illustrated arrangement, the proximal attachment disc 28240, the proximal-most annular disc member 28210P, annular proximal disc members 28210A, 28210B, 28210C and anvil mounting bracket 26240 all include fourth articulation cable passages 28214 that are configured to permit each of the distal cable portions 28416, 28426, 28436, and 28446 to pass therethrough. FIG. 127 illustrates the articulation rod 28424 slidably supported in a corresponding axial groove 28146 in the distal spine segment 28140 for axial travel therein. Each of the other articulation rods 28414, 28434, 28444 is similarly supported in axial grooves in the distal spine segment 28140 as well as corresponding grooves in the proximal spine segment 28120.

Referring now to FIGS. 119 and 128-130, the distal cable portion 28416 extends from the articulation rod 28414 through the articulation joint 28200 and is looped around two redirect pulleys 28550, 28560 that are supported on shafts 28502, 28512 that are rotatably mounted in the proximal end 26112 of the elongate channel 26110. The distal cable portion 28416 exits the articulation joint 28200 to be received within the first circumferential groove 28522 in the first lateral alpha wrap pulley 28520 where it is secure therein. The distal cable portion 28426 extends from the articulation rod 28424 through the articulation joint 28200 to be looped around the redirect pulleys 28560, 28550 to be received within the second circumferential groove 28524 in the first lateral alpha wrap pulley 28520 where it is secure therein.

In the illustrated example, distal cable portion 28436 extends from the articulation rod 28434 through the articulation joint 28200 to be received within a corresponding circumferential groove 28534 in the second lateral alpha wrap pulley 28530 where it is secured therein. In addition, the distal cable portion 28446 extends from the articulation rod 28444 through the articulation joint 28200 to be received within a corresponding circumferential groove 28532 in the second lateral alpha wrap pulley 28530 where it is secure therein.

In at least one example, to articulate the surgical end effector 26000 relative to the elongate shaft assembly 28000 through a first articulation plane, the cable control system 25030 is actuated to pull on the distal cable portion 28426 and the distal cable portion 28446 simultaneously with a same amount of tension being applied to each distal cable portion 28426, 28446. Because the distal cable portions 28426, 28446 apply equal amounts of tension on both sides of the pulley unit 28510, the pulley unit 28510 does not rotate. However, the pulling action of the distal cable portions 28426, 28446 is translated through the articulation joint 28200 to the surgical end effector 26000 which results in the articulation of the articulation joint 28200 through a first articulation plane. To articulate the surgical end effector 26000 through a second plane of articulation that is transverse to the first plane of articulation, the cable control system 25030 is actuated to pull the distal cable portion 28436 and the distal cable portion 28446 simultaneously with a same amount of tension being applied to each distal cable portion 28436, 28446. Because the distal cable portions 28436, 28446 apply equal amounts of tension on both sides of the second lateral alpha wrap pulley 25830 of the pulley unit 28510, the pulley unit 28510 does not rotate. However, the pulling action of the distal cable portions 28436, 28446 is translated through the articulation joint 28200 to the surgical end effector 26000 which results in the articulation of the articulation joint 28200 in a second articulation plane.

The cable control system 25030 may also be used to control the opening and closing of the anvil 26210 in the following manner. As indicated above, when the spiral closure cams 28526 on the first lateral alpha wrap pulley 28520 and the second lateral alpha wrap pulley 28530 are in a first position, the anvil 26210 may be pivoted to an open position by an anvil spring or springs (not shown) that are positioned in the proximal end 26112 of the elongate channel 26110 and are position to contact the anvil mounting portion 26230 or anvil closure arms 26234 to pivot the anvil 26210 to the open position. To close the anvil 26210 from that position, the cable control system 25030 is actuated to pull the distal cable portion 28416 and the distal cable portion 28446 simultaneously with a same amount of tension being applied to each distal cable portion 28416 and 28446. These distal cable portions 28416, 28446 will cause the pulley unit 28510 to rotate causing the spiral closure cams 28526, 28536 to contact the anvil closure arms 26234 and cam the anvil 26210 to a closed position. It will be appreciated that by applying equal amounts of tension into the distal cable portions 28416, 28446, no moment is applied to the articulation joint 28200 because there are equal amounts of tension being applied on each side of the shaft axis SA. Such arrangement allows the jaw closure to be profiled as desired. This cable-control system 25030 may allow for a faster closure when the anvil 26210 is fully open. The cable-control system 25030 can also function as a lower speed/higher force generating closure mechanism for clamping onto tissue. The present cable controlled system 25030 may not produce the backlash that commonly occurs with other cable-controlled systems and thus can also be used to control the articulation position of the end effector. The above-described articulation joint 28200 and cable controlled system 25030 can facilitate multiple plane articulation while also supplying an additional actuation motion to the surgical end effector 26000.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 25010 employs a firing system 27000 that may address many if not all of such issues.

Referring now to FIGS. 133 and 134, in at least one embodiment, the firing system 27000 comprises a firing member 27100 that includes a vertically-extending firing member body 27112 that comprises a top firing member feature 27120 and a bottom firing member feature 27130. A tissue cutting blade 27114 is attached to or formed in the vertically-extending firing member body 27112. In at least one arrangement, the top firing member feature 27120 comprises a top tubular body 27122 that has a top axial passage 27124 extending therethrough.

See FIG. 134. The bottom firing member feature 27130 comprises a bottom tubular body 27132 that has a bottom axial passage 27134 extending therethrough. In at least one arrangement, the top firing member feature 27120 and the bottom firing member feature 27130 are integrally formed with the vertically-extending firing member body 27112. In at least one example, the anvil body 26212 comprises an axially extending anvil slot that has a cross-sectional shape that resembles a "keyhole" to accommodate passage of the top firing member feature 27120 in the various manners discussed herein. Similarly, the elongate channel 26110 comprises an axially extending channel slot that also has a keyhole cross-sectional shape for accommodating passage of the bottom firing member feature 27130 as described above.

In the illustrated arrangement, the firing system 27000 comprises an upper firing assembly 27200 that operably interfaces with the top firing member feature 27120. The upper firing assembly 27200 includes an upper flexible outer tube or conduit 27210 that has a proximal end 27212 that is fixed to an upper insert 27214 that is non-movably attached to the shaft spine assembly 28100. For example, the upper insert 27214 may be welded to the shaft spine assembly 28100 or otherwise be attached thereto by adhesive or other appropriate fastening means. The flexible outer tube or conduit 27210 extends through upper passages 28216 provided through the proximal attachment disc assembly 28240, the proximal-most annular disc member 28210P, the annular disc members 28210A, 28210B, 28210C and the anvil mounting bracket 26240. A distal end 27216 of the flexible outer tube or conduit 27210 may be affixed to the anvil mounting bracket 26240.

In the illustrated embodiment, the upper firing assembly 27200 further includes an upper push rod 27220 that is slidably supported in a corresponding axial passage in the shaft spine assembly 28100. The upper firing assembly 27200 further comprises an upper push coil 27230 that is supported in an inner flexible upper sleeve 27240 which extends through the upper flexible outer tube or conduit 27210. A proximal end 27232 of the upper push coil 27230 and a proximal end 27242 of the inner flexible upper sleeve 27240 abut a distal end 27222 of the upper push rod 27220. The upper push coil 27230 is hollow and may comprise a coil spring that is fabricated from Nitinol, titanium, stainless steel, etc. In other arrangements, the upper push coil 27230 comprises a laser cut "hypotube" that essentially comprises a hollow tubular member with offset laser cuts therein which enable the hypotube to flex and bend while being capable of transmitting axial forces or motions. The inner flexible upper sleeve 27240 may be fabricated from a polymer or similar material and prevent tissue, fluid, and/or debris from infiltrating into the upper push coil 27230 which may hamper its ability to flex and bend during articulation of the surgical end effector relative to the elongate shaft assembly.

As can be seen in FIG. 134, a distal end 27234 of the upper push coil 27230 as well as a distal end 27244 of the inner flexible upper sleeve 27240 abut a proximal end 27123 of the top tubular body 27122 or the top firing member feature 27120. Also in the illustrated arrangement, the upper firing assembly further comprises an upper push coil cable 27250 that extends through the hollow upper push coil 27230. The upper push coil cable 27250 comprises an upper cable proximal end 27252 that is secured to the distal end 27222 of the upper push rod 27220 and an upper cable distal end 27254 that is secured within the top axial passage 27124 in the top tubular body 27122 of the top firing member feature 27120 by an upper attachment lug 27256. The upper push coil cable 27250 is held in tension between the top firing member feature 27120 an the upper push rod 27220 which serves to retain the distal end 27234 of the upper push coil 27230 as well as a distal end 27244 of the inner flexible upper sleeve 27240 in abutting contact with the proximal end 27123 of the top tubular body 27122 of the top firing member feature 27120 and the proximal end 27232 of the upper push coil 27230 and a proximal end 27242 of the inner flexible upper sleeve 27240 in abutting contact with the distal end 27222 of the upper push rod 27220.

In the illustrated example, the firing system 27000 further comprises a lower firing assembly 27300 that operably interfaces with the bottom firing member feature 27130. The lower firing assembly 27300 includes a lower flexible outer tube or conduit 27310 that has a proximal end 27312 that is fixed to a lower insert 27314 that is non-movably attached to the shaft spine assembly 28100. For example, the lower insert 27314 may be welded to the shaft spine assembly 28100 or otherwise be attached thereto by adhesive or other appropriate fastening means. The lower flexible outer tube or conduit 27310 extends through lower passages 28218 provided in each of the proximal attachment disc assembly 28240, the proximal-most annular disc member 28210P, annular disc members 28210A, 28210B, 28210C and anvil mounting bracket 26240. A distal end 27316 of the flexible outer tube or conduit 27310 is affixed to the anvil mounting bracket 26240.

In the illustrated embodiment, the lower firing assembly 27300 further includes a lower push rod 27320 that is slidably supported in a corresponding axial passage in the shaft spine assembly 28100. The lower firing assembly 27300 further comprises a lower push coil 27330 that is supported in an inner flexible lower sleeve 27340 which extends through the lower flexible outer tube or conduit 27310. A proximal end 27332 of the lower push coil 27330 and a proximal end 27342 of the inner flexible lower sleeve 27340 abut a distal end 27322 of the lower push rod 27320. The lower push coil 27330 is hollow and may comprise a coil spring that is fabricated from Nitinol, titanium, stainless steel, etc. In other arrangements, the lower push coil 27330 comprises a laser cut hypotube that essentially comprises a hollow tubular member with offset laser cuts therein which enable the hypotube to flex and bend. The inner flexible lower sleeve 27340 may be fabricated from a polymer or similar material and prevent tissue, fluid, and/or debris from infiltrating into the lower push coil 27330 which may hamper its ability to flex during articulation.

As can be seen in FIG. 134, a distal end 27334 of the lower push coil 27330 as well as a distal end 27344 of the inner flexible lower sleeve 27340 abut a proximal end 27133 of the bottom tubular body 27132 of the bottom firing member feature 27130. Also in the illustrated arrangement, the lower firing assembly 27300 further comprises a lower push coil cable 27350 that extends through the hollow lower push coil 27330. The lower push coil cable 27350 comprises a lower cable proximal end 27352 that is secured to the distal end 27322 of the lower push rod 27320 and a lower cable distal end 27354 that is secured within the bottom axial passage 27134 in the bottom tubular body 27132 of the bottom firing member feature 27130 by a lower attachment lug 27356. The lower push coil cable 27350 is held in tension between the bottom firing member feature 27130 an the lower push rod 27320 which serves to retain the distal end 27334 of the lower push coil 27330 as well as a distal end 27344 of the inner flexible lower sleeve 27340 in abutting contact with the proximal end 27133 of the bottom tubular body 27132 of the bottom firing member feature 27130 and the proximal end 27332 of the lower push coil 27330 and a proximal end 27342 of the inner flexible lower sleeve 27340 in abutting contact with the distal end 27322 of the lower push rod 27320.

In the illustrated arrangement, the firing system 27000 further comprises a differential drive assembly 27400 that is configured to axially drive the upper firing assembly 27200 and the lower firing assembly 27300. Turning to FIGS. 136-139, in at least one arrangement, a proximal end 27224 of the upper push rod 27220 is coupled to a first or upper gear rack 27410 of the differential drive assembly 27400. As can be seen in FIG. 136, the first or upper gear rack 27410 is slidably supported in an upper proximal axial cavity 28122 in the proximal spine segment 28120. Similarly, a proximal end 27324 of the lower push rod 27320 is coupled to a second or lower gear rack 27420 that is supported for axial travel within a lower proximal axial cavity 28124 in the proximal spine segment 28120. The differential drive assembly 27400 further comprises an axially movable carrier member 27430 that is centrally disposed between the first or upper gear rack 27410 and the second or lower gear rack 27420 and is supported for axial travel within a proximal axial cavity 28126 in the proximal spine segment 28120. See FIG. 136. Still referring to FIGS. 136-139, a pinion gear 27432 is pivotally pinned to the axially movable carrier member 27430 such that the pinion gear 27432 is meshing engagement with the first or upper gear rack 27410 and the second or lower gear rack 27420. The axially movable carrier member 27430 is driven axially within the proximal axial cavity 28126 in the proximal spine segment 28120 by a firing drive actuator 27440. See FIG. 137. In one arrangement, the firing drive actuator 27440 comprises a firing drive gear rack 27442 that drivingly interfaces with a drive gear 27444 that is driven by a firing motor 27446 that may be operably supported in or otherwise associated with the housing of the surgical instrument 25010. In other arrangements, the firing drive actuator 27440 may be axially driven distally and proximally by a cylinder arrangement or other suitable actuator interfacing therewith. As can be seen in FIGS. 137-139, the firing drive actuator 27440 may be attached to the axially movable carrier member 27430 by a pair of spaced coupler pins 27448 that are attached to the firing drive actuator 27440 and are received within corresponding axial slots 27434 in the axially movable carrier member 27430. Such arrangement permits some relative axial movement between the firing drive actuator 27440 and the axially movable carrier member 27430. For example, when the firing drive actuator 27440 is driven distally in the distal direction DD, the axially movable carrier member 27430 will not move distally until the coupler pins 27448 reach the distal ends of their corresponding axial slots 27434 at which point the axially movable carrier member 27430 will move distally. Likewise, the when the firing drive actuator 27440 is driven in the proximal direction PD, the axially movable carrier member 27430 will not move proximally until the coupler pins 27448 reach the proximal ends of their corresponding axial slots 27434 at which point the axially movable carrier member 27430 will move proximally.

Surgical stapling devices need to apply a high force on the firing member over a long displacement to form the staples and cut tissue. Transmitting that force through an articulated joint is especially challenging because it is difficult to redirect the forces in the desired direction and withstand the loads applied to it. The differential drive assembly 27400 described herein addresses and solves many, if not all of such challenges by employing two flexible outer tubes or conduits 27210, 27310 to constrain the paths of the flexible push coils 27230, 27330, respectively. As described herein, the upper flexible outer tube or conduit 27210 surrounds a portion of the upper push coil 27230 and the upper flexible outer tube or conduit 27310 surrounds a portion of the lower push coil 27330. Each of the outer tubes or conduits 27210, 27310 can bend but they also can resolve an axial tensile load. The ability to bend allows for the firing member force to be redirected through the articulated joint, and the ability to resolve tension allows for it to change the direction in which the push coil goes. When the push coil 27230, 27330 is put in compression, the flexible outer tube or conduit 27210, 27310 is put in tension. The outer tubes or conduits 27210, 27310 prevent the push coils 27230, 27330 from buckling. The outer tubes 27210, 27310 are terminated in a manner to resolve the tensile loads. As described above, the distal end 27216 of the flexible outer tube or conduit 27210 and the distal end 27316 of the flexible outer tube or conduit 27310 are both affixed to the anvil mounting bracket 26240. The proximal end 27212 of the flexible outer tube or conduit 27210 and the proximal end 27312 of the flexible outer tube or conduit 27310 are both affixed to the shaft spine assembly 28100. The pinion gear 27432 is in meshing engagement with the first or upper gear rack 27410 and the second or lower gear rack 27420 such that when one of the racks 27410, 27420 moves in one axial direction, the other rack 27410, 27420 axially moves in an opposite direction. As can be seen in FIGS. 138 and 139, during articulation, the pinion gear 27432 rotates so the flexible outer tubes or conduits 27210, 27310 can move to account for the change in path length. However, when the firing drive actuator 27440 is driven in the distal direction DD, the axially movable carrier member 27430 is actuated to push the push coils 27230, 27330 distally through the outer tubes or conduits 27210, 27310 to fire (i.e., drive the firing member 27100 distally) the tensile loads in the two flexible outer tubes or conduits 27210, 27310 react against one another without any motion of the pinion gear 27432.

In accordance with one general aspect, the upper passages 28216 form an upper pathway 28221 (FIG. 117) through the articulation joint 28200. Similarly, the lower passages 28218 form a lower pathway 28223 through the articulation joint 28200. When the surgical end effector 26000 is in an unarticulated position (i.e., the surgical end effector is axially aligned with the elongate shaft assembly 28000 on the shaft axis SA—FIGS. 115, 117, 118), the upper pathway 28221 and the lower pathway 28223 are parallel to each other. See FIG. 117. When the surgical end effector 26000 is in an articulated position relative to the elongate shaft assembly 28000, the upper pathway 28221 and the lower pathway 28223 are concentric to each other. See FIG. 116.

When the surgical end effector 26000 is in the unarticulated position, the firing system 27000 may be actuated to drive the firing member 27100 from a starting position within the proximal end 26112 of the elongate channel 26100 to an ending position within the distal end 26114 of the elongate channel 26110. When the surgical end effector 26000 is in the unarticulated position, and the firing system 27000 is actuated, the differential drive assembly 27400 drives the upper firing assembly 27200 and the lower firing assembly 27300 equal axial distances in a same axial direction (i.e., the distal direction DD) to apply an upper axial drive motion and a lower axial drive motion to the firing member 27100. The upper axial drive motion and the lower axial drive motion are substantially equal in magnitude which serves to distally advance the firing member 27100 through the surgical end effector 26000 without binding which might otherwise occur should the upper axial drive motion and the lower axial drive motions be different in magnitude. Similarly, when the surgical end effector 26000 is in an articulated position relative to the elongate shaft assembly 28000, the firing system 27000 may be actuated to drive the firing member 27100 from the starting position to the ending position. In such instances, the differential drive assembly 27400 is configured to permit the upper firing assembly 27200 and the lower firing assembly 27300 to move in substantially equal distances in opposite axial directions to accommodate the articulated position. The differential drive assembly 27400 may then apply an upper axial drive motion and a lower axial drive motion that are equal to each other to the firing member 27100. For example, depending upon the articulated position of the surgical end effector 26000 relative to the elongate shaft assembly 28000, the upper firing assembly 27200, upon articulation of the surgical end effector 26000, may be moved proximally a first distance and the lower firing assembly 27300 may be positioned relative thereto distally a second distance that is substantially equal to the first distance by the pinion gear 27432. Thereafter, distal actuation of the firing drive actuator 27440 will cause the upper firing assembly 27200 and the lower firing assembly 27300 to apply an upper axial drive motion and a lower axial drive motion that are equal to each other to the firing member 27100. As used herein, when the carrier is moved distally, the carrier may apply "axial control motions" to the upper firing assembly 27200 and the lower firing assembly 27300. Thus, when the surgical end effector 26000 is in an unarticulated configuration, the carrier may apply equal amounts of axial control motions to the upper firing member 27200 and the lower firing member 27300 in the same axial direction (distal direction DD) and when the surgical end effector 26000 is in an articulated configuration, the carrier may apply "other equal amounts" of axial control motions to the upper firing member 27200 and the lower firing member 27300 in the same axial direction (distal direction DD) to move the firing member 27100 from the starting position to the ending position.

FIGS. 140-152 illustrate another surgical instrument 30010 that employs another form of articulation joint 30200 for coupling a surgical end effector 31000 to an elongate shaft assembly 32000. The elongate shaft assembly 32000 may be identical or very similar to various other elongate shaft assemblies described herein. As can be seen in FIGS. 140-143, the articulation joint 30200 comprises a proximal joint member 30210 and a distal joint member 30250. The proximal joint member 30210 is configured to be attached to a distal end of the elongate shaft assembly 32000 that is coupled to a housing or other portion of a surgical instrument. The distal joint member 30250 is configured to be attached to the surgical end effector 31000. For example, the distal joint member 30250 may be attached to the elongate channel 31200 of the surgical end effector 31000. The end effector 31000 may be identical or very similar to various surgical end effectors disclosed herein.

As can be seen in FIGS. 143 and 150, the proximal joint member 30210 comprises a proximal face 30212 that defines a proximal apex 30218. Similarly, the distal joint member 30250 comprises a distal face 30252 that defines a distal apex 30254. See FIG. 151. The proximal joint member 30210 and the distal joint member 30250 are pivotally retained together with their respective apex portions 30218, 30254 in "rolling inter-engagement" by a linkage assembly 30300. As can be seen in FIGS. 141-143, the linkage assembly 30300 comprises a first link 30310 and a second link 30320. In the illustrated example, the first link 30310 and the second link 30320 are coupled to the proximal joint member 30210 by a proximal cross pin assembly 30330. In accordance with one aspect, the proximal cross pin assembly 30330 comprises a first proximal cross pin 30332 that defines a first proximal pivot axis FPPA. See FIG. 152. A proximal end 30312 of the first link 30310 is configured to receive a first proximal threaded fastener 30314 therethrough that is configured to be threadably received in a first threaded hole 30334 in the first proximal cross pin 30332. See FIG. 143. Likewise, a proximal end 30322 of the second link 30320 is configured to receive a second proximal threaded fastener 30324 therethrough that is configured to be threadably received in a second threaded hole 30336 in the first proximal cross pin 30332.

In at least one embodiment, the first proximal cross pin assembly 30330 further comprises a second proximal cross pin 30340 that is rotatably journaled on the first proximal cross pin 30332. In one arrangement, the first proximal cross pin 30332 may comprise a first proximal bushing or low friction sleeve 30338 that is configured to facilitate free rotation between the first proximal cross pin 30332 and the second proximal cross pin 30340. The second proximal cross pin 30340 defines a second proximal pivot axis SPPA that is transverse to the first proximal pivot axis FPPA and a shaft axis SA that is defined by the elongate shaft assembly 32000. As can be seen in FIG. 143, the second proximal cross pin 30340 is received within laterally aligned proximal pin openings 30220 in the proximal joint member 30210 to attach the linkage assembly 30300 to the proximal joint member 30210 such that the linkage assembly 30300 may pivot relative to the proximal joint member 30210 about the first proximal pivot axis FPPA and the second proximal pivot axis SPPA.

In the illustrated example, the first link 30310 and the second link 30320 are coupled to the distal joint member 30250 by a distal cross pin assembly 30350. In accordance with one aspect, the distal cross pin assembly 30350 comprises a first distal cross pin 30352 that defines a first distal pivot axis FDPA. A distal end 30316 of the first link 30310 is configured to receive a first distal threaded fastener 30318 therethrough that is configured to be threadably received in a third threaded hole 30354 in the first distal cross pin 30352. Likewise, a distal end 30326 of the second link 30320 is configured to receive a second distal threaded fastener 30328 therethrough that is configured to be threadably received in a fourth threaded hole 30356 in the first distal cross pin 30352.

In at least one embodiment, the first distal cross pin assembly 30350 further comprises a second distal cross pin 30360 that is rotatably journaled on the first distal cross pin 30352. In one arrangement, the first distal cross pin 30352 may comprise a first proximal bushing or low friction sleeve 30358 that is configured to facilitate free rotation between the first distal cross pin 30352 and the second distal cross pin 30360. The second distal cross pin 30360 defines a second distal pivot axis SDPA that is transverse to the first distal pivot axis FDPA and the shaft axis SA. As can be seen in FIG. 142, the second distal cross pin 30360 is received within laterally aligned distal pin openings 30256 in the distal joint member 30250 to attach the linkage assembly 30300 to the distal joint member 30250 such that the linkage assembly 30300 may pivot relative to the distal joint member 30250 about the first distal pivot axis FDPA and the second distal pivot axis SDPA.

Turning now to FIG. 150, the proximal face 30212 of the proximal joint member 30210 defines a proximal apex 30218 that comprises a plurality of radially-spaced recessed regions 30222 formed thereon. In the illustrated arrangement, six total recessed regions 30222 are equally spaced about a center 30219 of the proximal apex 30218. As can be seen in FIG. 151, the distal face 30252 of the distal joint member 30250 comprises a total of six distal fins or protuberances 30262 that are equally spaced about a center 30255 of the distal apex 30254 such that each fin 30262 is corresponds to one of the recessed regions 30222 when the surgical end effector is in an unarticulated position. For example, angle B may be approximately sixty degrees. See FIG. 151. Each of the fins 30262 and each of the recessed regions 30222 comprise rounded edges configured to facilitate rolling inter-engagement between the proximal apex 30218 and the distal apex 30254 during articulation of the surgical end effector 31000 relative to the elongate shaft assembly 32000. Such rolling inter-engagement may be somewhat similar to the rolling inter-engagement between the teeth of intermeshing bevel gears, for example such that the proximal apex 30218 and the distal apex 30254 remain in engagement with each other during articulation of the surgical end effector 31000.

Returning to FIG. 141, the surgical instrument 30010 also comprises an articulation system 30500 that is configured to apply articulation motions to the surgical end effector 31000 to articulate the surgical end effector 31000 relative to the elongate shaft assembly 32000. In at least one arrangement, the articulation system 30500 comprises four articulation cables 30510, 30520, 30530, and 30540 that extend through the elongate shaft assembly 32000. In the illustrated arrangement, the articulation cables 30510, 30520, 30530, and 30540 pass through the proximal joint member 30210 and the distal joint member 30250 and are secured to the surgical end effector 31000 in the various manners disclosed herein. The articulation cables 30510, 30520, 30530, and 30540 operably interface with an articulation control system that is supported in or otherwise associated with the housing of the surgical instrument 300010. For example, as was discussed above, a proximal portion of each cable 30510, 30520, 30530, and 30540 may be spooled on a corresponding rotary spool or cable-management system 2007 (FIG. 2) in the housing portion of the surgical instrument 30010 that is configured to payout and retract each cable 30510, 30520, 30530, and 30540 in desired manners. The spools/cable management system may be motor powered or manually powered (ratchet arrangement, etc.). FIGS. 140, 141, and 144-146 illustrate the position of the articulation joint 30200 when the surgical end effector is in an unarticulated position and FIGS. 142 and 147-149 illustrate various positions of the articulation joint 30200 when the surgical end effector has been articulated in various positions relative to the elongate shaft assembly 32000. The surgical instrument 30010 may also employ a firing system 30600 of the various types and constructions disclosed in detail herein to drive a firing member (not shown) within the surgical end effector 31000. For example, the proximal joint member 30210 may be provided with an upper proximal firing member passage 30214 that is configured to accommodate passage of an upper flexible firing assembly 30610 therethrough. The upper flexible firing assembly 30610 may span across an area generally designated as 30700 between the proximal face 30212 of the proximal joint member 30210 and the distal face 30252 of the distal joint member 30250 to and slidably pass through an upper distal firing member passage 30257 in the distal joint member 30250. Similarly, the proximal joint member 30210 is provided with a lower proximal firing member passage 30216 that is configured to accommodate passage of a lower flexible firing assembly 30620 member therethrough. The lower flexible firing assembly 30620 spans area 30700 and is received in a lower distal firing member passage 30259 in the distal joint member 30250. The upper flexible firing assembly 30610 and the lower flexible firing assembly 30620 operably interface with a firing member in the surgical end effector 31000. The upper flexible firing assembly 30610 and the lower flexible firing assembly 30620 may be identical or very similar in construction to the various flexible firing member drive arrangements disclosed herein.

FIG. 153 illustrates another form of articulation joint 30200' that is identical in construction and operation to articulation joint 30200 described above, except that the first link 30310 and the second link 30320 are connected together by an annular ring 30380 that is located in the area 30700 between the proximal face 30212 of the proximal joint member 30210 and the distal face 30252 of the distal joint member 30250. In at least one arrangement, the annular ring 30380 comprises an outer diameter which is equal to or less than an outer diameter of the proximal joint member 30210 and an outer diameter of the distal joint member 30250. In one arrangement, for example, the outer diameter of the distal joint member 30250 is equal to the outer diameter of the proximal joint member 30210 which is equal to or less than the maximum outer diameter of the elongate shaft assembly 32000. Thus, such arrangement permits the surgical instrument 30010 to be inserted into a patient through a trocar cannula that can accommodate the maximum outer diameter of the elongate shaft assembly 32000. The annular ring 30380 may be particularly advantageous as it may prevent tissue or a flexible exterior joint cover (not shown) from potentially getting caught between the joint components.

The articulation joints 30200, 30200' utilize an outer linkage assembly 30300 arrangement that connects the proximal cross pin assembly 30330 and the distal cross pin assembly 30350 together and resolve torsional and axial loads that are applied to the joint which may be particular important for resolving loads in the instrument during firing of the firing member. Such joint arrangement further leaves space between the proximal joint member and distal joint member to accommodate additional components/features. As can be seen in the various Figures, the proximal joint member and the distal joint member each are provided with clearance pockets/features/contours to accommodate the linkage assembly when the joint articulates.

FIGS. 154-156 illustrate another form of articulation joint 33000 that may be used to couple a surgical end effector of the various types disclosed herein to an elongate shaft assembly 34000 of a surgical instrument 33010. The elongate shaft assembly 34000 comprises a central spine member 34100 (FIG. 155) that may be coupled to or otherwise operably interfaces with a housing (not shown) of the surgical instrument 33010. The elongate shaft assembly 34000 further comprises an outer tube member 34110 that is extends over the central spine member 34100. In at least one form, the articulation joint 33000 comprises a proximal joint member 33100 that is attached to the central spine member 34100 and a distal joint member 33300 that is attached to a surgical end effector (not shown). For example, the distal joint member 33300 may be attached to an elongate channel of an endo-cutter arrangement in the various manners disclosed herein.

In the illustrated arrangement, the proximal joint member 33100 comprises a first or right half segment 33100A and a second or left half segment 33100B that are attached to a distal end of the central spine member 34100. The first half segment 33100A and the second half segment 33100B may be attached to the central spine member 34100 or other similar component of the elongate shaft assembly 34000 by welding, adhesive, mechanical fasteners, pins, etc. In accordance with one aspect, the surgical instrument 33010 comprises a firing system 35000 that comprises a distal differential drive assembly 35100 and a proximal differential drive assembly 35500.

As can be seen in FIG. 156, the proximal joint member 33100 operably supports the distal differential drive assembly 35100. In one arrangement, the distal differential drive assembly 35100 comprises an upper distal rack assembly 35110 that is supported for axial travel within the proximal joint member 33100. As can be seen in FIGS. 156, 157, and 158, the upper distal rack assembly 35110 is supported in meshing engagement with a distal differential gear 35130 that is rotatably supported on a pivot axle 35132 that is supported in the proximal joint member 33100. The upper distal rack assembly 35110 is supported for axial travel within the proximal joint member 33100. The distal differential drive assembly 35100 also comprises a lower distal rack assembly 35120 that is supported in meshing engagement with the distal differential gear 35130 and is configured to travel axially within the proximal joint member 33100.

In accordance with one aspect, the firing system 35000 further comprises an upper flexible firing assembly 35300 and a lower flexible firing assembly 35400 that are configured to operably interface with a firing member 35200. As can be seen in FIGS. 156 and 159, the firing member 35200 includes a vertically-extending firing member body 35212 that comprises a top firing member feature 35220 and a bottom firing member feature 35230. A tissue cutting blade 35214 is attached to or formed in the vertically-extending firing member body 35212. In at least one arrangement, the top firing member feature 35220 comprises a top finned portion 35222 that has a top axial passage 35224 extending therethrough. The bottom firing member feature 35230 comprises a bottom finned portion 35232 that has a bottom axial passage 35234 extending therethrough. In at least one arrangement, the top firing member feature 35220 and the bottom firing member feature 35230 are integrally formed with the vertically-extending firing member body 35212. In at least one example, the anvil body comprises an axially extending anvil slot that is configured to accommodate passage of the top firing member feature 35220 in the various manners discussed herein. Similarly, the elongate channel comprises an axially extending channel slot that is configured to accommodate passage of the bottom firing member feature 35230 as described herein.

In one example, the upper flexible firing assembly 35300 comprises an upper flexible tube or conduit 35310 that has a proximal end 35312 that is supported in a distal socket 3512 in the upper distal rack assembly 35110 and is secured thereto by welding, adhesive, etc. The upper flexible tube or conduit 35310 extends through an upper opening 33218 in the proximal joint member 33100 and spans across the articulation joint 33000. The upper flexible tube or conduit 35310 comprises a distal end 35314 that is received in an opening 33330 in the distal joint member 33300 and is terminated or secured therein by welding, adhesive, etc. The upper flexible firing assembly 35300 further comprises an upper push coil 35320. The upper push coil 35320 is hollow and may comprise a coil spring that is fabricated from Nitinol, titanium, stainless steel, etc. In other arrangements, the upper push coil 35320 comprises a laser cut hypotube that essentially comprises a hollow tubular member with offset laser cuts or spiral cuts therein which enable the hypotube to flex and bend. The upper push coil 35320 may additionally be received within an inner flexible upper sleeve 35330 that may be fabricated from a polymer or similar material and prevent tissue, fluid, and/or debris from infiltrating into the upper push coil 35320 which may hamper its ability to flex and bend during articulation.

The upper push coil 35320 extends through the upper flexible tube 35310 and through an axial passage in the upper distal rack 35110. An upper support beam 35140 is supported by the central spine member 34100 and has an upper passage 35142 to constrain and permit passage of the upper push coil 35320 therethrough. As can be seen in FIG. 159, a distal end 35322 of the upper push coil 35320 as well as a distal end 35332 of the inner flexible upper sleeve 35330 abut a proximal end 35223 of the top finned portion 35222 of the top firing member feature 35220. Also in the illustrated arrangement, the upper firing assembly 35300 further comprises an upper cable 35340 that extends through the hollow upper push coil 35320. The upper cable 35340 comprises an upper cable distal end 35342 that is secured within the top axial passage 35224 in the top finned portion 35222 of the top firing member feature 35220 by an upper attachment lug 35343.

Turning to FIGS. 156-161, the proximal differential drive assembly 35500 comprises an upper gear rack 35510 that is slidably supported within the central spine member 34100. The proximal differential drive assembly 35500 further comprises a lower proximal gear rack 35520 that is supported for axial travel within the central spine member 34100. The proximal differential drive assembly 35500 also comprises an axially movable carrier member 35530 that is centrally disposed between the upper proximal gear rack 35510 and the lower proximal gear rack 35520 and is supported for axial travel within the central spine member 34100. A proximal pinion gear 35532 is pivotally supported on a pin 35533 that is mounted to the axially movable carrier member 35530 such that the proximal pinion gear 35532 is meshing engagement with the upper proximal gear rack 35510 and the lower proximal gear rack 35520. The axially movable carrier member 35530 is driven axially within an axial cavity in the central spine member 34100 by a firing drive actuator 35540. As can be seen in FIG. 160, the firing drive actuator 35540 comprises a firing drive gear rack 35542 that drivingly interfaces with a drive gear 35544 that is driven by a firing motor 35546 that may be operably supported in the housing of the surgical instrument 33010. In other arrangements, the firing drive actuator 35540 may be axially driven distally and proximally by a cylinder arrangement or other suitable actuator interfacing therewith. As can be seen in FIGS. 156 and 160, the firing drive actuator 35540 may be attached to the axially movable carrier member 35530 by a pair of spaced coupler pins 35548.

In the illustrated arrangement, the upper proximal gear rack 35510 further comprises an upper cable attachment feature 35512 that protrudes therefrom and is configured to slide within the upper passage 35142 in the upper support beam 35140. In accordance with one aspect, the upper cable 35340 extends through the hollow upper push coil 35320 and a proximal end of the upper cable 35340 is secured to the upper cable attachment feature 35512. The upper cable 35340 is held in tension between the top firing member feature 35220 and the upper cable attachment feature 35512 which serves to retain the distal end 35322 of the upper push coil 35320 as well as a distal end 35332 of the inner flexible upper sleeve 35330 in abutting contact with the proximal end 35323 of the top finned portion 35222 of the top firing member feature 35220 and the proximal end of the upper push coil 35320 and a proximal end of the inner flexible upper sleeve 35330 in abutting contact with the distal end of the upper cable attachment feature 35512.

In one example, the lower flexible firing assembly 35400 comprises a lower flexible tube or conduit 35410 that has a proximal end 35412 that is supported in a distal socket 35122 in the lower distal rack 35120 and is secured thereto by welding, adhesive, etc. The lower flexible tube or conduit 35410 extends through a lower opening 33219 in the proximal joint member 33100 and spans across the articulation joint 33000. The lower flexible tube or conduit 35410 comprises a distal end 35414 that is received in an opening 33340 in the distal joint member 33300 and is terminated or secured therein by welding, adhesive, etc. The lower flexible firing assembly 35400 further comprises a lower push coil 35420. The lower push coil 35420 is hollow and may comprise a coil spring that is fabricated from Nitinol, titanium, stainless steel, etc. In other arrangements, the lower push coil 35420 comprises a laser cut hypotube that essentially comprises a hollow tubular member with offset laser cuts or spiral cuts therein which enable the hypotube to flex and bend. The lower push coil 35420 may additionally be received within an inner flexible lower sleeve 35430 may be fabricated from a polymer or similar material and prevent tissue, fluid, and/or debris from infiltrating into the lower push coil 35420 which may hamper its ability to flex and bend during articulation.

The lower push coil 35420 extends through the lower flexible tube 35410 and through an axial passage in the lower distal rack 35120. A lower support beam 35150 is supported by the central spine member 34100 and has a lower passage 35152 to constrain and permit passage of the lower push coil 35420 therethrough. As can be seen in FIG. 159, a distal end 35422 of the lower push coil 35420 as well as a distal end 35432 of the inner flexible lower sleeve 35430 abut a proximal end 35233 of the bottom finned portion 35232 of the bottom firing member feature 35230. Also in the illustrated arrangement, the lower flexible firing assembly 35400 further comprises a lower cable 35440 that extends through the hollow lower push coil 35420. The lower cable 35440 comprises a lower cable distal end 35442 that is secured within the bottom axial passage 35234 in the bottom finned portion 35232 of the bottom firing member feature 35230 by a lower attachment lug 35443. In accordance with one aspect, the lower cable 35440 extends through the hollow lower push coil 35420 and a distal end of the lower cable 35440 is secured to a lower cable attachment feature 35522 on the lower proximal gear rack 35520. The lower cable 35440 is held in tension between the bottom firing member feature 35230 and the lower cable attachment feature 35522 which serves to retain the distal end 35422 of the lower push coil 35420 as well as a distal end 35332 of the inner flexible upper sleeve 35330 in abutting contact with the proximal end 35233 of the bottom finned portion 35232 of the bottom firing member feature 35230 and the proximal end of the lower push coil 35420 and a proximal end of the inner flexible lower sleeve 35430 in abutting contact with the distal end of the lower cable attachment feature 35522.

Surgical stapling devices need to apply a high force on the firing member over a long displacement to form the staples and cut tissue. Transmitting that force through an articulated joint is especially challenging because it is difficult to redirect the forces in the desired direction and withstand the loads applied to it. The firing system 35000 described herein addresses and solves many, if not all of such challenges by employing two flexible tubes 35310, 35410 to constrain the paths of the push coils 35320, 35420, respectively. As described herein, the upper flexible tube 35310 surrounds the upper push coil 35320 and the lower flexible tube 35410 surrounds the lower push coil 35420. Each of the tubes 35310, 35410 can bend but they also can resolve an axial tensile load. See FIGS. 164 and 165. The ability to bend allows for the firing member force to be redirected through the articulated joint, and the ability to resolve tension allows for it to change the direction in which the push coil goes. When the push coil 35320, 35420 is put in compression, the flexible tube 35310, 35410 is put in tension. The tube 35310, 35410 prevents the push coil 35320, 35420 from buckling. To resolve the tensile loads the tubes 35310, 35410 need to be terminated in a manner to resolve the loads. In the illustrated example, the respective distal ends 35314, 35414 of the flexible tubes 35310, 35410, respectively are secured to the distal joint member 33300. The proximal ends 35312, 35412 of the flexible tubes 35310, 35410 are secured to the upper distal rack assembly 35110 and the lower distal rack 35120, respectively. The distal differential gear 35130 is in meshing engagement with each of the upper distal rack assembly 35110 and the lower distal rack 35120 such that when one of the rack assemblies 35110, 35120 moves in one axial direction, the other rack assembly 35110, 35120 would axially move in an opposite axial direction. As can be seen in FIGS. 163-165, during articulation, the distal differential gear 35130 rotates so the flexible tubes 35310, 35410 can move to account for the change in path length. However, when the firing drive system is actuated to push the push coils 35320, 35420 distally through the tubes 35310, 35410 to fire (i.e., drive the firing member distally) the tensile loads in the two flexible tubes 35310, 35410 react against one another without any motion of the distal differential gear 35130.

In accordance with one aspect, the upper flexible tube or conduit 35310 forms an upper pathway that spans the articulation joint 33000 and the lower flexible tube or conduit 35410 forms a lower pathway that spans the articulation joint 33000. The upper pathway supports the upper push coil 35320 for axial travel therethrough and the lower push coil 35420 for axial travel therethrough. When the surgical end effector to which the articulation joint 33000 is attached is in an unarticulated position (i.e., the surgical end effector is axially aligned articulated with the elongate shaft assembly along the shaft axis) the upper pathway and the lower pathway are parallel. Stated another way, when the surgical end effector is in an unarticulated position, an end effector axis is axially aligned with the shaft axis and the upper pathway and the lower pathway are parallel. When the surgical end effector is in an unarticulated position (i.e., the end effector axis is not axially aligned with the shaft axis), the upper pathway and the lower pathway are concentric to each other. When the surgical end effector is in the unarticulated position, the proximal differential drive assembly is configured to drive the upper push coil 35320 and the lower push coil 35420 equal distances in the same axial direction (distal direction DD) to apply an upper axial drive motion and a lower axial drive motion to the firing member. The upper axial drive motion and the lower axial drive motion are substantially equal in magnitude which serves to distally advance the firing member through the surgical end effector without binding which might otherwise occur should the upper axial drive motion and the lower axial drive motions be different in magnitude. Similarly, the when the surgical end effector is in an articulated position relative to the elongate shaft assembly, the proximal differential drive assembly is configured to permit the upper push coil 35320 and the lower push coil 35420 to move in substantially equal distances in opposite axial directions and thereafter apply an upper axial drive motion and a lower axial drive motion that are equal to each other to the firing member.

As can be seen in FIG. 156, the proximal joint member 33100 defines a proximal face 33200 that is configured to receive a spherical proximal end of 33410 of a central link member 33400. In the illustrated arrangement, the spherical proximal end 33410 is configured to be pivotally received in a proximal socket 33210 in the proximal face 33200 of the proximal joint member 33100. The spherical proximal end 33410 of the central link member 33400 is retained within the proximal socket 33210 by a proximal cross pin assembly 33500. In accordance with one aspect, the proximal cross pin assembly 33500 comprises a first proximal cross pin 33510 that defines a first proximal pivot axis FPPA. The first proximal cross pin 33510 is pivotally supported in a pair of attachment lugs 33220 formed on the proximal face 33200 of the proximal joint member 33100 and extends through two opposing arcuate slots 33412 to permit pivotal as well as rotational travel of the first proximal cross pin 33510 within the spherical proximal end 33410 of the central link member 33400. Stated another way, the spherical proximal end 33410 of the central link member 33400 is rotatable about the first proximal cross pin 33510 as well as pivotable through a proximal pivot angle PPA defined by the arcuate slots 33412.

The proximal cross pin assembly 33500 further comprises a second proximal cross pin 33520 that is rotatably journaled on the first proximal cross pin 33510 to permit relative pivotal rotation between the first proximal cross pin 33510 and the second proximal cross pin 33520. The second proximal cross pin 33520 is pivotally supported within the spherical proximal end 33410 of the central link member 33400 and defines a second proximal pivot axis SPPA. The first proximal pivot axis FPPA is transverse to the shaft axis SA. The second proximal pivot axis SPPA is transverse to the shaft axis SA as well as the first proximal pivot axis FPPA. The proximal cross pin assembly 33500 facilitates pivotal travel of the spherical proximal end 33410 of the central link member 33400 relative to the proximal joint member 33100 about the first proximal pivot axis FPPA as well as the second proximal pivot axis SPPA.

In the illustrated arrangement, the distal joint member 33100 defines a distal face 33310 that is configured to receive a spherical distal end 33420 of a central link member 33400. In the illustrated arrangement, the spherical distal end 33420 is configured to be pivotally received in a distal socket 33312 in the distal face 33310 of the distal joint member 33300. The spherical distal end 33420 of the central link member 33400 is retained within the distal socket 33312 by a distal cross pin assembly 33600. In accordance with one aspect, the distal cross pin assembly 33600 comprises a first distal cross pin 33610 that defines a first distal pivot axis FDPA. The first distal cross pin 33610 is pivotally supported in a pair of attachment lugs 33314 formed on the distal face 33312 of the distal joint member 33300 and extends through two opposing arcuate slots 33422 to permit pivotal as well as rotational travel of the first distal cross pin 33610 within the spherical distal end 33420 of the central link member 33400. Stated another way, the spherical distal end 33420 of the central link member 33400 is rotatable about the first distal cross pin 33610 as well as pivotable through a distal pivot angle DPA defined by the arcuate slots 33412.

The distal cross pin assembly 33600 further comprises a second distal cross pin 33620 that is rotatably journaled on the first distal cross pin 33610 to permit relative pivotal rotation between the first distal cross pin 33610 and the second distal cross pin 33620. The second distal cross pin 33620 is pivotally supported within the spherical distal end 33420 of the central link member 33400 and defines a second distal pivot axis SDPA. The first distal pivot axis FDPA is transverse to the shaft axis SA. The second distal pivot axis SDPA is transverse to the shaft axis SA as well as the first distal pivot axis FDPA. The distal cross pin assembly 33600 facilitates pivotal travel of the spherical distal end 33420 of the central link member 33400 relative to the distal joint member 33300 about the first distal pivot axis FDPA as well as the second distal pivot axis SDPA.

In accordance with at least one aspect, the articulation joint 33000 further comprises a flexible joint support assembly generally designated as 33700 which provides flexible support between the proximal joint member 33100 and the distal joint member 33200 during articulation as well as to assist the articulation joint 33000 in returning to an unarticulated position (FIGS. 155-158). In at least one arrangement, the flexible joint support assembly 33700 comprises a series of flexible members 33710, 33720, 33730, and 33740 that cross through a hollow central link portion 33430 that is attached to the spherical proximal end 33410 and the spherical distal end 33420 and extends therebetween. The flexible members 33710, 33720, 33730, and 33740 may comprise cables or spring members that are fabricated from, for example, spring steel, stainless steel, Nitinol, titanium, etc. More particularly and with reference to FIG. 166, a first flexible member 33710 comprises a central portion 33712 and a proximal end portion 33714 that is configured to be received in a corresponding attachment hole 33212 (FIG. 156) in the first or right half segment 33100A of the proximal joint member 33100 and attached or secured therein. The first flexible member 33710 further comprises a distal end portion 33716 that is configured to be received in a corresponding slotted hole 33320 in the distal joint member 33300 and be attached therein. In such arrangement, the central portion 33712 of the first flexible member 33710 extends diagonally through the hollow central link portion 33430. The second flexible member 33720 comprises a central portion 33722 and a proximal end portion 33724 that is configured to be received in a corresponding attachment hole 33214 (FIG. 156) in the second or left segment 33100B of the proximal joint member 33100 and be secured therein. The second flexible member 33720 further comprises a distal end portion 33726 that is configured to be received in a corresponding slotted hole 33322 in the distal joint member 33300 and be secured therein. In such arrangement, the central portion 33722 of the second flexible member 33720 extends diagonally through the hollow central link portion 33430. The third flexible member 33730 comprises a central portion 33732 and a proximal end portion (not shown) that is configured to be inserted into a corresponding attachment hole (not shown) in the first or right segment 33100A of the proximal joint member 33100 and be secured therein. The third flexible member 33730 further comprises a distal end portion 33736 that is configured to be received in a corresponding slotted hole 33324 in the distal joint member 33300 and be secured therein. In such arrangement, the central portion 33732 of the third flexible member 33730 extends diagonally through the hollow central link portion 33430. The fourth flexible member 33740 comprises a central portion 33742 and a proximal end portion 33744 that is configured to be inserted into a corresponding attachment hole 33216 in the second or left segment 33100B of the proximal joint member 33100 and be secured therein. The fourth flexible member 33740 further comprises a distal end portion 33746 that is configured to be received in a corresponding slotted hole 33326 in the distal joint member 33300 and be secured therein. In such arrangement, the central portion 33742 of the fourth flexible member 33740 extends diagonally through the hollow central link portion 33430.

The surgical instrument 33010 also comprises an articulation system 33800 that is configured to apply articulation motions to the surgical end effector to articulate the surgical end effector relative to the elongate shaft assembly 34000. In at least one arrangement, the articulation system 33800 comprises four articulation cables 33810, 33820, 33830, and 33840 that extend through the elongate shaft assembly 34000. In the illustrated arrangement, the articulation cables 33810, 33820, 33830, and 33840 pass through the proximal articulation joint member 33100 and the distal articulation joint member 33300 and are secured to the surgical end effector in the various manners disclosed herein. The articulation cables 33810, 33820, 33830, and 33840 operably interface with an articulation control system that is supported in or is otherwise associated with the housing of the surgical instrument 33010. For example, as was discussed above, a proximal portion of each cable 33810, 33820, 33830, and 33840 may be spooled on a corresponding rotary spool or cable-management system 2007 (FIG. 2) in the housing portion of the surgical instrument 330010 that is configured to payout and retract each cable 33810, 33820, 33830, and 33840 in desired manners. The spools/cable management system may be motor powered or manually powered (ratchet arrangement, etc.). FIGS. 154, 155, 157, 158, 162, and 167 illustrate the position of the articulation joint 33000 when the surgical end effector is in an unarticulated position and FIGS. 163 and 169 illustrate various positions of the articulation joint 33000 when the surgical end effector has been articulated in various positions relative to the elongate shaft assembly.

The articulation joint 33000 comprises a spherical pitch and yaw joint that is controlled by cables and is used for articulation of the surgical end effector. The articulation joint comprises a double spherical joint, meaning that it has a pair of joints that each can perform pitch and yaw. This arrangement creates redundancy in the joint as now there are two joints that can perform pitch and yaw. The flexible joint support assembly 33700 serves to constrain how each joint moves during articulation so that the four degrees of freedom act as two. The flexible joint support assembly 33700 ties the two spherical joints together such that if one rotates, the other one rotates the same amount. When a joint rotates it applies tension in the cable that forces the other joint to rotate as well. Such joint arrangement has a very compact form factor and very little backlash in the wrist design.

FIGS. 170-177 illustrate another form of articulation joint 14200 that comprises a proximal joint member 14210 and a distal joint member 14250. The proximal joint member 14210 is configured to be attached to a distal end of an elongate shaft assembly that is coupled to a housing or other portion of a surgical instrument. The distal joint member 14250 is configured to be attached to a surgical end effector. For example, the distal joint member 14250 may be attached to an elongate channel of an endo-cutter arrangement in the various manners disclosed herein. As can be seen in FIGS. 170-173, the proximal joint member 14210 comprises a proximal face 14212 that defines two face segments 14214, 14216 that angle away from an arcuate proximal apex 14218. Similarly, the distal joint member 14250 comprises a distal face 14252 that defines two face segments 14254, 14256 that angle away from an arcuate distal apex 14258. The proximal joint member 14210 and the distal joint member 14250 are pivotally retained together with their respective arcuate apex portions 14218, 14258 in a confronting arrangement by at least one and preferably two linkage assemblies 15000, 15002.

As can be seen in FIGS. 171-175, the first linkage assembly 15000 comprises a first link 15101 and a second link 15020 that are located on one lateral side of the shaft axis SA. The second linkage assembly 15002 comprises a first link 15010 and a second link 15020 that are located on an opposite lateral side of the shaft axis SA from the first linkage assembly 15000. As can be seen in FIGS. 171-175, the first link 15010 of each linkage assembly 15000, 15002 comprises a rigid body 15012 that defines a proximal end 15014 and a distal end 15016. The proximal end 15014 is pivotally coupled to or pinned to the proximal joint 14210 on one side (side A—FIG. 174) of a first reference plane $RP_1$ that is defined by the shaft axis SA. The proximal end 15014 pivots about a first pivot axis FPA that is transverse to the shaft axis SA. See FIG. 170. The distal end 15016 is pivotally coupled to or pinned to the distal joint member 14250 on an opposite side (Side B—FIG. 174) of the first reference plane $RP_1$ such that the first link 15010 crosses through the first reference plane $RP_1$. The distal end 15016 pivots about a second pivot axis SPA that is also transverse to the shaft axis SA.

The second link 15020 of each linkage assembly 15000, 15002 comprises a rigid body 15022 that defines a proximal end 15024 and a distal end 15026. The proximal end 15024 is pivotally coupled to or pinned to the proximal joint member 14210 on side B of the first reference plane $RP_1$ and the distal end 15016 is pivotally coupled to or pinned to the distal joint member 14250 on side A of the first reference plane $RP_1$ such that the second link 15020 crosses the first link 15010 and passes through the first reference plane $RP_1$. The proximal end 15024 pivots about a third pivot axis TPA that is transverse to the shaft axis SA and the distal end 15026 pivots about a fourth pivot axis FTPA that is transverse to the shaft axis. In at least one example, all of the pivot axes FPA, SPA, TPA, FTPA are parallel to each other and transverse to the shaft axis SA.

Turning now to FIGS. 176 and 177, the linkage assemblies 15000, 15002 of links 15010, 15020 serve to position the proximal joint member 14210 and the distal joint member 14250 relative to each other for pivotal travel about two virtual pivot points $VPP_P$ and $VPP_D$. In at least one arrangement, the proximal joint member 14210 defines the proximal virtual pivot point $VPP_P$ which is located a proximal radius PR from the arcuate proximal apex 14218 on the shaft axis SA. The distal joint member 14250 defines the distal virtual pivot point $VPP_D$ which is located a distal radius DR from the arcuate distal apex 14228 on an end effector axis EA. The virtual pivot points $VPP_P$ and $VPP_D$ lie on a common joint axis JA that has a length of PR+DR which is held constant by the link assemblies 15000, 15002. FIG. 176 illustrates the articulation joint 14200 in an unarticulated orientation wherein the end effector axis EA, the joint axis JA and the shaft axis SA are axially aligned. FIG. 177 illustrates the articulation joint 14200 in an articulated orientation. During articulation, the linkage assemblies 15000, 15002 facilitate rotation of the distal joint member 14250 relative to the proximal joint member 14210 such that the angle Θ1 between the shaft axis SA and the joint axis JA is equal to the angle Θ2 between the end effector axis EA and the joint axis JA. See FIG. 177.

Returning to FIG. 170, in the illustrated example, the articulation joint 14200 is operably controlled by a cable control system that comprises four cables 15040, 15050, 15060, and 15070 that extend through the elongate shaft assembly to operably interface with a cable control system 9030 that may be supported within the housing of the surgical instrument. The cable control system 9030 may comprise a plurality of cable support members/capstans, pulleys, etc. that are controlled by one or more corresponding motors that are controlled by a control circuit portion of the surgical instrument. The cable control system 9030 is configured to manage the tensioning (pulling) and paying out of cables at precise times during the articulation process. As can be seen in FIG. 170, the cables 15040, 15050 extend through passages in the proximal joint member 14210 on side A of the first reference plane $RP_1$ and into corresponding passages in the distal joint member 14250. Cable 15040 has a retainer lug 15042 thereon to prevent it from pulling through the distal joint member 14250. Cable 15050 also has a retainer lug 15052 to prevent cable 15050 from pulling through the distal joint member 14250. Cables 15060, 15070 extend through passages in the proximal joint member 14210 on side B of the first reference plane $RP_1$ and into corresponding passages in the distal joint member 14250. Cable 15060 has a retainer lug 15062 thereon to prevent it from pulling through the distal joint member 14250. Cable 15070 also has a retainer lug 15072 to prevent cable 15050 from pulling through the distal joint member 14250.

FIG. 171 illustrates the articulation joint 14200 in an unarticulated orientation. FIG. 172 illustrates articulation of the distal joint member 14250 in a first articulation direction on one side of the shaft axis SA which is accomplished by applying tension to the cables 15040, 15050 and allowing cables 15060 and 15070 to slacken. FIG. 173 illustrates the distal joint member 14250 articulated in a maximum articulated orientation that has an articulation angle relative to the shaft axis SA of approximately ninety degrees. The distal joint member 14250 may be articulated in an opposite direction by applying tension to cables 15060 and 15070 and allowing cables 15040, 15050 to slacken. In this arrangement, the links 15010, 15020 retain the proximal joint member 14210 and the distal joint member 14250 together without relying on maintaining tension in the cables 15040, 15050, 15060, and 15070. The virtual pivot point arrangement also allows the pairs 15000, 15002 of links 15010, 15020 to be attached to the proximal joint member 14210 and distal joint member 14250 away from those virtual pivot points. Such arrangement provides maximum clearance in the center area of the articulation joint 14200 to accommodate a variety of actuation members/shafts. As can be seen in FIG. 170, the proximal joint member 41210 comprises a central proximal opening 14211 and the distal joint member 14250 comprises a central distal opening 14251. In various embodiments, various control members/drive members 14300 may extend through the openings 14211, 14251 to provide drive/control motions to the end effector. Such drive members 14300 must be flexible to accommodate articulation of the articulation joint components. In one arrangement, the apex areas 14218, 14528 may contact each other and in other embodiments, the apex areas 14218, 14258 are spaced from each other. Such arrangement also enables pivotal travel of the distal joint member 14250 relative to the proximal joint member 14210 without the use of intermeshing gear segments that are employed in other embodiments.

FIGS. 178-180 illustrate another form of articulation joint 16200 that can facilitate articulation of a surgical end effector in multiple planes of articulation. In one arrangement, the articulation joint 16200 comprises a proximal joint member 16210, a central joint member 16230 and a distal joint member 16250. The proximal joint member 16210 is configured to be attached to a distal end of an elongate shaft assembly that is coupled to a housing or other portion of a surgical instrument. The distal joint member 16250 is configured to be attached to a surgical end effector. For example, the distal joint member 16250 may be attached to an elongate channel of an endo-cutter arrangement in the various manners disclosed herein. The proximal joint member 16210 comprises a proximal joint distal face 16212 that defines two face segments 16214, 16216 that angle away from an arcuate proximal apex 16218.

The central joint member 16230 comprises proximal face 16232 that defines two face segments 16234, 16236 that angle away from a first arcuate center apex 16238. The central joint member 16230 further comprises a central joint distal face 16240 that defines two face segments 16244, 16246 that angle away from a second arcuate center apex 16248. The distal joint member 16250 comprises a distal joint proximal face 16252 that defines two face segments 16254, 16256 that angle away from an arcuate distal apex 16258. In the illustrated example, the proximal joint member 16210 and the central joint member 14230 are pivotally retained together with their respective apex portions 16218, 16238 in a confronting arrangement by a first proximal linkage assembly 17000 that comprises proximal links 17010, 17020 that are located on one side (side A) of a first reference plane $RP_1$ that extends through the shaft axis SA and a second proximal linkage assembly 17002 that comprises proximal links 17030, 17040 that are located on side B of the first reference plane $RP_1$. The first proximal link 17010 comprises a rigid body 17012 that defines a proximal end 17014 and a distal end 17016. The proximal end 17014 is pivotally coupled to or pinned to the proximal joint member 16210 on side C of a second reference plane $RP_2$ that is defined by the shaft axis SA and is orthogonal to the first reference plane $RF_1$. The proximal end 17014 pivots about a first pivot axis FPA that is transverse to the shaft axis SA. See FIG. 179. The distal end 17016 is pivotally coupled to or pinned to the central joint member 16230 on an opposite side (Side D) of the second reference plane $RP_2$ such that the first proximal link 17010 crosses through the second reference plane $RP_2$. The distal end 17016 pivots about a second pivot axis SPA that is also transverse to the shaft axis SA.

The second proximal link 17020 of the proximal linkage assembly 17000 comprises a rigid body 17022 that defines a proximal end 17024 and a distal end 17026. The proximal end 17024 is pivotally coupled to or pinned to the proximal joint member 16210 on side D of the second reference plane $RP_2$ and the distal end 17026 is pivotally coupled to or pinned to the central joint member 16230 on side C of the second reference plane $RP_2$ such that the second proximal link 17020 crosses the first proximal link 17010 and passes through the second reference plane $RP_2$. The proximal end 17024 pivots about a third pivot axis TPA that is transverse to the shaft axis SA and the distal end 17026 pivots about a fourth pivot axis FTPA that is transverse to the shaft axis SA. In at least one example, all of the pivot axes FPA, SPA, TPA, FTPA are parallel to each other and transverse to the shaft axis SA.

A "third" proximal link 17030 in the second proximal linkage assembly 17002 comprises a rigid body 17032 that defines a proximal end 17034 and a distal end 17036. The proximal end 17034 is pivotally coupled to or pinned to the proximal joint member 16210 on side D of the second reference plane $RP_2$. The proximal end 17014 pivots about the third pivot axis TPA. The distal end 17036 is pivotally coupled to or pinned to the central joint member 16230 on side C) of the second reference plane $RP_2$ such that the third proximal link 17030 crosses through the second reference plane $RP_2$. The distal end 17016 pivots about the fourth pivot axis FTPA.

The "fourth" proximal link 17040 of the proximal linkage assembly 17002 comprises a rigid body 17042 that defines a proximal end 17044 and a distal end 17046. The proximal end 17044 is pivotally coupled to or pinned to the proximal joint member 16210 on side C of the second reference plane $RP_2$ and the distal end 17046 is pivotally coupled to or pinned to the central joint member 16230 on side D of the second reference plane $RP_2$ such that the fourth proximal link 17040 crosses the third proximal link 17030 and passes through the second reference plane $RP_2$. The proximal end 17044 pivots about the first pivot axis TPA and the distal end 17046 pivots about the second pivot axis STPA.

In the illustrated example, the distal joint member 16250 and the central joint member 16230 are pivotally retained together with their respective arcuate apexes 16258, 16248 in a confronting arrangement by a third distal linkage assembly 17004 that comprises distal links 17050, 17060 that are located on side D of the second reference plane $RP_2$ and a fourth distal linkage assembly 17006 that comprises distal links 17070, 17080 that are located on side C of the second reference plane $RP_2$. A first distal link 17050 comprises a rigid body 17052 that defines a proximal end 17054 and a distal end 17056. The proximal end 17054 is pivotally coupled to or pinned to the central joint member 16230 on side A of the first reference plane $RP_1$. The proximal end 17054 pivots about a fifth pivot axis FFPA that is transverse to the shaft axis SA. The distal end 17016 is pivotally coupled to or pinned to the distal joint member 16250 on side B of the first reference plane $RP_1$ such that the first distal link 17050 crosses through the first reference plane $RP_1$. The distal end 17056 pivots about a sixth pivot axis SXPA that is also transverse to the shaft axis SA.

A second distal link 17060 comprises a rigid body 17062 that defines a proximal end 17064 and a distal end 17066. The proximal end 17064 is pivotally coupled to or pinned to the central joint member 16230 on side B of the first reference plane $RP_1$ and the distal end 17066 is pivotally coupled to or pinned to the distal joint member 16250 on side A of the first reference plane $RP_1$ such that the second distal link 17060 crosses the first distal link 17050 and passes through the first reference plane $RP_1$. The proximal end 17064 pivots about a seventh pivot axis SVPA that is transverse to the shaft axis SA and the distal end 17066 pivots about an eighth pivot axis EPA that is transverse to the shaft axis SA. In at least one example, all of the pivot axes FFPA, SXPA, SVPA and EPA are parallel to each other and transverse to the shaft axis SA.

A "third" distal link 17070 comprises a rigid body 17072 that defines a proximal end 17074 and a distal end 17076. The proximal end 17074 is pivotally coupled to or pinned to the central joint 16230 on side B of the first reference plane $RP_1$. The proximal end 17074 pivots about the seventh pivot axis SVPA. The distal end 17036 is pivotally coupled to or pinned to the distal joint member 16250 on side A of the first reference plane $RP_1$ such that the third distal link 17070 crosses through the first reference plane $RP_1$. The distal end 17076 pivots about the eighth pivot axis EPA.

The "fourth" distal link 17080 comprises a rigid body 17082 that defines a proximal end 17084 and a distal end 17086. The proximal end 17084 is pivotally coupled to or pinned to the central joint member 16230 on side A of the first reference plane $RP_1$ and the distal end 17086 is pivotally coupled to or pinned to the distal joint member 16250 on side B of the first reference plane $RP_1$ such that the fourth distal link 17080 crosses the third distal link 17070 and passes through the first reference plane $RP_1$. The proximal end 17084 pivots about the fifth pivot axis FFPA and the distal end 17086 pivots about the sixth pivot axis SXPA.

In the illustrated example, the articulation joint 16200 is operably controlled by a cable control system that comprises four cables 16310, 16320, 16330, and 16340 that extend through the elongate shaft assembly to operably interface with a cable control system that is supported within the housing of the surgical instrument. The cable control system may comprise a plurality of cable support members/capstans, pulleys, etc. that are controlled by one or more corresponding motors that are controlled by a control circuit portion of the surgical instrument. The cable control system is configured to manage the tensioning (pulling) and paying out of cables at precise times during the articulation process. As can be seen in FIGS. 178 and 180, the cable 16310 extends through corresponding passage in the proximal joint member 16210 on side A of the first reference plane $RP_1$ and side C of the second reference plane $RP_2$ into a corresponding passage in the central joint member 14530 located on side D of the second reference plane $RP_2$. The cable 16310 exits the central joint member 16230 and enters a corresponding passage in the distal joint member 16250 that crosses through the first reference plane $RP_1$ to exit the distal joint member 16250 at a location that is on side B of the first reference plane $RP_1$ and side D of the second reference plane $RP_2$. Cable 16310 has a retainer lug 163122 thereon to prevent it from pulling through the distal joint member 16250.

Still referring to FIGS. 178 and 180, the cable 16320 extends through a corresponding passage in the proximal joint member 16210 on side A of the first reference plane $RP_1$ and side D of the second reference plane $RP_2$ into a corresponding passage in the central joint member 14530 located on side C of the second reference plane $RP_2$. The cable 16320 exits the central joint member 16230 and enters a corresponding passage in the distal joint member 16250 that crosses through the first reference plane $RP_1$ to exit the distal joint member 16250 at a location that is on side B of the first reference plane $RP_1$ and side C of the second reference plane $RP_2$. Cable 16320 has a retainer lug 16322 thereon to prevent it from pulling through the distal joint member 16250.

As can also be seen in FIGS. 178 and 180, the cable 16330 extends through a corresponding passage in the proximal joint member 16210 on side B of the first reference plane $RP_1$ and side C of the second reference plane $RP_2$ into a corresponding passage in the central joint member 14530 located on side D of the second reference plane $RP_2$. The cable 16330 exits the central joint member 16230 and enters a corresponding passage in the distal joint member 16250 that crosses through the first reference plane $RP_1$ to exit the distal joint member 16250 at a location that is on side A of the first reference plane $RP_1$ and side D of the second reference plane $RP_2$. Cable 16330 has a retainer lug 16332 thereon to prevent it from pulling through the distal joint member 16250.

As can be further seen in FIGS. 178 and 180, the cable 16340 extends through a corresponding passage in the proximal joint member 16210 on side B of the first reference plane $RP_1$ and side D of the second reference plane $RP_2$ into a corresponding passage in the central joint member 14530 located on side C of the second reference plane $RP_2$. The cable 16330 exits the central joint member 16230 and enters a corresponding passage in the distal joint member 16250 that crosses through the first reference plane $RP_1$ to exit the distal joint member 16250 at a location that is on side A of the first reference plane $RP_1$ and side C of the second reference plane $RP_2$. Cable 16340 has a retainer lug 16342 thereon to prevent it from pulling through the distal joint member 16250.

To articulate the distal joint member 16250 in a first articulation direction FAD relative to the central joint member 16230, the cable control system is actuated to apply tension to cables 16330 and 16340 while allowing cables 16310 and 16320 to sufficiently slacken. To articulate the distal joint member 16250 in a second articulation direction SAD, the cable control system is actuated to apply tension to cables 16310 and 16320 while allowing cables 16330 and 16340 to sufficiently slacken. To articulate the central joint member 16230 relative to the proximal joint member 16210 in a third articulation direction TAD, the cable control system is actuated to apply tension to cables 16320 and 16340 while allowing cables 16310 and 16330 to sufficiently slacken. To articulate the central joint member 16230 relative to the proximal joint member 16210 in a fourth articulation direction FRD, the cable control system is actuated to apply tension to cables 16310 and 16330 while allowing cables 16320 and 16340 to sufficiently slacken.

FIGS. 181-183 illustrate another form of articulation joint 18200 that comprises a proximal joint member 18210 and a distal joint member 18250. The proximal joint member 18210 is configured to be attached to a distal end of an elongate shaft assembly 18100 (FIG. 182) that is coupled to a housing or other portion of a surgical instrument in the various manners disclosed herein. The distal joint member 18250 may be attached to a closure tube arrangement 18110 (FIG. 182) that is configured to apply closing and/or opening motions to a movable jaw of an end effector 18000. In alternative arrangements, the distal joint member 18250 may be attached to one of the end effector jaws or other mounting portion of the end effector 18000. For example, the distal joint member 18250 may be attached to an elongate channel of an endo-cutter arrangement in the various manners disclosed herein. In at least one arrangement, for example, the shaft assembly 18100 defines a shaft axis SA and the end effector 18000 defines and end effector axis EA. The articulation joint facilitates selective articulation of the end effector 18000 relative to the shaft assembly 18100 in an articulation plane between an unarticulated position wherein the end effector axis EA is axially aligned with the shaft axis SA and articulated positions wherein the end effector axis EA is not aligned with the shaft axis SA.

As can be seen in FIGS. 181-183, the proximal joint member 18210 comprises a proximal mounting hub 18212. The proximal mounting hub, for example, may be configured to be inserted into a hollow outer shaft or tube portion 18102 of an elongate shaft assembly 18100 and be attached thereto by welding, adhesive, etc. The illustrated example further comprises a distally-facing collar portion 18214 that defines a distally-facing mounting area, generally designated as 18220. See FIG. 183. To accommodate passage of various control shafts/drive members through the articulation joint 18200, the proximal joint member 18210 further comprises a proximal central passage 18216 that extends through the proximal mounting hub 18212 into the distally-facing mounting area 18220. In the illustrated example, the proximal central passage 18216 is configured to accommodate a proximal drive shaft 18310 that is a portion of a rotary drive system 18300. In other arrangements, a flexible drive shaft (not shown) may extend through the proximal central passage 18216.

The distal joint member 18250 comprises a distal mounting hub 18252 that is configured to be inserted into a hollow outer shaft 18114 or closure tube or mounting hub of a surgical end effector 18000 and be attached thereto by welding, adhesive, etc. The surgical end effector 18000 may comprise any of the surgical end effector examples disclosed herein. The illustrated example further comprises a proximally-facing collar portion 18254 that defines a proximally-facing mounting area, generally designated as 18260. In addition, the distal joint member 18250 further comprises a distal central passage 18256 that extends from the distally-facing mounting area 18220 through the distal mounting hub 18252. In the illustrated example, the distal central passage 18256 is configured to accommodate a distal drive shaft 18330 that is a portion of the rotary drive system 18300 or in other embodiments, the distal central passage 18256 may support another portion of a flexible drive shaft arrangement.

The illustrated example further comprises an articulation linkage assembly 19000 that extends between the proximal joint member 18210 and the distal joint member 18250 and is configured to operably interface therewith to facilitate articulation of the distal joint member 18250 (and the surgical end effector coupled thereto) relative to proximal joint member 18210 (and the elongate shaft assembly 18100 coupled thereto). As can be seen in FIG. 183, the articulation linkage assembly 19000 comprises a first link 19010, a second link 19030, and a third link 19050. Each of the links 19010, 19030 and 19050 is movably captured between the proximal joint member 18210 and the distal joint member 18250, but, as will be discussed in further detail below, none of the links 19010, 19030, 19050 are directly attached to either of the proximal joint member 18210 and the distal joint member 18250.

In one example, the first link 19010 comprises a rigid first link body 19012 that defines a first proximal end 19014 and a first distal end 19018. The first proximal end 19104 has a first proximal saddle 19016 formed therein that is configured to be pivotally received on a corresponding first proximal mounting lug 18222 formed in the distally-facing mounting area 18220. The first proximal mounting lug 18222 has an arcuate proximal pivot surface 18223 thereon and defines a first proximal pivot axis FPPA. See FIG. 184. The first proximal saddle 19016 comprises a U-shaped proximal pivot surface 19017 that is configured to rollably or movably interface with the arcuate proximal pivot surface 18223 on the first proximal mounting lug 18222 such that the first link 19010 is movable relative to proximal joint member 18210 about the first proximal pivot axis FPPA in multiple directions or in multiple proximal travel paths. For example, the first proximal saddle 19016 can move relative to the first proximal pivot axis FPPA in a first proximal travel path FPTP and a second proximal travel path SPTP. In at least one arrangement, the first proximal travel path FPTP is transverse to the second proximal travel path SPTP. See FIGS. 184 and 186-189.

The first distal end 19108 comprises a first distal saddle 19020 formed therein that is configured to be pivotally received on a corresponding first distal mounting lug 18262 formed in the proximally-facing mounting area 18260. The first distal mounting lug 18262 has an arcuate pivot surface 18263 and defines a first distal pivot axis FDPA. See FIG. 185. The first distal saddle 19020 comprises a U-shaped pivot surface 19022 that is configured to rollably or movably interface with the arcuate pivot surface 18263 on the first distal mounting lug 18262 such that the first link 19010 is movable relative to the distal proximal joint member 18250 about the first distal pivot axis FDPA in multiple directions or multiple distal travel paths. For example, the first distal saddle 19020 can move relative to the first distal pivot axis FDPA in a first distal travel path FDTP and a second distal travel path SDTP. In at least one arrangement, the first distal travel path FDTP is transverse to the second distal travel path SDTP. See FIG. 185.

The second link 19030 comprises a rigid second link body 19032 that defines a second proximal end 19034 and a second distal end 19038. The second proximal end 19034 has a second proximal saddle 19036 formed therein that is configured to be pivotally received on a corresponding second proximal mounting lug 18224 formed in the distally-facing mounting area 18220. The second proximal mounting lug 18224 has a second arcuate proximal pivot surface 18225 thereon and defines a second proximal pivot axis SPPA. See FIG. 184. The second proximal saddle 19036 comprises a second U-shaped proximal pivot surface 19037 that is configured to rollably or movably interface with the second arcuate proximal pivot surface 18225 on the second proximal mounting lug 18224 such that the second link 19030 is movable relative to proximal joint member 18210 about the second proximal pivot axis SPPA in multiple directions or multiple proximal travel paths. For example, the second proximal saddle 19036 can move relative to the second proximal pivot axis SPPA in a first proximal travel path FPTP and a second proximal travel path SPTP. In at least one arrangement, the first proximal travel path FPTP is transverse to the second proximal travel path SPTP. See FIG. 184.

The second distal end 19038 comprises a second distal saddle 19040 that is configured to be pivotally received on a corresponding second distal mounting lug 18264 formed in the proximally-facing mounting area 18260. See FIG. 185. The second distal mounting lug 18264 has a second arcuate distal pivot surface 18265 and defines a second distal pivot axis SDPA. The second distal saddle 19040 comprises a second U-shaped distal pivot surface 19042 that is configured to rollably interface with the second arcuate distal pivot surface 18265 on the second distal mounting lug 18264 such that the second link 19030 is movable relative to the distal joint member 18250 about the second distal pivot axis SDPA in multiple directions or multiple distal paths. For example, the second distal saddle 19040 can move relative to the second distal pivot axis SDPA in a first distal travel path FDTP and a second distal travel path SDTP. In at least one arrangement, the first distal travel path FDTP is transverse to the second distal travel path SDTP. See FIG. 185.

The third link 19050 comprises a rigid third link body 19052 that defines a third proximal end 19054 and a third distal end 19058. The third proximal end 19054 has a third proximal saddle 19056 formed therein that is configured to be pivotally received on a corresponding third proximal mounting lug 18226 formed in the distally-facing mounting area 18220. The third proximal mounting lug 18226 has a third arcuate proximal pivot surface 18227 and defines a third proximal pivot axis TPPA. See FIG. 184. The third proximal saddle 19056 comprises a third U-shaped proximal pivot surface 19057 that is configured to rollably or movably interface with the third arcuate proximal pivot surface 18227 on the third proximal mounting lug 18226 such that the third link 19050 is movable relative to proximal joint member 18210 about the third proximal pivot axis TPPA in multiple directions or multiple travel paths. For example, the third proximal saddle 19056 can move relative to the third proximal pivot axis TPPA in a first proximal travel path FPTP and a second proximal travel path SPTP. In at least one arrangement, the first proximal travel path FPTP is transverse to the second proximal travel path SPTP. See FIG. 184.

The third distal end 19058 comprises a third distal saddle 19060 that is configured to be pivotally received on a corresponding third distal mounting lug 18266 formed in the proximally-facing mounting area 18260. See FIG. 185. The third distal mounting lug 18266 comprises a third arcuate distal pivot surface 18267 and defines a third distal pivot axis TDPA. The third distal saddle 19060 comprises a third U-shaped distal pivot surface 19062 that is configured to rollably or movably interface with the third arcuate distal pivot surface 18267 on the third distal mounting lug 18266 such that the third link 19050 is movable relative to the distal joint member 18250 about the third distal pivot axis TDPA in multiple directions or multiple distal travel paths. For example, the third distal saddle 19060 can move relative to the third distal pivot axis TDPA in a first distal travel path FDTP and a second distal travel path SDTP. In at least one arrangement, the first distal travel path FDTP is transverse to the second distal travel path SDTP. See FIG. 185.

In the illustrated arrangement, none of the links 19010, 19030, and 19050 are directly attached to either of the proximal joint member 18210 or the distal joint member 18250. Instead, the link assembly 19000 is supported in movable pivotal engagement with the proximal joint member 18210 and the distal joint member 18250 by a cable-based articulation system 18400. In the illustrated example, the articulation joint 18200 is operably controlled by a cable control system 18400 that comprises four flexible actuator members in the form of cables 18410, 18420, 18430, and 18440 that extend through the elongate shaft assembly to operably interface with a cable control system that may be supported within the housing of the surgical instrument. The cable control system may comprise a plurality of cable support members/capstans, pulleys, etc. that are controlled by one or more corresponding motors that are controlled by a control circuit portion of the surgical instrument. The cable control system is configured to manage the tensioning (pulling) and paying out of cables at precise times during the articulation process. As can be seen in FIG. 181, the cable 18410 extends through a corresponding passage 18412 in the proximal joint member 18210 into a corresponding passage 18414 in the distal joint member 18250 and has a retainer lug (not shown) thereon to prevent it from pulling through the distal joint member 18250. The cable 18420 extends through a corresponding passage 18422 in the proximal joint member 18210 and enters a corresponding passage in the distal joint member 18250 and has a retainer lug (not shown) thereon to prevent it from pulling through the distal joint member 18250. The cable 18430 extends through a corresponding passage 18432 in the proximal joint member 18210 into a corresponding passage 18434 in the distal joint member 18250 and has a retainer lug (not shown) thereon to prevent it from pulling through the distal joint member 18250. The cable 18440 extends through a corresponding passage 18442 in the proximal joint member 18210 into a corresponding passage 18444 in the distal joint member 18250 and has a retainer lug (not shown) thereon to prevent it from pulling through the distal joint member 18250. Thus, in one sense, the cables 18410, 18420, 18430, and 18440 span the articulation joint 18200 to apply articulation motions to the distal joint member 18250.

The distal joint member 18250 is selectively articulatable in multiple directions relative to the proximal joint member 18210 by applying tension to the various cables while enabling the remaining cables to slacken. As can be seen in FIGS. 190 and 191, the link assembly 19000 facilitates articulation motions that essentially approximate a distal virtual sphere VDS that rolls relative to a virtual proximal sphere VPS. In the illustrated arrangement, the rotary drive system 18300 further comprises a central "dog bone" drive shaft 18320 that has a spherical proximal end 18322 that is received in a proximal socket 18312 in the proximal drive shaft 18310 and is movably retained therein by corresponding pins 18324. The central drive shaft 18320 further has a spherical distal end 18326 that is received within a distal socket 18332 in the distal drive shaft 18330 and is movably retained therein by corresponding pins 18328. Other flexible drive shaft arrangements (rotary and/or non-rotary) may also be employed. As can also be seen in FIG. 190, the three links 19010, 19030, and 19050 are configured with a geometry that places the distal end of each link at 180 degrees (about the longitudinal axis) from the proximal end of the link. Each respective link 19010, 19030, and 19050 "reaches around" the central drive shaft 18320. Stated another way, the first link 19010 defines a first link axis FLA. The second link 19030 defines a second link axis SLA and the third link 19050 defines a third link axis TLA. In one arrangement, the links 19010, 19030, and 19050 are supported relative to each other such that the first link axis FLA, the second link axis SLA, and the third think axis TLA are transverse to each other. See FIG. 183. The specific geometric location of the lugs and saddle arrangements define a linkage 19000 that moves the distal joint member 18250 relative to the proximal joint member 18210 as if it was a ball rolling on another ball. The cables hold the links in compression so that the saddles are retained in movable engagement with their corresponding lugs in the proximal joint member 18210 and the distal joint member 18250 without being otherwise directly coupled thereto (e.g., without pins or other arrangements).

Closing an anvil requires a system that meets many requirements. The closure system needs to respond fast to the hand motions of the surgeon who is either operating the robotic system or the hand held system to which the end effector is attached. The closure system must also be capable of applying enough load on the tissue to ensure proper staple formation. It should also be easy to bail out in the event of failure while closing. These features should all be attainable within a footprint that is as small as possible to ensure adequate maneuverability within the patient.

FIGS. 192-194 illustrate a surgical end effector 20000 that comprises a closure system 20400 that may address many if not all of the foregoing challenges. In the illustrated example, the surgical end effector 20000 comprises an elongate channel 20100 that is configured to operably support a surgical staple cartridge 20300 therein. The surgical end effector 20000 further comprises an anvil 20200 that is configured to move between an open position and a closed position relative to the surgical staple cartridge 20300 to clamp tissue therebetween. As can be seen in FIGS. 194 and 195, the closure system 20400 comprises a rotary driven closure cam member 20410 that is configured to apply closure motions to the anvil 20200. In one arrangement, the closure cam member 20410 is supported on a rotatable cam shaft 20420 that has a driven gear 20422 formed thereon.

The driven gear 20422 is supported in meshing engagement with a rotary closure gear 20660 that may be driven by a motor/gearbox arrangement supported in a housing of the surgical instrument to which the surgical end effector is operably attached. As can be seen in FIGS. 196 and 197, the cam shaft 20420 comprises a spiral drive groove 20424 that is configured to receive a drive pin 20412 on the closure cam member 20410. Rotation of the cam shaft 20420 in a first rotary direction will cause the closure cam member 20410 to move in the distal direction DD from a starting position (FIGS. 194 and 196) to an ending position (FIGS. 195 and 197).

In one arrangement, the anvil 20200 comprises an anvil mounting portion 20210 that comprises two mounting arms 20212 that each have a slot therein that is configured to receive a corresponding pivot pin 20216 that protrudes from a proximal end of the elongate channel 20100. See FIG. 193. The closure cam member 20410 further comprises two closure cams 20414 that correspond to the anvil mounting arms 20212 of the anvil 20200. In one arrangement, the anvil 20200 may be biased into the open position shown in FIGS. 193 and 194 by a spring (not shown). The anvil 20200 is moved to a closed position by actuating the rotary closure gear 20660 to drive the closure cam member 20410 distally from the starting position to the ending position. As the closure cam member 20410 is driven distally, the closure cams 20414 contact the corresponding mounting arms 20212 and causes the anvil 20200 to pivot to the closed position shown in FIG. 195.

FIG. 198 illustrates the surgical end effector 20000 attached to an articulation joint 20500 that employs a rotary drive assembly 20600 for transmitting rotary drive motions across the articulation joint 20500. In the illustrated example, the rotary drive assembly 20600 comprises nested universal joints that can permit the surgical end effector 20000 to roll distal to the articulation joint 20500. A two-side joint arrangement wherein each joint can angle approximately seventy degrees (one hundred forty degrees total) may be employed, for example.

In one arrangement, the articulation joint 20500 comprises a proximal joint member 20510 that may be attached to an outer tube member of an elongate shaft assembly that is coupled to or operably interfaces with a housing of a surgical instrument. In alternative arrangements, the proximal joint member 20510 may be integrally formed on a distal end of the outer tube member of the elongate shaft. As can be seen in FIGS. 198-200, the proximal joint member 20510 comprises a distally protruding upper pivot tang 20520 and a distally protruding lower pivot tang 20530. The articulation joint 20500 further comprises a distal joint member 20540 that is attached to the surgical end effector 20000. In one example, the distal joint member 20540 is attached to the proximal end of the elongate channel 20100 and includes a proximally protruding upper pivot tang 20550 and a proximally protruding lower pivot tang 20560. In the illustrated example, the distally protruding upper pivot tang 20520 is formed with a series of proximal articulation gear teeth 20522 and the proximally protruding upper pivot tang 20550 is formed with a series of distal articulation gear teeth 20552. The distally protruding lower pivot tang 20530 is formed with an arcuate proximal surface 20532 and the proximally protruding lower pivot tang 20560 is formed with an arcuate distal surface 20562. In one example, the rotary drive assembly 20600 extends through the articulation joint 20500 and serves to retain the proximal articulation gear teeth 20522 in meshing engagement with the distal articulation gear teeth 20552 to facilitate pivotal travel therebetween. In addition, in at least one arrangement, the arcuate distal surface 20562 and the arcuate proximal surface 20532 may be supported in rocking engagement with each other. Such arrangement permits the surgical end effector 20000 to articulate through a single articulation plane relative to the elongate shaft assembly upon application of articulation control motions to the surgical end effector 20000. Such articulation control motions may be applied to the surgical end effector by cables or other articulation members (not shown) that extend from control systems in the surgical instrument housing and span the articulation joint 20500 to operably interface with the surgical end effector.

Turning to FIG. 200, the rotary drive system 20600 comprises a series of nested shaft systems 20610, 20710, and 20810. As can be seen in FIG. 200, the centermost "first" shaft system 20610 comprises a first proximal shaft member 20620 that is attached to or otherwise operably interfaces with a corresponding first rotary drive system supported by the housing of the surgical instrument. For example, the first rotary drive system may comprise a corresponding motor/gear arrangement configured to rotate the first proximal shaft member 20620. The first shaft system 20610 further comprises a first central shaft 20630 that comprises a shaft body 20632 that has a first spherical proximal end 20634 that is rotatably supported in a first spherical proximal cup 20622 on the first proximal shaft member 20620. The first central shaft 20630 is movably pinned within a cavity 20624 in the first spherical proximal cup 20622 by a first proximal pin 20636 that extends through an arcuate slot 20635 in the first spherical proximal end 20634. The first central shaft 20630 further comprises a first spherical distal end 20640 that is rotatably supported in a first spherical distal cup 20652 that is attached to a first distal shaft member 20650. The first central shaft 20630 is movably pinned within a cavity 20654 in the first spherical distal cup 20652 by a first distal pin 20644 that extends through an arcuate slot 20642 in the first spherical distal end 20640. In one arrangement, for example, the first distal shaft member 20650 may be configured to apply rotary motions to the closure gear 20660 to apply rotary closure motions to the rotatable cam shaft 20420 in the manners described above. See FIGS. 194 and 195, for example. Thus, in at least one arrangement, actuation of the first rotary drive system to cause rotation of the first proximal shaft member 20620 will result in actuation of the closure system 20400 to move the anvil 20200 from an open position to a closed position.

Referring to FIGS. 200-202, the second shaft system 20710 comprises a second proximal shaft member 20720 that is attached to or otherwise operably interfaces with a corresponding second rotary drive system supported by the housing of the surgical instrument. For example, the second rotary drive system may comprise a corresponding motor/gear arrangement configured to rotate the second proximal shaft member 20720. The second shaft system 20710 further comprises a second hollow central shaft 20730 that comprises a hollow shaft body 20732 that has a second spherical proximal end 20734. In one arrangement, the second hollow central shaft 20730 may be fabricated in two segments that are welded or otherwise coupled together. The second spherical proximal end 20734 defines a second central proximal cavity 20735 that is configured to movably receive therein the first spherical proximal cup 20622 of the first proximal shaft member 20620 therein. The second spherical proximal end 20734 is configured to be rotatably supported in a second spherical proximal cup 20722 on the second proximal shaft member 20720. The second hollow central shaft 20730 is movably pinned within a cavity 20724 in the second spherical proximal cup 20722 by second proximal pin segments 20736 that extend from the second spherical proximal end 20734 to be movably received within corresponding arcuate slots 20726 in the second spherical proximal cup 20722 on the second proximal shaft member 20720. The second hollow central shaft 20730 further comprises a second spherical distal end 20740. The second spherical distal end 20740 defines a second central distal cavity 20742 that is configured to movably receive therein the first spherical distal cup 20652 of the first distal shaft member 20650 therein. The second hollow central shaft 20730 is movably pinned within a cavity 20754 in the second spherical distal cup 20752 by second distal pin segments 20746 that extend from the second spherical distal end 20740 to be movably received within corresponding arcuate slots 20756 in the second spherical distal cup 20752 on the second distal shaft member 20750.

In one arrangement, the second distal shaft member 20750 may be configured to apply rotary motions to a first rotary drive gear 20760 that is in meshing engagement with a driven gear 20762 that is attached to a rotary drive shaft 20770 that is rotatably supported in the elongate channel 20100. See FIGS. 194, 195, and 203. As can be seen in FIGS. 194, 195, and 203, the surgical end effector 20000 further comprises a firing member 20310 that is in threaded engagement with the rotary drive shaft 20770. Rotation of the rotary drive shaft 20770 in a first rotary direction will cause the firing member 20310 to move distally from a starting position (FIG. 194) through the surgical end effector 20000 to an ending position. Rotation of the rotary drive shaft 20770 in an opposite rotary motion will drive the firing member 20310 from the ending position back to the starting position. Thus, in at least one arrangement, actuation of the second rotary drive system to cause rotation of the second proximal shaft member 20720 will result in actuation of the firing member 20310 to cut and staple tissue that is clamped between the anvil 20200 and the surgical staple cartridge 20300.

Referring to FIGS. 200-202, the third shaft system 20810 comprises a third proximal shaft member 20820 that is attached to or otherwise operably interfaces with a corresponding third rotary drive system supported by the housing of the surgical instrument. For example, the third rotary drive system may comprise a corresponding motor/gear arrangement configured to rotate the third proximal shaft member 20820. The third shaft system 20810 further comprises a third hollow central shaft 20830 that comprises a hollow shaft body 20832 that has a third spherical proximal end 20834. In one arrangement, the third hollow central shaft 20830 may be fabricated in two segments that are welded or otherwise coupled together. The third spherical proximal end 20834 defines a third proximal cavity 20835 that is configured to movably receive therein the second spherical proximal cup 20722 of the second proximal shaft member 20720 therein. The third spherical proximal end 20834 is configured to be movably supported in a third proximal socket 20824 in the third proximal shaft member 20820. The third spherical proximal end 20834 is axially movable within the third proximal socket 20824 and is attached thereto by third proximal pin segments 20836 that extend from the third spherical proximal end 20834 to be movably received within corresponding axial slots 20824 in the third proximal socket 20824 on the third proximal shaft member 20820. The third central shaft 20830 further comprises a third spherical distal end 20840. The third spherical distal end 20840 defines a third central distal cavity 20842 that is configured to movably receive therein the second spherical distal cup 20752 of the second distal shaft member 20750 therein. The third spherical distal end 20840 is movably pinned within a third distal socket 20852 on a third distal shaft 20850. The third spherical distal end 20840 is axially movable within the third distal socket 20852 and is attached thereto by third distal pin segments 20846 that extend from the third spherical distal end 20840 to be movably received within corresponding axial slots 20854 in the third distal socket 20850.

In one arrangement, the third distal shaft member 20850 may be configured to apply rotary motions to the surgical end effector 20000 to rotate the surgical end effector 20000 about the shaft axis SA. In one arrangement, for example, the third distal shaft member 20850 may be directly attached to (welded) the elongate channel 20100. Thus, in at least one arrangement, actuation of the third rotary drive system to cause rotation of the third proximal shaft member 20820 will result in rotation of the third distal shaft member 20850 and the surgical end effector 20000. In the illustrated arrangement, the intermeshing gear teeth 20522 and 20552 on the upper proximal pivot tang 20520 and upper distal pivot tang 20550 force the centers of the shaft systems to stay in the same center distance when undergoing articulation. Such shaft systems are very strong and robust while maintaining a tight articulation joint while also facilitating distal roll of the surgical end effector.

Highly articulated robotic and handheld endo mechanical staplers need to generate a lot of force to clamp onto thick tissue. Moving forces through a highly articulated joint (sixty degrees and greater for example) is challenging. Many robotic and handheld motors are slow and their ability to produce sufficient torque is limited. FIGS. 204-210 illustrate a surgical end effector 21000 that can address many of not all of those challenges. As can be seen in FIG. 204, the surgical end effector 21000 comprises a first jaw 21100 that comprises an elongate channel 21110 that is configured to operably support a surgical staple cartridge 21300 therein. The surgical end effector 21000 further comprises a second jaw 21200 that comprises an anvil 21210 that is pivotally coupled to the elongate channel 21110 about a fixed pivot axis PA. The anvil 21210 is pivotable between an open position (FIG. 206) and a closed position (FIG. 205) by a rotary driven closure system 21400.

In one arrangement, the closure system 21400 comprises a closure drive shaft 21410 that is configured to be rotated by a corresponding source of rotary motion (motor, etc.) in the housing of the surgical instrument to which the surgical end effector is attached. The closure drive shaft 21410 may comprises a flexible shaft arrangement that can flex while transferring torque through an articulation joint. The closure drive shaft 21410 is attached to a rotary cam shaft 21420 that has a closure cam lobe 21422 formed thereon. In one arrangement, an opening bushing 21430 is movably journaled on the rotary cam shaft 21420 and is configured to engage an opening tab 21222 on an anvil mounting portion 21220 of the anvil 21210. An opening spring 21440 is positioned on the rotary cam shaft 21420 to bias the opening bushing 21430 distally into contact with the opening tab 21222 on the anvil 21210. As can be seen in FIG. 126, as the opening bushing 21430 moves distally, it contacts the opening tab 21222 which causes the anvil 21210 to pivot about the pivot axis PA to the open position (FIG. 206).

In one example, the anvil 21210 is pivoted from the open position to a closed position by rotating the rotary cam shaft 21420 from a first rotary position shown in FIG. 207 to a final rotary position shown in FIG. 209. As can be seen in FIGS. 204 and 205, the closure system 21400 further comprises a cam follower 21450 that is movably supported in the anvil mounting portion 21220 and is configured for movable engagement with the closure cam lobe 21422 on the rotary cam shaft 21420. FIGS. 206 and 207 illustrate the position of the closure cam lobe 21422 when the anvil 21210 is in the open position. When in that position, the anvil mounting portion 21220 has pivoted past the closure cam lobe 21422 such that the cam follower 21450 is not contacted by the closure cam lobe 21422. As the rotary cam shaft 21420 begins to rotate, the closure can lobe 21422 contacts the cam follower 21450 (FIG. 208) and cams the cam follower 21450 into contact with a pivot cradle 12224 in the anvil mounting portion 21220 (upward in FIG. 208) to the position shown in FIG. 209 wherein the cam follower 21452 has pivoted the anvil 21210 to the closed position (FIG. 210). As the anvil 21210 pivots to the closed position, the opening tab 21222 biases the opening bushing 21430 proximally on the rotary cam shaft 21420 against the bias of the opening spring 21440. Thus, when the rotary cam shaft 21420 is rotated in an opposite direction, the anvil opening spring 21440 biases the opening bushing 21430 distally into contact with the opening tab 21222 to pivot the anvil 21210 back to the open position.

FIG. 211 illustrates another rotary cam shaft 21420' that is identical to the rotary cam shaft 21420 except that a distal end 21426 of the rotary cam shaft 21420' further comprises an opening cam 21426 that is configured to engage the opening tab 21222 on the anvil 21210 to move the anvil 21210 to an open position. Thus, when the rotary cam shaft 21420' is in a first rotary position, the opening cam 21426 has cammed the anvil opening tab 21222 to pivot the anvil 21210 to the open position. See FIG. 212. To close the anvil, the rotary cam shaft 21420' is rotated in a closure direction to cause the cam lobe 21422 to cam the cam follower 21450 upward to pivot the anvil 21210 into the closed position. The anvil 21210 can then be returned to the open position by rotating the rotary cam shaft 21420' back to the first rotary position. In alternative arrangements, the opening bushing 21430 and opening spring 21440 may be used in conjunction with the rotary cam shaft 21420'.

It will be appreciated that the foregoing embodiments of the closure system 21400 facilitates the application of relatively quick closure and opening motions to the anvil 21210. In various arrangements, the cam profile(s) may be formed to establish a low mechanical advantage at the start and a relatively high mechanical advantage at the end when the anvil 21210 starts to compress tissue. Such closure system arrangement employs fewer components than many other closure system designs. This arrangement also provides additional space at the proximal end of the end effector to accommodate electronics and other mechanisms in the end effector.

Example Set No. 1

Example 1—A surgical instrument comprising an elongate shaft. A surgical end effector is coupled to the elongate shaft by an articulation joint that is configured to facilitate selective articulation of the surgical end effector relative to the elongate shaft. The surgical end effector comprises a first jaw and a second jaw that is configured to move relative to the first jaw between an open position and a closed position. A firing member is supported for axial travel within the surgical end effector between a starting position and an ending position. The surgical instrument further comprises an upper flexible spine assembly that is attached to a top portion of the firing member. A lower flexible spine assembly is attached to a bottom portion of the firing member. A rotary drive member operably interfaces with the upper flexible spine assembly at an upper location. The rotary drive member also operably interfaces with the lower flexible spine assembly at a lower location. The upper location and the lower location are distal to the articulation joint. The rotary drive member is configured to cause the upper flexible spine assembly and the lower flexible spine assembly to apply axial drive motions to the firing member to move the firing member between the starting position and the ending position.

Example 2—The surgical instrument of Example 1, wherein the rotary drive member is centrally disposed between the upper flexible spine assembly and the lower flexible spine assembly.

Example 3—The surgical instrument of Examples 1 or 2, wherein the upper flexible spine assembly comprises an upper series of upper vertebra members that are loosely coupled together and the lower flexible spine assembly comprises a lower series of lower vertebra members that are loosely coupled together.

Example 4—The surgical instrument of Example 3, wherein the upper vertebra members are movably supported relative to each other by an upper flexible coupler member that is coupled to the top portion of the firing member and extends through each upper vertebra member. The lower vertebra members are movably supported relative to each other by a lower flexible coupler member that is coupled to the bottom portion of the firing member and extends through each lower vertebra member.

Example 5—The surgical instrument of Example 4, wherein each upper vertebra member comprises an upper vertebra body portion that defines an upper proximal end and an upper distal end. An upper hollow passage extends through the upper vertebra body portion between the upper proximal end and the upper distal end to permit the upper flexible coupler member to extend therethrough. An upper proximal mating feature is provided on the upper proximal end and an upper distal mating feature is provided on the upper distal end. The upper proximal mating feature on each upper vertebra member is configured to movably interface with the upper distal mating feature on an adjacent upper vertebra member. An upper vertebra drive feature is configured to operably engage the rotary drive member.

Example 6—The surgical instrument of Example 5, wherein the upper proximal mating feature comprises an upper concave recess in the upper proximal end of the upper vertebra body portion. The upper distal mating feature comprises an upper convex protrusion on the upper distal end of the upper vertebra body portion. The upper convex protrusion on each upper vertebra member is sized and shaped to matingly engage the upper concave recess in an adjacent upper vertebra member.

Example 7—The surgical instrument of Examples 5 or 6, wherein the each lower vertebra member comprises a lower vertebra body portion that defines a lower proximal end and a lower distal end. A lower hollow passage extends through the lower vertebra body portion between the lower proximal end and the lower distal end to permit the lower flexible coupler member to extend therethrough. A lower proximal mating feature is provided on the lower proximal end and a lower distal mating feature is provided on the lower distal end. The lower proximal mating feature on each lower vertebra member is configured to movably interface with the lower distal mating feature on an adjacent lower vertebra member. A lower vertebra drive feature is configured to operably engage the rotary drive member.

Example 8—The surgical instrument of Example 7, wherein the lower proximal mating feature comprises a lower concave recess in the lower proximal end of the lower vertebra body portion and the lower distal mating feature comprises a lower convex protrusion on the lower distal end of the lower vertebra body portion. The lower convex protrusion on each lower vertebra member is sized and shaped to matingly engage the lower concave recess in an adjoining lower vertebra member.

Example 9—The surgical instrument of Examples 7 or 8, wherein the upper vertebra drive feature comprises an upper tooth that is configured to interface with the rotary drive member, and wherein the lower vertebra drive feature comprises a lower tooth that is configured to interface with the rotary drive member.

Example 10—The surgical instrument of Example 9, wherein the rotary drive member comprises a rotary body portion that has a helical drive member on an external surface thereof. The helical drive member is configured to engage an upper helical surface that is formed on each upper tooth and a lower helical surface on each lower tooth.

Example 11—The surgical instrument of Examples 3, 4, 5, 6, 7, 8, 9 or 10, further comprising an upper vertebra biaser that is configured to apply a continuous upper compression to the upper series of upper vertebra members to retain the upper vertebra members in the upper series of upper vertebra members in movable contact with each other. The surgical instrument further comprises a lower vertebra biaser that is configured to apply a continuous lower compression to the lower series of lower vertebra members to retain the lower vertebra members in the lower series of lower vertebra members in movable contact with each other.

Example 12—The surgical instrument of Example 10, wherein the upper helical surface comprises two different pitches.

Example 13—The surgical instrument of Examples 4, 5, 6, 7, 8, 9, 10, 11 or 12, wherein the upper flexible coupler member and the lower flexible coupler member are configured to retract the firing member from a position that is distal to the starting position by applying retraction motions to each of the upper flexible coupler member and the lower flexible coupler member in a proximal direction.

Example 14—The surgical instrument of Examples 3, 4, 5, 6, 7, 8, 9, 10, 11, 12 or 13, wherein the articulation joint comprises an articulation joint length and wherein the upper series of upper vertebra members comprises an upper series length that is greater than or equal to the articulation joint length plus a distance from the starting position to the ending position of the firing member. The lower series of lower vertebra members comprises a lower series length that is greater than or equal to the articulation joint length plus the distance from the starting position to the ending position of the firing member.

Example 15—The surgical instrument of Examples 3, 4, 5, 6, 7, 8, 9, 10, 11, 12, 13 or 14, further comprising an upper sleeve that extends from a proximal end of the surgical end effector and spans the articulation joint. The upper sleeve is axially movable relative to the surgical end effector and is configured to slidably support a portion of the upper series of upper vertebra members that spans the articulation joint. A lower sleeve extends from the proximal end of the surgical end effector and spans the articulation joint. The lower sleeve is axially movable relative to the surgical end effector and is configured to slidably support another portion of the lower series of lower vertebra members that spans the articulation joint.

Example 16—A surgical instrument that comprises an elongate shaft that has a surgical end effector coupled thereto by an articulation joint that is configured to facilitate selective articulation of the surgical end effector relative to the elongate shaft. The surgical end effector comprises a firing member that is supported for axial travel within the surgical end effector between a starting position and an ending position. A rotary drive member is rotatably supported at a location that is distal to the articulation joint. An upper longitudinally-segmented nut assembly is attached to a top portion of the firing member and is in threaded engagement with the rotary drive member at an upper location that is distal to the articulation joint such that rotation of the rotary drive member causes the upper longitudinally-segmented nut assembly to apply an upper axial drive motion to the firing member. The upper longitudinally-segmented nut assembly is flexible to accommodate articulation of the surgical end effector. A lower longitudinally-segmented nut assembly is attached to a bottom portion of the firing member and is in threaded engagement with the rotary drive member at a lower location that is distal to the articulation joint such that rotation of the rotary drive member causes the lower longitudinally-segmented nut assembly to apply a lower axial drive motion to the firing member. The lower longitudinally-segmented nut assembly is flexible to accommodate articulation of the surgical end effector.

Example 17—The surgical instrument of Example 16, wherein the upper longitudinally-segmented nut assembly comprises an upper series of upper vertebra members that are movably supported relative to each other by an upper flexible coupler member that is coupled to the top portion of the firing member and extends through each upper vertebra member. The lower longitudinally-segmented nut assembly comprises a lower series of lower vertebra members that are movably supported relative to each other by a lower flexible coupler member that is coupled to the bottom portion of the firing member and extends through each lower vertebra member.

Example 18—The surgical instrument of Examples 16 or 17, wherein the rotary drive member comprises a helical thread that comprises at least two different pitches.

Example 19—The surgical instrument of Examples 17 or 18, further comprising means for permitting the upper vertebra members and the lower vertebra members that traverse the articulation joint to move out of axial alignment while facilitating serial threaded engagement with the rotary drive member.

Example 20—A surgical instrument that comprises an elongate shaft that has a surgical end effector coupled thereto by an articulation joint configured to facilitate selective articulation of the surgical end effector relative to the elongate shaft. The surgical end effector comprises a firing member that is supported for axial travel within the surgical end effector between a starting position and an ending position. A rotary drive member is rotatably supported at a location that is distal to the articulation joint. A flexible drive assembly is supported by the elongate shaft such that it axially traverses the articulation joint and is configured to accommodate articulation of the surgical end effector about the articulation joint. The flexible drive assembly is in threaded engagement with the rotary drive member at a drive location that is distal to the articulation joint such that rotation of the rotary drive member causes the flexible drive assembly to apply an axial drive motion to the firing member.

Example Set No. 2

Example 1—A surgical end effector comprising a first jaw and a second jaw that is configured to move relative to the first jaw between an open position and a closed position. A firing member is supported for axial travel within the surgical end effector between a home position corresponding to the open position of the second jaw and an ending position. The firing member is configured to apply a first closure motion to the second jaw to move the second jaw from the open position to the closed position as the firing member is moved in a distal direction from the home position to the ending position. The firing member is further configured to apply a second closure motion to the second jaw to move the second jaw towards the first jaw when the firing member is moved in a proximal direction from the home position.

Example 2—The surgical end effector of Example 1, wherein the firing member comprises a vertically-extending firing member body that includes a top firing member feature that is configured to apply the first closure motion to the second jaw. The firing member further comprises a bottom firing member feature that is configured to slidably engage the first jaw as the firing member is moved between the home position and the ending position. At least one pre-compression feature is configured to contact a portion of the second jaw when the firing member is moved in a proximal direction from the home position.

Example 3—The surgical end effector of Example 2, wherein the second jaw is supported for pivotal travel between the open position and the closed position relative to the first jaw about a jaw pivot axis. At least one pre-compression feature is configured to contact the portion of the second jaw at a pre-compression location that is distal to the jaw pivot axis.

Example 4—The surgical end effector of Examples 1, 2 or 3, wherein the second jaw comprises a second jaw body that includes a proximal end and a distal end. The second jaw further comprises pivot features on the proximal end that define the jaw pivot axis. A portion of the second jaw comprises a jaw closure arm that protrudes from the proximal end and is configured to be contacted by at least one pre-compression feature as the firing member is moved proximally from the home position.

Example 5—The surgical end effector of Examples 2, 3 or 4, wherein the top firing member feature comprises a top tubular feature that protrudes from a top end of the vertically-extending firing member body and wherein the bottom firing member feature comprises a bottom tubular feature that protrudes from a bottom end of the vertically-extending firing member body.

Example 6—The surgical end effector of Example 5, wherein the first jaw comprises a bottom keyhole-shaped passage that is configured to slidably accommodate the bottom tubular feature on the firing member when the firing member is moved between the home position and the ending position, and wherein the second jaw comprises a top keyhole-shaped passage that is configured to slidably accommodate the top tubular feature on the firing member when the firing member is moved between the home position and the ending position.

Example 7—The surgical end effector of Examples 1, 2, 3, 4, 5 or 6, wherein the firing member is configured to operably engage a rotary drive member that is configured to apply an initial drive motion to the firing member to drive the firing member distally from the home position to a closure position wherein the firing member applies the first closure motion to the second jaw. The rotary drive member is further configured to apply a reversing drive motion to the firing member to drive the firing member in the proximal direction from the home position.

Example 8—The surgical end effector of Example 5, wherein the firing member is configured to operably engage a rotary drive member that is configured to apply an initial drive motion to the firing member to drive the firing member distally from the home position to a closure position wherein the firing member applies the first closure motion to the second jaw. The rotary drive member is further configured to apply a reversing drive motion to the firing member to drive the firing member in the proximal direction.

Example 9—The surgical end effector of Examples 5, 6 or 8, wherein the top tubular feature comprises an upper tooth that is configured to interface with the rotary drive member, and wherein the bottom tubular feature comprises at least one lower tooth that is configured to interface with the rotary drive member.

Example 10—The surgical end effector of Examples 7, 8 or 9, further comprising means for applying a bailout motion to the firing member to move the firing member from a position that is distal to the home position in a proximal direction to the home position without applying the reversing drive motion to the firing member with the rotary drive member.

Example 11—The surgical end effector of Examples 1, 2, 3, 4, 5, 6, 7, 8, 9 or 10, wherein the surgical end effector is configured to be operably coupled to a surgical instrument that comprises an upper flexible spine assembly that is attached to a top portion of the firing member and a lower flexible spine assembly that is attached to a bottom portion of the firing member. The surgical instrument further comprises a rotary drive member that operably interfaces with the upper flexible spine assembly and the lower flexible spine assembly such that the rotary drive member causes the upper flexible spine assembly and the lower flexible spine assembly to apply axial drive motions to the firing member to move the firing member between the home position and the ending position.

Example 12—The surgical end effector of Example 11, wherein the upper flexible spine assembly comprises an upper series of upper vertebra members that are loosely coupled together, and wherein the lower flexible spine assembly comprises a lower series of lower vertebra members that are loosely coupled together.

Example 13—The surgical end effector of Example 12, wherein the upper vertebra members are movably supported relative to each other by an upper flexible coupler member that is coupled to the top portion of the firing member and extends through each upper vertebra member, and wherein the lower vertebra members are movably supported relative to each other by a lower flexible coupler member that is coupled to the bottom portion of the firing member and extends through each lower vertebra member.

Example 14—The surgical end effector of Examples 2, 3, 4, 5, 6, 8, 9, 10, 11, 12 or 13, wherein the first jaw comprises a channel that is configured to operably support a surgical staple cartridge that comprises a cartridge body that operably supports a plurality of surgical staples therein. A cartridge sled is movably supported in the cartridge body and is configured to move between a beginning position and a finished position in the cartridge body to drive the surgical staples from the cartridge body. The second jaw comprises an anvil that is supported for pivotal travel between the open position and the closed position relative to the surgical staple cartridge. At least one pre-compression feature on the firing member is configured to drive the cartridge sled from the beginning position to the finished position when the firing member is distally driven from the home position to the ending position.

Example 15—A surgical instrument that comprises an elongate shaft that operably supports a firing drive system therein. A surgical end effector is operably coupled to the elongate shaft and comprises a first jaw and a second jaw that is configured to move relative to the first jaw between an open position and a closed position. A firing member operably interfaces with the firing drive system such that the firing drive system is configured to move the firing member between a home position that corresponds to the open position of the second jaw and an ending position. When the firing member is moved distally from the home position, the firing member applies a first closure motion to the second jaw to move the second jaw from the open position to the closed position. The firing drive system is configured to move the firing member proximally from the home position such that, when the firing member moves proximally from the home position, the firing member applies a second closure motion to the second jaw to move the second jaw towards the first jaw.

Example 16—The surgical instrument of Example 15, wherein the firing drive system comprises a rotary drive member that is configured to apply axial drive motions to the firing member.

Example 17—The surgical instrument of Example 16, further comprising an upper flexible spine assembly that is attached to a top portion of the firing member and operably interfaces with the rotary drive member such that rotation of the rotary drive member causes the upper flexible spine assembly to apply an upper axial drive motion to the firing member. A lower flexible spine assembly is attached to a bottom portion of the firing member and operably interfaces with the rotary drive member such that rotation of the rotary drive member causes the lower flexible spine assembly to apply a lower axial drive motion to the firing member.

Example 18—The surgical instrument of Example 17, wherein the upper flexible spine assembly comprises an upper series of upper vertebra members that are loosely coupled together, and wherein the lower flexible spine assembly comprises a lower series of lower vertebra members that are loosely coupled together.

Example 19—A surgical instrument comprising an elongate shaft that operably supports a firing drive system therein. A surgical end effector is operably coupled to the elongate shaft and comprises a first jaw and a second jaw that is configured to move relative to the first jaw between an open position and a closed position. A firing member operably interfaces with the firing drive system such that the firing drive system is configured to move the firing member between a home position that corresponds to the open position of the second jaw and an ending position. When the firing member is moved distally from the home position, the firing member applies a first closure motion to the second jaw to move the second jaw from the open position to the closed position. When the firing member is moved proximally from the home position, the firing member applies a second closure motion to the second jaw. The surgical instrument further comprises means for applying a rotary motion to the firing member to move the firing member distally from the home position and proximally from the home position. The means for applying is further configured to apply additional rotary motions to a drive arrangement that interfaces with the firing member to apply axial drive motions to the firing member.

Example 20—The surgical instrument of Example 19, further comprising means for applying a retraction force to the firing member to move the firing member from a position that is distal to the home position to the home position without actuating the means for applying.

Example Set No. 3

Example 1—A surgical instrument comprising an elongate shaft that has a surgical end effector coupled thereto by an articulation joint that is configured to facilitate selective articulation of the surgical end effector relative to the elongate shaft. The surgical end effector comprises a firing member that is supported for axial travel within the surgical end effector between a starting position and an ending position. A drive assembly comprises a series of drive components that are operably supported by the elongate shaft and are configured to traverse the articulation joint and operably interface with the firing member. The drive components are loosely linked to each other when traversing the articulation joint and are configured to serially engage a rotary drive member that is located distal to the articulation joint such that the rotary drive member causes each drive component to become rigidly latched to a proceeding drive component to form an axially ridged distal series of drive components that is configured to apply an axial drive motion to the firing member to drive the firing member between the starting position and the ending position.

Example 2—The surgical instrument of Example 1, wherein each drive component is configured to threadably engage the rotary drive member.

Example 3—The surgical instrument of Examples 1 or 2, wherein the rotary drive member comprises a hollow threaded member that is supported for rotation at a location that is distal to the articulation joint and wherein the drive components in at least a portion of the series of drive components are configured to serially threadably engage the hollow threaded member.

Example 4—The surgical instrument of Example 3, wherein when the hollow threaded member is rotated in a first rotary direction, a distal drive component in the series of loosely-linked drive components threadably engages the rotary drive member to cause the loosely-linked drive components to be pulled distally in series into operable threaded engagement with the rotary drive member. Each drive component in the series of loosely-linked drive component is latched into rigid engagement with a distally-adjacent drive components to form the axially rigid distal series of drive components Example 5—The surgical instrument of Example 4, wherein when the rotary drive member is rotated in a second rotary direction, the rotary drive member pulls the axially ridged distal series of drive components proximally such that as each drive component in the axially rigid distal series of drive components operably engages the rotary drive member and the rotary drive member de-latches the drive component from a distally-adjacent drive component in the axially rigid distal series of drive components to re-establish the series of loosely linked drive components.

Example 6—The surgical instrument of Examples 1, 2, 3, 4 or 5, wherein each drive component in at least a portion of the series of drive components comprises a thread portion on an outer perimeter thereof.

Example 7—The surgical instrument of Examples 1, 2, 3, 4 or 6, wherein each drive component is loosely-linked to adjacent drive components in the series of drive components by corresponding flexible members.

Example 8—The surgical instrument of Examples 1, 2, 3, 4, 5, 6 or 7, wherein at least some of the drive components in the series of drive components comprises a drive component body that has a latch feature distally protruding therefrom and a latch cavity located in a proximal end of the drive component body. The latch cavity is configured to latchingly receive therein the latch feature of a proximally adjacent drive component in the series of drive components.

Example 9—The surgical instrument of Example 8, wherein the drive component body is configured to threadably engage the rotary drive member.

Example 10—The surgical instrument of Example 9, wherein the hollow threaded member comprises an internal thread comprising a variable pitch.

Example 11—The surgical instrument of Examples 1, 2, 3, 4, 5, 6, 7, 8, 9 or 10, wherein the surgical end effector comprises a first jaw that comprises a first passage that is configured to slidably accommodate an upper portion of the firing member. The surgical end effector further comprises a second jaw that is configured to move relative to the first jaw between an open position and a closed position and comprises a second passage that is configured to accommodate a lower portion of the firing member. The first passage and the second passage are also configured to accommodate corresponding portions of drive component in the axially rigid distal series of drive components.

Example 12—A surgical instrument comprising an elongate shaft that has a surgical end effector coupled thereto by an articulation joint that is configured to facilitate selective articulation of the surgical end effector relative to the elongate shaft. The surgical end effector comprises a firing member that is supported for axial travel within the surgical end effector between a starting position and an ending position. A drive conversion member is supported at a location that is distal to the articulation joint. A flexible drive assembly is supported by the elongate shaft and axially traverses the articulation joint. The flexible drive assembly is configured to accommodate articulation of the surgical end effector and is in operable engagement with the drive conversion member such that when the drive conversion member is actuated, the drive conversion member converts a portion of the flexible drive assembly into an axially rigid drive member segment that is axially driven distally by the drive conversion member to apply axial drive motions to move the firing member between the starting position and the ending position.

Example 13—The surgical instrument of Example 12, wherein the drive conversion member is configured to threadably engage the flexible drive assembly.

Example 14—The surgical instrument of Examples 12 or 13, wherein the drive conversion member comprises a hollow threaded member that comprises an internal thread comprising a variable pitch.

Example 15—The surgical instrument of Examples 12, 13 or 14, wherein the surgical end effector comprises a first jaw and a second jaw that is configured to move relative to the first jaw between an open position and a closed position. The firing member is configured to apply a closure motion to the second jaw to move the second jaw from the open position to the closed position as the firing member is moved in a distal direction from the starting position to the ending position by the axially rigid drive member segment.

Example 16—The surgical instrument of Example 15, wherein the first jaw comprises a channel that is configured to operably support a surgical staple cartridge that comprises a cartridge body that operably supports a plurality of surgical staples therein. The surgical staple cartridge further comprises a cartridge sled that is movably supported in the cartridge body and is configured to move between a beginning position and a finished position in the cartridge body to drive the surgical staples from the cartridge body. The second jaw comprises an anvil that is supported for pivotal travel between the open position and the closed position relative to the surgical staple cartridge. The firing member is configured to drive the cartridge sled from the beginning position to the finished position when the firing member is driven from the starting position to the ending position.

Example 17—The surgical instrument of Examples 12, 13, 14, 15 or 16, wherein the drive conversion member is actuatable in a first actuation direction and a second actuation direction. When the drive conversion member is actuated in the first actuation direction, the drive conversion member converts the portion of the flexible drive assembly into the axially rigid drive member segment and when the drive conversion member is actuated in the second actuation direction, the drive conversion member drives the axially rigid drive member segment in a proximal direction.

Example 18—The surgical instrument of Example 17, wherein when the drive conversion member is actuated in the second actuation direction, the drive conversion member reconverts the axially rigid drive member segment into the portion of the flexible drive assembly.

Example 19—The surgical instrument of Examples 12, 13, 14, 15, 16, 17 or 18, wherein the firing member is movable from a position distal to the starting position to the starting position without actuating the drive conversion member by applying an axial bailout motion to the flexible drive assembly.

Example 20—A surgical instrument comprising an elongate shaft that has a surgical end effector coupled thereto by an articulation joint that is configured to facilitate selective articulation of the surgical end effector relative to the elongate shaft. The surgical end effector comprises a firing member that is supported for axial travel within the surgical end effector between a starting position and an ending position. A loosed-linked drive member is operably supported by the elongate shaft and traverses the articulation joint to accommodate articulation of the surgical end effector relative to the elongate shaft. The surgical instrument further comprises means for converting a portion of the loose-linked drive member that is distal to the articulation joint into a rigid drive member that is configured to apply axial drive motions to the firing member to drive the firing member between the starting position and the ending position.

Example Set No. 4

Example 1—A surgical instrument comprising a surgical end effector that includes a firing member that is supported for axial travel within the surgical end effector. An upper chain-drive assembly operably interfaces with a top portion of the firing member and a lower chain-drive assembly operably interfaces with a bottom portion of the firing member. A drive member operably interfaces with the upper chain-drive assembly and the lower chain-drive assembly to cause the upper chain-drive assembly and the lower chain-drive assembly to apply axial drive motions to the firing member to move the firing member between a starting position and an ending position within the surgical end effector.

Example 2—The surgical instrument of Example 1, wherein the upper chain-drive assembly comprises a plurality of upper chain link features that are movably interconnected by an upper flexible member and wherein the lower chain-drive assembly comprises a plurality of lower chain link features that are movably interconnected by a lower flexible member.

Example 3—The surgical instrument of Example 2, further comprising an upper tensioner that is attached to a proximal end of the upper flexible member to maintain variable tension in the upper chain-drive assembly and a lower tensioner that is attached to a proximal end of the lower flexible member to maintain variable tension in the lower chain-drive assembly.

Example 4—The surgical instrument of Examples 2 or 3, wherein each upper chain-link feature comprises an upper sphere and wherein each lower chain-link feature comprises a lower sphere.

Example 5—The surgical instrument of Examples 1, 2, 3 or 4, further comprising an elongate shaft that is coupled to the surgical end effector by an articulation joint that is configured to facilitate selective articulation of the surgical end effector relative to the elongate shaft. The drive member operably interfaces with the upper chain-drive assembly at an upper location and the drive member operably interfaces with the lower chain-drive assembly at a lower location. The upper location and the lower location are distal to the articulation joint.

Example 6—The surgical instrument of Example 5, wherein the articulation joint comprises a multi-axis articulation joint.

Example 7—The surgical instrument of Examples 1, 2, 3, 4 or 6, wherein a proximal upper portion of the upper chain-drive assembly that is proximal to the drive member is loosely coupled together and an upper distal portion of the upper chain-drive assembly that is distal to the drive member is compressed into a substantially rigid upper state that is configured to apply an upper axial drive motion to the firing member. A lower proximal portion of the lower chain-drive assembly that is proximal to the drive member is loosely coupled together and a lower distal portion of the lower chain-drive assembly that is distal to the drive member is compressed into a substantially rigid lower state that is configured to apply a lower axial drive motion to the firing member.

Example 8—The surgical instrument of Examples 1, 2, 3, 4, 5, 6 or 7, wherein the upper chain-drive assembly comprises an upper proximal end and an upper distal end that operably interfaces with the top portion of the firing member. The lower chain-drive assembly comprises a lower proximal end and a lower distal end that operably interfaces with the bottom portion of the firing member. The upper proximal end is coupled to the lower proximal end by a coupler member that is supported in operable engagement with a proximal support member that facilitates movement of the coupler member and the upper chain-drive assembly and the lower chain drive assembly. The proximal support member is configured to translate axially as the upper chain-drive assembly and the lower chain-drive assembly translate axially.

Example 9—The surgical instrument of Examples 5 or 6, wherein the drive member is located between the upper chain-drive assembly and the lower chain-drive assembly and is supported in a position that is distal to the articulation joint.

Example 10—A surgical instrument comprising an elongate shaft that has a surgical end effector coupled thereto by an articulation joint that is configured to facilitate selective articulation of the surgical end effector relative to the elongate shaft. The surgical end effector comprises a first jaw and a second jaw that is configured to move relative to the first jaw between an open position and a closed position. A firing member is supported for axial travel within the surgical end effector between a starting position and an ending position. The surgical instrument further comprises an upper chain-drive assembly that is attached to a top portion of the firing member and a lower chain-drive assembly that is attached to a bottom portion of the firing member. A rotary drive member operably interfaces with the upper chain-drive assembly at an upper location and with the lower chain-drive assembly at a lower location. The upper location and the lower location are distal to the articulation joint. The rotary drive member causes the upper chain-drive assembly and the lower chain-drive assembly to apply axial drive motions to the firing member to move the firing member between the starting position and the ending position.

Example 11—The surgical instrument of Example 10, wherein the upper chain-drive assembly comprises a plurality of upper chain link features that are movably interconnected by an upper flexible member and the lower chain-drive assembly comprises a plurality of lower chain link features that are movably interconnected by a lower flexible member.

Example 12—The surgical instrument of Example 11 further comprising an upper tensioner that is attached to a proximal end of the upper flexible member to maintain variable tension in the upper chain-drive assembly and a lower tensioner that is attached to a proximal end of the lower flexible member to maintain variable tension in the lower chain-drive assembly.

Example 13—The surgical instrument of Examples 10, 11 or 12, wherein each upper chain-link feature comprises an upper sphere and each lower chain-link feature comprises a lower sphere.

Example 14—The surgical instrument of Examples 10, 11, 12 or 13, wherein the first jaw comprises a bottom passage that is configured to slidably accommodate the bottom portion of the firing member and a distal portion of the lower chain-drive assembly and the second jaw comprises a top passage that is configured to slidably accommodate the top portion of the firing member and a distal portion of the upper chain-drive assembly when the firing member is moved between the starting position and the ending position.

Example 15—The surgical instrument of Example 14, wherein the bottom passage is sized and shaped relative to each lower sphere in the distal portion of the lower chain-drive assembly to prevent the distal portion of the lower chain-drive assembly from buckling as the firing member is driven from the starting position to the ending position. The top passage is sized and shaped relative to each upper sphere in the distal portion of the upper chain-drive assembly to prevent the distal portion of the upper chain-drive assembly from buckling as the firing member is driven from the starting position to the ending position.

Example 16—The surgical instrument of Examples 14 or 15, wherein the bottom passage comprises a bottom keyhole shape and the top passage comprises a top keyhole shape.

Example 17—The surgical instrument of Examples 10, 11, 12, 13, 14, 15 or 16, wherein the firing member is movable from a position distal to the starting position to the starting position without actuating the rotary drive member by applying an axial bailout motion to each of the upper chain-drive assembly and the lower chain-drive assembly.

Example 18—A surgical instrument, comprising an elongate shaft that has a surgical end effector coupled thereto by an articulation joint that is configured to facilitate selective articulation of the surgical end effector relative to the elongate shaft. The surgical end effector comprises a firing member that is supported for axial travel within the surgical end effector between a starting position and an ending position. An upper loosely-linked chain-drive assembly is supported by the elongate shaft and traverses the articulation joint to operably interface with a top portion of the firing member. A lower loosely-linked chain-drive assembly is supported by the elongate shaft and traverses the articulation joint to operably interface with a bottom portion of the firing member. The surgical instrument further comprises means for converting an upper portion of the upper loosely-linked chain-drive assembly that is distal to the articulation joint into a rigid drive member that is configured to apply axial drive motions to the firing member to drive the firing member between the starting position and the ending position.

Example 19—The surgical instrument of Example 18, wherein the upper loosely-linked chain-drive assembly comprises a plurality of upper chain link features that are movably interconnected by an upper flexible member and the lower loosely-linked chain-drive assembly comprises a plurality of lower chain link features that are movably interconnected by a lower flexible member.

Example 20—The surgical instrument of Example 19, wherein each upper chain-link feature comprises an upper sphere and wherein each lower chain-link feature comprises a lower sphere.

Example Set No. 5

Example 1—A surgical instrument comprising a shaft assembly that defines a shaft axis. The surgical instrument further comprises a surgical end effector that defines an end effector axis and is coupled to the shaft assembly by an articulation joint that is configured to facilitate articulation of the surgical end effector relative to the shaft assembly in an articulation plane between an unarticulated position wherein the end effector axis is axially aligned with the shaft axis and articulated positions wherein the end effector axis is not axially aligned with the shaft axis. The articulation joint comprises a proximal joint member that is coupled to the shaft assembly and a distal joint member that is coupled to the surgical end effector. The articulation joint further comprises an articulation linkage assembly that comprising a plurality of links. Each link is configured to operably interface with the proximal joint member for movable travel relative thereto in a first proximal travel path and a second proximal travel path that is transverse to the first proximal travel path. Each link is further configured to operably interface with the distal joint member for movable travel relative thereto in a first distal travel path and a second distal travel path that is transverse to the first distal travel path. The articulation linkage assembly defines a central passage that extends between the plurality of links. The surgical instrument further comprises a drive member that extends through the proximal joint member, the central passage and the distal joint member to operably interface with the surgical end effector. At least two flexible actuator members span the articulation joint and operably interface with the distal joint member to apply articulation motions thereto.

Example 2—The surgical instrument of Example 1, wherein the plurality of links comprises three links.

Example 3—The surgical instrument of Example 2, wherein the three links comprises a first link that is configured to operably interface with the proximal joint member for movable travel relative thereto in a first proximal travel path and another first proximal travel path that is transverse to the first proximal travel path. The first link is further configured to operably interface with the distal joint member for movable travel relative thereto in a first distal travel path and another first distal travel path that is transverse to the first distal travel path. The three links further comprise a second link that is configured to operably interface with the proximal joint member for movable travel relative thereto in a second proximal travel path and another second proximal travel path that is transverse to the second proximal travel path. The second link is configured to operably interface with the distal joint member for movable travel relative thereto in a second distal travel path and another second distal travel path that is transverse to the second distal travel path. The three links further comprise a third link that is configured to operably interface with the proximal joint member for movable travel relative thereto in a third proximal travel path and another third travel path that is transverse to the third proximal travel path. The third link is further configured to operably interface with the distal joint member for movable travel relative thereto in a third distal travel path and another third distal travel path that is transverse to the third distal travel path.

Example 4—The surgical instrument of Examples 1, 2 or 3, wherein each link comprises a proximal saddle that is configured to movably interface with a corresponding proximal mounting lug on the proximal joint member and a distal saddle that is configured to movably interface with a corresponding distal mounting lug on the distal joint member.

Example 5—The surgical instrument of Example 4, wherein each proximal mounting lug defines an arcuate proximal pivot surface. Each proximal saddle comprises a U-shaped proximal pivot surface that is configured to movably interface with the arcuate proximal pivot surface on the proximal mounting lug to facilitate travel of the link in the first proximal travel path and the second proximal travel path on the proximal mounting lug. Each distal mounting lug defines an arcuate distal pivot surface. Each distal saddle comprises a U-shaped distal pivot surface that is configured to movably interface with the arcuate distal pivot surface on the distal mounting lug to facilitate travel of the link in the first distal travel path and the second distal travel path on the distal mounting lug.

Example 6—The surgical instrument of Example 5, wherein each proximal mounting lug defines a proximal lug axis and wherein the first proximal travel path comprises a first arcuate proximal travel path along the proximal lug axis. The second proximal travel path comprises a second arcuate proximal travel path around the proximal lug axis. Each distal mounting lug defines a distal lug axis and wherein the first distal travel path comprises a first arcuate distal travel path along the distal lug axis. The second distal travel path comprises a second arcuate distal travel path around the distal lug axis.

Example 7—The surgical instrument of Examples 1, 2, 3, 4 or 6, wherein a portion of the drive member that extends through the articulation joint is flexible.

Example 8—The surgical instrument of Examples 1, 2, 3, 4, 5, 6 or 7, wherein the drive member comprises a proximal drive shaft that includes a distal end that is operably supported in the proximal joint member. A distal drive shaft comprises a proximal end that is operably supported in the distal joint member. A central drive shaft spans between the proximal joint member and the distal joint member distal and comprises a proximal end that is configured to operably interface with the distal end of the proximal drive shaft. The central drive shaft further comprises a distal end that is configured to operably interface with the proximal end of the distal drive shaft.

Example 9—The surgical instrument of Example 8, wherein the proximal drive shaft is configured to apply rotary drive motions to the central drive shaft.

Example 10—The surgical instrument of Examples 1, 2, 3, 4, 5, 6, 7, 8 or 9, wherein the at least two flexible actuator members comprises four cables that span the articulation joint and operably interface with the distal articulation joint member to apply articulation motions thereto.

Example 11—The surgical instrument of Examples 1, 2, 3, 4, 5, 6, 7, 8, 9 or 10, wherein each link is not attached to the proximal joint member and the distal joint member.

Example 12—The surgical instrument of Examples 1, 2, 3, 4, 5, 6, 7, 8, 9, 10 or 11, wherein each link is retained in movable contact with the proximal joint member and the distal joint member.

Example 13—A surgical instrument comprising a shaft assembly that defines a shaft axis and a surgical end effector that defines an end effector axis. The surgical end effector is coupled to the shaft assembly by an articulation joint that is configured to facilitate articulation of the surgical end effector relative to the shaft assembly in an articulation plane between an unarticulated position wherein the end effector axis is axially aligned with the shaft axis in the articulation plane and articulated positions wherein the end effector axis is not axially aligned with the shaft axis. The articulation joint comprises a proximal joint member that is coupled to the shaft assembly and a distal joint member that is coupled to the surgical end effector. The articulation joint further comprises an articulation linkage assembly that comprises a first link that is configured to operably interface with the proximal joint member for movable travel relative thereto in a first proximal travel path and another first proximal travel path that is transverse to the first proximal travel path. The first link is further configured to operably interface with the distal joint member for movable travel relative thereto in a first distal travel path and another first distal travel path that is transverse to the first distal travel path. The articulation linkage assembly further comprises a second link that is configured to operably interface with the proximal joint member for movable travel relative thereto in a second proximal travel path and another second proximal travel path that is transverse to the second proximal travel path. The second link is further configured to operably interface with the distal joint member for movable travel relative thereto in a second distal travel path and another second distal travel path that is transverse to the second distal travel path. The articulation linkage assembly further comprises a third link that is configured to operably interface with the proximal joint member for movable travel relative thereto in a third proximal travel path and another third travel path that is transverse to the third proximal travel path. The third link is further configured to operably interface with the distal joint member for movable travel relative thereto in a third distal travel path and another third distal travel path that is transverse to the third distal travel path. The surgical instrument further comprises at least two flexible actuator members that span the articulation joint and operably interface with the distal joint member to apply articulation motions thereto.

Example 14—The surgical instrument of Example 13, wherein the first link defines a first link axis. The second link defines a second link axis. The third link defines a third link axis. The first link axis, the second link axis, and the third link axis are transverse to each other.

Example 15—The surgical instrument of Examples 13 or 14, wherein the first link, the second link, and the third link are arranged relative to each other to define a central passage that extends between the first link, the second link, and the third link and is configured to operably support a drive member therein.

Example 16—The surgical instrument of Examples 13, 14 or 15, wherein the first link comprises a first proximal saddle that is configured to movably interface with a corresponding first proximal mounting lug on the proximal joint and a first distal saddle that is configured to movably interface with a corresponding first distal mounting lug on the distal joint. The second link comprises a second proximal saddle that is configured to movably interface with a corresponding second proximal mounting lug on the proximal joint and a second distal saddle that is configured to movably interface with a corresponding second distal mounting lug on the distal joint. The third link comprises a third proximal saddle that is configured to movably interface with a corresponding third proximal mounting lug on the proximal joint and a third distal saddle that is configured to movably interface with a corresponding third distal mounting lug on the distal joint.

Example 17—The surgical instrument of Example 16, wherein the first proximal mounting lug defines a first arcuate proximal pivot surface. The first proximal saddle comprises a first U-shaped proximal pivot surface that is configured to movably interface with the first arcuate proximal pivot surface on the first proximal mounting lug to facilitate travel of the first link in the first proximal travel path and another first proximal travel path on the first proximal mounting lug. The second proximal mounting lug defines a second arcuate proximal pivot surface. The second proximal saddle comprises a second U-shaped proximal pivot surface that is configured to movably interface with the second arcuate proximal pivot surface on the second proximal mounting lug to facilitate travel of the second link in the second proximal travel path and another second proximal travel path on the second proximal mounting lug. The third proximal mounting lug defines a third arcuate proximal pivot surface. The third proximal saddle comprises a third U-shaped proximal pivot surface that is configured to movably interface with the third arcuate proximal pivot surface on the third proximal mounting lug to facilitate travel of the third link in the third proximal travel path and another third proximal travel path on the third proximal mounting lug.

Example 18—The surgical instrument of Example 17, wherein the first distal mounting lug defines a first arcuate distal pivot surface. The first distal saddle comprises a first U-shaped distal pivot surface that is configured to movably interface with the first arcuate distal pivot surface on the first distal mounting lug to facilitate travel of the first link in the first distal travel path and another first distal travel path on the first distal mounting lug. The second distal mounting lug defines a second arcuate distal pivot surface. The second distal saddle comprises a second U-shaped distal pivot surface that is configured to movably interface with the second arcuate distal pivot surface on the second distal mounting lug to facilitate travel of the second link in the second distal travel path and another second distal travel path on the second distal mounting lug. The third distal mounting lug defines a third arcuate distal pivot surface. The third distal saddle comprises a third U-shaped distal pivot surface that is configured to movably interface with the third arcuate distal pivot surface on the third distal mounting lug to facilitate travel of the third link in the third distal travel path and another third distal travel path on the third distal mounting lug.

Example 19—The surgical instrument of Example 18, wherein the first proximal mounting lug defines a first proximal lug axis. The first proximal travel path comprises a first arcuate proximal travel path along the first proximal lug axis and the another first proximal travel path comprises another first proximal arcuate travel path that extends around the first proximal lug axis. The second proximal mounting lug defines a second proximal lug axis. The second proximal travel path comprises a second arcuate proximal travel path along the second proximal lug axis and the another second proximal travel path comprises another second proximal arcuate travel path that extends around the second proximal lug axis. The third proximal mounting lug defines a third proximal lug axis. The third proximal travel path comprises a third arcuate proximal travel path that extends along the third proximal lug axis. The another third proximal travel path comprises another third proximal arcuate travel path that extends around the third proximal lug axis. The first distal mounting lug defines a first distal lug axis. The first distal travel path comprises a first arcuate distal travel path that extends along the first distal lug axis. The another first distal travel path comprises another first distal arcuate travel path that extends around the first distal lug axis. The second distal mounting lug defines a second distal lug axis. The second distal travel path comprises a second arcuate distal travel path that extends along the second distal lug axis. The another second distal travel path comprises another second distal arcuate travel path that extends along the second distal lug axis. The third distal mounting lug defines a third distal lug axis. The third distal travel path comprises a third arcuate distal travel path that extends along the third distal lug axis. The another third distal travel path comprises another third distal arcuate travel path that extends around the third distal lug axis.

Example 20—The surgical instrument of Example 19, wherein the first proximal lug axis, the second proximal lug axis, and the third proximal lug axis are transverse to each other and wherein the first distal lug axis, the second distal lug axis, and the third distal lug axis are transverse to each other.

Example Set No. 6

Example 1—A surgical instrument comprising a shaft assembly that defines a shaft axis and a surgical end effector that defines an end effector axis. The surgical end effector is coupled to the shaft assembly by an articulation joint that is configured to facilitate articulation of the surgical end effector relative to the shaft assembly in an articulation plane between an unarticulated position wherein the end effector axis is axially aligned with the shaft axis in the articulation plane and articulated positions wherein the end effector axis is not axially aligned with the shaft axis. The articulation joint comprises a proximal joint member that is coupled to the shaft assembly and comprises a proximal face that defines an arcuate proximal apex. A distal joint member coupled to the surgical end effector and comprises a distal face that defines an arcuate distal apex. The articulation joint further comprises at least one linkage assembly that comprises a first link that is coupled to the proximal joint member and the distal joint member and a second link that is coupled to the proximal joint member and the distal joint member. The second link crosses the first link and the first link and the second link pivotally couple the proximal joint member to the distal joint member such that the arcuate distal apex confronts the arcuate proximal apex. The surgical instrument further comprises at least two flexible actuator members that span the articulation joint and operably interface with the distal articulation joint member to apply articulation motions thereto.

Example 2—The surgical instrument of Example 1, wherein at least one linkage assembly movably affixes the proximal joint member to the distal joint member such that the arcuate distal apex is spaced from the arcuate proximal apex.

Example 3—The surgical instrument of Example 1, wherein at least one linkage assembly movably affixes the proximal joint member to the distal joint member such that the arcuate distal apex is supported in rolling contact with the arcuate proximal apex.

Example 4—The surgical instrument of Examples 1, 2 or 3, wherein at least one linkage assembly comprises a first linkage assembly that comprises the first link and the second link, wherein the first link and second link are located on one side of the shaft axis. The at least one linkage assembly further comprises a second linkage assembly that comprises another first link that is coupled to the proximal joint member and the distal joint member. The second linkage assembly further comprises another second link that is coupled to the proximal joint member and the distal joint member, wherein the another second link crosses the another first link. The second linkage assembly is located on another side of the shaft axis.

Example 5—The surgical instrument of Examples 1, 2, 3 or 4, wherein the surgical end effector is articulatable relative to the shaft assembly through articulation angles on each side of the shaft axis. Each articulation angle may range between zero degrees and ninety degrees.

Example 6—The surgical instrument of Examples 1, 2, 3, 4 or 5, wherein the arcuate distal apex defines a distal radius that extends between a distal virtual pivot point and the arcuate distal apex. The arcuate proximal apex defines a proximal radius that extends between a proximal virtual pivot point and the arcuate proximal face. The distal virtual pivot point and the proximal virtual pivot point lie on a common joint axis that extends between the distal virtual pivot point and the proximal virtual pivot point.

Example 7—The surgical instrument of Examples 1, 2, 3, 4 or 6, wherein when the surgical end effector is articulated relative to the shaft assembly, a proximal angle between the shaft axis and the joint axis is equal to a distal angle between the end effector axis and the joint axis.

Example 8—The surgical instrument of Examples 6 or 7, wherein the first link of each link assembly is attached to the proximal joint member at a corresponding proximal location that is offset from a proximal virtual pivot axis that is perpendicular to the shaft axis and extends through the proximal virtual pivot point. The first link of each link assembly is also attached to the distal joint member at a corresponding distal location that is offset from a distal virtual pivot axis that is perpendicular to the end effector axis and extends through the distal virtual pivot point.

Example 9—The surgical instrument of Example 8, wherein the second link of each link assembly is attached to the proximal joint member at another corresponding proximal location that is offset from the proximal virtual pivot axis. The second link of each link assembly is attached to the distal joint member at another corresponding distal location that is offset from the distal virtual pivot axis.

Example 10—The surgical instrument of Examples 1, 2, 3, 4, 5, 6, 7, 8 or 9, wherein the proximal joint member comprises a proximal central passage and the distal joint member comprises a distal central passage. The surgical instrument further comprises a flexible drive member that extends through the proximal central passage and the distal central passage.

Example 11—A surgical instrument comprising a shaft assembly that defines a shaft axis and a surgical end effector that defines an end effector axis. The surgical end effector is coupled to the shaft assembly by an articulation joint that is configured to facilitate articulation of the surgical end effector relative to the shaft assembly in an articulation plane between an unarticulated position wherein the end effector axis is axially aligned with the shaft axis in the articulation plane and articulated positions wherein the end effector axis is not axially aligned with the shaft axis. The articulation joint comprises a proximal joint member that is coupled to the shaft assembly and comprises a proximal arcuate apex. The articulation joint further comprises a central joint member that comprises a proximal facing first arcuate apex and a distal facing second arcuate apex. A distal joint member is coupled to the surgical end effector and defines a distal arcuate joint apex. The articulation joint further comprises at least one proximal linkage assembly that includes a first proximal link that is coupled to the proximal joint member and the central joint member. A second proximal link is coupled to the proximal joint member and the central joint member and crosses the first proximal link. The first proximal link and the second proximal link pivotally couple the proximal joint member to the central joint member such that the proximal facing first arcuate apex confronts the proximal arcuate apex to facilitate articulation of the central joint member relative to the proximal joint member through a first articulation plane. The surgical instrument further comprises at least one distal linkage assembly that includes a first distal link that is coupled to the central joint member and the distal joint member. A second distal link is coupled to the central joint member and the distal joint member and crosses the first distal link, The first distal link and the second distal link pivotally couple the central joint member to the distal joint member such that the arcuate distal apex confronts the arcuate distally facing second arcuate apex to facilitate articulation of the distal joint member relative to the central joint member through a second articulation plane that differs from the first articulation plane. The surgical instrument further comprises four flexible actuator members that span the articulation joint and operably interfaces with the distal joint member to apply articulation motions thereto.

Example 12—The surgical instrument of Example 11, wherein the proximal linkage assembly movably affixes the central joint member to the proximal joint member such that the proximal facing first arcuate apex is spaced from the proximal arcuate apex and wherein the distal linkage assembly movably affixes the distal joint member to the central joint member such that the distal arcuate apex is spaced from the distal facing second arcuate apex.

Example 13—The surgical instrument of Example 11, wherein the proximal linkage assembly movably affixes the central joint member to the proximal joint member such that the proximally facing first arcuate apex is in rolling contact with the proximal arcuate apex and wherein the distal linkage assembly movably affixes the distal joint member to the central joint member such that the distal arcuate apex is in rolling contact with the distal facing second arcuate apex.

Example 14—The surgical instrument of Examples 11, 12 or 13, wherein the proximal linkage assembly comprises a first proximal linkage assembly that comprises the first proximal link and the second proximal link. The first proximal link and the second proximal link are located on one side of the shaft axis. A second proximal linkage assembly comprises another proximal first link that is coupled to the proximal joint member and the central joint member. The second proximal linkage assembly further comprises another proximal second link that is coupled to the proximal joint member and the central joint member and crosses the another proximal first link. The second proximal linkage assembly is located on another side of the shaft axis.

Example 15—The surgical instrument of Examples 11, 12, 13 or 14, wherein at least one distal linkage assembly comprises a first distal linkage assembly that comprises the first distal link and the second distal link. The first distal link and the second distal link are located on one side of the shaft axis. A second distal linkage assembly comprises another first distal link that is coupled to the central joint member and the distal joint member. Another second distal link is coupled to the central joint member and the distal joint member. The another second distal link crosses the another first distal link. The second distal linkage assembly is located on the another side of the shaft axis.

Example 16—The surgical instrument of Examples 11, 12, 13, 14 or 15, wherein the second articulation plane is perpendicular to the first articulation plane.

Example 17—The surgical instrument of Examples 11, 12, 13, 14, 15 or 16, wherein the proximal joint member comprises a proximal passage that extends therethrough and the central joint member comprises a central passage that extends therethrough. The distal joint member comprises a distal passage that extends therethrough. The surgical instrument further comprises at least one drive member that extends through the proximal passage, the central passage and the distal passage to convey drive motions to the end effector.

Example 18—The surgical instrument of Examples 11, 12, 13, 14, 15, 16 or 17, further comprising a first reference plane that extends through the shaft axis and a second reference plane that extends through the shaft axis at a right angle relative to the first reference plane. A first one of the cables passes through the proximal joint member on a first side of the first reference plane and a first side of the second reference plane and extends through the first reference plane into the central joint member on a second side of the first reference plane and extends through the second reference plane into the distal joint member on the second side of the first reference plane and a second side of the second reference plane. A second one of the cables extends through the proximal joint member on the second side of the first reference plane and the first side of the second reference plane and extends through the second reference plane into the central joint member on the first side of the first reference plane and passes through the second reference plane to extend into the distal joint member on the first side of the first reference plane and the second side of the second reference plane.

Example 19—A surgical instrument comprising a shaft assembly that defines a shaft axis and has a surgical end effector coupled thereto by an articulation joint. The articulation joint comprises a proximal joint member that is coupled to the shaft assembly and a distal joint member that is coupled to the surgical end effector. The articulation joint further comprises a first linkage assembly that includes a first link that is coupled to the proximal joint member and the distal joint member on a first side of the shaft axis. A second link is coupled to the proximal joint member on the first side of the shaft axis. The second link crosses the first link and is attached to the distal joint member on the first side of the shaft axis. The articulation joint further comprises a second linkage assembly that includes a third link that is coupled to the proximal joint member and the distal joint member on a second side of the shaft axis. A fourth link is coupled to the proximal joint member on the second side of the shaft axis. The fourth link crosses the third link on the second side of the shaft axis and is attached to the distal joint member on the second side of the shaft axis. The first linkage assembly and the second linkage assembly facilitate articulation of the surgical end effector through an articulation plane relative to the shaft assembly. The surgical instrument further comprises at least two flexible actuator members that span the articulation joint and operably interfaces with the distal joint member to apply articulation motions thereto.

Example 20—The surgical instrument of Example 19, wherein the proximal joint member defines a proximal central passage that extends therethrough, and wherein the distal joint member defines a distal central passage that extends therethrough. The surgical instrument further comprises a flexible drive member that extends through the proximal central passage and the distal central passage to apply drive motions to the surgical end effector.

Example Set No. 7

Example 1—A surgical instrument comprising a shaft assembly that defines a shaft axis and has a surgical end effector operably coupled thereto by an articulation joint. The surgical end effector comprises a first jaw and a second jaw that is selectively movable between an open position and a closed position relative to the first jaw. The articulation joint comprises a distal joint member that is coupled to the surgical end effector. A central joint member operably interfaces with the distal joint member such that the distal joint member is selectively articulatable relative to the central joint member about a distal articulation axis that is transverse to the shaft axis. A proximal joint member is coupled to the shaft assembly and operably interfaces with the central joint member such that the central joint member is selectively articulatable relative to the proximal joint member about a proximal articulation axis that is transverse to the shaft axis and the distal articulation axis. The surgical instrument further comprises an articulation control system that operably interfaces with the articulation joint and the surgical end effector. The articulation control system is configured to apply articulation motions to the surgical end effector to selectively articulate the surgical end effector about the distal articulation axis and the proximal articulation axis.

Example 2—The surgical instrument of Example 1, wherein the articulation control system is configured to apply closing motions to the second jaw of the surgical end effector.

Example 3—The surgical instrument of Examples 1 or 2, wherein the articulation control system comprises a plurality of flexible actuators that extend through the proximal joint member, the central joint member, and the distal joint member and operably interface with a jaw closure system that is operably supported in the surgical end effector and configured to apply the closing motions to the second jaw.

Example 4—The surgical instrument of Example 3, wherein the jaw closure system comprises a closure pulley assembly that is configured to apply the closing motions to the second jaw.

Example 5—The surgical instrument of Example 4, wherein the closure pulley assembly comprises at least one closure cam that is configured to cammingly engage a mounting portion on the second jaw to apply the closure motions thereto.

Example 6—The surgical instrument of Examples 3, 4 or 5, wherein the plurality of flexible actuators comprises a first cable, a second cable, a third cable, and a fourth cable. The first cable and the second cable extend through the proximal joint member, the central joint member, and the distal joint member on one side of the shaft axis. The third cable and the fourth cable extend through the proximal joint member, the central joint member, and the distal joint member on another side of the shaft axis.

Example 7—The surgical instrument of Example 6, wherein the jaw closure system comprises a pulley unit that is supported by the surgical end effector and comprises a first pulley that is rotatably supported on one side of the shaft axis. A second pulley is supported on another side of the shaft axis and is coupled to the first pulley for rotational travel therewith. The first cable and the second cable operably interface with the first pulley and the third cable and the fourth cable operably interface with a third pulley and a fourth pulley.

Example 8—The surgical instrument of Example 7, wherein the pulley unit is rotatable through a rotational travel path of at least three hundred thirty degrees by applying tension to one or more of the first cable, the second cable, the third cable, and the fourth cable.

Example 9—The surgical instrument of Examples 7 or 8, wherein the first cable extends through a lower portion of the proximal joint member. The central joint member comprises a cable redirection unit that is configured to redirect the first cable out through an upper portion of the central joint member to pass through an upper portion of the distal joint member and engage the first pulley. The second cable extends through an upper portion of the proximal joint member and engages the redirection unit in the central jaw member which redirects the second cable out through a lower portion of the central jaw member to pass through a lower portion of the distal joint member to operably engage the first pulley.

Example 10—The surgical instrument of Examples 1, 2, 3, 4, 5, 6, 7, 8 or 9, wherein the proximal joint member comprises a proximal joint distal face. The central joint member comprises a center joint proximal face that confronts the proximal joint distal face and wherein the central joint member further comprises a central joint distal face. The distal joint member comprises a distal joint proximal face that confronts the central joint distal face.

Example 11—The surgical instrument of Example 10, wherein the proximal joint distal face comprises a plurality of proximal joint gear teeth that are configured for meshing engagement with corresponding central joint proximal gear teeth that are associated with the central joint proximal face. The central joint distal face comprises a plurality of central joint distal gear teeth that are configured for meshing engagement with corresponding distal joint proximal gear teeth that are associated with the distal joint proximal face.

Example 12—The surgical instrument of Example 10, wherein the proximal joint distal face comprises a pair of spaced proximal joint distal apex portions. The central joint proximal face comprises a pair of spaced central joint proximal apex portions that are configured to confront the pair of spaced proximal joint distal apex portions. The central joint distal face comprises a pair of spaced central joint distal apex portions. The distal joint proximal face comprises a pair of spaced distal joint proximal apex portions that are configured to confront the pair of spaced central joint distal apex portions.

Example 13—The surgical instrument of Example 12, wherein each proximal joint distal apex portion comprises a first arcuate distal surface that is configured to rockingly engage a first arcuate proximal surface on a corresponding central joint proximal apex portion. Each central joint distal apex portion comprises a second arcuate distal surface that is configured to rockingly engage a second arcuate proximal surface on a corresponding distal joint proximal apex portion.

Example 14—The surgical instrument of Examples 1, 2, 3, 4, 5, 6, 7, 8, 9, 10, 11, 12 or 13, further comprising a drive shaft arrangement that extends through the proximal joint member, the central joint member, and the distal joint member to operably interface with the surgical end effector to apply drive motions thereto.

Example 15—The surgical instrument of Example 14, wherein the drive shaft arrangement comprises a rotary drive shaft arrangement.

Example 16—The surgical instrument of Example 15, wherein the rotary drive shaft arrangement comprises a proximal rotary drive shaft that has a distal end that is rotatably supported in the proximal joint member. The rotary drive shaft arrangement further comprises a first rotary drive shaft that has a first distal end that is rotatably coupled to the distal end of the proximal rotary drive shaft. The first rotary drive shaft spans between the proximal joint member and the central joint member and further comprises a first distal end that is rotatably coupled to a central bearing that is supported in the central joint member. A second rotary drive shaft comprises a second proximal end that is rotatably coupled in the central bearing in the central joint member. The second rotary drive shaft spans between the central joint member and the distal joint member to be operably coupled to a rotary drive member.

Example 17—The surgical instrument of Examples 3, 4, 5, 6, 7, 8, 9, 14, 15 or 16, wherein the central joint member is not directly attached to the proximal joint member, wherein the distal joint member is not directly attached to the central joint member, wherein the central joint member is held in operable pivotal engagement with the proximal joint member by the plurality of flexible actuators, and wherein the distal joint member is held in operable pivotal engagement with the central joint member by the plurality of flexible actuators.

Example 18—A surgical instrument comprising a shaft assembly that defines a shaft axis. The surgical instrument further comprises a surgical end effector that is operably coupled to the shaft assembly by an articulation joint. The surgical end effector comprises an elongate channel that is configured to operably support a surgical staple cartridge therein. An anvil is pivotally supported relative to the elongate channel and is selectively movable between an open position and a closed position relative to the surgical staple cartridge supported in the elongate channel. The articulation joint comprises a distal joint member that is coupled to the elongate channel. A central joint member operably interfaces with the distal joint member such that the distal joint member is selectively articulatable relative to the central joint member about a distal articulation axis that is transverse to the shaft axis. A proximal joint member is coupled to the shaft assembly and operably interfaces with the central joint member such that the central joint member is selectively articulatable relative to the proximal joint member about a proximal articulation axis that is transverse to the shaft axis and the distal articulation axis. The surgical instrument further comprises an articulation control system that operably interfaces with the articulation joint and the surgical end effector. The articulation control system is configured to apply articulation motions to the surgical end effector to selectively articulate the surgical end effector about the distal articulation axis and the proximal articulation axis. The articulation control system is configured to apply closing motions to the second jaw of the surgical end effector.

Example 19—The surgical instrument of Example 18, wherein the articulation control system comprises a plurality of flexible actuators that extend through the proximal joint member, the central joint member, and the distal joint member and operably interface with an anvil closure system that is operably supported in the elongate channel and is configured to apply closing motions to the anvil.

Example 20—The surgical instrument of Examples 18 or 19, wherein the anvil closure system comprises a closure pulley assembly configured to apply the closing motions to the anvil.

Example 21—The surgical instrument of Examples 18, 19 or 20, wherein the surgical end effector further comprises a firing member that is configured to axially move between a starting position and an ending position within the surgical end effector in response to firing motions applied to the firing member by a rotary drive system that extends through the proximal joint member, the central joint member, and the distal joint member.

Example Set No. 8

Example 1—A method of operating a surgical instrument that comprises a surgical end effector that is articulatable relative to a shaft assembly of the surgical instrument about an articulation joint. The method comprises providing a rotary drive motion to a rotary drive member of the surgical end effector, wherein the rotary drive member extends through the articulation joint. The method further comprises converting the rotary drive motion to an upper axial motion and a lower axial motion at locations that are distal to the articulation joint and applying the upper axial motion to an upper portion of the firing member. The method further comprises applying the lower axial motion to a lower portion of the firing member such that the upper axial motion and lower axial motion drives the firing member distally through the surgical end effector from a starting position to an ending position.

Example 2—The method of Example 1, wherein providing a rotary drive motion comprises providing a rotary motion to the rotary drive member in a first rotary direction until the firing member reaches the ending position. The method further comprises providing another rotary drive motion to the rotary drive member in a second rotary direction after the firing member has reached the ending position to drive the firing member from the ending position to the starting position.

Example 3—The method of Examples 1 or 2, wherein applying the upper axial motion comprises applying an upper axial motion in a distal direction and wherein applying the lower axial motion comprises applying a lower axial motion in a distal direction.

Example 4—The method of Example 3, further comprising converting the another rotary drive motion to another upper axial motion and another lower axial motion at the locations that are distal to the articulation joint. The method further comprises applying the another upper axial motion to the upper portion of the firing member and applying the another lower axial motion to the lower portion of the firing member such that the another upper axial motion and the another lower axial motion drives the firing member proximally through the surgical end effector from the ending position to the starting position.

Example 5—The method of Examples 1, 2, 3 or 4, wherein the upper axial motion comprises a first magnitude, wherein the lower axial motion comprises a second magnitude, and wherein the second magnitude equals the first magnitude.

Example 6—The method of Examples 1, 2, 3, 4 or 5, wherein the method further comprises applying an articulation motion to the surgical end effector.

Example 7—The method of Examples 1, 2, 3, 4 or 6, wherein the surgical end effector comprises a first jaw and a second jaw that is movable relative to the first jaw between an open position and a closed position. The second jaw is moved from the open position to the closed position by the firing member as the firing member is driven distally from the starting position.

Example 8—The method of Examples 1, 2, 3, 4, 5, 6 or 7, wherein the surgical end effector comprises a first jaw and a second jaw that is movable relative to the first jaw between an open position and a closed position. The method further comprises applying a closure motion to the second jaw before applying the upper axial motion to an upper portion of the firing member and applying the lower axial motion to a lower portion of the firing member.

Example 9—The method of Examples 1, 2, 3, 4, 5, 6, 7 or 8, wherein the method further comprises applying an articulation motion to an articulation control member that spans the articulation joint and operably interfaces with the surgical end effector to articulate the surgical end effector to an articulated orientation relative to the shaft assembly.

Example 10—The method of Example 9, wherein applying a closure motion comprises applying another actuation motion to the articulation control member to cause the second jaw to move from the closed position to the open position.

Example 11—A method for operating a surgical instrument. The method comprises providing a surgical end effector that is coupled to a shaft assembly by an articulation joint. The surgical end effector comprises a firing member that is movable between a starting position and an ending position through the surgical end effector by a firing drive system that comprises a series of loosely-linked firing components that extend through the articulation joint. The method further comprises converting the series of loosely-linked firing components into a rigid series of the firing components at a location that is distal to the articulation joint to generate an axial drive motion and applying the axial drive motion to the firing member to drive the firing member from the starting position to the ending position.

Example 12—The method of Example 11, wherein converting comprises applying a rotary drive motion to the series of loosely-linked firing components at the location that is distal to the articulation joint.

Example 13—The method of Examples 11 or 12, wherein the series of loosely-linked firing components comprises an upper series of loosely-linked upper firing components and a lower series of loosely-linked lower firing components.

The action of converting comprises converting the upper series of loosely linked upper firing components into a rigid upper series of the upper firing components at the location that is distal to the articulation joint to generate an upper axial drive motion and converting the lower series of loosely-linked lower firing components into a rigid lower series of the lower firing components at the location that is distal to the articulation joint to generate a lower axial drive motion.

Example 14—The method of Examples 11, 12 or 13, wherein applying the axial drive motion to the firing member comprises applying the upper axial drive motion to an upper portion of the firing member and applying the lower axial drive motion to a lower portion of the firing member.

Example 15—The method of Examples 11, 12, 13 or 14, wherein the surgical end effector comprises a first jaw and a second jaw that is movable relative to the first jaw between an open position and a closed position. The second jaw is moved from the open position to the closed position by the firing member as the firing member is driven distally from the starting position.

Example 16—The method of Examples 11, 12, 13 or 14, wherein the surgical end effector comprises a first jaw and a second jaw that is movable relative to the first jaw between an open position and a closed position. The method further comprises applying a closure motion to the second jaw before applying the upper axial drive motion to the upper portion of the firing member and before applying the lower axial drive motion to the lower portion of the firing member.

Example 17—The method of Examples 11, 12, 13, 14, 15 or 16, wherein the method further comprises applying an articulation motion to an articulation control member that spans the articulation joint and operably interfaces with the surgical end effector to articulate the surgical end effector to an articulated orientation relative to the shaft assembly.

Example 18—The method of Example 17, wherein applying a closure motion comprises applying another actuation motion to the articulation control member to cause the second jaw to move from the closed position to the open position.

Example 19—The method of Examples 11, 12, 13, 14, 15, 16, 17 or 18, wherein converting comprises drivingly engaging each of the loosely-linked firing components in the series of loosely-linked firing components with a rotary drive member and latching each loosely-linked firing component serially together with an adjacent one of the loosely-linked firing components as the adjacent one of the loosely-linked firing components disengages the rotary drive member such that the latched firing components form the rigid series of firing components.

Example 20—The method of Example 19, wherein drivingly engaging each of the loosely-linked firing components in the series of loosely-linked firing components with a rotary drive member further comprises rotating the rotary drive member in a first rotary direction until the firing member has reached the ending position. The method further comprises rotating the rotary drive member in a second rotary direction after the firing member has reached the ending position to drive the firing member from the ending position to the starting position.

Example Set No. 9

Example 1—A surgical instrument comprising a shaft assembly that defines a shaft axis and has a surgical end effector coupled thereto by an articulation joint. The articulation joint comprises a proximal joint member that is coupled to the shaft assembly and comprises a proximal face that defines a proximal apex. The articulation joint further comprises a distal joint member that is coupled to the surgical end effector and comprises a distal face that defines a distal apex. A linkage assembly is configured to retain the proximal apex in rolling inter-engagement with the distal apex. The linkage assembly comprises a first link that is coupled to the proximal joint member for pivotal travel relative thereto about a first proximal pivot axis that is transverse to the shaft axis and a second proximal pivot axis that is transverse to the first pivot axis and the shaft axis. The first link is further coupled to the distal joint member for pivotal travel relative thereto about a first distal pivot axis that is transverse to the shaft axis and a second distal pivot axis that is transverse to the shaft axis and the first distal pivot axis. The linkage assembly further comprises a second link that is coupled to the proximal joint member for pivotal travel relative thereto about the first proximal pivot axis and the second proximal pivot axis. The second link is further coupled to the distal joint member for pivotal travel relative thereto about the first distal pivot axis and the second distal pivot axis.

Example 2—The surgical instrument of Example 1, wherein the first link is attached to the second link.

Example 3—The surgical instrument of Example 2, wherein the first link is attached to the second link by an annular ring that extends between the first link and the second link.

Example 4—The surgical instrument of Example 3, wherein the proximal joint member comprises a proximal outer diameter and wherein the distal joint member comprises a distal outer diameter that is equal to the proximal outer diameter. The annular ring comprises a ring outer diameter that is equal to or less than the proximal outer diameter and the distal outer diameter.

Example 5—The surgical instrument of Examples 1, 2, 3 or 4, further comprising a proximal cross-pin assembly that defines the first proximal pivot axis and the second proximal pivot axis. The surgical instrument further comprises a distal cross-pin assembly that defines the first distal pivot axis and the second distal pivot axis.

Example 6—The surgical instrument of Example 5, wherein the proximal cross-pin assembly comprises a first proximal cross-pin and a second proximal cross-pin. The second proximal cross-pin is rotatably journaled on the first proximal cross-pin to facilitate rotation of the first proximal cross-pin relative to the second proximal cross-pin. The distal cross-pin assembly comprises a first distal cross-pin and a second distal cross-pin. The second distal cross-pin is rotatably journaled on the first distal cross-pin to facilitate rotation of the first distal cross-pin relative to the second distal cross-pin.

Example 7—The surgical instrument of Example 6, wherein the first link is removably coupled to the first proximal cross-pin and the first distal cross-pin. The second link is removably coupled to the first proximal cross-pin and the first distal cross-pin.

Example 8—The surgical instrument of Examples 1, 2, 3, 4, 5, 6 or 7, wherein the proximal apex comprises a plurality of proximal engagement features and the distal apex comprises a plurality of distal engagement features that are in rolling engagement with the proximal engagement features.

Example 9—The surgical instrument of Example 8, wherein the plurality of proximal engagement features comprises a plurality of radially projecting fin members, and wherein the distal engagement features comprises a plurality of radial recesses that are spaced between the plurality of radially projecting fin members.

Example 10—The surgical instrument of Examples 1, 2, 3, 4, 5, 6, 7, 8 or 9, further comprising a plurality of flexible articulation actuators that extend through the proximal joint member and the distal joint member. Each flexible articulation member is coupled to the surgical end effector and is configured to apply articulation motions thereto.

Example 11—A surgical instrument comprising a shaft assembly that defines a shaft axis and has a surgical end effector that defines an end effector axis coupled thereto by an articulation joint. The articulation joint is configured to facilitate articulation of the surgical end effector relative to the shaft assembly between an unarticulated position in which the end effector axis is axially aligned with the shaft axis and articulated positions in which the end effector axis is not axially aligned with the shaft axis. The articulation joint comprises a proximal joint member that is coupled to the shaft assembly and a distal joint member that is coupled to the surgical end effector. The articulation joint further comprises a central link member that comprises a proximal end that is coupled to the proximal joint member for pivotal travel relative thereto about a first proximal pivot axis that is transverse to the shaft axis and a second proximal pivot axis that is transverse to the first proximal pivot axis and the shaft axis. The central link further comprises a distal end that is coupled to the distal joint member for pivotal travel relative thereto about a first distal pivot axis that is transverse to the shaft axis and a second distal pivot axis that is transverse to the first distal pivot axis and the shaft axis.

Example 12—The surgical instrument of Example 11, wherein the proximal end of the central link member is coupled to the proximal joint member by a proximal cross-pin assembly that defines the first proximal pivot axis and the second proximal pivot axis. The distal end of the central link member is coupled to the distal joint member by a distal cross-pin assembly that defines the first distal pivot axis and the second distal pivot axis.

Example 13—The surgical instrument of Examples 11 or 12, wherein the proximal end of the central link member comprises a proximal spherical member that is rollably retained in a proximal socket in the proximal joint member and the distal end of the central link member comprises a distal spherical member that is rollably retained in a distal socket in the distal joint member.

Example 14—The surgical instrument of Examples 12 or 13, wherein the proximal cross-pin assembly comprises a first proximal cross-pin and a second proximal cross-pin. The second proximal cross-pin is rotatably journaled on the first proximal cross-pin to facilitate rotation of the first proximal cross-pin relative to the second proximal cross-pin. The distal cross-pin assembly comprises a first distal cross-pin and a second distal cross-pin. The second distal cross-pin is rotatably journaled on the first distal cross-pin to facilitate rotation of the first distal cross-pin relative to the second distal cross-pin.

Example 15—The surgical instrument of Example 14, wherein the first proximal cross-pin is rotatably supported in the proximal joint member and the second proximal cross-pin is rotatably supported in the proximal spherical member. The first distal cross-pin is rotatably supported in the distal joint member and the second distal cross-pin is rotatably supported in the distal spherical member.

Example 16—The surgical instrument of Examples 11, 12, 13, 14 or 15, further comprising a plurality of flexible articulation actuators that extend through the proximal joint member and the distal joint member. Each flexible articulation member is coupled to the surgical end effector and is configured to apply articulation motions thereto.

Example 17—The surgical instrument of Examples 11, 12, 13, 14, 15 or 16, wherein the central link member comprises a central link portion that is coupled to the proximal spherical member and the distal spherical member and extends therebetween.

Example 18—The surgical instrument of Example 17, further comprising a flexible joint support that surrounds the central link member and is coupled to the proximal joint member and the distal joint member.

Example 19—The surgical instrument of Example 18, wherein the flexible joint support comprises a first flexible member that is coupled to the proximal joint member and the distal joint member. A second flexible member is coupled to the proximal joint member and the distal joint member. A third flexible member is coupled to the proximal joint member and the distal joint member and a fourth flexible member is coupled to the proximal joint member and the distal joint member.

Example 20—The surgical instrument of Example 19, wherein each of the first flexible member, the second flexible member, the third flexible member, and the fourth flexible member pass through a central portion of the central link member.

Example Set No. 10

Example 1—A surgical instrument comprising an elongate shaft assembly that is coupled to a surgical end effector by an articulation joint that is configured to facilitate selective articulation of the surgical end effector relative to the elongate shaft assembly in multiple articulation planes. A firing member is supported for axial travel within the surgical end effector between a starting position and an ending position. A firing system is configured to selectively move the firing member between the starting position and the ending position. The firing system comprises an upper flexible firing assembly that comprises a flexible upper hollow member that has an upper proximal end and an upper distal end. The upper proximal end is supported within the elongate shaft assembly and the flexible upper hollow member spans the articulation joint and the upper distal end is fixed to the surgical end effector. The flexible firing assembly further comprises a flexible upper drive member that has an upper drive member proximal end that operably interfaces with a source of axial drive motions. The flexible upper drive member is slidably constrained in the flexible upper hollow member for axial movement therein. The flexible upper drive member spans the articulation joint and further comprises an upper drive member distal end that operably interfaces with an upper portion of the firing member to apply upper axial drive motions thereto to move the firing member from the starting position to the ending position. The firing system further comprises a lower flexible firing assembly that comprises a flexible lower hollow member that has a lower proximal end and a lower distal end. The lower proximal end is supported within the elongate shaft assembly and the flexible lower hollow member spans the articulation joint and the lower distal end is fixed to the surgical end effector. The lower flexible firing assembly further comprises a flexible lower drive member that has a lower drive member proximal end that operably interfaces with the source of axial drive motions. The flexible lower drive member is slidably constrained in the flexible lower hollow member for axial movement therein and spans the articulation joint and further comprises a lower drive member distal end that operably interfaces with a lower portion of the firing member to apply lower axial drive motions thereto to move the firing member from the starting position to the ending position.

Example 2—The surgical instrument of Example 1, wherein the flexible upper drive member comprises an upper hollow coiled member and the flexible lower drive member comprises a lower hollow coiled member.

Example 3—The surgical instrument of Examples 1 or 2, wherein the flexible upper hollow member forms an upper pathway that spans the articulation joint for slidably supporting the flexible upper drive member therethrough. The flexible lower hollow member forms a lower pathway that spans the articulation joint for slidably supporting the flexible lower drive member therethrough. The upper pathway and the lower pathway are parallel to each other when the surgical end effector is in an unarticulated position and the upper pathway and the lower pathway are concentric to each other when the surgical end effector is articulated relative to the elongate shaft assembly.

Example 4—The surgical instrument of Examples 1, 2 or 3, wherein the upper proximal end of the flexible upper hollow member and the lower proximal end of the flexible lower hollow member are coupled to a distal differential assembly that is operably supported by the elongate shaft assembly. The distal differential assembly is configured to enable the flexible upper hollow member and the flexible lower hollow member to move in opposite axial directions when the surgical end effector is articulated relative to the elongate shaft assembly.

Example 5—The surgical instrument of Example 4, wherein the distal differential assembly comprises an upper distal gear rack that is supported for axial travel in two axial directions and is coupled to the proximal end of the flexible upper hollow member. The distal differential assembly further comprises a lower distal gear rack that is supported for axial travel in the two axial directions and is coupled to the proximal end of the flexible lower hollow member. A distal pinion gear is rotatably supported in meshing engagement with the upper distal rack and the lower distal gear rack.

Example 6—The surgical instrument of Examples 4 or 5, wherein the source of axial drive motions comprises a proximal differential drive assembly that is supported proximal to the articulation joint and operably interfaces with the flexible upper drive member and the flexible lower drive member such that when the surgical end effector is in the unarticulated position, the proximal differential drive assembly is configured to drive the flexible upper drive member and the flexible lower drive member equal axial distances in a same axial direction to apply an upper axial drive motion and a lower axial drive motion that is equal to the upper axial drive motion to the firing member. When the surgical end effector is in an articulated position, the proximal differential drive assembly is configured to permit the flexible upper drive member and the flexible lower drive member to move equal distances in opposite axial directions while applying the upper axial drive motion and lower axial drive motion that is equal to the upper axial drive motion to the firing member.

Example 7—The surgical instrument of Example 6, wherein the proximal differential drive assembly comprises an upper proximal gear rack that operably interfaces with the flexible upper drive member and a lower proximal gear rack that operably interfaces with the flexible lower drive member. A carrier is supported for axial movement relative to the upper proximal gear rack and the lower proximal gear rack. The carrier comprises a rotatable proximal pinion gear in meshing engagement with the upper proximal gear rack and the lower proximal gear rack.

Example 8—The surgical instrument of Example 7, wherein the carrier further comprises a carrier rack in meshing engagement with a motor-driven drive gear.

Example 9—The surgical instrument of Examples 1, 2, 3, 4, 5, 6, 7 or 8, wherein the flexible upper drive member comprises an upper push coil and the flexible lower drive member comprises a lower push coil.

Example 10—The surgical instrument of Example 9, wherein the flexible upper drive member further comprises an upper push coil cable that extends through the upper push coil and comprises an upper cable distal end that is coupled to the top portion of the firing member and an upper cable proximal end that is coupled to the upper proximal gear rack. The flexible lower drive member further comprises a lower push coil cable that extends through the lower push coil and comprises a lower cable distal end that is coupled to the bottom portion of the firing member and a lower cable proximal end that is coupled to the lower proximal gear rack.

Example 11—The surgical instrument of Example 10, further comprising an upper support beam that is supported by the elongate shaft assembly and extends proximally from the upper distal gear rack. The upper support beam defines an upper axial passage therein that is configured to slidably constrain a portion of the upper push coil that extends from the distal upper gear rack to the proximal upper gear rack. The surgical instrument further comprises a lower support beam that is supported by the elongate shaft assembly and extends proximally from the lower distal gear rack. The lower support beam defines a lower axial passage therein that is configured to slidably constrain a portion of the lower push coil that extends from the distal gear rack to the proximal gear rack.

Example 12—The surgical instrument of Examples 9, 10 or 11, wherein the upper push coil is received within an upper flexible sleeve and the lower push coil is received within a lower flexible sleeve.

Example 13—The surgical instrument of Examples 1, 2, 3, 4, 5, 6, 7, 8, 9, 10, 11 or 12, wherein the articulation joint comprises a proximal joint member hat is attached to the elongate shaft assembly and a distal joint member that is attached to the surgical end effector. A linkage assembly pivotally couples the proximal joint member to the distal joint member.

Example 14—The surgical instrument of Example 13, further comprising a plurality of flexible articulation actuators that extend through the elongate shaft assembly and the proximal joint member and are attached to the distal articulation joint member.

Example 15—A surgical instrument comprising an elongate shaft assembly that has a surgical end effector coupled thereto by an articulation joint that is configured to facilitate selective articulation of the surgical end effector relative to the elongate shaft assembly in multiple articulation planes. A firing member is supported for axial travel within the surgical end effector between a starting position and an ending position. A firing system is configured to selectively move the firing member between the starting position and the ending position. The firing system comprises an upper flexible firing assembly that comprises a flexible upper hollow member that includes an upper proximal end and an upper distal end. The upper proximal end is supported within the elongate shaft assembly for axial travel in two directions. The flexible upper hollow member spans the articulation joint and the upper distal end is fixed to the surgical end effector. The upper flexible firing assembly further comprises a flexible upper push coil that operably interfaces with a source of axial drive motions. The flexible upper push coil is slidably constrained in the flexible upper hollow member for axial movement therein. The flexible upper push coil spans the articulation joint inside of the flexible upper hollow member and operably interfaces with an upper portion of the firing member to apply upper axial drive motions thereto to move the firing member from the starting position to the ending position. The firing system further comprises a lower flexible firing assembly that includes a flexible lower hollow member that comprises a lower proximal end and a lower distal end. The lower proximal end is supported within the elongate shaft assembly for axial travel in the two axial directions. The flexible lower hollow member spans the articulation joint and the lower distal end is fixed to the surgical end effector. The upper proximal end of flexible upper hollow member and the lower proximal end of the flexible hollow lower member are configured to move equal distances relative to each other in opposite axial directions when the surgical end effector is articulated relative to the elongate shaft assembly. The lower flexible firing assembly further comprises a flexible lower push coil that operably interfaces with the source of axial drive motions. The flexible lower push coil is slidably constrained in the flexible lower hollow member for axial movement therein. The flexible lower push coil spans the articulation joint inside of the flexible lower hollow member and operably interfaces with a lower portion of the firing member to apply lower axial drive motions thereto to move the firing member from the starting position to the ending position.

Example 16—The surgical instrument of Example 15, wherein the source of axial drive motions comprises a proximal differential drive assembly that is supported proximal to the articulation joint and operably interfaces with the flexible upper push coil and the flexible lower push coil such that when the surgical end effector is in an unarticulated position, the proximal differential drive assembly is configured to drive the flexible upper push coil and the flexible lower push coil equal axial distances in a same axial direction to apply an upper axial drive motion and a lower axial drive motion that is equal to the upper axial drive motion to the firing member. When the surgical end effector is in an articulated position, the proximal differential drive assembly is configured to permit the flexible upper push coil and the flexible lower push coil to move equally in opposite axial directions while applying the upper axial drive motion and lower axial drive motion that is equal to the upper axial drive motion to the firing member.

Example 17—The surgical instrument of Example 16, wherein the proximal differential drive assembly comprises an upper proximal gear rack that operably interfaces with the flexible upper push coil and a lower proximal gear rack that operably interfaces with the flexible lower push coil. A carrier is supported for axial movement relative to the upper proximal gear rack and the lower proximal gear rack. The carrier comprises a rotatable proximal pinion gear that is in meshing engagement with the upper proximal gear rack and the lower proximal gear rack.

Example 18—The surgical instrument of Example 17, wherein carrier further comprises a carrier rack in meshing engagement with a motor-driven drive gear.

Example 19—The surgical instrument of Examples 15, 16, 17 or 18, wherein the flexible upper push coil further comprises an upper push coil cable that extends through the flexible upper push coil and comprises an upper cable distal end that coupled to the top portion of the firing member and an upper cable proximal end that is coupled to the upper proximal gear rack. The flexible lower push cable further comprises a lower push coil cable that extends through the lower push coil and comprises a lower cable distal end that is coupled to the bottom portion of the firing member and a lower cable proximal end that is coupled to the lower proximal gear rack.

Example 20—The surgical instrument of Examples 15, 16, 17, 18 or 19, wherein the upper push coil is received within an upper flexible sleeve and the lower push coil is received within a lower flexible sleeve.

Example Set No. 11

Example 1—A surgical instrument comprising an elongate shaft that has a surgical end effector coupled thereto by an articulation joint that is configured to facilitate selective articulation of the surgical end effector relative to the elongate shaft. A constant velocity drive shaft assembly spans the articulation joint and is configured to apply rotary motions to a portion of the surgical end effector. The constant velocity drive shaft assembly comprises a series of movable drive joints. Each movable drive joint is capable of moving in multiple planes relative to each other. A movable exoskeleton spans the articulation joint and comprises a series of movably interfacing annular rib members. Each annular rib member comprises a first end and a second end. The first end of one annular rib member is configured to movably interface with the second end of an adjacent annular rib member to facilitate relative movement therebetween in multiple directions. Each annular rib member comprises a central opening such that the central opening in each annular rib member cooperate to form a passage through the series of movably interfacing annular rib members for receiving the constant velocity drive shaft assembly therethrough.

Example 2—The surgical instrument of Example 1, further comprising a flexible drive cover configured to movably support the series of movable drive joints therein. The flexible drive cover is configured to maintain each movable drive joint in the series of movable drive joints in movable engagement with each other and is sized to pass through the passage in the series of movably interfacing annular rib members.

Example 3—The surgical instrument of Example 2, wherein the flexible drive cover comprises heat shrink tubing.

Example 4—The surgical instrument of Example 2, wherein the flexible drive cover comprises a coiled member.

Example 5—The surgical instrument of Example 2, wherein the flexible drive cover comprises a tube comprising a series of offset slits therein.

Example 6—The surgical instrument of Examples 1, 2, 3, 4 or 5, wherein each movable drive joint comprises a first sphere portion that includes a socket cavity. A second sphere portion is sized to be rotatably received in the socket cavity in the first sphere portion of an adjacent movable drive joint in the series of movable drive joints. A pair of diametrically opposed pins protrudes from the second sphere portion. Each pin is configured to be movably received in a corresponding pin slot in the first sphere portion of the adjacent drive joint and is configured to rotate and move axially in therein.

Example 7—The surgical instrument of Examples 1, 2, 3, 4, 5 or 6, further comprising a proximal rotary drive shaft that is configured to apply rotary drive motions to the constant velocity drive shaft assembly.

Example 8—The surgical instrument of Example 7, further comprising a proximal attachment shaft that comprises a proximal attachment portion that is configured to operably interface with the proximal rotary drive shaft. An attachment shaft socket portion is configured to rotatably receive therein the second sphere portion of a proximal-most movable drive joint.

Example 9—The surgical instrument of Examples 1, 2, 3, 4, 5, 6, or 8, further comprising a distal drive shaft configured to operably interface with a movable distal-most drive joint.

Example 10—The surgical instrument of Example 9, further comprising a firing member that is supported for axial travel within the surgical end effector between a starting position and an ending position. An upper flexible spine assembly is attached to a top portion of the firing member. A lower flexible spine assembly is attached to a bottom portion of the firing member. The distal drive shaft is configured to apply rotary drive motions to the upper flexible spine assembly and the lower flexible spine assembly.

Example 11—The surgical instrument of Example 10, wherein each annular rib member comprises an upper spine passage that is configured to accommodate passage of the upper flexible spine assembly therethrough. A lower spine passage is configured to accommodate passage of the lower flexible spine assembly therethrough.

Example 12—The surgical instrument of Example 1, 2, 3, 4, 5, 6, 7, 8, 9, 10 or 11 further comprising a plurality of flexible articulation actuation members that are configured to span the articulation joint and apply articulation motions to the surgical end effector. Each annular rib member comprises an articulation passage therein that corresponds to each flexible articulation actuation member to permit movable passage therethrough.

Example 13—A movable exoskeleton assembly for a surgical instrument. The movable exoskeleton assembly comprises a series of movably interfacing annular rib members that are configured to span an articulation joint of the surgical instrument. Each movably interfacing annular rib member comprises a cupped end and a domed end. The cupped end of one movably interfacing annular rib member is configured to movably interface with the domed end of an adjacent movably interfacing annular rib member to facilitate relative movement therebetween in multiple directions. Each movably interfacing annular rib member comprises a central opening such that the central opening in each interfacing annular rib member cooperate to form a passage through the series of movably interfacing annular rib members for permitting passage of drive components therethrough.

Example 14—The movable exoskeleton assembly of Example 13, further comprising a flexible hollow support member that is configured to be received in the passage and operably support the drive components therethrough.

Example 15—The movable exoskeleton assembly of Example 14, wherein the flexible hollow support member comprises heat shrink tubing.

Example 16—The movable exoskeleton assembly of Example 14, wherein the flexible hollow support member comprises heat shrink tubing.

Example 17—The movable exoskeleton assembly of Example 14, wherein the flexible cover comprises a tube comprising a series of offset slits therein.

Example 18—A surgical instrument, comprising an elongate shaft that has a surgical end effector coupled thereto by an articulation joint that is configured to facilitate selective articulation of the surgical end effector relative to the elongate shaft. The surgical end effector comprises a first jaw and a second jaw that is configured to move relative to the first jaw between an open position and a closed position. A firing member is supported for axial travel within the surgical end effector between a starting position and an ending position. The surgical instrument further comprises an upper flexible spine assembly that is attached to a top portion of the firing member. A lower flexible spine assembly is attached to a bottom portion of the firing member. A rotary drive is configured to move the firing member between the starting position and the ending position. A movable exoskeleton spans the articulation joint and comprises a series of movably interfacing annular rib members. Each annular rib member comprises a proximal end and a distal end. The proximal end of one of the annular rib members is configured to movably interface with the distal end of an adjacent annular rib member to facilitate relative movement therebetween in multiple directions. Each annular rib member comprises a central opening. The central opening in each annular rib member cooperates to form a passage through the series of annular rib members for receiving a portion of the rotary drive therethrough.

Example 19—The surgical instrument of Example 18, wherein each annular rib member comprises a proximal cupped end and a distal domed end. The proximal cupped end of one annular rib member is configured to movably interface with a distal domed end of an adjacent annular rib member to facilitate relative movement therebetween in multiple directions.

Example 20—The surgical instrument of Examples 18 or 19 further comprising a flexible hollow support member received in the passage and is configured to permit passage of the portion of the rotary drive therethrough.

Example Set No. 12

Example 1—A surgical instrument comprising a surgical end effector comprising a firing member that is supported for axial travel within the surgical end effector between a starting position and an ending position. The surgical instrument further comprises an elongate shaft that is coupled to the surgical end effector by an articulation joint that is configured to facilitate selective articulation of the surgical end effector relative to the elongate shaft. The articulation joint is configured to establish an upper pathway and a lower pathway through the articulation joint. The upper pathway and the lower pathway are parallel to each other when the surgical end effector is in an unarticulated position and the upper pathway and the lower pathway are concentric to each other when the surgical end effector is articulated relative to the elongate shaft assembly. The surgical instrument further comprises a firing system that is configured to selectively move the firing member between the starting position and the ending position. The firing system comprises an upper flexible firing assembly that slidably extends through the upper pathway and operably interfaces with a top portion of the firing member. A lower flexible firing assembly slidably extends through the lower pathway and operably interfaces with a bottom portion of the firing member. The firing system further comprises a differential drive assembly that is supported proximal to the articulation joint and operably interfaces with the upper firing assembly and the lower firing assembly such that when the surgical end effector is in the unarticulated position, the differential drive assembly is configured to drive the upper flexible firing assembly and the lower flexible firing assembly equal axial distances in a same axial direction to apply an upper axial drive motion and a lower axial drive motion that are equal to each other to the firing member. When the surgical end effector is in an articulated position, the differential drive assembly is configured to permit the upper firing assembly and the lower firing assembly to move in in equal but opposite axial directions while applying the upper axial drive motion and the lower axial drive motion to the firing member.

Example 2—The surgical instrument of Example 1, wherein the differential drive assembly comprises an axially movable carrier assembly that operably interfaces with the upper flexible firing assembly and the lower flexible firing assembly such that when the surgical end effector is in the unarticulated position relative to the elongate shaft assembly, the axially movable carrier assembly simultaneously applies equal amounts of axial control motions in the same axial direction to the upper flexible firing assembly and the lower flexible firing assembly to move the firing member from the starting position to the ending position. When the surgical end effector is in the articulated position relative to the elongate shaft assembly, the axially movable carrier assembly applies other equal amounts of axial control motions in the same axial direction to the upper flexible firing assembly and the lower flexible firing assembly to move the firing member from the starting position to the ending position.

Example 3—The surgical instrument of Example 2, wherein the upper firing assembly proximal end portion comprises a first gear rack and the lower firing assembly proximal end portion comprises a second gear rack. The axially movable carrier assembly comprises an axially movable carrier member that is supported for axial travel relative to the first gear rack and the second gear rack and comprises a rotatable pinion gear that is in meshing engagement with the first gear rack and the second gear rack.

Example 4—The surgical instrument of Example 3, wherein the axially movable carrier member comprises a carrier rack that is in meshing engagement with a motor-driven drive gear.

Example 5—The surgical instrument of Example 4, wherein the upper flexible firing assembly further comprises an upper flexible coil member that comprises an upper coil distal end and an upper coil proximal end. The upper coil distal end operably interfaces with the top portion of the firing member and the upper coil proximal end is coupled to the upper gear rack. The lower flexible firing assembly further comprises a lower flexible coil member that comprises a lower coil distal end and a lower coil proximal end. The lower coil distal end operably interfaces with the bottom portion of the firing member and the lower coil proximal end is coupled to the lower gear rack.

Example 6—The surgical instrument of Example 5, further comprising an upper cable that extends through the upper flexible coil member and comprises an upper cable distal end and an upper cable proximal end. The upper cable distal end is coupled to the top portion of the firing member and the upper cable proximal end operably interfaces with a source of articulation motions. The surgical instrument further comprises a lower cable that extends through the lower flexible coil member and comprises a lower cable distal end and a lower cable proximal end. The lower cable distal end is coupled to the bottom portion of the firing member. The lower cable proximal end operably interfaces with the source of articulation motions.

Example 7—The surgical instrument of Examples 1, 2, 3, 4, 5 or 6, wherein the articulation joint comprises a series of movably interfacing annular disc members. Each annular disc member comprises a first face and a second face. The first face of one annular disc member is configured to movably interface with the second face of an adjacent annular disc member to facilitate relative movement therebetween in multiple directions. Each annular disc member has an upper opening extending therethrough such that the upper opening in each annular disc member in the series of movably interfacing annular disc members cooperate to form the upper pathway for receiving the upper flexible firing assembly therethrough. Each annular disc member further has a lower opening extending therethrough such that the lower opening in each annular disc member in the series of movably interfacing annular disc members cooperate to form the lower pathway for receiving the lower flexible firing assembly therethrough.

Example 8—The surgical instrument of Example 7, wherein the first face of each annular disc member comprises a centrally-disposed spherical feature. The second face of each annular disc member comprises a centrally-disposed spherical socket that is configured to movably receive therein the centrally-disposed spherical feature of an adjacent annular disc member.

Example 9—The surgical instrument of Example 8, further comprising means for limiting the pivotal travel of the centrally disposed spherical feature within a centrally-disposed spherical socket of an adjacent annular disc member to a predetermined range of pivotal travel.

Example 10—The surgical instrument of Examples 7, 8 or 9, further comprising a resilient spacer member between each annular disc member.

Example 11—The surgical instrument of Examples 1, 2, 3, 4, 5, 6, 7, 8, 9 or 10, wherein the surgical end effector comprises a first jaw and a second jaw that is supported for movable travel relative to the first jaw between an open position and a closed position.

Example 12—The surgical instrument of Examples 1, 2, 3, 4, 5, 6, 7, 8, 9, 10 or 11, further comprising a plurality of actuation cables that are configured to apply articulation motions to the surgical end effector to articulate the surgical end effector relative to the elongate shaft assembly.

Example 13—The surgical instrument of Example 12, wherein the plurality of actuation cables are configured to apply opening motions to the surgical end effector to cause the second jaw to move between the open position and the closed position.

Example 14—A surgical instrument comprising a surgical end effector that comprises a channel that is configured to operably support a surgical staple cartridge therein. The surgical end effector further comprises an anvil that is pivotally supported on the channel for movement between an open position and a closed position relative to a surgical staple cartridge that is supported in the channel. A tissue cutting member is supported for axial travel within the surgical end effector between a starting position and an ending position. The surgical instrument further comprises an elongate shaft assembly that is coupled to the channel by an articulation joint that is configured to facilitate selective articulation of the surgical end effector relative to the elongate shaft assembly. The articulation joint is configured to establish an upper pathway and a lower pathway through the articulation joint. The upper pathway and the lower pathway are parallel to each other when the surgical end effector is in an unarticulated position and the upper pathway and the lower pathway are concentric to each other when the surgical end effector is articulated relative to the elongate shaft assembly. A firing system is configured to selectively move the tissue cutting member between the starting position and the ending position. The firing system comprises an upper flexible coil member that extends through the upper pathway and comprises an upper coil proximal end and an upper coil distal end. The upper coil distal end is coupled to a top portion of the tissue cutting member. The firing system further comprises a lower flexible coil member that extends through the lower pathway and comprises a lower coil proximal end and a lower coil distal end. The lower coil distal end is coupled to a bottom portion of the tissue cutting member. A differential drive assembly is supported proximal to the articulation joint and operably interfaces with the upper flexible coil member and the lower flexible coil member such that when the surgical end effector is in the unarticulated position, the differential drive assembly is configured to drive the upper flexible coil member and the lower flexible coil member equal axial distances in a same axial direction to apply an upper axial drive motion and a lower axial drive motion that are equal to each other to the tissue cutting member. When the surgical end effector is in an articulated position, the differential drive assembly is configured to permit the upper flexible coil member assembly and the lower flexible coil member to move in in equal but opposite axial directions while applying the equal upper axial drive motion and lower axial drive motion to the tissue cutting member.

Example 15—The surgical instrument of Example 14, further comprising an upper axial push rod that has an upper push rod proximal end that operably interfaces with the differential drive assembly and an upper push rod distal end that operably interfaces with the upper coil proximal end. An upper push coil cable extends through the upper flexible coil member and comprises an upper cable distal end that is coupled to the top portion of the tissue cutting member and an upper cable proximal end that is coupled to the upper push rod distal end. The surgical instrument further comprises a lower axial push rod that has a lower push rod proximal end that operably interfaces with the differential drive assembly and a lower push rod distal end that operably interfaces with the lower coil proximal end. A lower push coil cable extends through the lower flexible coil member and comprises a lower cable distal end that is coupled to the bottom portion of the tissue cutting member and a lower cable proximal end that is coupled to the lower push rod distal end.

Example 16—The surgical instrument of Example 15, wherein upper flexible coil member and a portion of the upper axial push rod is constrained for axial movement within an upper outer tube member that is supported within the upper pathway and comprises an upper tube member distal end that is supported in the surgical end effector and an upper tube member proximal end that is fixed within the elongate shaft assembly. The lower flexible coil member and a portion of the lower axial push rod is constrained for axial movement within a lower outer tube member that is supported within the lower pathway and comprises a lower tube member distal end that is supported in the surgical end effector and a lower tube member proximal end that is fixed within the elongate shaft assembly.

Example 17—The surgical instrument of Examples 15 or 16, wherein the differential drive assembly comprises an upper gear rack that is coupled to the upper push rod proximal end and a lower gear rack that is coupled to the lower push rod proximal end. A carrier is supported for axial movement relative to the upper gear rack and the lower gear rack. The carrier comprises a rotatable pinion gear that is in meshing engagement with the upper gear rack and the lower gear rack.

Example 18—The surgical instrument of Example 17, wherein the carrier further comprises a carrier rack that is in meshing engagement with a motor-driven drive gear.

Example 19—The surgical instrument of Examples 14, 15, 16, 17 or 18 further comprising a plurality of actuation cables extending through the elongate shaft assembly and the articulation joint to provide actuation motions to the surgical end effector.

Example 20—The surgical instrument of Example 19, wherein the plurality of actuation cables are configured to apply articulation motions to the surgical end effector to articulate relative to the elongate shaft assembly and opening and closing motions to the anvil.

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S.

Pat. No. 9,072,535, for example, discloses several examples of a robotic surgical instrument system in greater detail.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A method of operating a surgical instrument comprising a surgical end effector that is articulatable relative to a shaft assembly of the surgical instrument about an articulation joint, wherein said method comprises:
providing a rotary drive motion to a rotary drive member of the surgical end effector, wherein the rotary drive member extends through the articulation joint;
converting the rotary drive motion to an upper axial motion and a lower axial motion at locations that are distal to the articulation joint;
applying the upper axial motion to an upper portion of a firing member; and
applying the lower axial motion to a lower portion of the firing member such that the upper axial motion and lower axial motion drives the firing member distally through the surgical end effector from a starting position to an ending position.

2. The method of claim 1, wherein said providing a rotary drive motion comprises providing a rotary motion to the rotary drive member in a first rotary direction until the firing member reaches the ending position, and wherein said method further comprises providing another rotary drive motion to the rotary drive member in a second rotary direction after the firing member has reached the ending position to drive the firing member from the ending position to the starting position.

3. The method of claim 2, wherein said applying the upper axial motion comprises applying an upper axial motion in a distal direction, wherein said applying the lower axial motion comprises applying a lower axial motion in a distal direction.

4. The method of claim 3, further comprising:
converting the another rotary drive motion to another upper axial motion and another lower axial motion at the locations that are distal to the articulation joint;
applying the another upper axial motion to the upper portion of the firing member; and
applying the another lower axial motion to the lower portion of the firing member such that the another upper axial motion and the another lower axial motion drives the firing member proximally through the surgical end effector from the ending position to the starting position.

5. The method of claim 1, wherein the upper axial motion comprises a first magnitude, wherein the lower axial motion comprises a second magnitude, and wherein the second magnitude equals the first magnitude.

6. The method of claim 1, further comprising applying an articulation motion to the surgical end effector.

7. The method of claim 1, wherein the surgical end effector comprises a first jaw and a second jaw, wherein the second jaw is movable relative to the first jaw between an open position and a closed position, and wherein the second jaw is moved from the open position to the closed position by the firing member as the firing member is driven distally from the starting position.

8. The method of claim 1, wherein the surgical end effector comprises a first jaw and a second jaw, wherein the second jaw is movable relative to the first jaw between an open position and a closed position, and wherein said method further comprises applying a closure motion to the second jaw before said applying the upper axial motion to an upper portion of the firing member and said applying the lower axial motion to a lower portion of the firing member.

9. The method of claim 8, further comprising applying an articulation motion to an articulation control member that spans the articulation joint and operably interfaces with the surgical end effector to articulate the surgical end effector to an articulated orientation relative to the shaft assembly.

10. The method of claim 9, wherein said applying a closure motion comprises applying another actuation motion to the articulation control member to cause the second jaw to move from the closed position to the open position.

11. A method for operating a surgical instrument, wherein said method comprises:
providing a surgical end effector that is coupled to a shaft assembly by an articulation joint, wherein the surgical end effector comprises a firing member that is movable between a starting position and an ending position through the surgical end effector by a firing drive system that comprises a series of loosely-linked firing components extending through the articulation joint, and wherein said method further comprises:
converting the series of loosely-linked firing components into a rigid series of the firing components at a location that is distal to the articulation joint to generate an axial drive motion; and
applying the axial drive motion to the firing member to drive the firing member from the starting position to the ending position.

12. The method of claim 11, wherein said converting comprises applying a rotary drive motion to the series of loosely-linked firing components at the location that is distal to the articulation joint.

13. The method of claim 11, wherein the series of loosely-linked firing components comprises:
an upper series of loosely-linked upper firing components; and
a lower series of loosely-linked lower firing components, and wherein said converting comprises:
converting the upper series of loosely linked upper firing components into a rigid upper series of the upper firing components at the location that is distal to the articulation joint to generate an upper axial drive motion; and
converting the lower series of loosely-linked lower firing components into a rigid lower series of the lower firing components at the location that is distal to the articulation joint to generate a lower axial drive motion.

14. The method of claim 13, wherein said applying the axial drive motion to the firing member comprises:
applying the upper axial drive motion to an upper portion of the firing member; and
applying the lower axial drive motion to a lower portion of the firing member.

15. The method of claim 11, wherein the surgical end effector comprises a first jaw and a second jaw, wherein the second jaw is movable relative to the first jaw between an open position and a closed position, and wherein the second jaw is moved from the open position to the closed position by the firing member as the firing member is driven distally from the starting position.

16. The method of claim 14, wherein the surgical end effector comprises a first jaw and a second jaw, wherein the second jaw is movable relative to the first jaw between an open position and a closed position, and wherein said method further comprises applying a closure motion to the second jaw before said applying the upper axial drive motion to the upper portion of the firing member and said applying the lower axial drive motion to the lower portion of the firing member.

17. The method of claim 16, further comprising applying an articulation motion to an articulation control member that spans the articulation joint and operably interfaces with the surgical end effector to articulate the surgical end effector to an articulated orientation relative to the shaft assembly.

18. The method of claim 17, wherein said applying a closure motion comprises applying another actuation motion to the articulation control member to cause the second jaw to move from the closed position to the open position.

19. The method of claim 11, wherein said converting comprises:
drivingly engaging each of the loosely-linked firing components in the series of loosely-linked firing components with a rotary drive member; and
latching each loosely-linked firing component serially together with an adjacent one of the loosely-linked firing components as the adjacent one of the loosely-linked firing components disengages the rotary drive member such that the latched firing components form the rigid series of firing components.

20. The method of claim 19, wherein said drivingly engaging each of the loosely-linked firing components in the series of loosely-linked firing components with a rotary drive member further comprises rotating the rotary drive member in a first rotary direction until the firing member has reached the ending position, and wherein said method further comprises rotating the rotary drive member in a second rotary direction after the firing member has reached the ending position to drive the firing member from the ending position to the starting position.

* * * * *